United States Patent
Park et al.

(10) Patent No.: US 12,279,525 B2
(45) Date of Patent: Apr. 15, 2025

(54) ORGANIC ELECTROLUMINESCENT COMPOUND, A PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyo-Soon Park, Gyeonggi-do (KR); Kyoung-Jin Park, Gyeonggi-do (KR); Sang-Hee Cho, Gyeonggi-do (KR); So-Mi Park, Gyeonggi-do (KR); Dong-Hyung Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 778 days.

(21) Appl. No.: 17/391,166

(22) Filed: Aug. 2, 2021

(65) Prior Publication Data

US 2022/0069228 A1    Mar. 3, 2022

(30) Foreign Application Priority Data

Aug. 11, 2020   (KR) .................. 10-2020-0100503
Jun. 15, 2021   (KR) .................. 10-2021-0077495

(51) Int. Cl.

| | | |
|---|---|---|
| *H01L 51/50* | (2006.01) | |
| *C07D 307/91* | (2006.01) | |
| *C07D 403/10* | (2006.01) | |
| *H10K 85/60* | (2023.01) | |
| *H10K 50/11* | (2023.01) | |
| *H10K 101/00* | (2023.01) | |

(52) U.S. Cl.
CPC ......... *H10K 85/654* (2023.02); *C07D 307/91* (2013.01); *C07D 403/10* (2013.01); *H10K 85/633* (2023.02); *H10K 85/636* (2023.02); *H10K 85/6572* (2023.02); *H10K 50/11* (2023.02); *H10K 85/623* (2023.02); *H10K 85/6574* (2023.02); *H10K 85/6576* (2023.02); *H10K 2101/90* (2023.02)

(58) Field of Classification Search
CPC ........ H10K 50/10; H10K 50/15; H10K 50/30; H10K 50/113; H10K 50/622; H10K 50/631; H10K 50/155; H10K 50/852; H10K 50/342; H10K 85/342; H10K 85/636; H10K 85/6574; H10K 85/6572
See application file for complete search history.

(56) References Cited

U.S. PATENT DOCUMENTS

| | | | |
|---|---|---|---|
| 2015/0031896 A1* | 1/2015 | Vestweber | ........... H10K 85/633 564/429 |
| 2018/0208837 A1 | 7/2018 | Ahn | |
| 2018/0323397 A1 | 11/2018 | Ahn et al. | |
| 2019/0393427 A1 | 12/2019 | Moon et al. | |

FOREIGN PATENT DOCUMENTS

| | | | | |
|---|---|---|---|---|
| KR | 101577104 B | 12/2015 | | |
| KR | 101577104 B1 * | 12/2015 | ............. | H10K 50/00 |

* cited by examiner

*Primary Examiner* — Gregory D Clark
(74) *Attorney, Agent, or Firm* — G. Creston Campbell

(57) ABSTRACT

The present disclosure relates to an organic electroluminescent compound represented by formula 1, a plurality of host materials comprising a combination of specific compounds, and an organic electroluminescent device comprising the same. The organic electroluminescent device having improved driving voltage, luminous efficiency and/or lifespan properties can be provided by including the organic electroluminescent compound or a specific combination of compounds according to the present disclosure as a host material(s).

14 Claims, No Drawings

ORGANIC ELECTROLUMINESCENT COMPOUND, A PLURALITY OF HOST MATERIALS AND ORGANIC ELECTROLUMINESCENT DEVICE COMPRISING THE SAME

TECHNICAL FIELD

The present disclosure relates to an organic electroluminescent compound, host materials comprising a combination of specific compounds, and an organic electroluminescent device comprising the same.

BACKGROUND ART

In 1987, Tang et al. of Eastman Kodak first developed a small molecule green organic electroluminescent device (OLED) of TPD/Alq$_3$ bilayer consisting of a light-emitting layer and a charge transport layer. Thereafter, the development of OLEDs was rapidly effected and OLEDs have been commercialized. Currently, the organic electroluminescent device mainly uses a phosphor having excellent luminous efficiency in realizing a panel. OLEDs having high luminous efficiency and/or long lifespan are required for long-term use and high resolution of the display.

In order to improve luminous efficiency, driving voltage, and/or lifespan, various materials or concepts for the organic layer of an organic electroluminescent device have been proposed, but they have not been satisfactory in practical use. Accordingly, there has been a continuous need to develop an organic electroluminescent device having improved performance, for example, improved driving voltage, luminous efficiency, power efficiency, and/or lifespan properties, compared to the previously known organic electroluminescent device.

Korean Patent No. 10-1577104 discloses a fused dihydrophenanthrene derivative, but fails to specifically disclose a compound containing a substituted dihydrophenanthrene. It is still required to develop an organic electroluminescent material for improving OLED performance.

DISCLOSURE OF INVENTION

Technical Problems

The objective of the present disclosure is to provide an organic electroluminescent compound having a novel structure suitable for applying it to an organic electroluminescent device. Another object of the present disclosure is to provide an improved organic electroluminescent material capable of providing an organic electroluminescent device having properties of reduced driving voltage, improved luminous efficiency and/or long lifespan. Another object of the present disclosure is to provide an organic electroluminescent device having improved driving voltage, luminous efficiency and/or lifespan properties by including a specific combination of compounds as host materials.

Solution to Problem

The present inventors have completed the present disclosure by discovering that the compound represented by the following formula 1 achieves the above-described object. The compound represented by formula 1 of the present disclosure may be combined with a compound represented by formula 2, formula 3, or formula 4 to be applied to an organic electroluminescent device as a plurality of host materials.

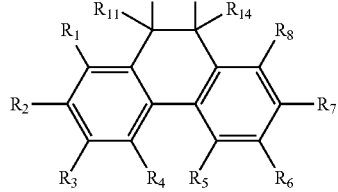

(1)

In formula 1, $R_{11}$ to $R_{14}$ each independently represent hydrogen, deuterium, a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring, with a proviso that at least one of $R_{11}$ to $R_{14}$ is neither hydrogen nor deuterium;

$R_1$ to $R_8$ each independently represent hydrogen, deuterium, or -L-Ar, or may be linked to an adjacent substituent to form a ring, with a proviso that at least one pair of $R_1$ and $R_2$, $R_2$ and $R_3$, $R_3$ and $R_4$, $R_5$ and $R_6$, $R_6$ and $R_7$, and $R_7$ and $R_8$ is linked to each other to be fused as the following formula a:

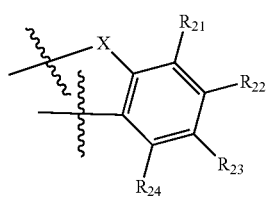

(a)

wherein

X represents $NR_{31}$, O, S, $CR_{32}R_{33}$, or $-CR_{34}=CR_{35}-$;

$R_{31}$ represents $-L_1-Ar_1$;

$R_{32}$ and $R_{33}$ each independently represent a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring;

$R_{34}$ and $R_{35}$ each independently represent hydrogen, deuterium, or $-L_5-Ar_5$;

$R_{21}$ to $R_{24}$ each independently represent hydrogen, deuterium, or $-L_2-Ar_2$, or may be linked to an adjacent substituent to form a ring;

L, $L_1$, $L_2$, and $L_5$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30) cycloalkylene;

Ar, $Ar_1$, $Ar_2$, and $Ar_5$ each independently represent a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, or a substituted or unsubstituted (C1-C30) alkoxy, or are represented by the following formula b or c:

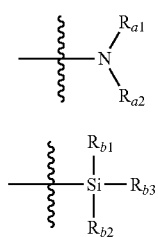

(b)

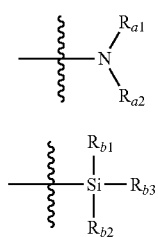

(c)

wherein $R_{a1}$, $R_{a2}$, $R_{b1}$, $R_{b2}$, and $R_{b3}$ each independently represent a substituted or unsubstituted (C6-C30)aryl, a substituted or unsubstituted (3- to 30-membered)heteroaryl, or a substituted or unsubstituted (C3-C30)cycloalkyl;

⸹ in formula a represents a bonding site with $R_1$ to $R_8$; and

⸹ in formulas b and c represents a bonding site with L, $L_1$, $L_2$, or $L_5$, respectively.

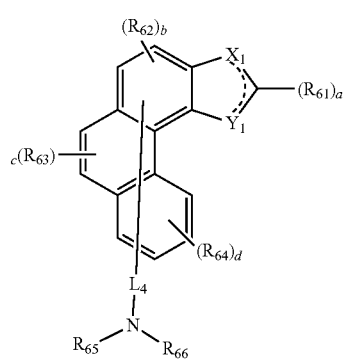

(2)

In formula 2, $X_1$ and $Y_1$ each independently represent —N═, —NR$_{67}$—, —O—, or —S—, with a proviso that any one of $X_1$ and $Y_1$ represents —N═, and the other one of $X_1$ and $Y_1$ represents —NR$_{67}$—, —O—, or —S—;

$R_{61}$ represents a substituted or unsubstituted (C6-C30)aryl or a substituted or unsubstituted (3- to 30-membered) heteroaryl;

$R_{62}$ to $R_{64}$ and $R_{67}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -L$_3$"-N(Ar$_3$")(Ar$_4$"); or may be linked to an adjacent substituent to form a ring;

L$_3$" each independently represents a single bond, a substituted or unsubstituted (C6-C30)arylene, or a substituted or unsubstituted (3- to 30-membered)heteroarylene;

Ar$_3$" and Ar$_4$" each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl;

$R_{65}$ and $R_{66}$ each independently represent a substituted or unsubstituted (C6-C30)aryl or a substituted or unsubstituted (3- to 30-membered)heteroaryl;

$L_4$ represents a single bond, a substituted or unsubstituted (C6-C30)arylene, or a substituted or unsubstituted (3- to 30-membered)heteroarylene; and a represents 1, b and c each independently represent 1 or 2, d represents an integer of 1 to 4, and when b to d are an integer of 2 or more, each of $R_{62}$ to each of $R_{64}$ may be the same or different from each other.

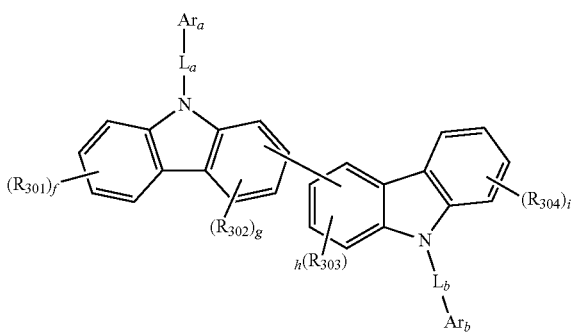

(3)

In formula 3, $L_a$ and $L_b$ each independently represents a single bond, a substituted or unsubstituted (C6-C30)arylene, or a substituted or unsubstituted (3- to 30-membered)heteroarylene;

Ar$_a$ and Ar$_b$ each independently represent a substituted or unsubstituted (C1-C30)alkyl, a substituted or unsubstituted (C6-C30)aryl, or a substituted or unsubstituted (3- to 30-membered)heteroaryl;

$R_{301}$ to $R_{304}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring of a (C3-C30)aliphatic ring(s) and a (C6-C30)aromatic ring(s), or -L$_3$'''-N(Ar$_3$''')(Ar$_4$'''); or may be linked to an adjacent substituent to form a ring;

L$_3$''' each independently represents a single bond, a substituted or unsubstituted (C6-C30)arylene, or a substituted or unsubstituted (3- to 30-membered)heteroarylene;

Ar$_3$''' and Ar$_4$''' each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s)

and a (C6-C30)aromatic ring(s), a substituted or unsubstituted (C6-C30)aryl, or a substituted or unsubstituted (3- to 30-membered)heteroaryl; and f and i each independently represent an integer of 1 to 4, g and h each independently represent an integer of 1 to 3, and when f to i are an integer of 2 or more, each of $R_{301}$ to each of $R_{304}$ may be the same or different from each other.

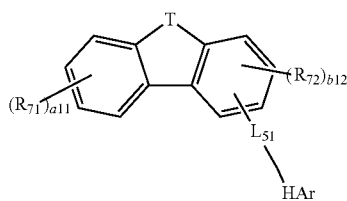

(4)

In formula 4,

T represents —O— or —S—;

HAr represents a substituted or unsubstituted nitrogen-containing (3- to 30-membered)heteroaryl;

$L_{51}$ represents a single bond, a substituted or unsubstituted (C6-C30)arylene, or a substituted or unsubstituted (3- to 30-membered)heteroarylene;

$R_{71}$ and $R_{72}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a ring; and $a_{11}$ represents an integer of 1 to 4, $b_{12}$ represents an integer of 1 to 3, and when $a_{11}$ and $b_{12}$ each represent an integer of 2 or more, each of $R_1$ and each of $R_{72}$ may be the same or different from each other.

Advantageous Effects of Invention

The organic electroluminescent compound according to the present disclosure exhibits suitable performance for use in organic electroluminescent devices. In addition, by including a specific combination of compounds according to the present disclosure as host materials, an organic electroluminescent device having a lower driving voltage, higher luminous efficiency and/or longer lifespan properties compared to a conventional organic electroluminescent device is provided. For example, by including the compound of the present disclosure, a red light-emitting organic electroluminescent device having a low driving voltage, high luminous efficiency and/or long lifespan properties can be provided.

MODE FOR THE INVENTION

Hereinafter, the present disclosure will be described in detail. However, the following description is intended to explain the invention, and is not meant to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, or an electron injection material.

The term "a plurality of organic electroluminescent material(s)" in the present disclosure means an organic electroluminescent material(s) comprising a combination of at least two compounds, which may be comprised in any organic layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent material(s) may be a combination of two or more compounds that may be included in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such two or more compounds may be included in the same layer or different layers through methods used in the art, and may be mixture-evaporated or co-evaporated, or individually deposited.

The term "a plurality of host material(s)" in the present disclosure means a host material(s) comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host material(s) of the present disclosure may be a combination of two or more host materials, and may optionally further include a conventional material comprised in organic electroluminescent materials. The two or more host materials comprised in the plurality of host materials of the present disclosure may be included in one light-emitting layer or may be respectively included in different light-emitting layers. For example, the two or more host materials may be mixture-evaporated or co-evaporated, or individually deposited.

The organic electroluminescent material of the present disclosure may comprise one or more types of the compound represented by formula 1. The compound of formula 1 may be comprised in a hole injection layer, a hole transport layer, a hole auxiliary layer, a light-emitting auxiliary layer, an electron blocking layer, a light-emitting layer, an electron buffer layer, a hole blocking layer, an electron transport layer and/or an electron injection layer, etc., but is not limited thereto. The compound of formula 1 may be comprised in a light-emitting layer, but is not limited thereto. When the compound of formula 1 is comprised in a light-emitting layer, it may be comprised as a host material. Here, the host material may be a host material of a blue, green or red light-emitting organic electroluminescent device.

Hereinafter, the compound represented by formula 1 will be described in more detail.

Herein, the term "(C1-C30)alkyl(ene)" is meant to be a linear or branched alkyl(ene) having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl(ene)" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7, preferably 5 to 7 ring backbone atoms, and including at least one heteroatom selected from the group consisting of B, N, O, S, Si, and P, preferably at least one heteroatom selected from the group consisting of O, S, and N. The above heterocycloalkyl may include tetrahydrofuran, pyrrolidine, thiolane, tetrahydropyran, etc. The term "(C6-C30)aryl(ene)" is meant to be a monocyclic or fused ring radical derived from an aromatic hydrocarbon having 6 to 30 ring backbone carbon atoms, which may be partially saturated. The number of ring backbone carbon atoms is preferably 6 to 25, and more preferably 6 to 18. The above aryl comprises those having a spiro structure. The above aryl may include phenyl, biphenyl, terphenyl, naphthyl, binaphthyl, phenylnaphthyl, naphthylphenyl, phenylterphenyl, fluorenyl, phenylfluorenyl, diphenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, tetramethyldihydrophenanthrenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene)" means an aryl group or arylene group having 3 to 30 ring backbone atoms and including at least one heteroatom(s) selected from the group consisting of B, N, O, S, Si, and P. The number of heteroatoms is preferably 1 to 4. The above heteroaryl(ene) may be a monocyclic ring or a fused ring condensed with at least one benzene ring, and may be partially saturated. In addition, the above heteroaryl(ene) comprises the form in which at least one heteroaryl or aryl group is linked to a heteroaryl group via a single bond(s), and also comprises those having a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolyl, benzofuroquinazolinyl, benzofuronaphthyridinyl, benzofuropyrimidinyl, naphthofuropyrimidinyl, benzothienoquinolyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, benzotriazolephenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-ted-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. In the present disclosure, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position: Para indicates that two substituents are at positions 1 and 4, and for example, when two substituents in a benzene derivative occupy positions 1 and 4, it is called a para position.

In addition, "substituted" in the expression "substituted or unsubstituted" means that a hydrogen atom in a certain functional group is replaced with another atom or another functional group (i.e., a substituent), and also comprises being substituted with a group in which two or more of the substituents are linked. For example, "a substituent in which two or more substituents are linked" may be pyridine-triazine. That is, pyridine-triazine may be interpreted as one heteroaryl substituent or the substituents in which two heteroaryl substituents are linked. In formulas of the present disclosure, the substituents of the substituted alkyl, the substituted alkylene, the substituted cycloalkyl, the substituted cycloalkylene, the substituted alkoxy, the substituted aryl, the substituted arylene, the substituted heteroaryl, and the substituted heteroarylene each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one (C6-C30)aryl(s); a (C6-C30)aryl unsubstituted or substituted with at least one of a (C1-C30)alkyl(s) and a (3- to 30-membered) heteroaryl(s); tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino(s) unsubstituted or substituted with a (C1-C30)alkyl(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of a (C1-C6)alkyl(s); a (5- to 15-membered)heteroaryl(s); a (C6-C15)aryl(s) unsubstituted or substituted with at least one (C1-C6)alkyl(s). Specifically, the substituents, each independently, may be at least one of methyl, phenyl, naphthyl, biphenyl, dimethylfluorenyl, tetramethyldihydrophenanthrenyl, pyridyl, dibenzothiophenyl, dibenzofuranyl, and carbazolyl.

In the formulas of the present disclosure, in case a substituent is linked to an adjacent substituent to form a ring, the ring may be a substituted or unsubstituted mono- or polycyclic (3- to 30-membered) alicyclic or aromatic ring, or the combination thereof formed from at least two adjacent substituents being linked. In addition, the formed ring may contain at least one heteroatom selected from B, N, O, S, Si, and P, preferably at least one heteroatom selected from N, O, and S. According to one embodiment of the present disclosure, the number of ring backbone atoms is 5 to 20, and according to another embodiment of the present disclosure, the number of ring backbone atoms is 5 to 15.

In the formulas of the present disclosure, the heteroaryl, the heteroarylene, and the heterocycloalkyl, each independently, may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

In formula 1, $R_{11}$ to $R_{14}$ each independently represent hydrogen, deuterium, a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring, with a proviso that at least one of $R_{11}$ to $R_{14}$ is neither hydrogen nor deuterium. According to one embodiment of the present disclosure, $R_{11}$ to $R_{14}$ each independently represent a substituted or unsubstituted (C1-C6)alkyl. According to another embodiment of the present disclosure, $R_{11}$ to $R_{14}$ each independently represent an unsubstituted (C1-C6) alkyl. For example, all of $R_{11}$ to $R_{14}$ may be methyl.

In formula 1, $R_1$ to $R_8$ each independently represent hydrogen, deuterium, or -L-Ar, or may be linked to an adjacent substituent to form a ring, with a proviso that at least one pair of $R_1$ and $R_2$, $R_2$ and $R_3$, $R_3$ and $R_4$, $R_5$ and $R_6$, $R_6$ and $R_7$, and $R_7$ and $R_8$ is linked to each other to be fused as the following formula a:

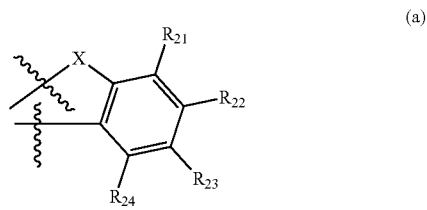

(a)

wherein X represents $NR_{31}$, O, S, $CR_{32}R_{33}$, or —$CR_{34}$=$CR_{35}$—, and $R_{31}$ represents -$L_1$-$Ar_1$.

Herein, $R_{32}$ and $R_{33}$ each independently represent a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring. According to one embodiment of the present disclosure, $R_{32}$ and $R_{33}$ each independently represent a substituted or unsubstituted (C1-C6)alkyl. According to another embodiment of the present disclosure, $R_{32}$ and $R_{33}$ each independently represent an unsubstituted (C1-C6)alkyl. For example, all of $R_{32}$ and $R_{33}$ may be methyl.

$R_{34}$ and $R_{35}$ each independently represent hydrogen, deuterium, or -$L_5$-$Ar_5$. According to one embodiment of the present disclosure, $R_{34}$ and $R_{35}$ each independently represent hydrogen or -$L_5$-$Ar_5$. For example, $R_{34}$ and $R_{35}$ may each independently be hydrogen, -$L_5$-$Ar_5$, etc.

In formula a, $R_{21}$ to $R_{24}$ each independently represent hydrogen, deuterium, or -$L_2$-$Ar_2$, or may be linked to an adjacent substituent to form a ring. According to one embodiment of the present disclosure, $R_{21}$ to $R_{24}$ each independently represent hydrogen or -$L_2$-$Ar_2$, or may be linked to an adjacent substituent to form a substituted or unsubstituted aromatic ring. According to another embodiment of the present disclosure, $R_{21}$ to $R_{24}$ each independently represent hydrogen or -$L_2$-$Ar_2$, or may be linked to an adjacent substituent to form an unsubstituted aromatic ring. For example, $R_{21}$ to $R_{24}$ may each independently be hydrogen or -$L_2$-$Ar_2$, or may be linked to an adjacent substituent to form a benzene ring.

In formula 1 and formula a, L, $L_1$, $L_2$, and $L_5$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, L, $L_1$, $L_2$, and $L_5$ each independently represent a single bond, a substituted or unsubstituted (C6-C15)arylene, or a substituted or unsubstituted (5- to 15-membered)heteroarylene. According to another embodiment of the present disclosure, L, $L_1$, $L_2$, and $L_5$ each independently represent a single bond, a (C6-C15) arylene unsubstituted or substituted with at least one (C6-C12)aryl(s), or an unsubstituted (5- to 15-membered)heteroarylene. For example, L may be a single bond, phenylene, quinazolinylene, quinoxalinylene, etc., $L_1$ may be a single bond, phenylene, naphthylene, biphenylene, phenylene substituted with phenyl, pyridylene, quinazolinylene, quinoxalinylene, carbazolylene, etc., $L_2$ may be a single bond, phenylene, quinazolinylene, quinoxalinylene, carbazolylene, etc., and $L_5$ may be a single bond, quinazolinylene, etc.

In formula 1 and formula a, Ar, $Ar_1$, $Ar_2$, and $Ar_5$ each independently represent a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, or a substituted or unsubstituted (C1-C30) alkoxy, or are represented by the following formula b or c:

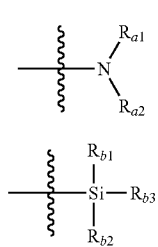

(b)

(c)

wherein $R_{a1}$, $R_{a2}$, $R_{b1}$, $R_{b2}$, and $R_{b3}$ each independently represent a substituted or unsubstituted (C6-C30)aryl, a substituted or unsubstituted (3- to 30-membered)heteroaryl, or a substituted or unsubstituted (C3-C30) cycloalkyl.

According to one embodiment of the present disclosure, Ar, $Ar_1$, $Ar_2$, and $Ar_5$ each independently represent a substituted or unsubstituted (C6-C20)aryl or a substituted or unsubstituted (5- to 15-membered)heteroaryl, or are represented by formula b. According to another embodiment of the present disclosure, Ar, $Ar_1$, $Ar_2$, and $Ar_5$ each independently represent a (C6-C20)aryl unsubstituted or substituted with at least one (5- to 15-membered)heteroaryl(s), or a (5- to 15-membered)heteroaryl unsubstituted or substituted with at least one of a (5- to 15-membered)heteroaryl(s) and a (C6-C15)aryl(s) unsubstituted or substituted with a (C1-C6) alkyl(s), or are represented by formula b. For example, Ar may be phenyl, phenyl substituted with carbazolyl, diphenyltriazinyl, triazinyl substituted with phenyl and dibenzofuranyl, quinazolinyl substituted with at least one phenyl, quinoxalinyl substituted with at least one phenyl, carbazolyl, diphenylamino, naphthylbiphenylamino, phenyldimethylfluorenylamino, phenyldibenzofuranylamino, phenyldibenzothiophenylamino, etc. $Ar_1$ may be phenyl, biphenyl, terphenyl, phenyl substituted with carbazolyl, diphenyltriazinyl, triazinyl substituted with phenyl and naphthyl, triazinyl substituted with phenyl and biphenyl, triazinyl substituted with phenyl and dimethylfluorenyl, triazinyl substituted with phenyl and tetramethyldihydrophenanthrenyl, triazinyl substituted with phenyl and pyridyl, triazinyl substituted with phenyl and dibenzofuranyl, triazinyl substituted with phenyl and dibenzothiophenyl, quinazolinyl substituted with at least one phenyl, quinoxalinyl substituted with at least one phenyl, carbazolyl, carbazolyl substituted with phenyl, diphenylamino, etc. $Ar_2$ may be phenyl, diphenyltriazinyl, triazinyl substituted with phenyl and dibenzofuranyl, quinazolinyl substituted with at least one phenyl, quinoxalinyl substituted with at least one phenyl, carbazolyl, carbazolyl substituted with phenyl, diphenylamino, phenylbiphenylamino, phenyldimethylfluorenylamino, phenyldibenzofuranylamino, phenyldibenzothiophenylamino, etc. $Ar_5$ may be biphenyl, diphenyltriazinyl, triazinyl substituted with phenyl and naphthyl, triazinyl substituted with phenyl and dibenzofuranyl, triazinyl substituted with phenyl and tetramethyldihydrophenanthrenyl, phenyldibenzofuranylamino, phenyldimethylfluorenylamino, etc.

In formula a, ⸺ represents a bonding site with $R_1$ to $R_8$.

In formulas b and c, ⸺ represents a bonding site with L, $L_1$, $L_2$, or $L_5$, respectively.

According to one embodiment of the present disclosure, formula 1 may be represented by at least one of the following formulas 1-1 to 1-6:

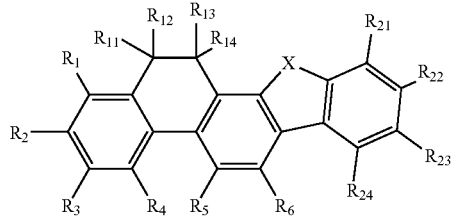

(1-1)

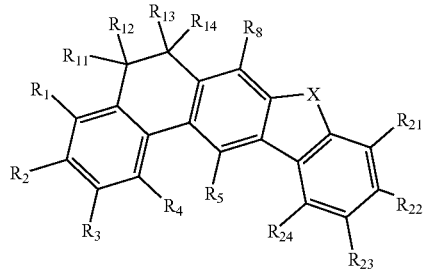

(1-2)

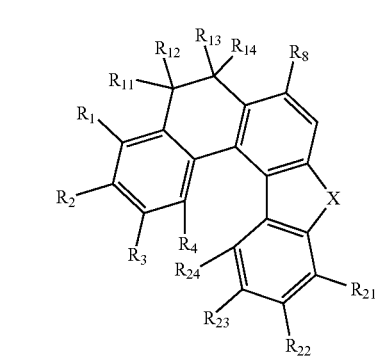

(1-3)

-continued (1-4)
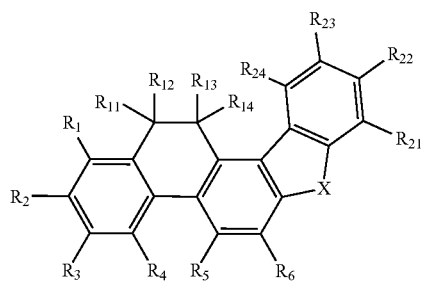

(1-5)
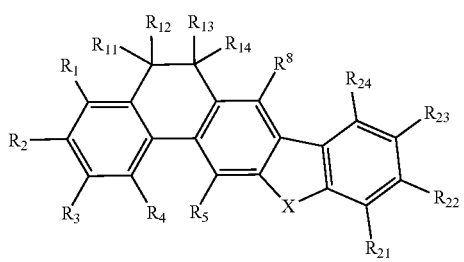

(1-6)
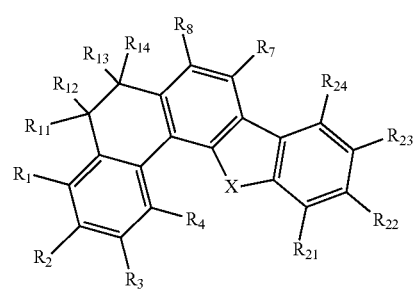

wherein $R_1$ to $R_8$, $R_7$ to $R_{14}$, $R_{21}$ to $R_{24}$, and X are as defined in formula 1.

According to one embodiment of the present disclosure, formula 1 may be represented by at least one of the following formulas 1-11 to 1-13:

(1-11)
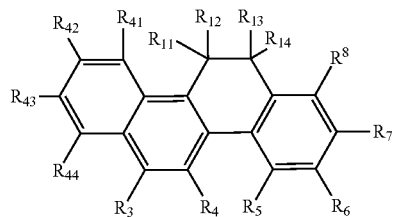

(1-12)
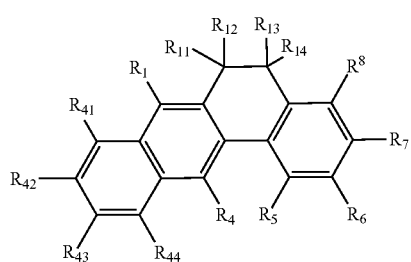

-continued (1-13)
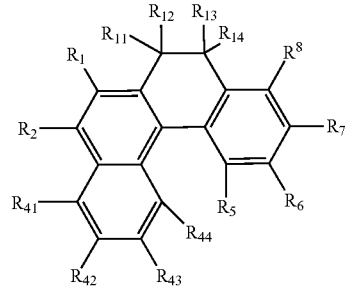

wherein $R_1$ to $R_8$ and $R_{11}$ to $R_{14}$ are as defined in formula 1;

$R_{41}$ to $R_{44}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or $-L_3-N(Ar_3)(Ar_4)$;

$L_3$ each independently represents a single bond, a substituted or unsubstituted (C6-C30)arylene, or a substituted or unsubstituted (3- to 30-membered)heteroarylene; and $Ar_3$ and $Ar_4$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

According to one embodiment of the present disclosure, $R_{41}$ to $R_{44}$ may each independently be hydrogen.

According to one embodiment of the present disclosure, formula a may be represented by at least one of the following formulas a-1 to a-3:

(a-1)
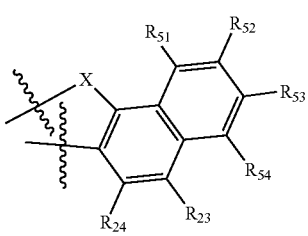

(a-2)
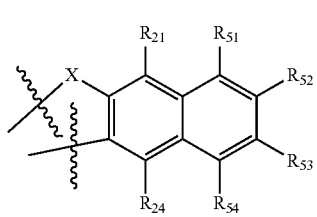

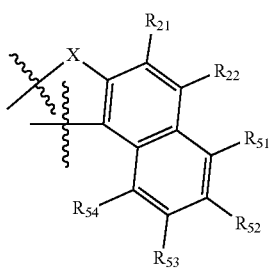

(a-3)

wherein
$R_{21}$ to $R_{24}$ and X are as defined in formula 1;
$R_{51}$ to $R_{54}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or $-L_3'-N(Ar_3')(Ar_4')$;
$L_3'$ each independently represents a single bond, a substituted or unsubstituted (C6-C30)arylene, or a substituted or unsubstituted (3- to 30-membered)heteroarylene; and
$Ar_3'$ and $Ar_4'$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

According to one embodiment of the present disclosure, $R_{51}$ to $R_{54}$ may each independently be hydrogen.

The compound represented by formula 1 may be at least one selected from the following compounds, but is not limited thereto.

C-1

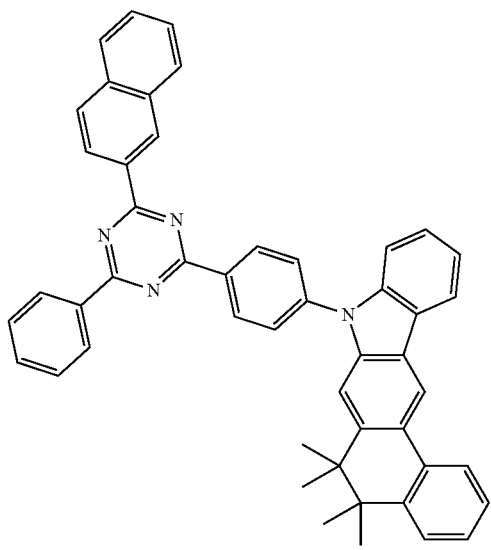

C-2

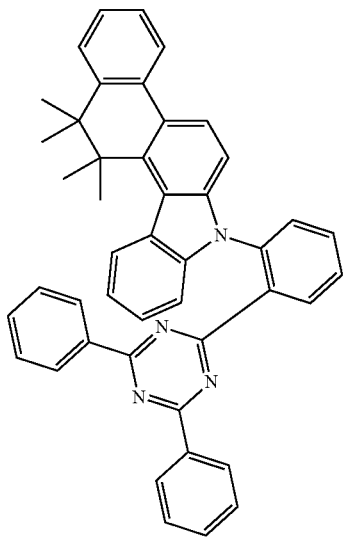

C-3

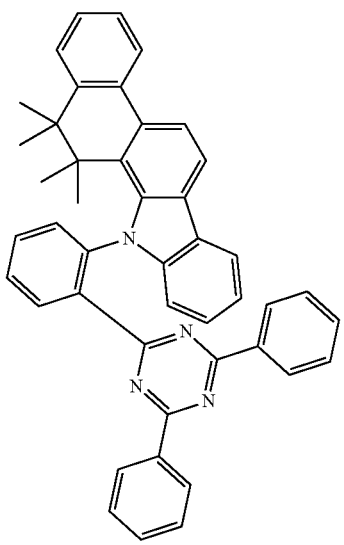

C-4

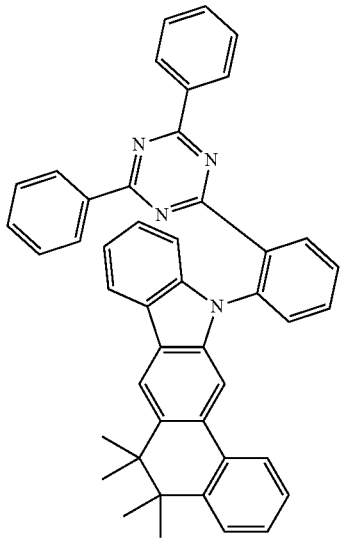

C-5
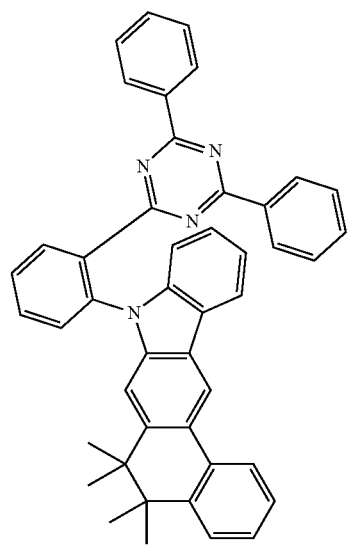
C-6
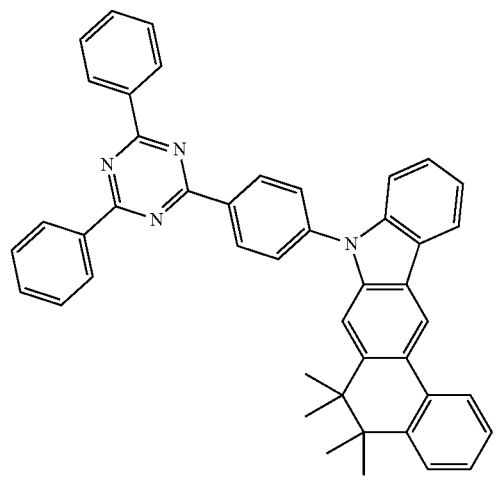
C-7
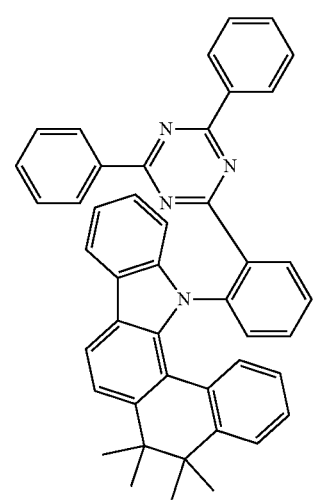
C-8
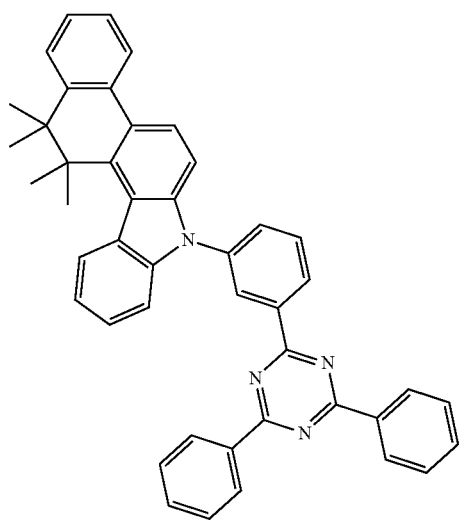
C-9
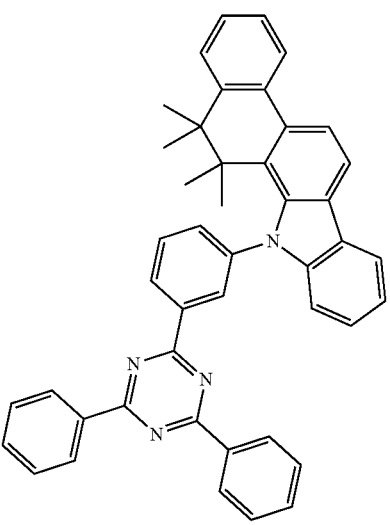
C-10
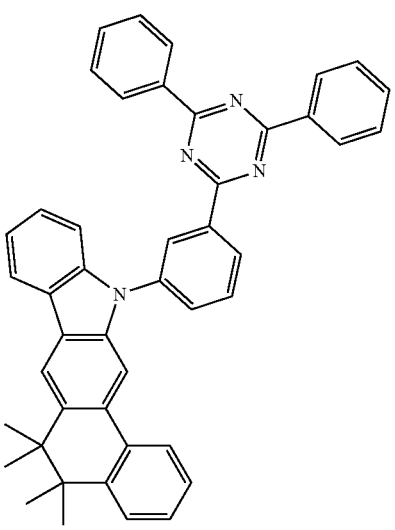

C-11
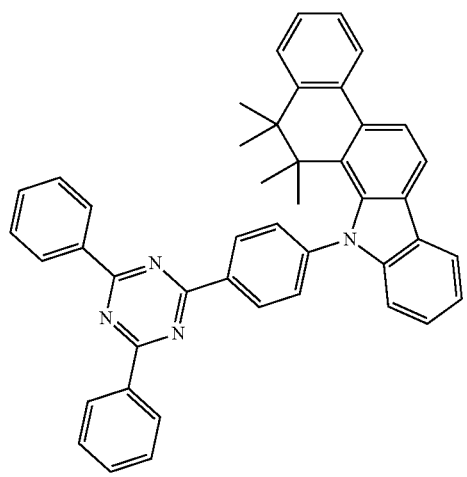
C-12
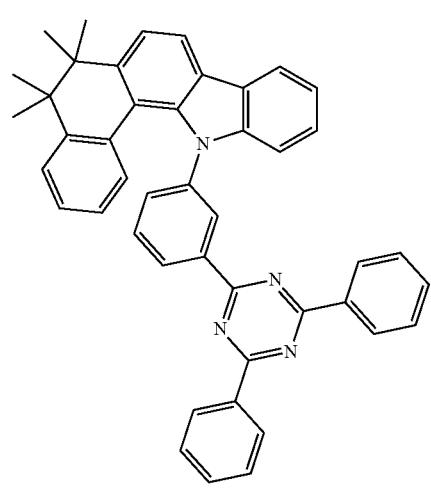
C-13
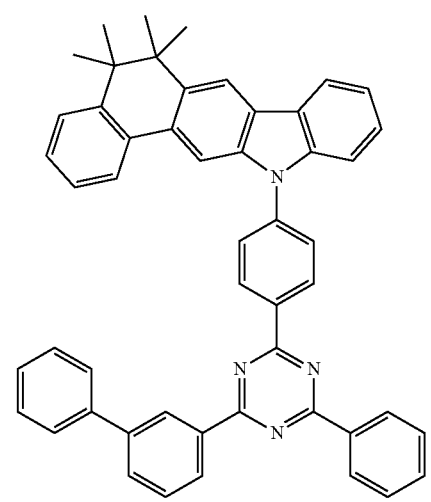
C-14
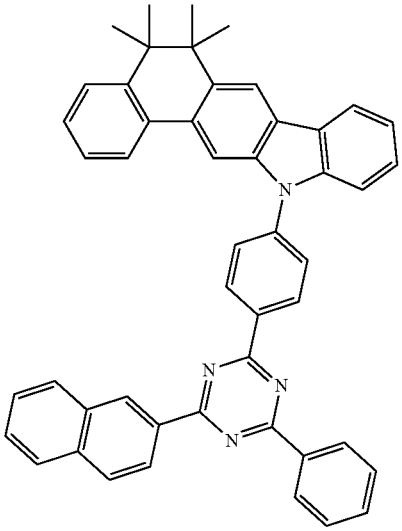
C-15
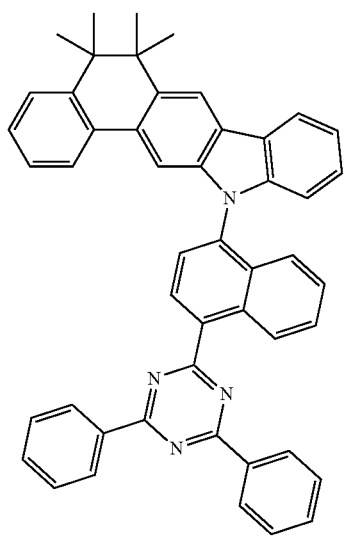
C-16
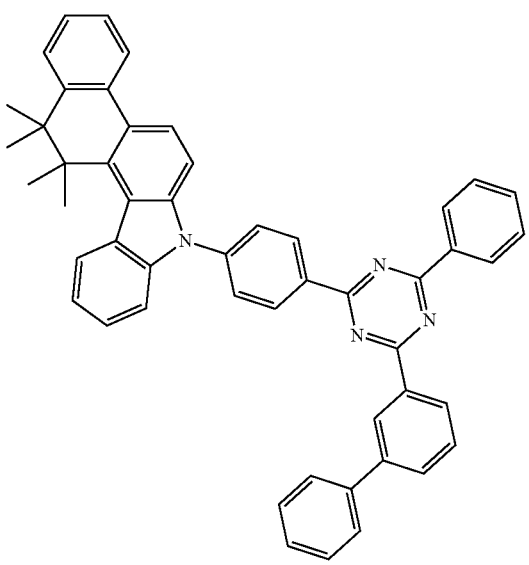

C-17
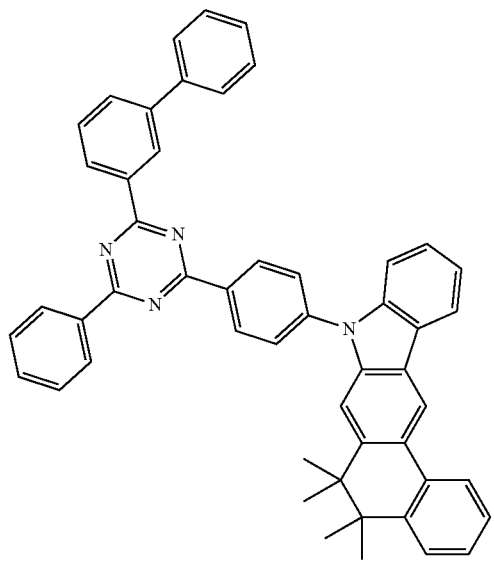
C-18
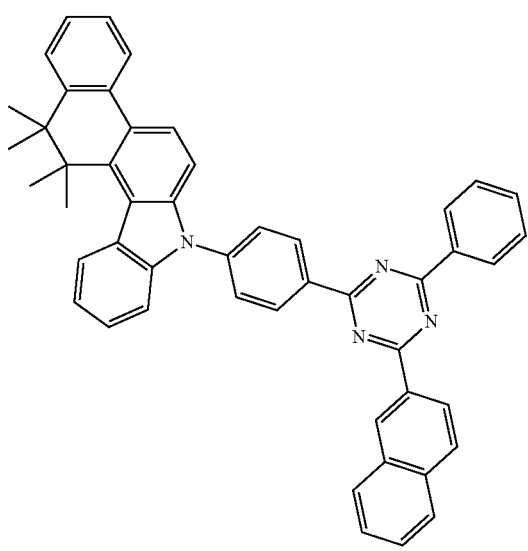
C-19
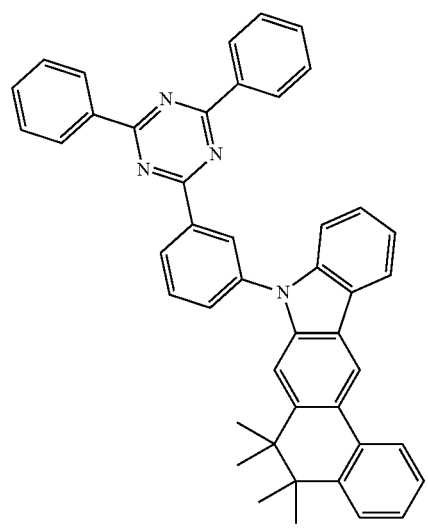
C-20
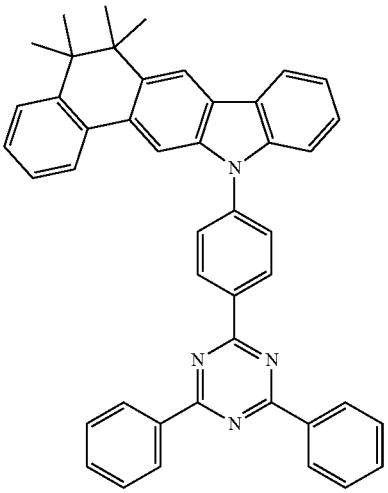
C-21
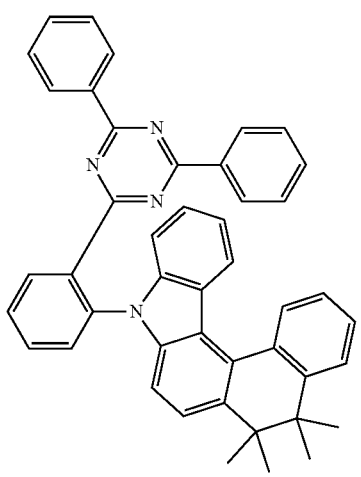
C-22
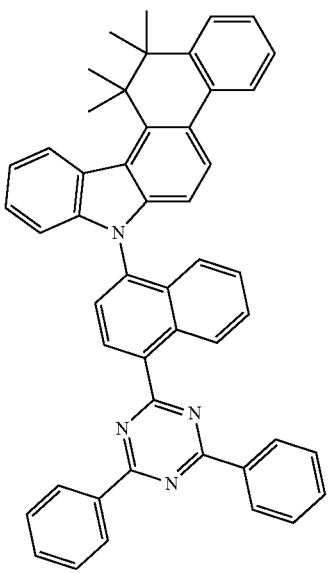

C-23
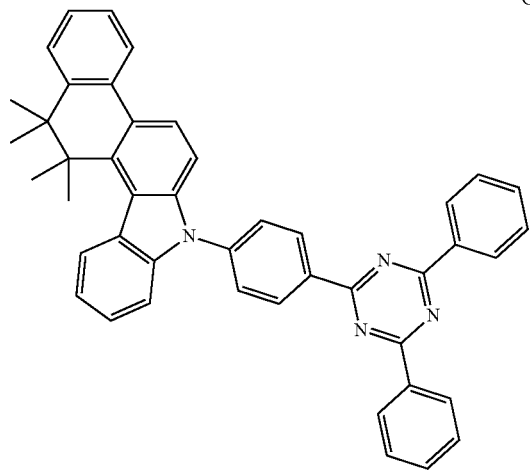
C-24
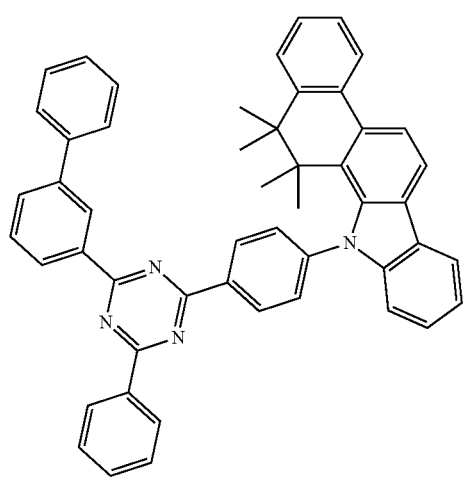
C-25
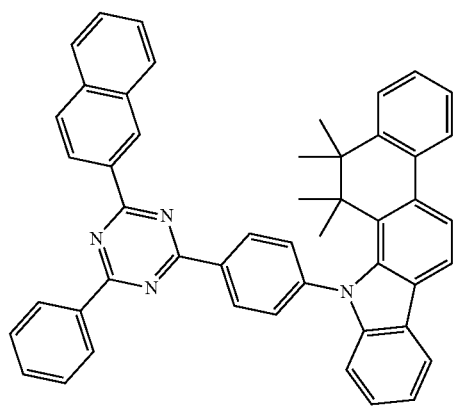
C-26
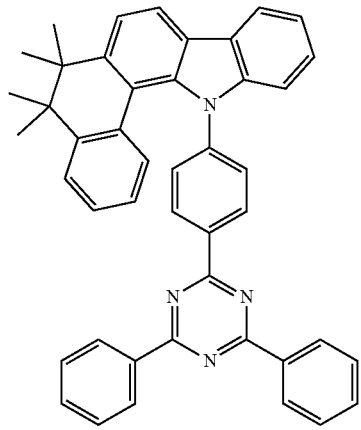
C-27
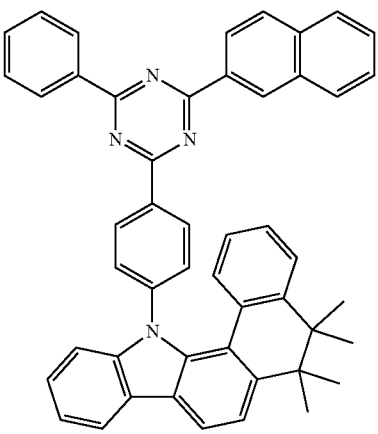
C-28
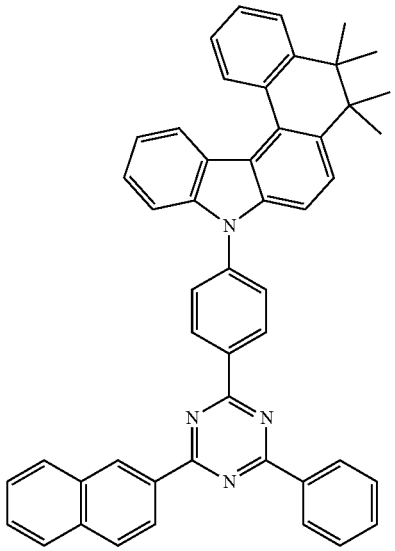

C-29
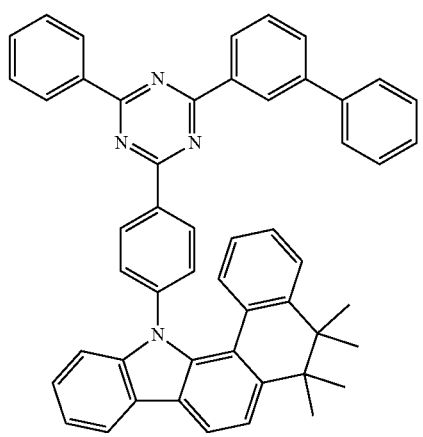
C-30
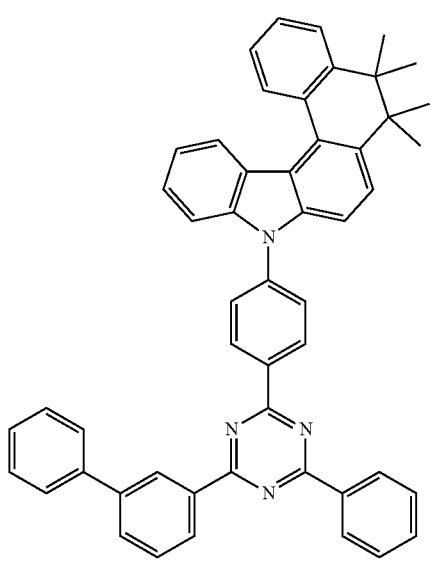
C-31
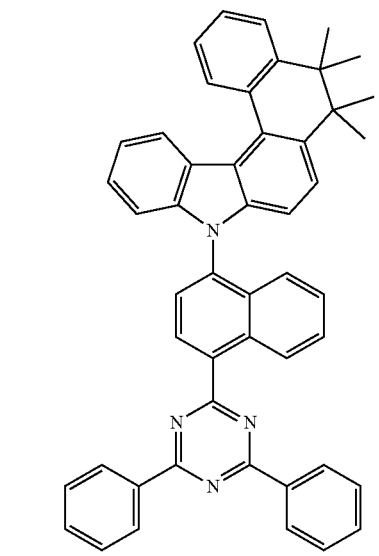
C-32
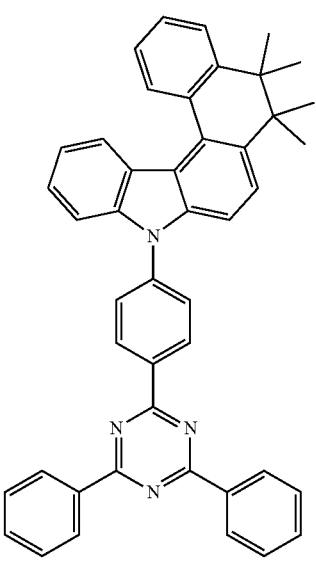
C-33
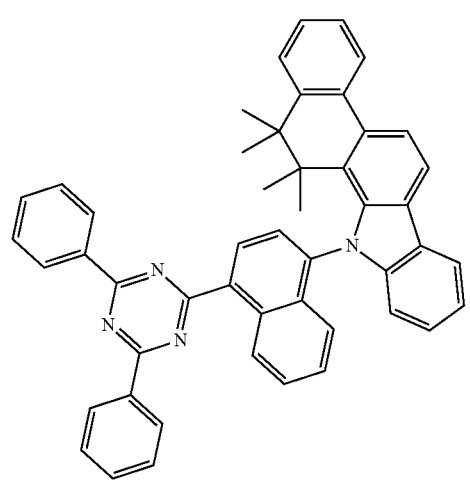
C-34
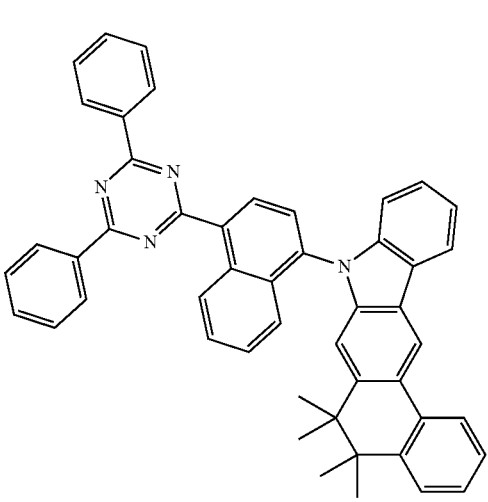

C-35
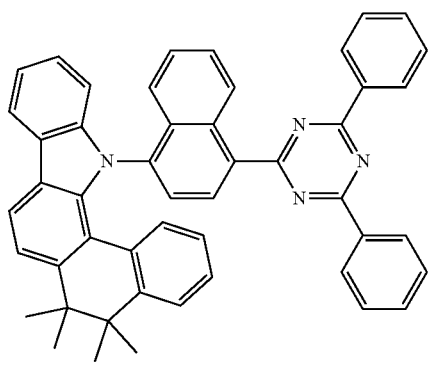
C-36
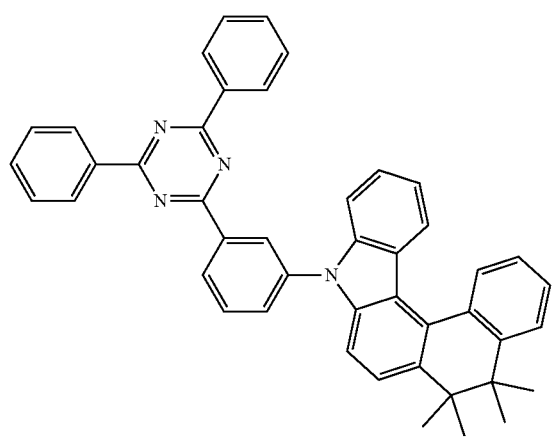
C-37
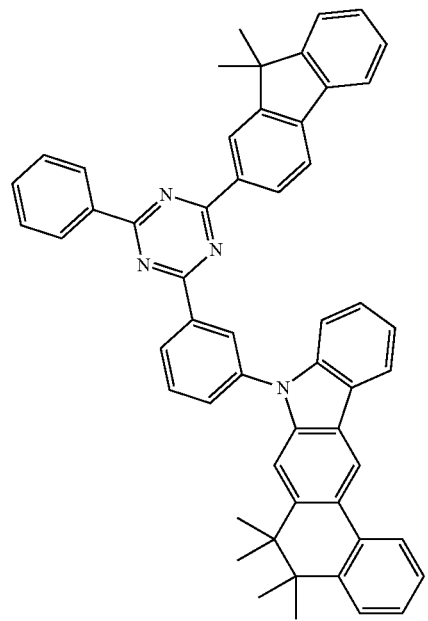
C-38
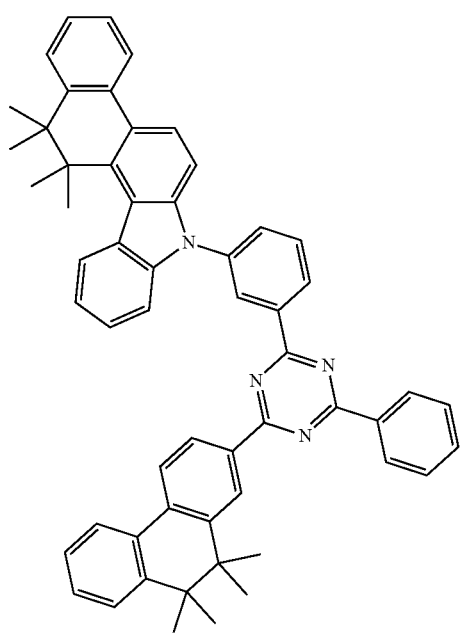
C-39
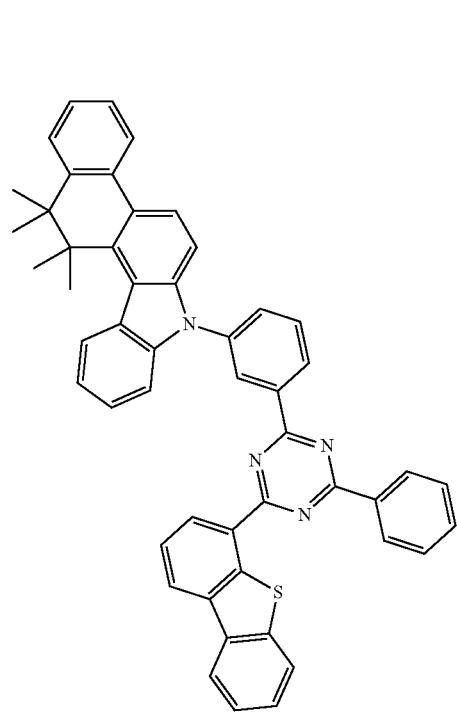

C-40
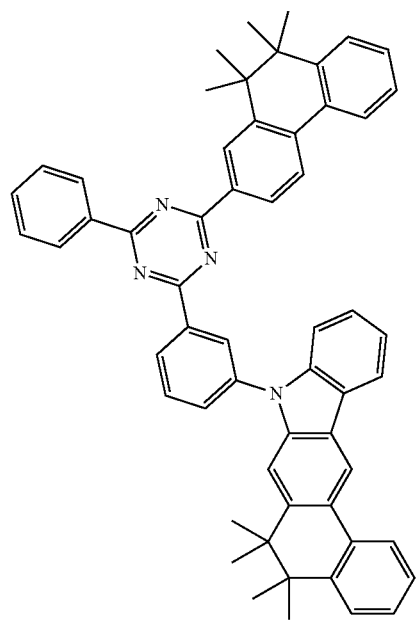
C-42
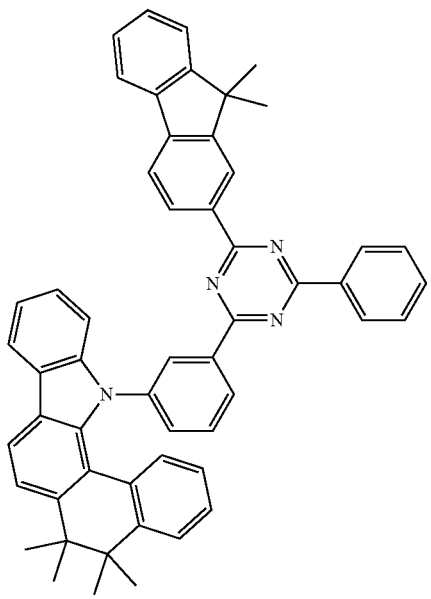
C-41
C-43
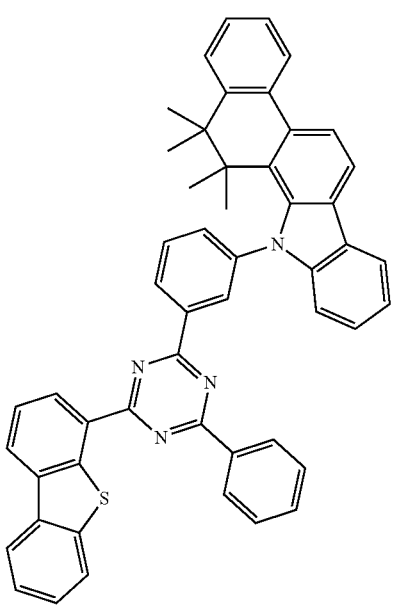

C-44
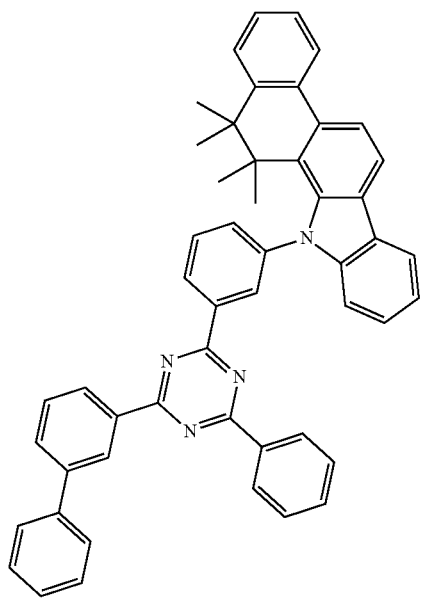
C-45
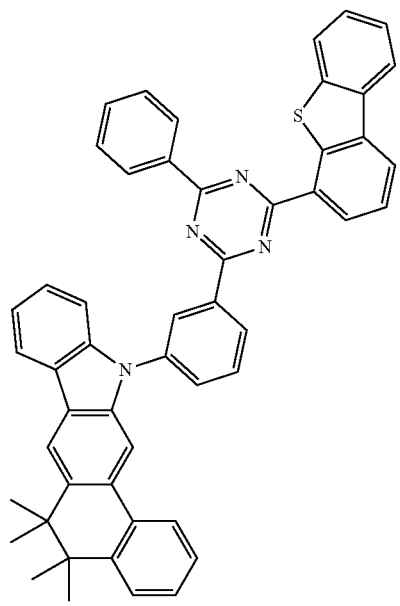
C-46
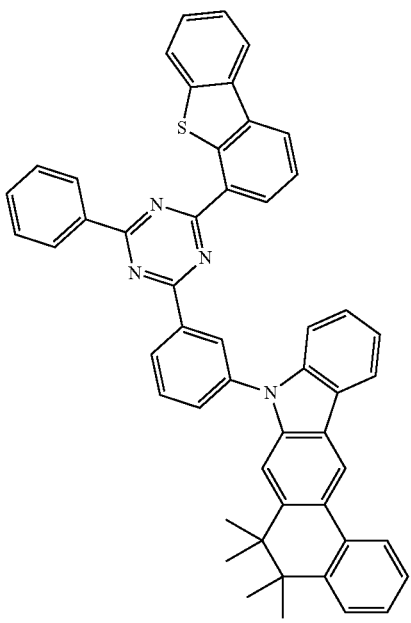
C-47
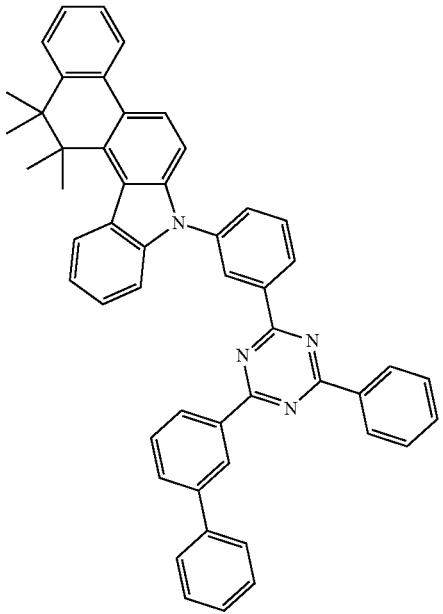

C-48
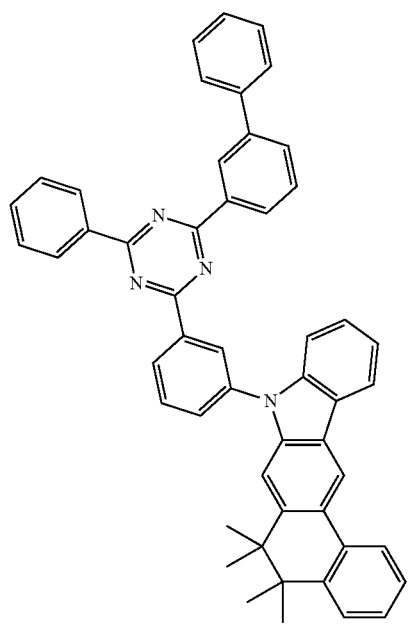
C-50
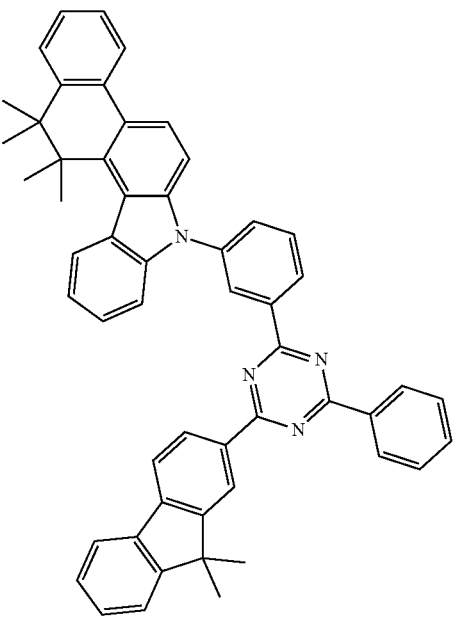
C-49
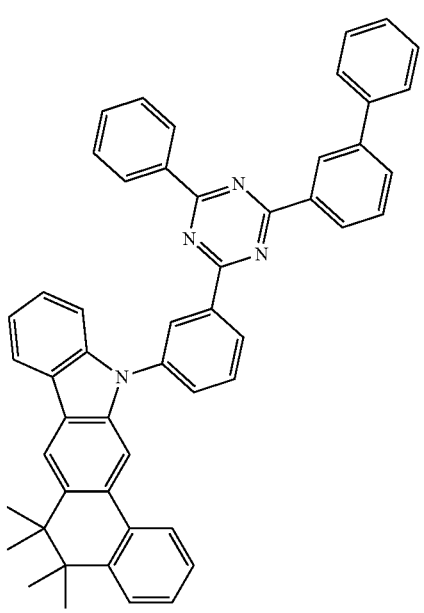
C-51
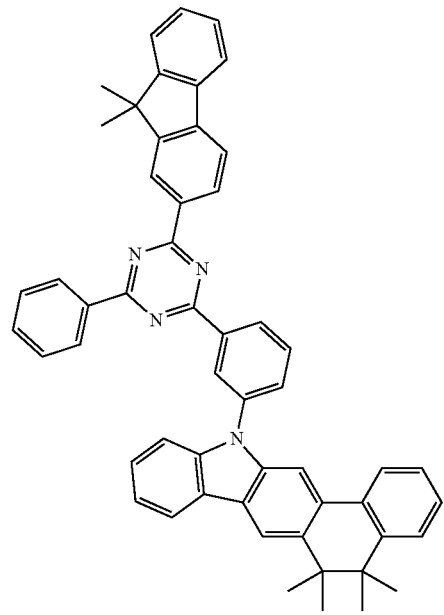

C-52
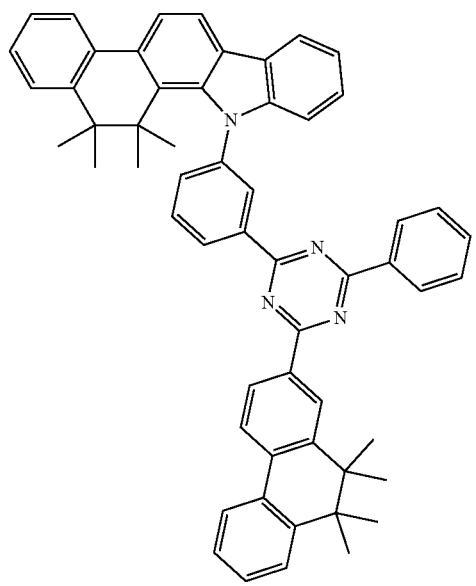
C-54
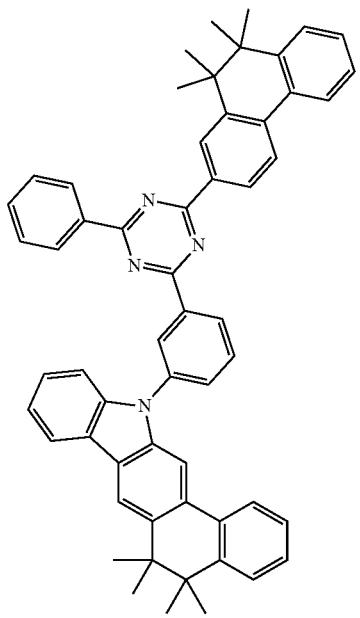
C-53
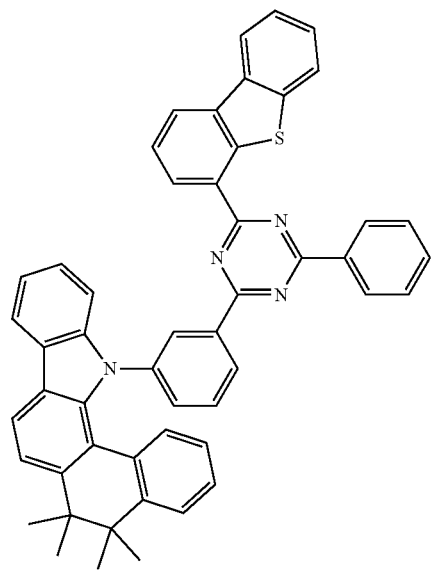
C-55
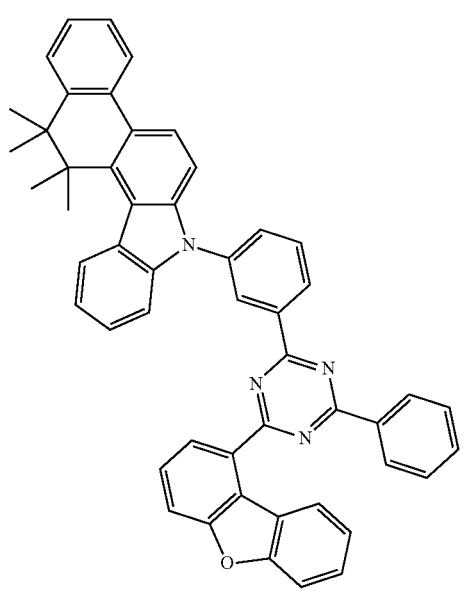

C-56
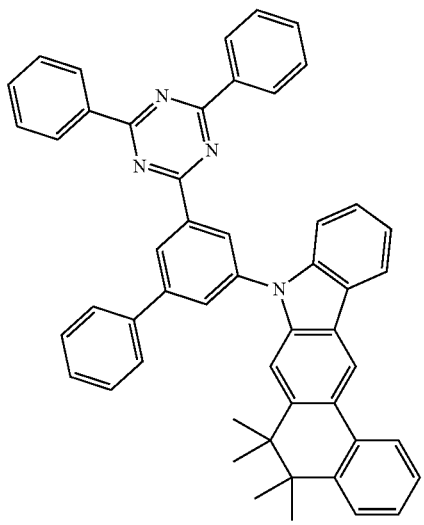
C-59
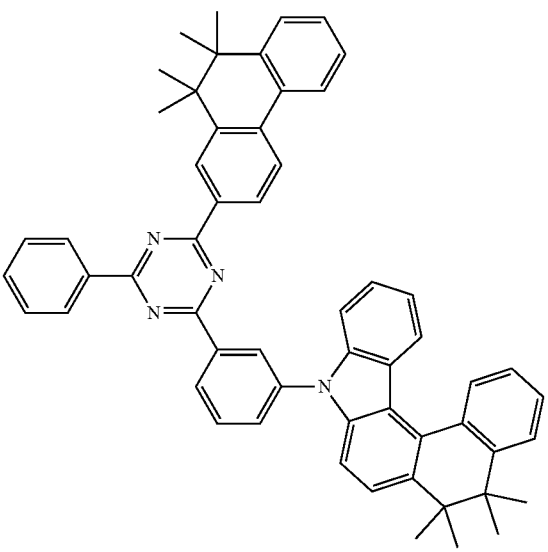
C-57
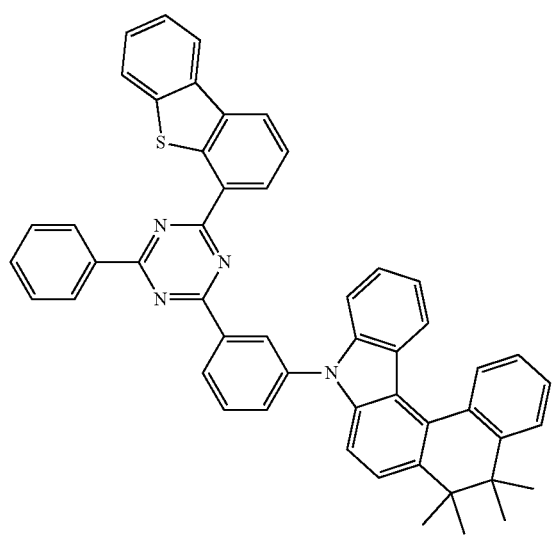
C-60
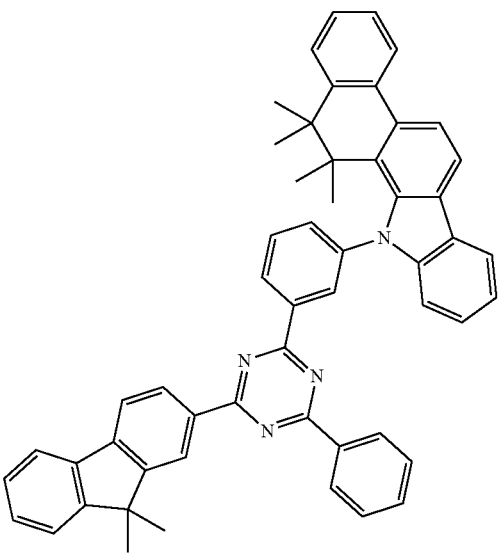
C-58
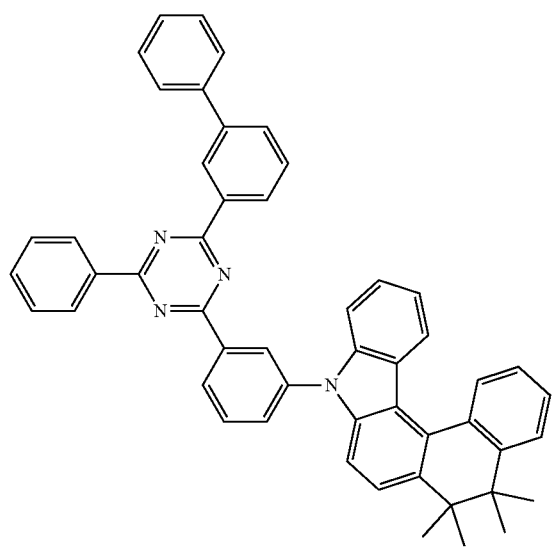
C-61
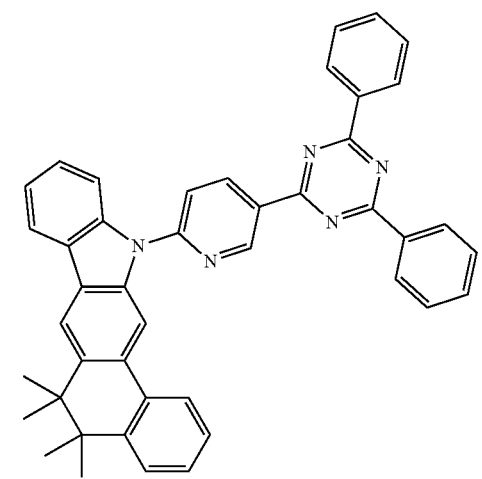

C-62
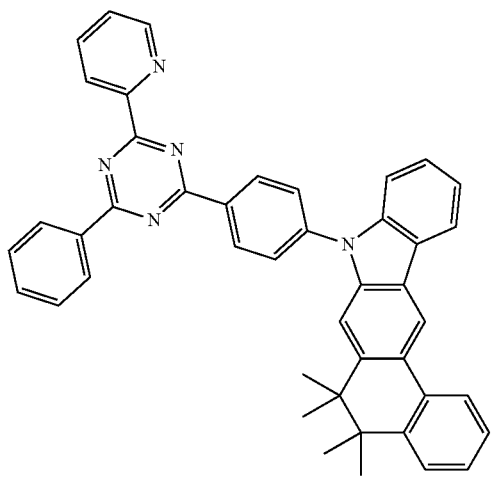
C-65
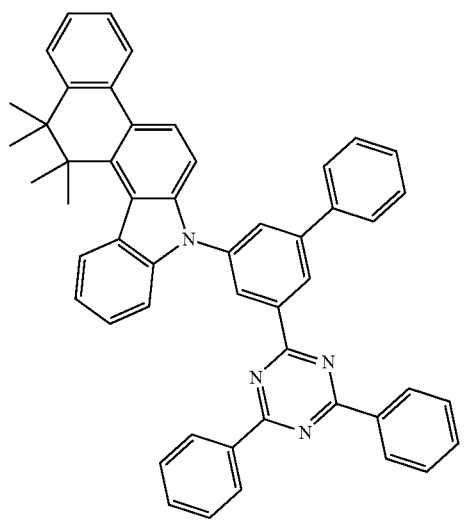
C-63
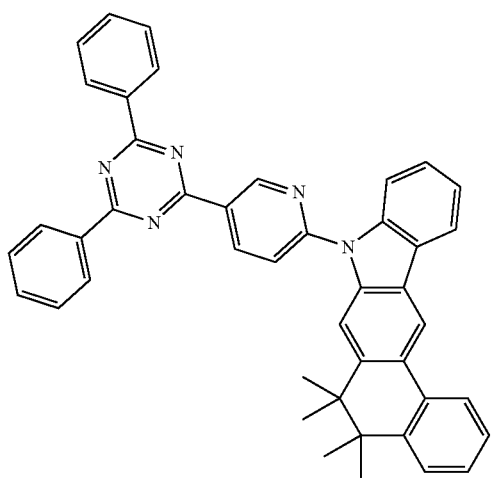
C-66
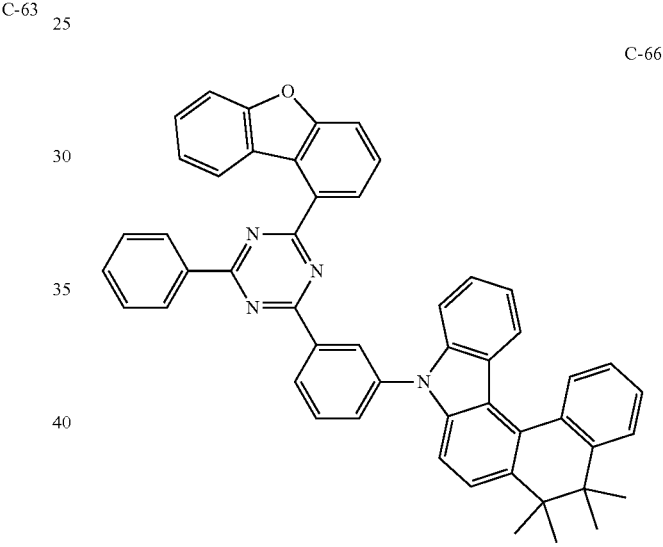
C-64
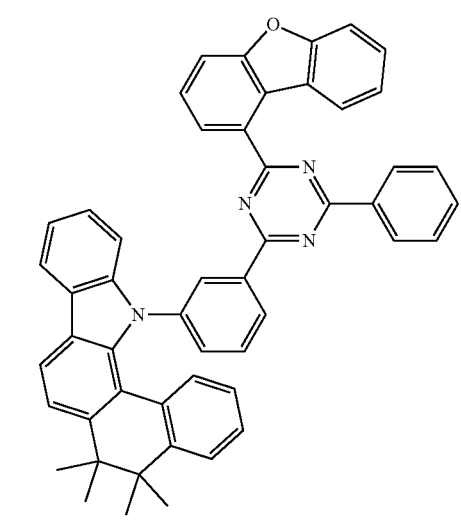
C-67
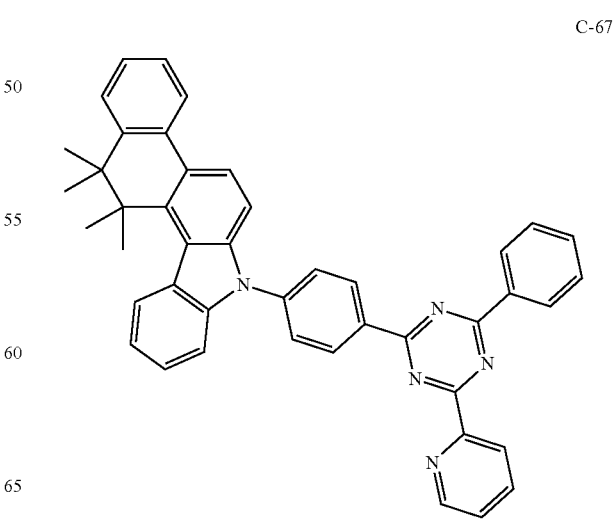

-continued
C-68
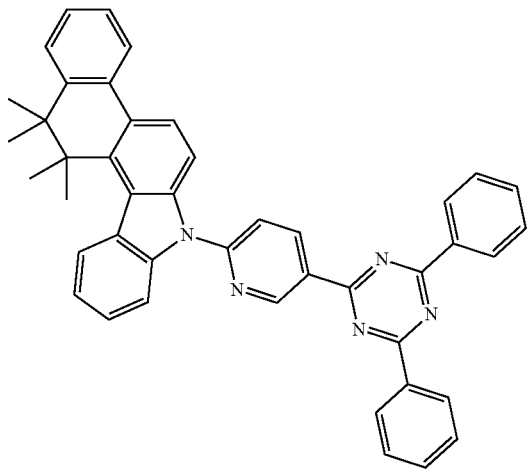
C-69
C-70
-continued
C-71
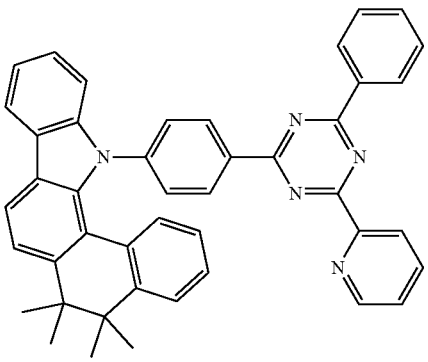
C-72
C-73
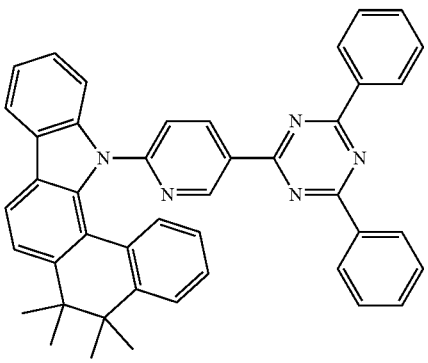
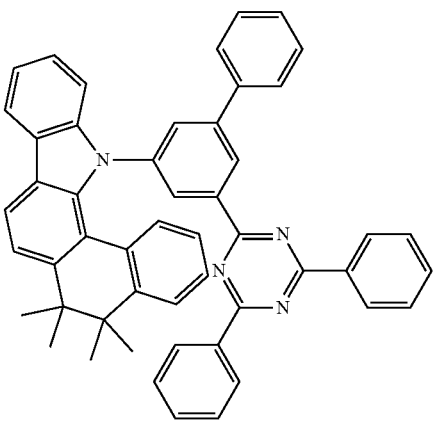
C-74
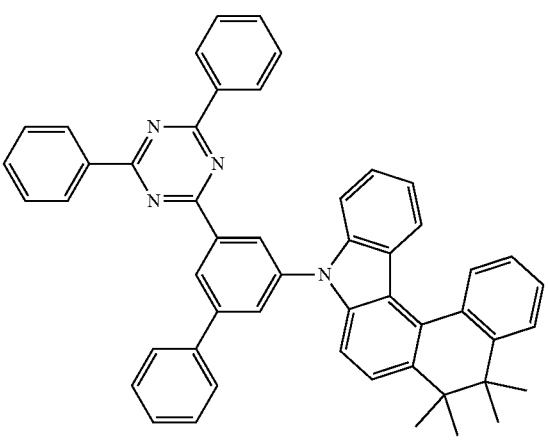

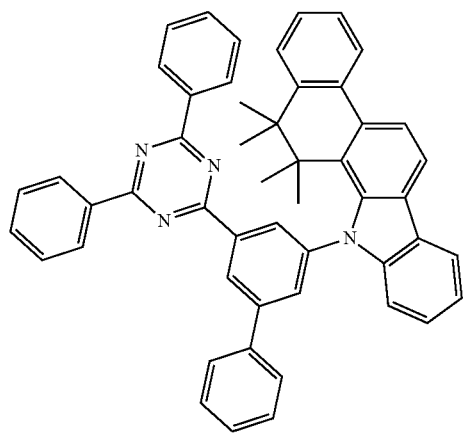
C-75
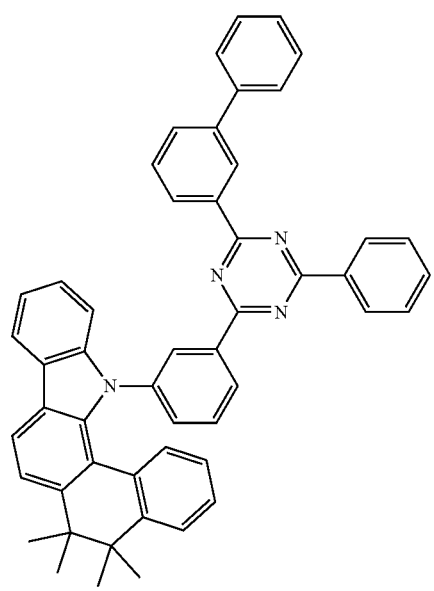
C-76
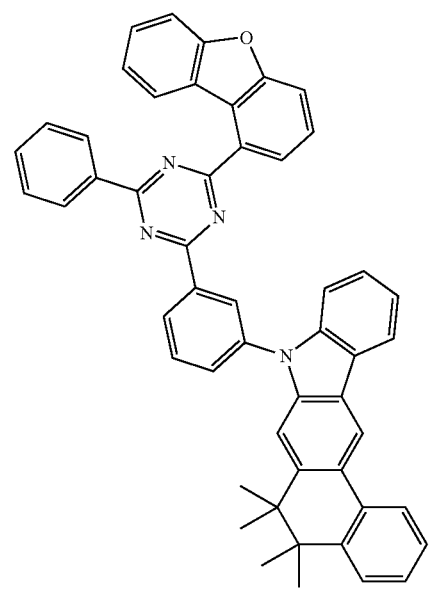
C-77
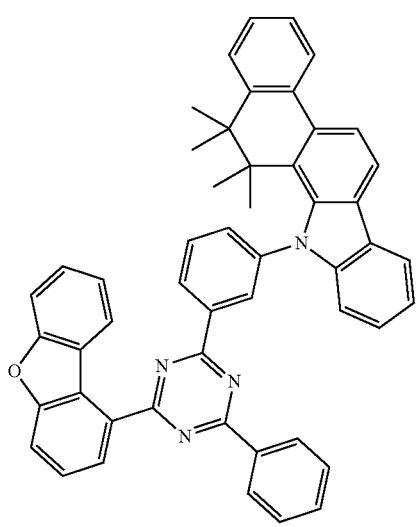
C-78
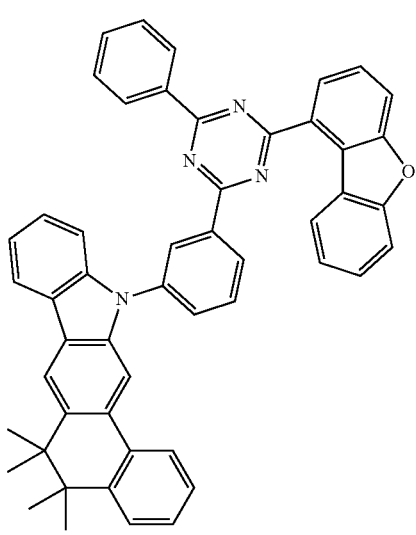
C-79
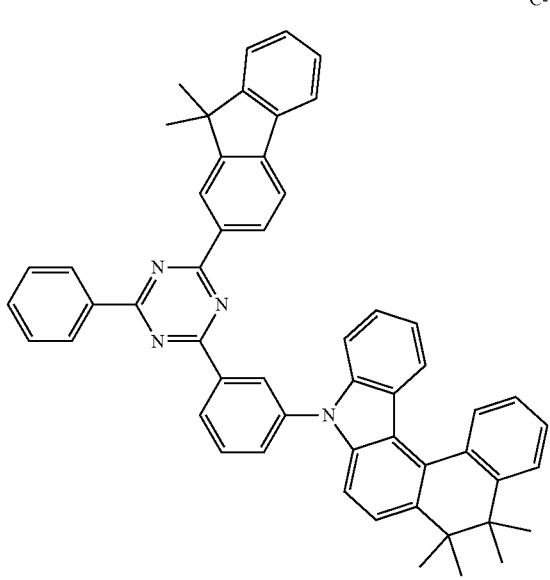
C-80

C-81
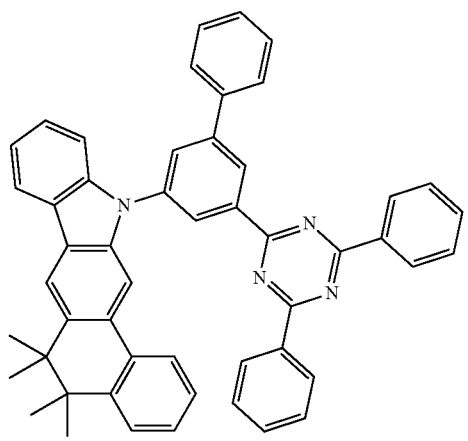
C-82
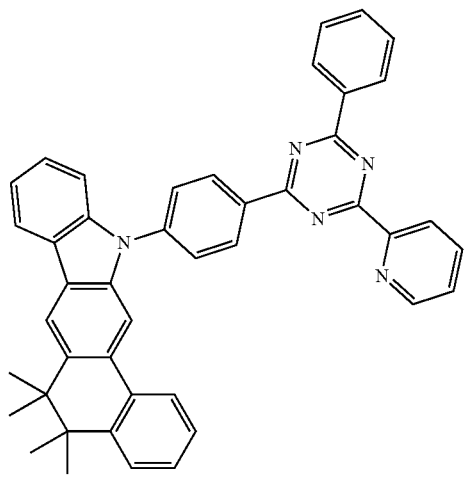
C-83
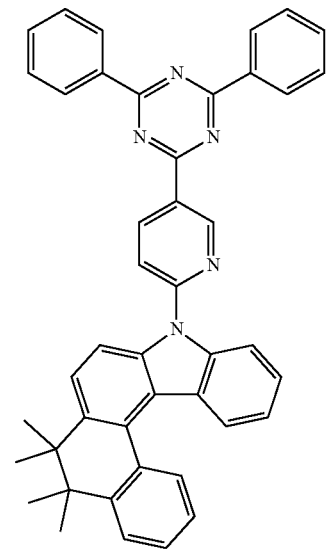
C-84
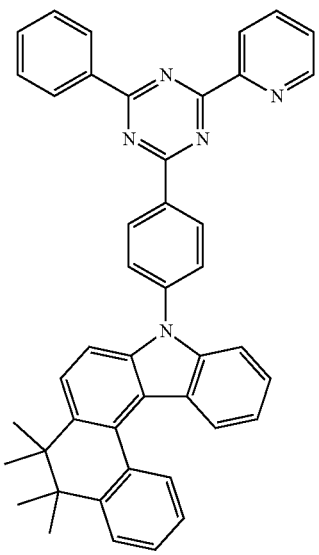
C-85
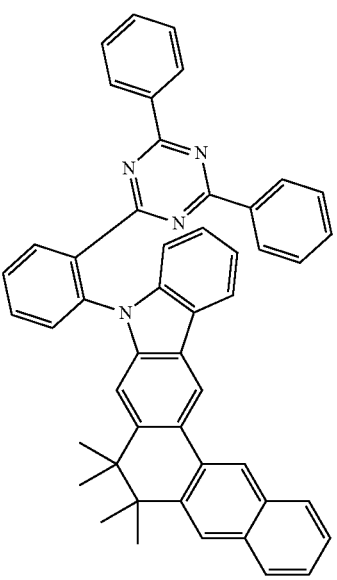

-continued
C-86
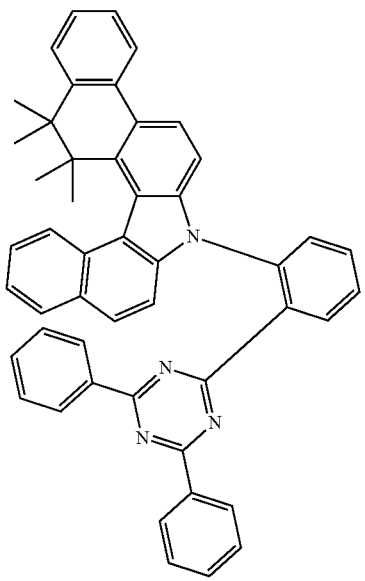
C-88
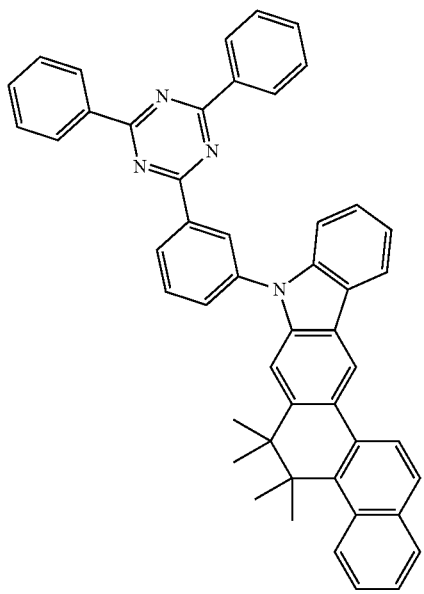
C-87
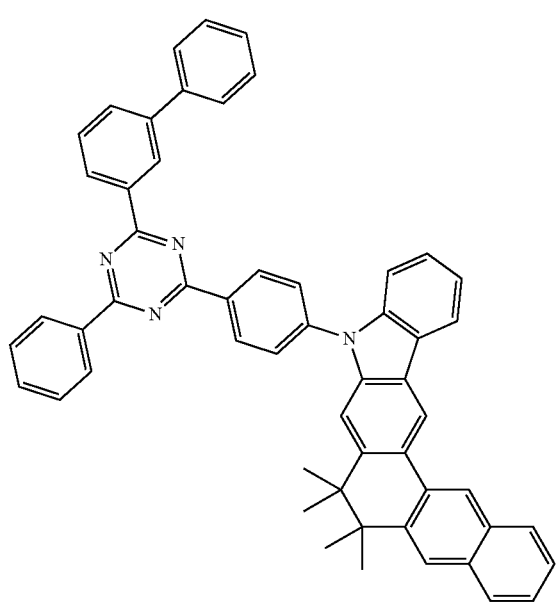
C-89
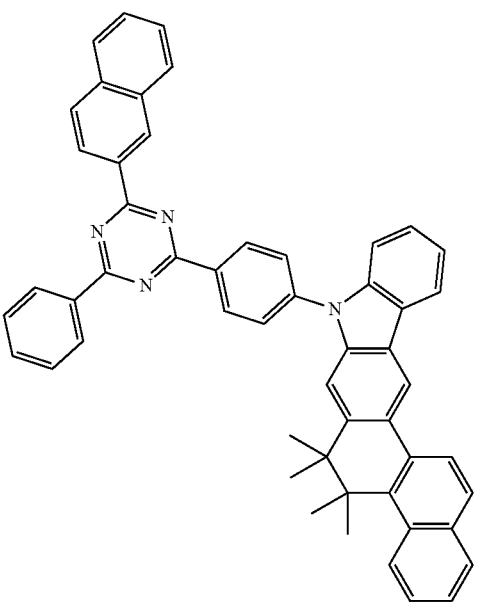

C-90
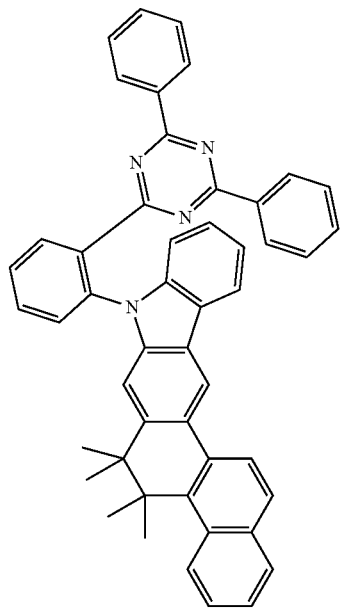
C-91
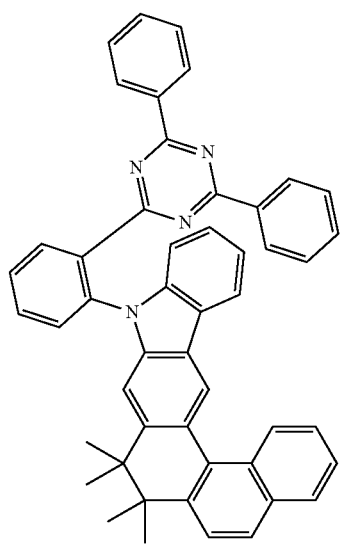
C-92
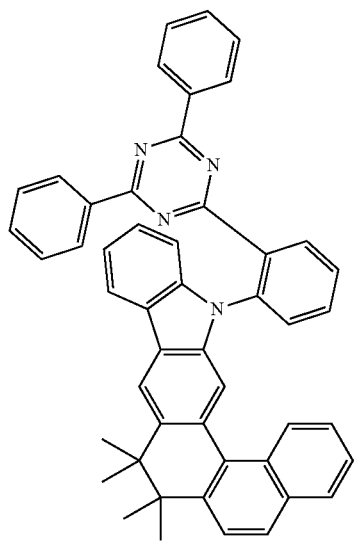
C-93
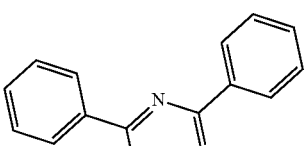
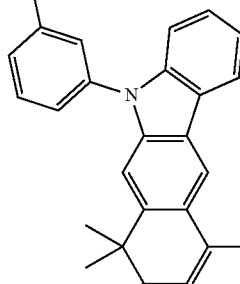
C-94
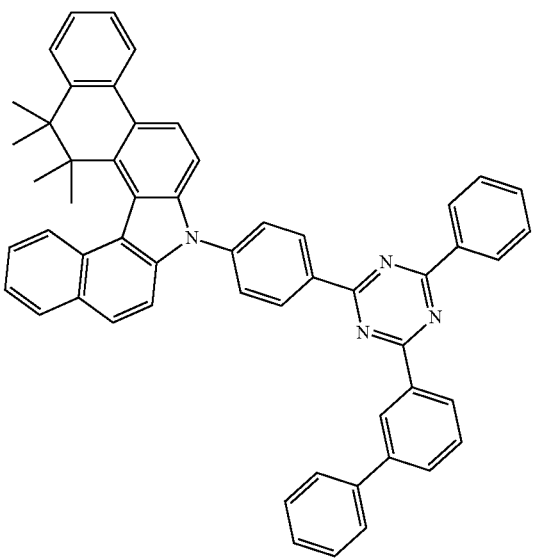

-continued
C-95
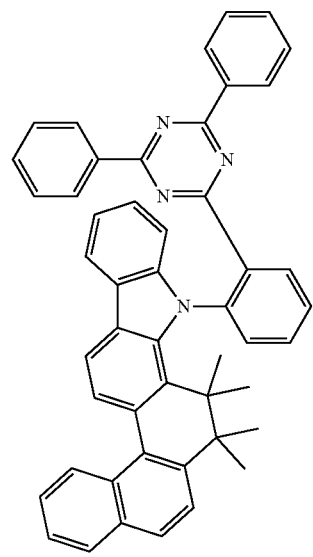
C-96
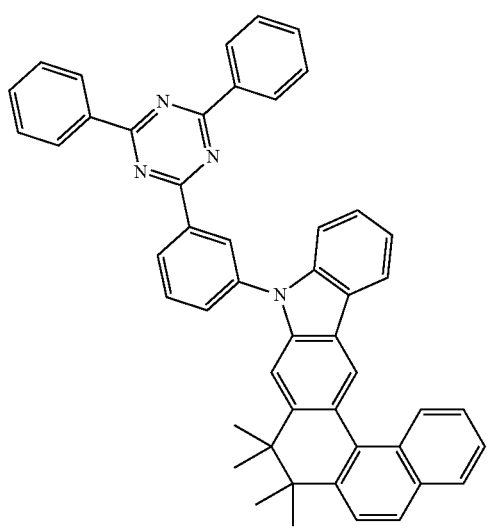
C-97
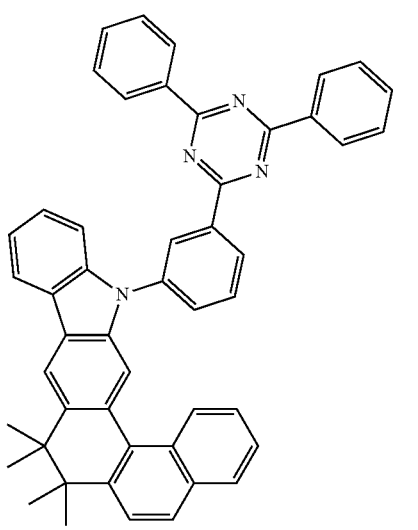
-continued
C-98
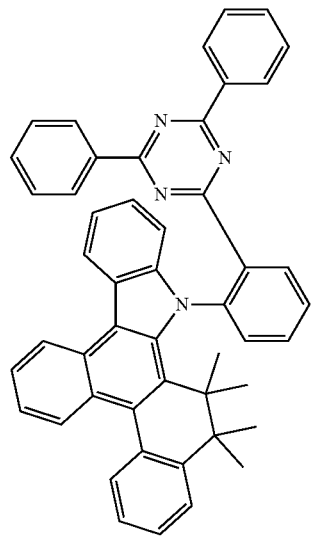
C-99
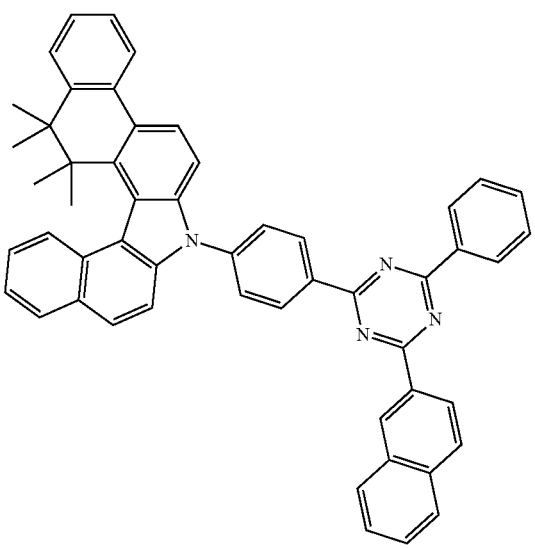
C-100
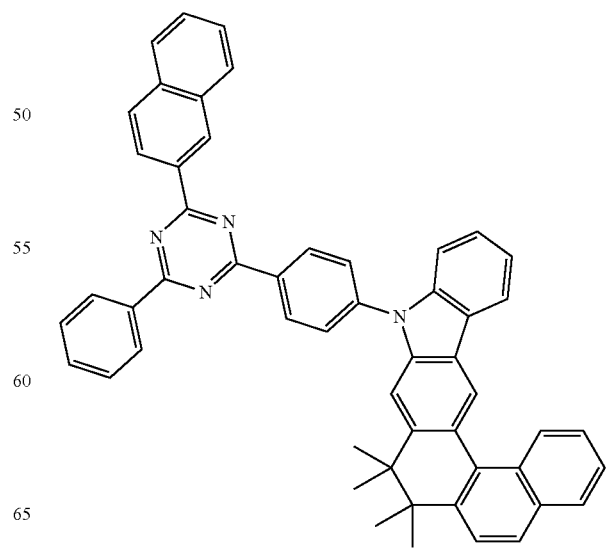

C-101
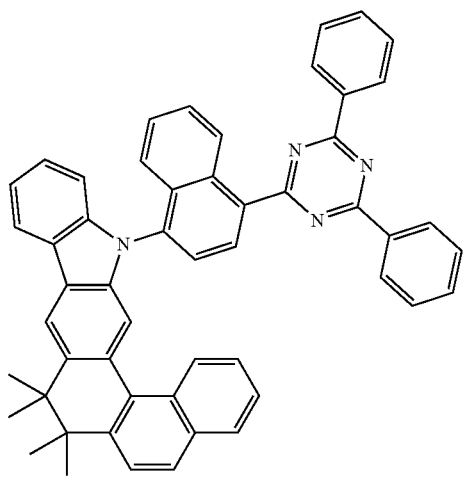
C-102
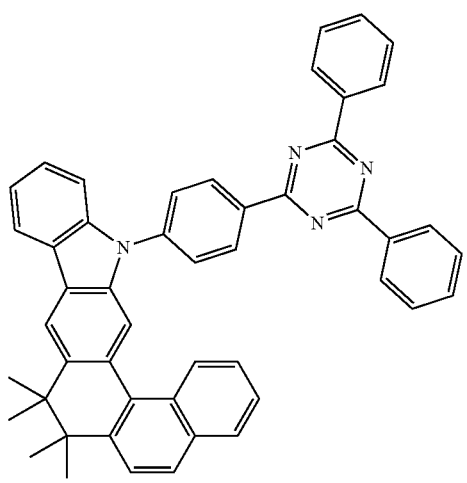
C-103
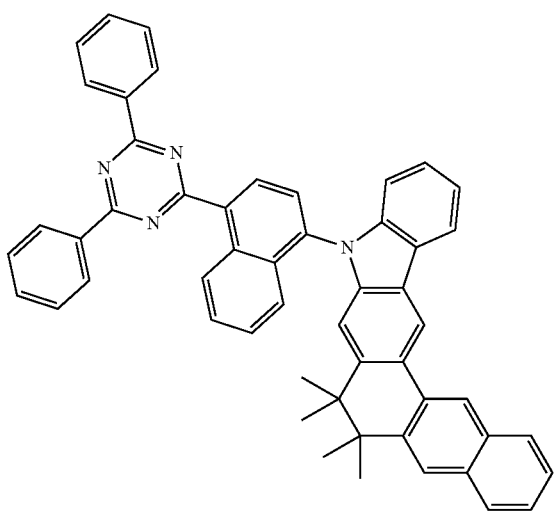
C-104
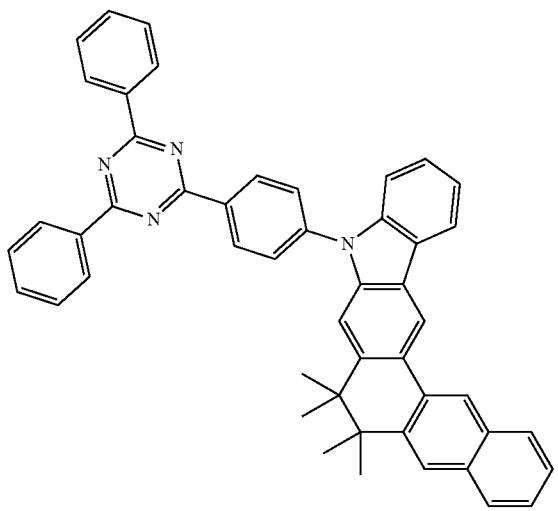
C-105
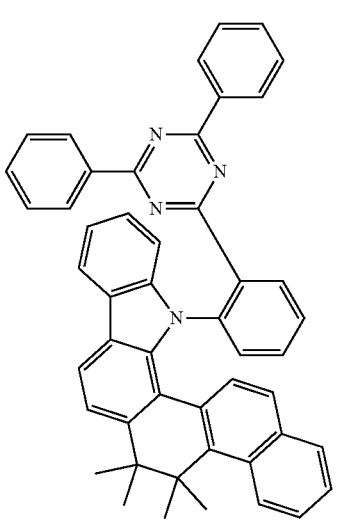
C-106
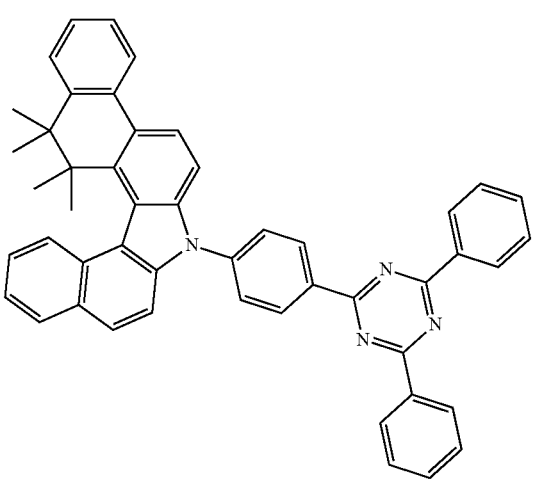

C-107
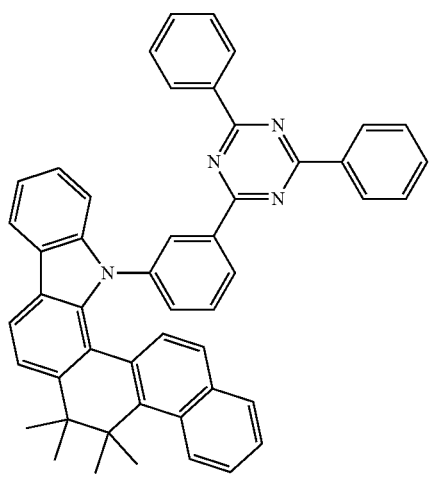
C-110
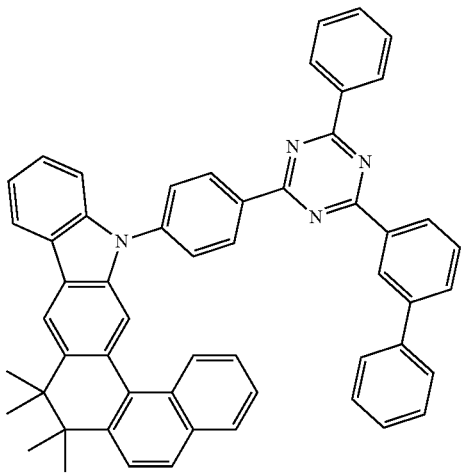
C-108
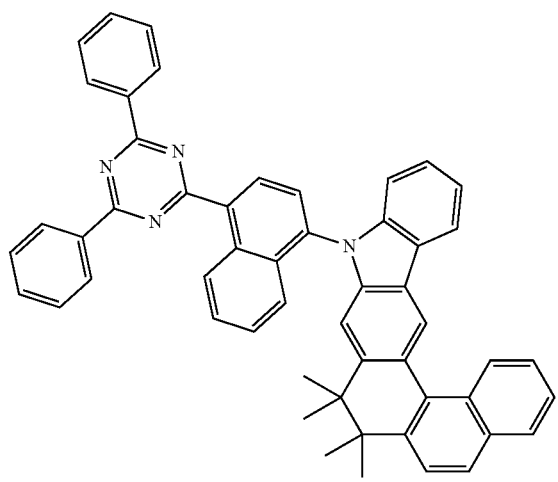
C-111
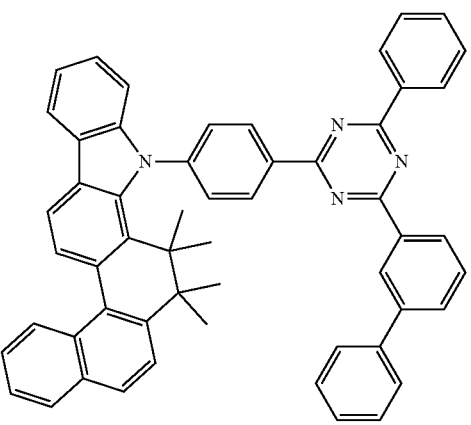
C-109
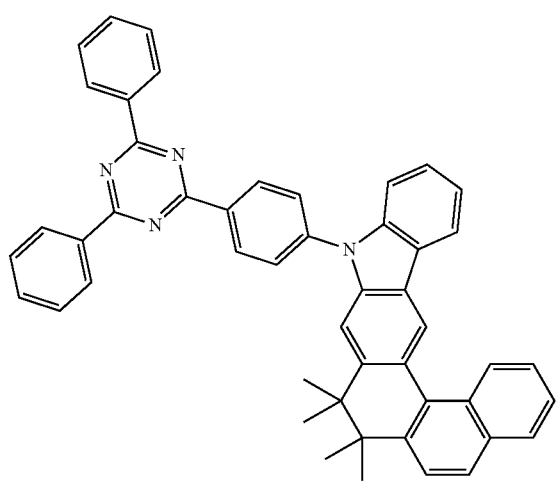
C-112
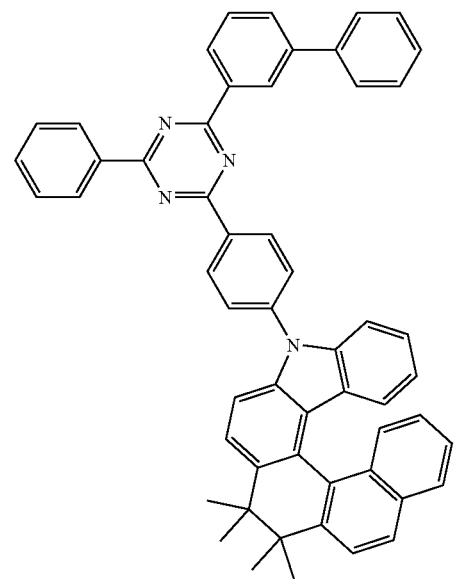

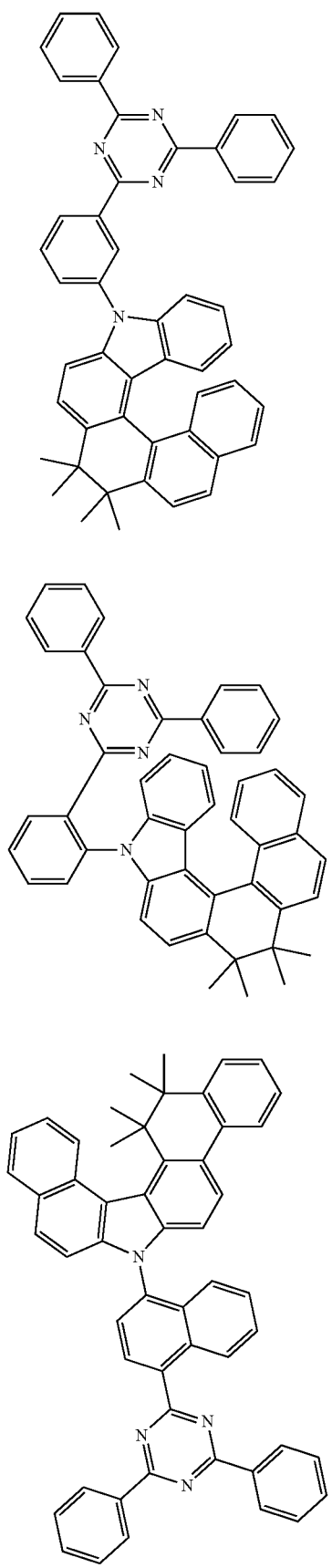
C-113
C-114
C-115
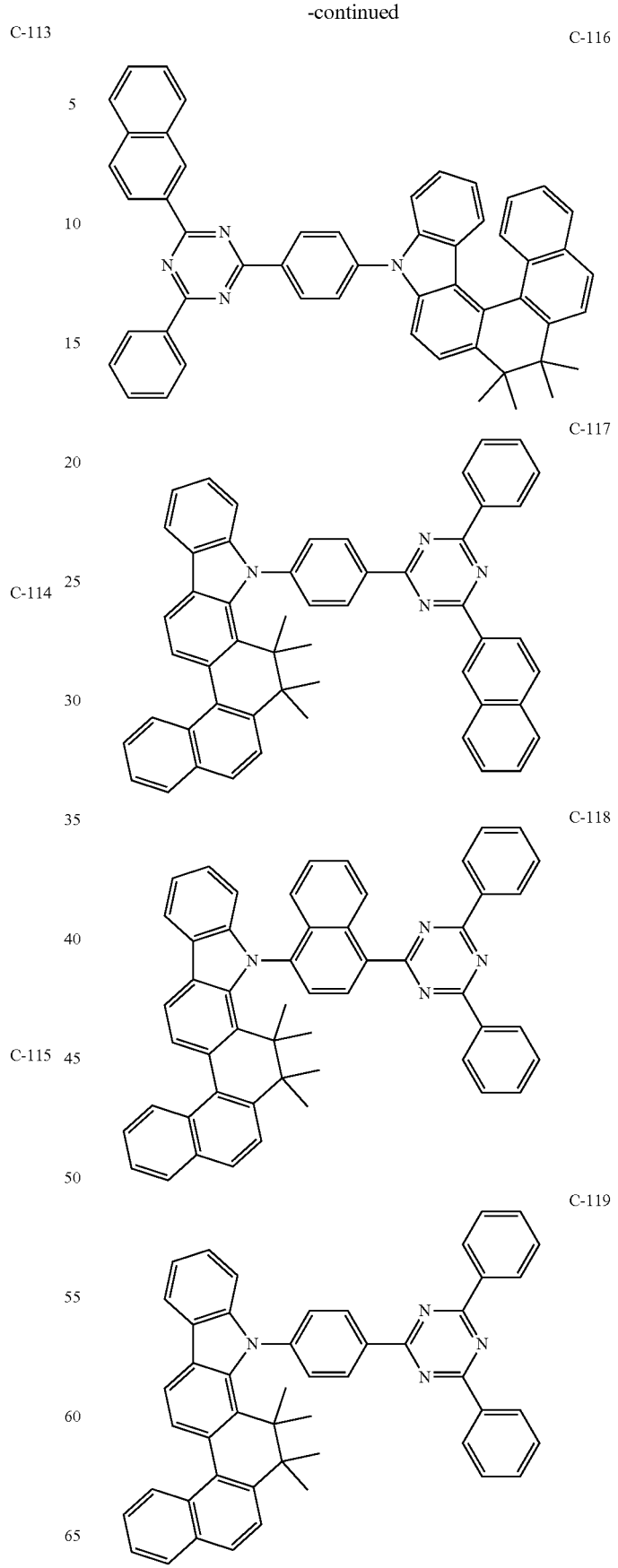
C-116
C-117
C-118
C-119

C-120
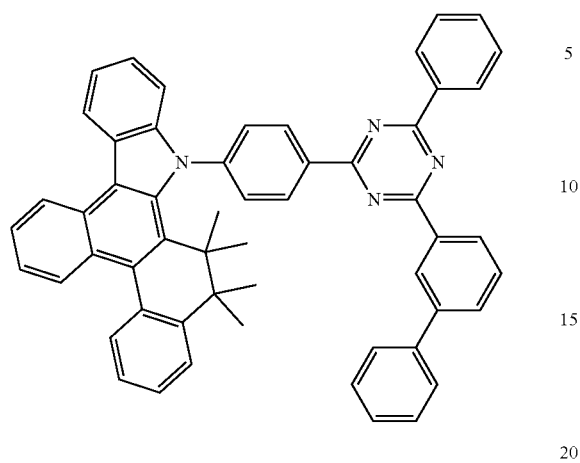
C-121
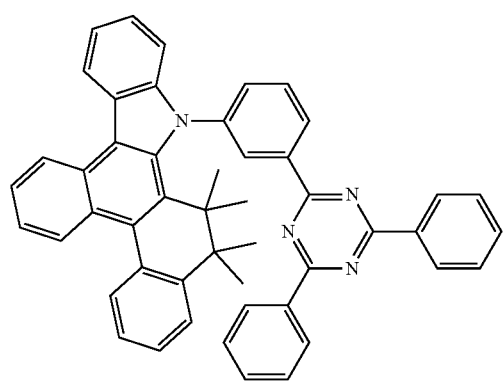
C-122
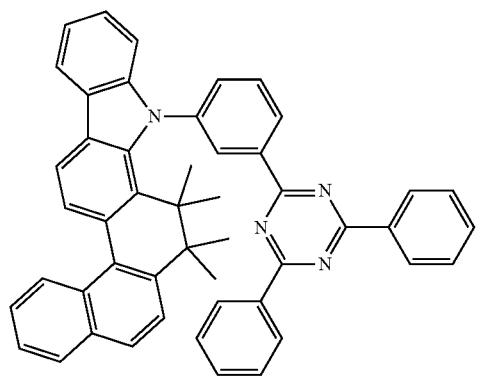
C-123
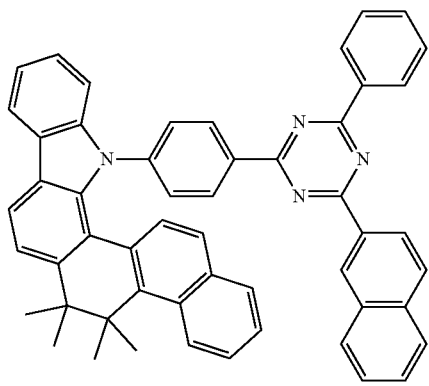
C-124
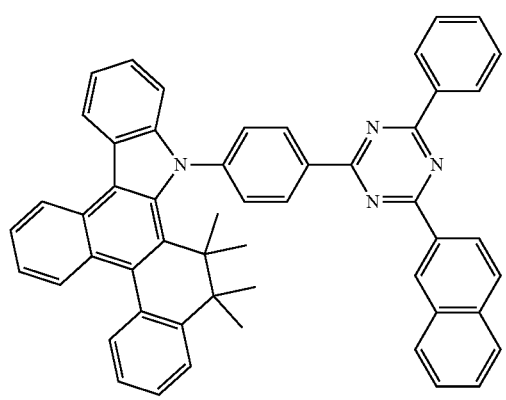
C-125
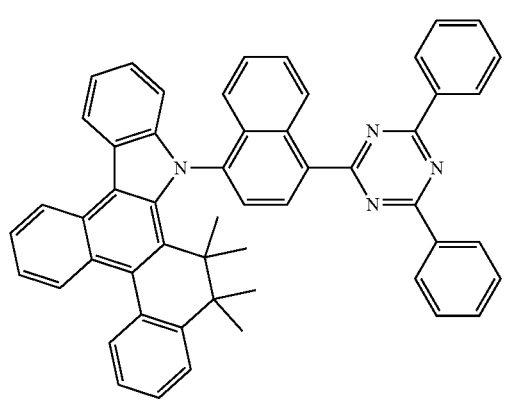

C-126
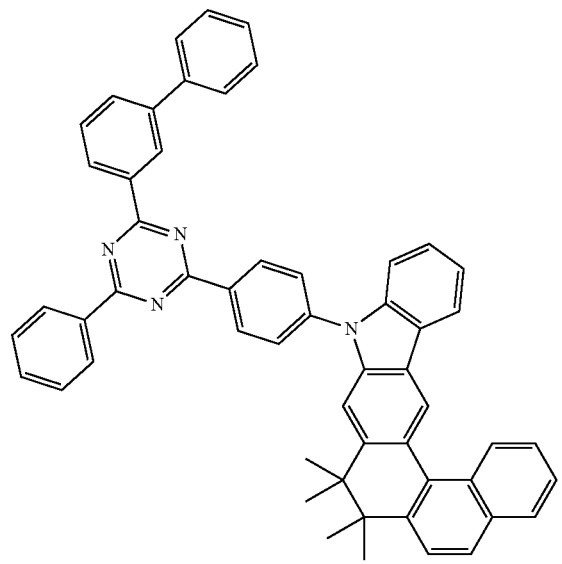
C-127
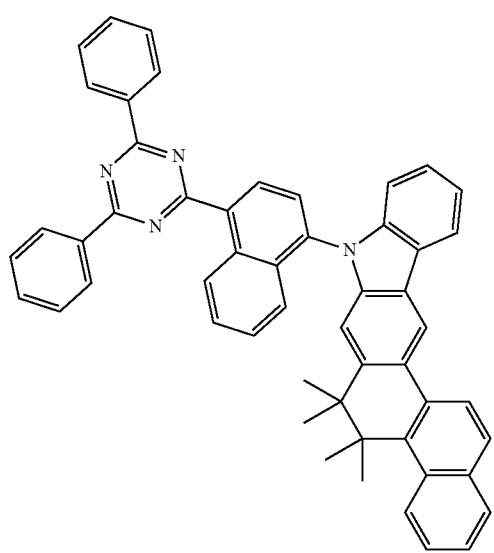
C-128
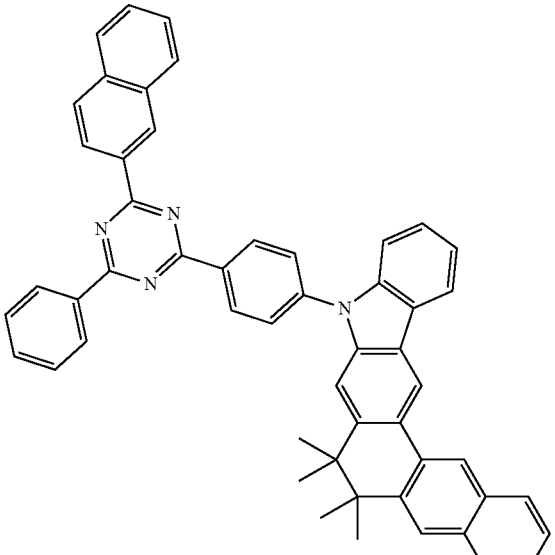
C-129
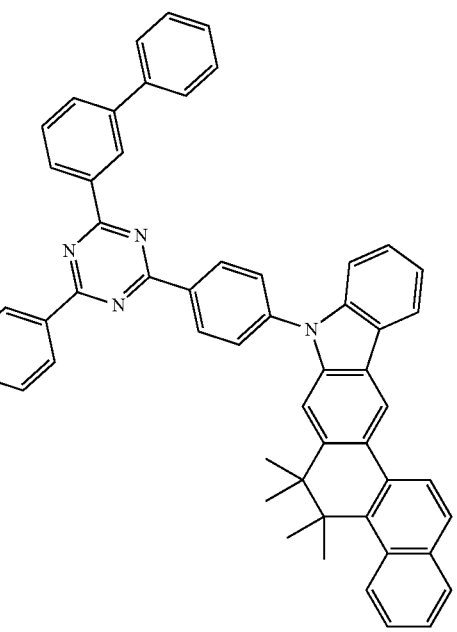
C-130

-continued
C-131
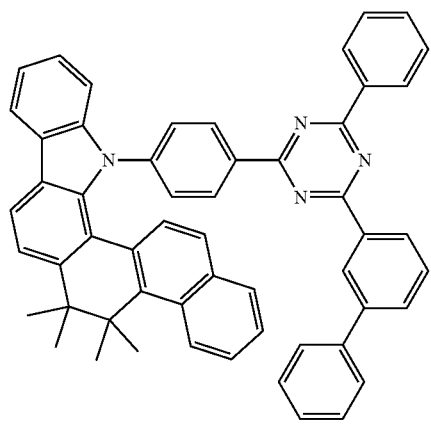
C-132
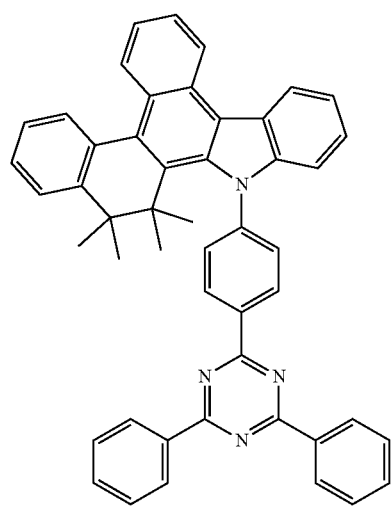
C-133
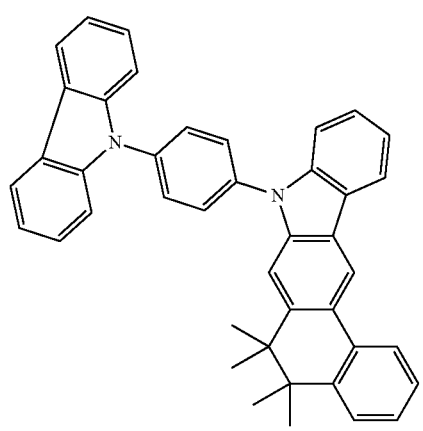
-continued
C-134
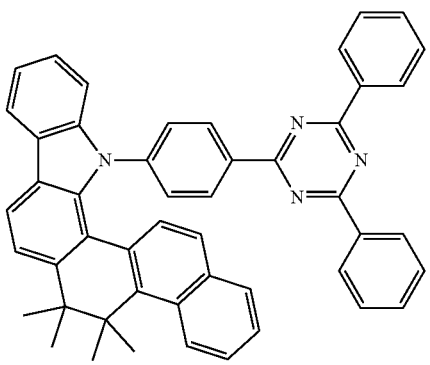
C-135
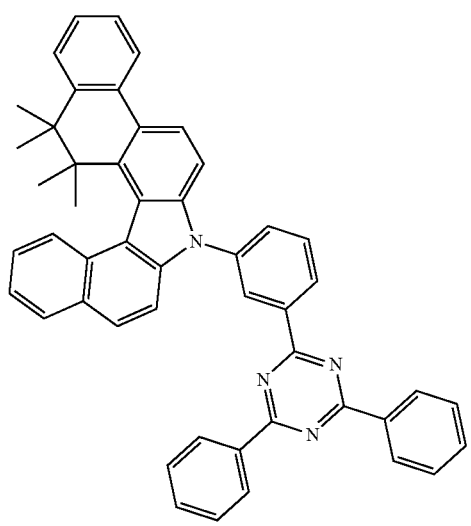
C-136
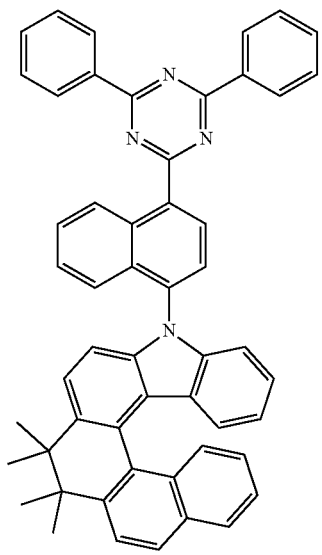

C-137
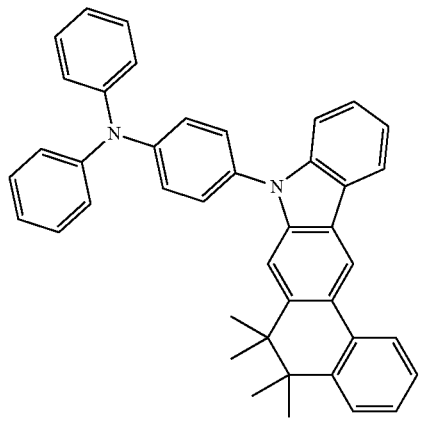
C-138
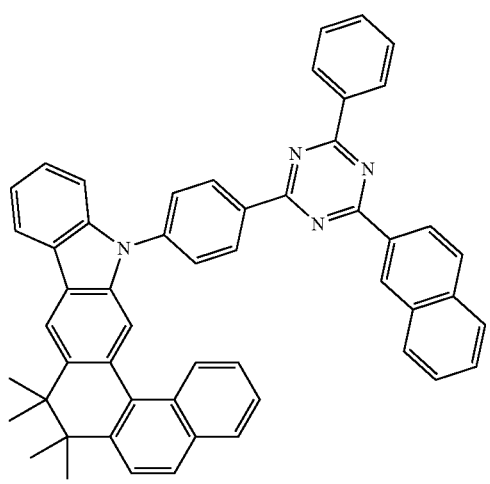
C-139
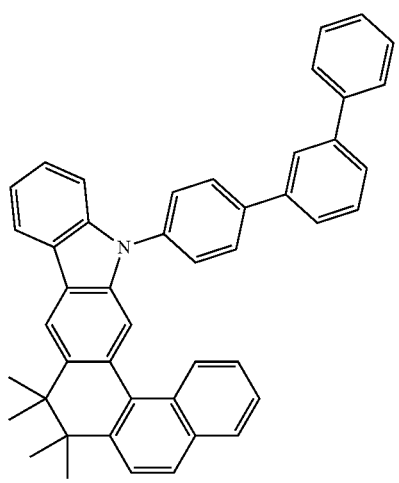
C-140
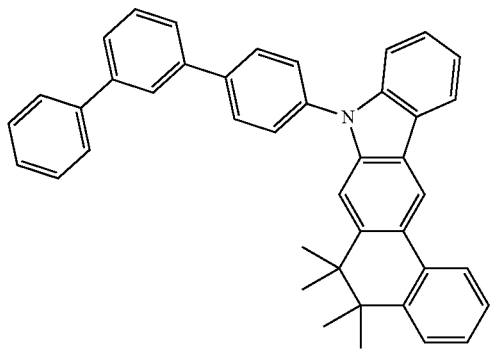
C-141
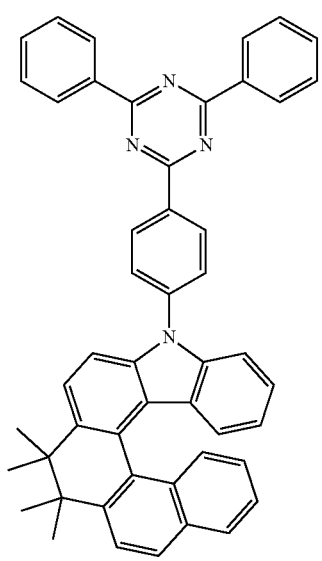
C-142
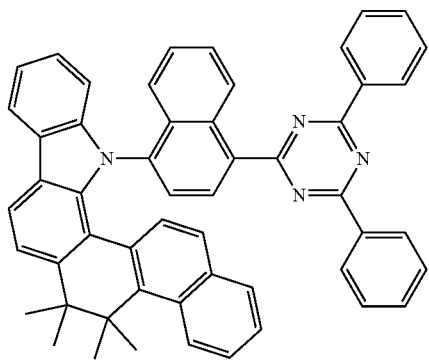

C-143
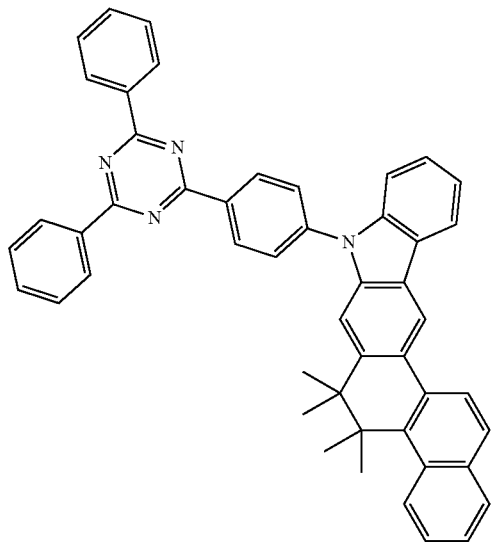
C-144
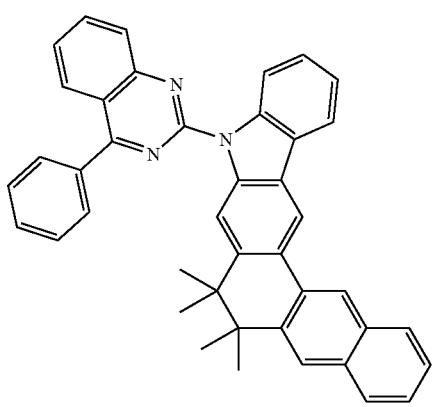
C-145
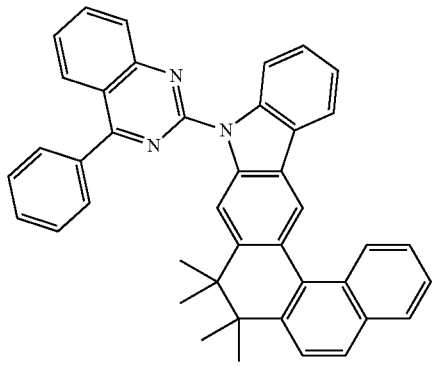
C-146
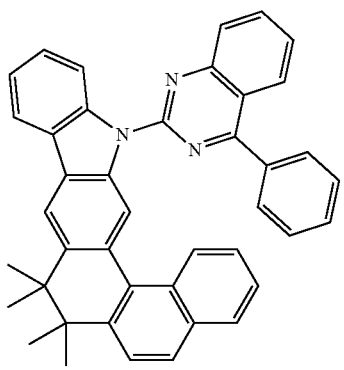
C-147
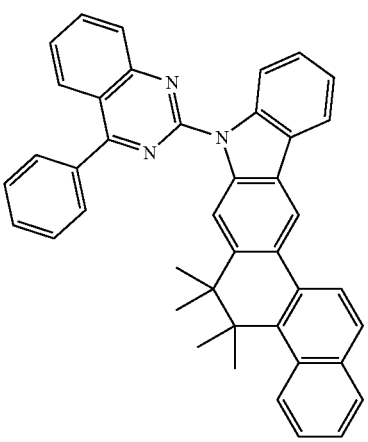
C-148
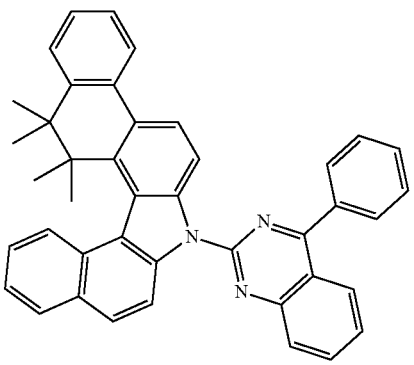
C-149

-continued
C-150
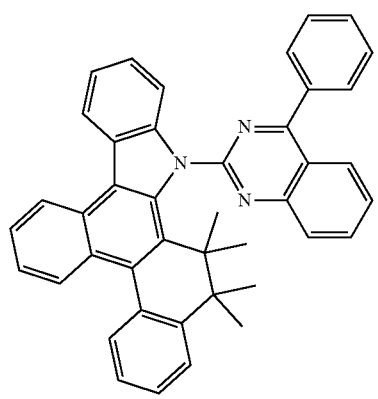
C-151
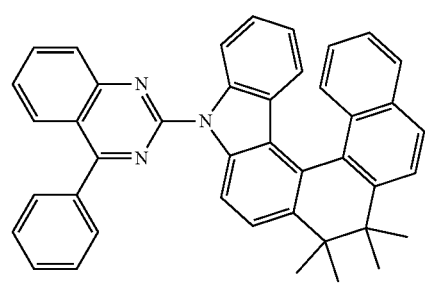
C-152
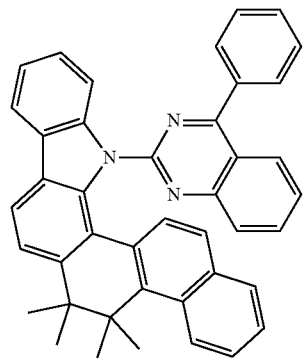
C-153
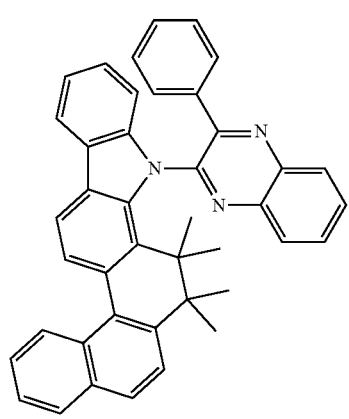
-continued
C-154
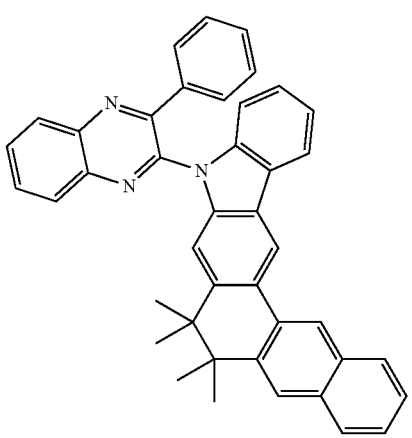
C-155
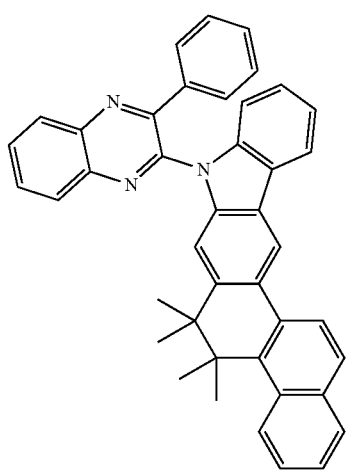
C-156
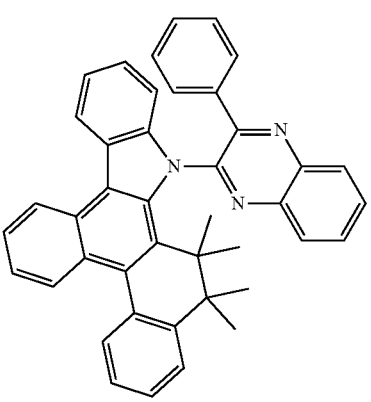

-continued
C-157
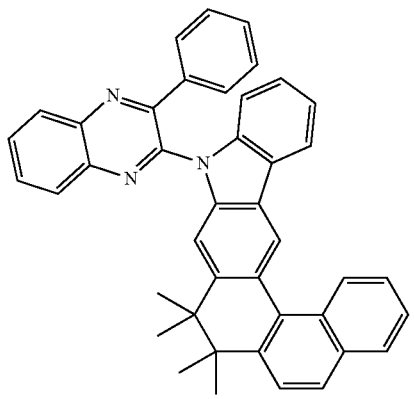
C-158
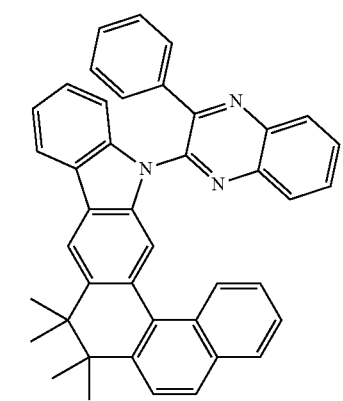
C-159
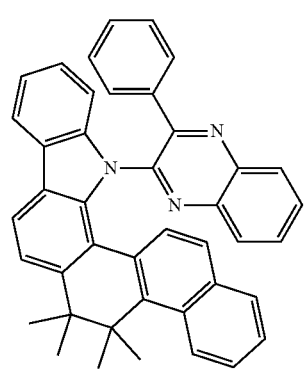
C-160
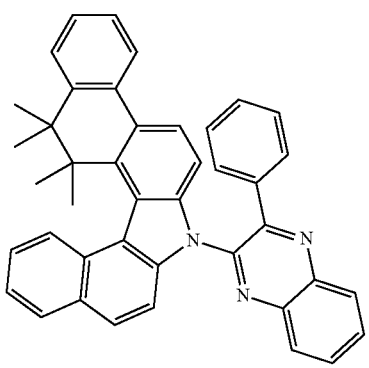
-continued
C-161
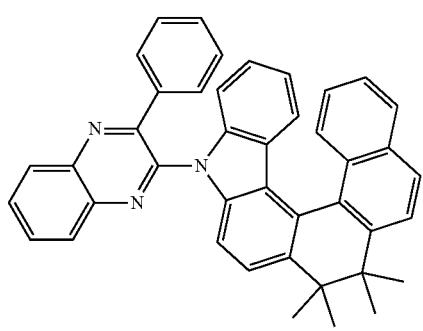
C-162
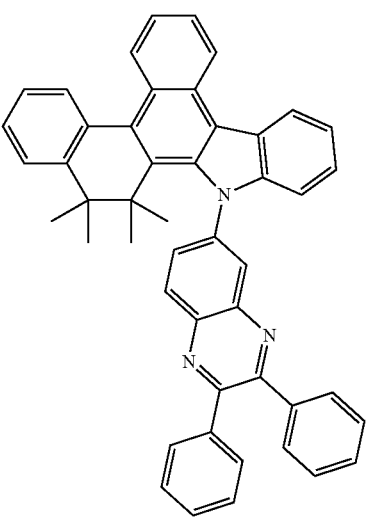
C-163
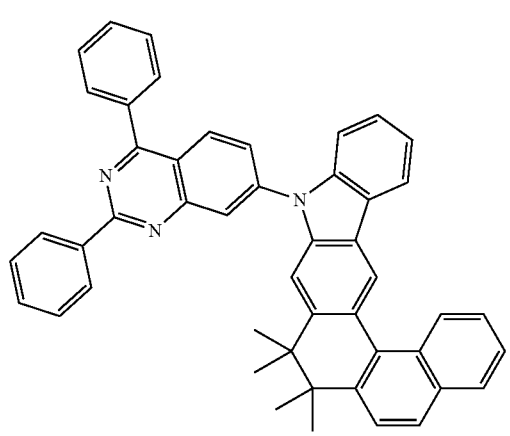

C-164
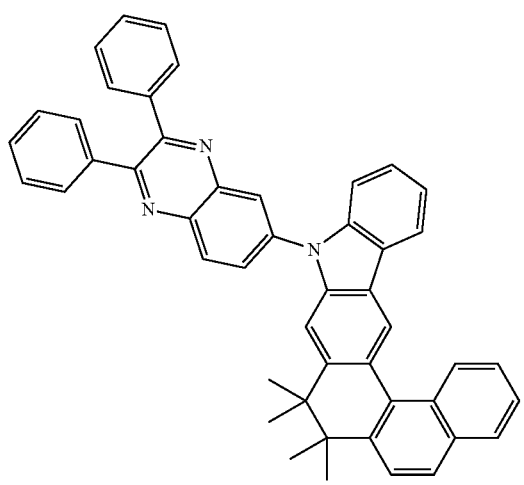
C-165
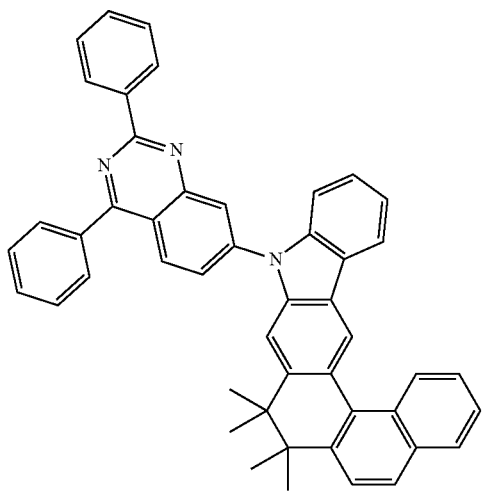
C-166
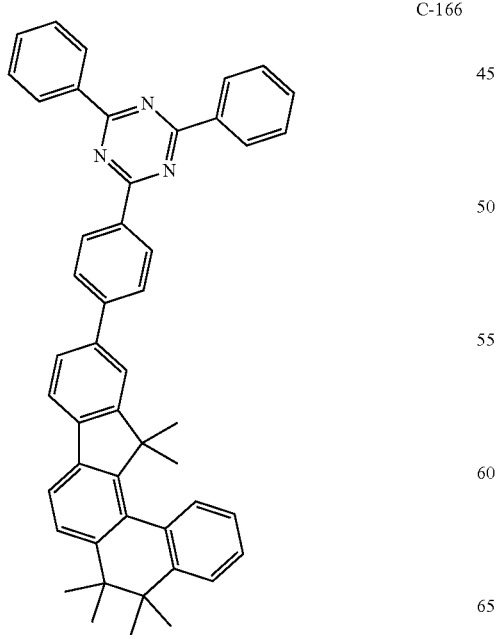
C-167
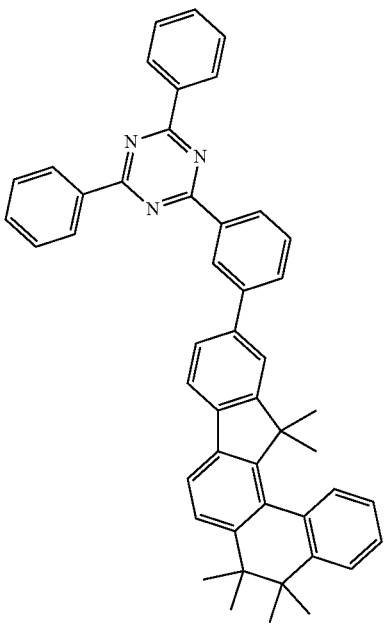
C-168
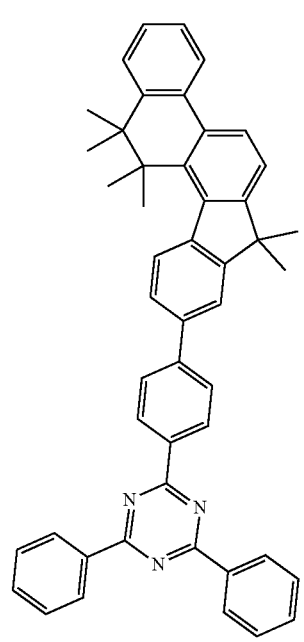

C-169
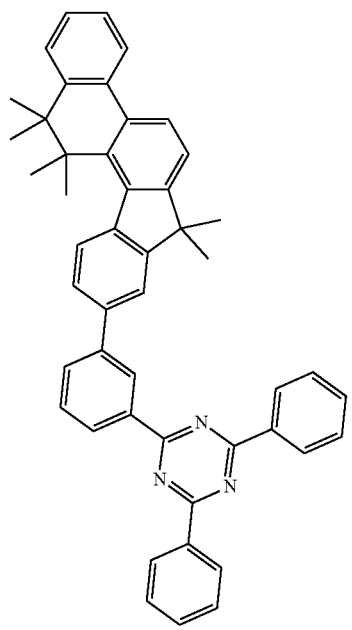
C-170
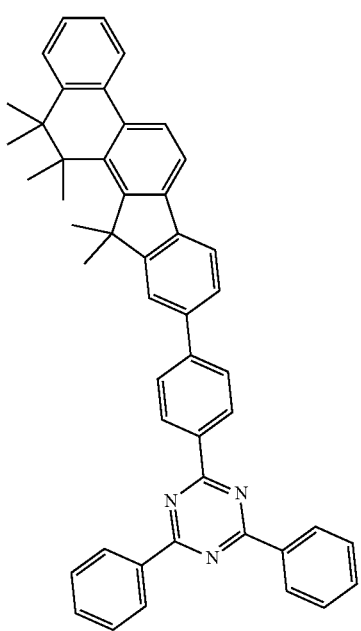
C-171
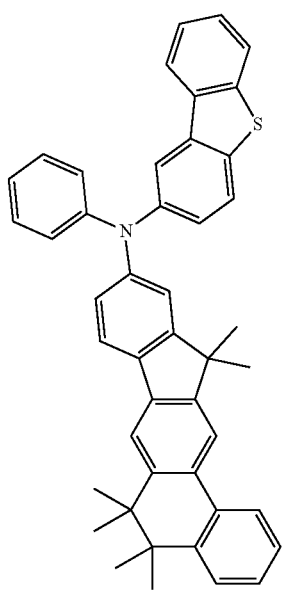
C-172
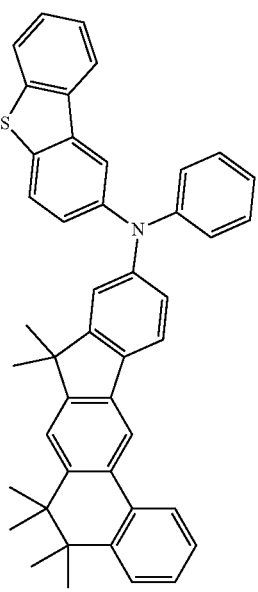

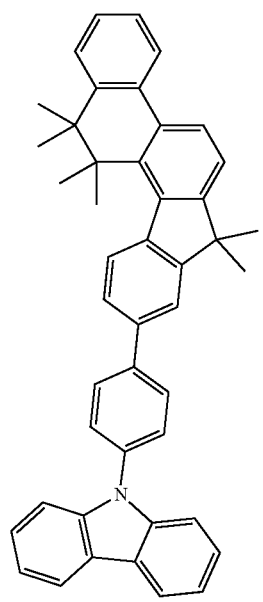
C-173
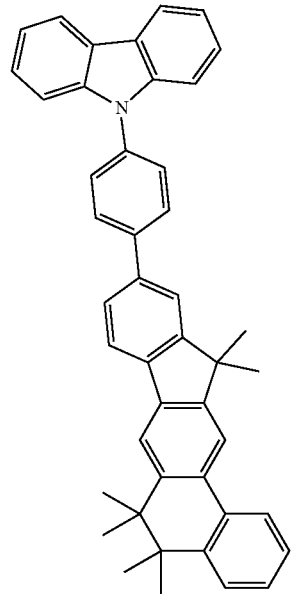
C-175
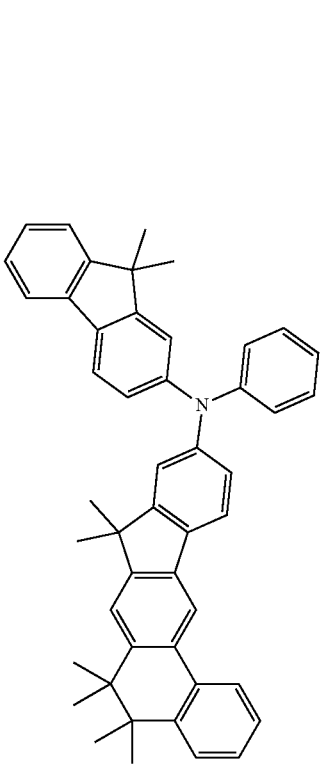
C-176
C-174

C-177 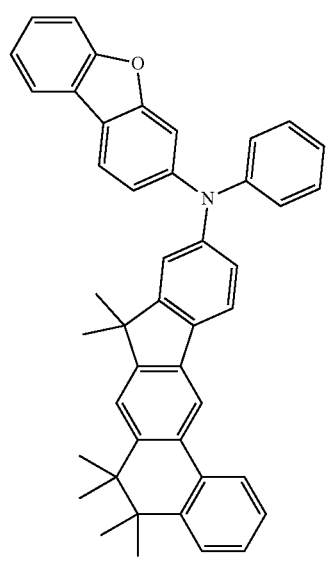
C-180 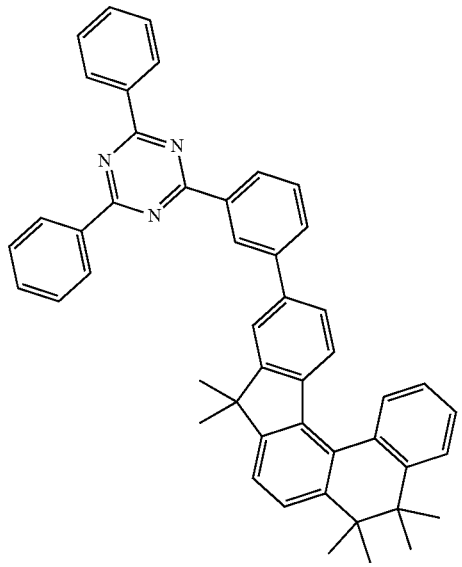
C-178 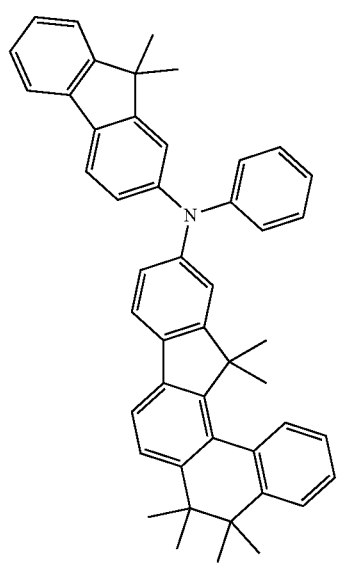
C-181 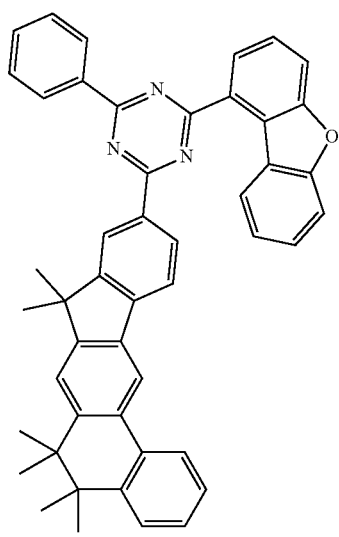
C-179 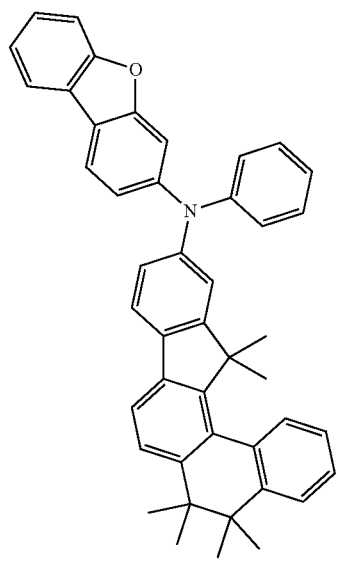
C-182 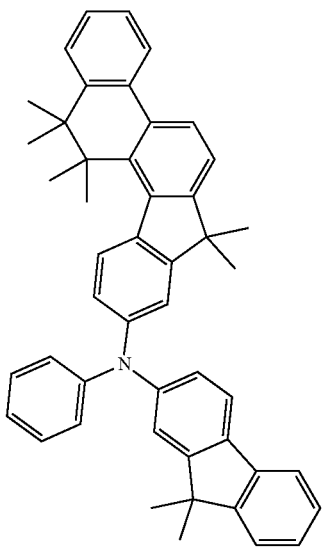

C-183
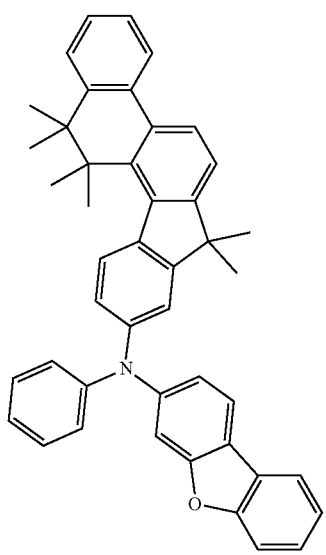
C-184
C-185
C-186
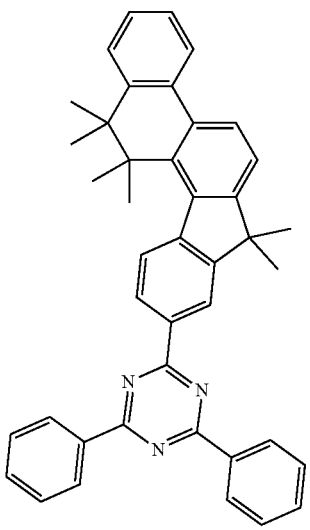
C-187
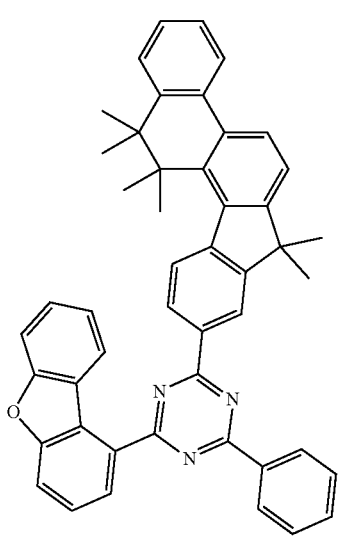
C-188
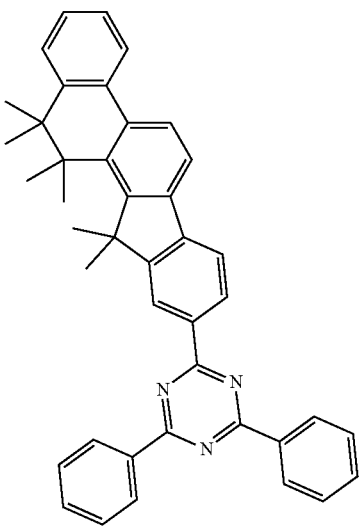

C-189
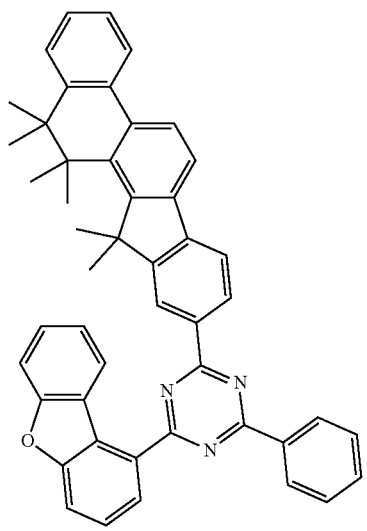
C-190
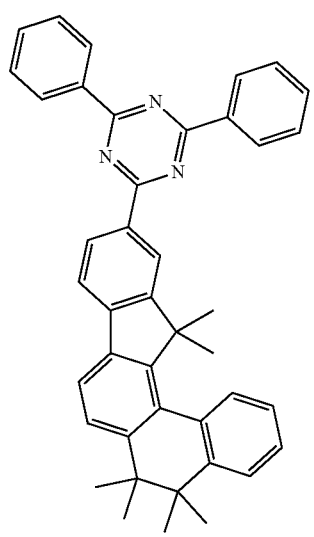
C-191
C-192
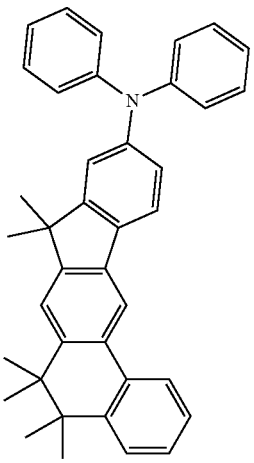
C-193
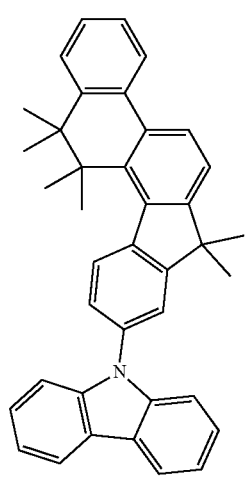
C-194
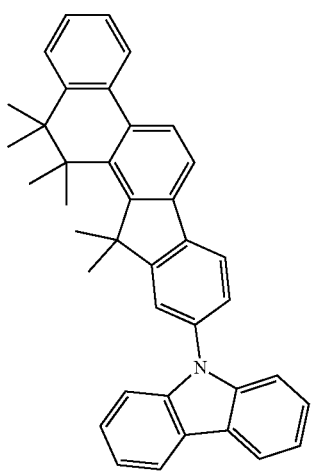

C-195
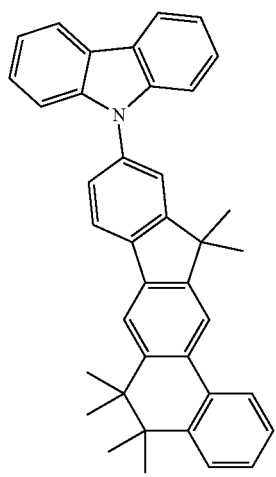
C-198
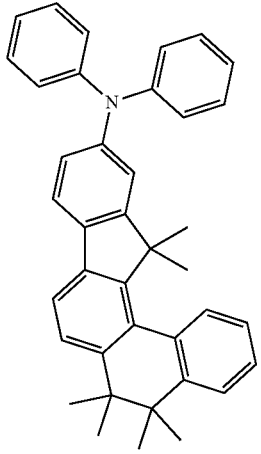
C-196
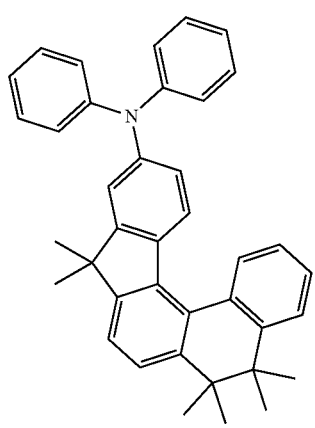
C-199
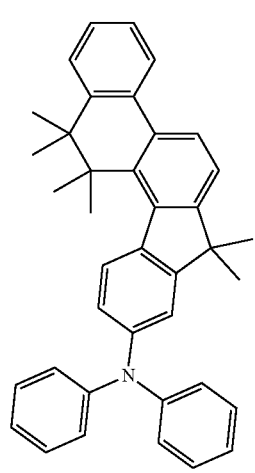
C-197
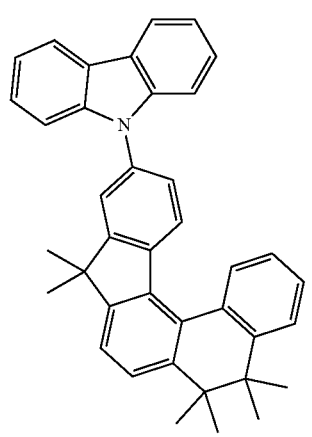
C-200
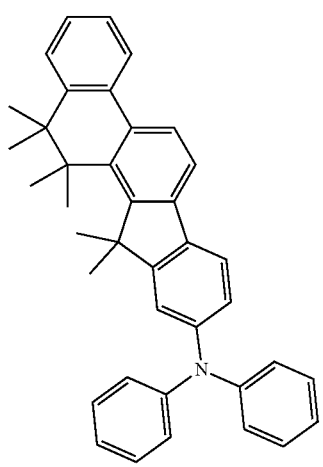

C-201
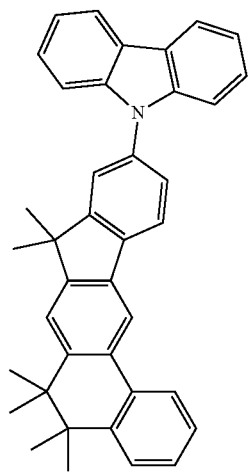
C-202
C-203
C-204
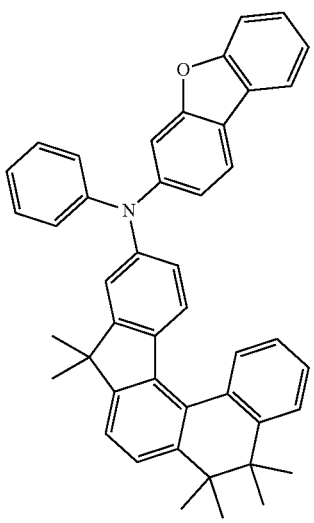
C-205
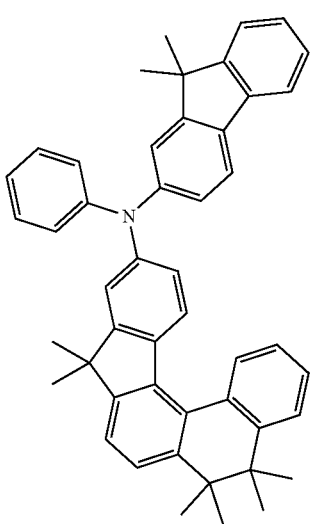
C-206
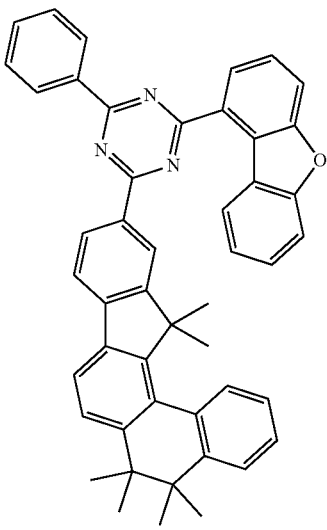

-continued
C-207
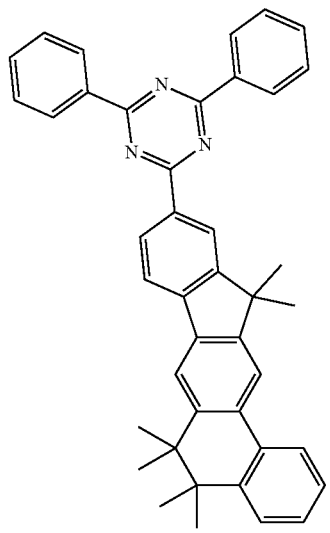
C-208
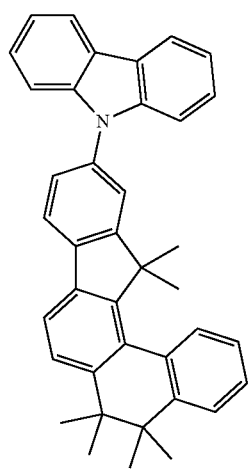
C-209
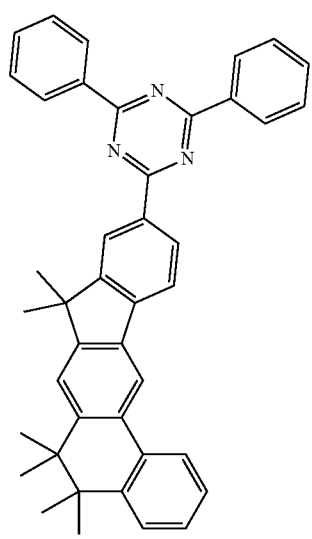
-continued
C-210
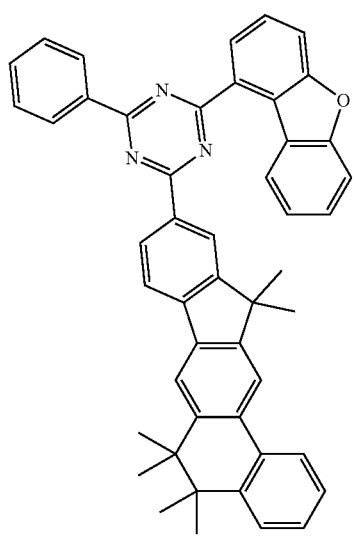
C-211
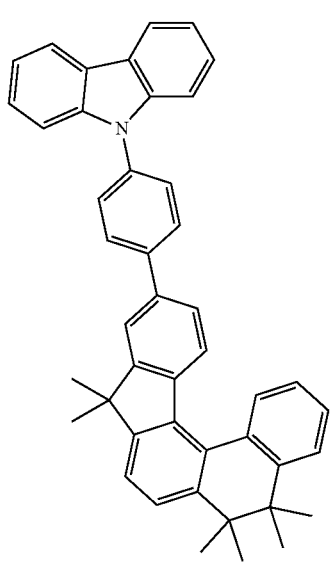
C-212
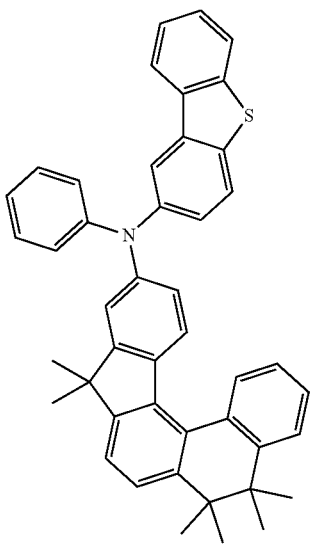

C-213
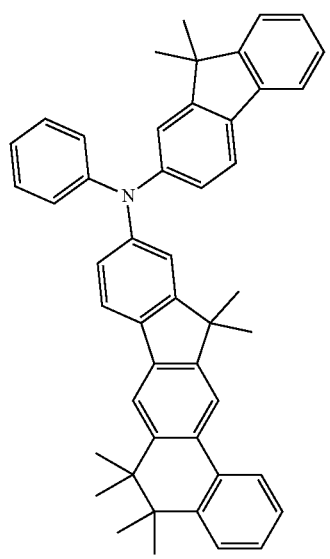
C-214
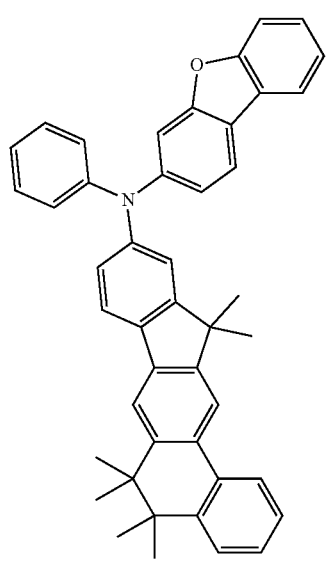
C-215
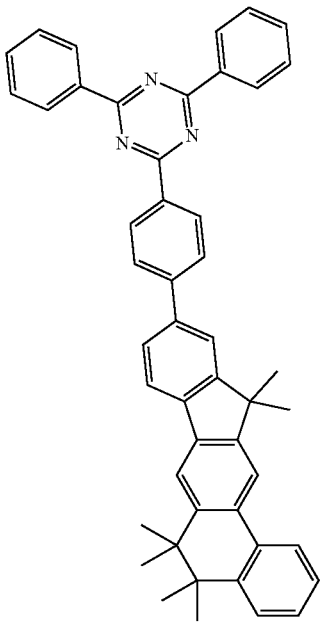
C-216

-continued
C-217
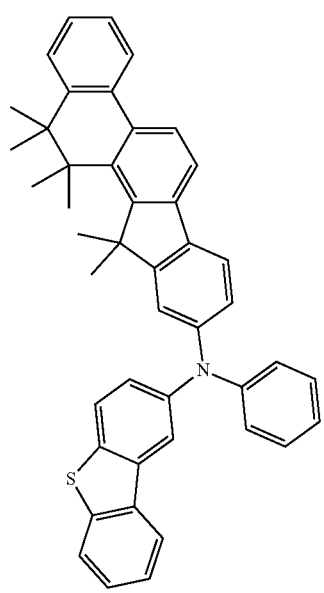
C-218
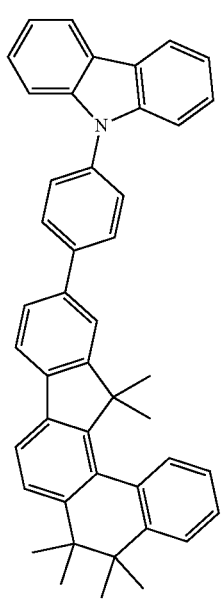
-continued
C-219
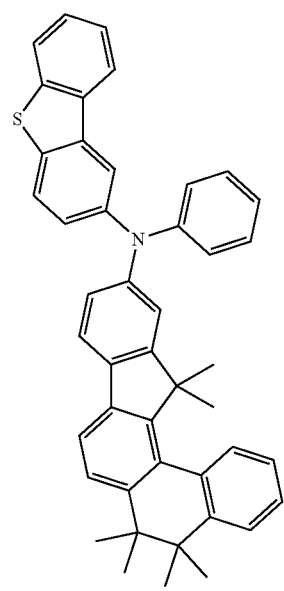
C-220
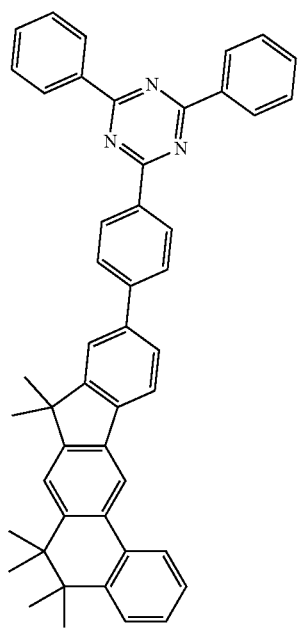

C-221
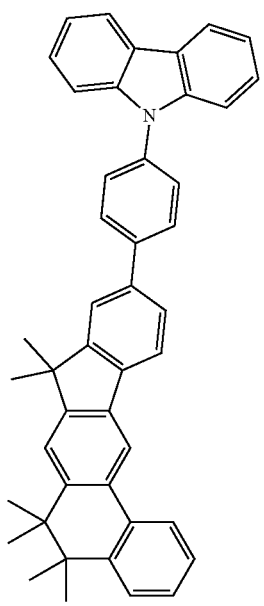
C-222
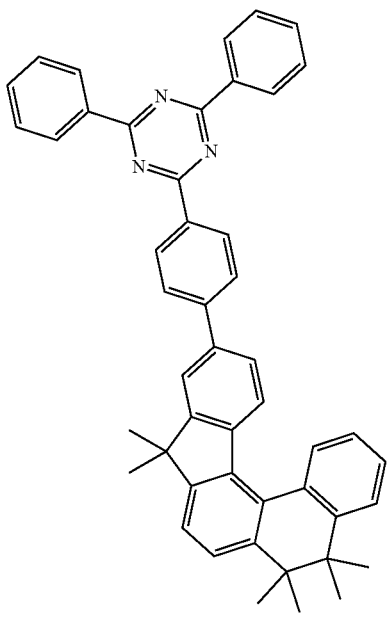
C-223
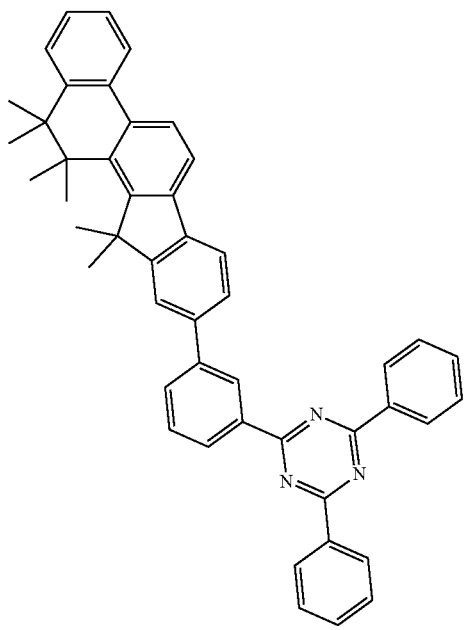
C-224

-continued
C-225
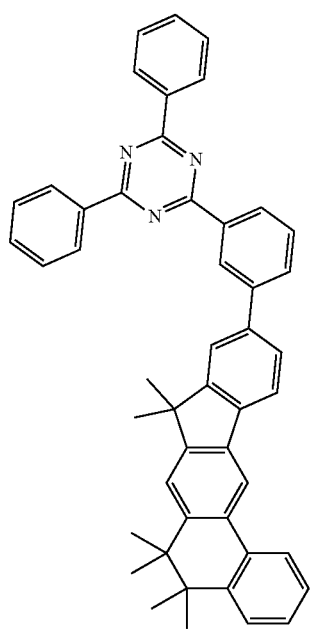
C-226
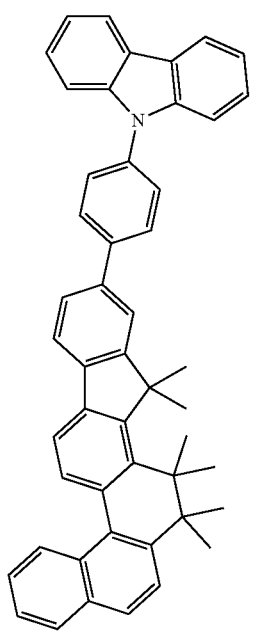
C-227
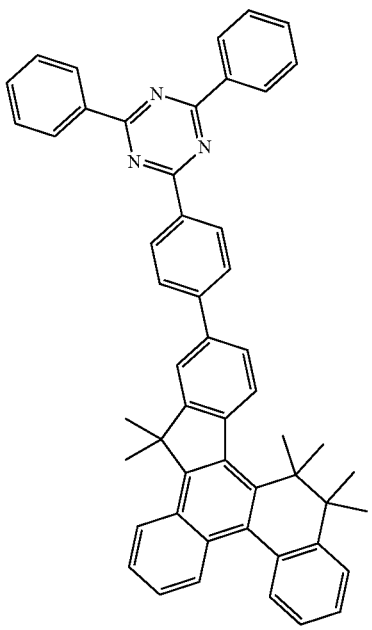
C-228
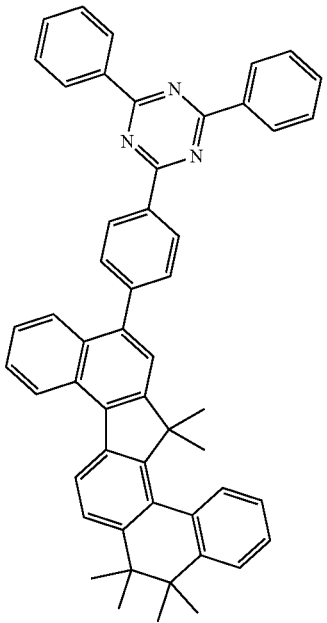

C-229
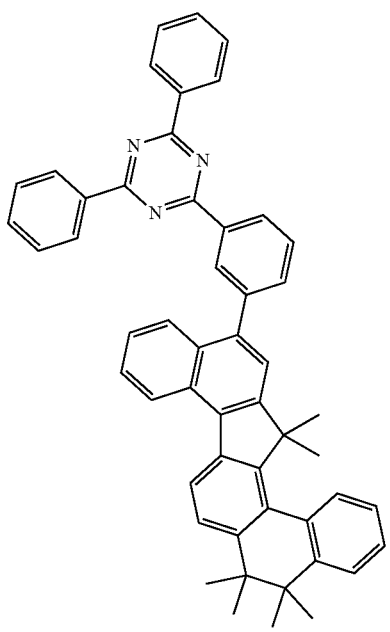
C-230
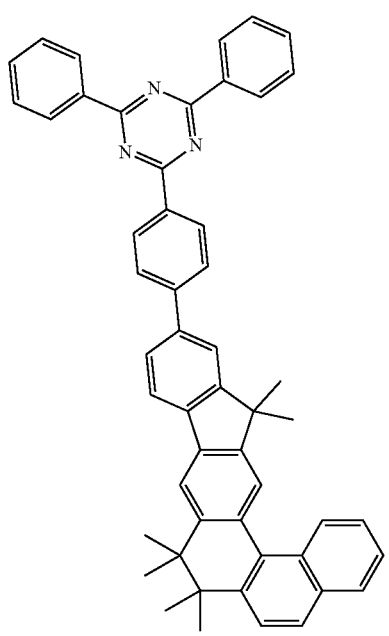
C-231
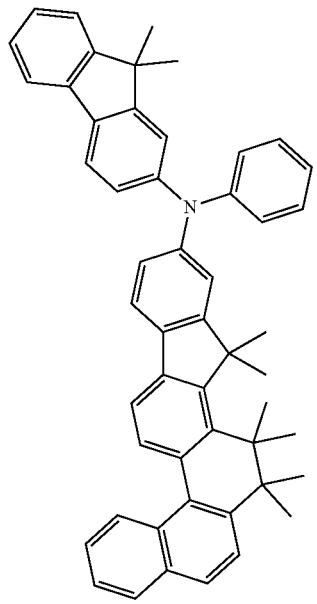
C-232
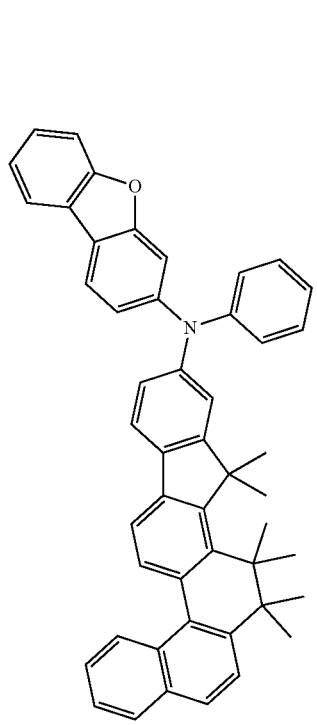

C-233
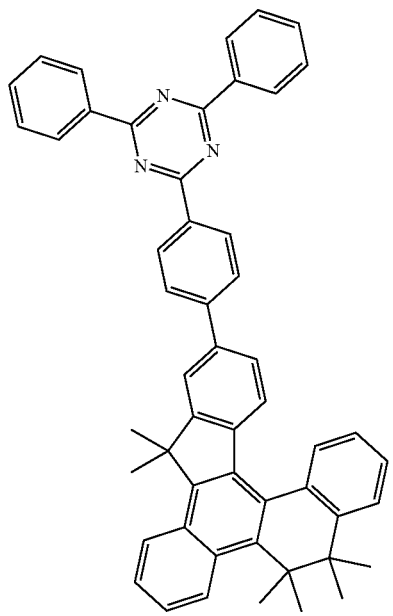
C-235
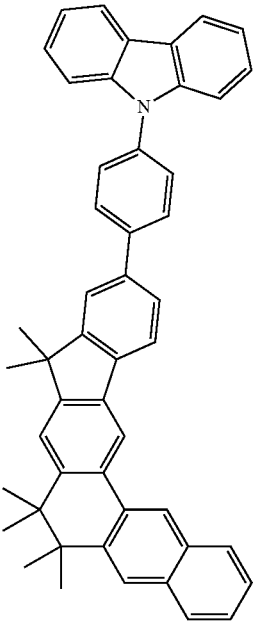
C-234
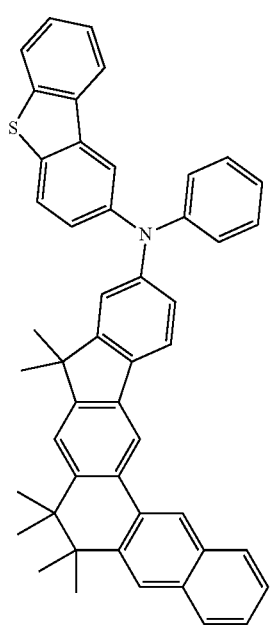
C-236
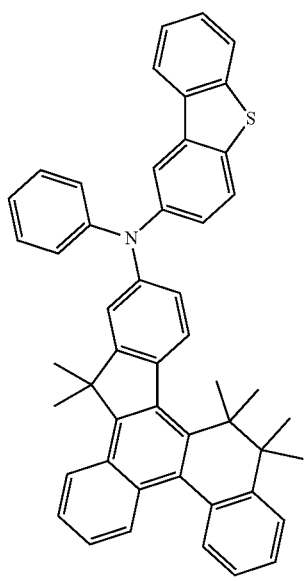

C-237
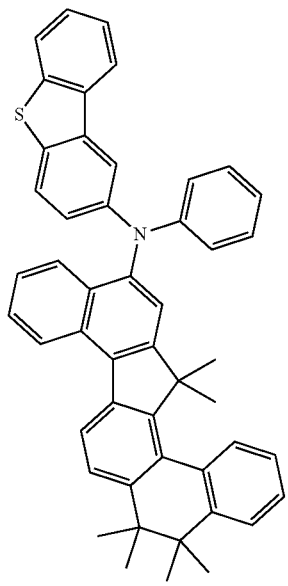
C-238
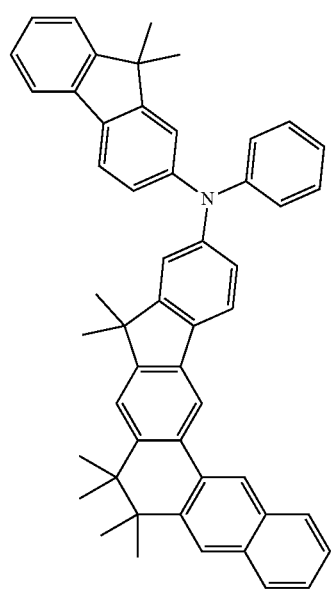
C-239
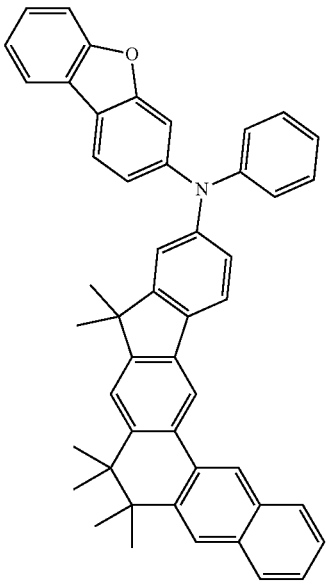
C-240
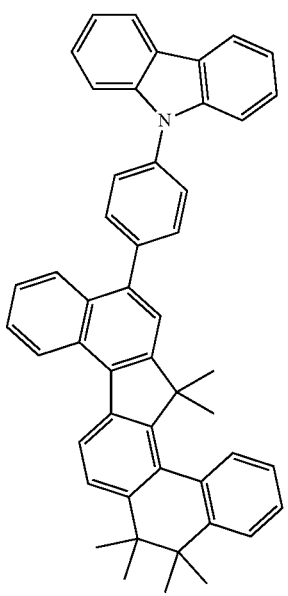

C-241
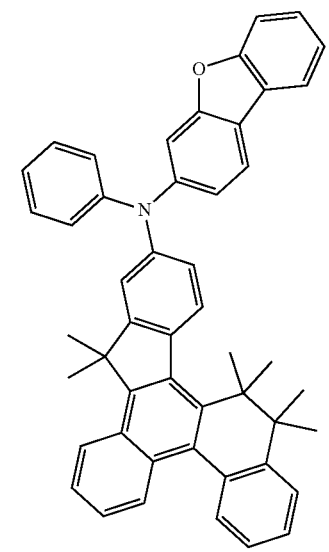
C-242
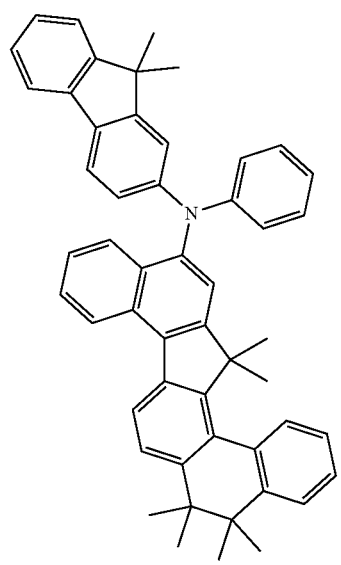
C-243
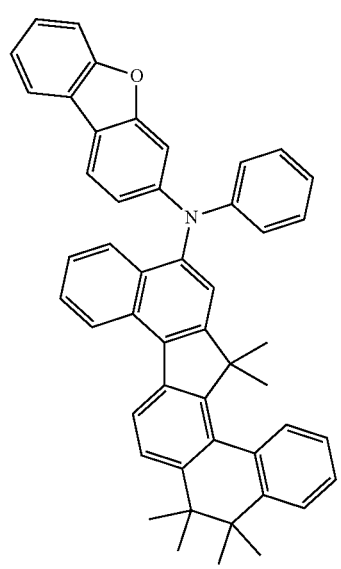
C-244
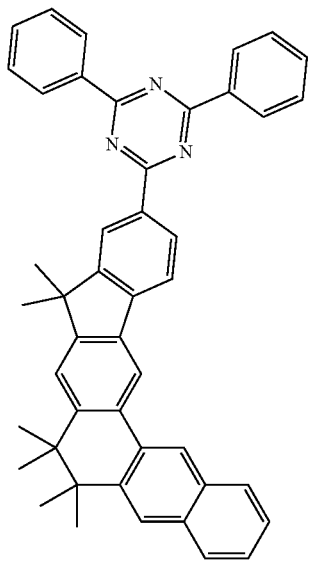
C-245
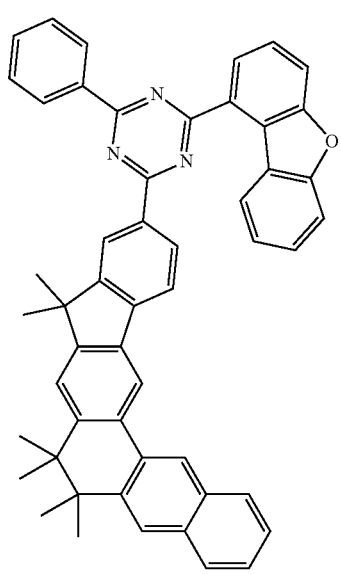
C-246
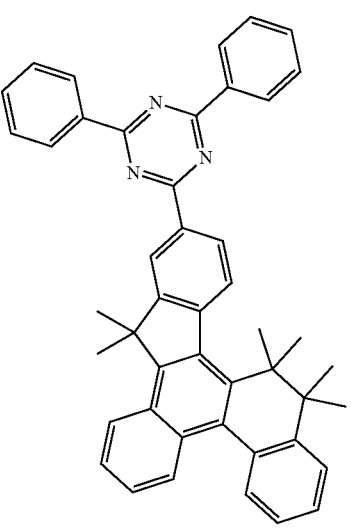

C-247
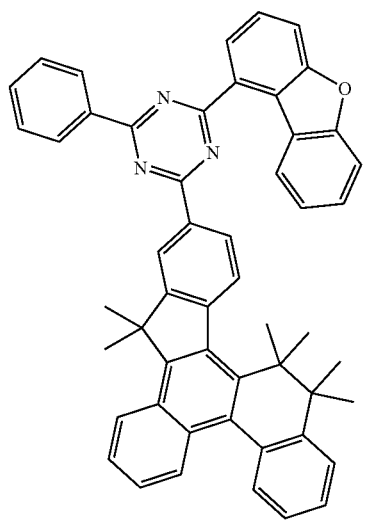
C-248
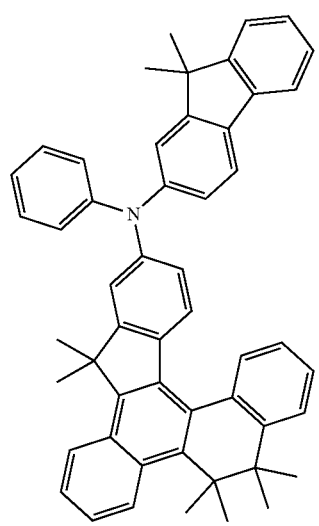
C-249
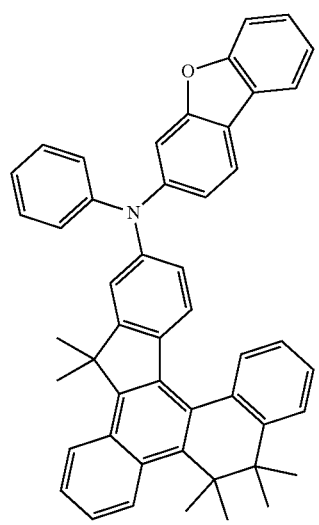
C-250
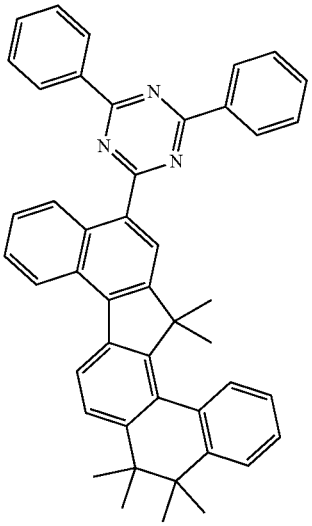
C-251
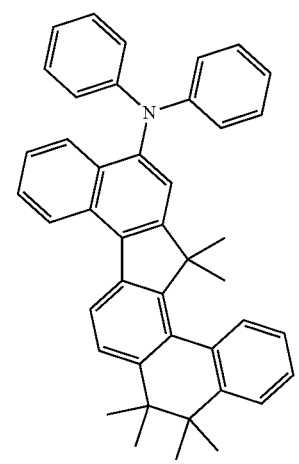
C-252
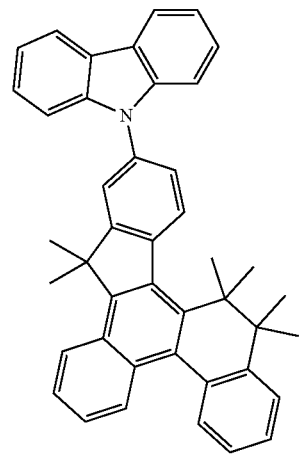

C-253
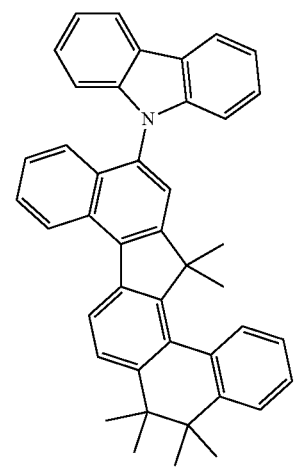
C-254
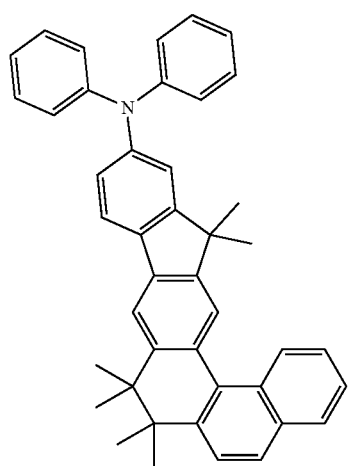
C-255
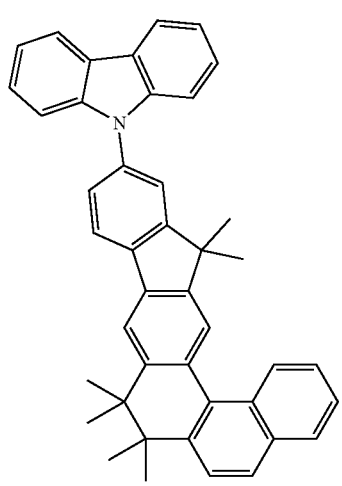
C-256
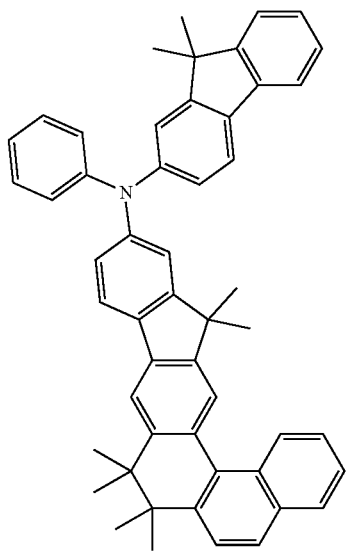
C-257
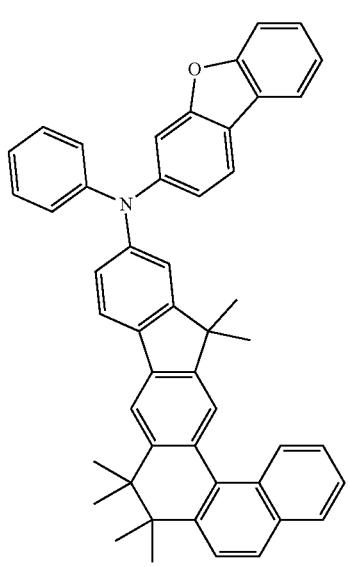
C-258
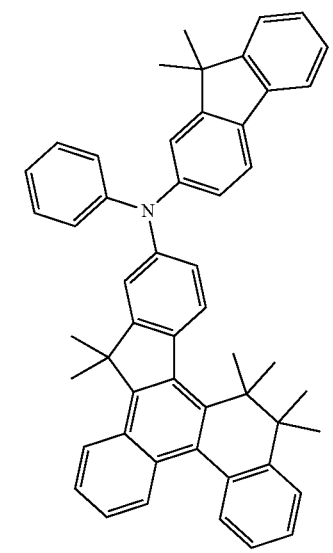

C-259
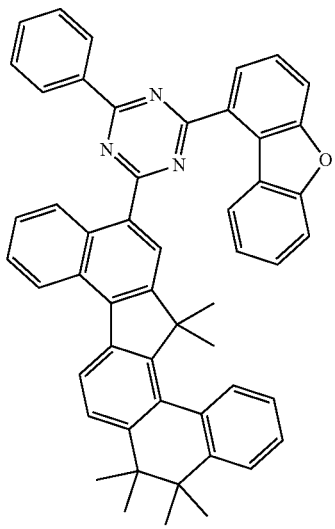
C-260
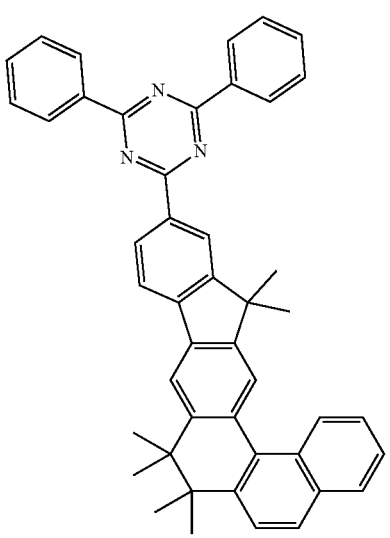
C-261
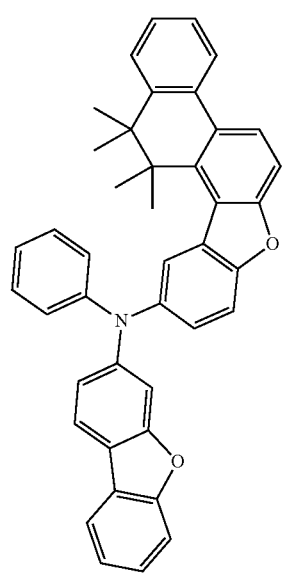
C-262
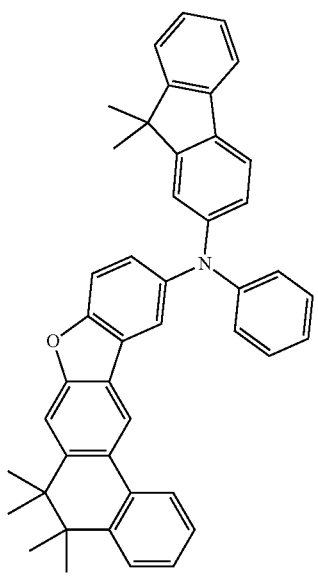
C-263
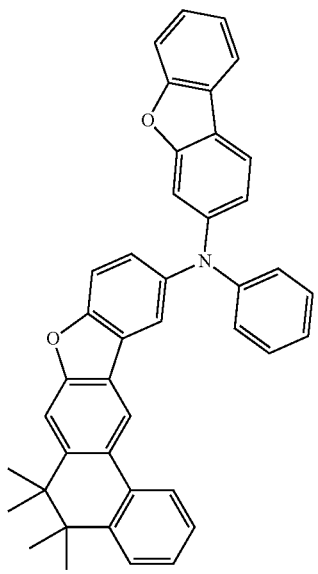

C-264
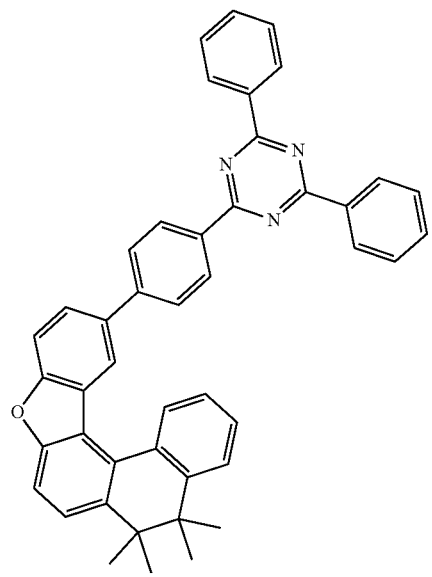
C-266
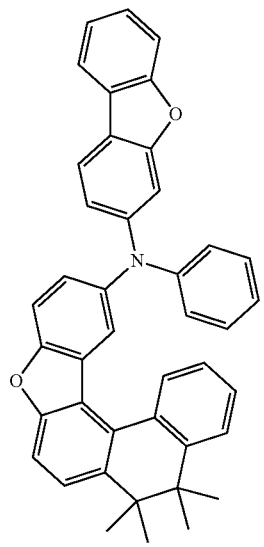
C-265
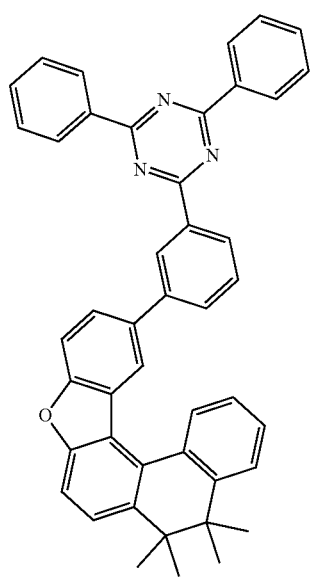
C-267
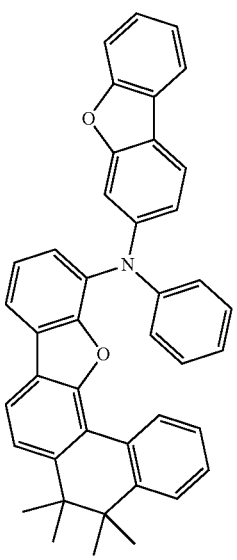

C-268
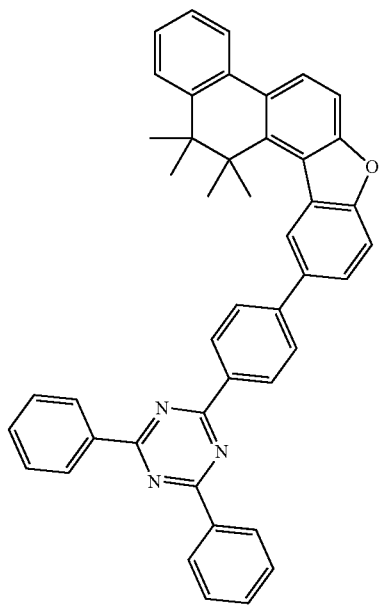
C-269
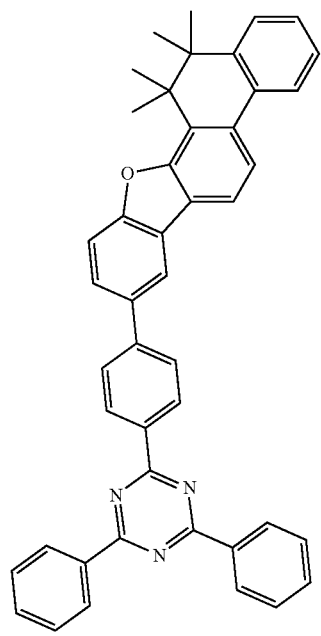
C-270
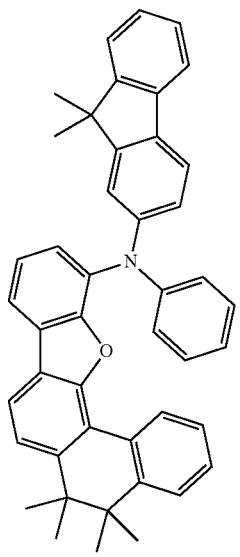
C-271
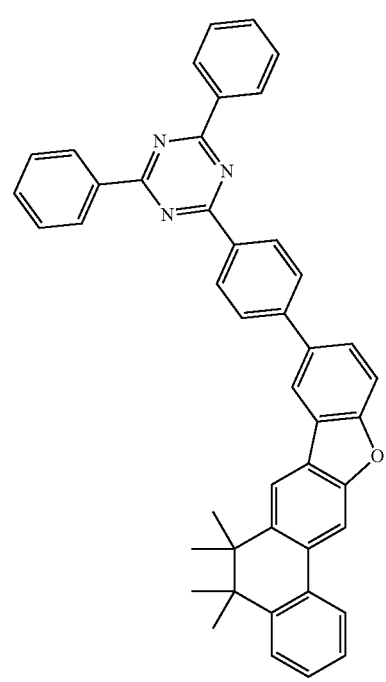

C-272
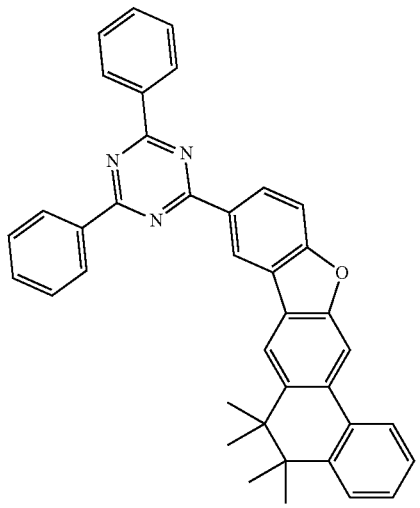
C-275
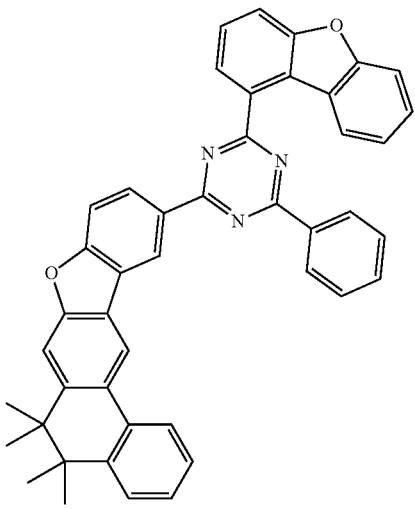
C-273
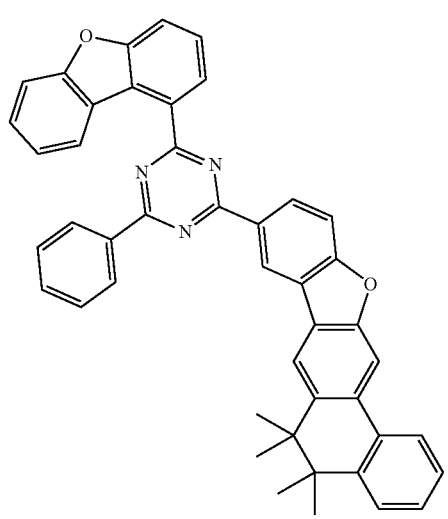
C-276
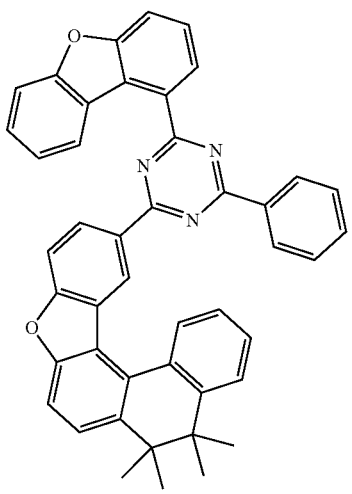
C-274
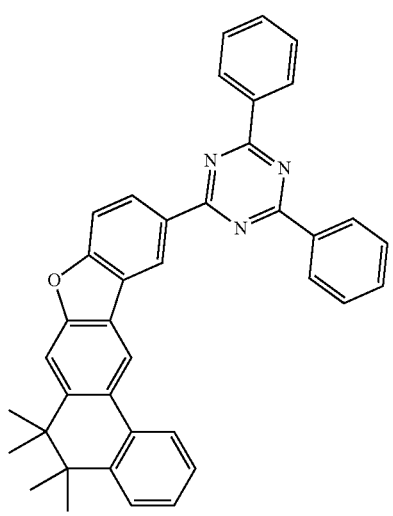
C-277
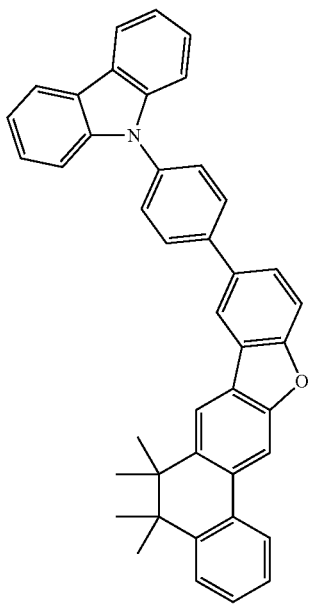

-continued
C-278
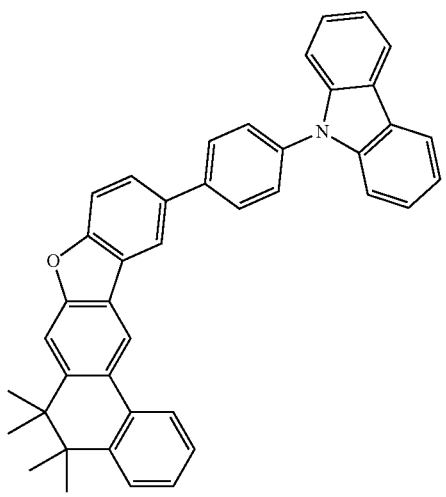
C-279
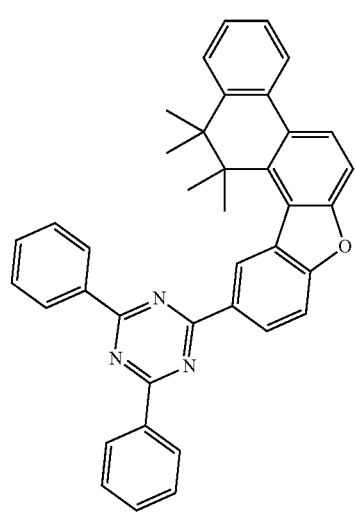
C-280
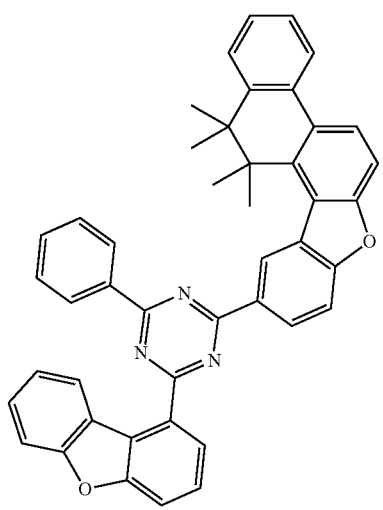
-continued
C-281
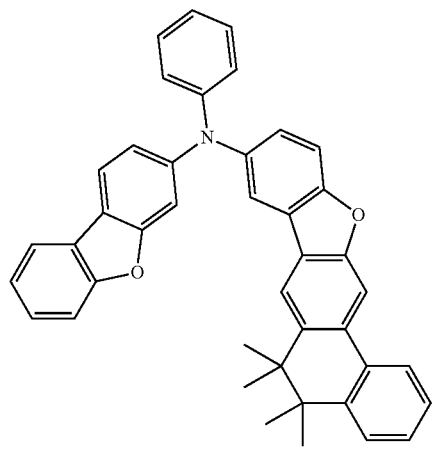
C-282
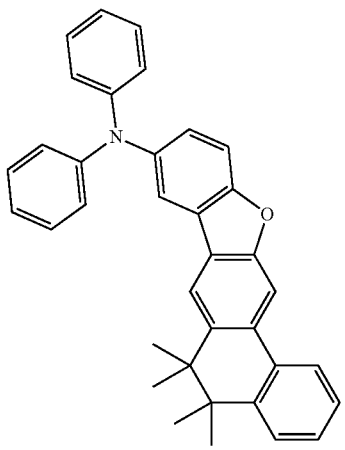
C-283
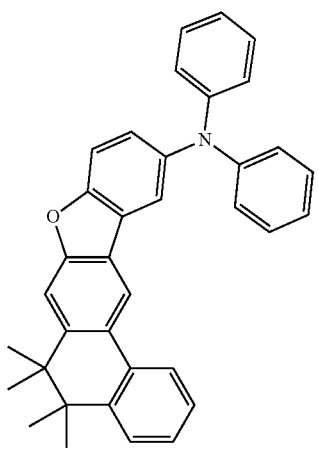

C-284
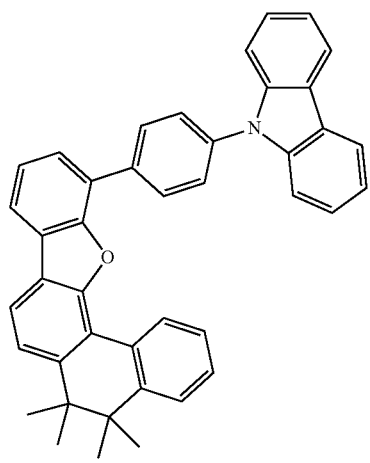
C-285
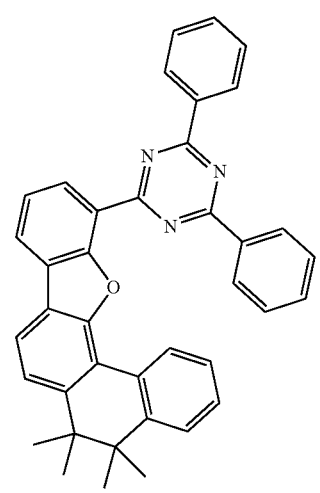
C-286
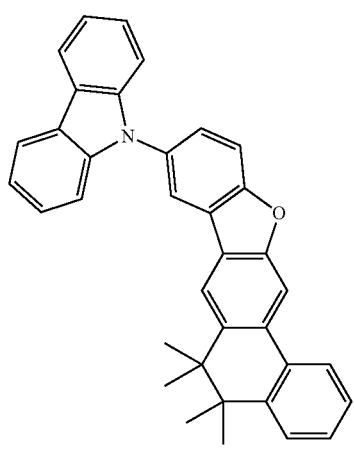
C-287
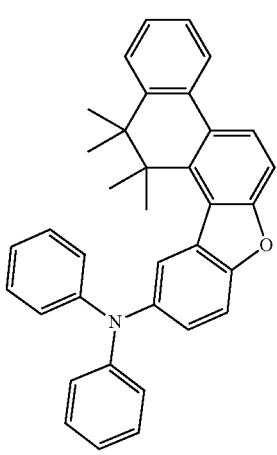
C-288
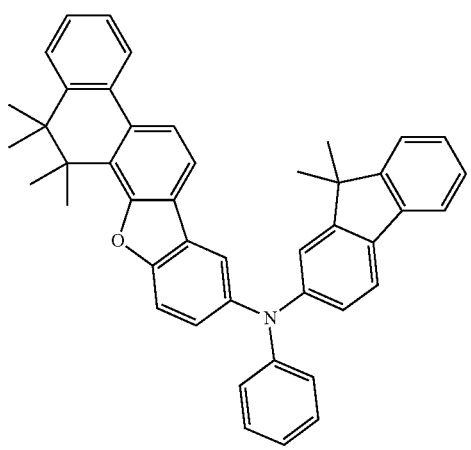
C-289
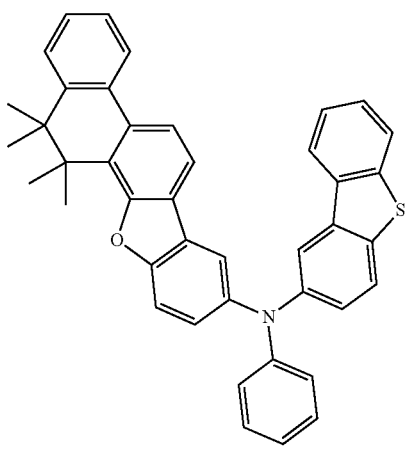

C-290
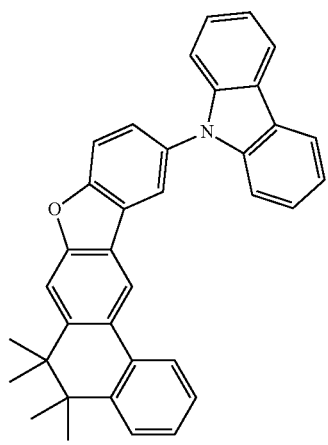
C-291
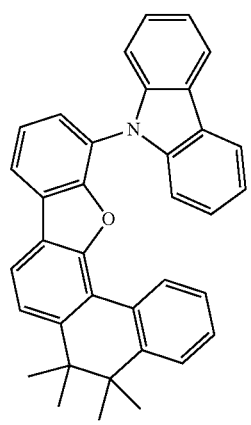
C-292
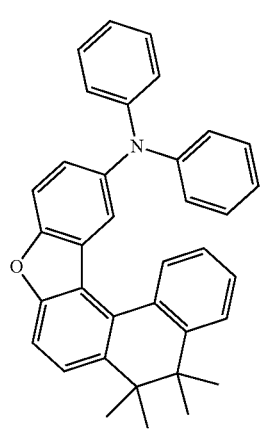
C-293
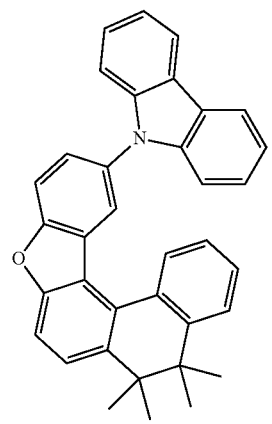
C-294
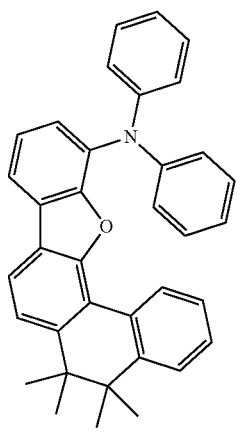
C-295
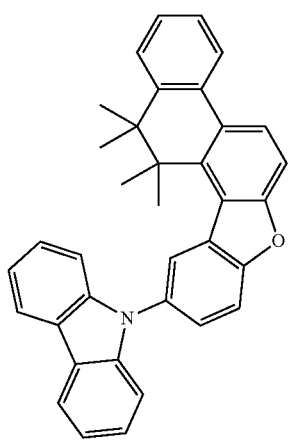

C-296 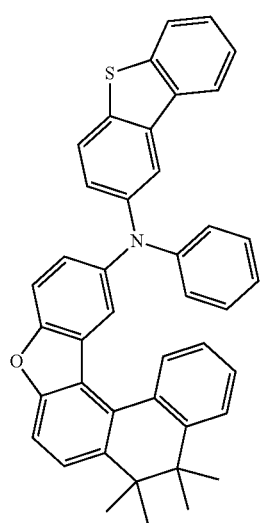
C-297 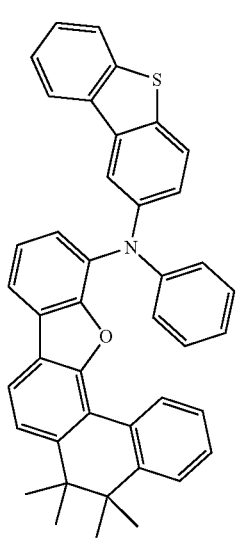
C-298 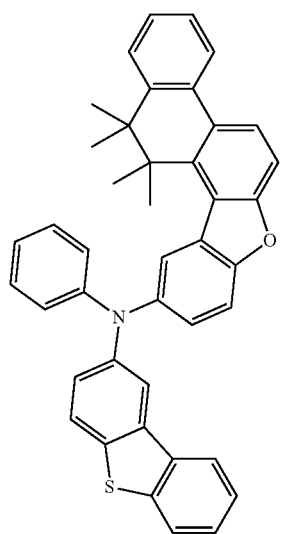
C-299 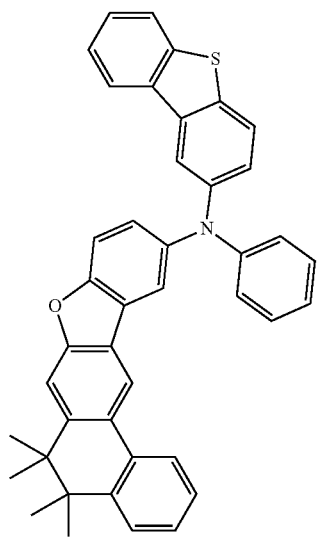
C-300 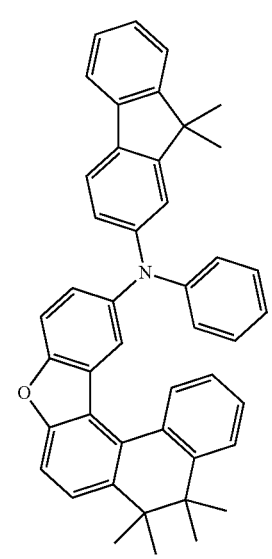
C-301 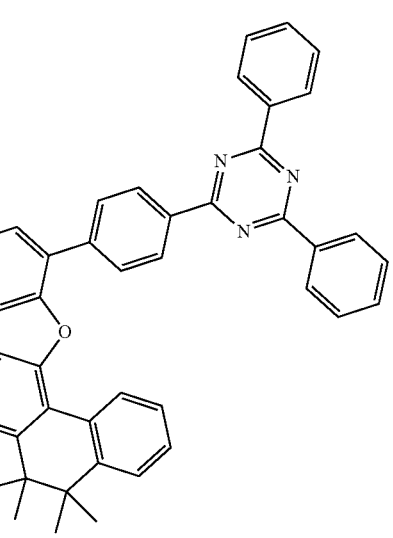

C-302
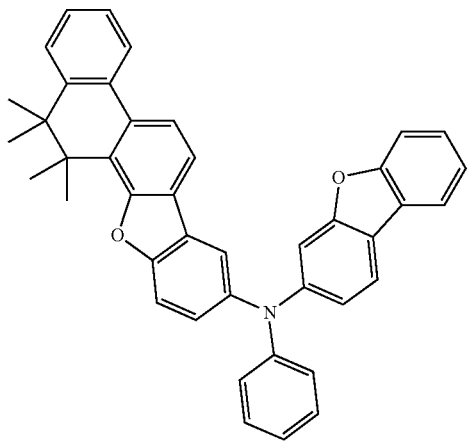
C-303
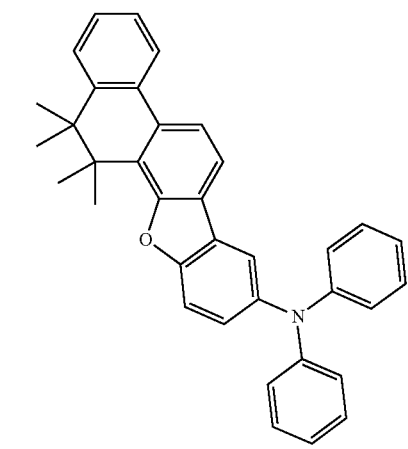
C-304
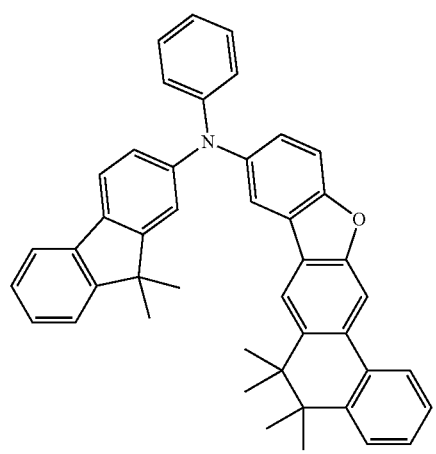
C-305
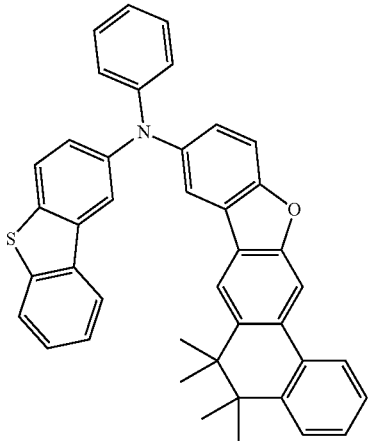
C-306
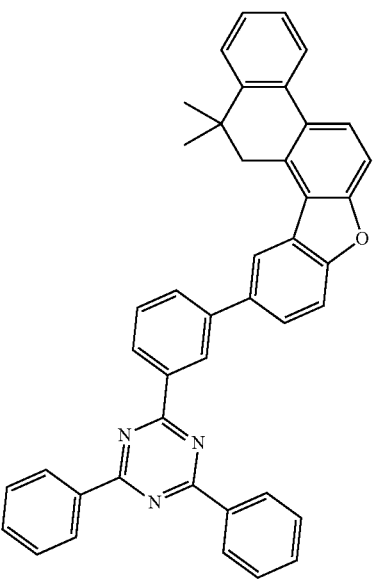
C-307
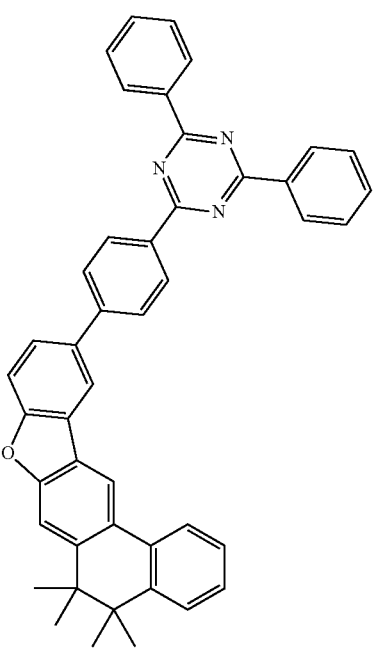

C-308
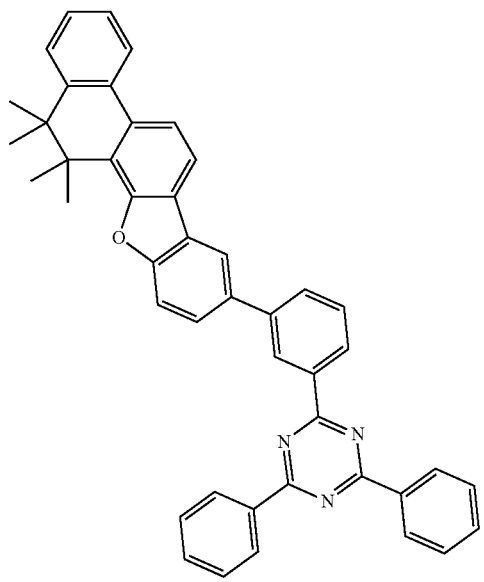
C-309
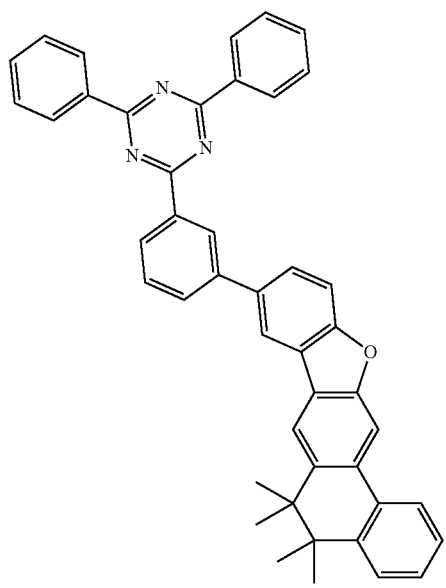
C-310
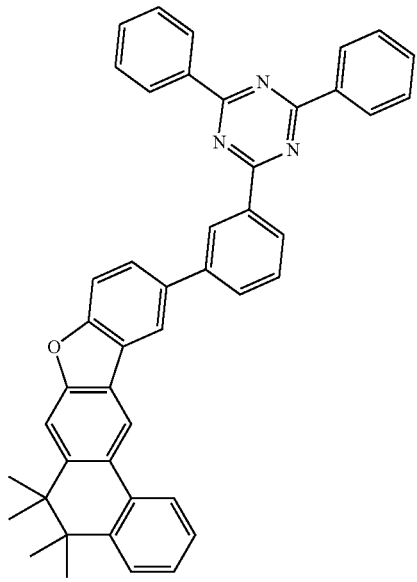
C-311
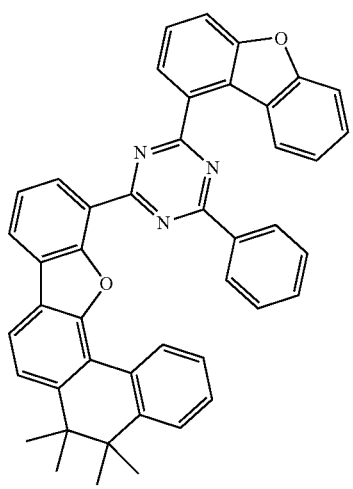
C-312
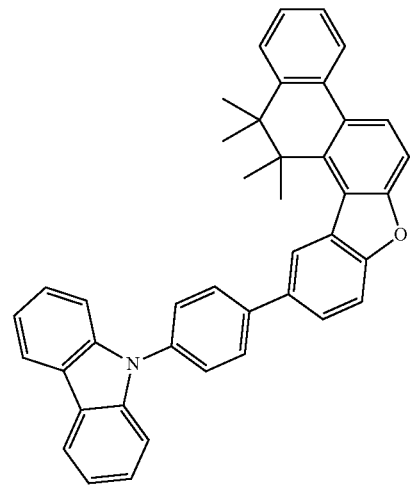

C-313
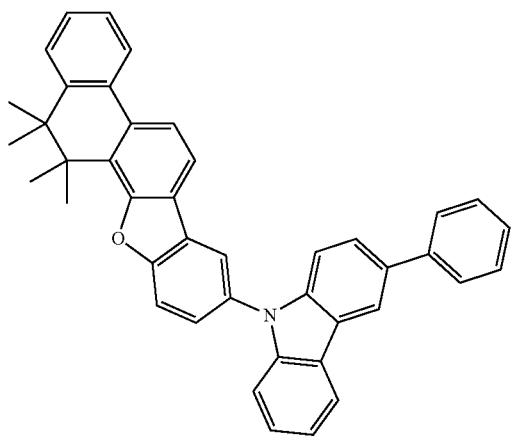
C-316
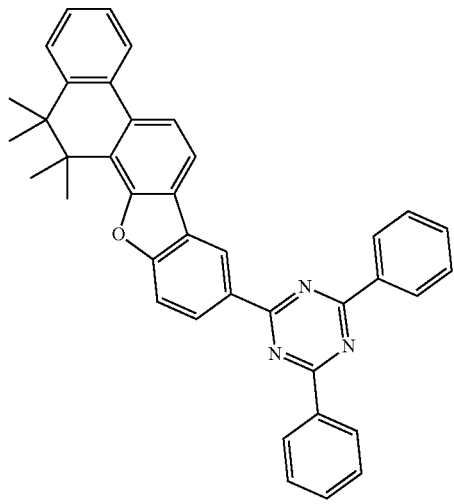
C-314
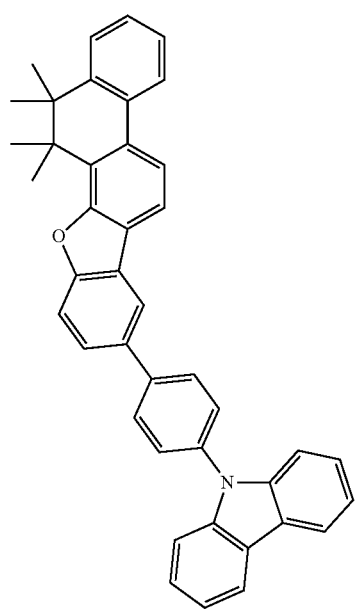
C-317
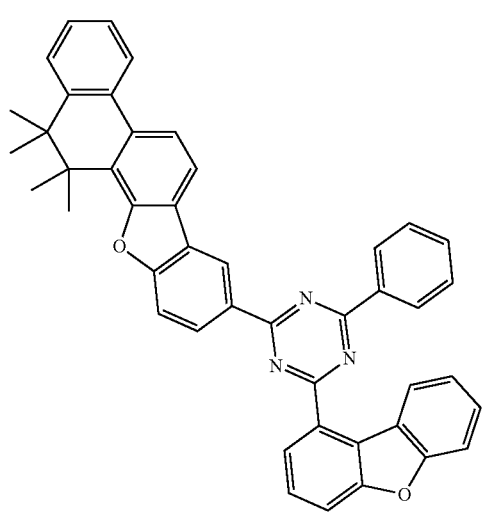
C-315
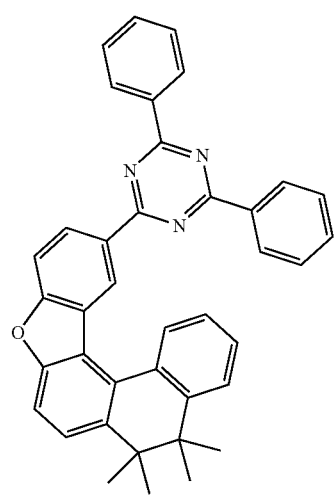
C-318
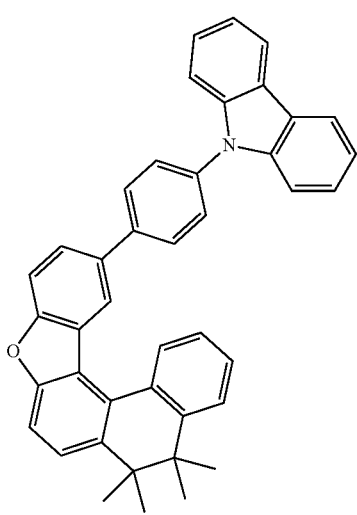

C-319
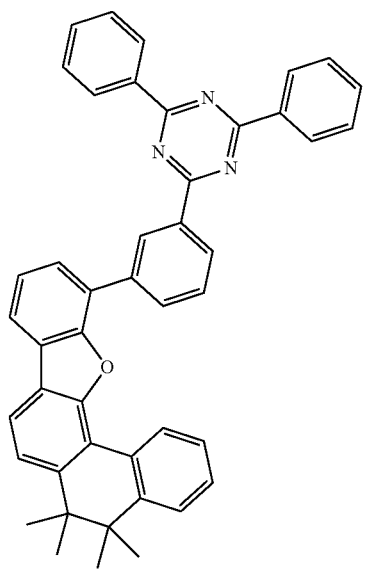
C-320
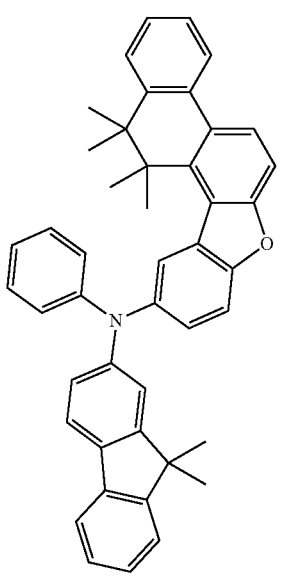
C-321
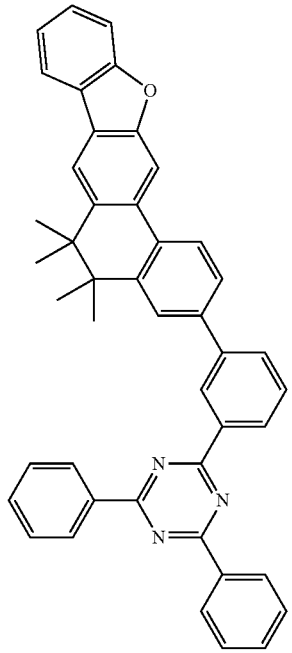
C-322
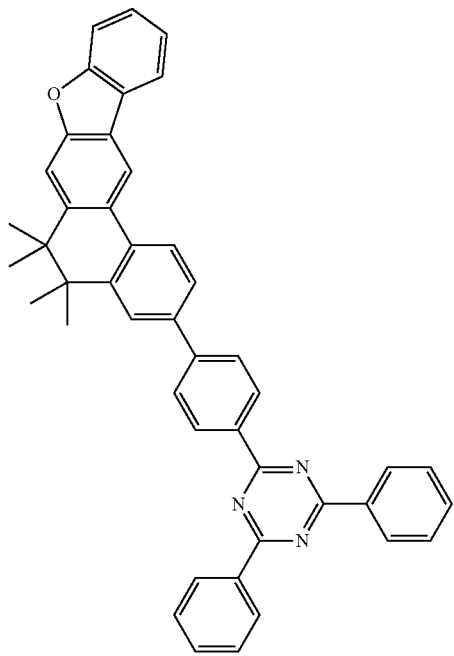

C-323
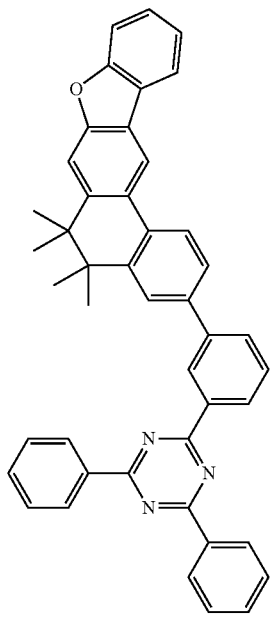
C-324
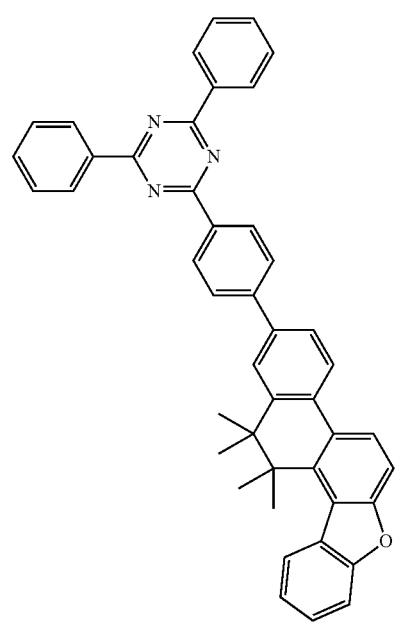
C-325
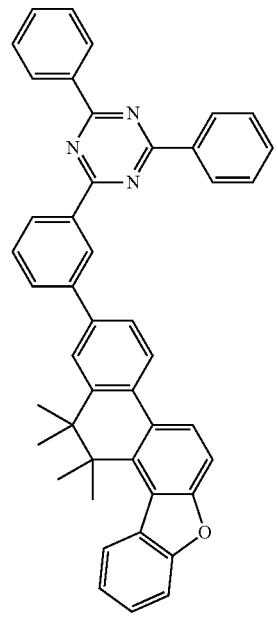
C-326
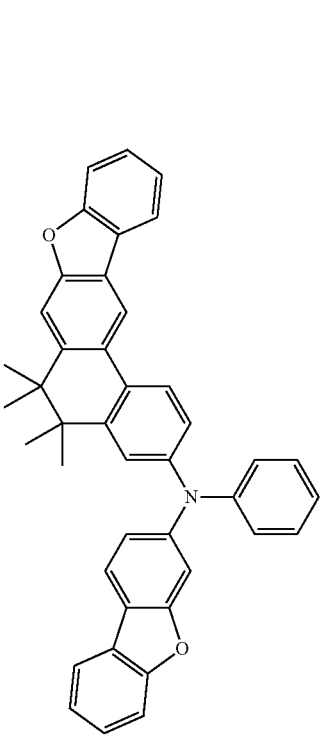

C-327
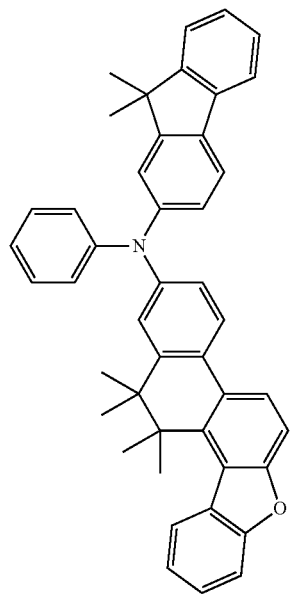
C-329
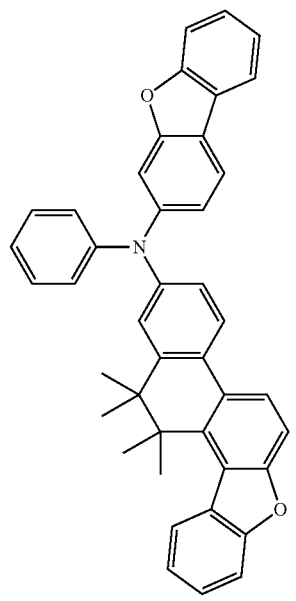
C-328
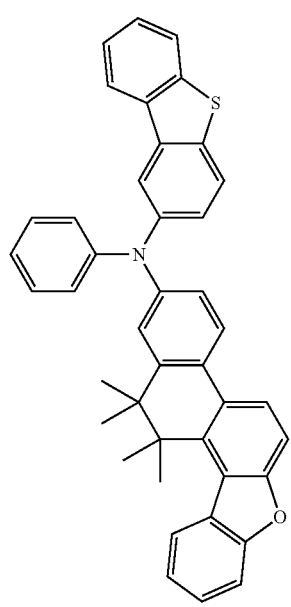
C-330
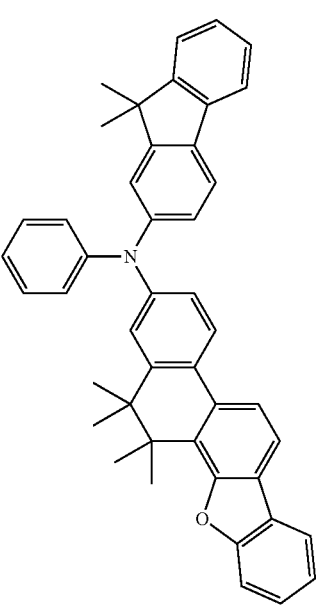

C-331
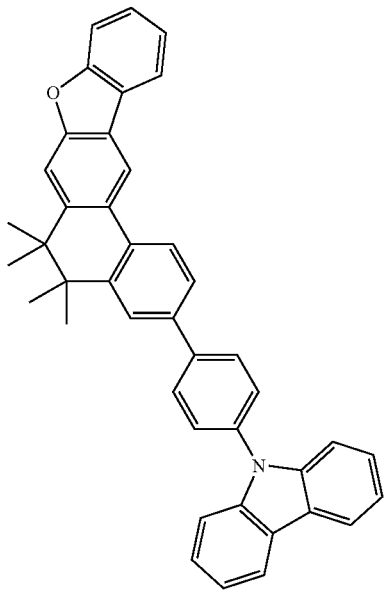
C-332
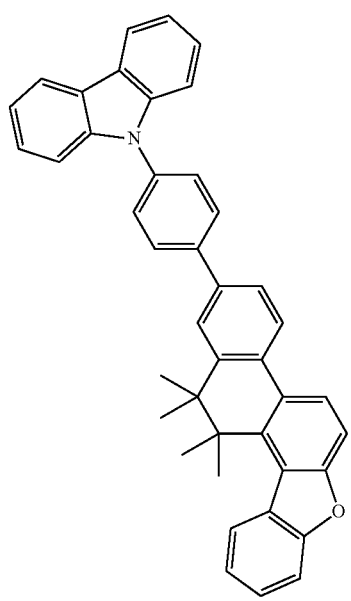
C-333
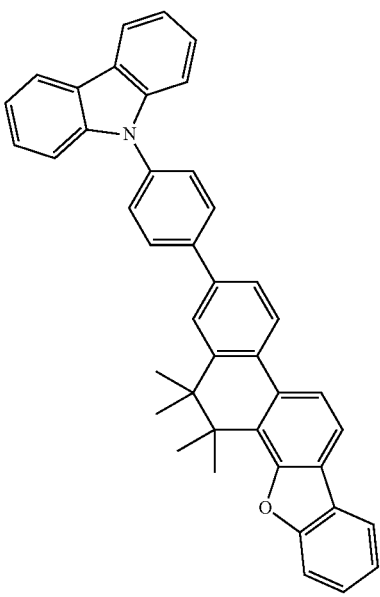
C-334
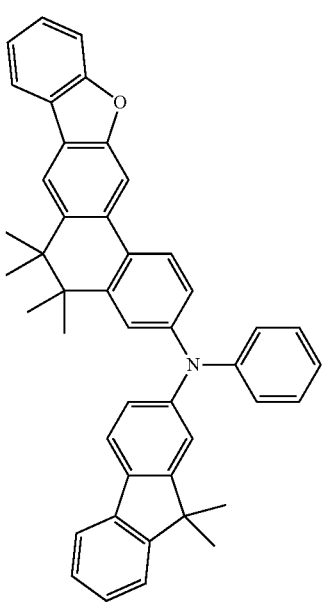

C-335
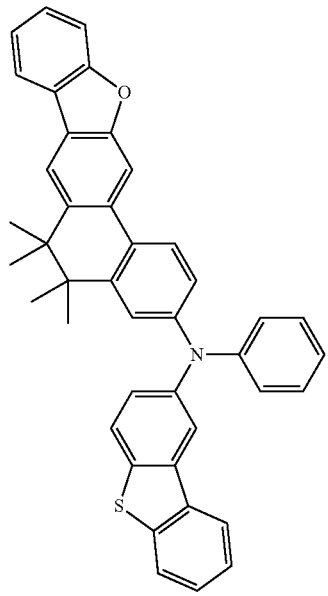
C-336
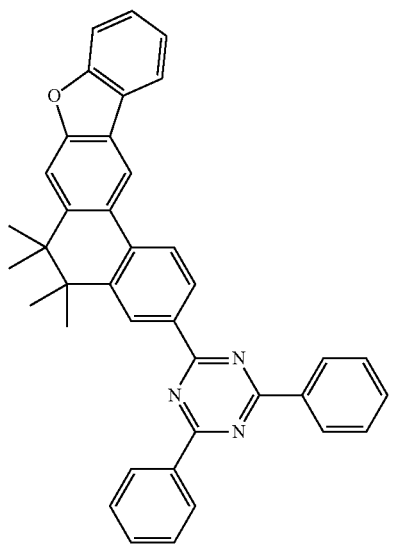
C-337
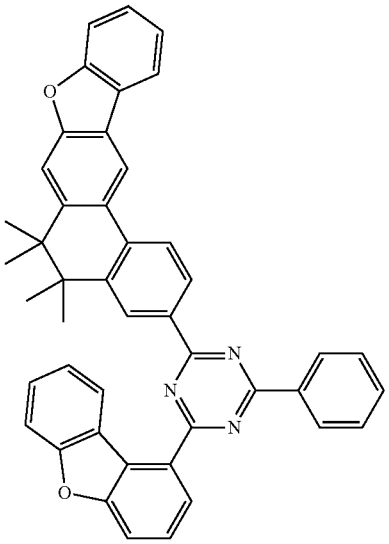
C-338
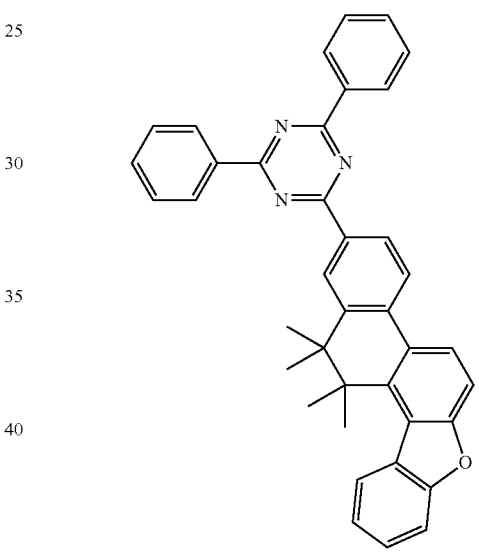
C-339
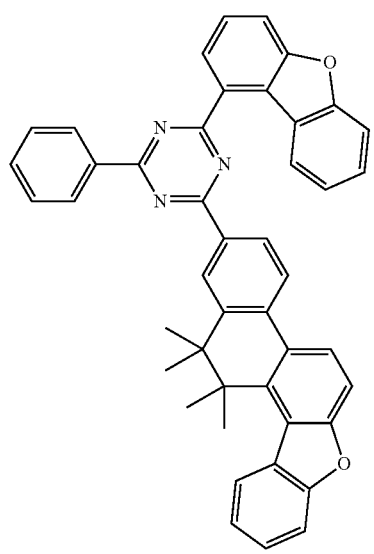

C-340
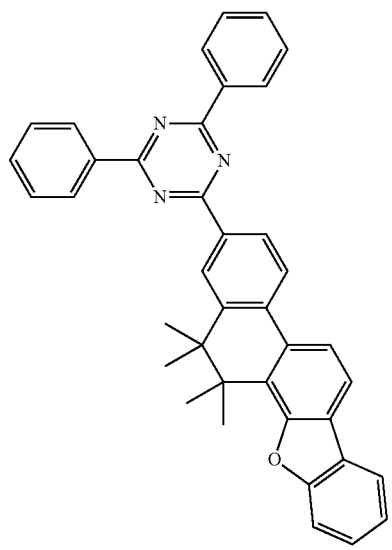
C-341
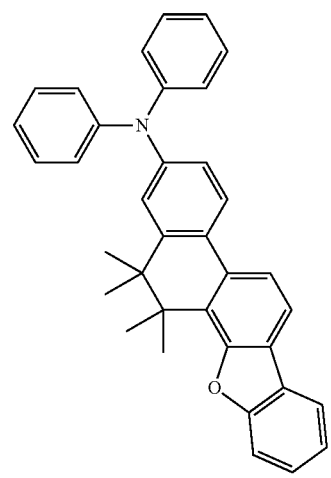
C-342
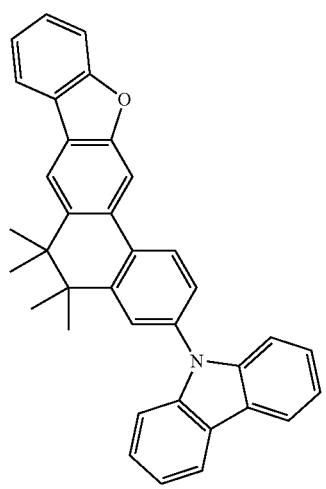
C-343
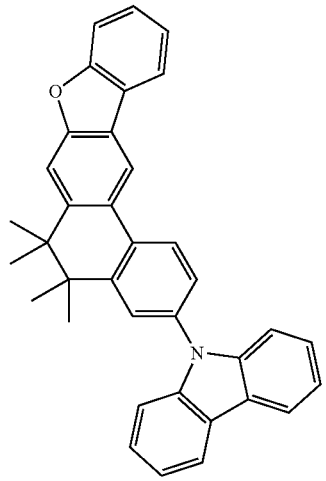
C-344
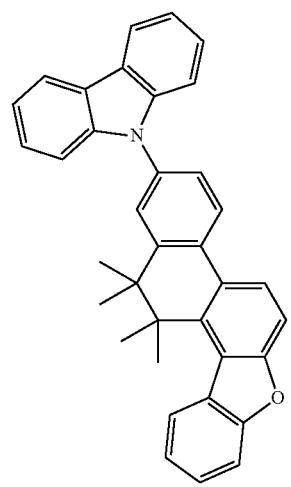
C-345
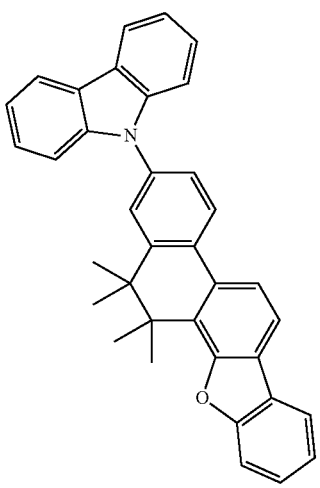

-continued
C-346
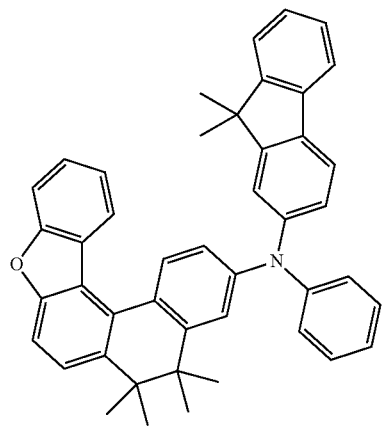
C-347
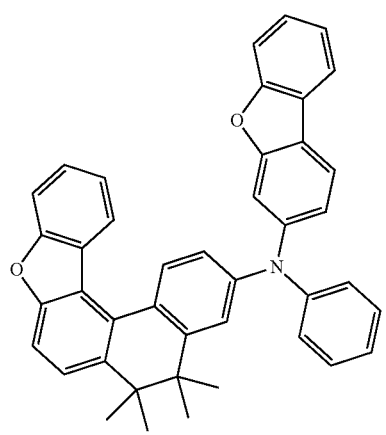
C-348
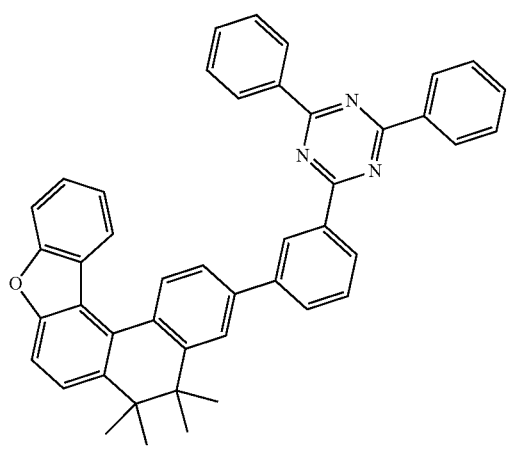
-continued
C-349
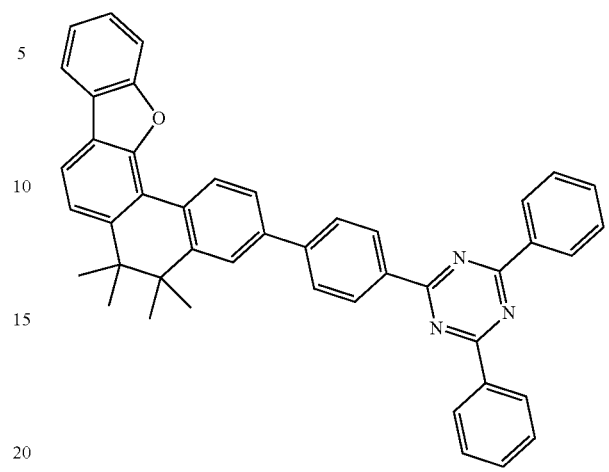
C-350
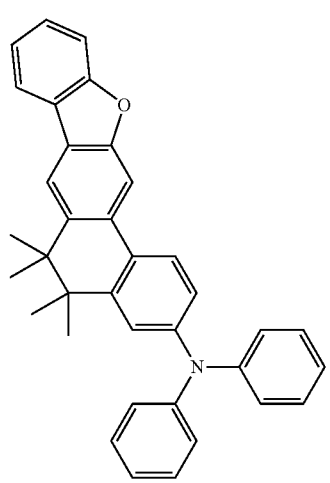
C-351
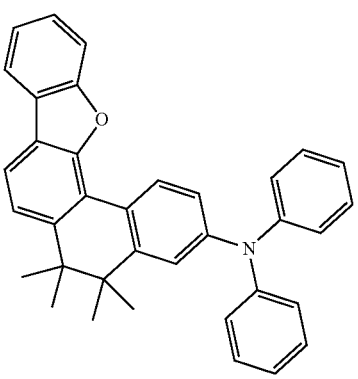

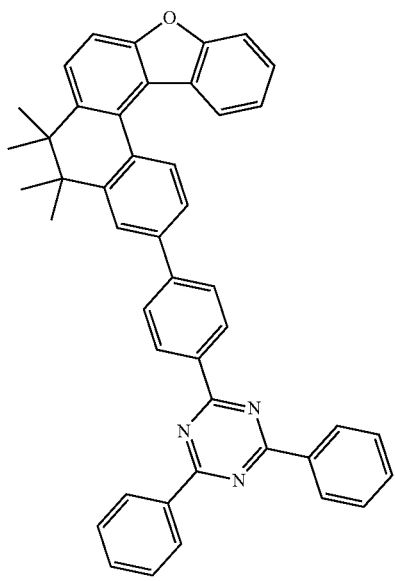
C-352
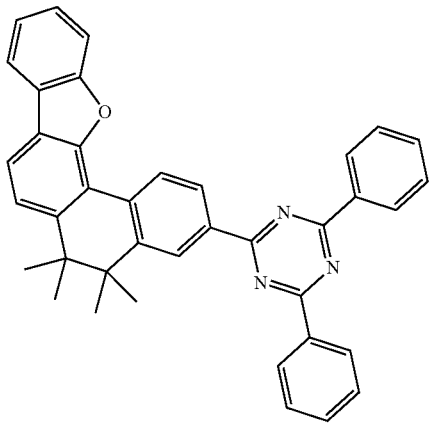
C-355
C-353
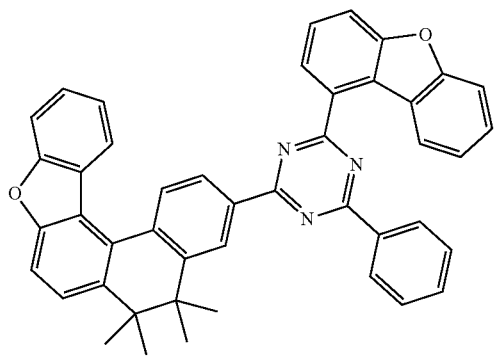
C-356
C-357
C-354
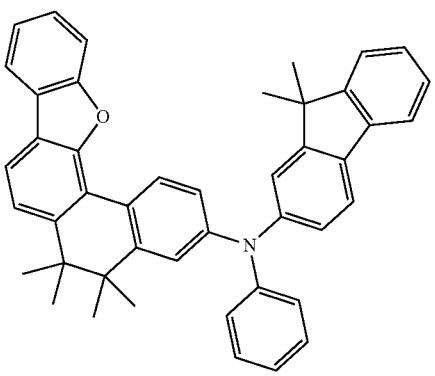
C-358

C-359
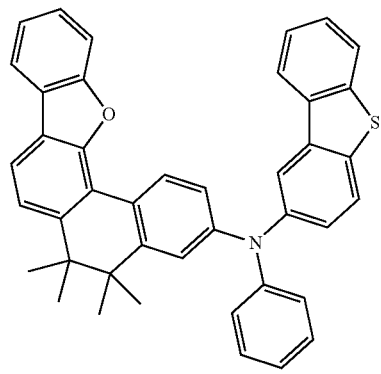
C-360
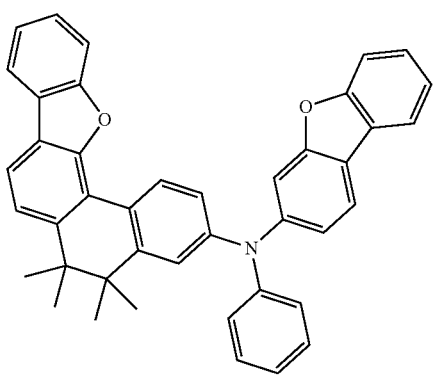
C-361
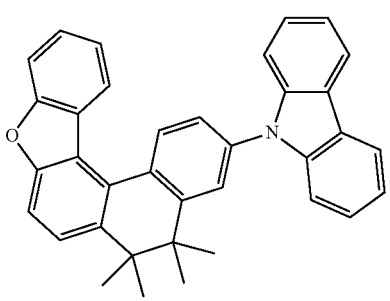
C-362
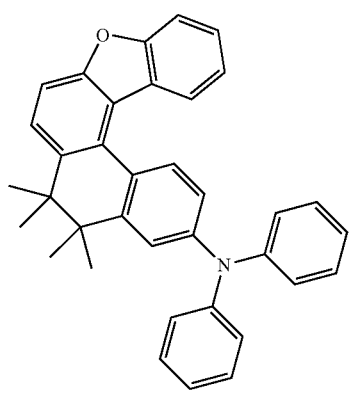
C-363
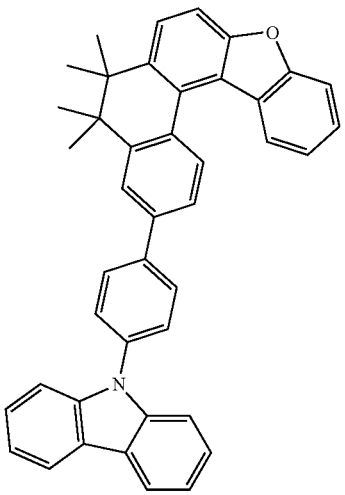
C-364
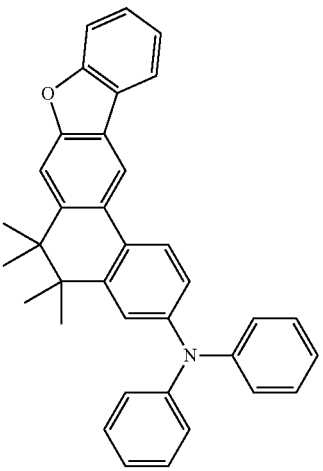
C-365
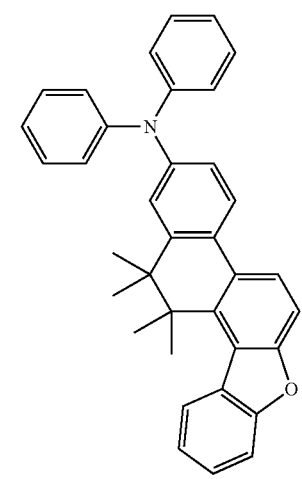

C-366
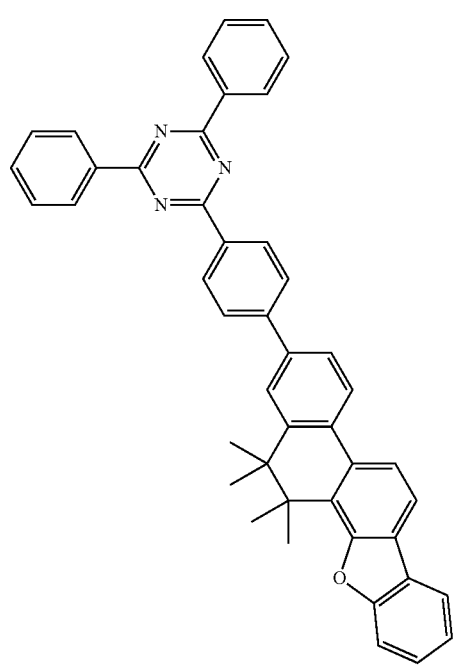
C-367
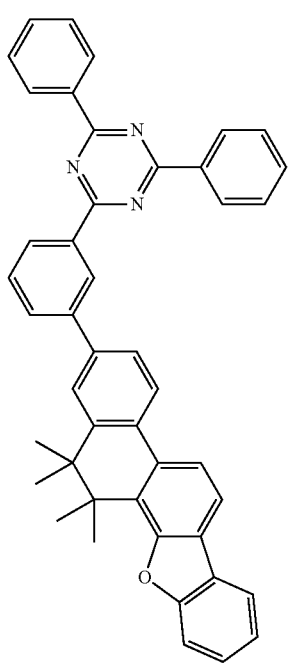
C-368
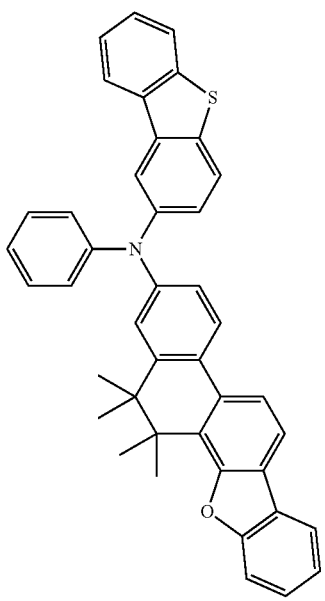
C-369
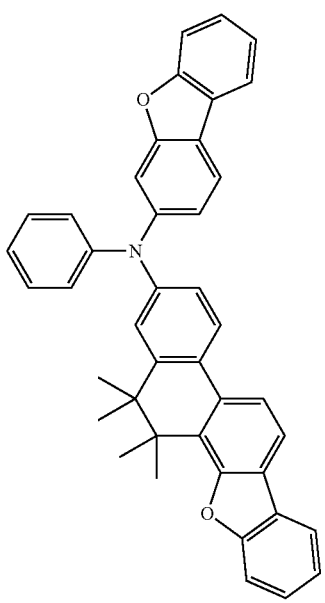

C-370
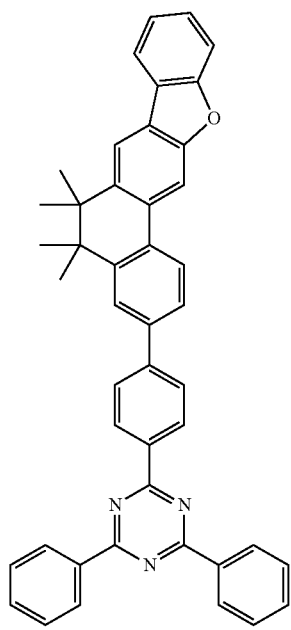
C-371
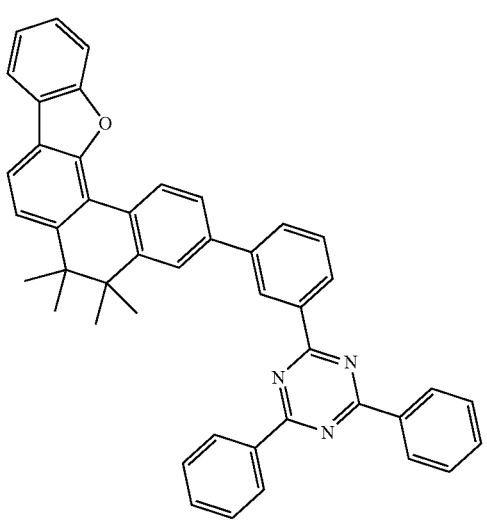
C-372
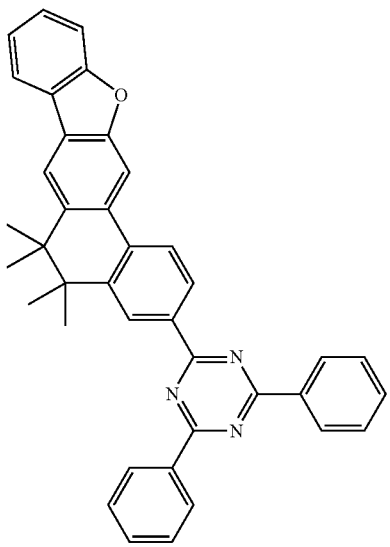
C-373
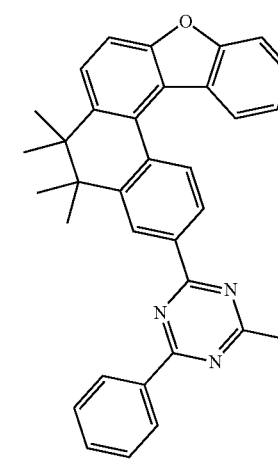
C-374

C-375
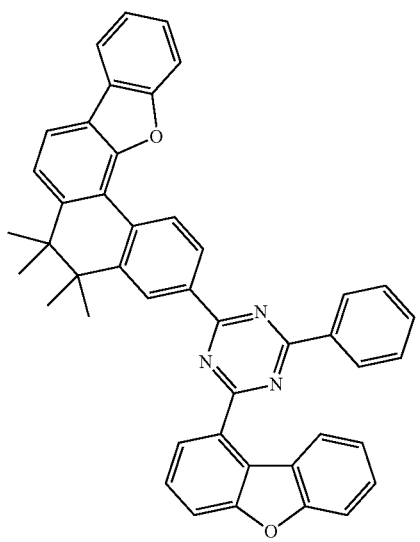
C-376
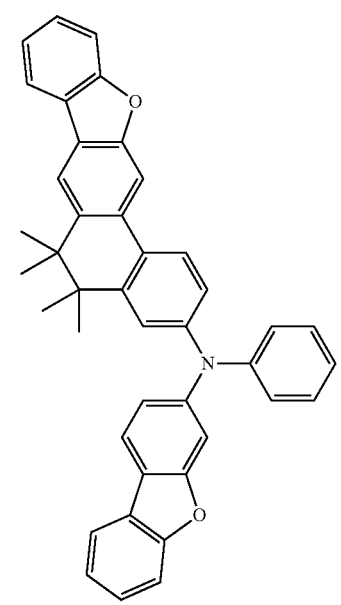
C-377
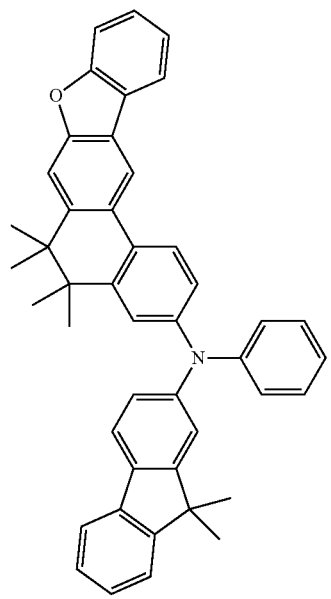
C-378
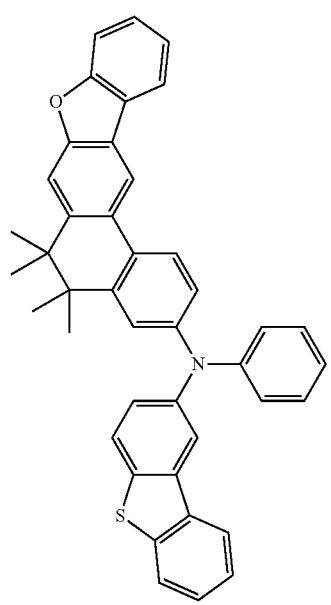

C-379
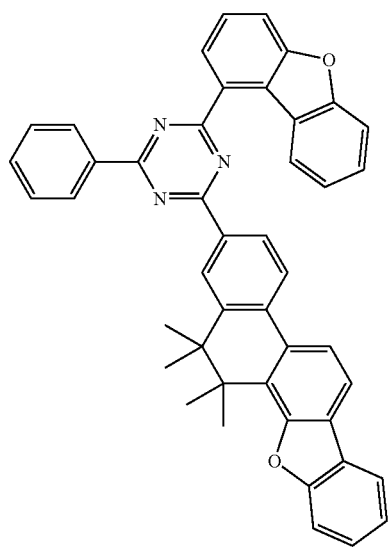
C-380
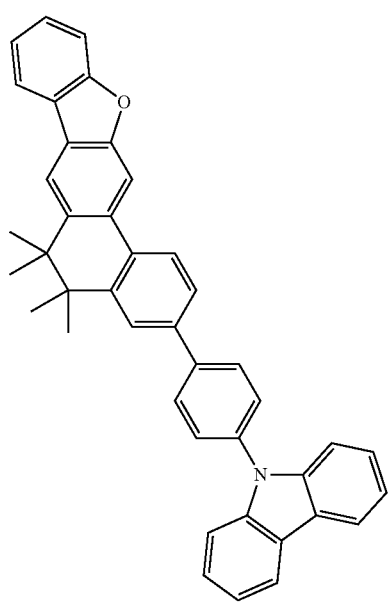
C-381
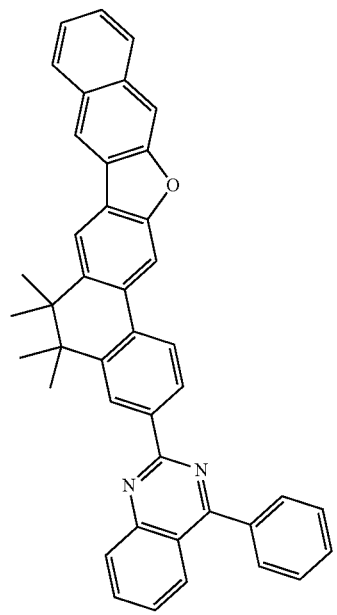
C-382
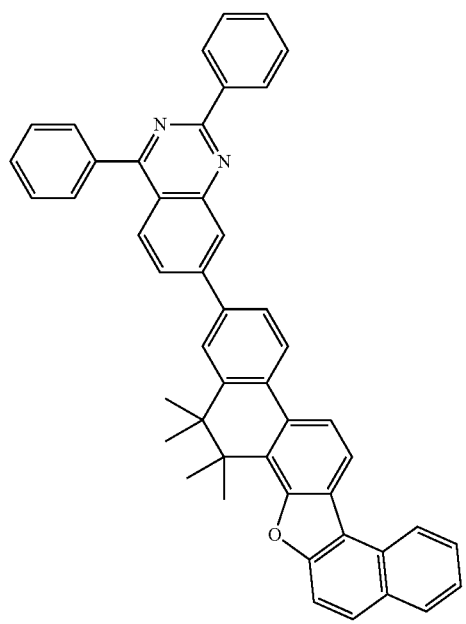

C-383
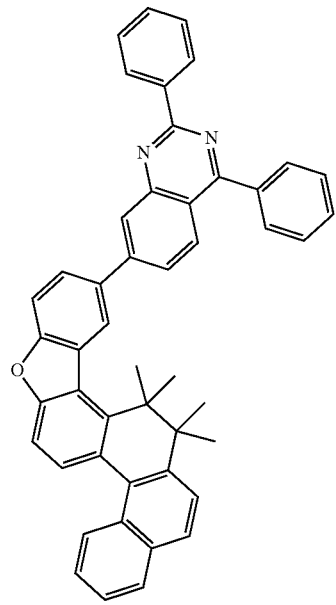
C-384
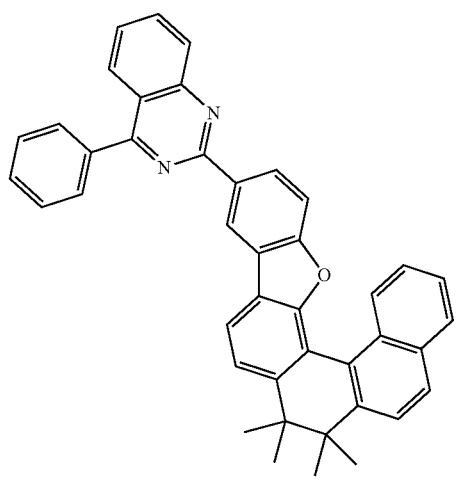
C-385
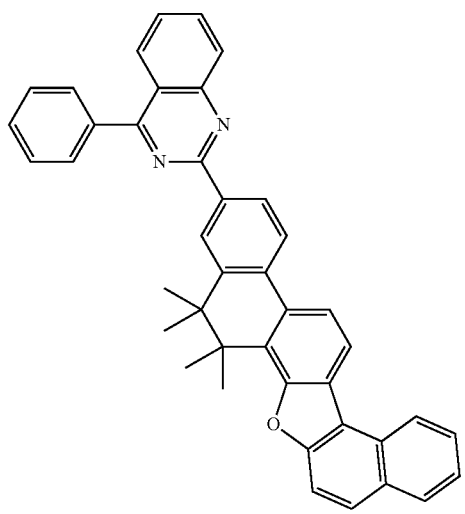
C-386
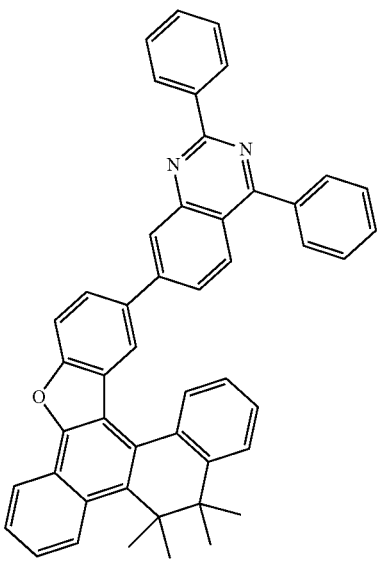
C-387
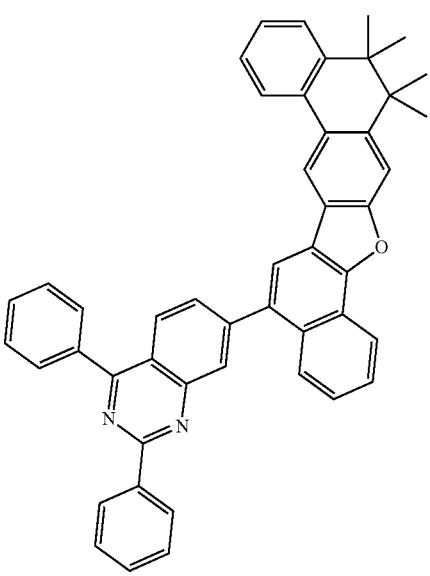

C-388
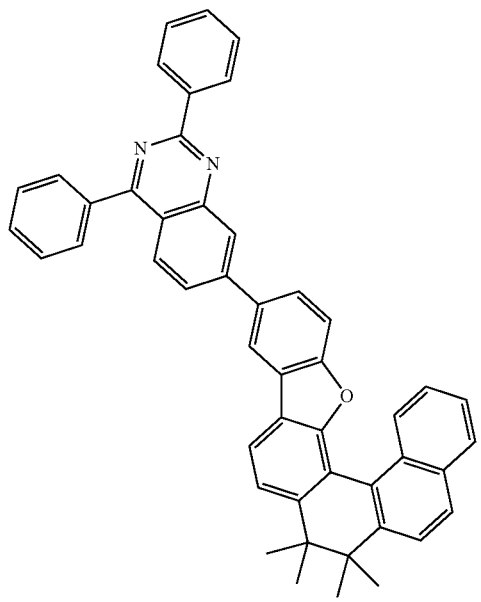
C-389
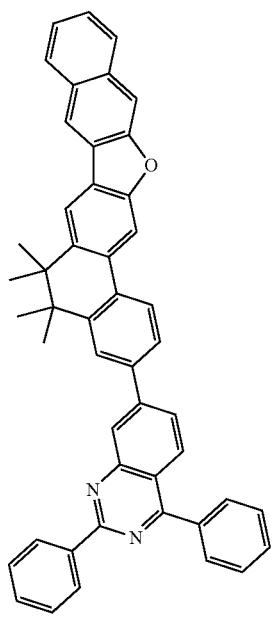
C-390
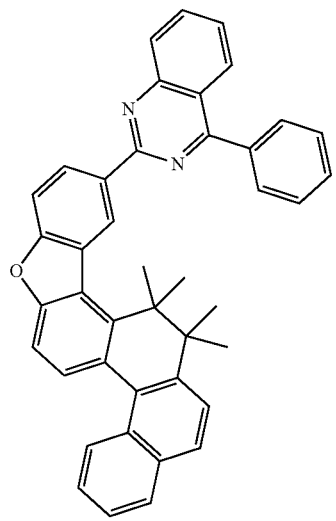
C-391
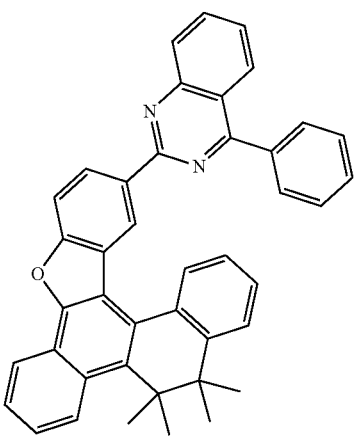
C-392
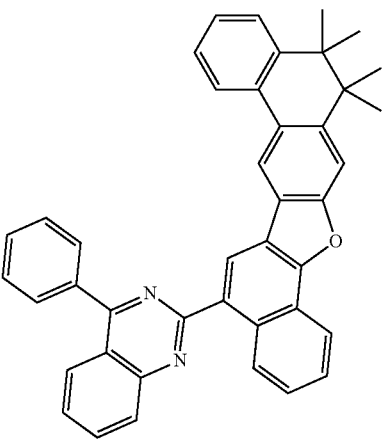

C-393
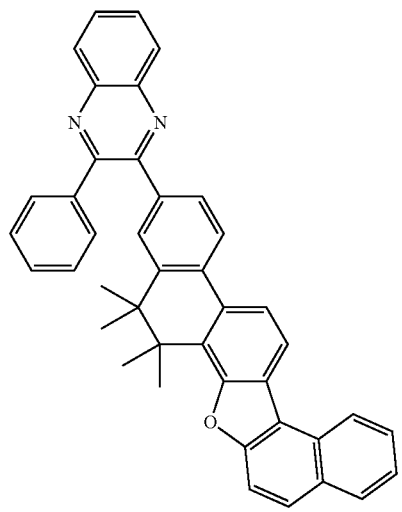
C-394
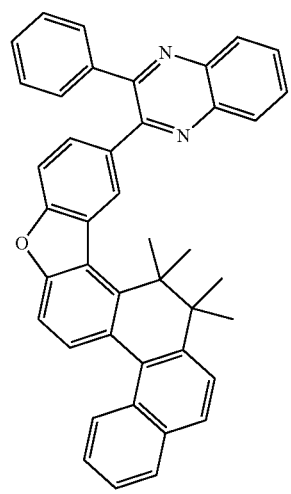
C-395
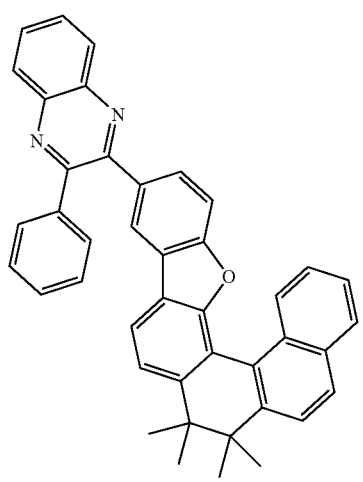
C-396
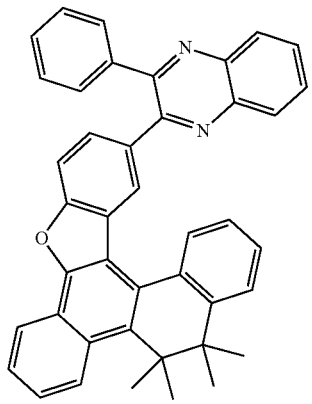
C-397
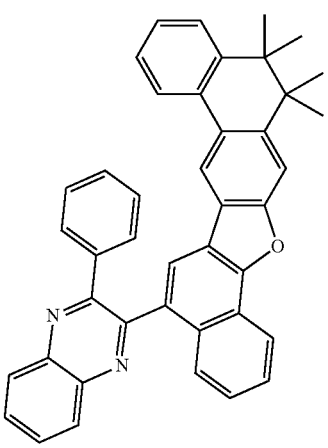
C-398
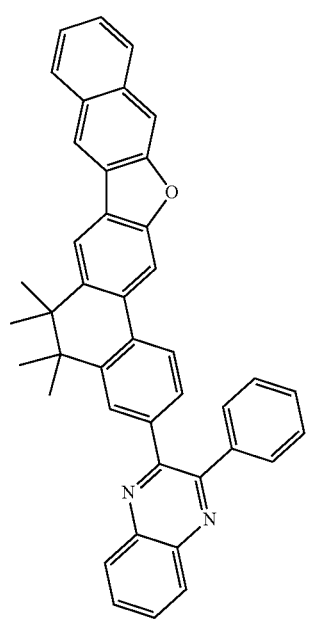

C-399
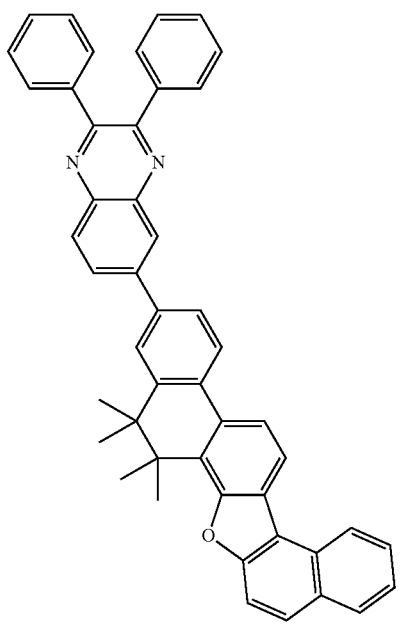
C-400
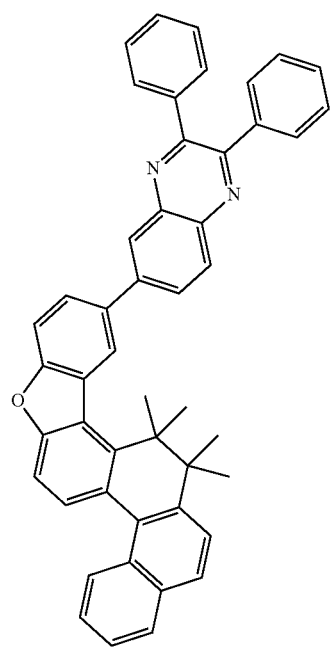
C-401
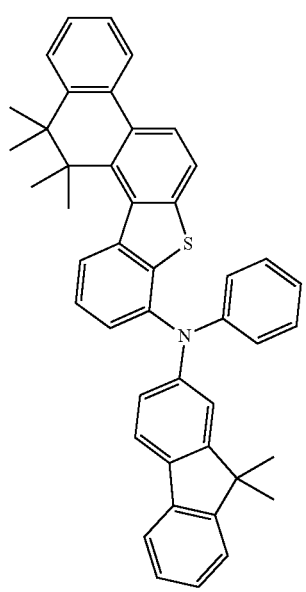
C-402
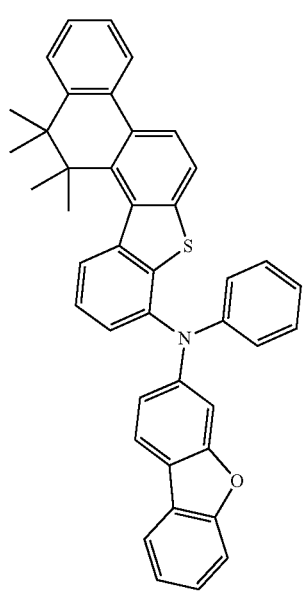

C-403
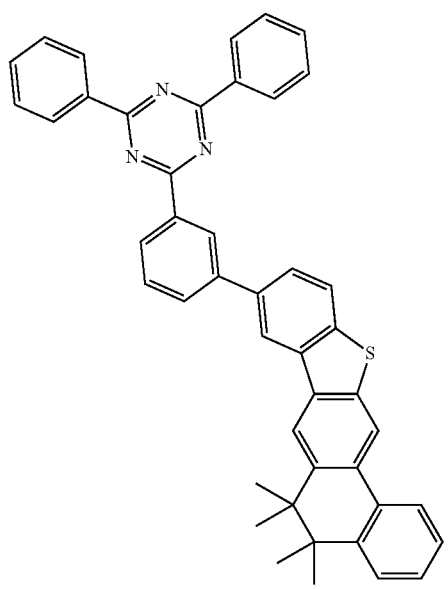
C-405
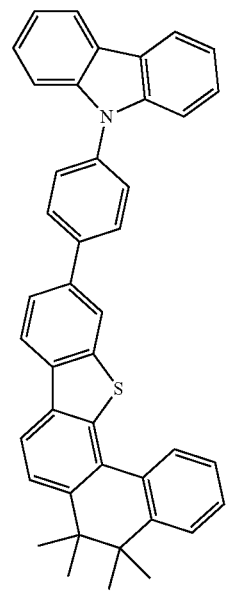
C-404
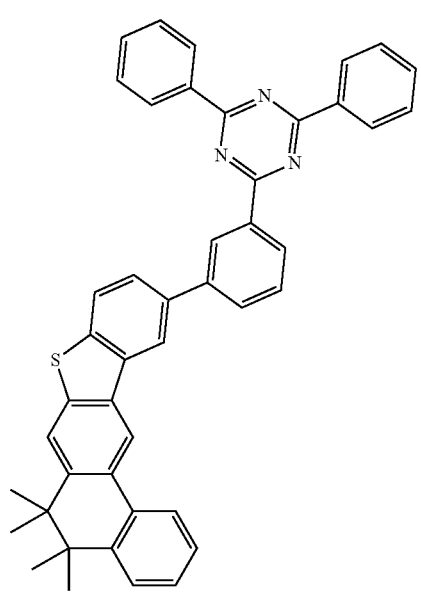
C-406
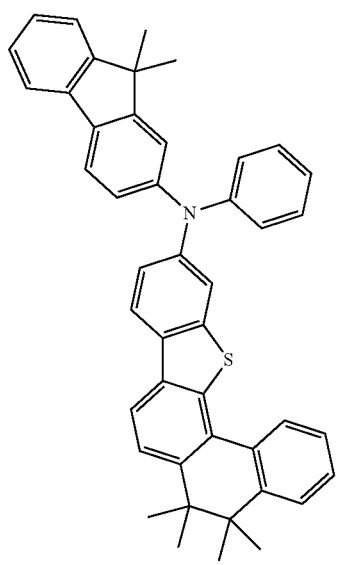

-continued
C-407
C-408
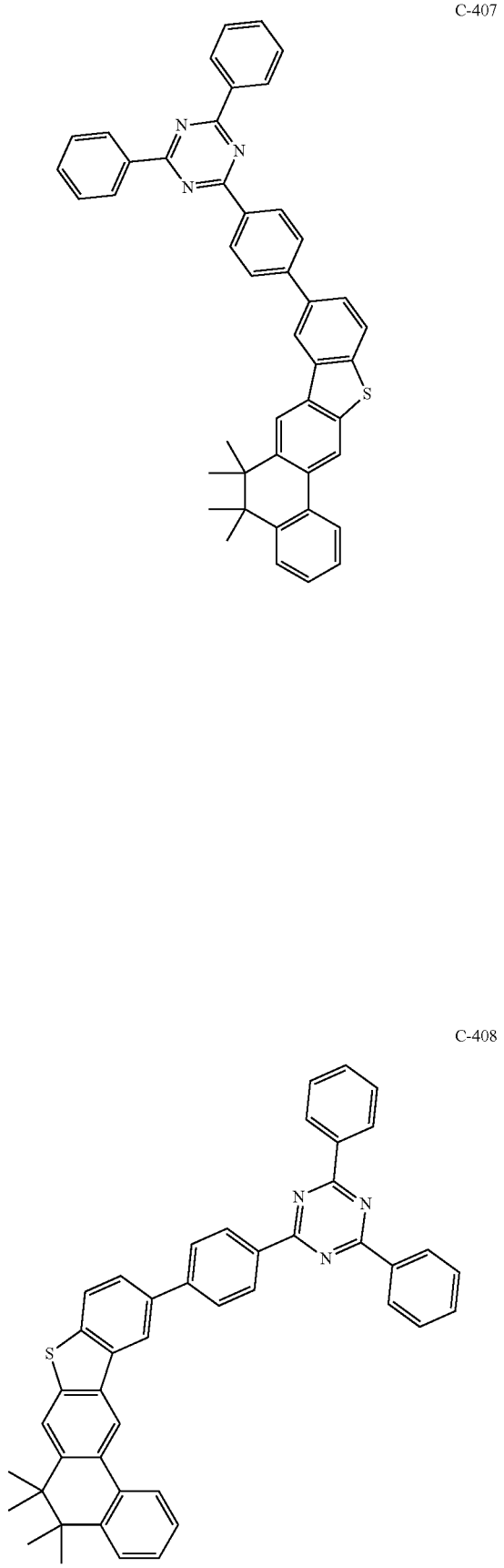
-continued
C-409
C-410
C-411
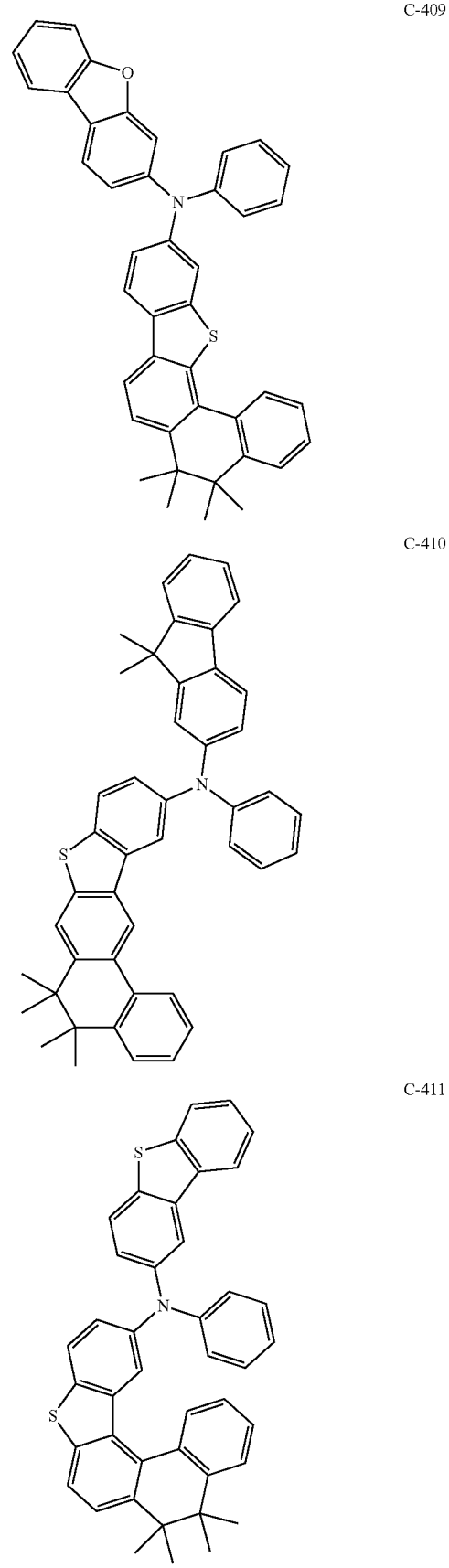

-continued
C-412
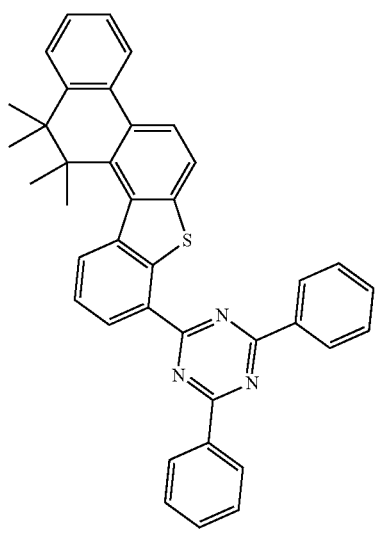
C-413
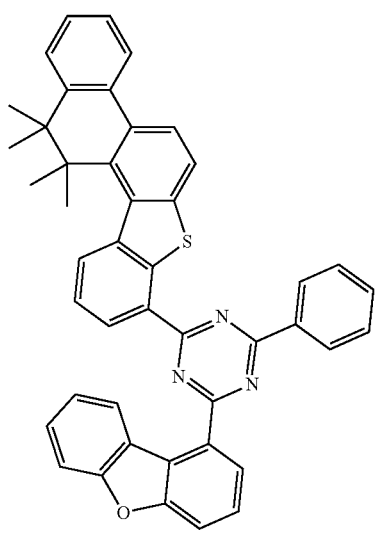
C-414
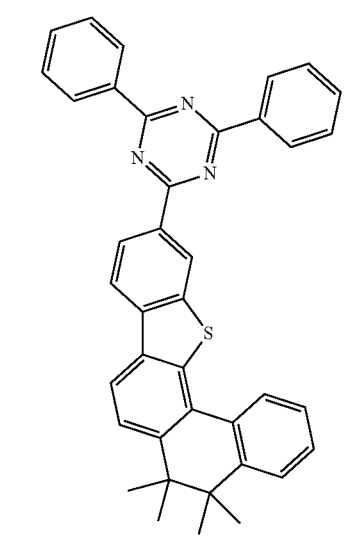
-continued
C-415
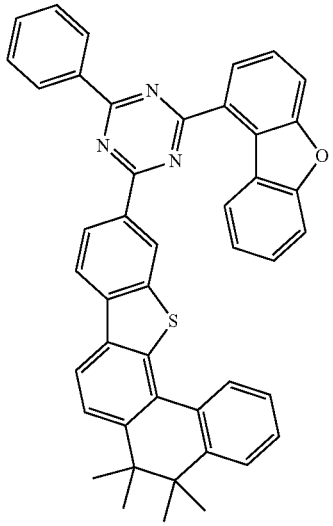
C-416
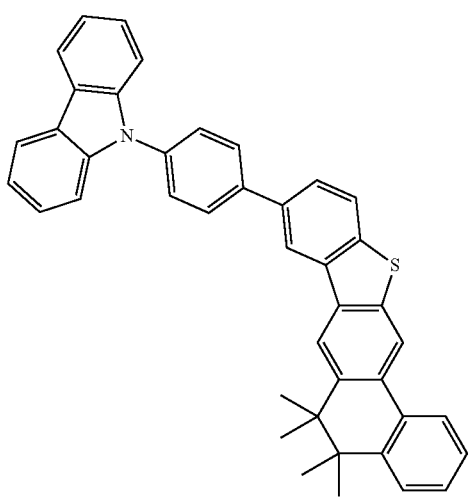
C-417
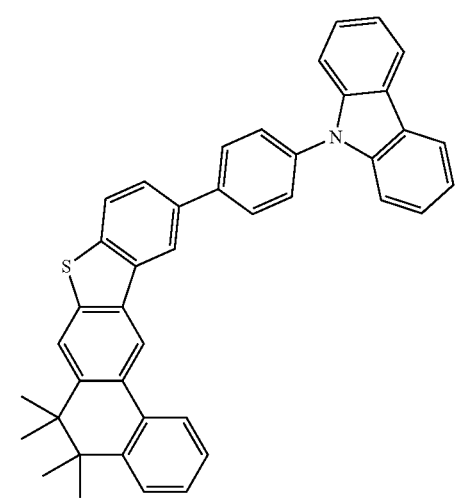

C-418
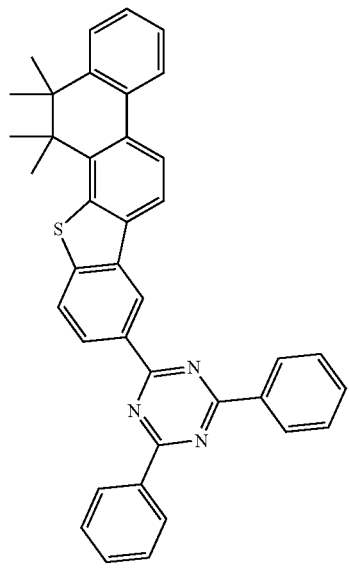
C-419
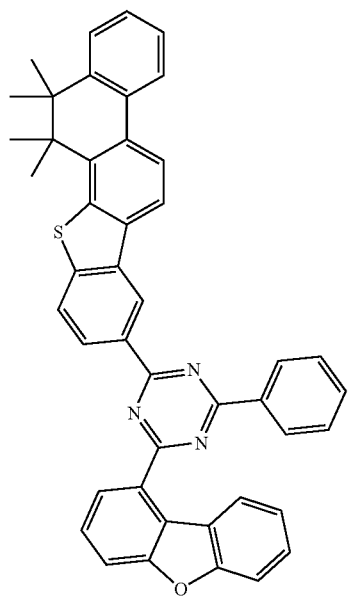
C-420
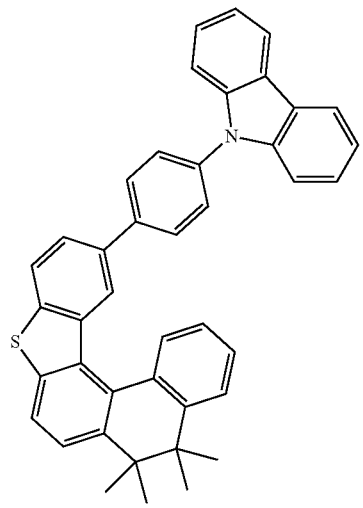
C-421
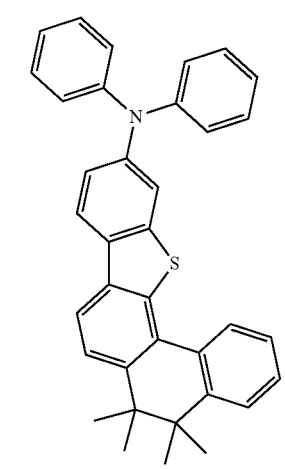
C-422
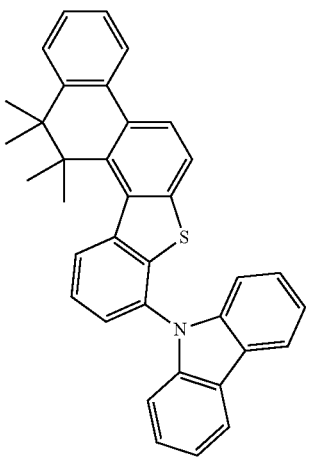

C-423
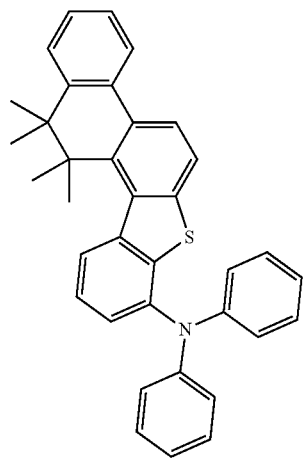
C-424
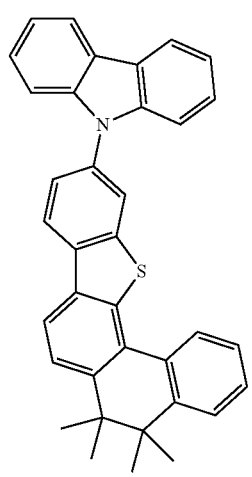
C-425
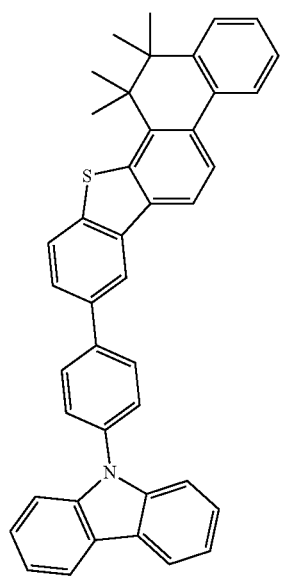
C-426
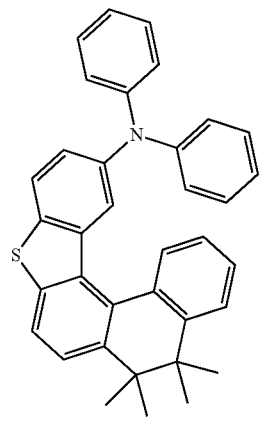
C-427
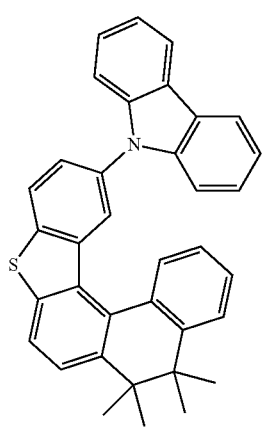
C-428
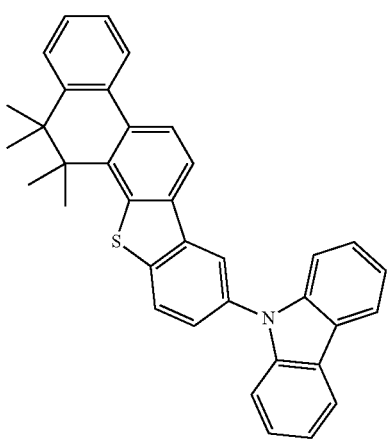

C-429
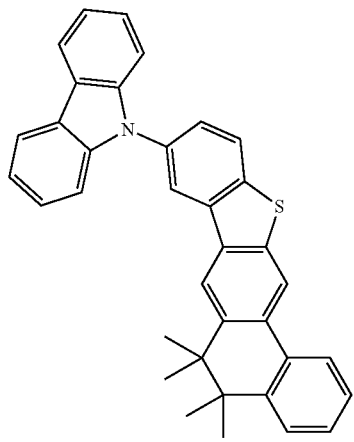
C-432
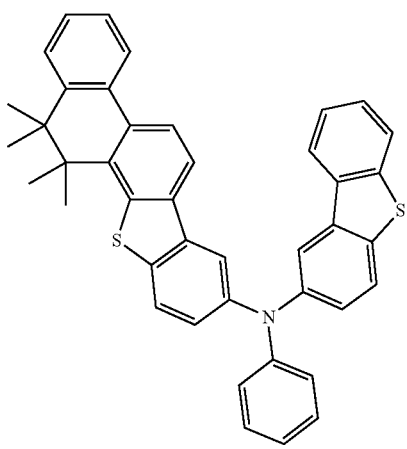
C-430
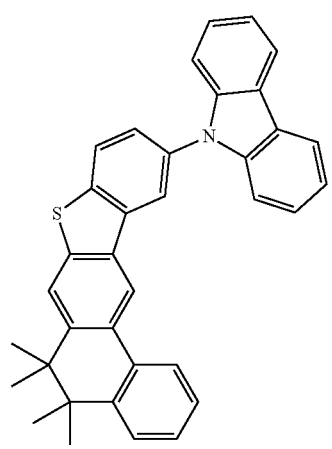
C-433
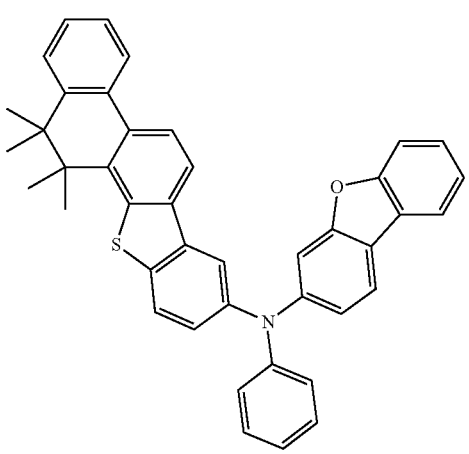
C-431
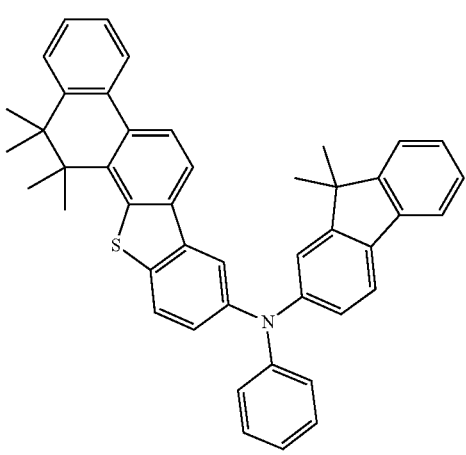
C-434
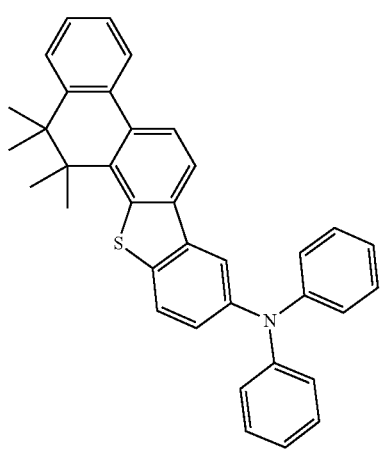

C-435
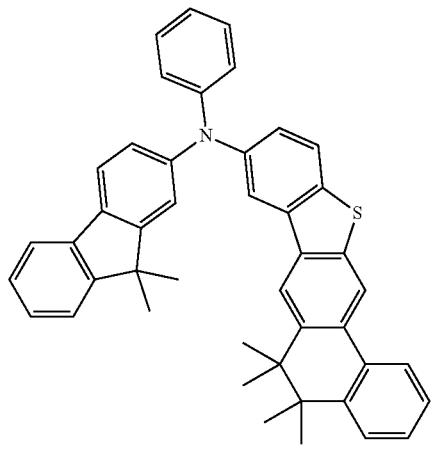
C-436
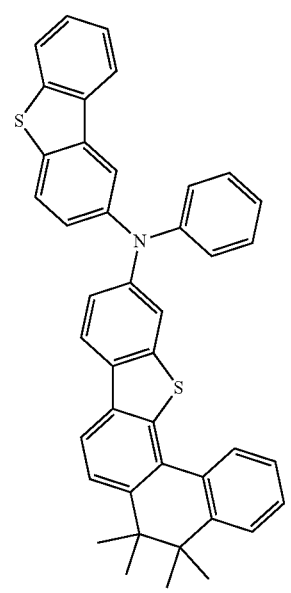
C-437
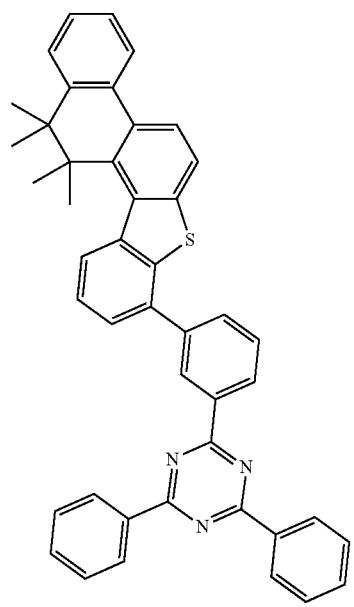
C-438
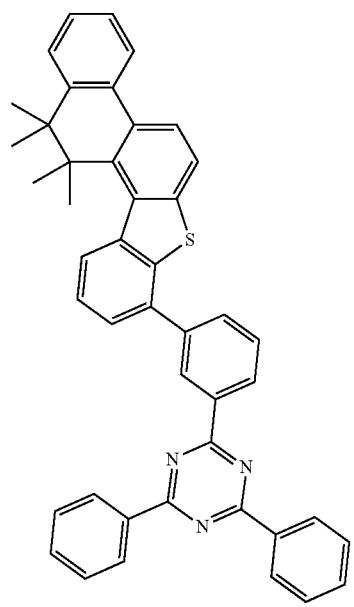
C-439
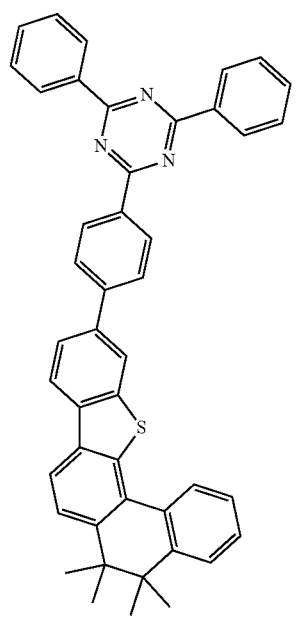

-continued
C-440
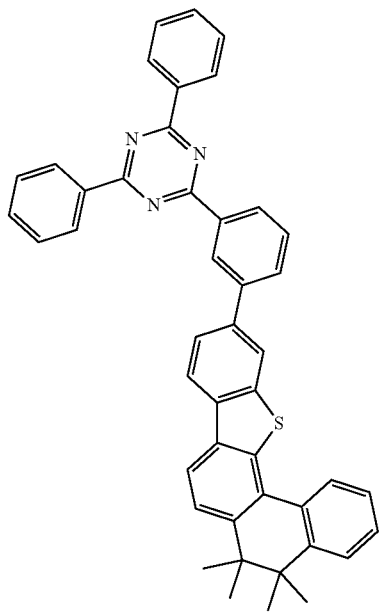
C-441
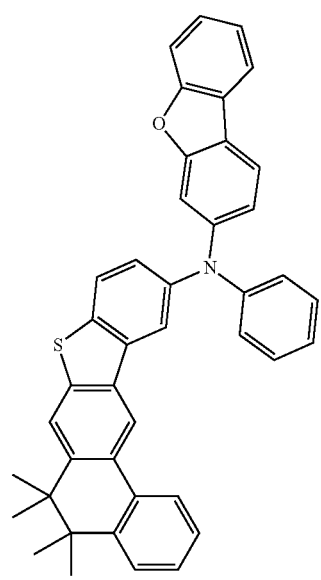
C-442
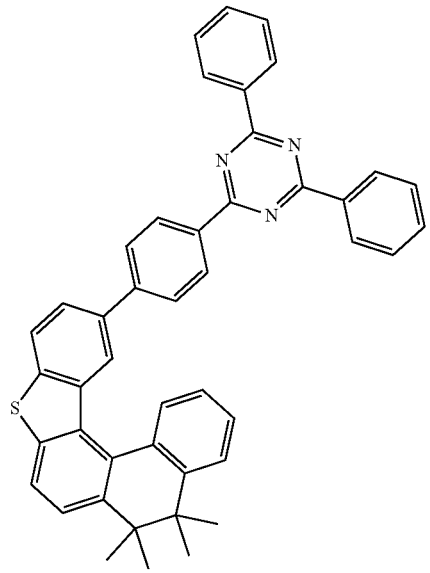
C-443
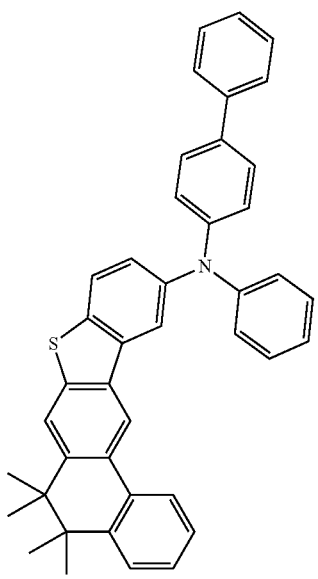

C-444
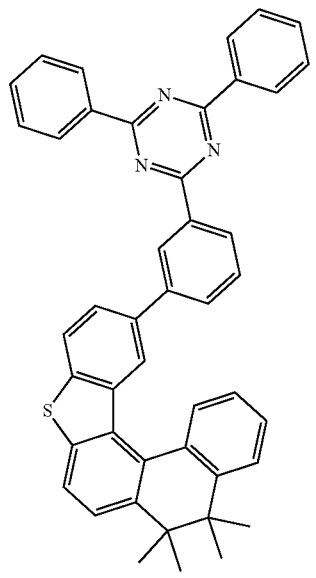
C-445
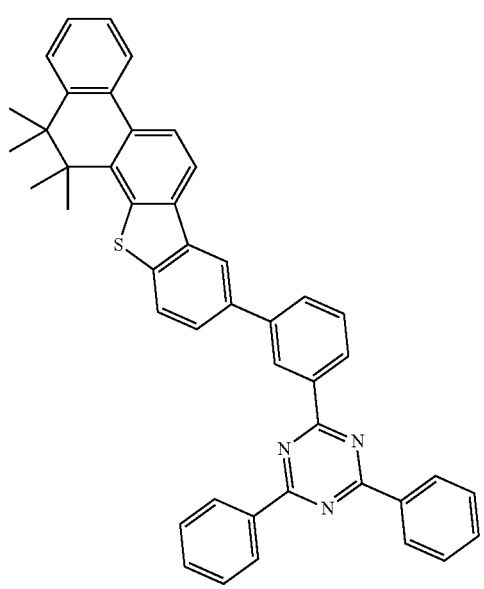
C-446
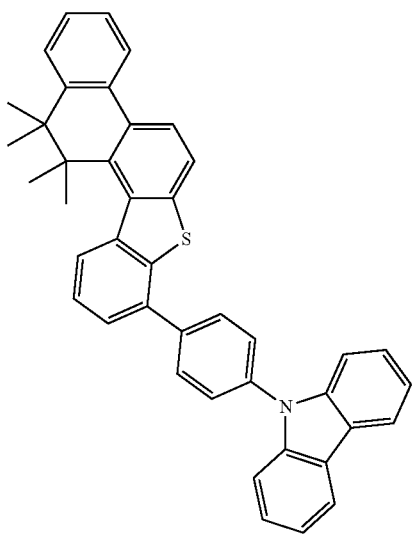
C-447
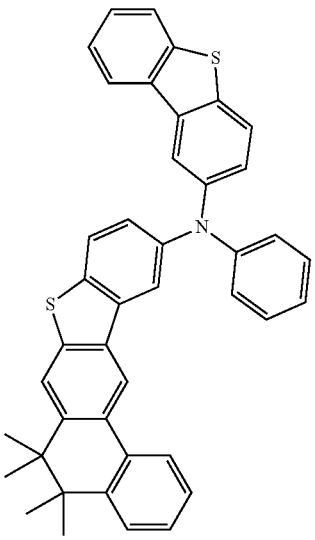
C-448

C-449
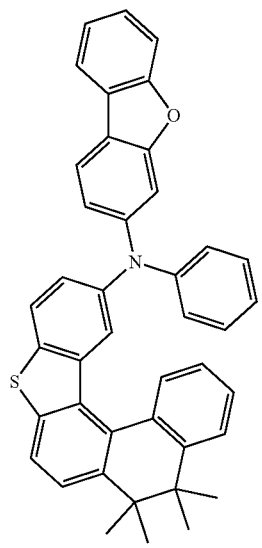
C-450
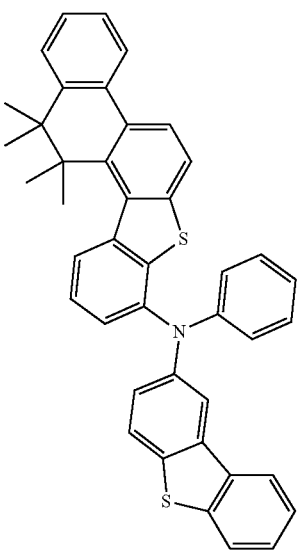
C-451
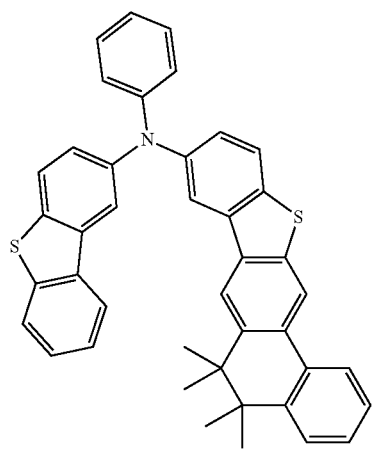
C-452
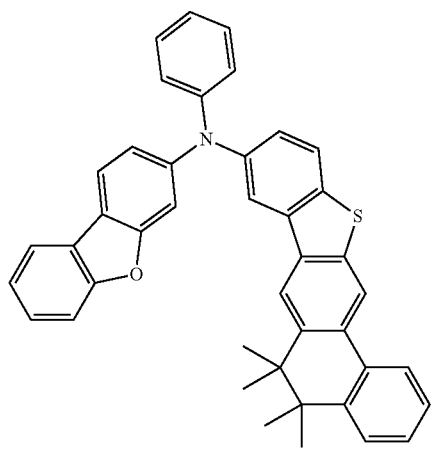
C-453
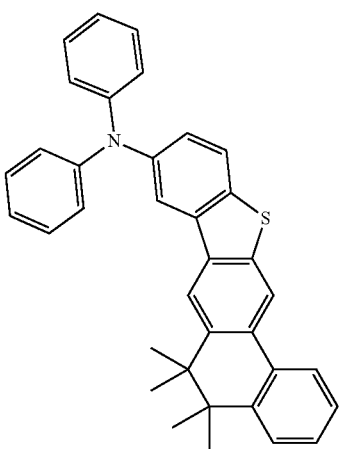
C-454
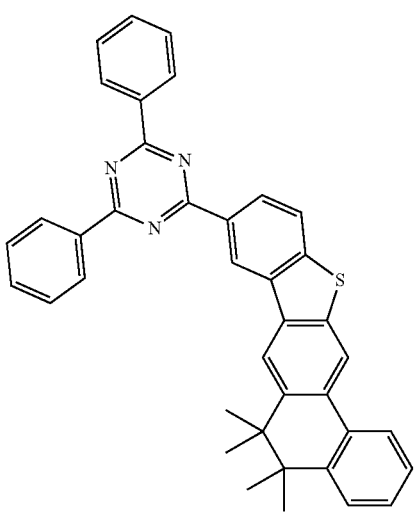

C-455
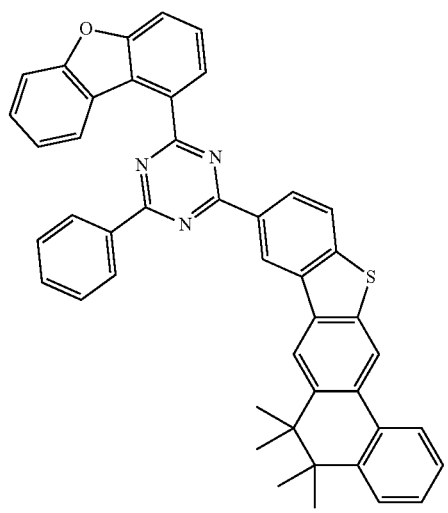
C-456
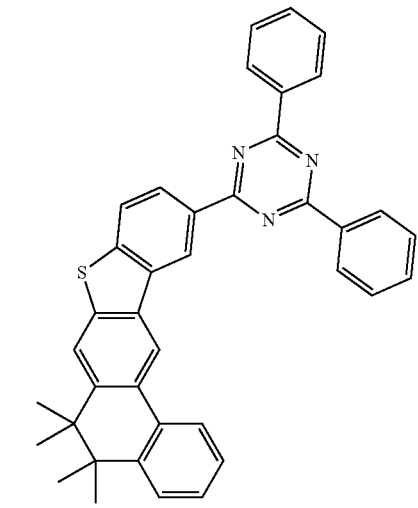
C-457
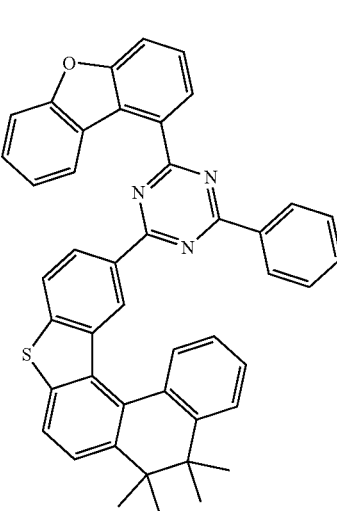
C-458
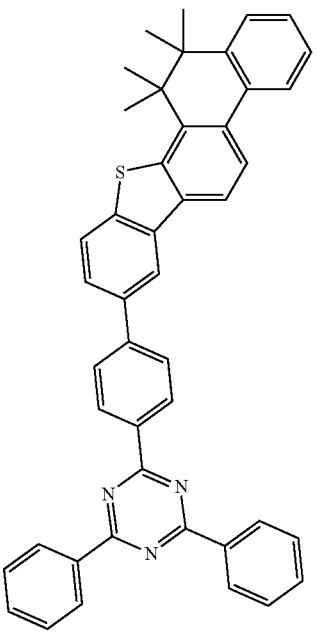
C-459
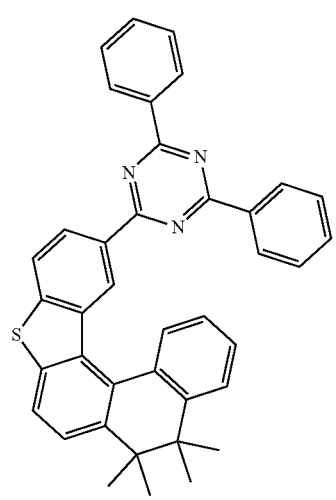
C-460
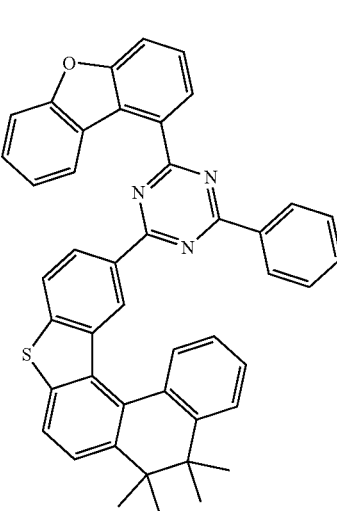

C-461
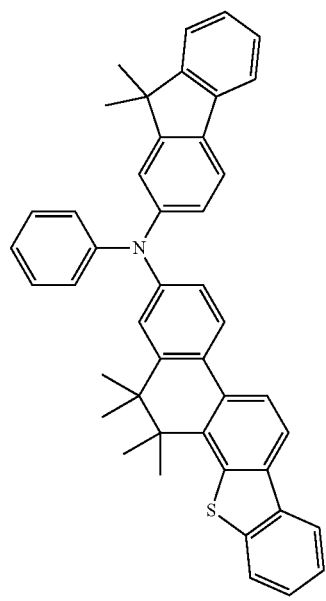
C-462
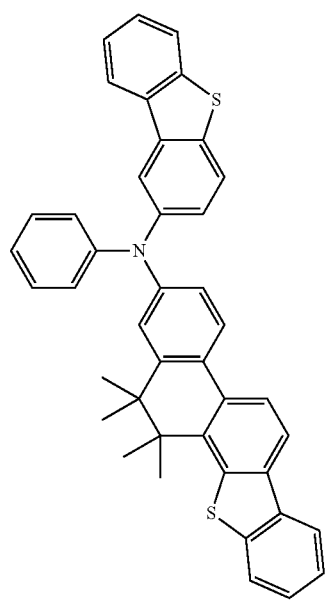
C-463
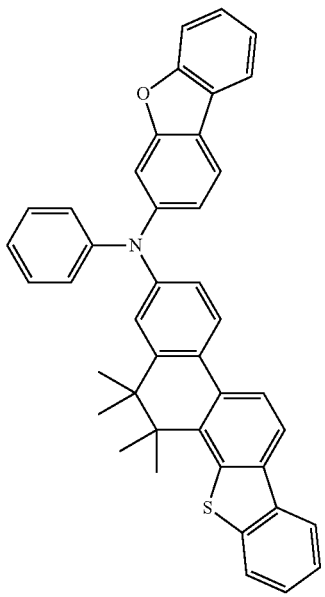
C-464
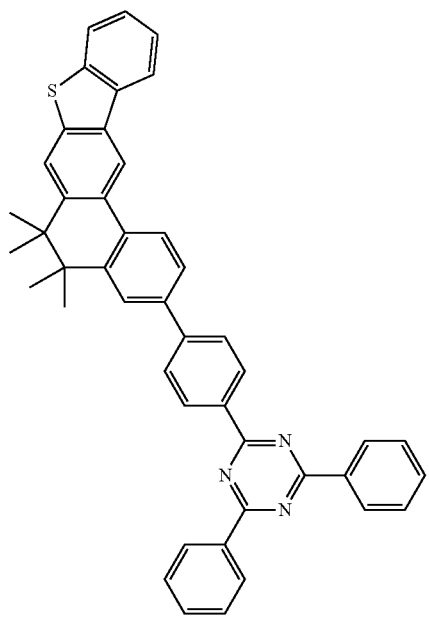

C-465
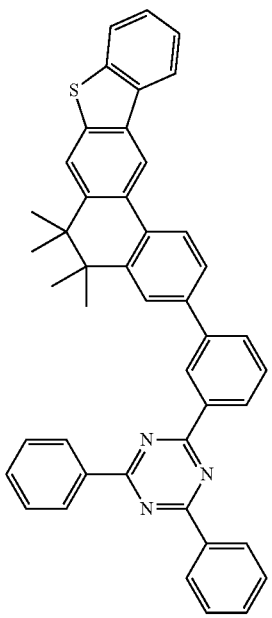
C-466
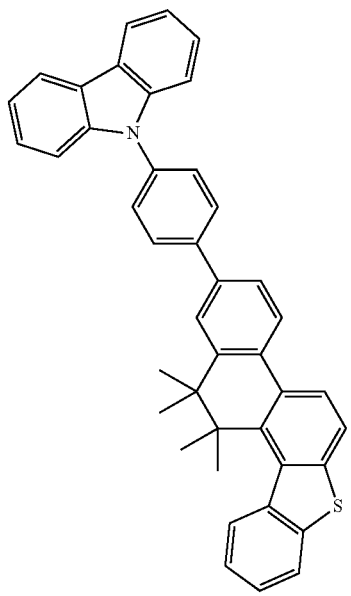
C-467
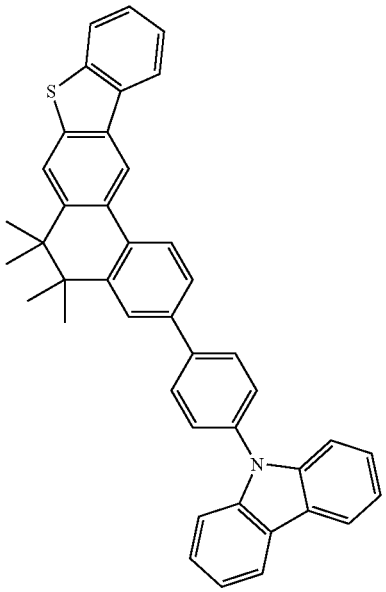
C-468
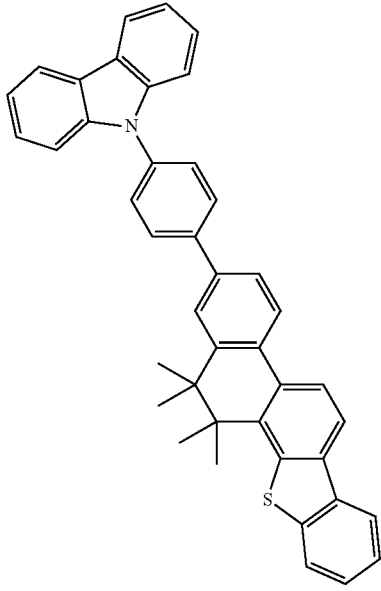

C-469
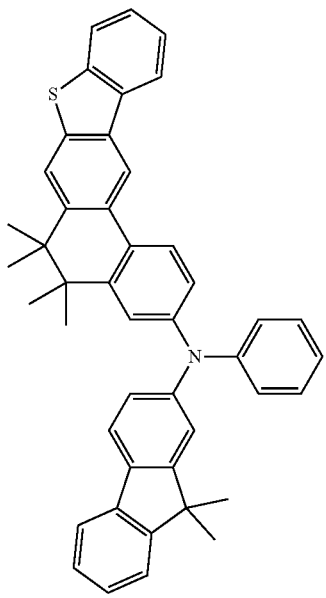
C-470
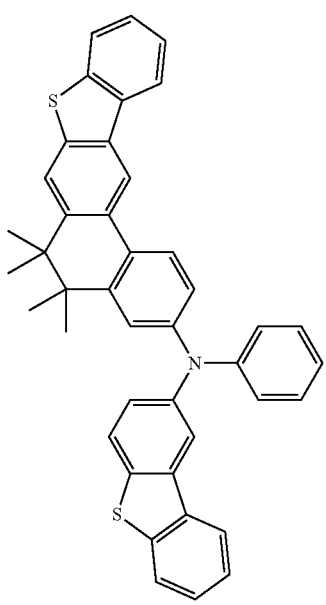
C-471
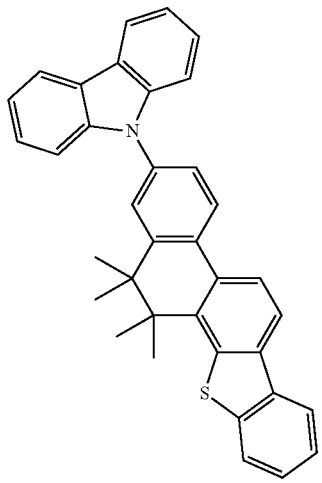
C-472
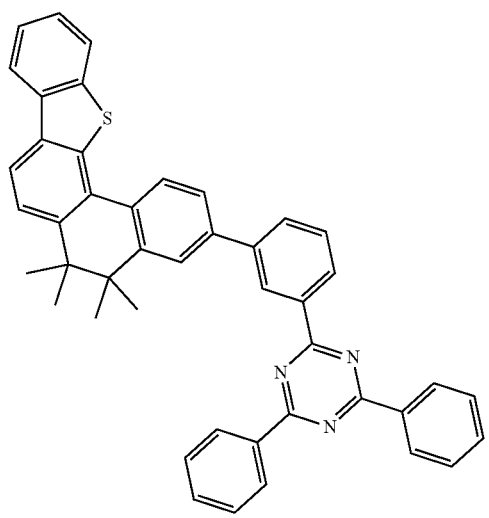
C-473
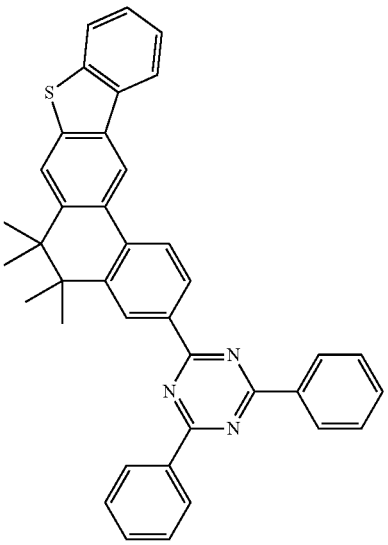

C-474
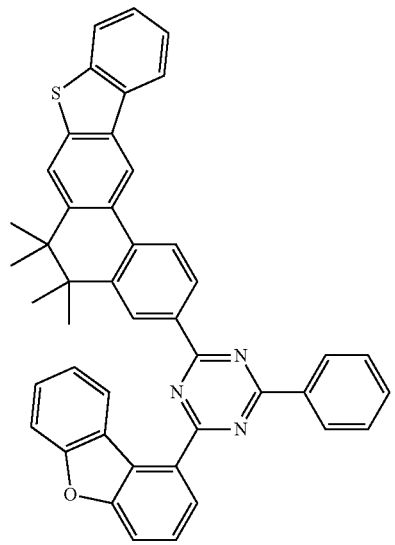
C-475
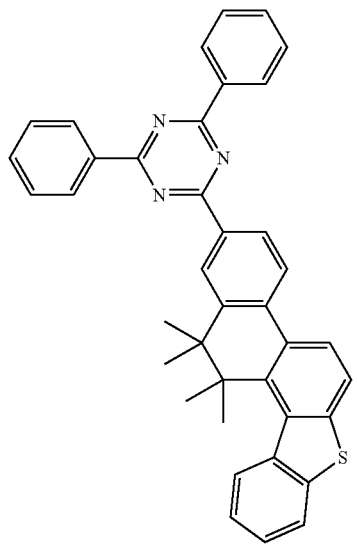
C-476
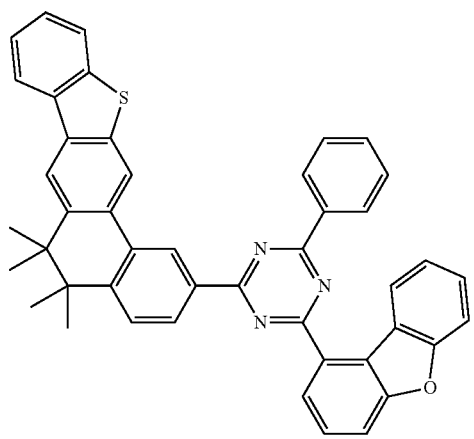
C-477
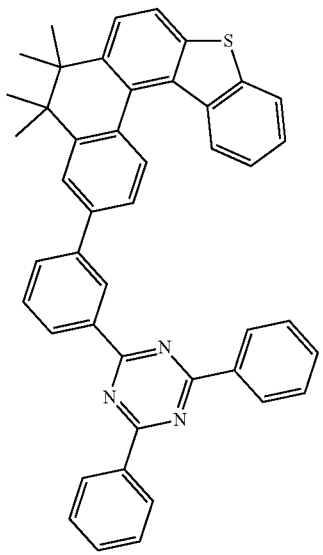
C-478
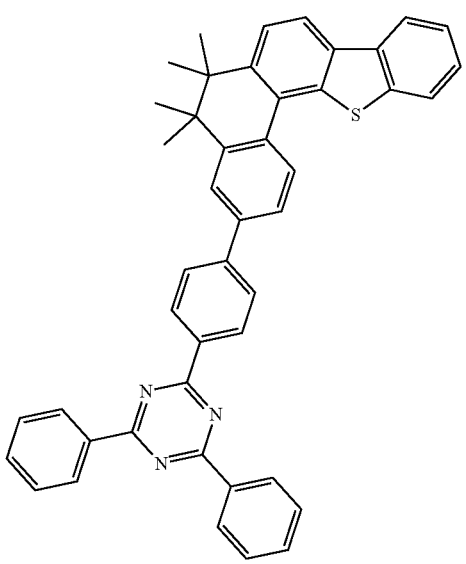
C-479
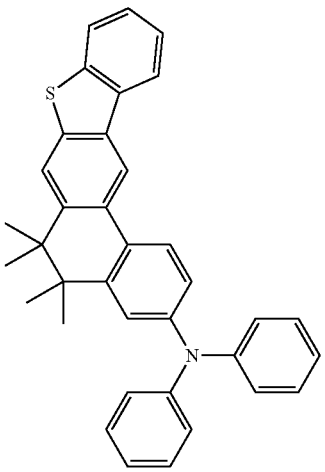

C-480
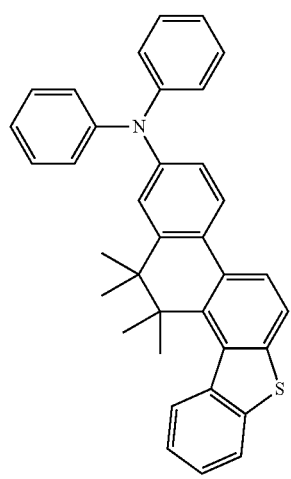
C-481
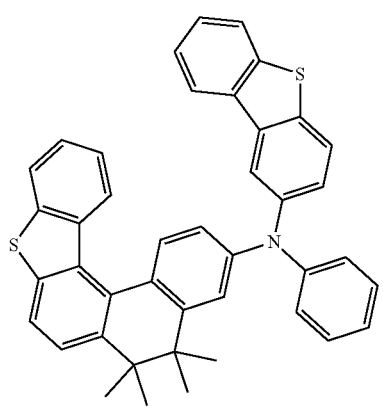
C-482
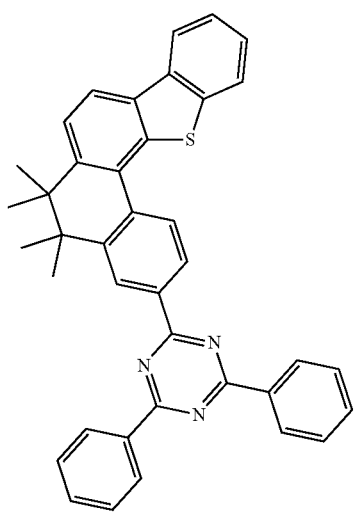
C-483
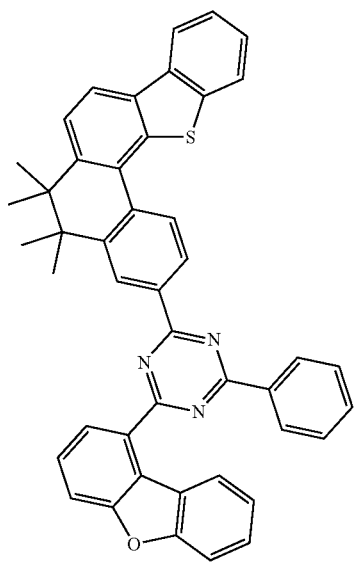
C-484
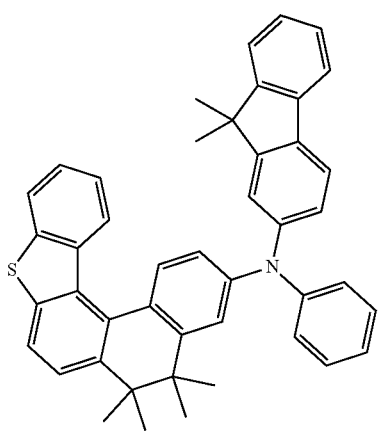
C-485
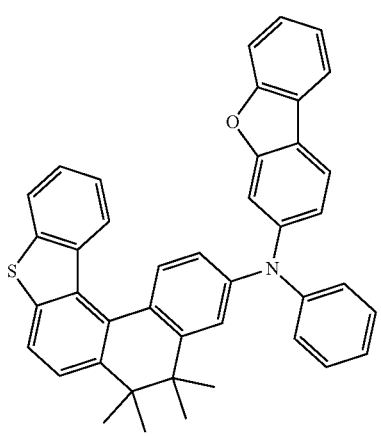

C-486
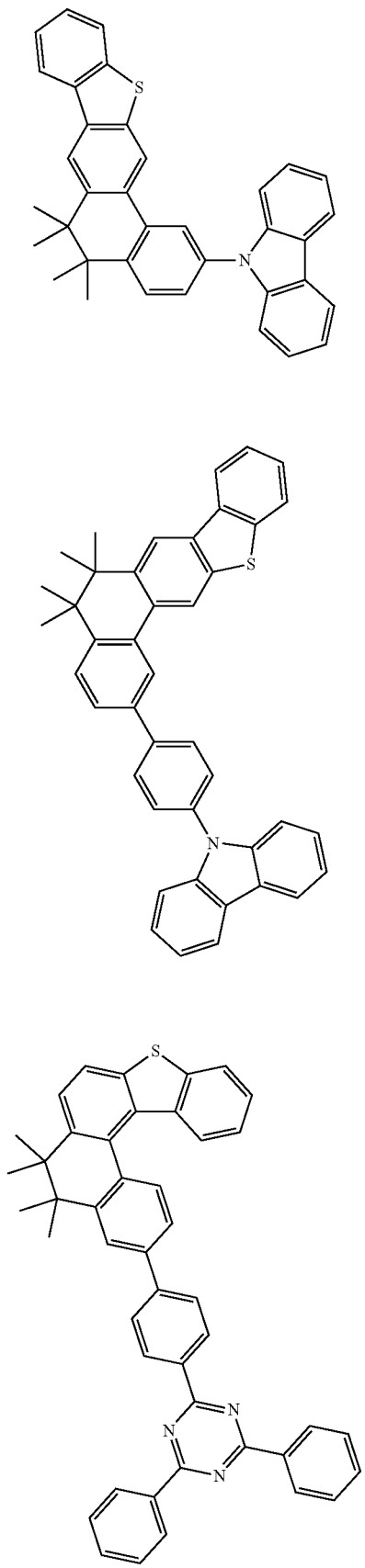
C-487
C-488
C-489
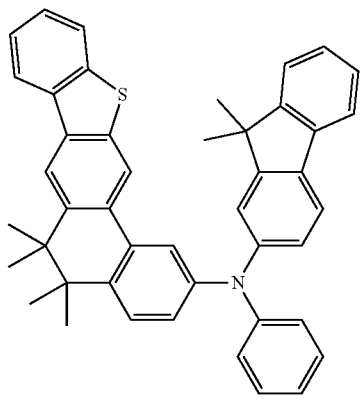
C-490
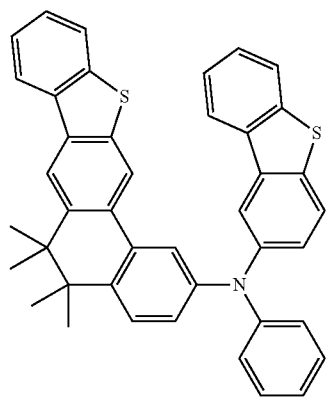
C-491
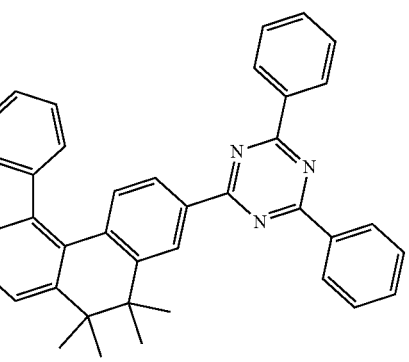
C-492
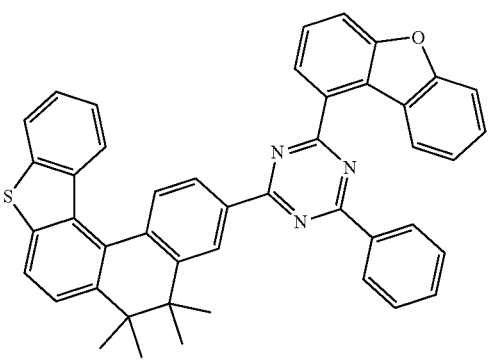

C-493
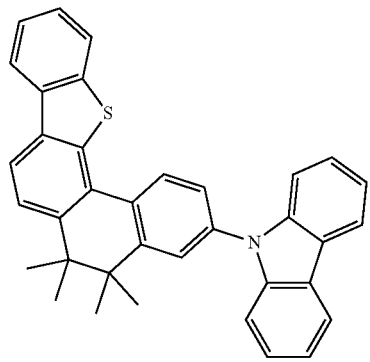
C-494
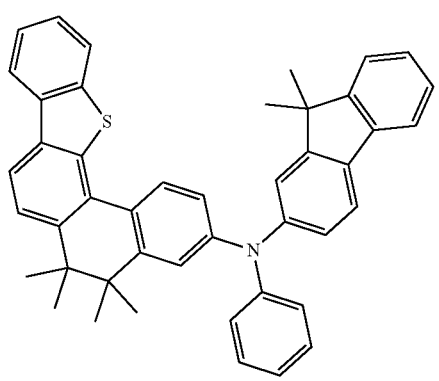
C-495
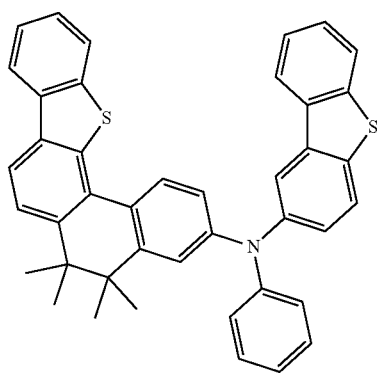
C-496
C-497
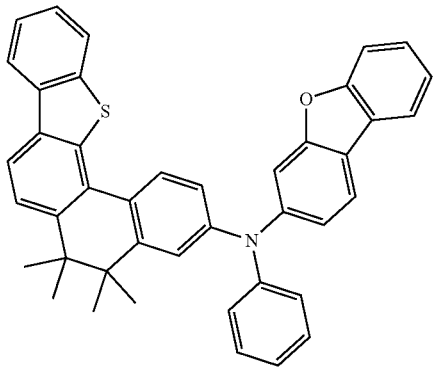
C-498
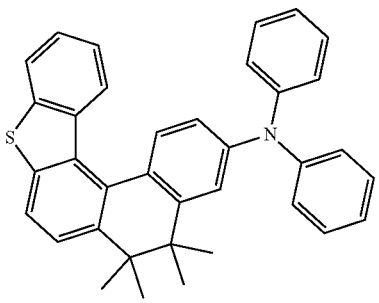
C-499
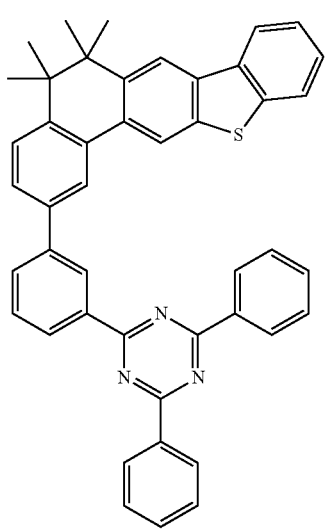

C-500
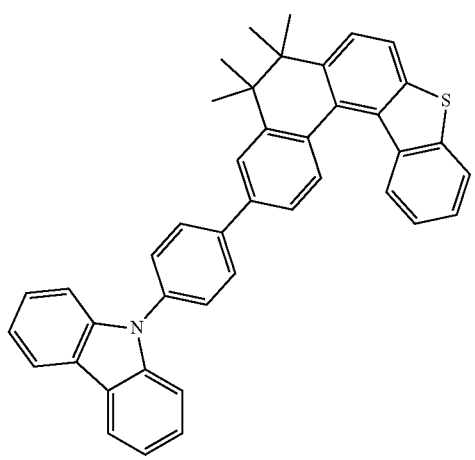
C-502
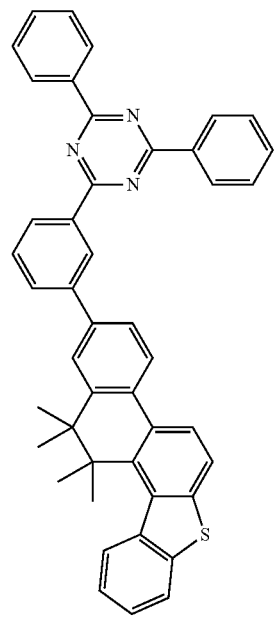
C-501
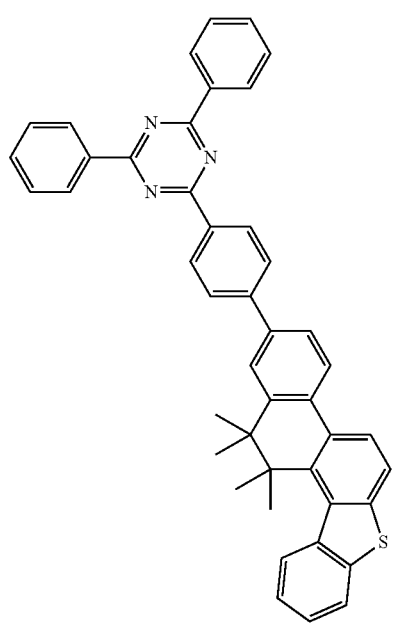
C-503
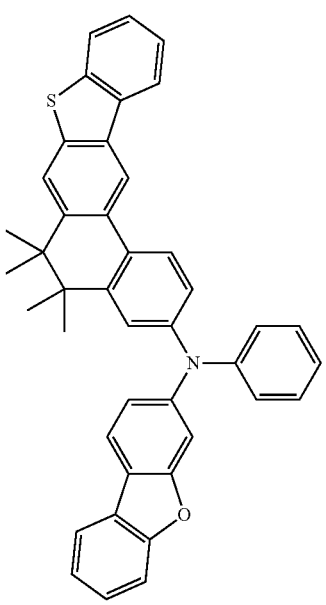

C-504
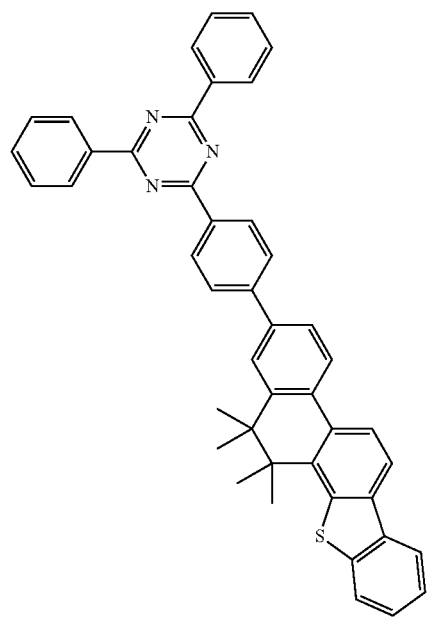
C-505
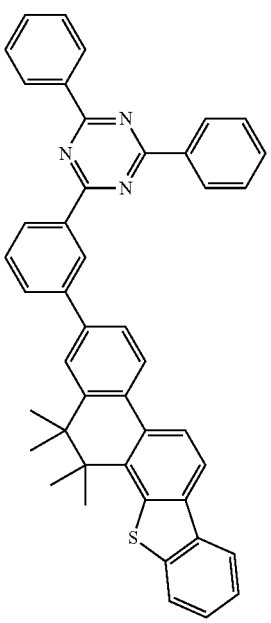
C-506
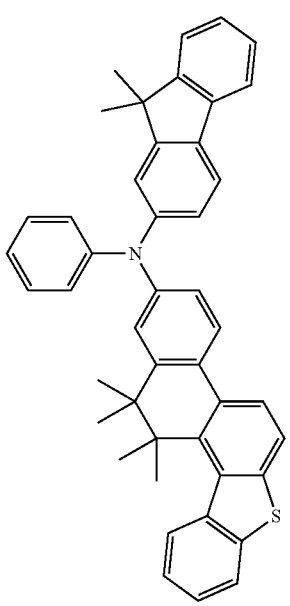
C-507
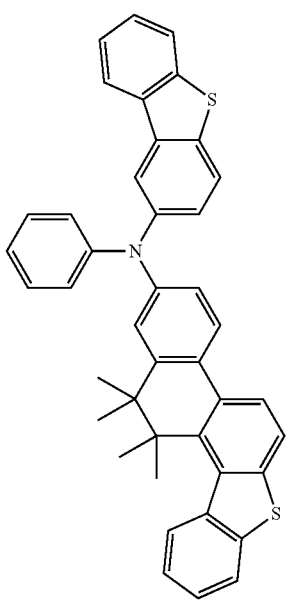

C-508
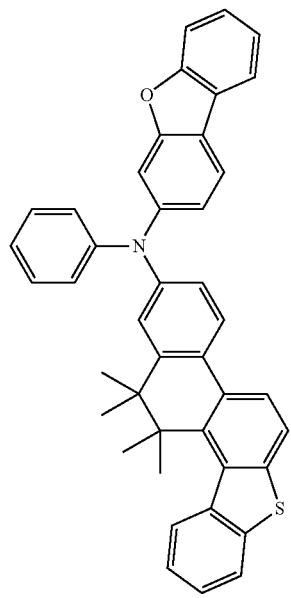
C-509
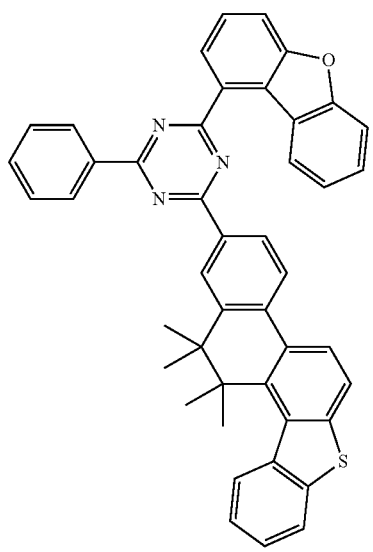
C-510
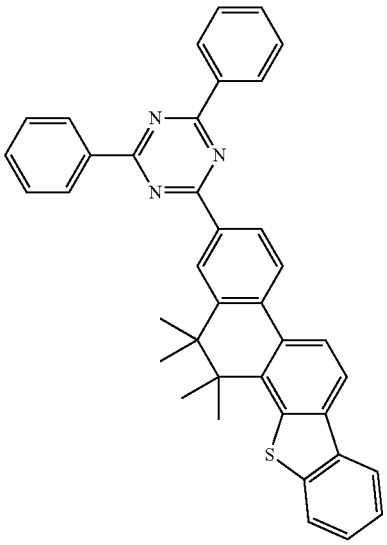
C-511
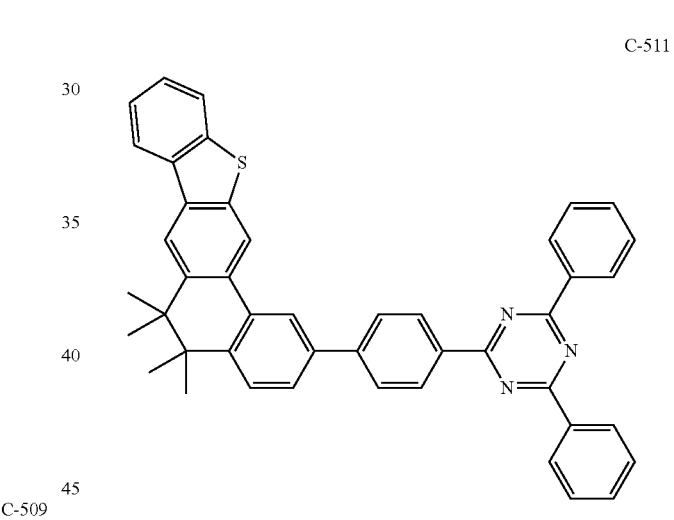
C-512
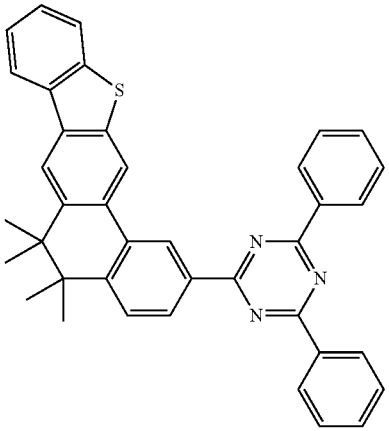

C-513
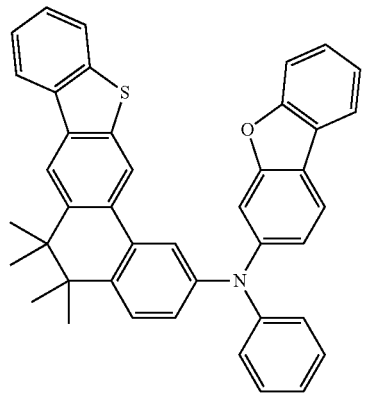
C-514
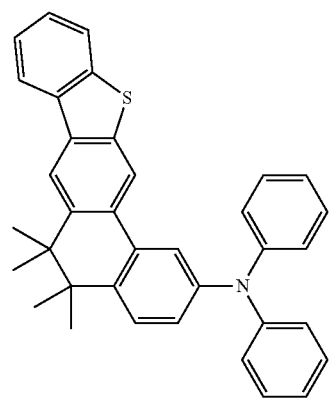
C-515
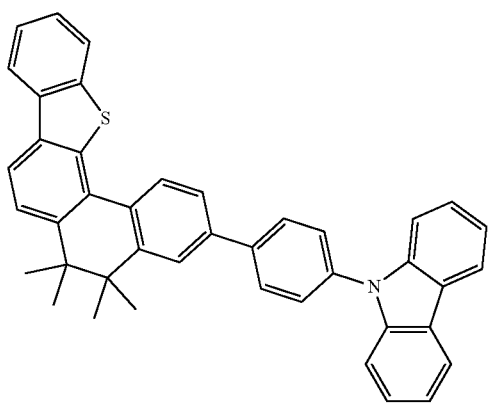
C-516
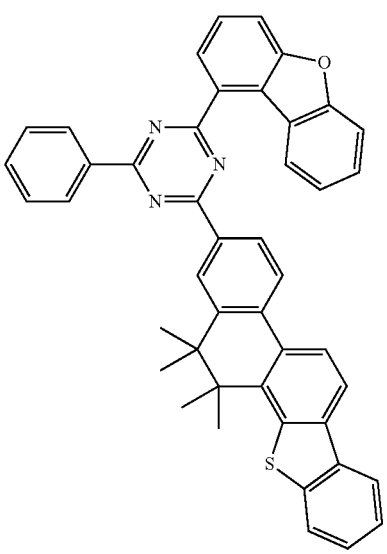
C-517
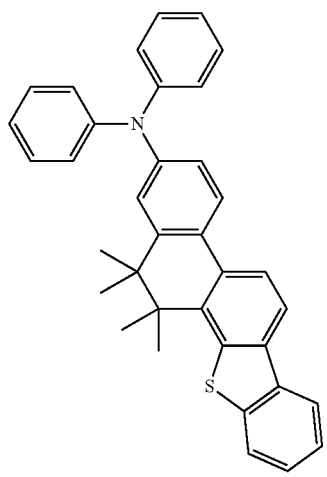
C-518
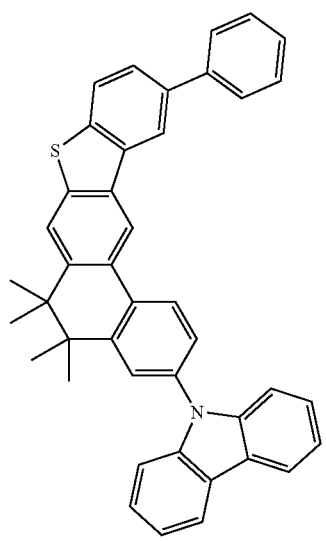

C-519
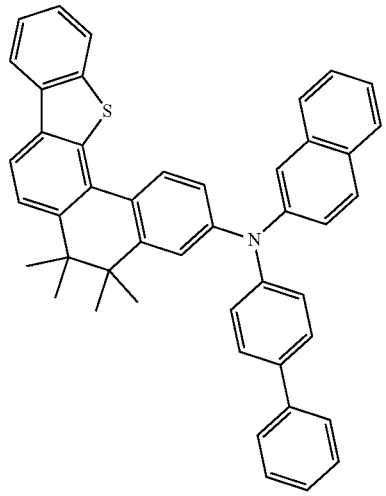
C-520
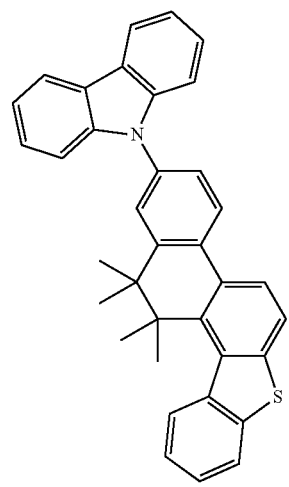
C-521
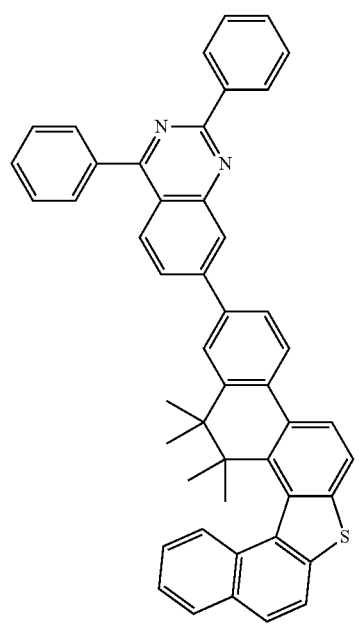
C-522
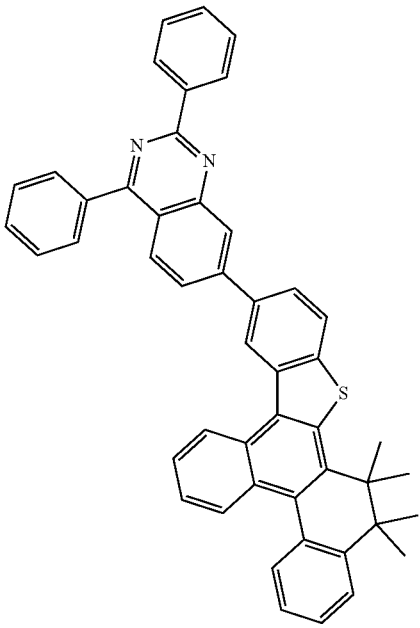
C-523
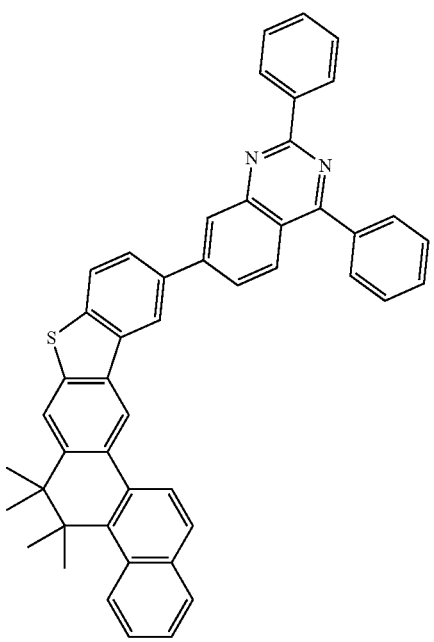

-continued
C-524
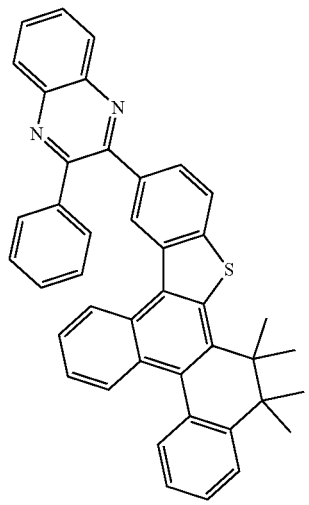
C-525
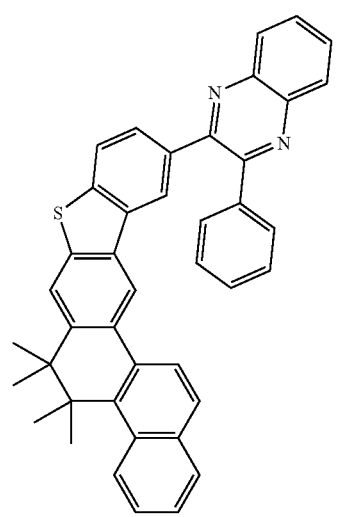
C-526
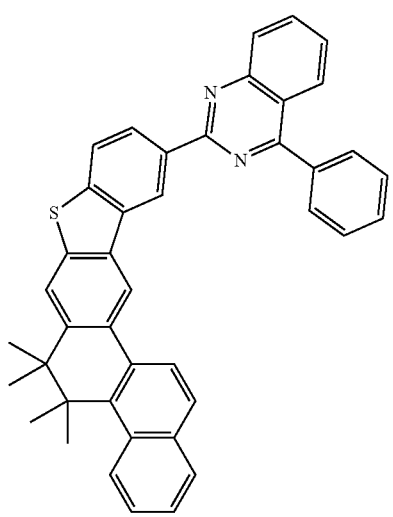
-continued
C-527
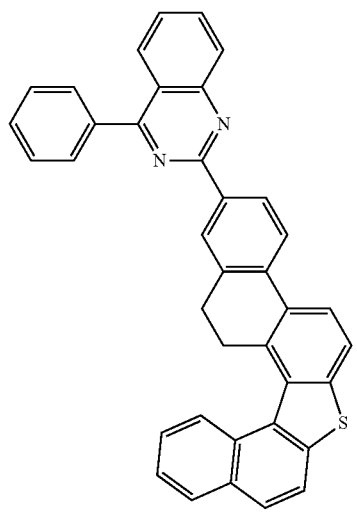
C-528
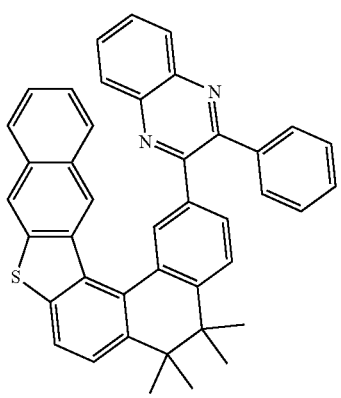
C-529
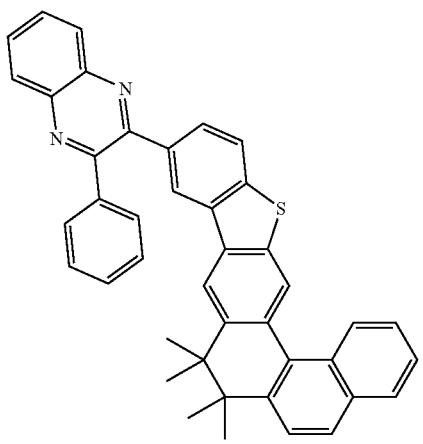

C-530
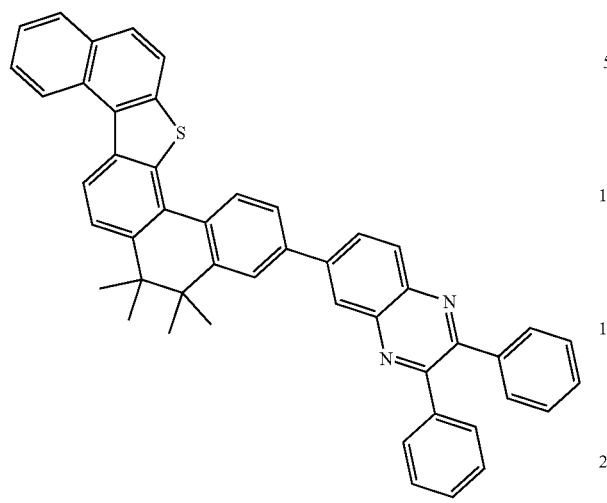
C-533
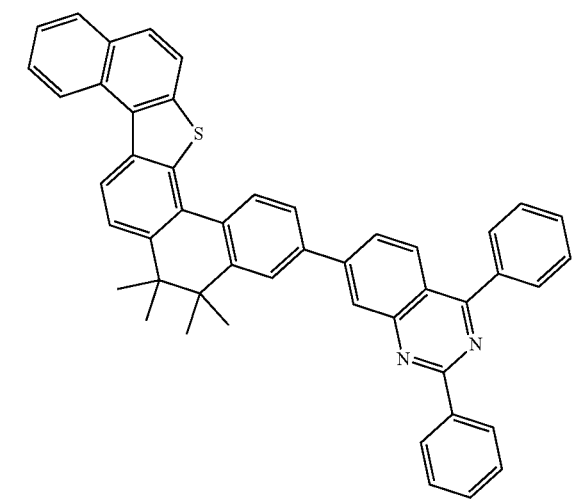
C-531
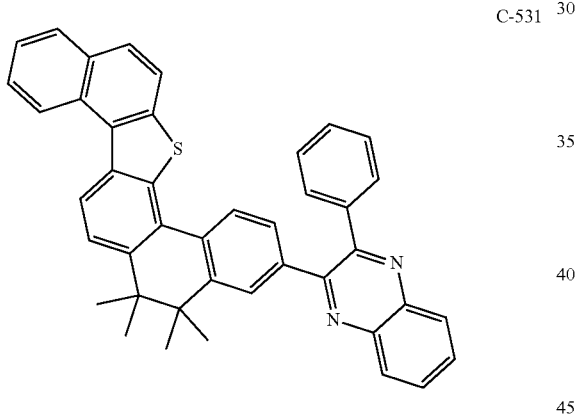
C-532
C-534
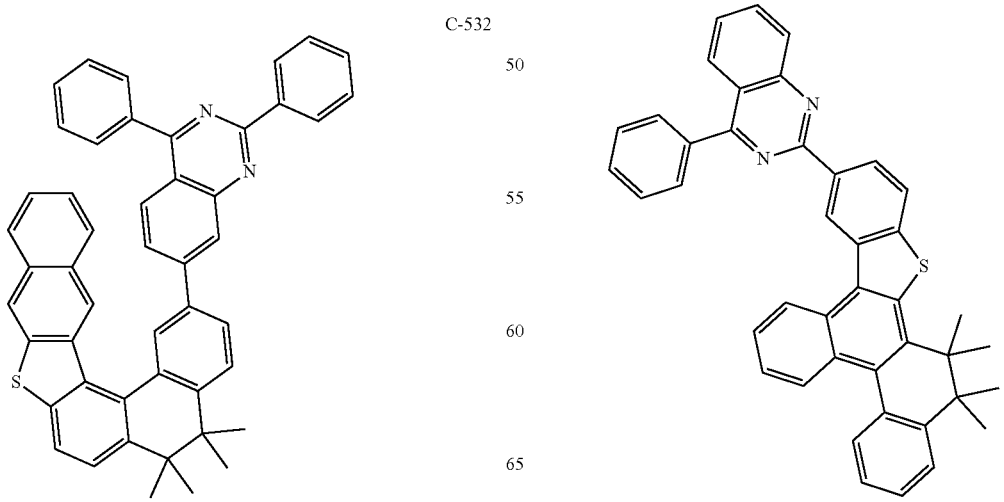

C-535
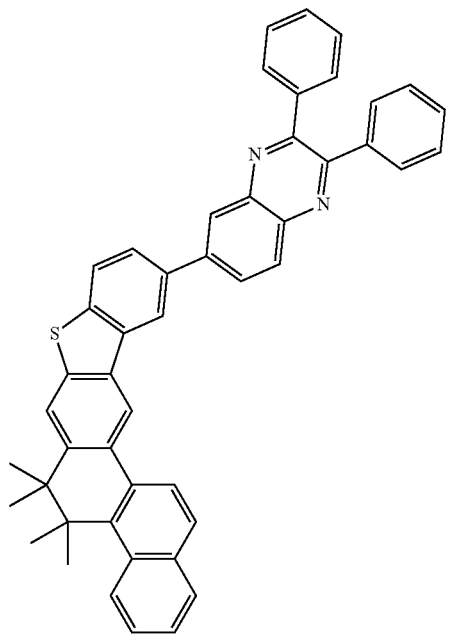
C-536
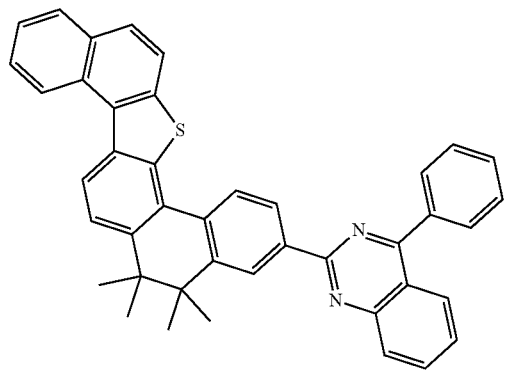
C-537
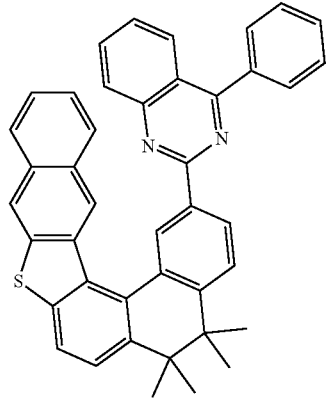
C-538
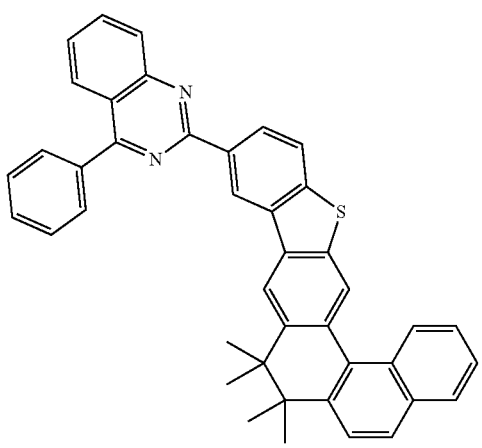
C-539
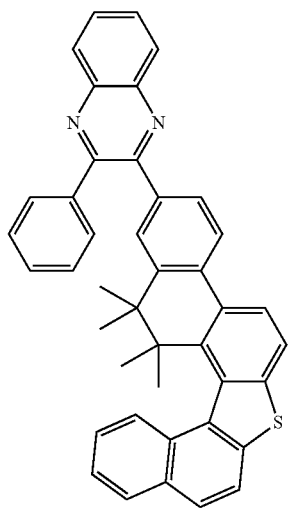
C-540
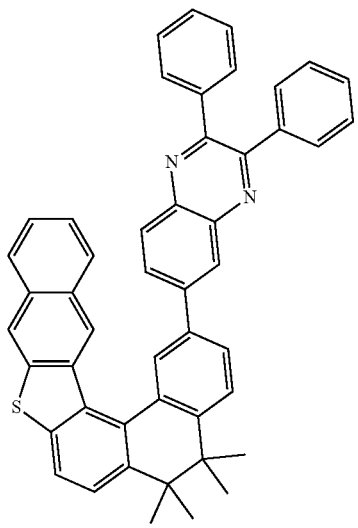

C-541
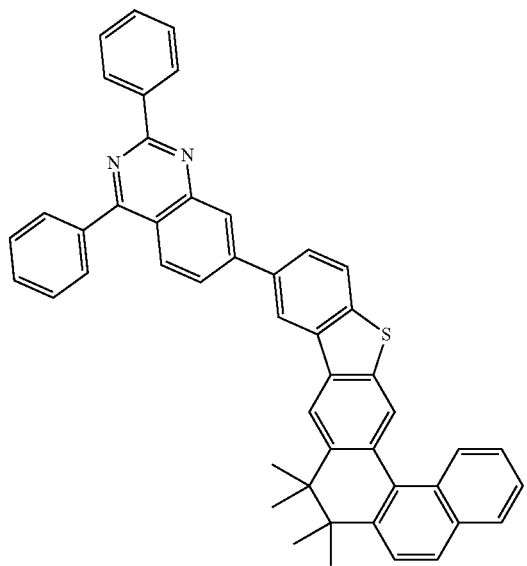
C-543
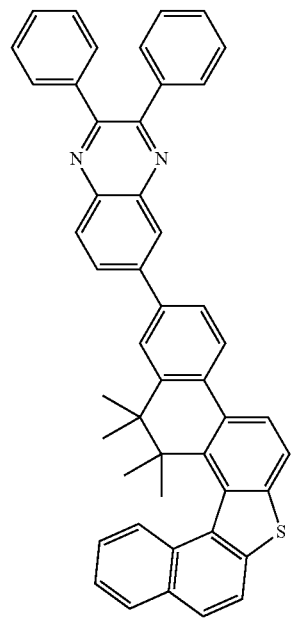
C-542
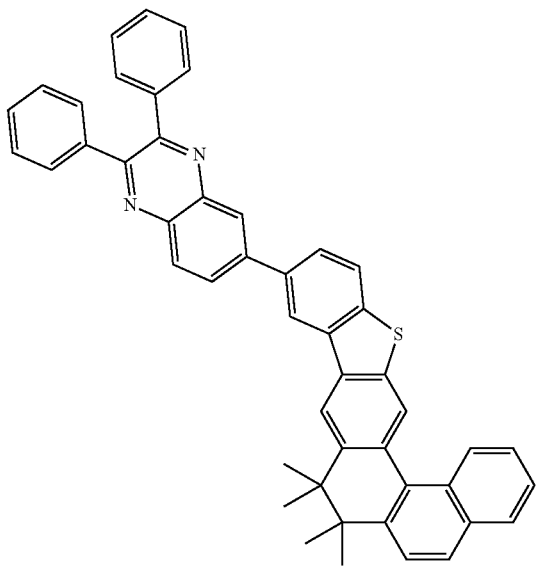
C-544
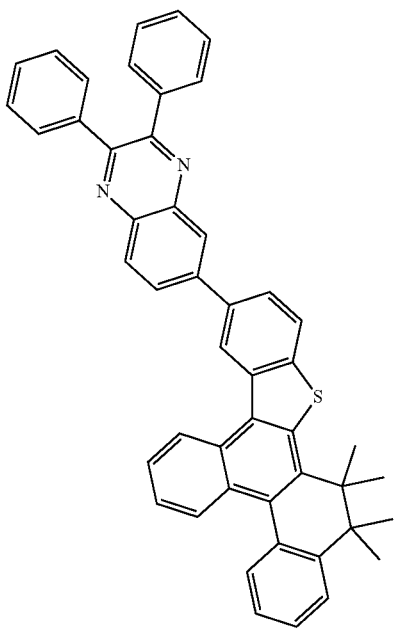

C-545
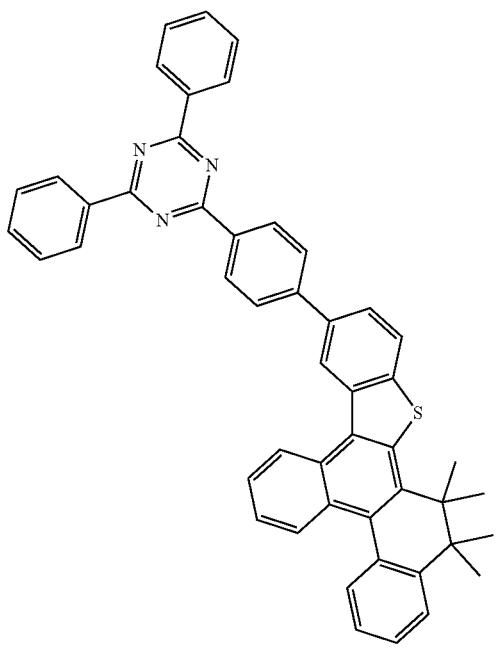
C-546
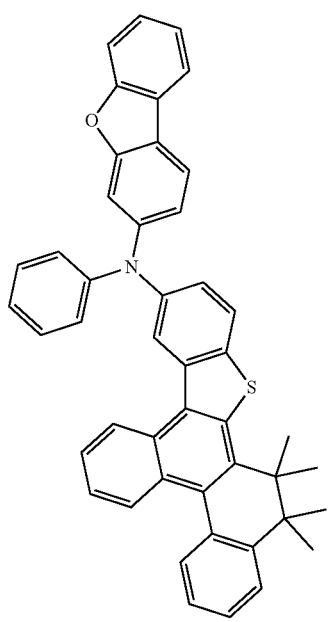
C-547
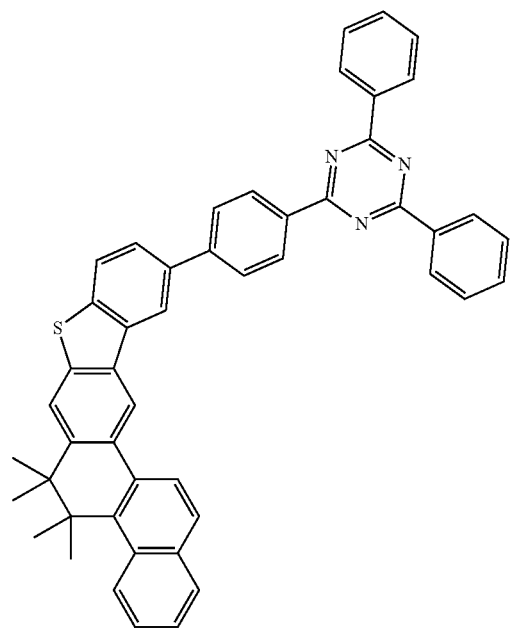
C-548
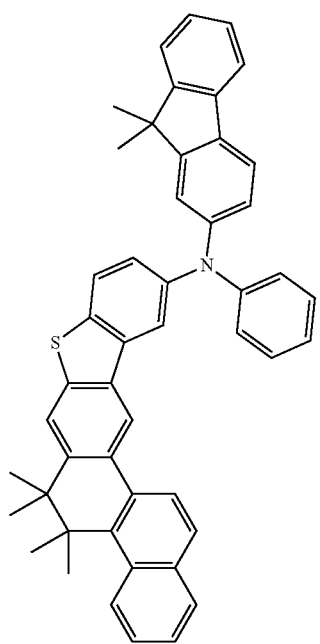

C-549
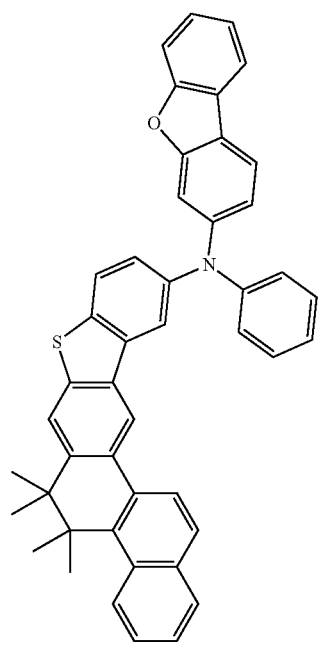
C-550
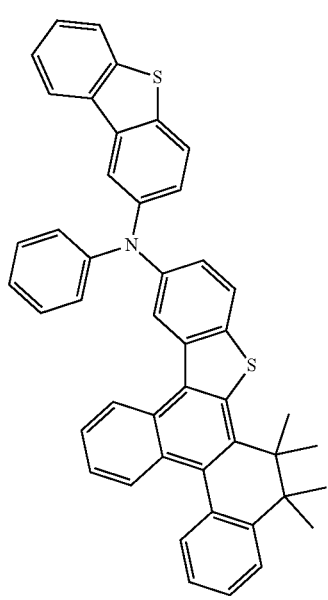
C-551
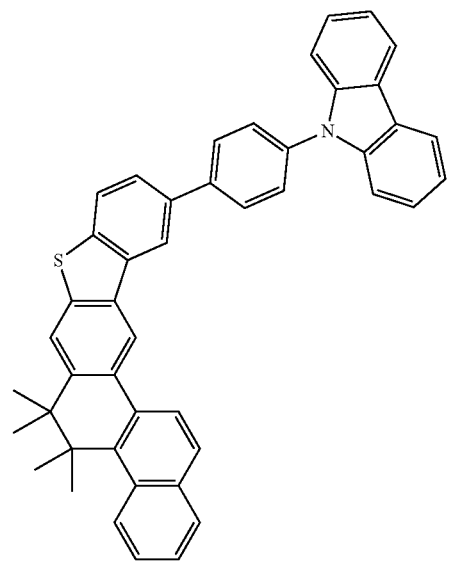
C-552
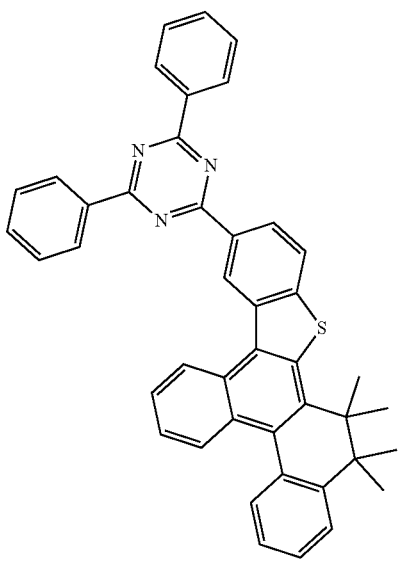

C-553
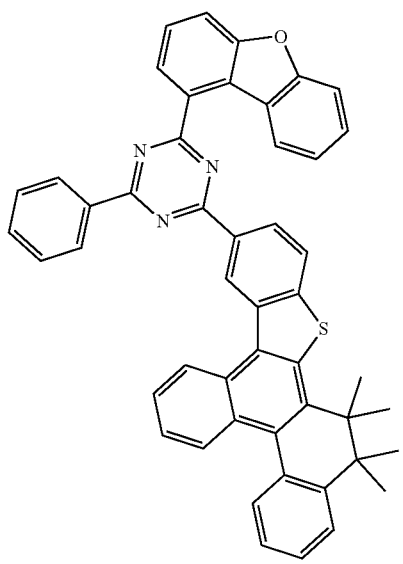
C-554
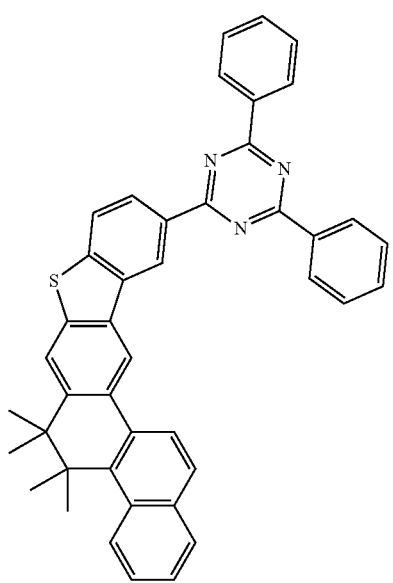
C-555
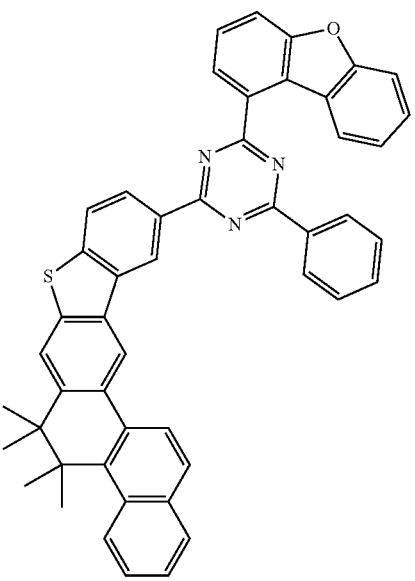
C-556
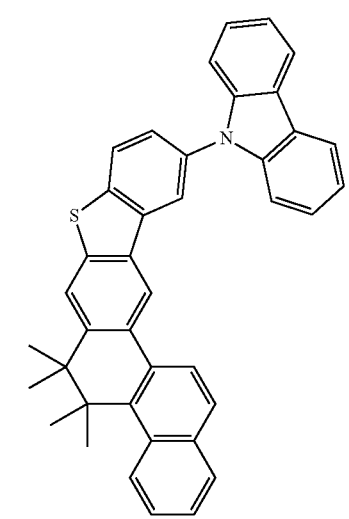

C-557
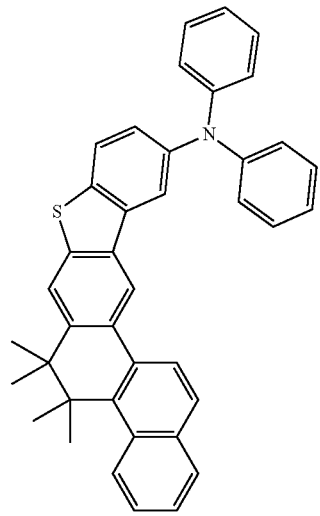
C-558
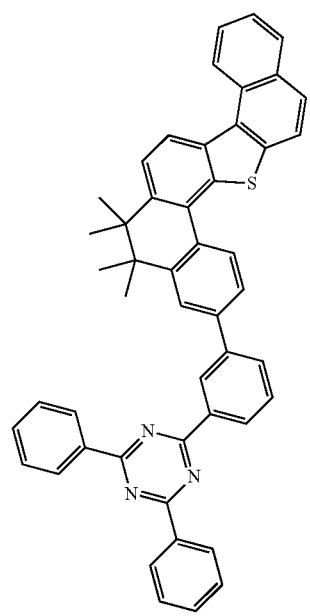
C-559
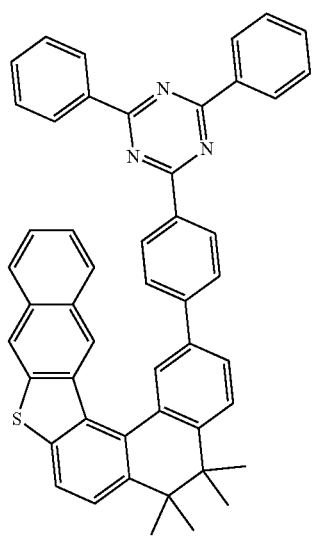
C-560
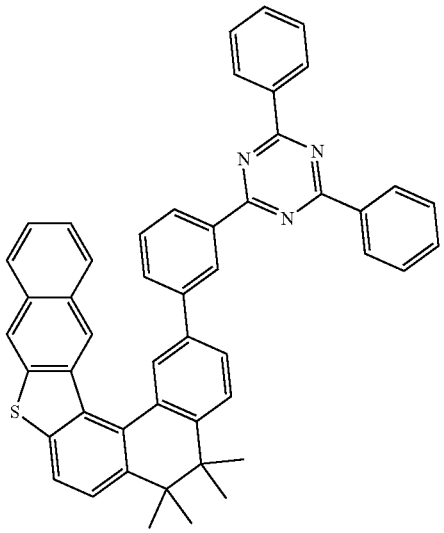
C-561
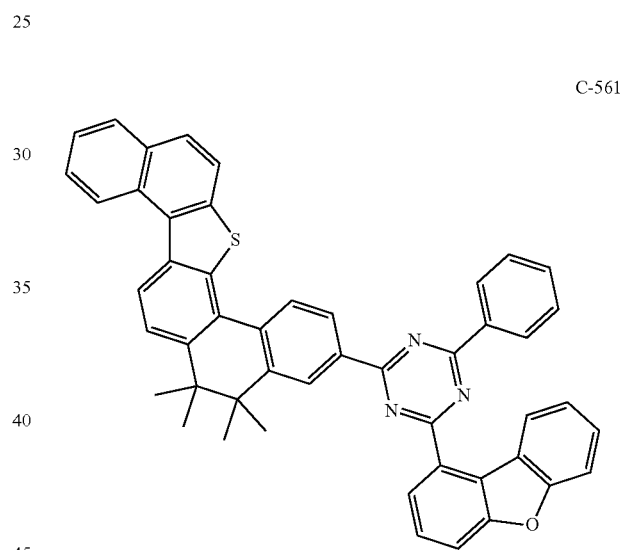
C-562
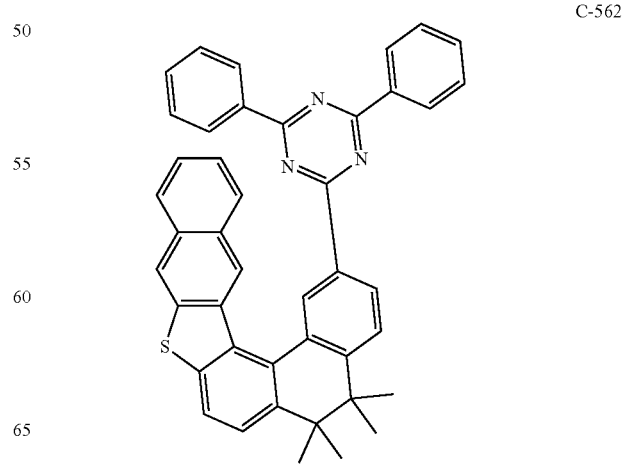

C-563
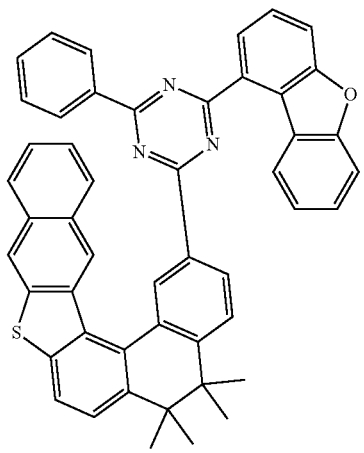
C-564
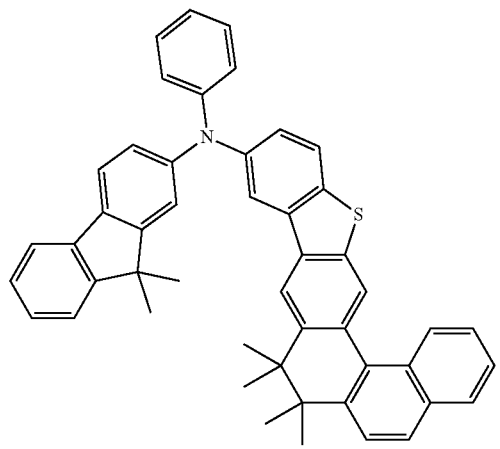
C-565
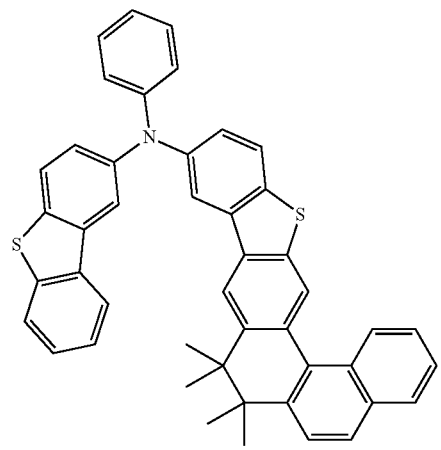
C-566
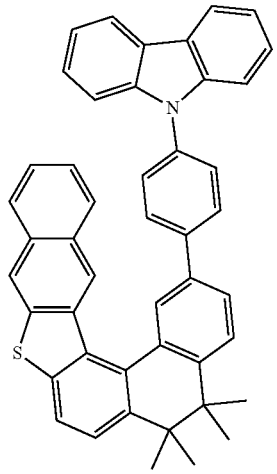
C-567
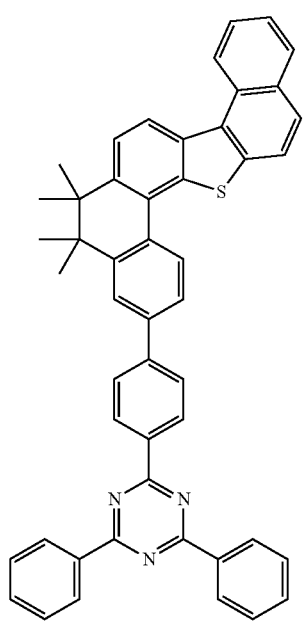
C-568
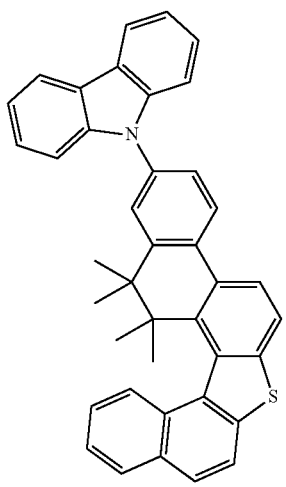

C-569
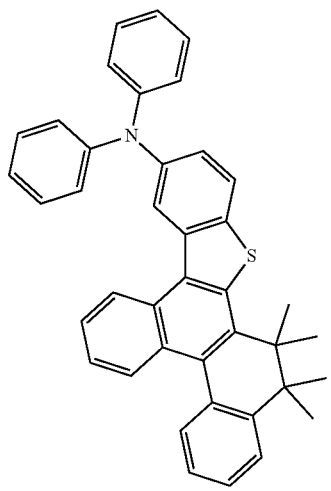
C-572
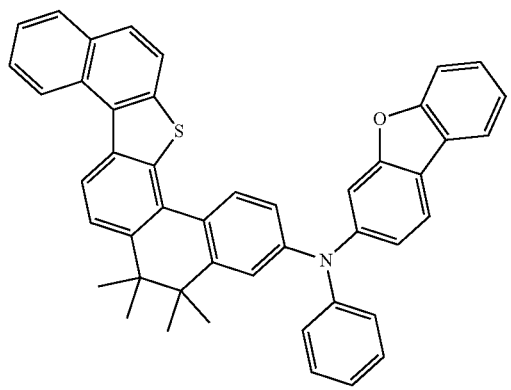
C-570
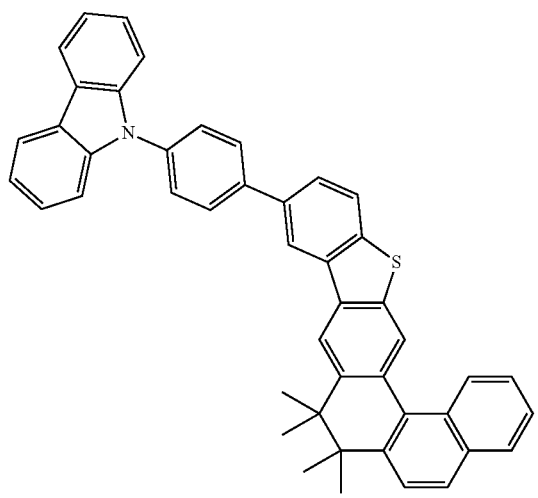
C-573
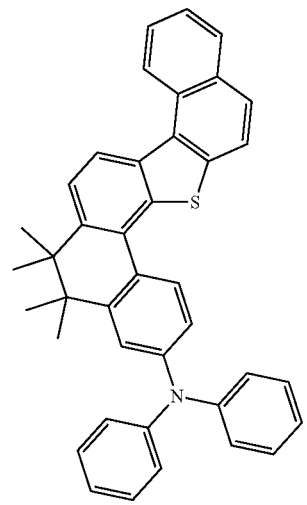
C-571
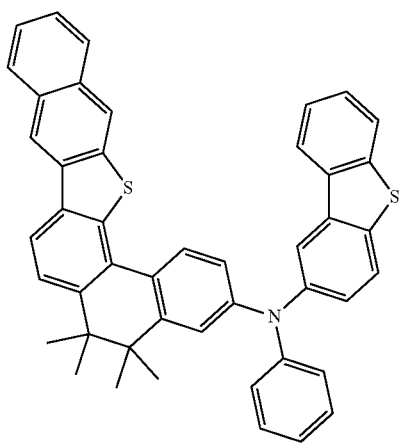
C-574
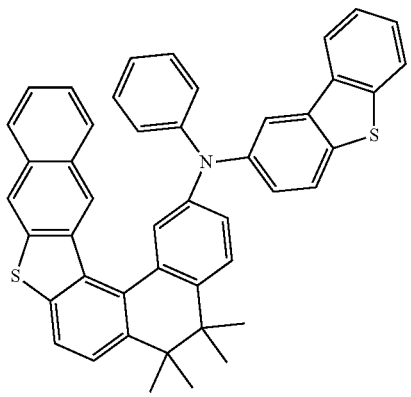

C-575
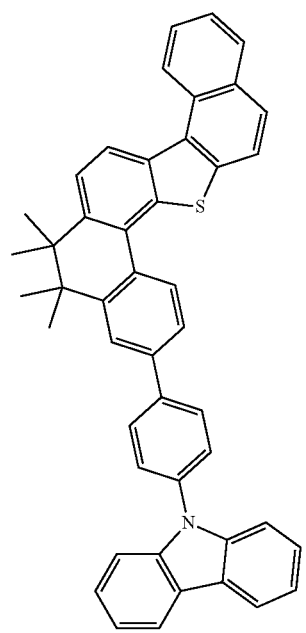
C-576
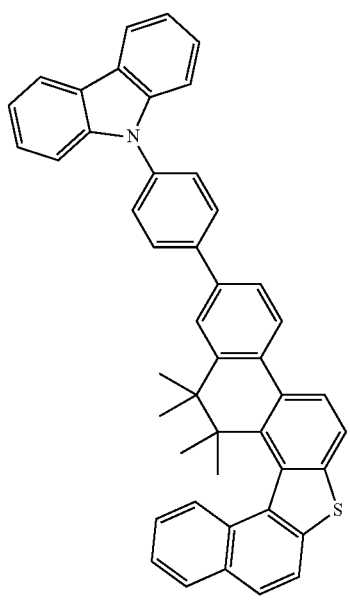
C-577
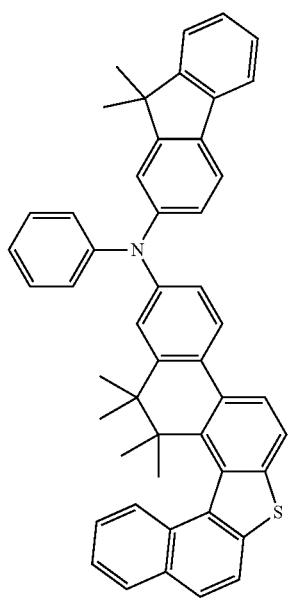
C-578
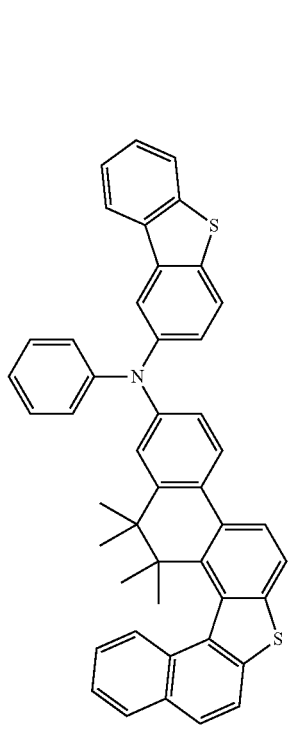

C-579
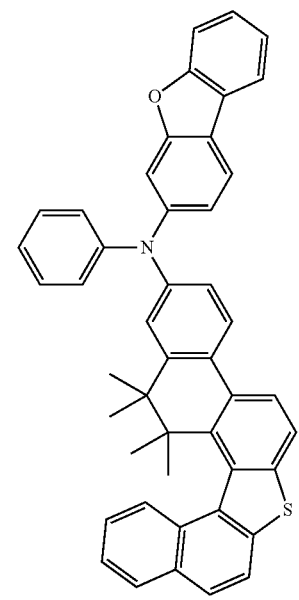
C-580
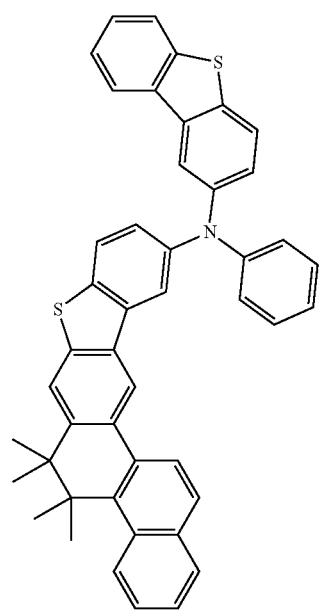
C-581
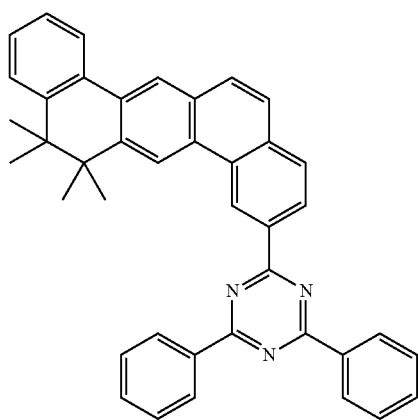
C-582
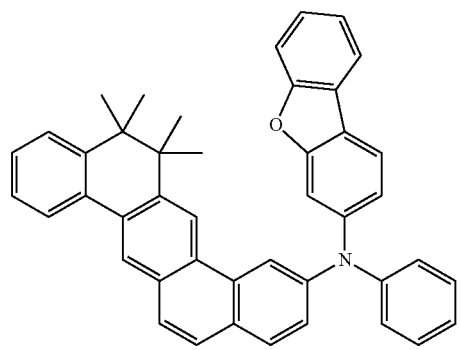
C-583
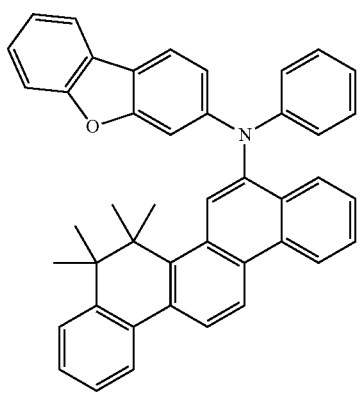
C-584
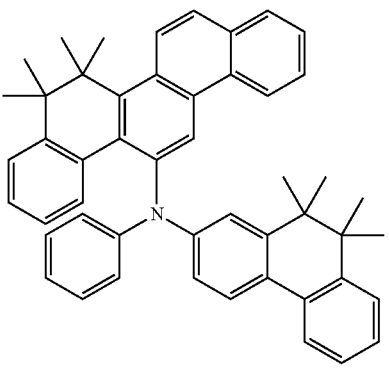
C-585
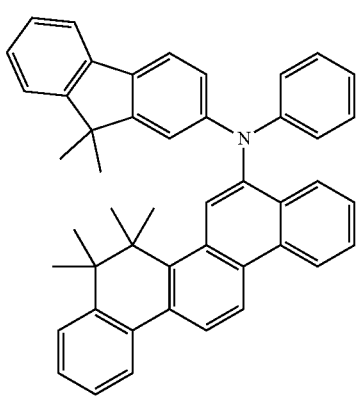

C-586
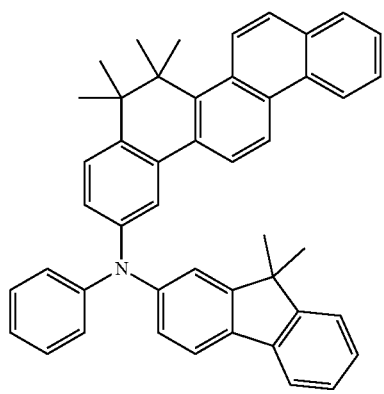
C-587
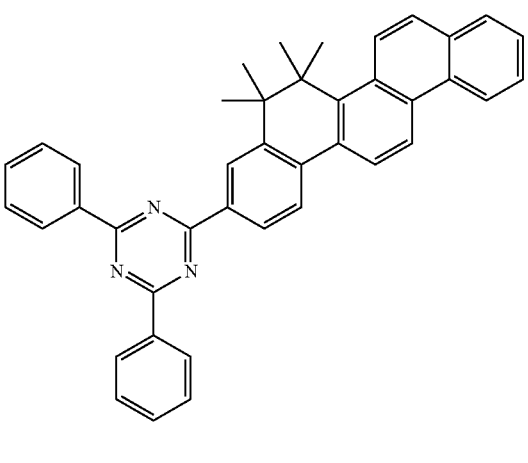
C-588
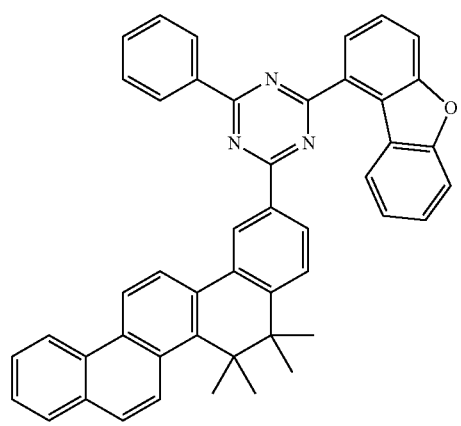
C-589
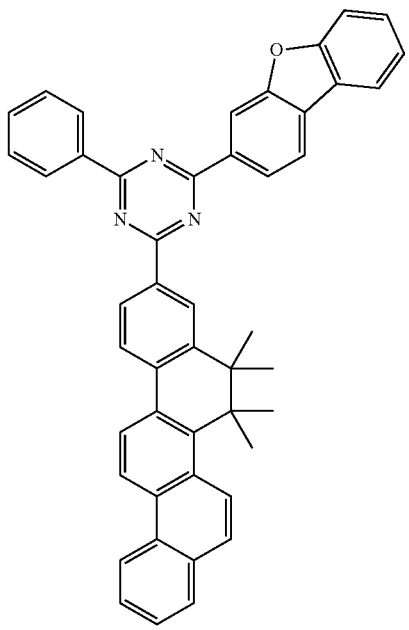
C-590
C-591
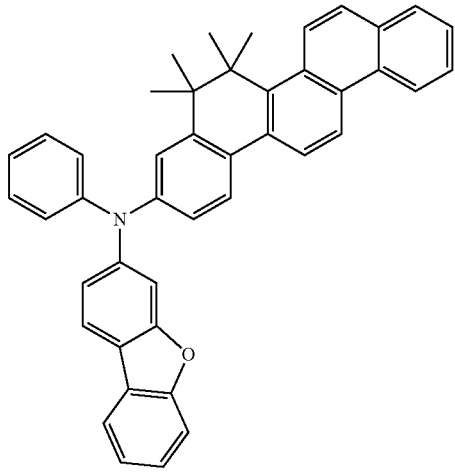

C-592
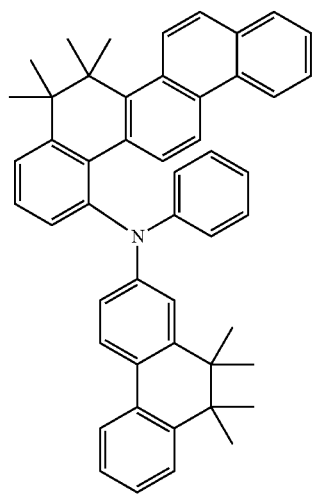
C-593
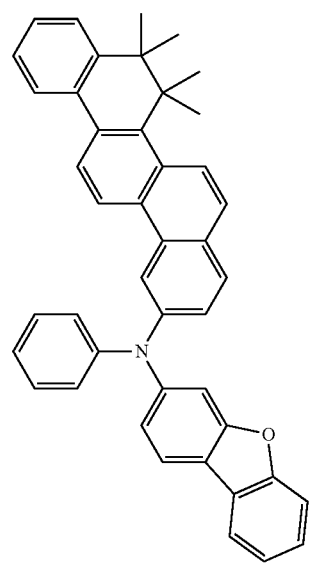
C-594
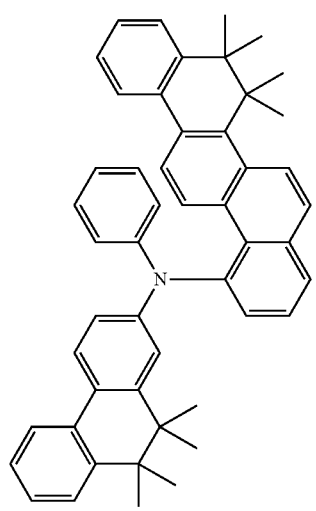
C-595
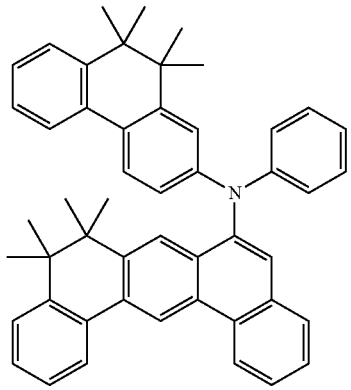
C-596
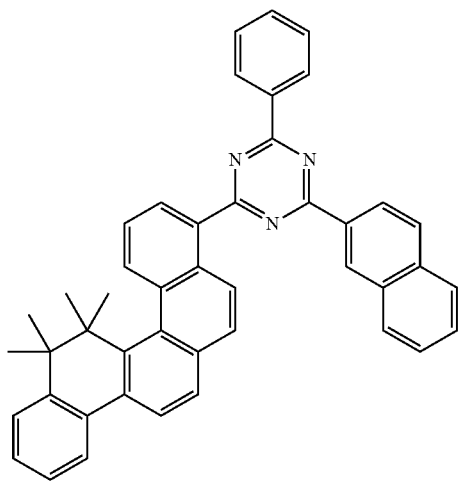
C-597
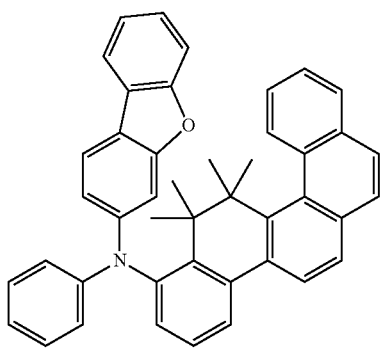

C-598
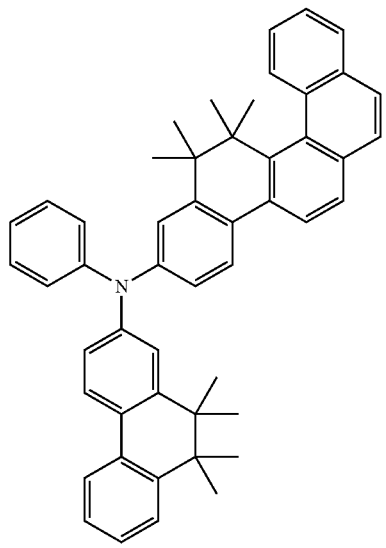
C-599
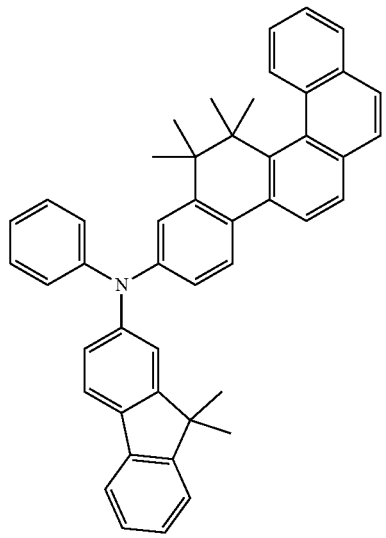
C-600
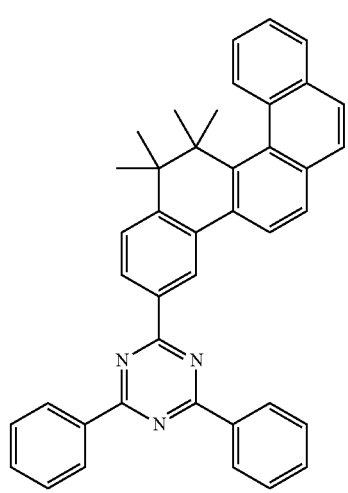
C-601
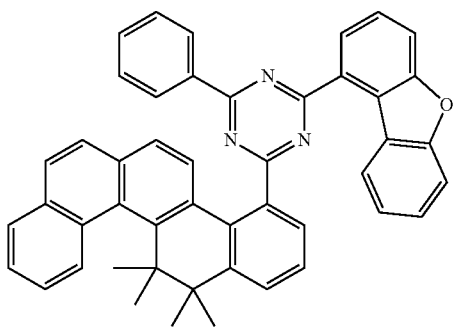
C-602
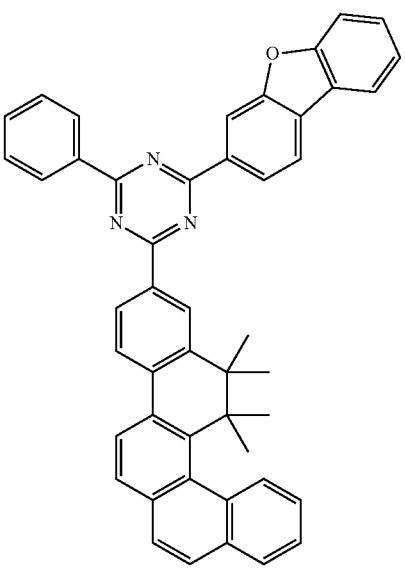
C-603
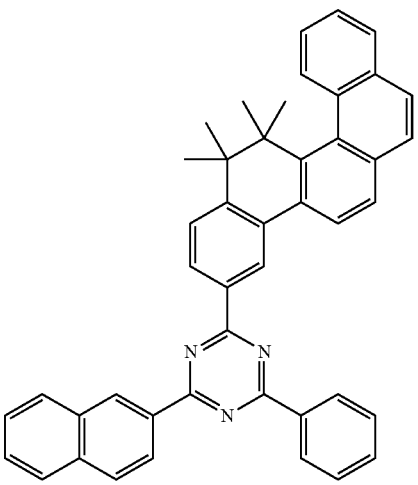

C-604
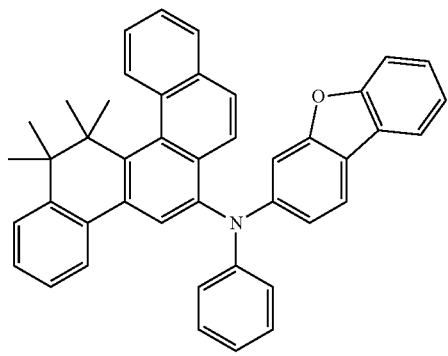
C-605
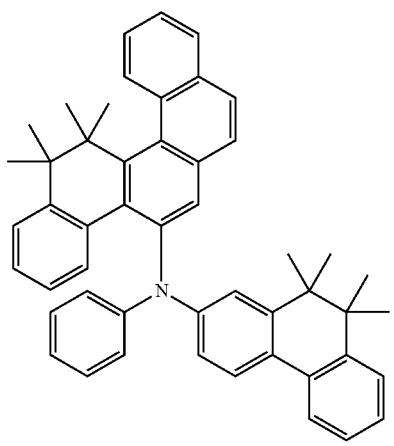
C-606
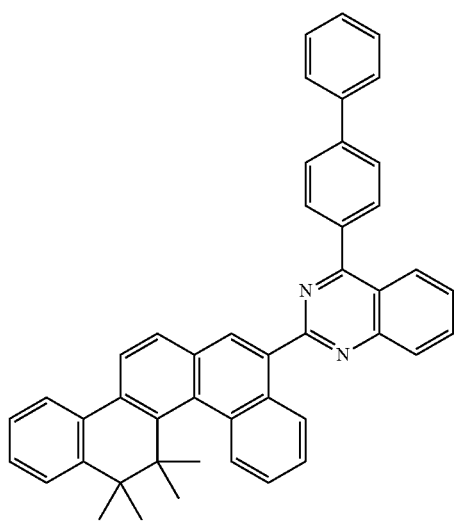
C-607
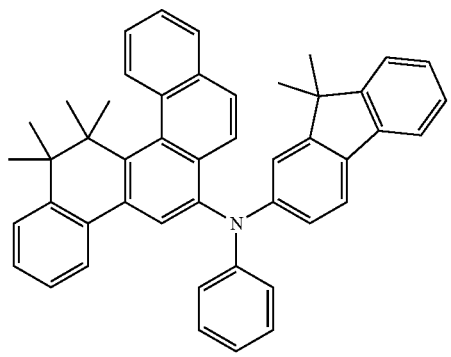
C-608
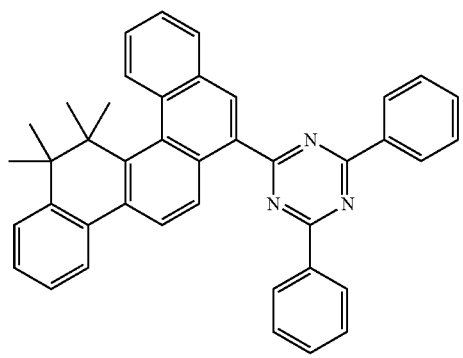
C-609
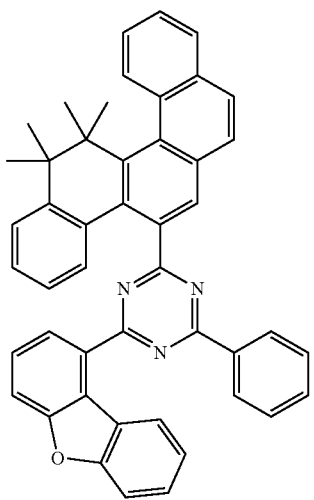

C-610
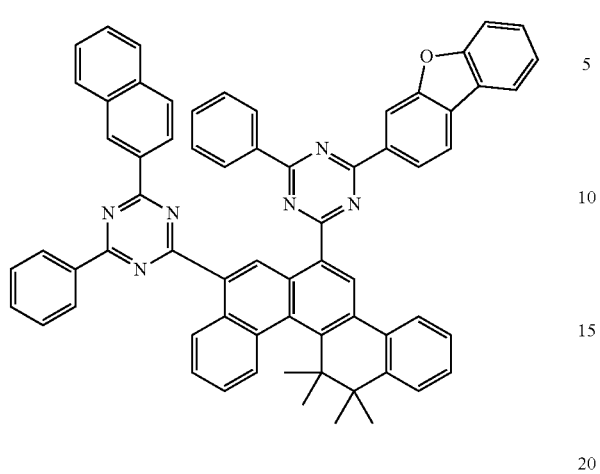
C-613
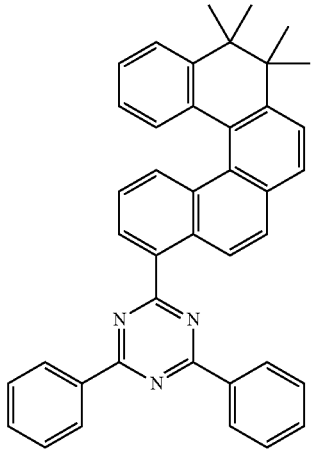
C-611
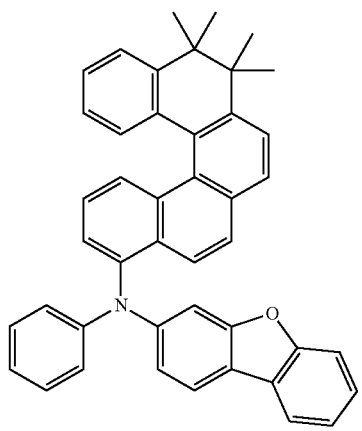
C-614
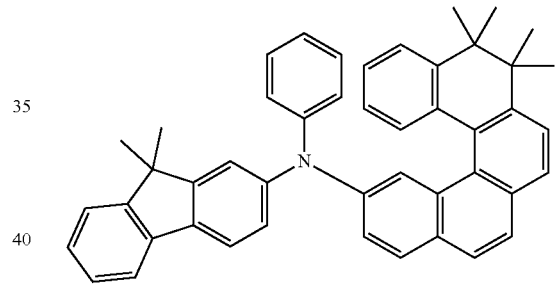
C-612
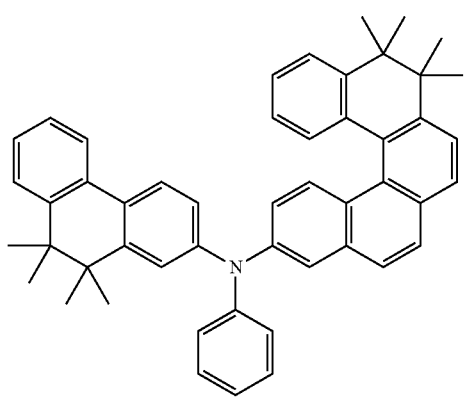
C-615
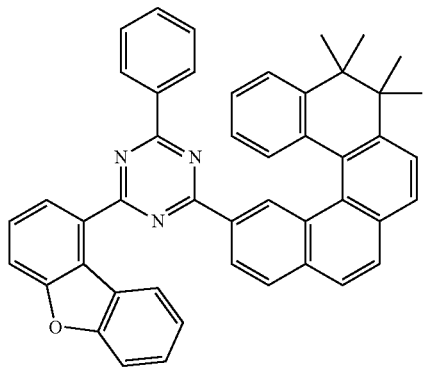

C-616
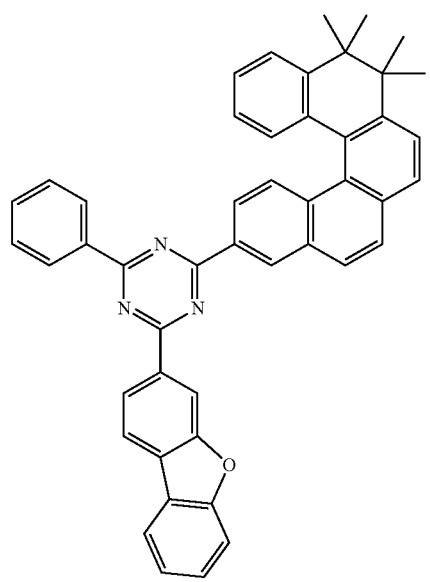
C-617
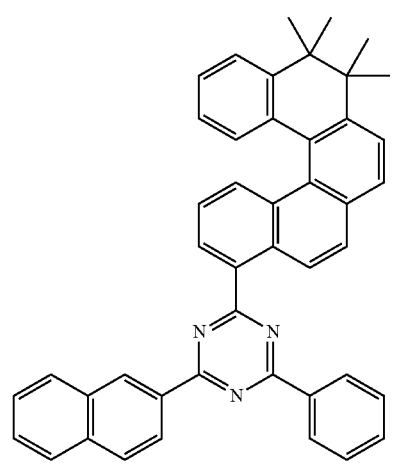
C-618
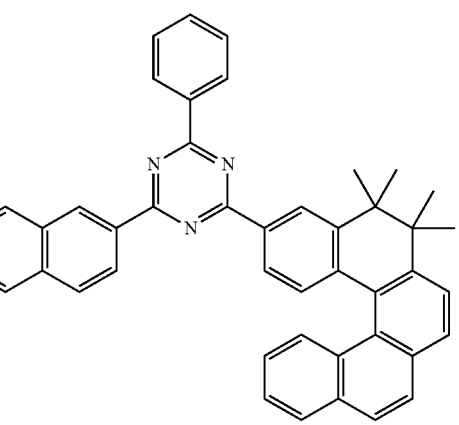
C-619
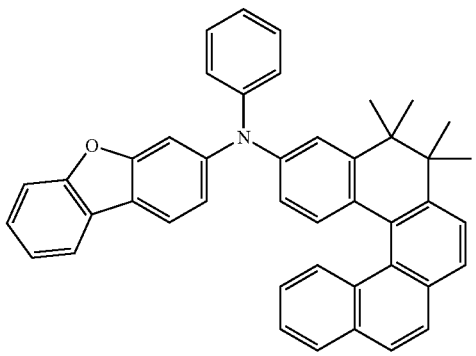
C-620
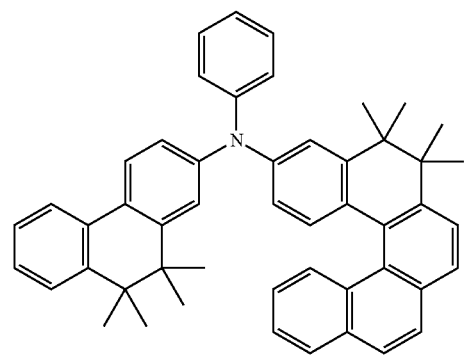
C-621
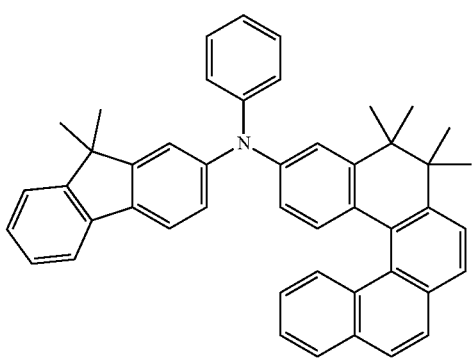
C-622
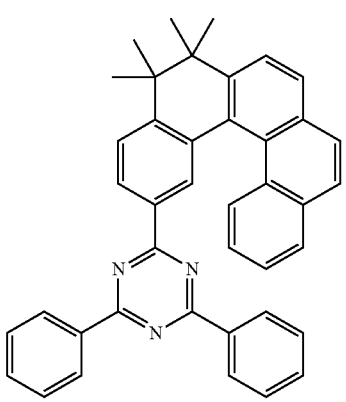

C-623
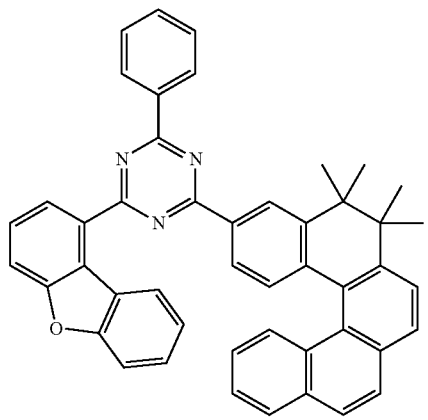
C-624
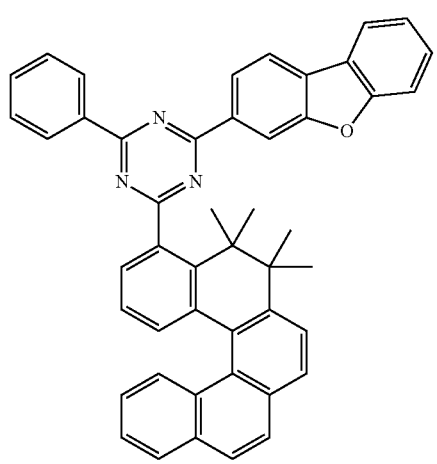
C-625
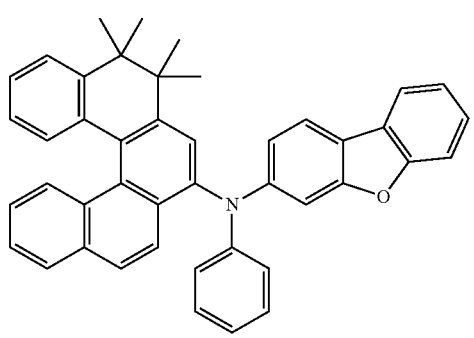
C-626
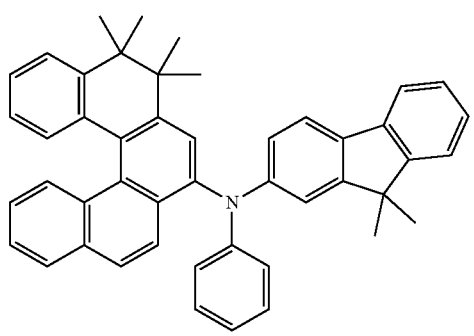
C-627
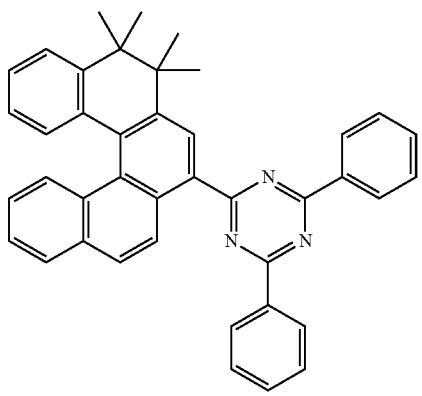
C-628
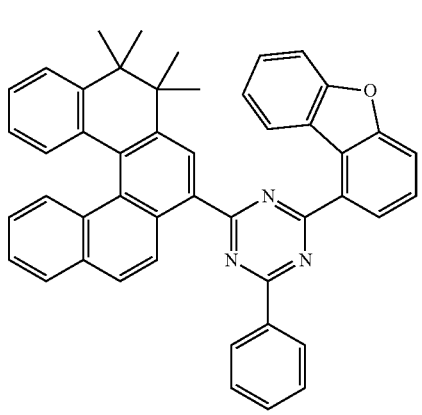
C-629
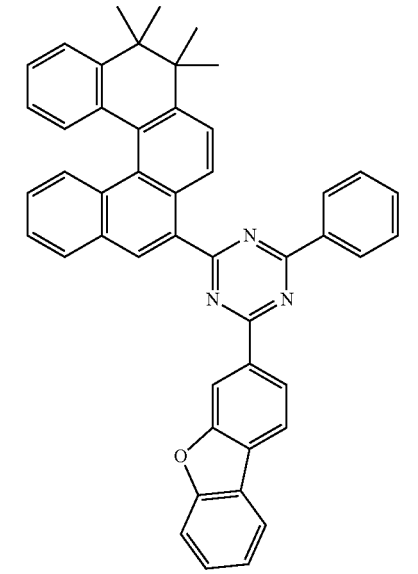

C-630
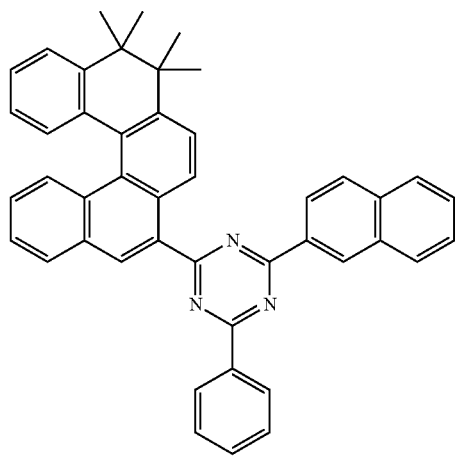
C-634
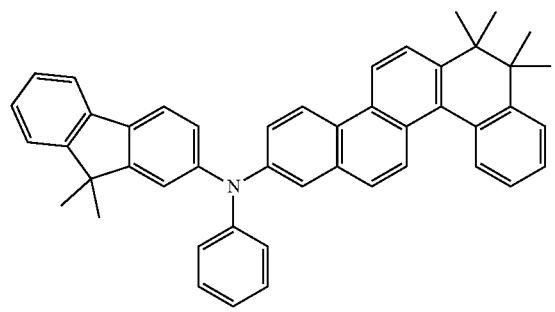
C-631
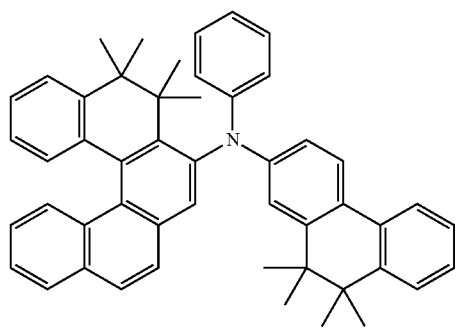
C-635
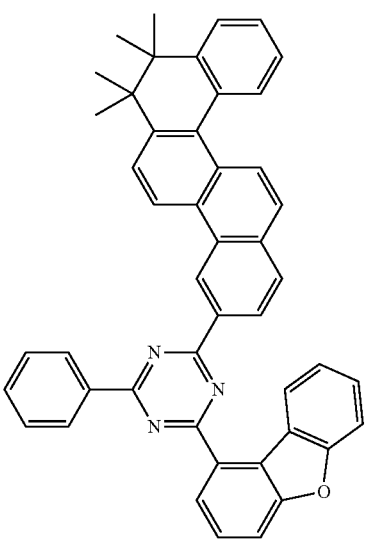
C-632
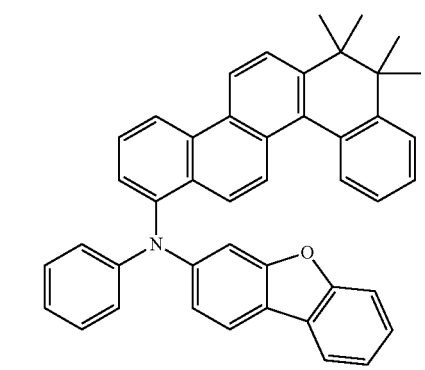
C-636
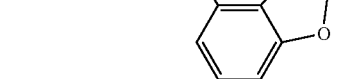
C-633
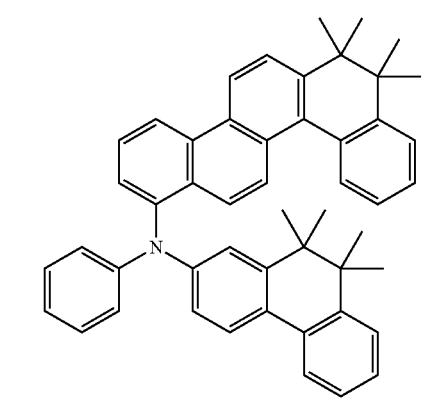
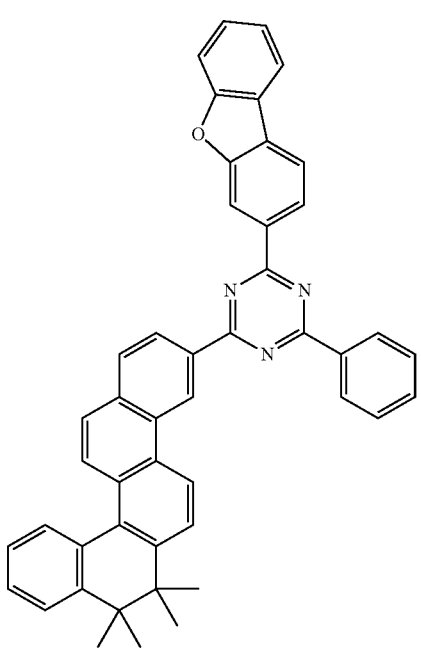

C-637
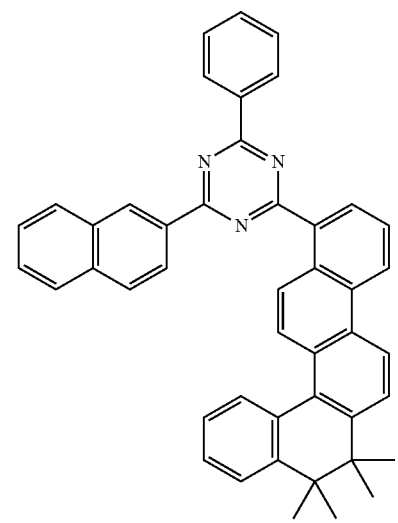
C-638
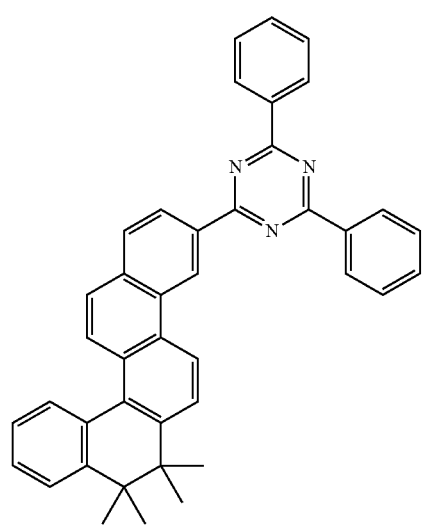
C-639
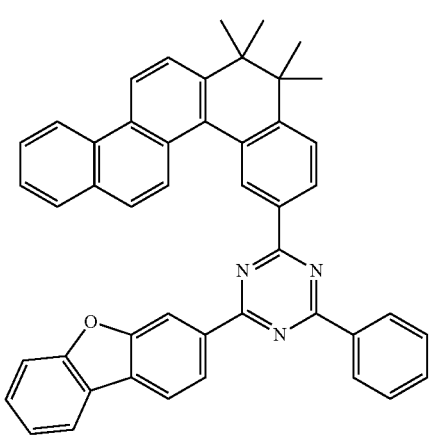
C-640
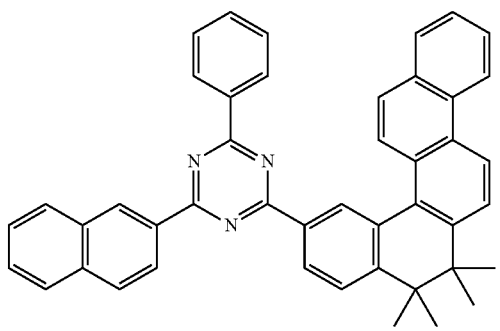
C-641
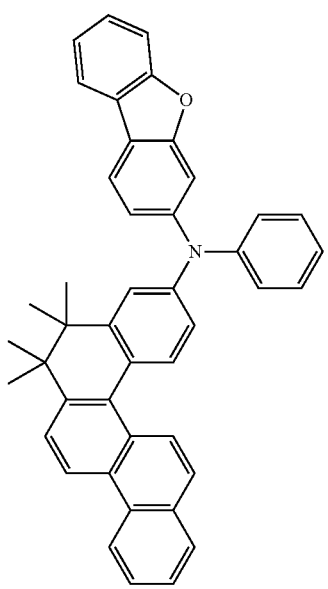
C-642
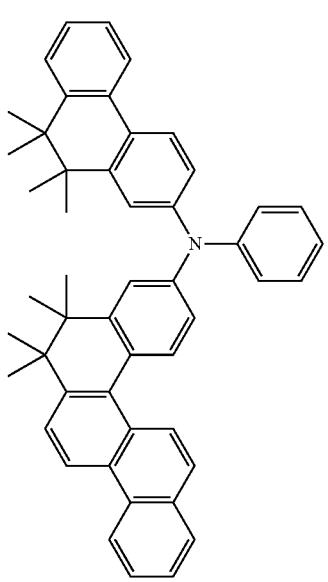

C-643
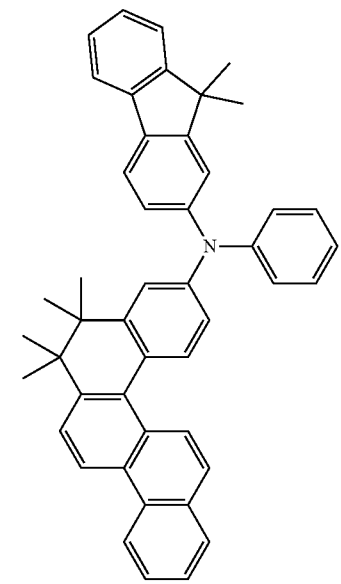
C-644
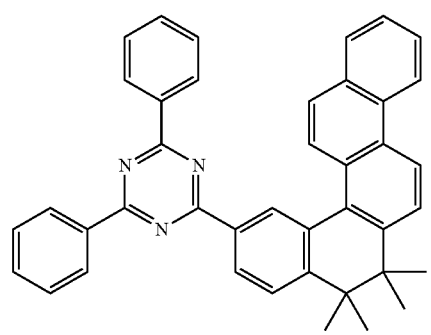
C-645
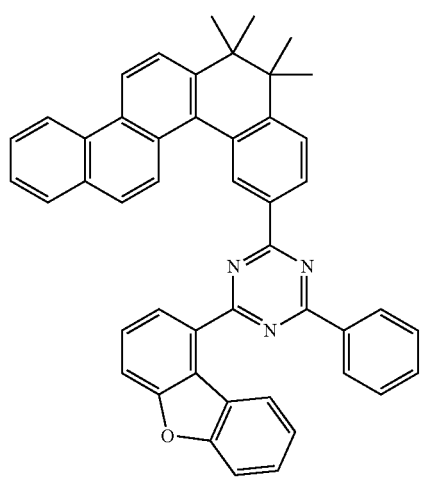
C-646
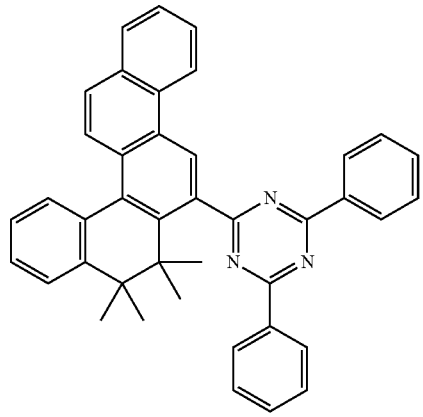
C-647
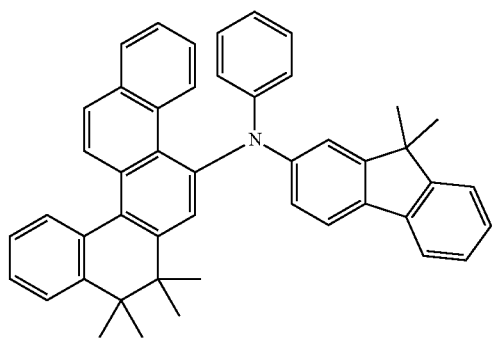
C-648
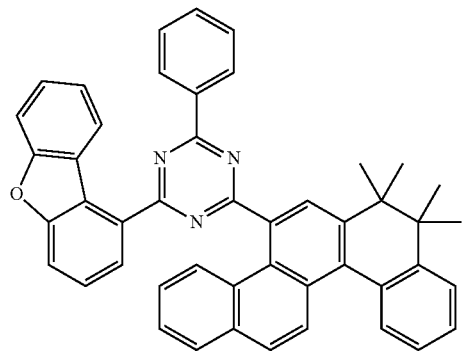
C-649
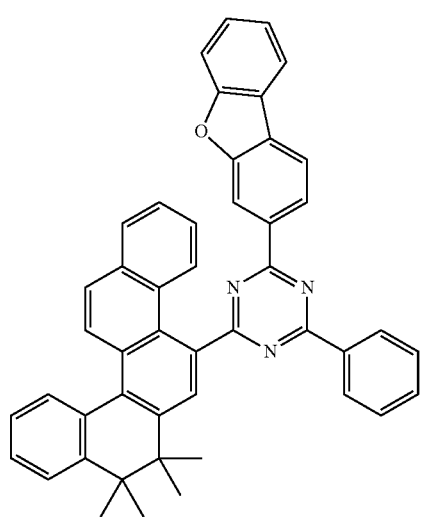

C-650
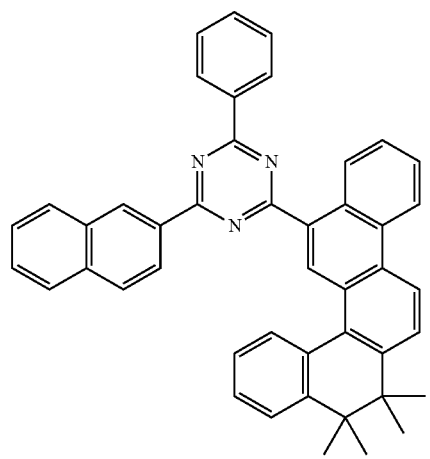
C-651
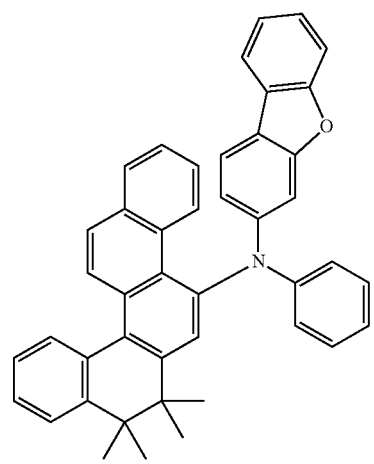
C-652
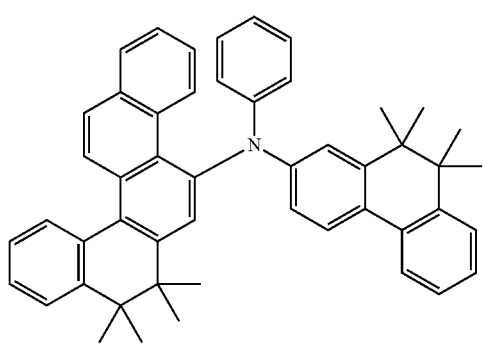
C-653
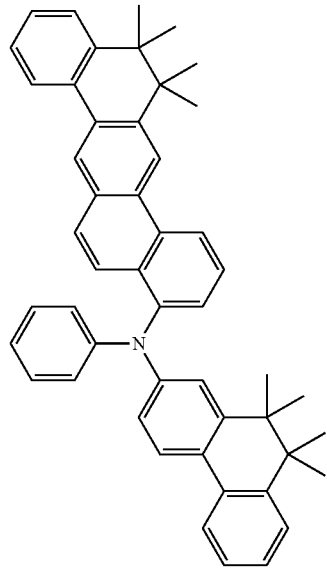
C-654
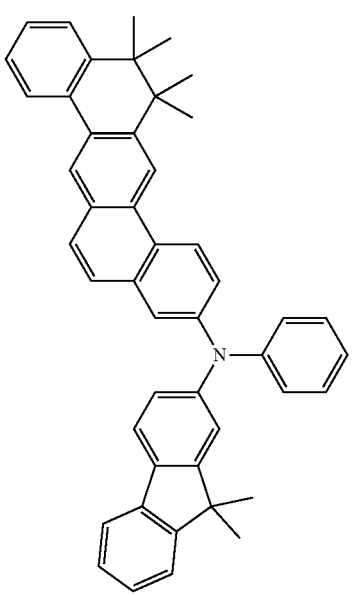

-continued
C-655
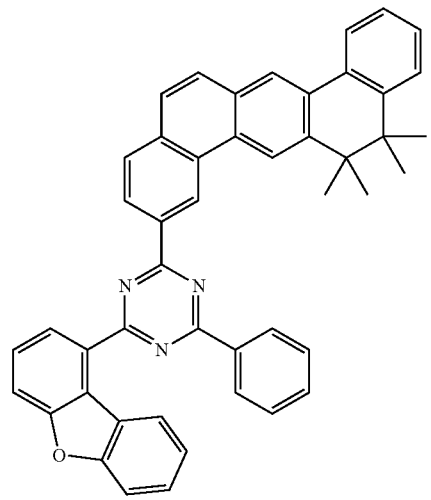
C-656
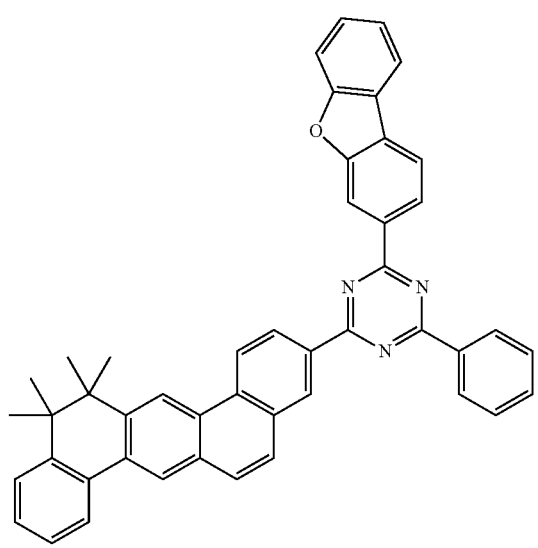
C-657
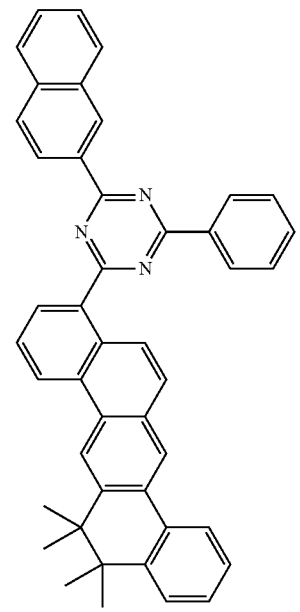
C-658
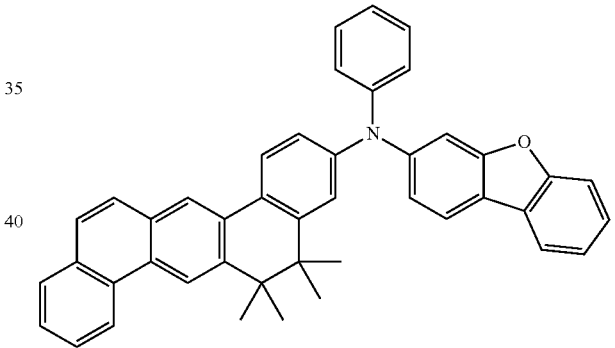
C-659
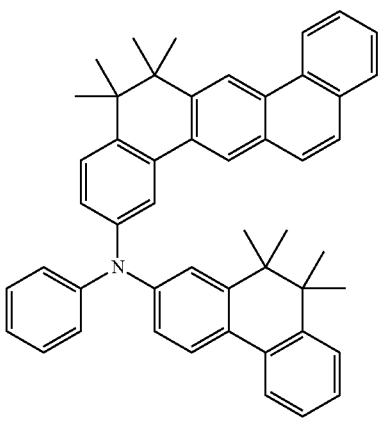

C-660
C-661
C-662
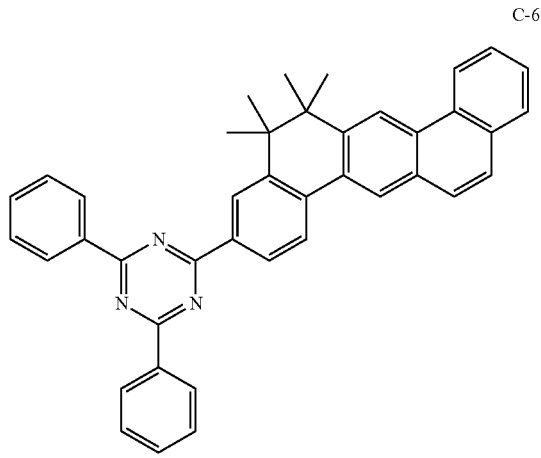
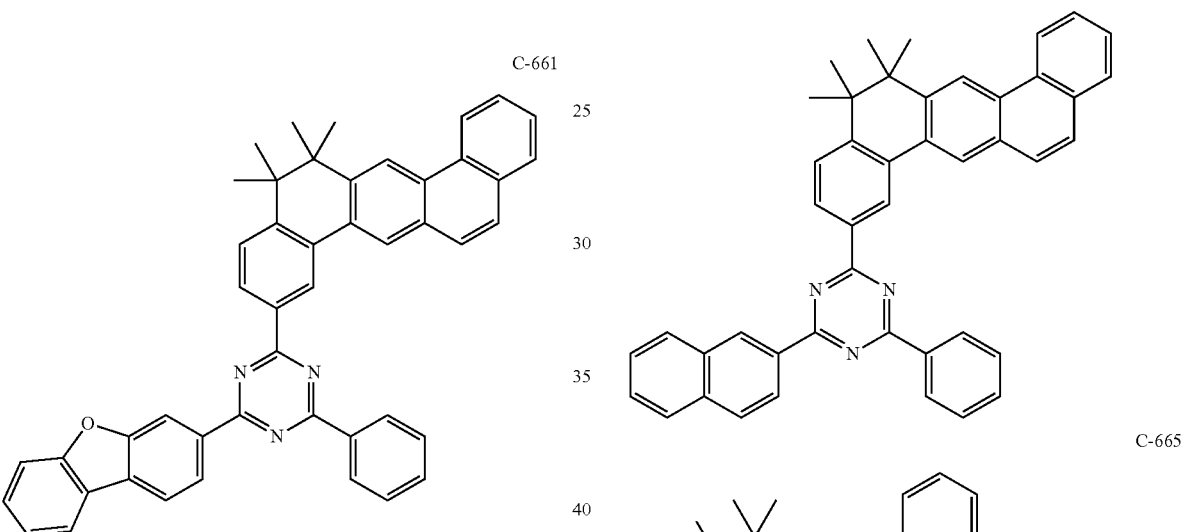
C-663
C-664
C-665
C-666
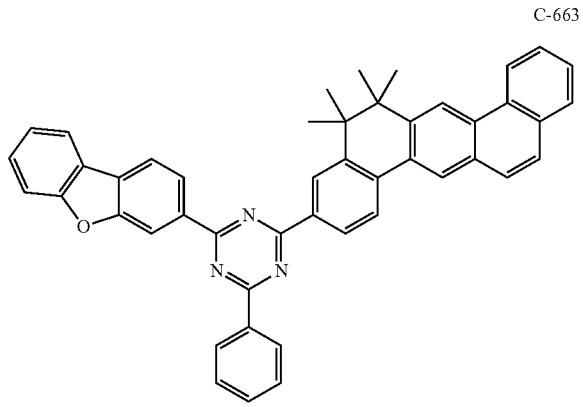
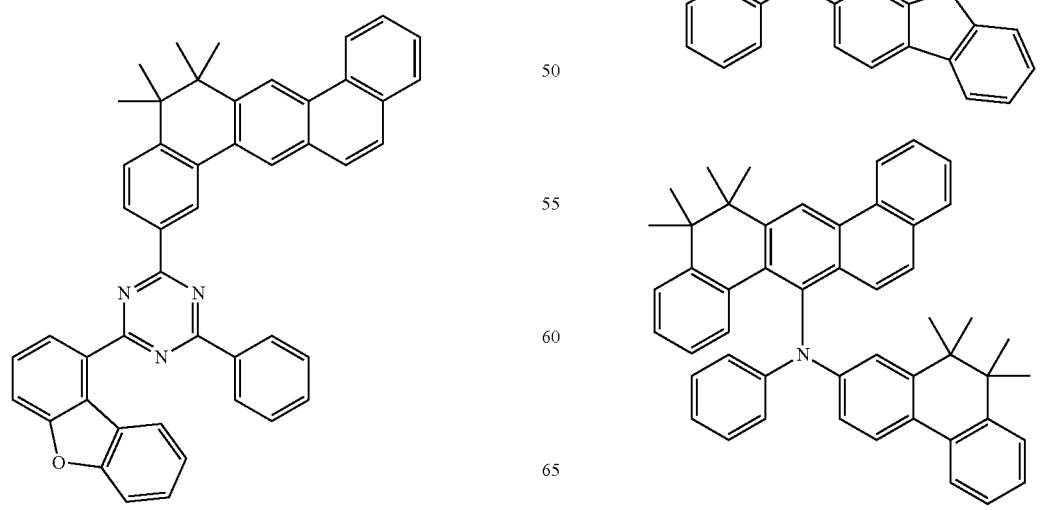

-continued
C-667
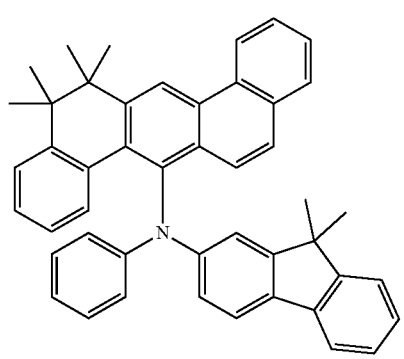
C-668
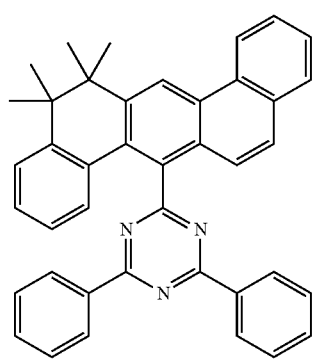
C-669
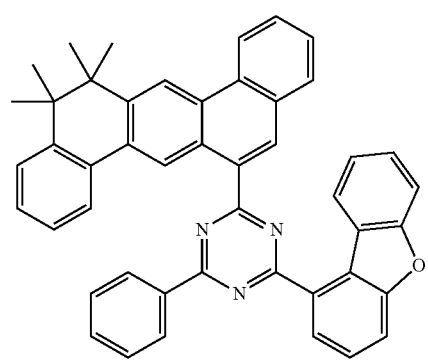
C-670
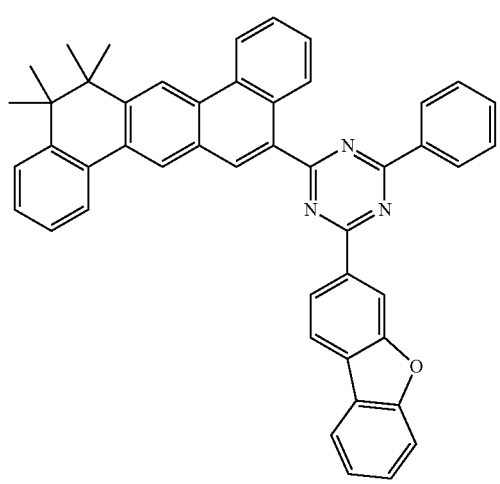
-continued
C-671
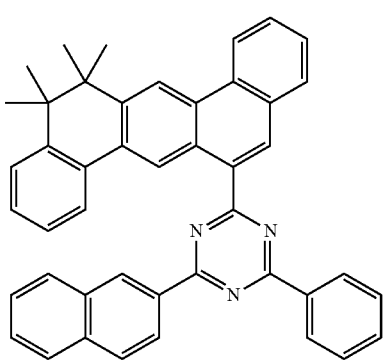
C-672
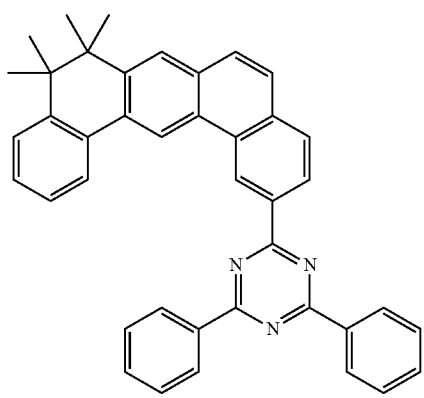
C-673
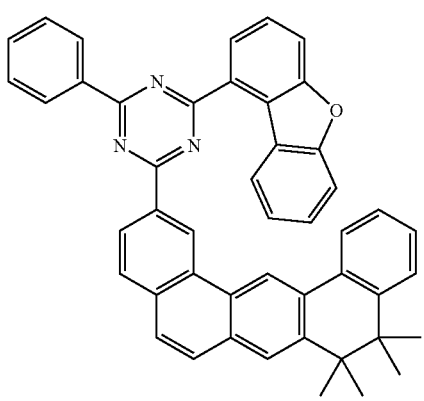

C-674
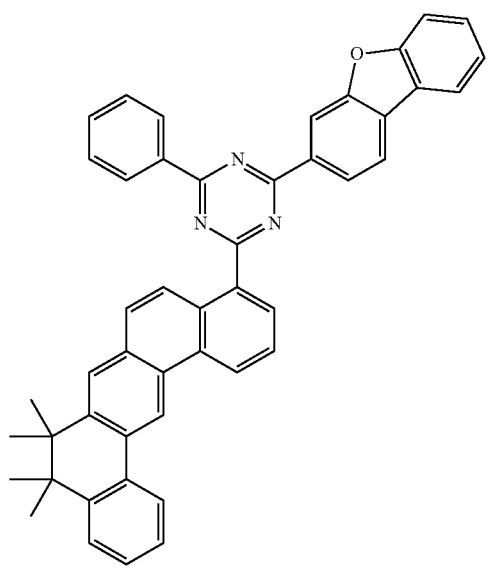
C-675
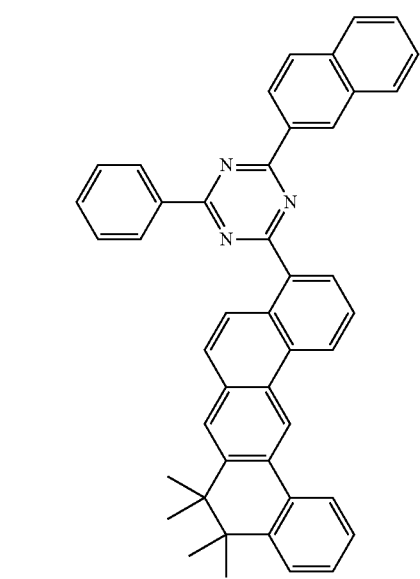
C-676
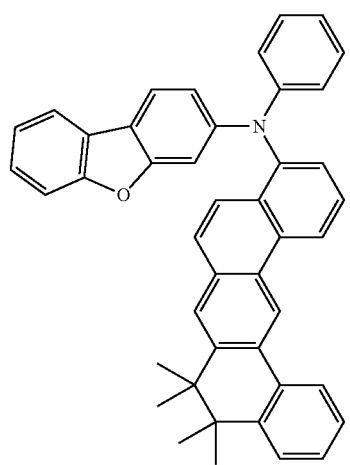
C-677
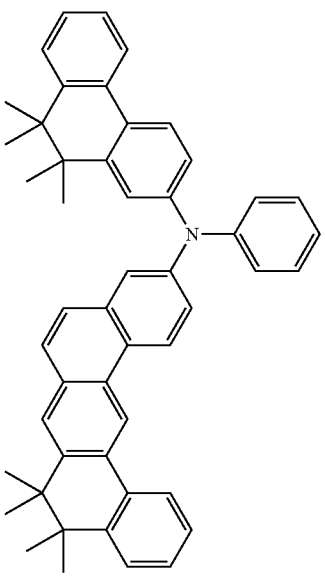
C-678
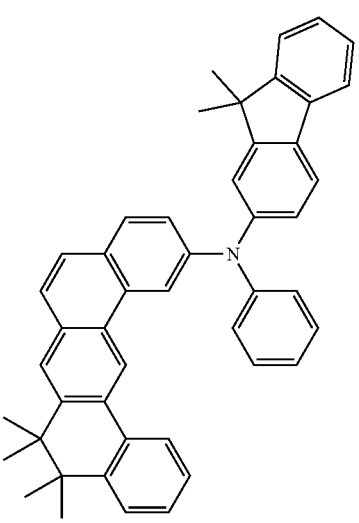
C-679
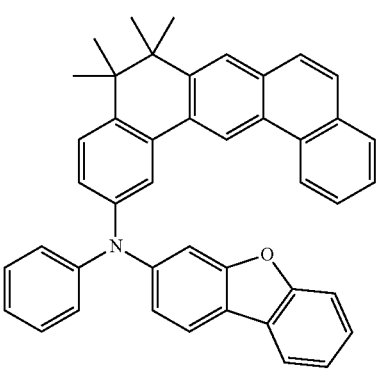

C-680
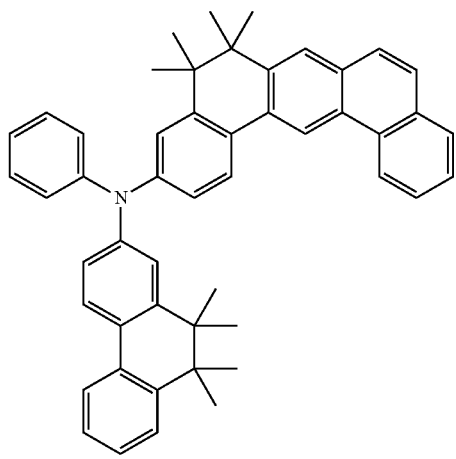
C-681
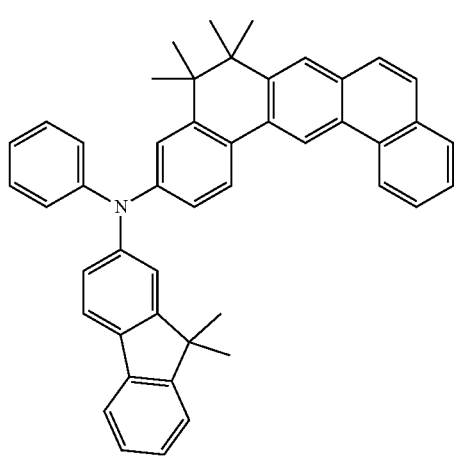
C-682
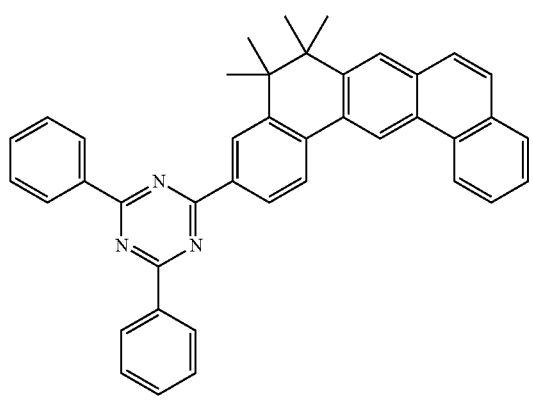
C-683
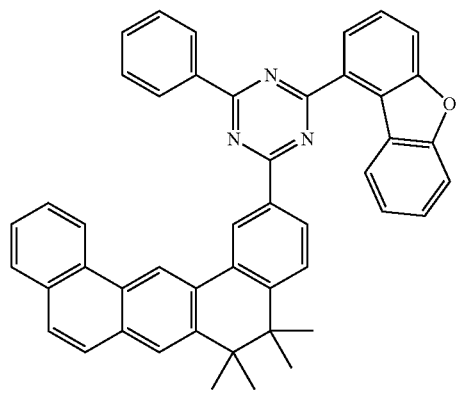
C-684
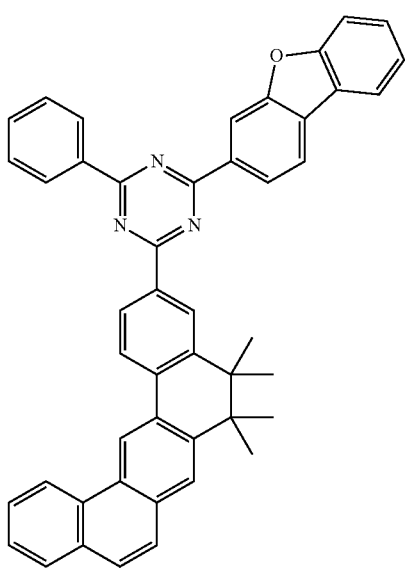
C-685
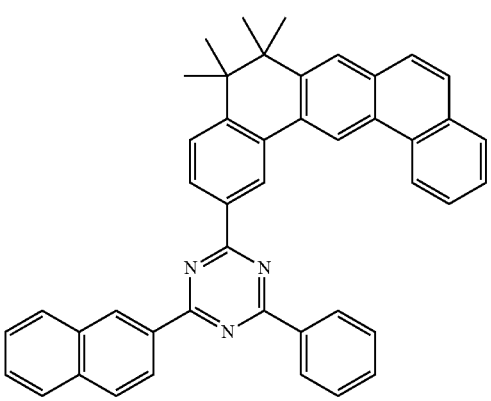

C-686
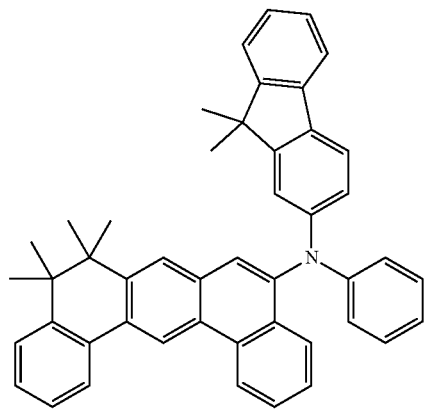
C-687
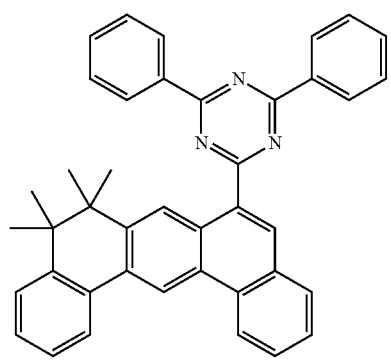
C-688
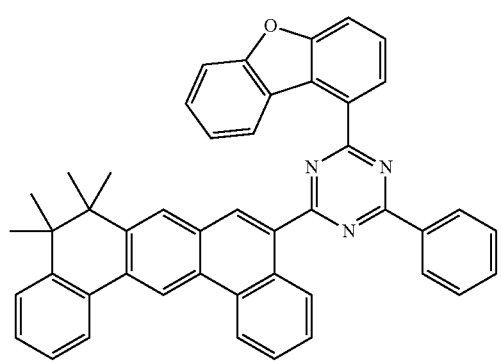
C-689
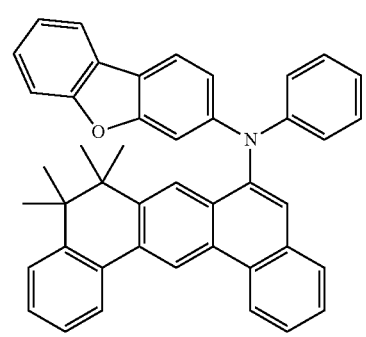
C-690
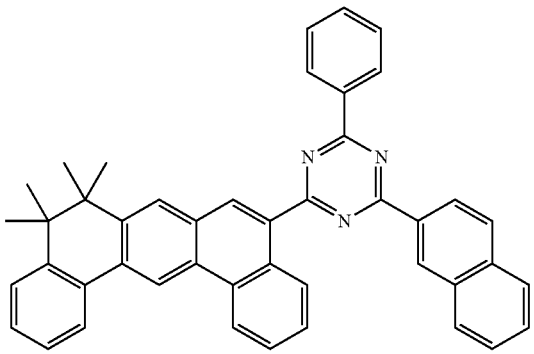
C-691
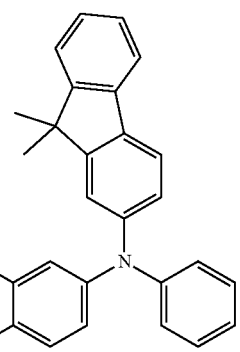
C-692
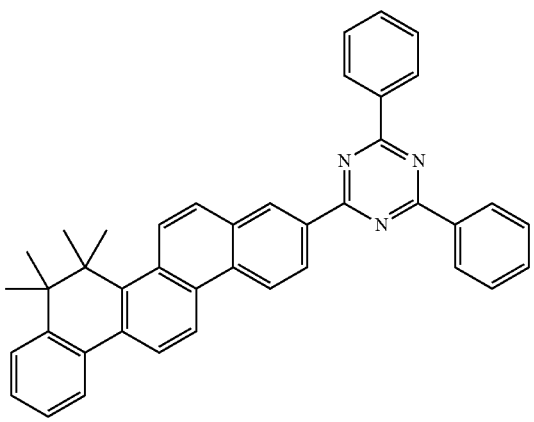

C-693

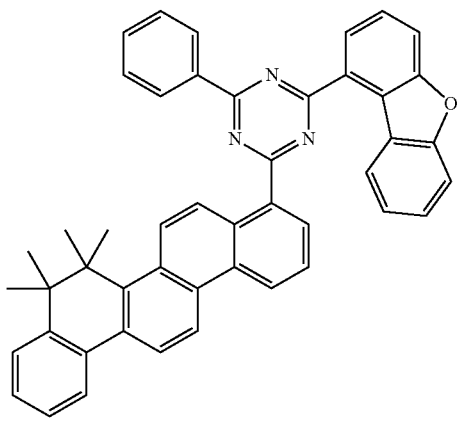

C-694

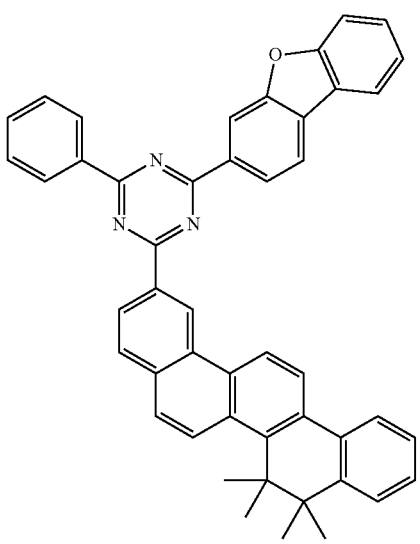

C-695

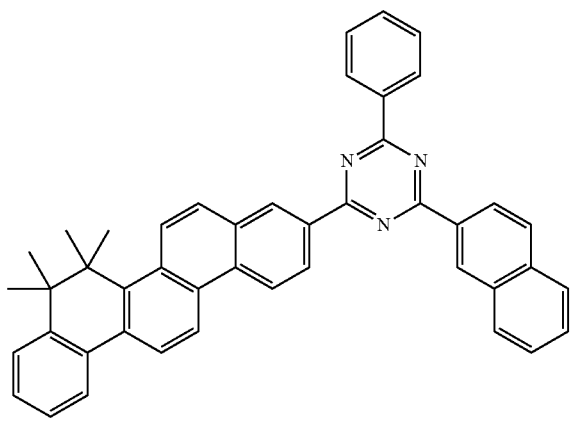

According to the present disclosure, a plurality of host materials comprising a first host material comprising the organic electroluminescent compound represented by formula 1 and a second host material different from the first host material are provided. Herein, the second host material may comprise the compound represented by any one of the following formulas 2 to 4, but is not limited thereto.

Hereinafter, the compound represented by formula 2 will be described in more detail.

In formula 2, $X_1$ and $Y_1$ each independently represent —N=, —NR$_{67}$—, —O—, or —S—, with a proviso that any one of $X_1$ and $Y_1$ represents —N=, and the other one of $X_1$ and $Y_1$ represents —NR$_{67}$—, —O—, or —S—. According to one embodiment of the present disclosure, any one of $X_1$ and $Y_1$ represents —N=, and the other one of $X_1$ and $Y_1$ represents —O— or —S—. That is, it may be that $X_1$ is —N=, and $Y_1$ is —O—; $X_1$ is —N=, and $Y_1$ is —S—; $X_1$ is —O—, and $Y_1$ is —N=; or $X_1$ is —S— and $Y_1$ is —N=.

In formula 2, $R_{61}$ represents a substituted or unsubstituted (C6-C30)aryl or a substituted or unsubstituted (3- to 30-membered)heteroaryl. According to one embodiment of the present disclosure, $R_{61}$ represents a substituted or unsubstituted (C6-C30)aryl or a substituted or unsubstituted (5- to 25-membered)heteroaryl. According to another embodiment of the present disclosure, $R_{61}$ represents a substituted or unsubstituted (C6-C30)aryl or a substituted (5- to 20-membered)heteroaryl. For example, $R_{61}$ may be an unsubstituted phenyl, unsubstituted biphenyl, unsubstituted naphthyl, fluorenyl substituted with methyl, benzofluorenyl substituted with methyl, unsubstituted dibenzofuranyl, unsubstituted dibenzothiophenyl, spiro[fluorene-fluoren]yl, spiro[fluorene-benzofluoren]yl, unsubstituted pyridyl, etc.

In formula 2, $R_{62}$ to $R_{64}$ and $R_{67}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -L$_3$"-N(Ar$_3$")(Ar$_4$"); or may be linked to an adjacent substituent to form a ring. Herein, L$_3$" each independently represents a single bond, a substituted or unsubstituted (C6-C30)arylene, or a substituted or unsubstituted (3- to 30-membered)heteroarylene; and Ar$_3$" and Ar$_4$" each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

According to one embodiment of the present disclosure, $R_{62}$ to $R_{64}$ and $R_{67}$ each independently represent hydrogen, or a substituted or unsubstituted (C6-C12)aryl. According to another embodiment of the present disclosure, $R_{62}$ to $R_{64}$ and $R_{67}$ each independently represent hydrogen or an unsubstituted (C6-C12)aryl. For example, $R_{62}$ and $R_{63}$ may be hydrogen, and $R_{67}$ may be hydrogen, phenyl, etc.

In formula 2, $L_4$ represents a single bond, a substituted or unsubstituted (C6-C30)arylene, or a substituted or unsubstituted (3- to 30-membered)heteroarylene. According to one embodiment of the present disclosure, $L_4$ represents a single bond, or a substituted or unsubstituted (C6-C18)arylene. According to another embodiment of the present disclosure, $L_4$ represents a single bond, or an unsubstituted (C6-C12)arylene. For example, $L_4$ may be a single bond, an unsubstituted phenylene, an unsubstituted naphthylene, etc.

In formula 2, $R_{65}$ and $R_{66}$ each independently represent a substituted or unsubstituted (C6-C30)aryl or a substituted or unsubstituted (3- to 30-membered)heteroaryl. According to one embodiment of the present disclosure, $R_{65}$ and $R_{66}$ each independently represent a substituted or unsubstituted (C6-

C25)aryl, or a substituted or unsubstituted (3-20 membered) heteroaryl. According to another embodiment of the present disclosure, $R_{65}$ and $R_{66}$ each independently represent a (C6-C25)aryl unsubstituted or substituted with at least one of deuterium, (C1-C6)alkyl, (C6-C25)aryl, (3- to 20-membered)heteroaryl, (C3-C7)cycloalkyl, and (C1-C6)alkyl(C6-C12)aryl; or a (3- to 20-membered)heteroaryl unsubstituted or substituted with at least one of (C6-C12)aryl and (5- to 15-membered)heteroaryl. For example, $R_{65}$ and $R_{66}$ may each independently be at least one of a substituted phenyl, naphthyl, biphenyl, phenanthrenyl, dimethylfluorenyl, diphenylfluorenyl, naphthylphenyl, phenylnaphthyl, dimethylbenzofluorenyl, terphenyl, spirobifluorenyl, benzofuranyl, benzothiophenyl, dibenzothiophenyl unsubstituted or substituted with phenyl, dibenzofuranyl unsubstituted or substituted with phenyl or pyridyl, carbazolyl substituted with phenyl, benzonaphthofuranyl, benzonaphthothiophenyl, benzofuropyridyl, etc.; wherein the substituent of the substituted phenyl may be at least one of phenyl substituted with at least one of deuterium, methyl, and tert-butyl; anthracenyl; fluoranthenyl; phenylfluorenyl; cyclohexyl; pyridyl substituted with phenyl; phenoxazinyl; and benzimidazolyl substituted with phenyl.

In formula 2, a represents 1; b and c each independently represent 1 or 2, preferably 1; d represents an integer of 1 to 4, preferably 1 or 2; and when b to d are an integer of 2 or more, each of $R_{62}$ to each of $R_{64}$ may be the same or different from each other.

The compound represented by formula 2 may be at least one selected from the following compounds, but is not limited thereto.

H1-1

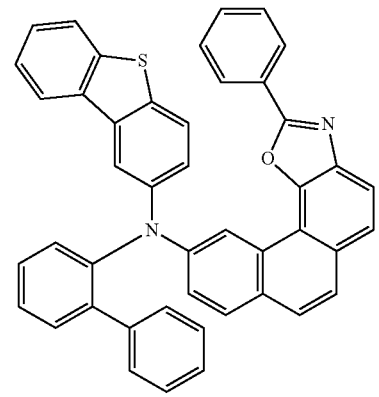

H1-2

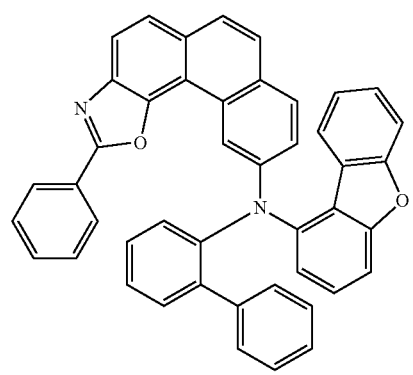

-continued

H1-3

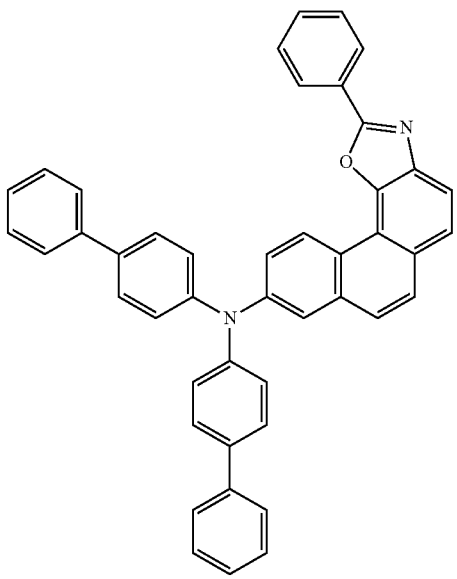

H1-4

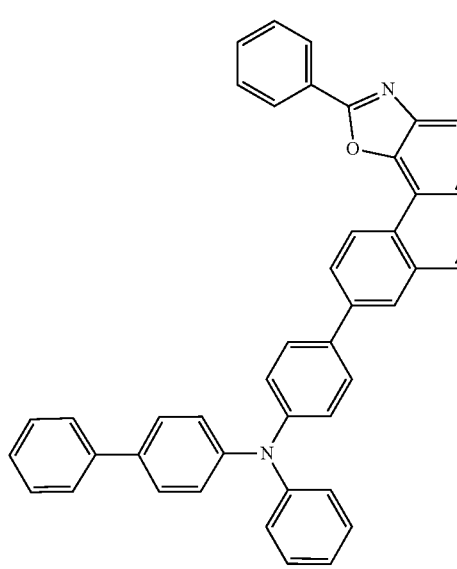

H1-5

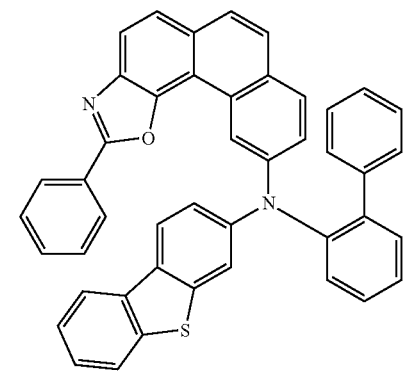

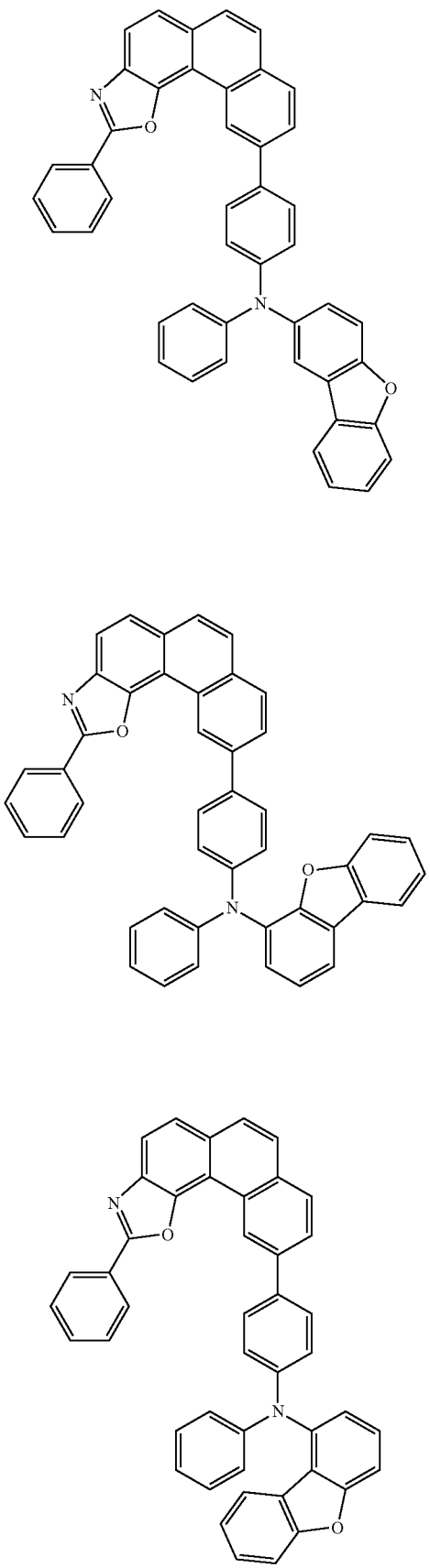
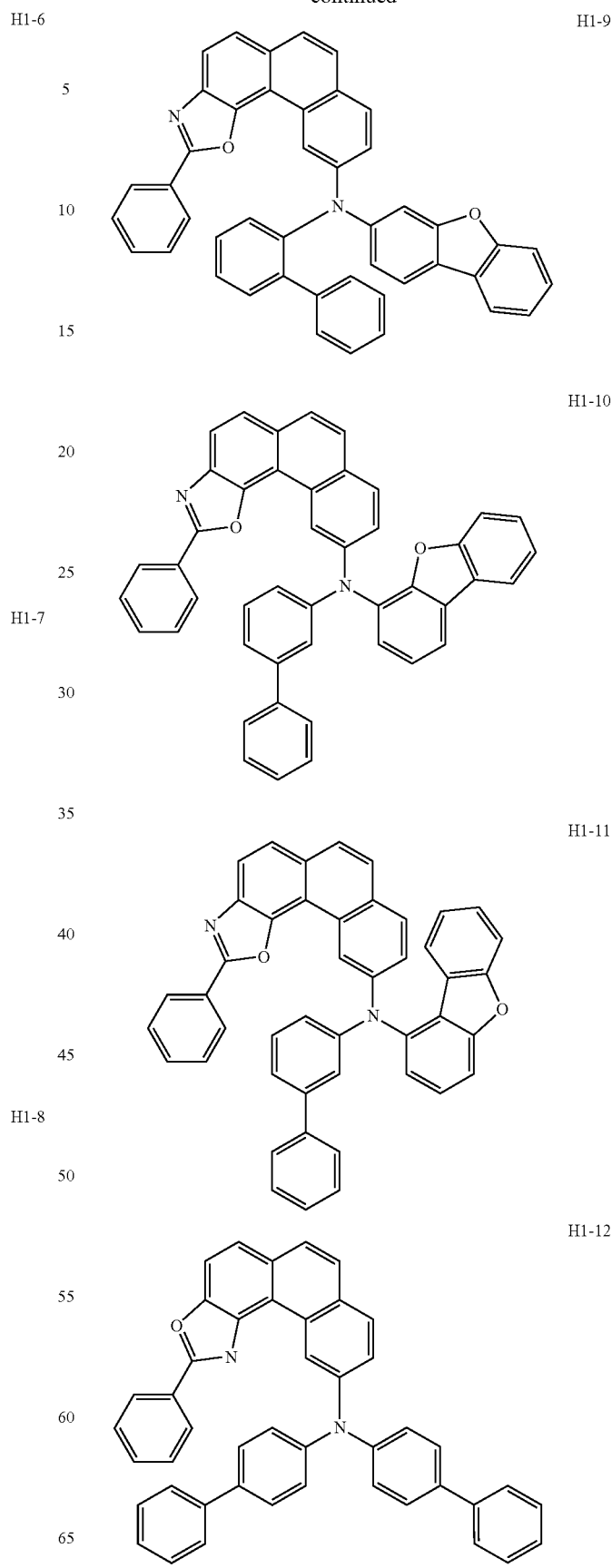

H1-13
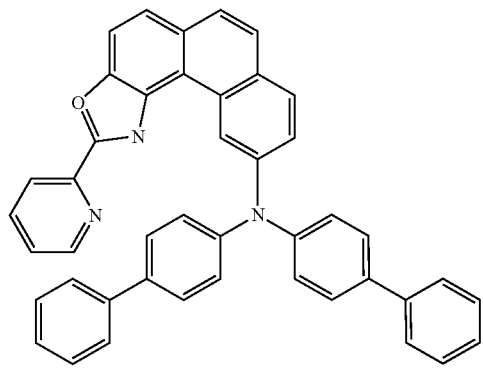
H1-14
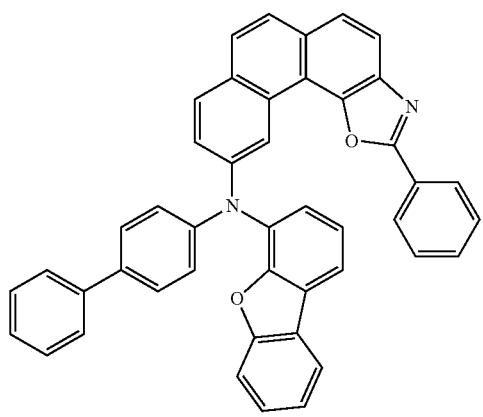
H1-15
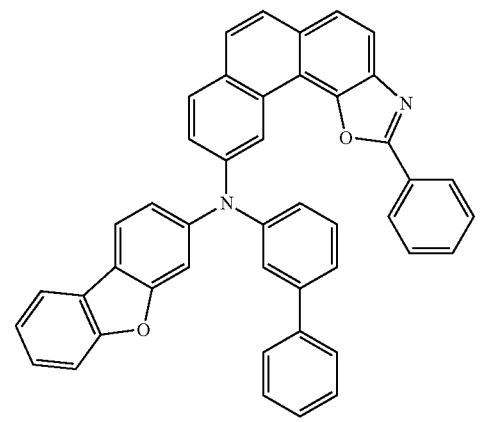
H1-16
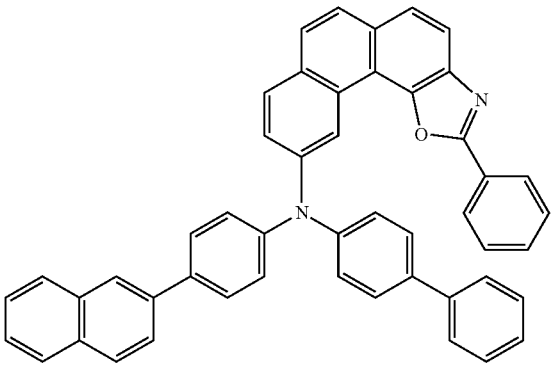
H1-17
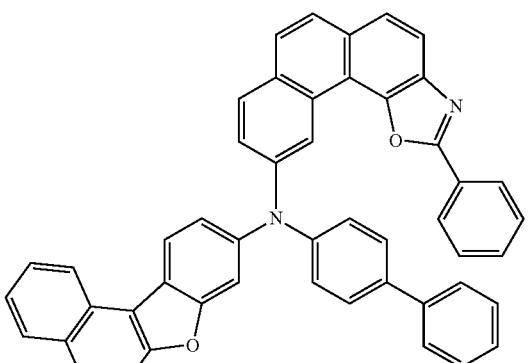
H1-18
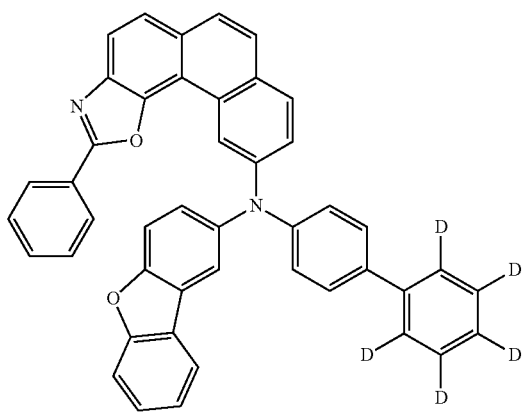
H1-19

H1-20
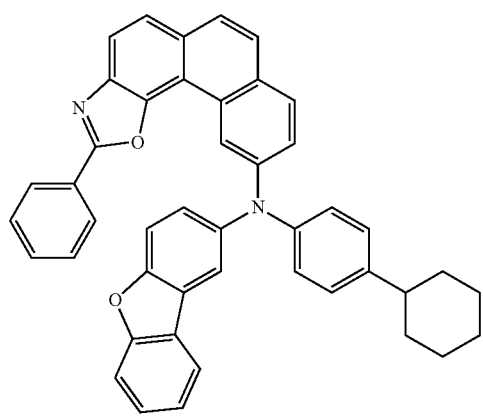
H1-21
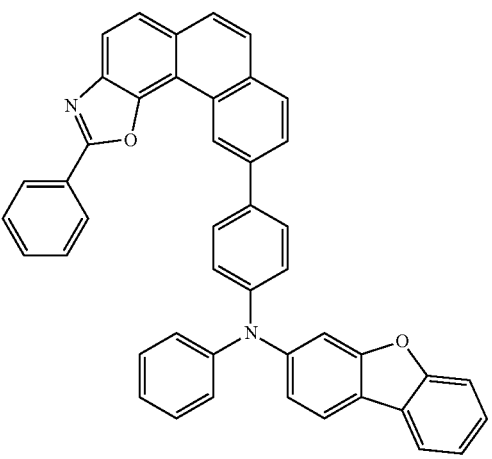
H1-22
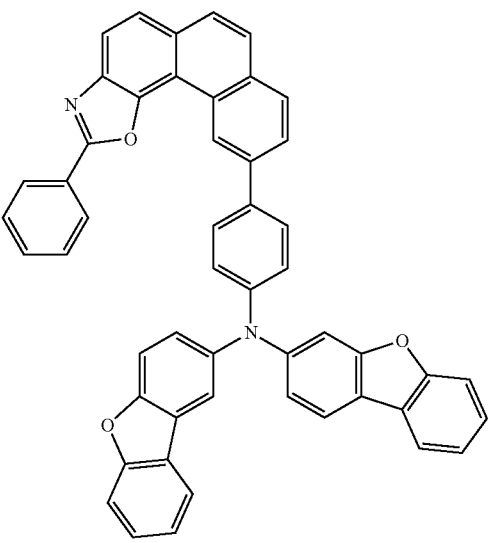
H1-23
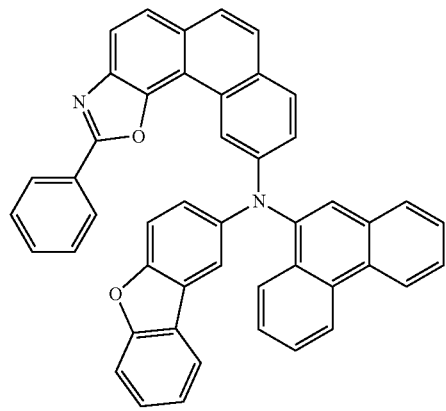
H1-24
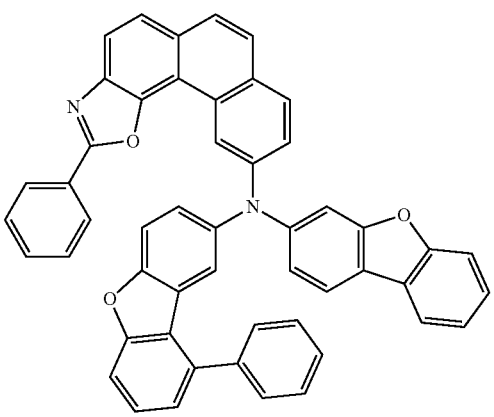
H1-25
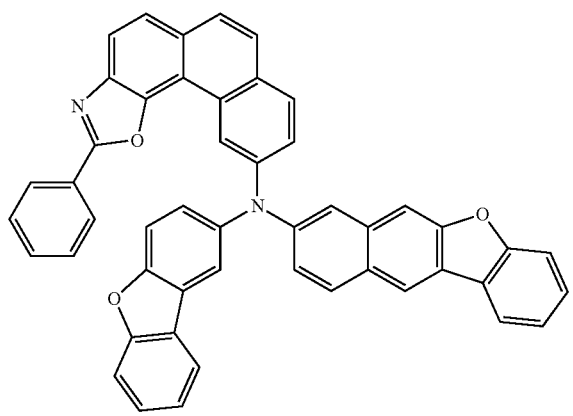

H1-26
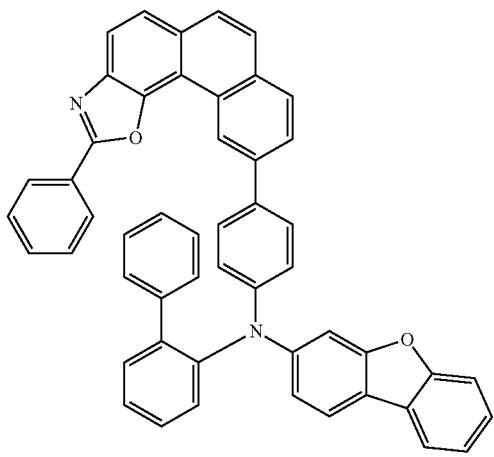
H1-27
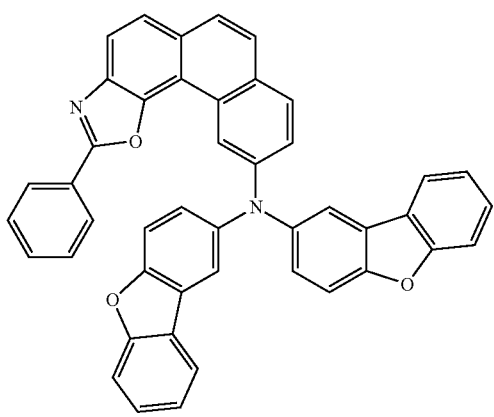
H1-28
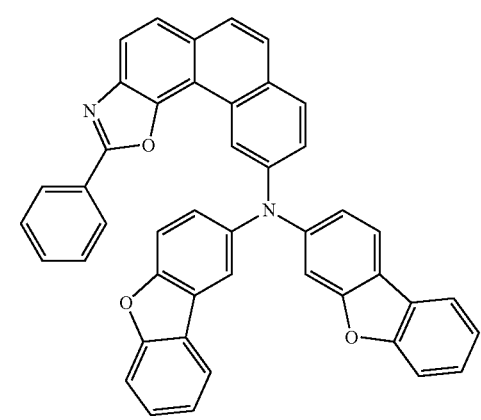
H1-29
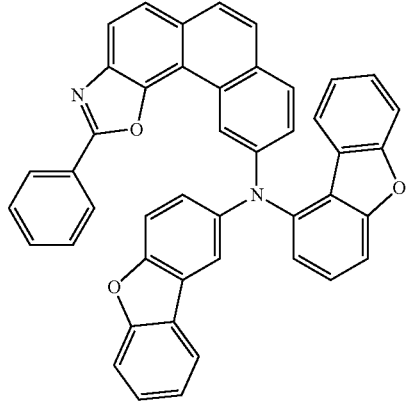
H1-30
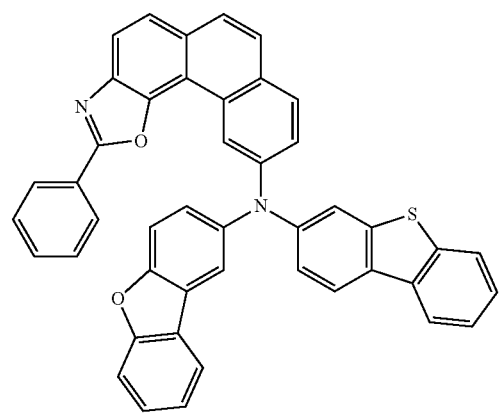
H1-31
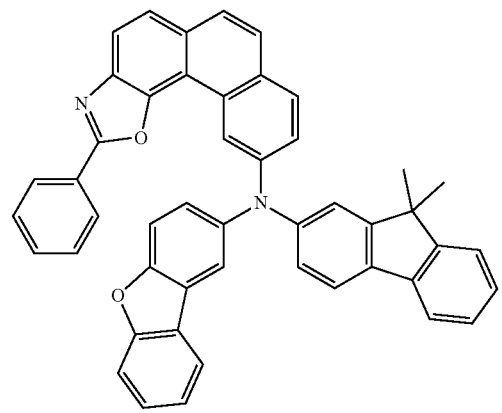
H1-32
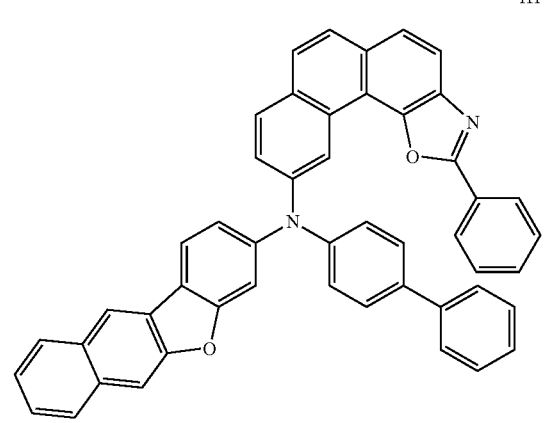

H1-33
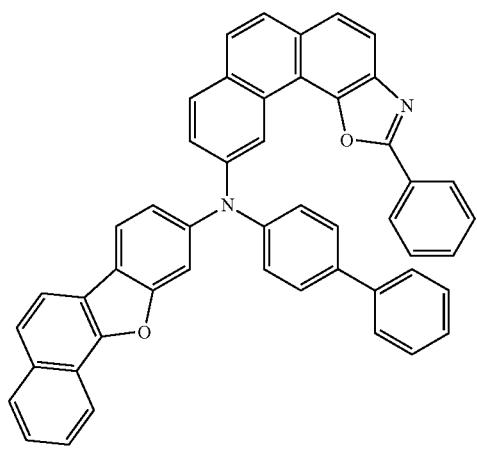
H1-34
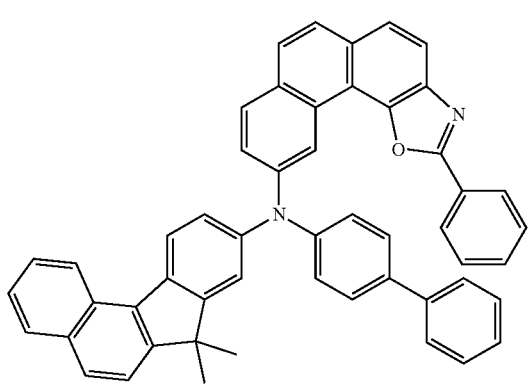
H1-35
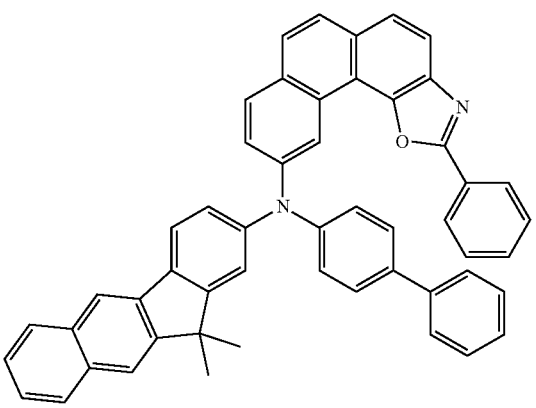
H1-36
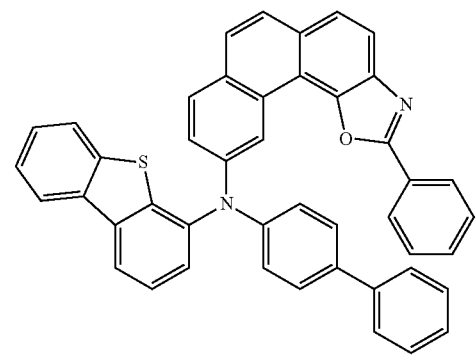
H1-37
H1-38
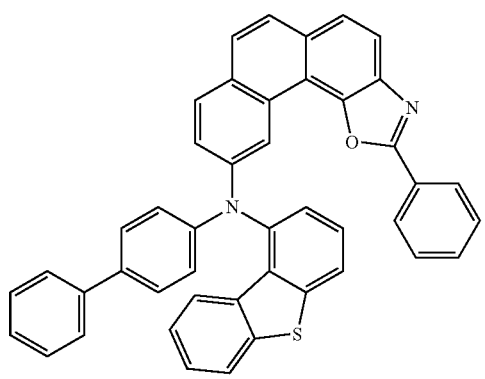
H1-39
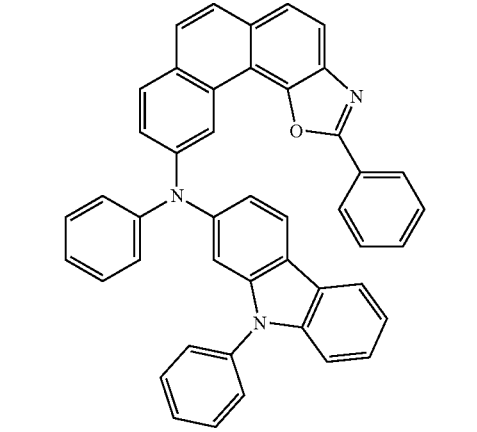
H1-40
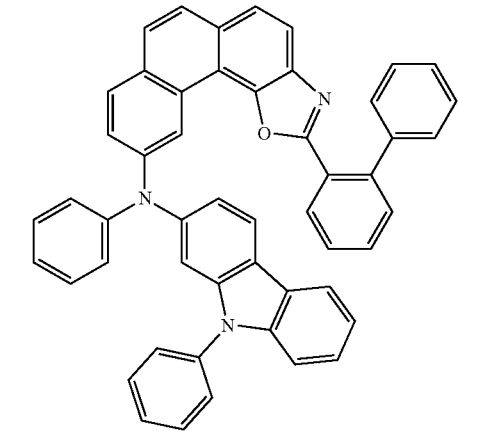

H1-41
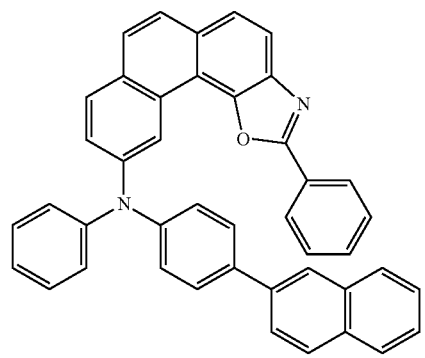
H1-42
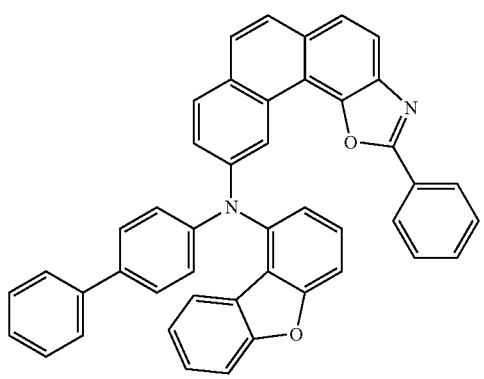
H1-43
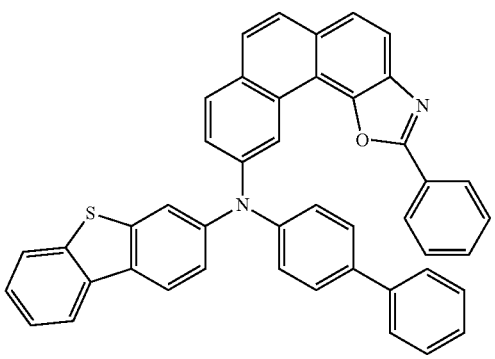
H1-44
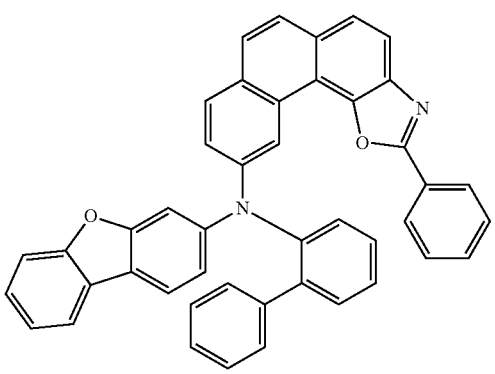
H1-45
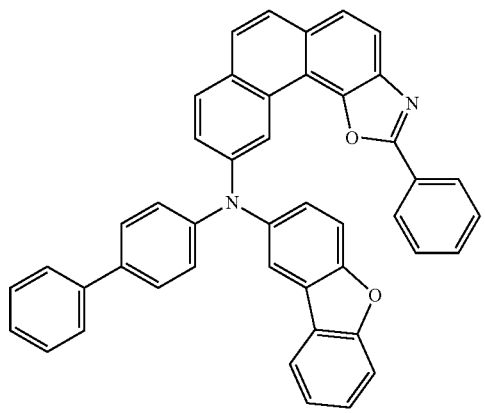
H1-46
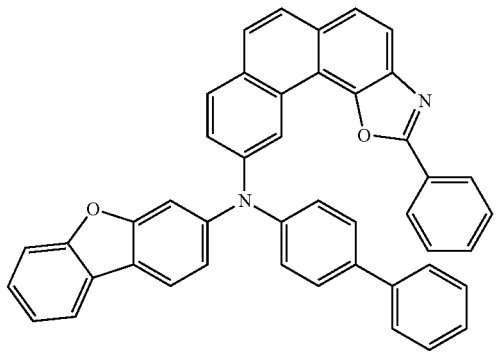
H1-47
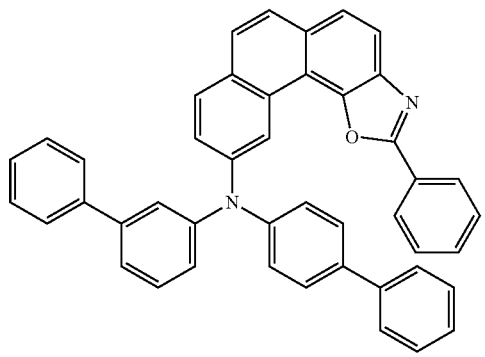
H1-48
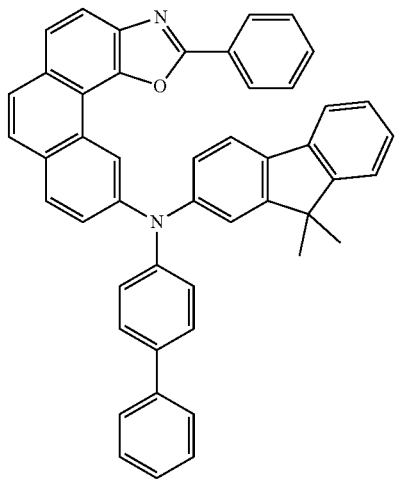

H1-49
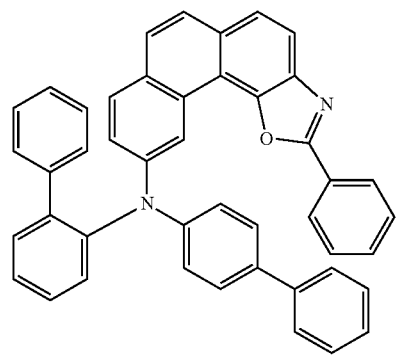
H1-50
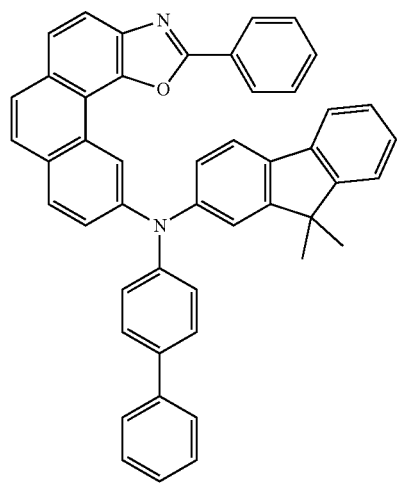
H1-51
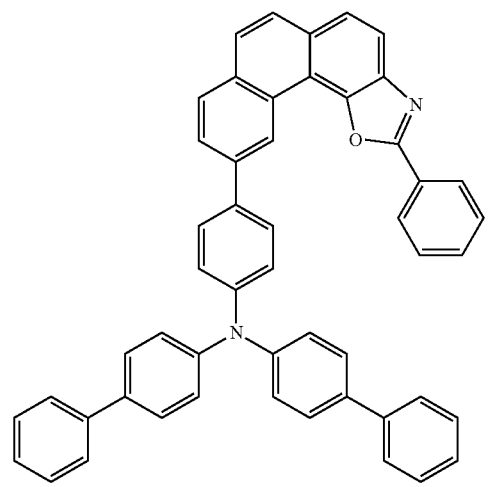
H1-52
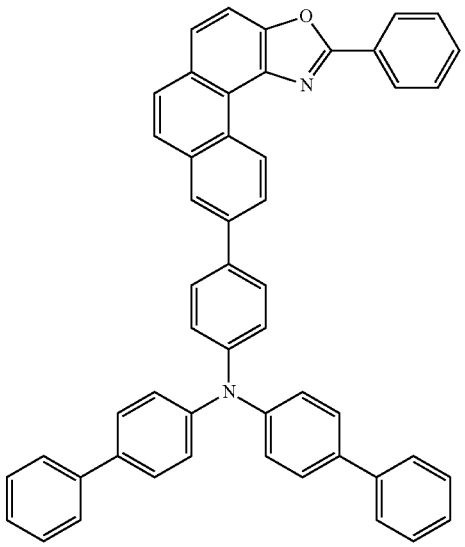
H1-53
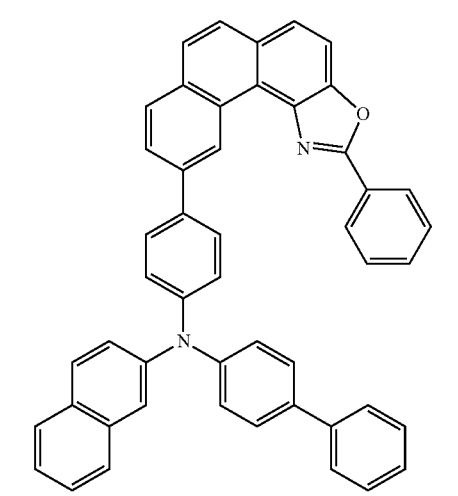
H1-54
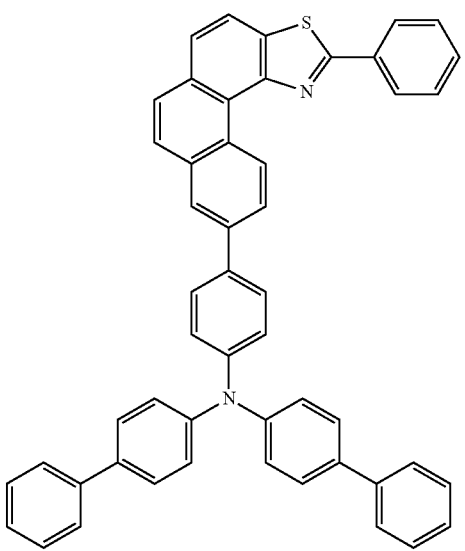

H1-55
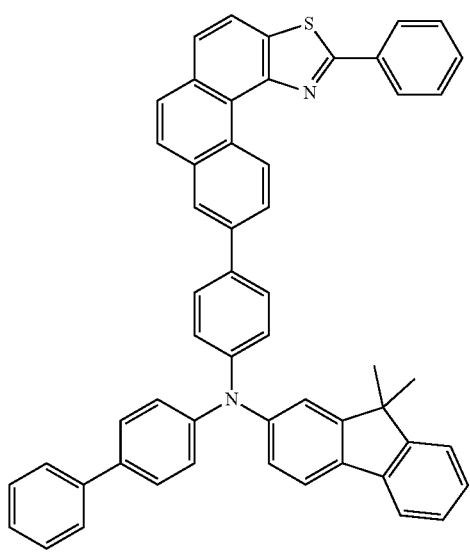
H1-56
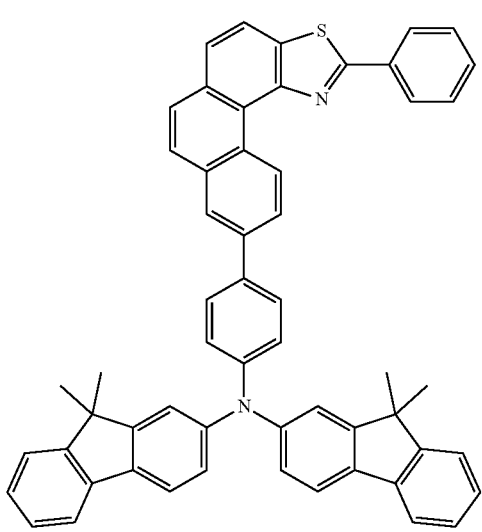
H1-57
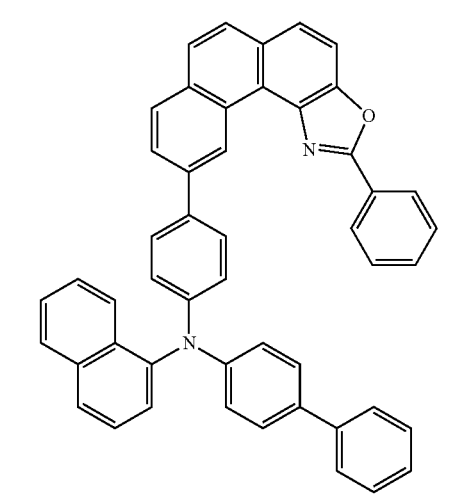
H1-58
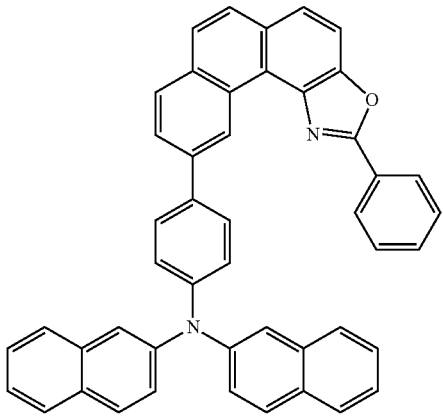
H1-59
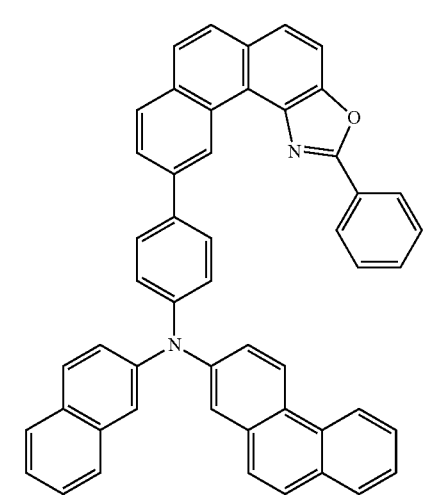
H1-60
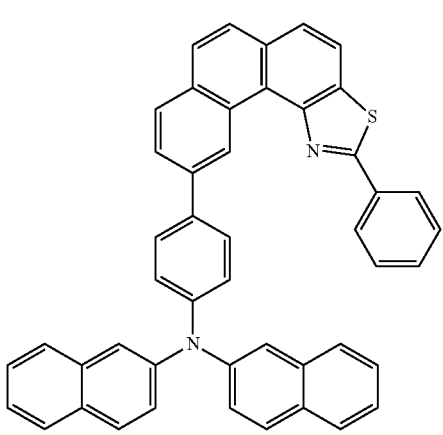

H1-61
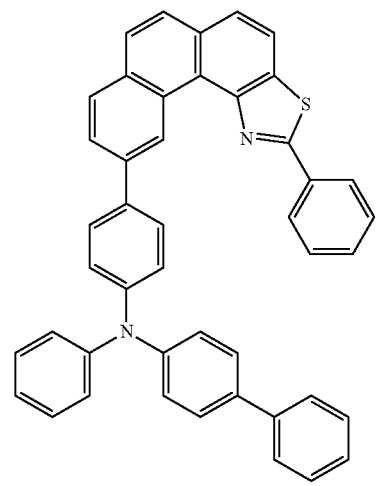
H1-62
H1-63
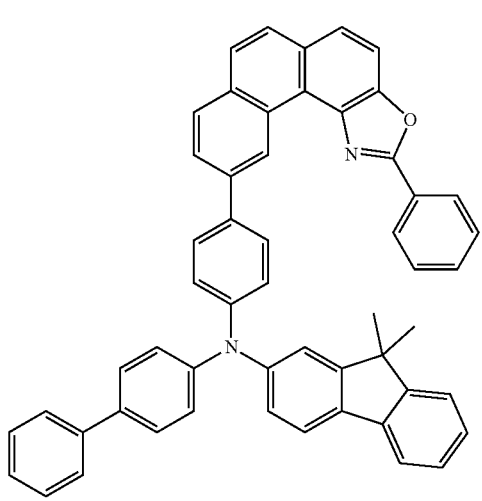
H1-64
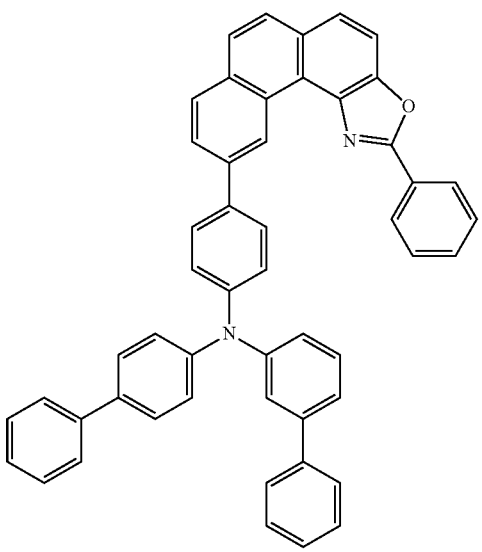
H1-65
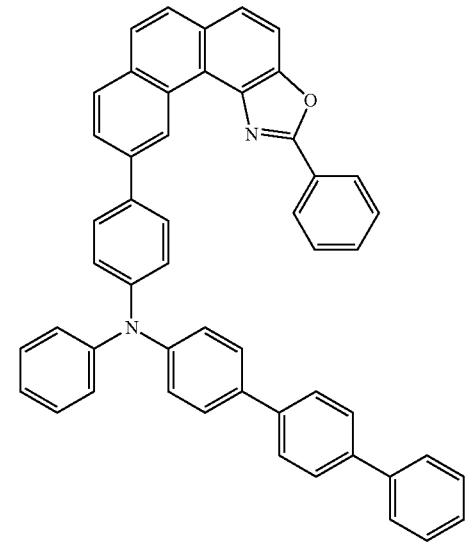
H1-66
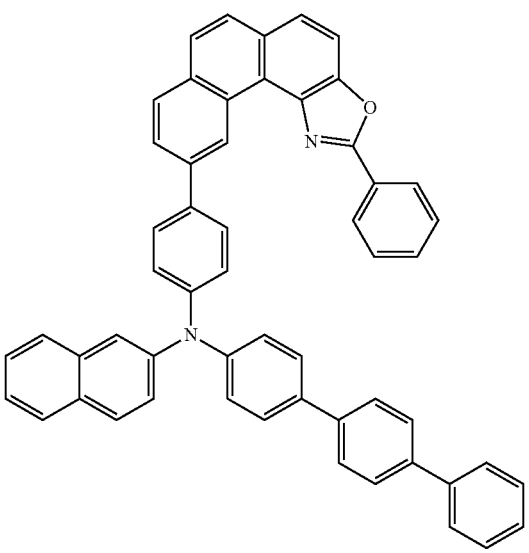

H1-67
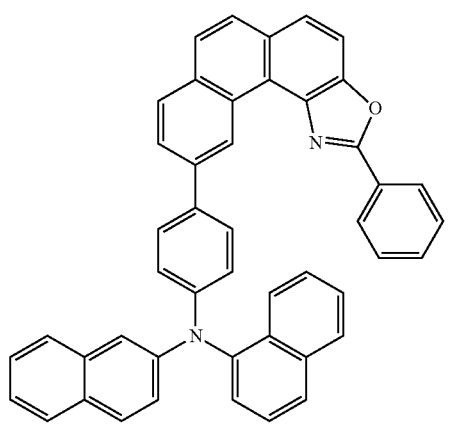
H1-68
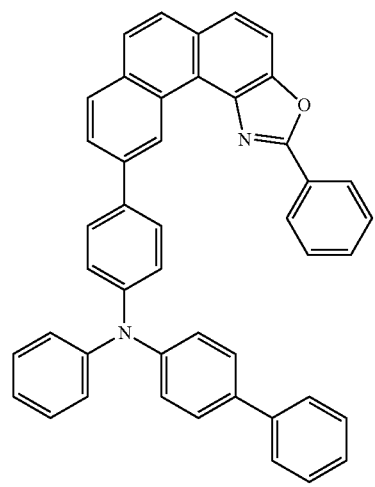
H1-69
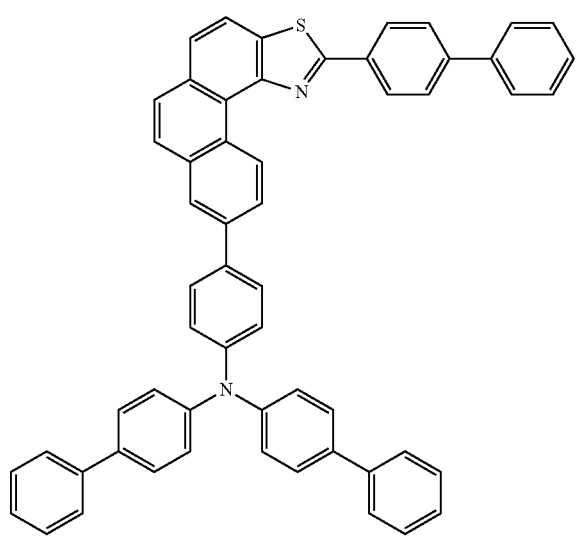
H1-70
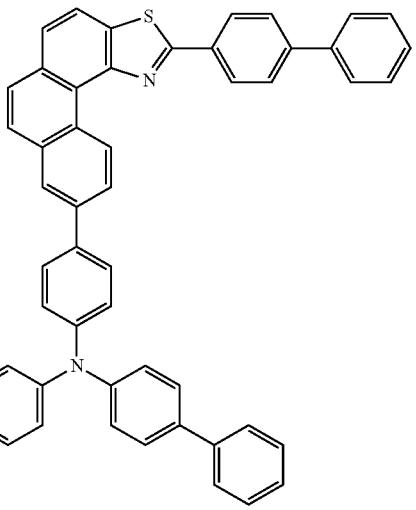
H1-71
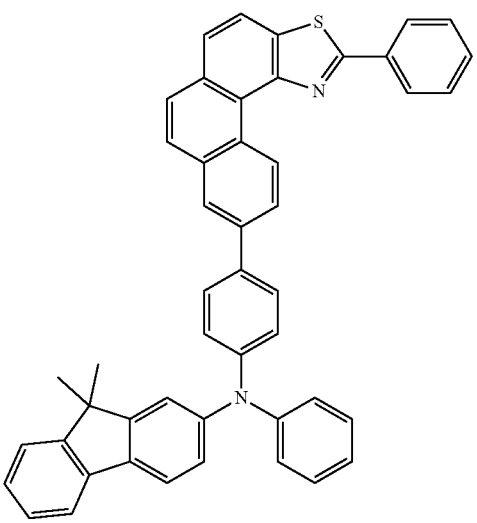
H1-72
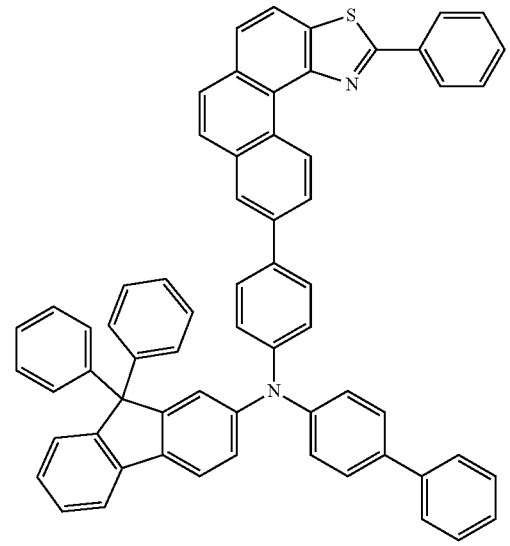

-continued
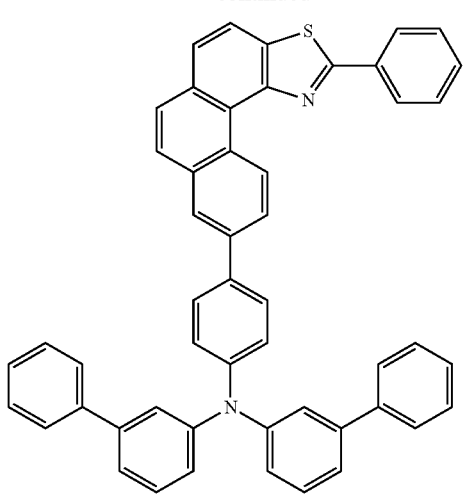
H1-73
H1-74
H1-75
-continued
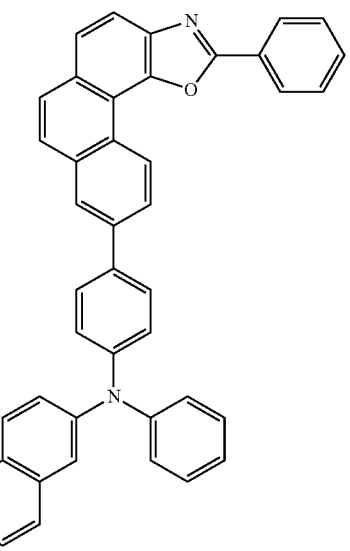
H1-76
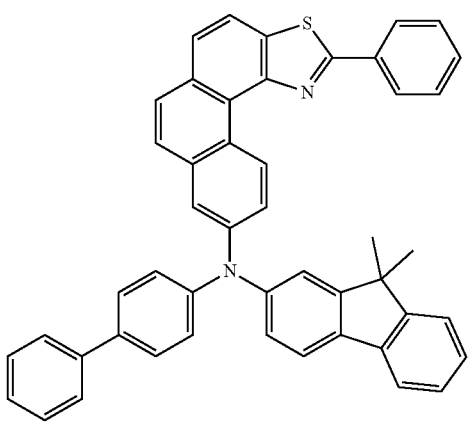
H1-77
H1-78

-continued
H1-79
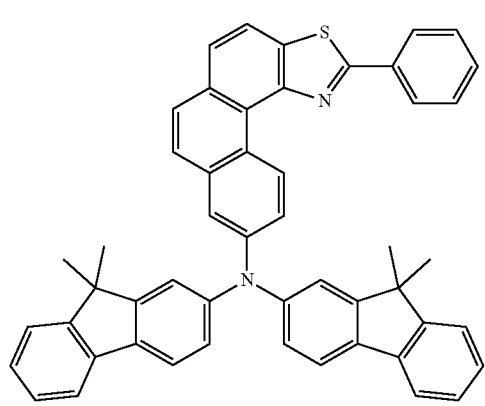
H1-80
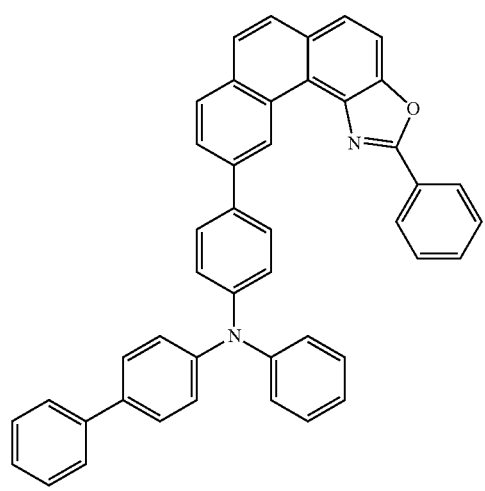
H1-81
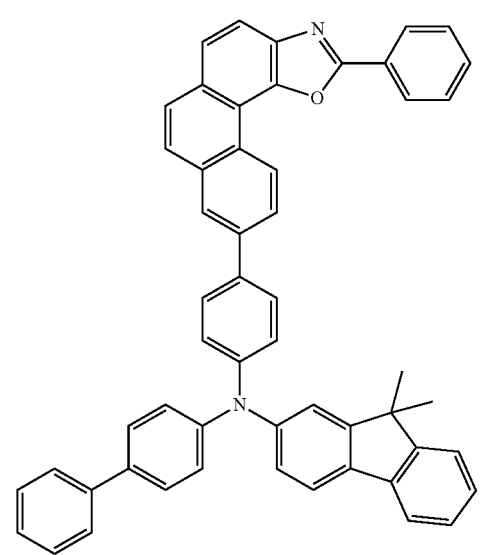
-continued
H1-82
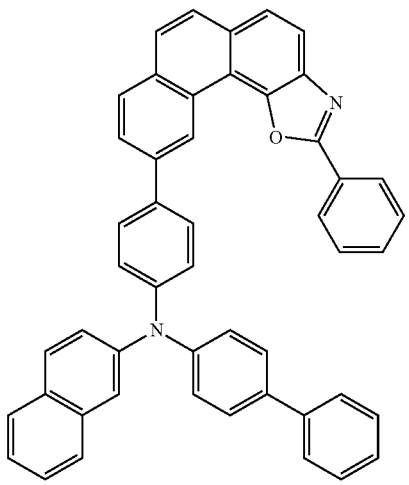
H1-83
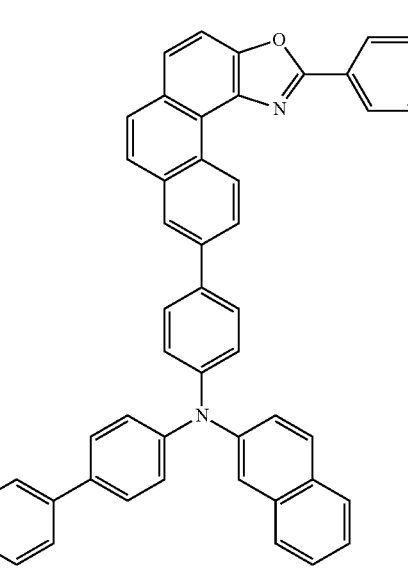
H1-84
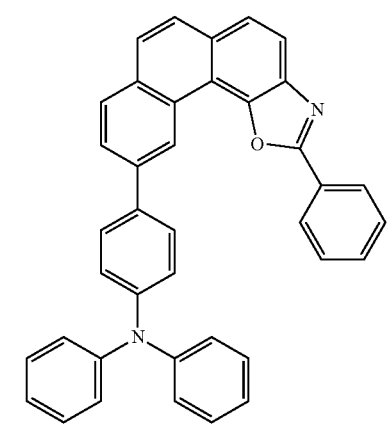

H1-85
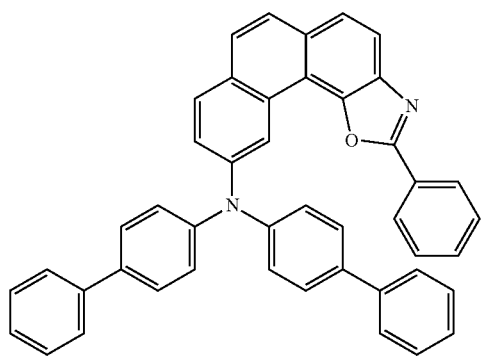
H1-86
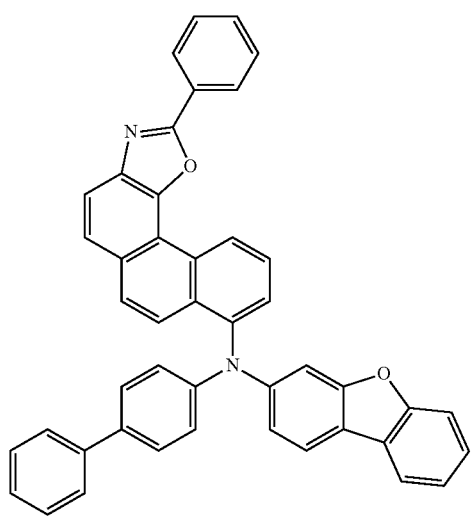
H1-87
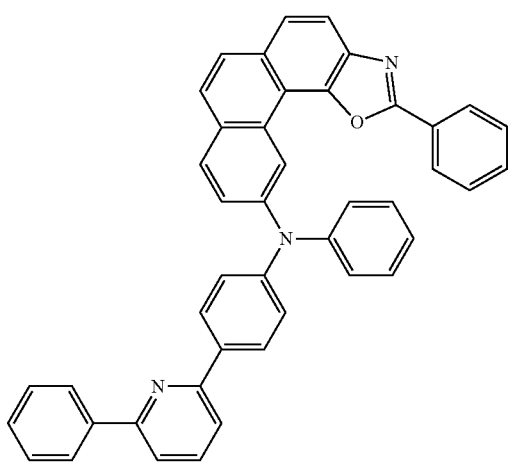
H1-88
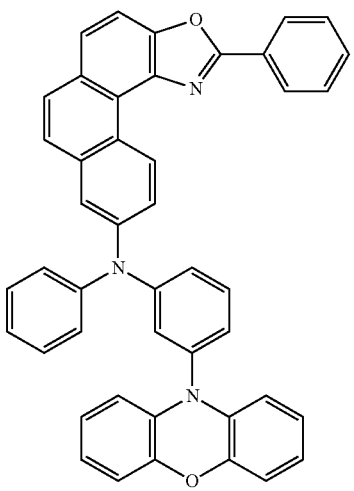
H1-89
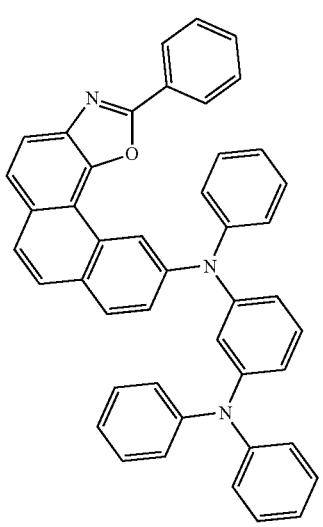
H1-90
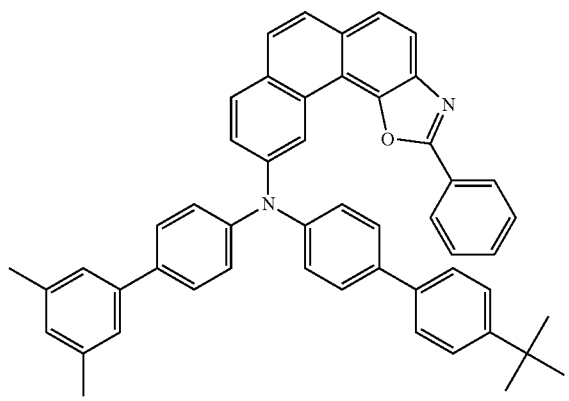

H1-91
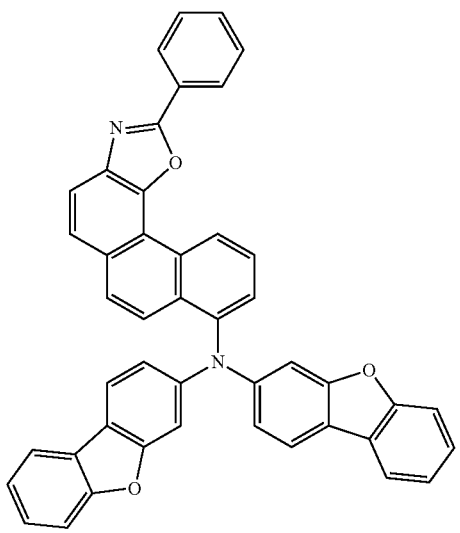
H1-92
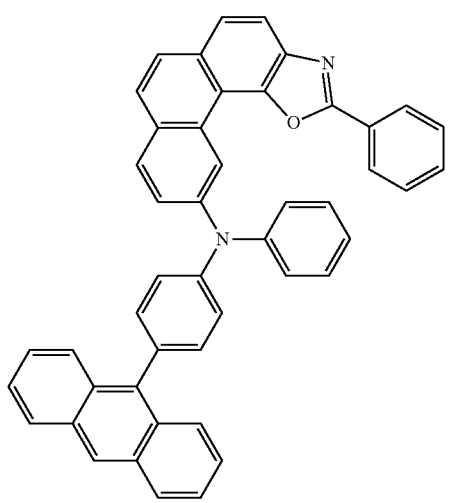
H1-93
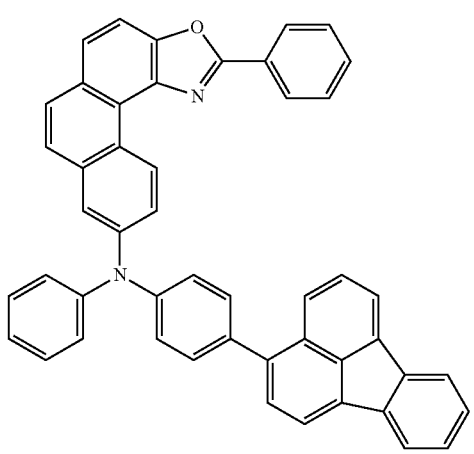
H1-94
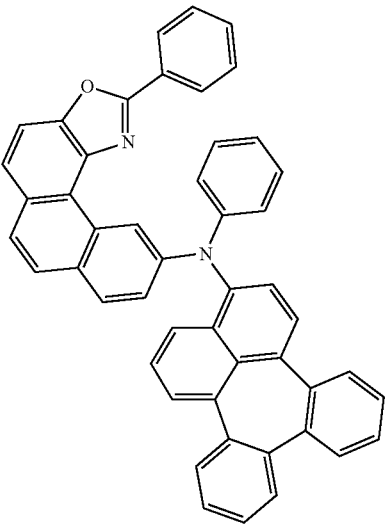
H1-95
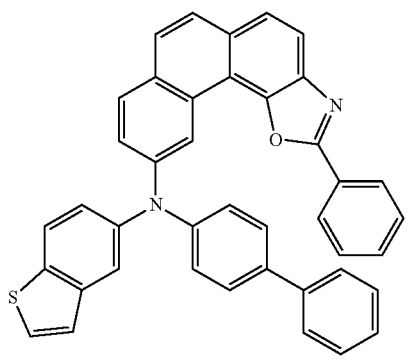
H1-96
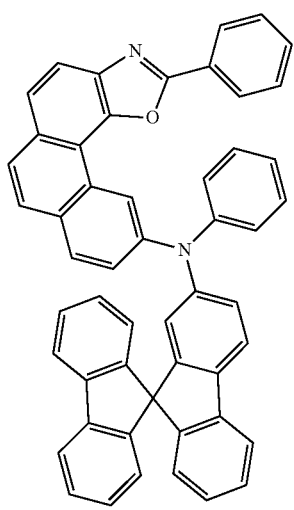

H1-97
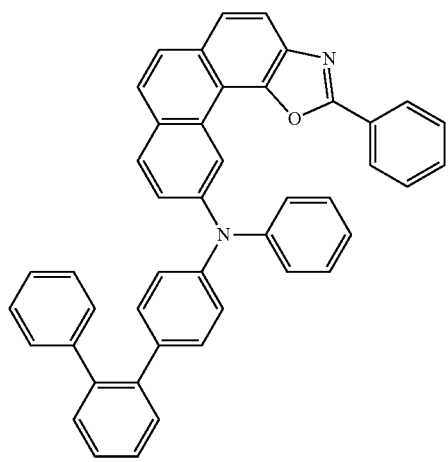
H1-98
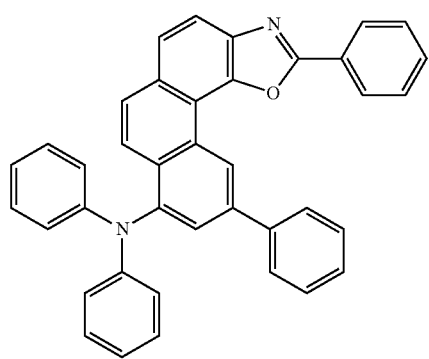
H1-99
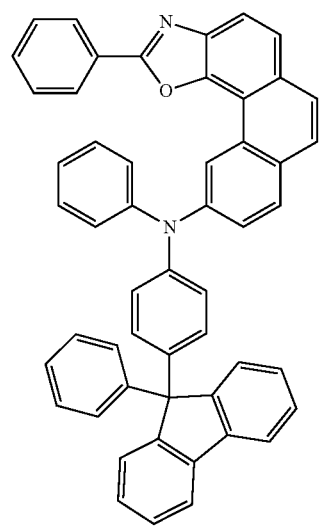
H1-100
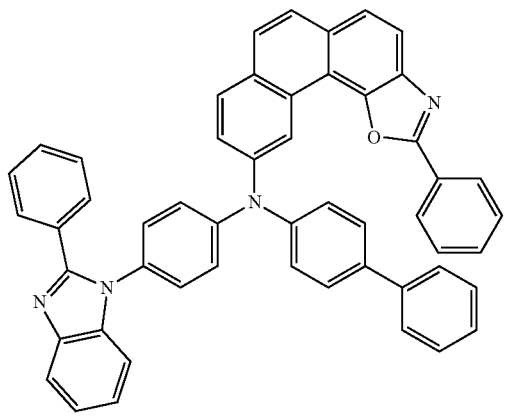
H1-101
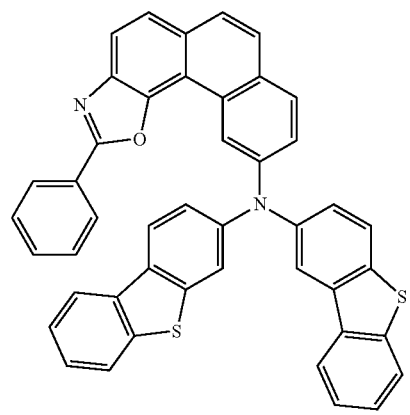
H1-102
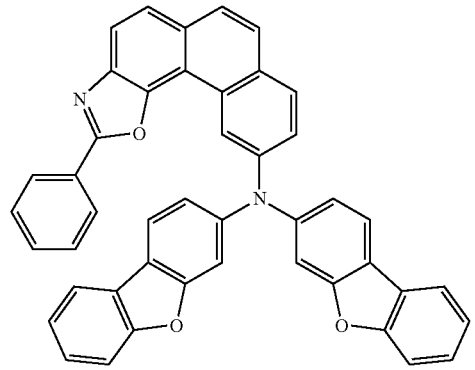
H1-103
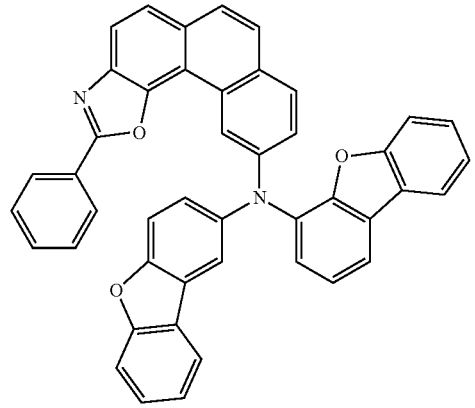

H1-104
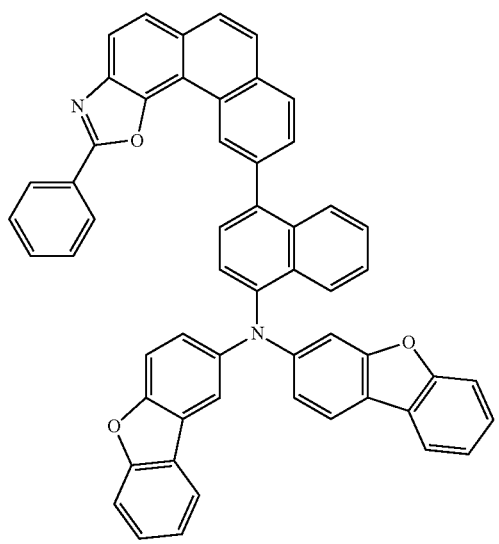
H1-105
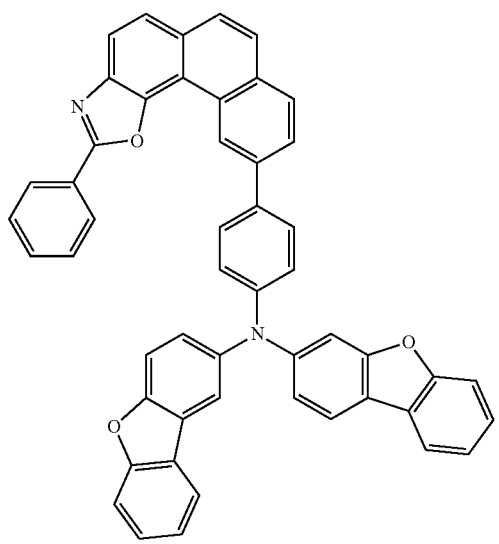
H1-106
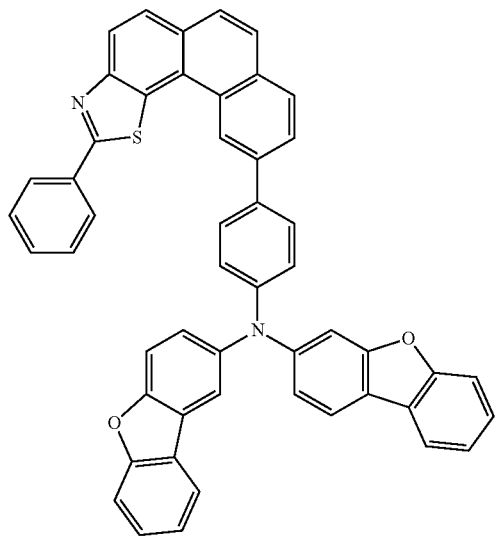
H1-107
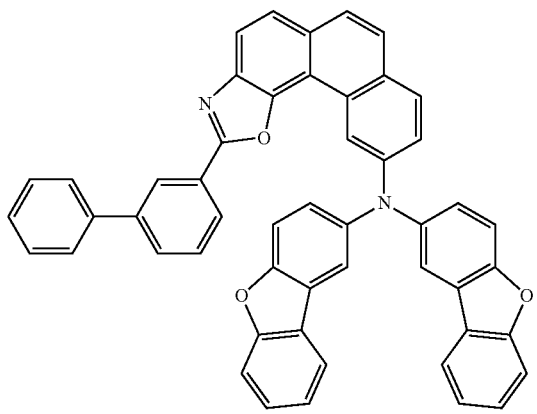
H1-108
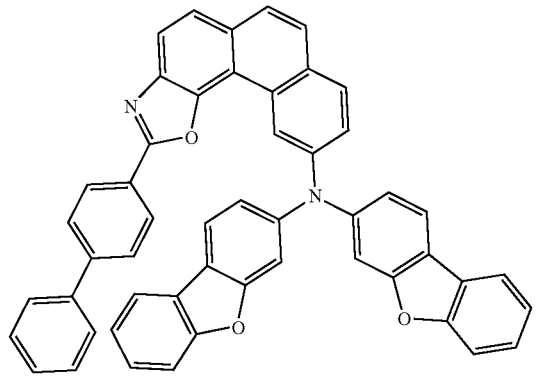

H1-109
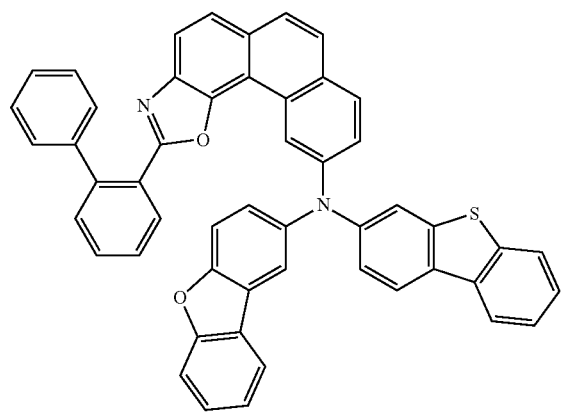
H1-112
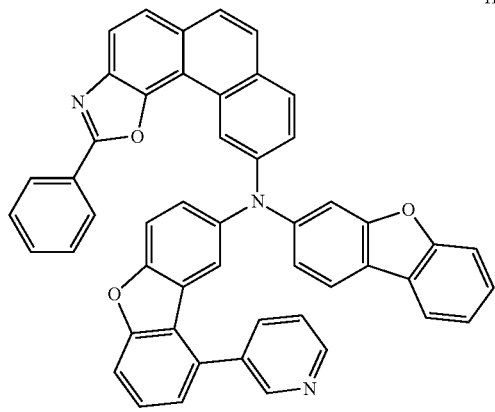
H1-110
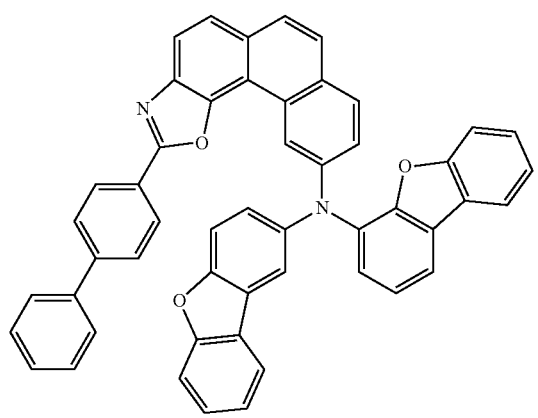
H1-113
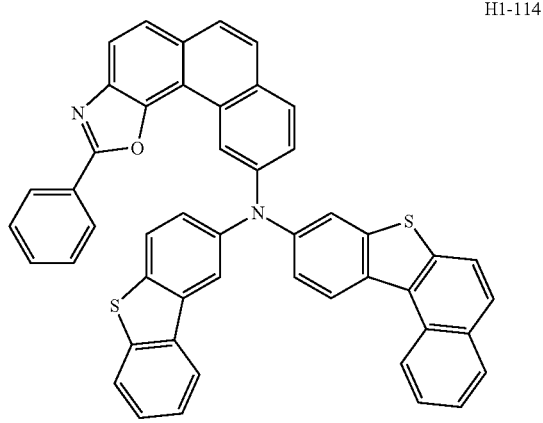
H1-111
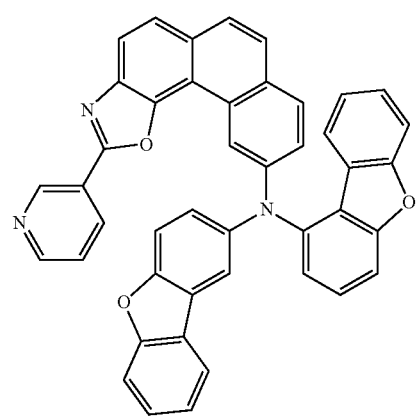
H1-114

H1-115 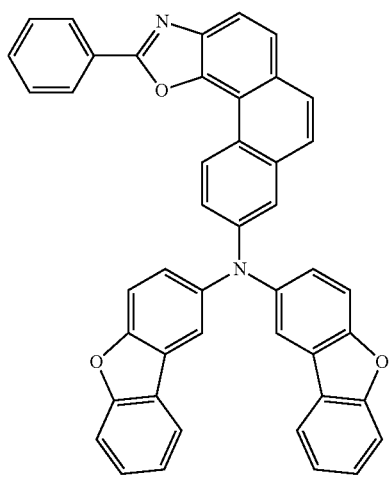
H1-118 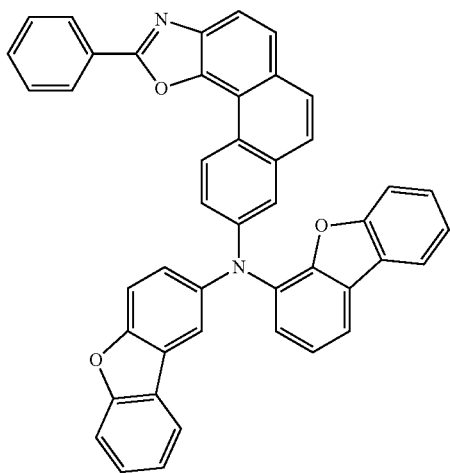
H1-116 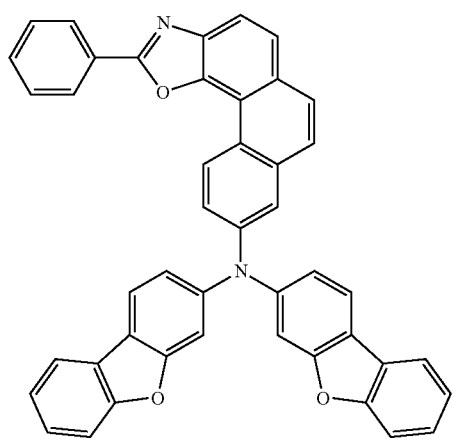
H1-119 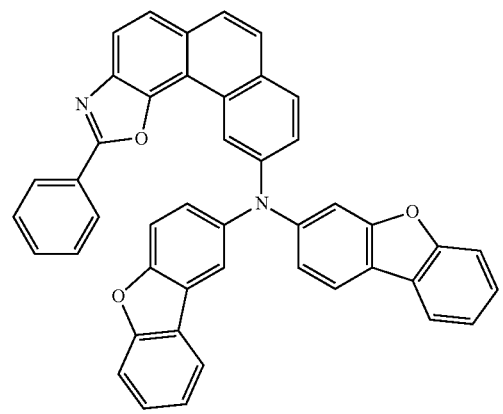
H1-117 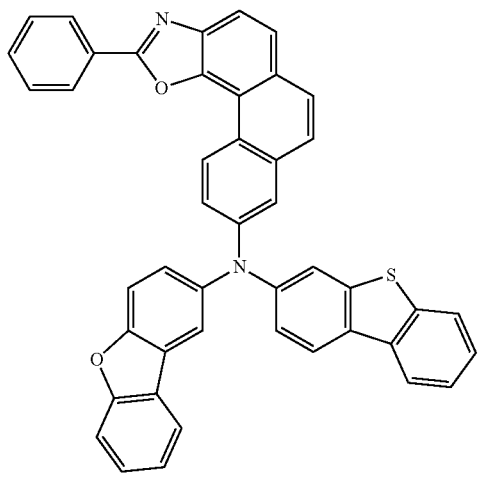
H1-120 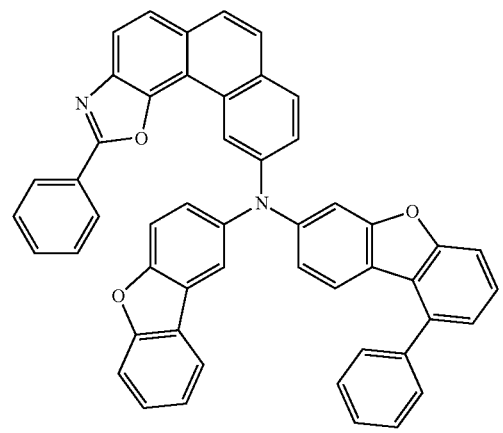

H1-121
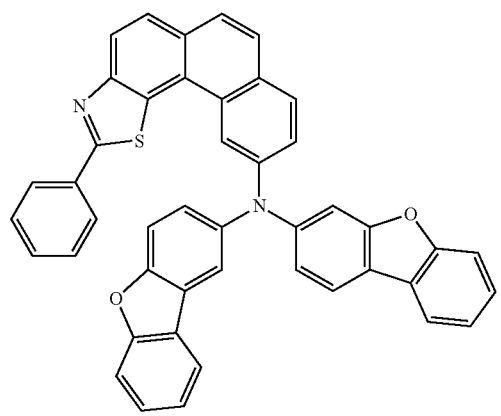
H1-124
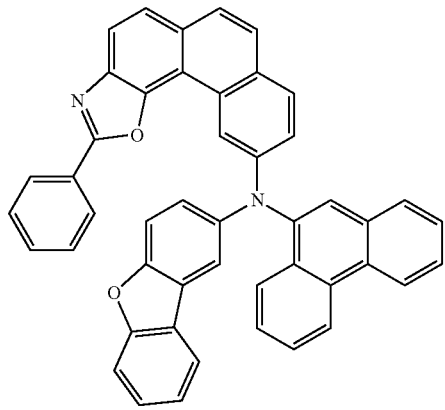
H1-122
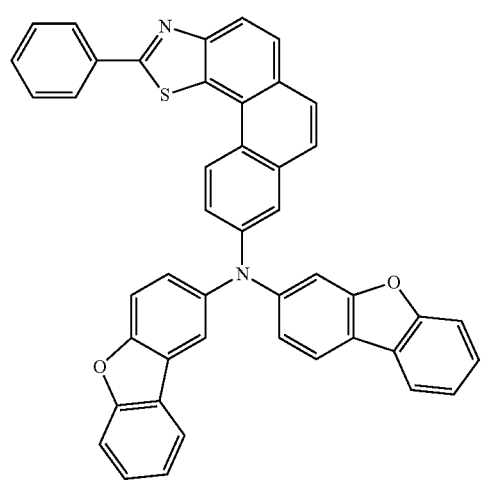
H1-125
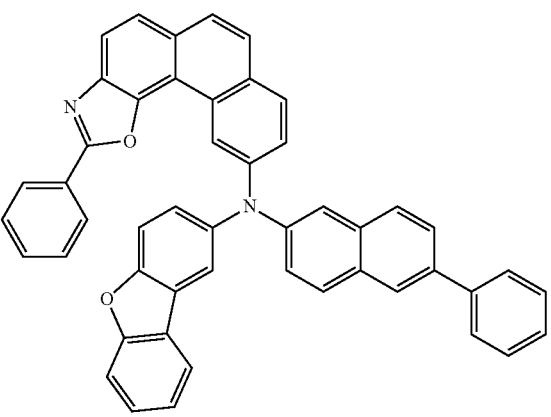
H1-123
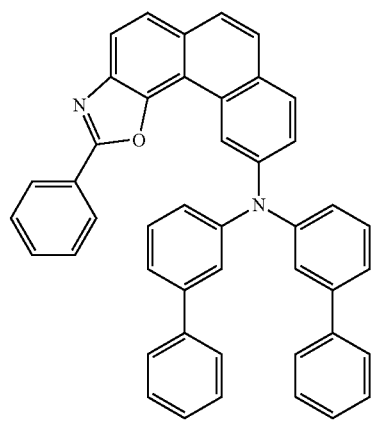
H1-126
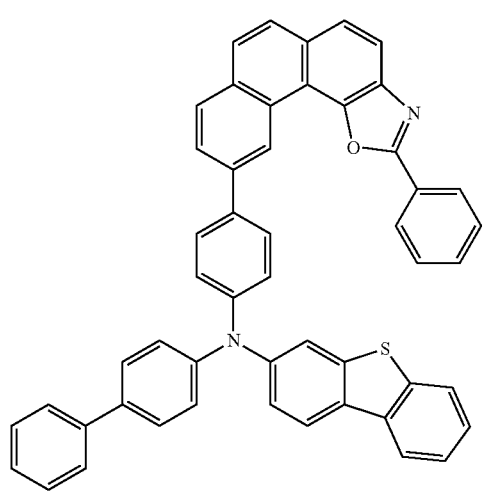

H1-127
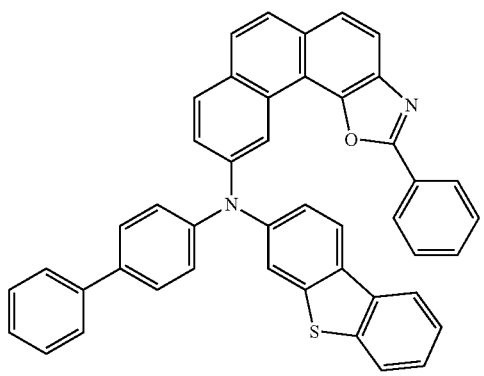
H1-128
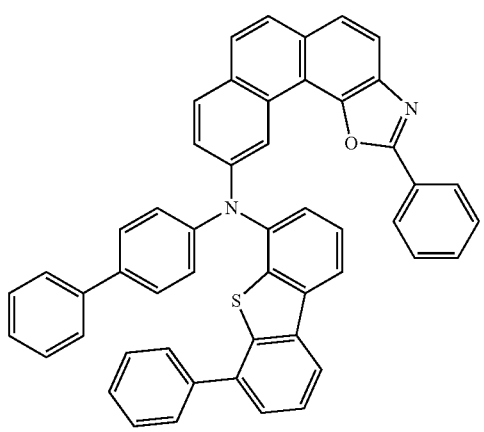
H1-129
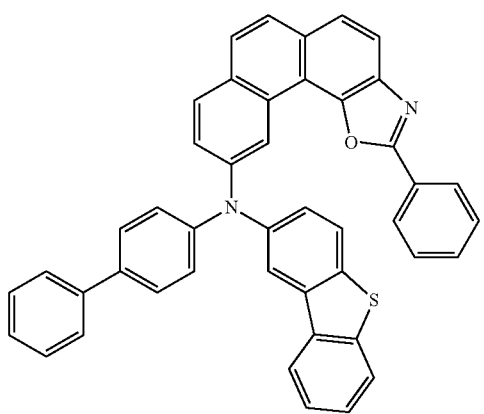
H1-130
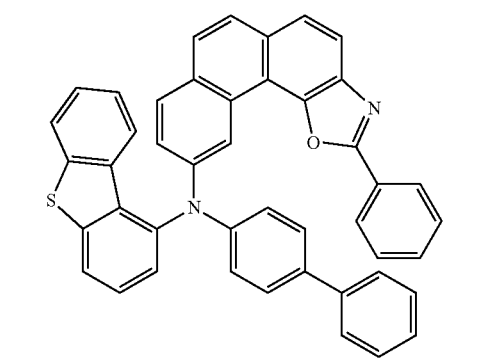
H1-131
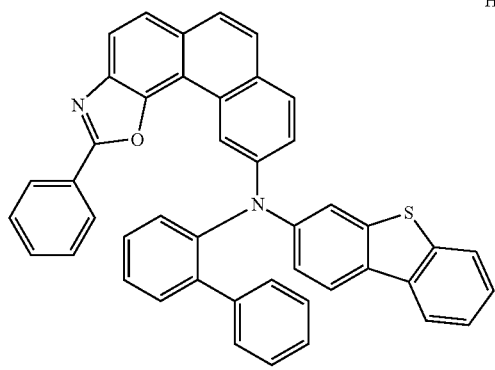
H1-132
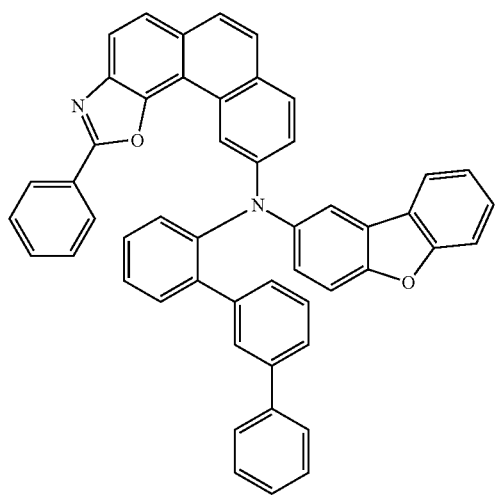
H1-133
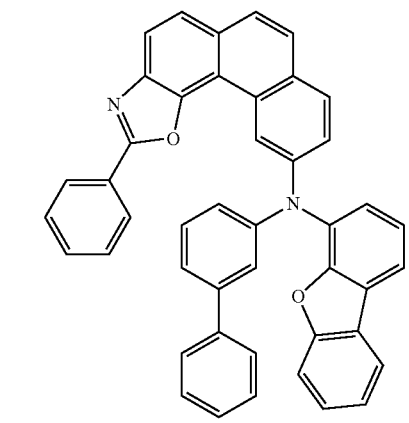

H1-134
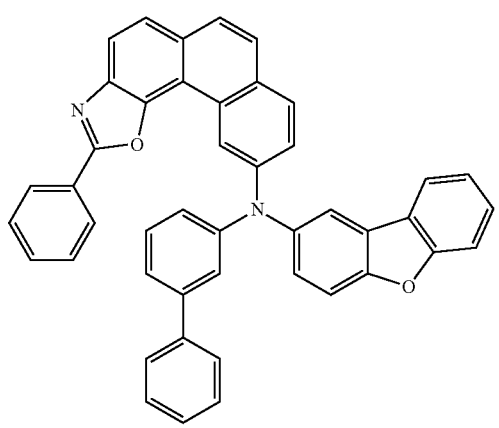
H-135
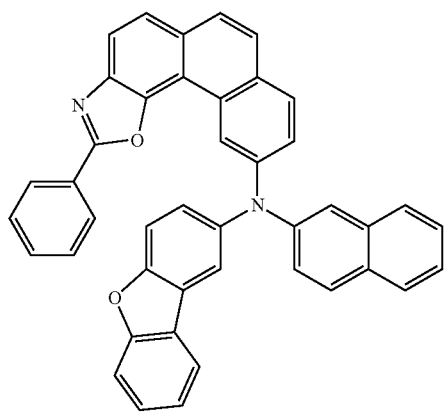
H-136
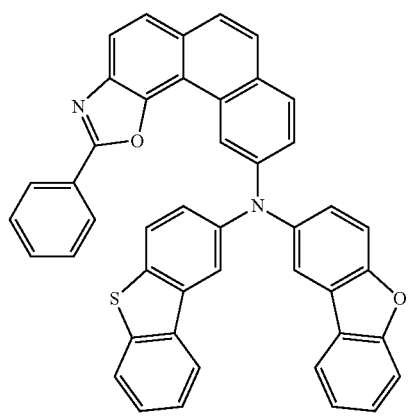
The compound represented by formula 3 may be at least one selected from the following compounds, but is not limited thereto.
H2-1
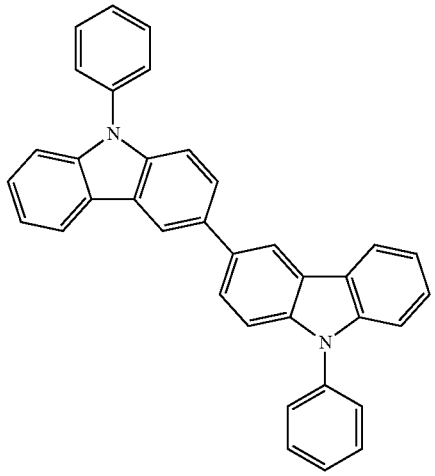
H2-2
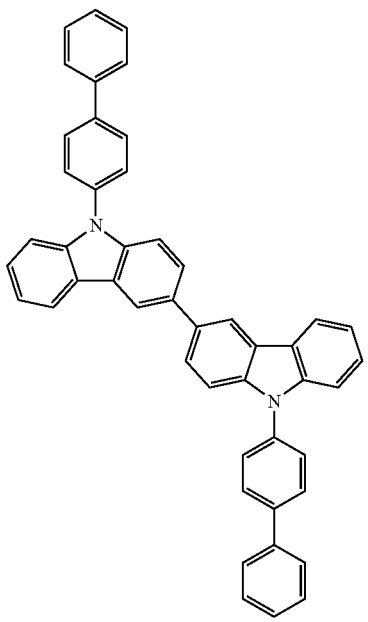

H2-3
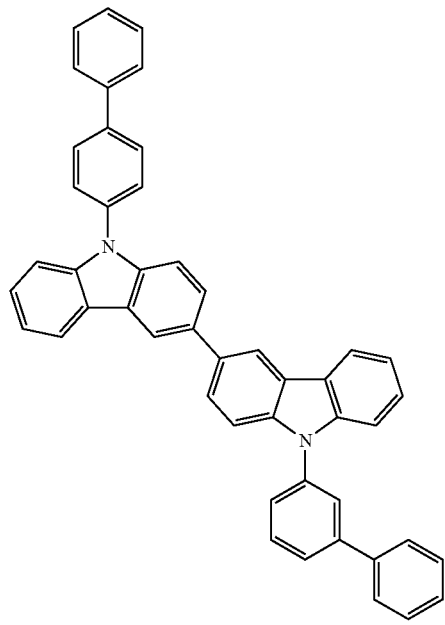
H2-4
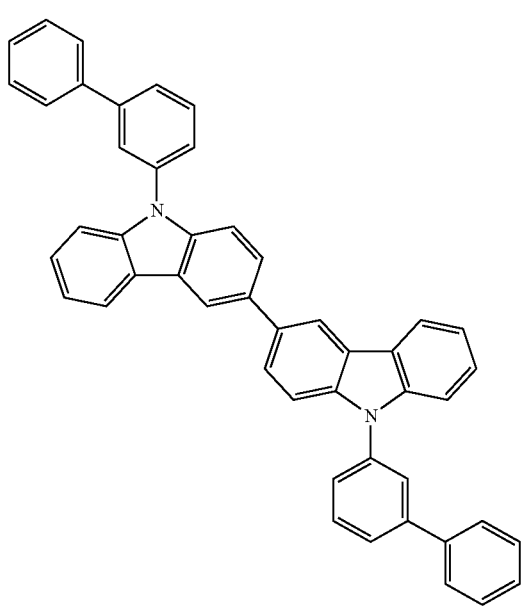
H2-5
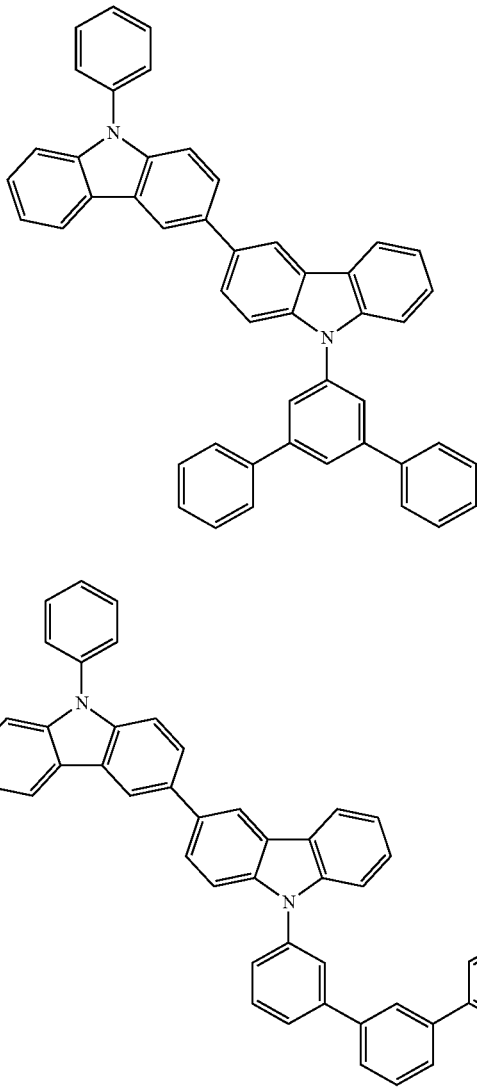
H2-6
H2-7
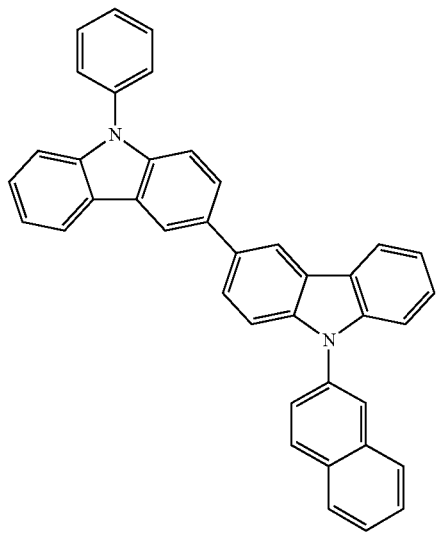

-continued
H2-8
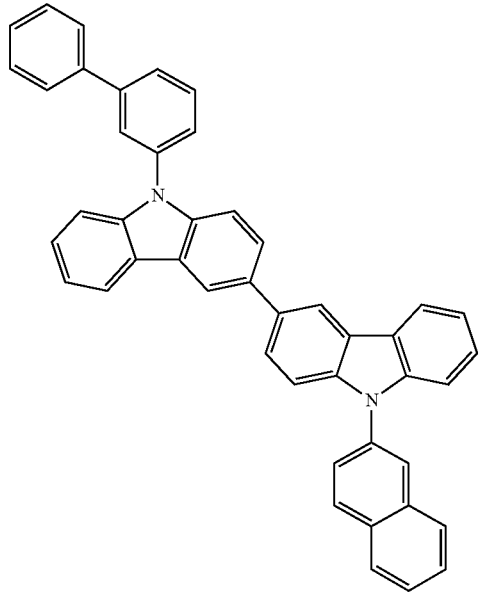
H2-9
H2-11
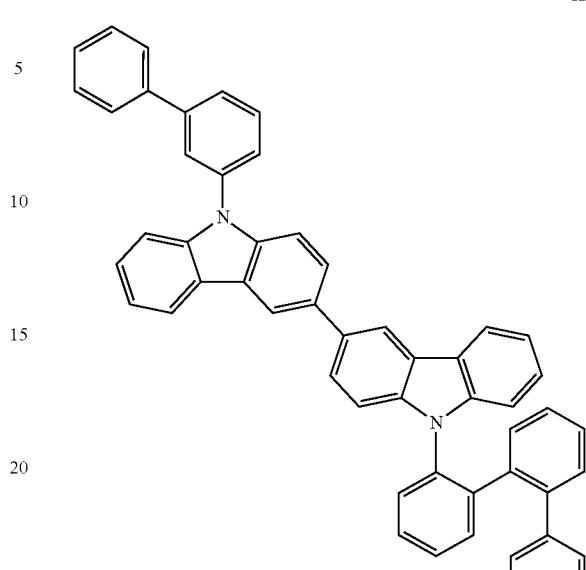
H2-10
H2-12
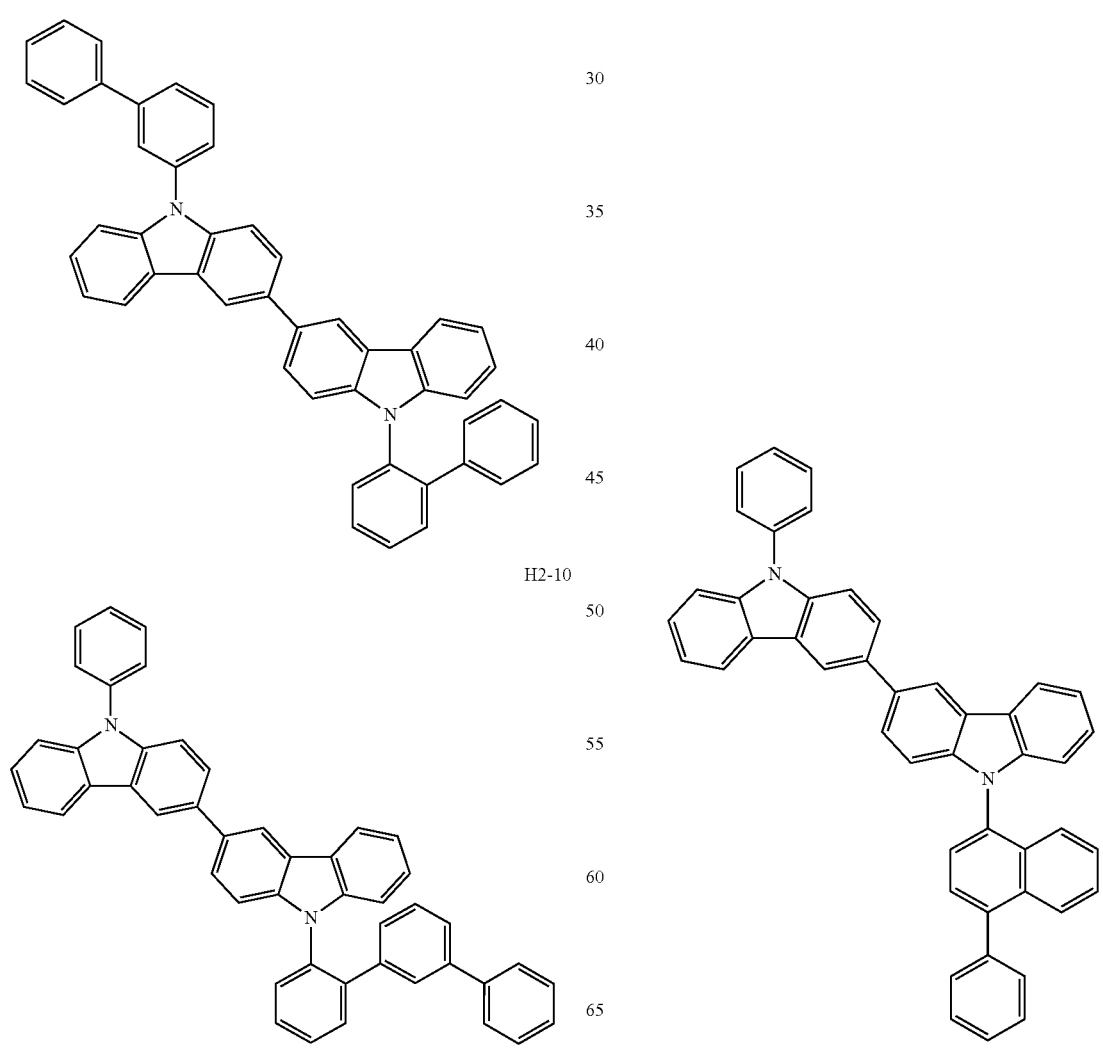

H2-13
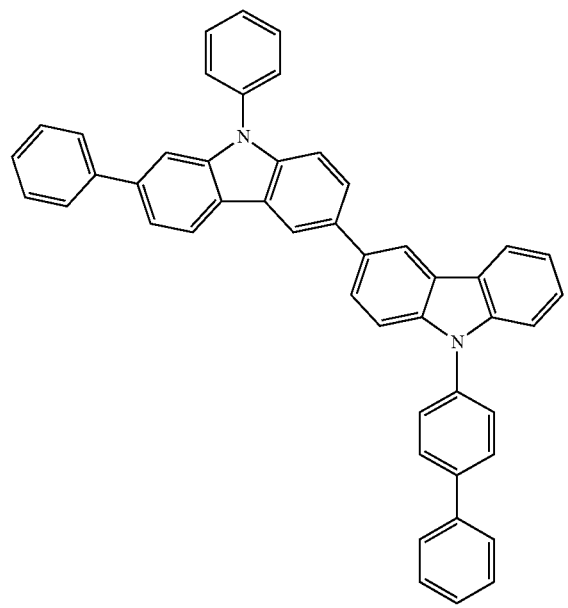
H2-14
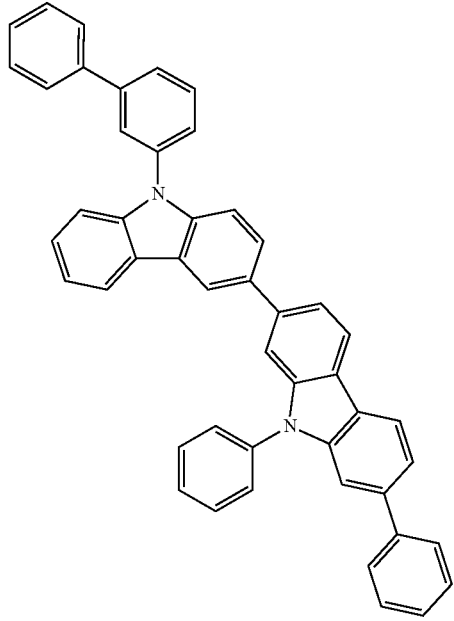
H2-15
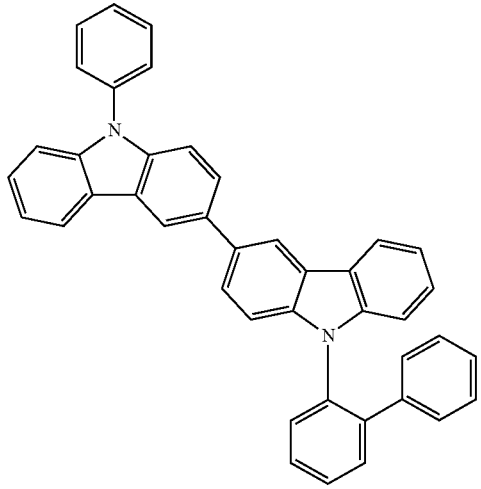
H2-16
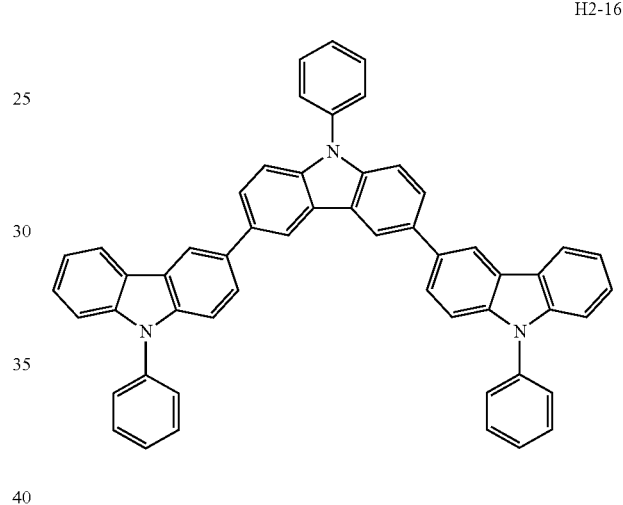
H2-17
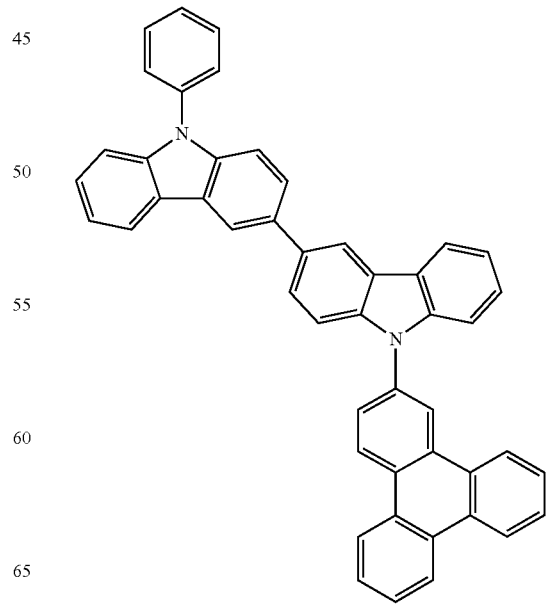

H2-18
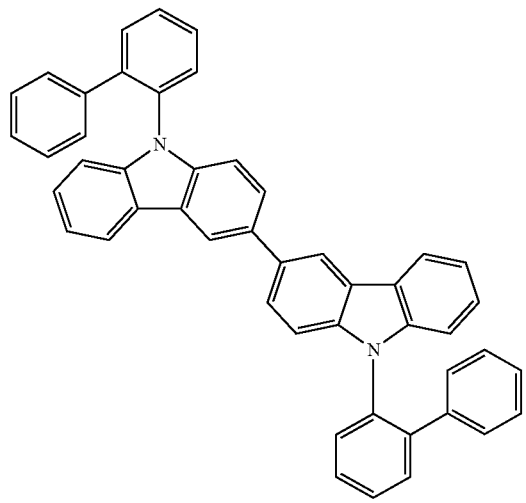
H2-19
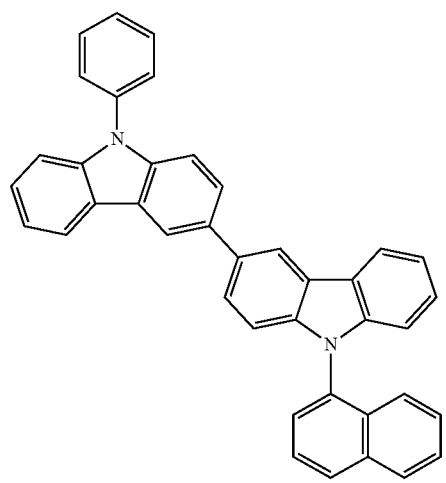
H2-20
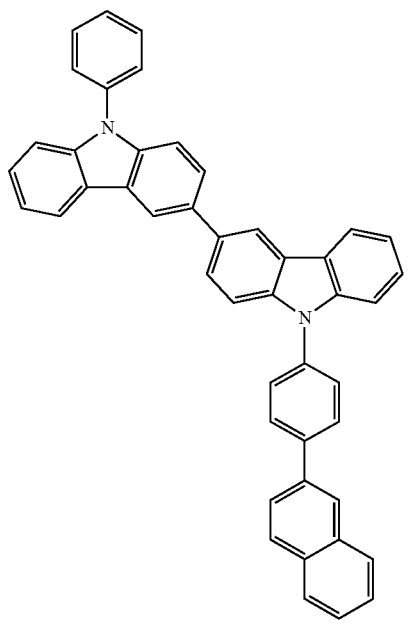
H2-21
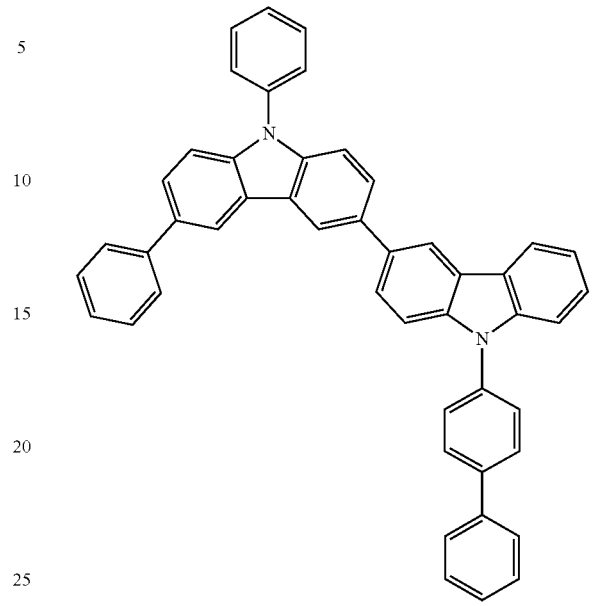
H2-22
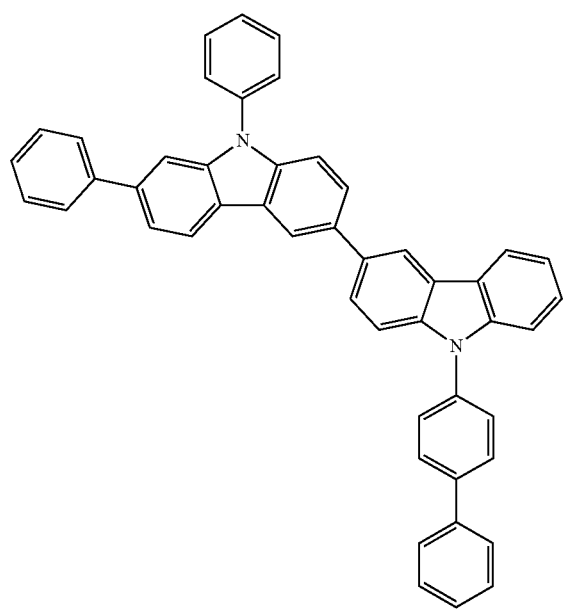

-continued
H2-23
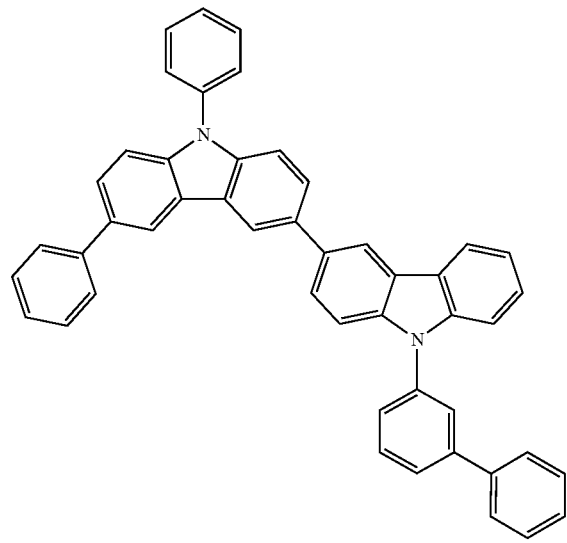
H2-25
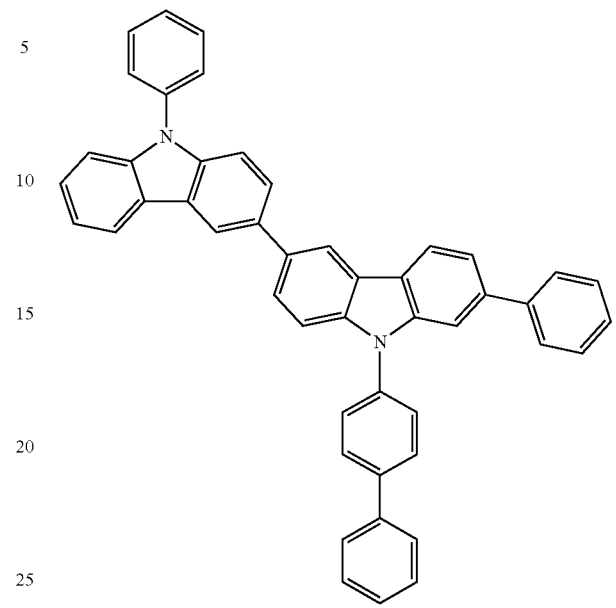
H2-24
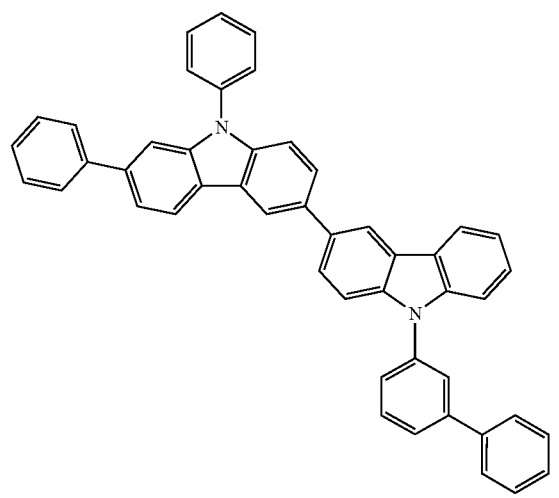
H2-26
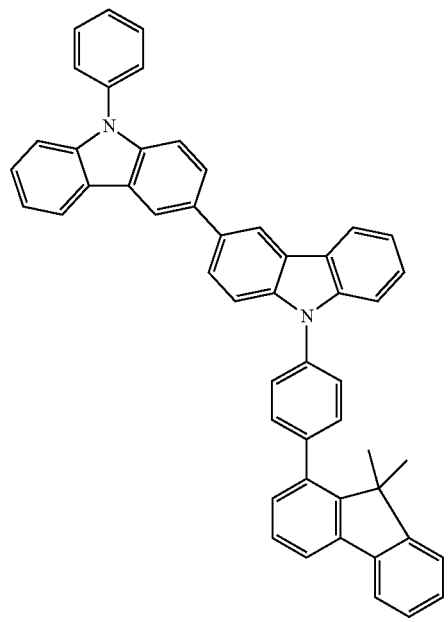

329
-continued
330
-continued
H2-27
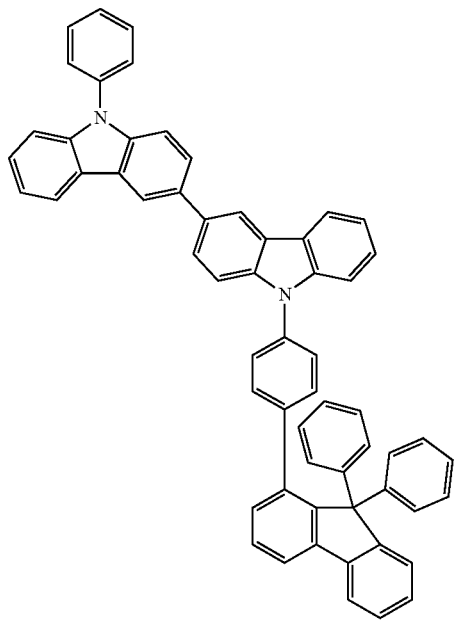
H2-29
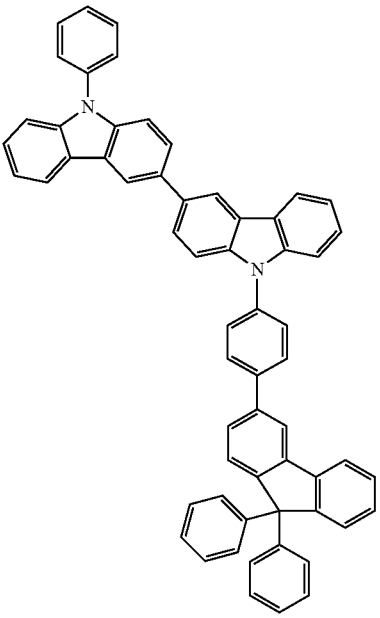
H2-28
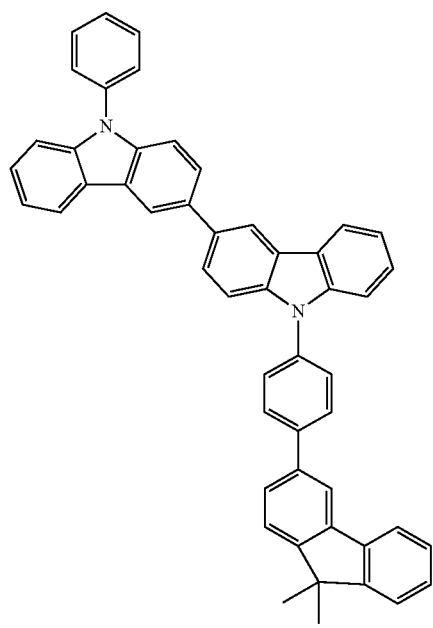
H2-30
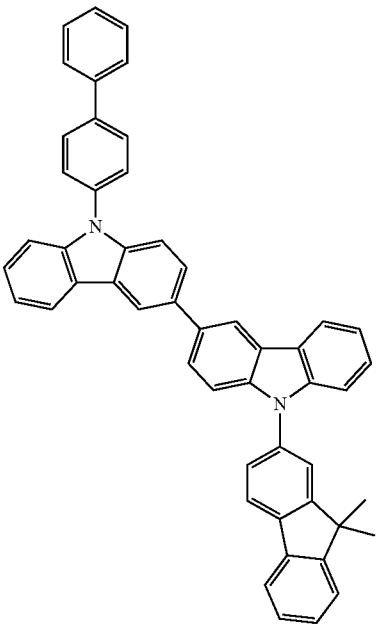

H2-31
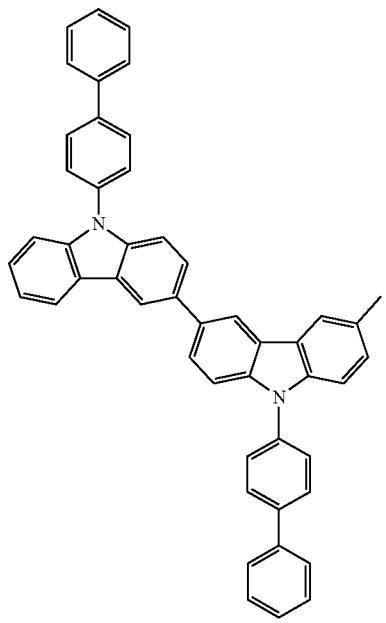
H2-33
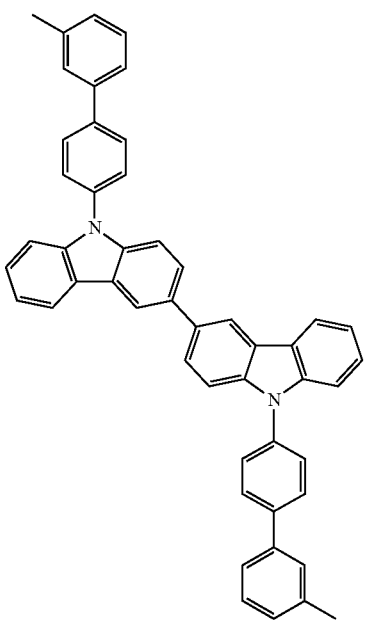
H2-32
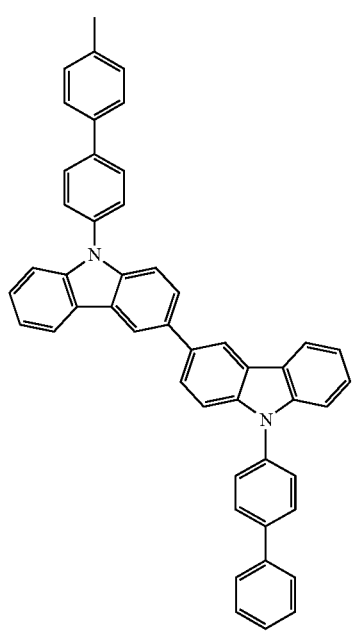
H2-34
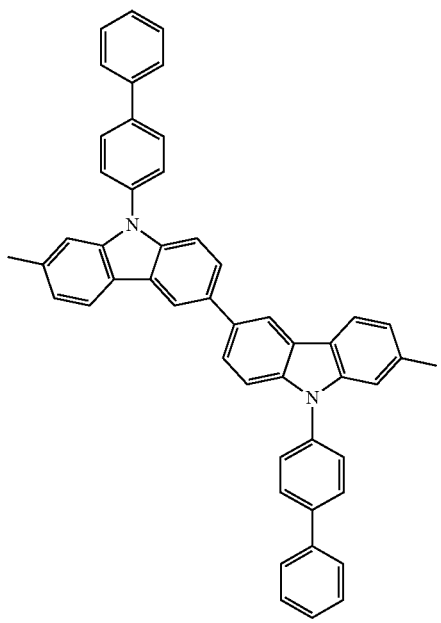

H2-35
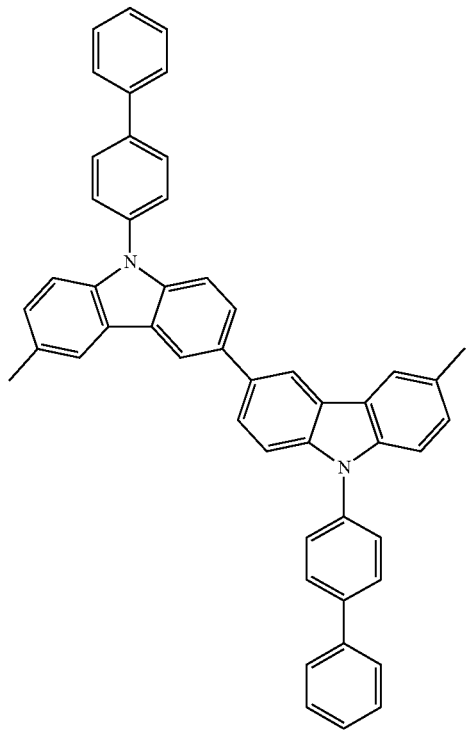
H4-2
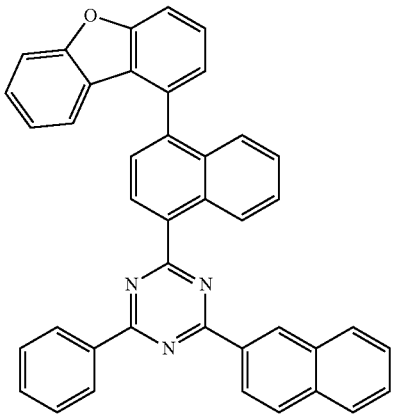
H4-3
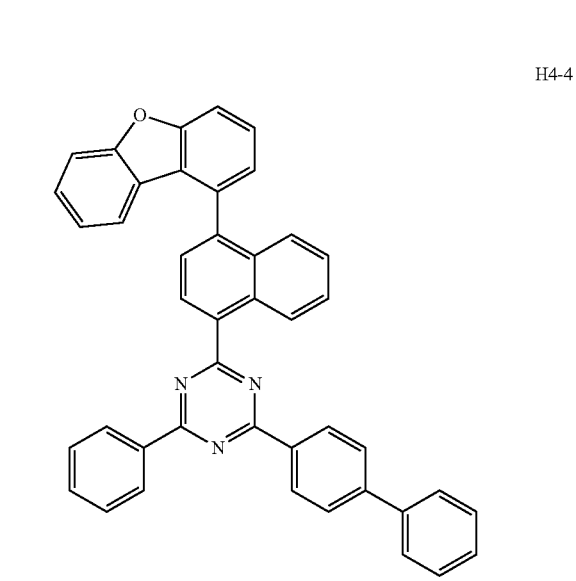
The compound represented by formula 4 may be at least one selected from the following compounds, but is not limited thereto.
H4-1
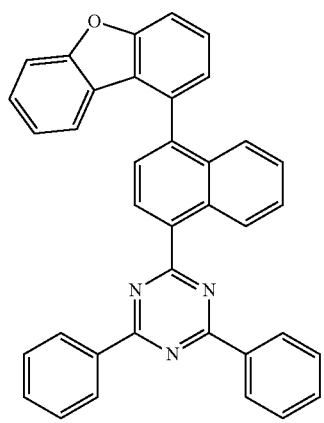
H4-4

H4-5
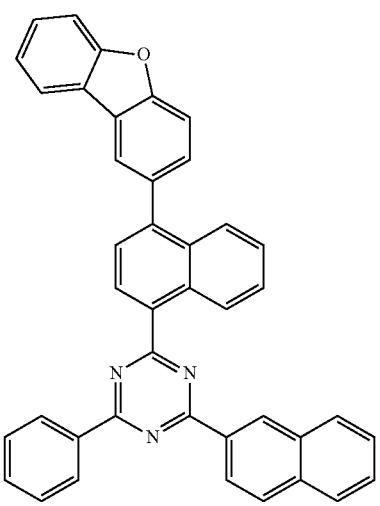
H4-6
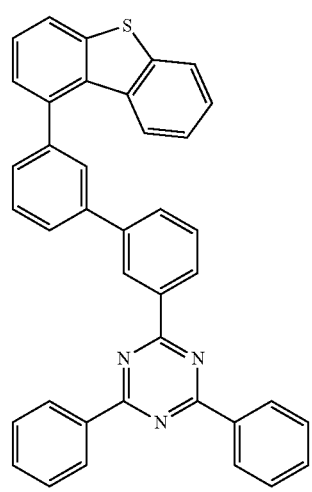
H4-7
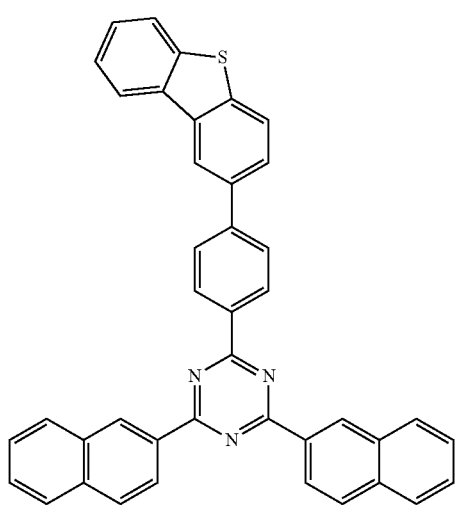
H4-8
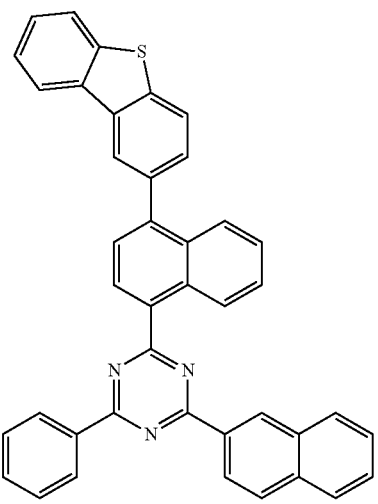
H4-9
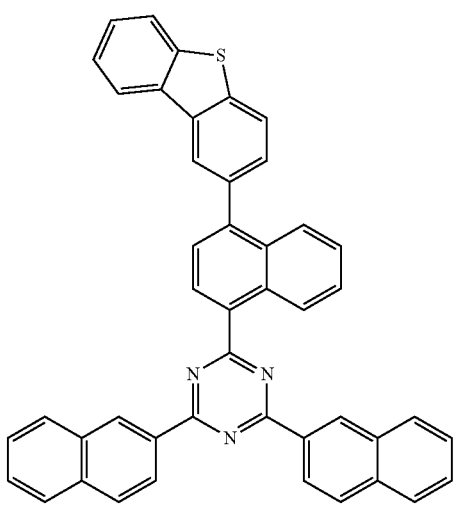
H4-10
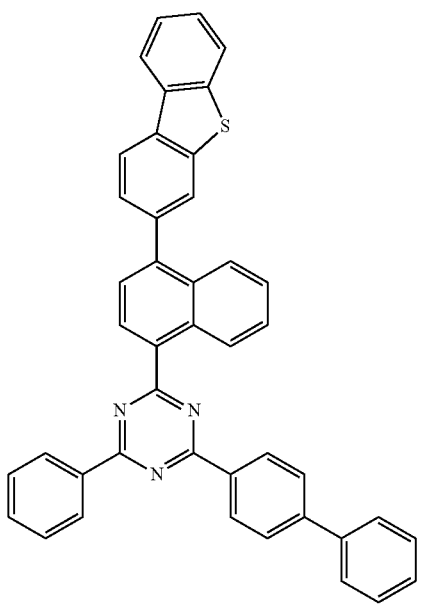

H4-11
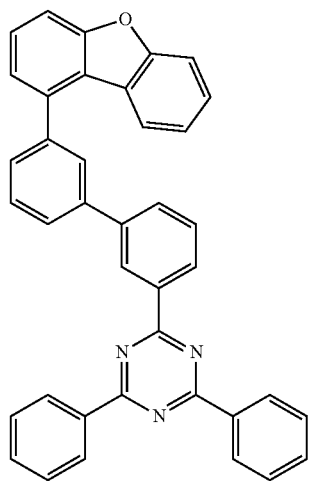
H4-12
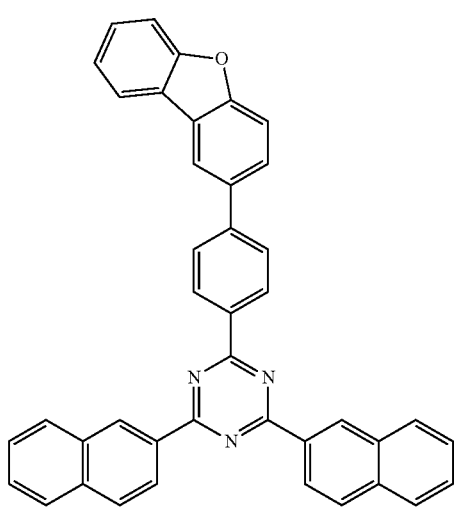
H4-13
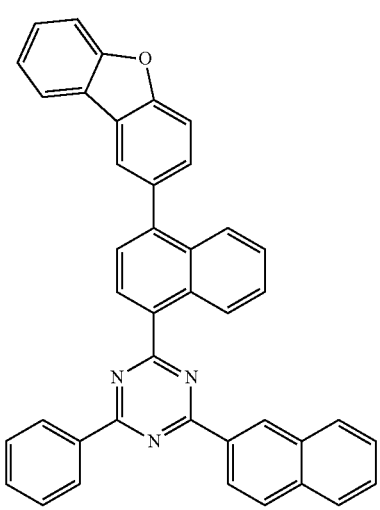
H4-14
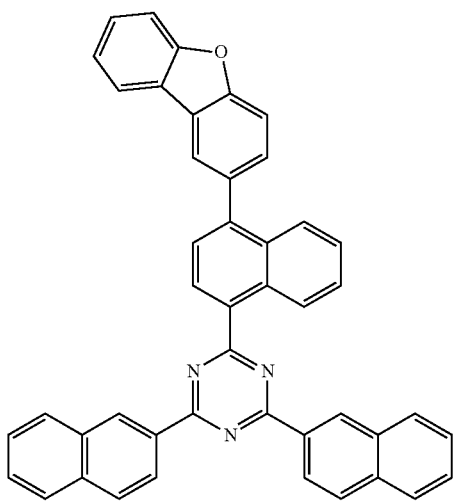
H4-15
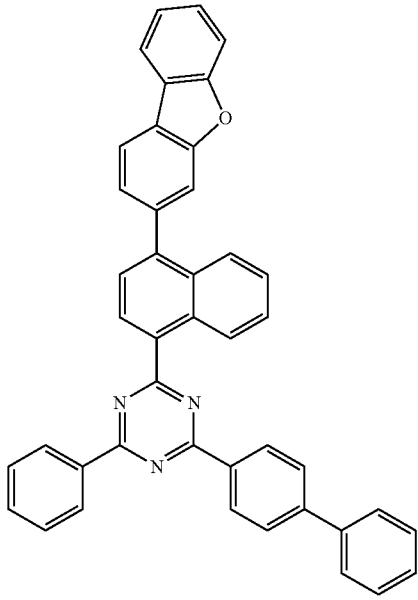
H4-16
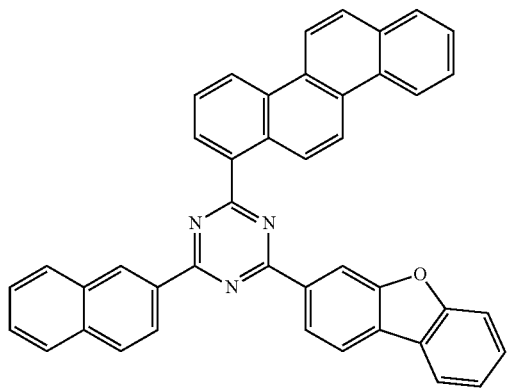

H4-17
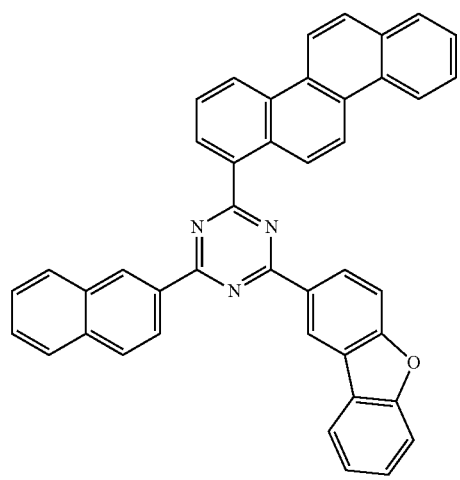
H4-18
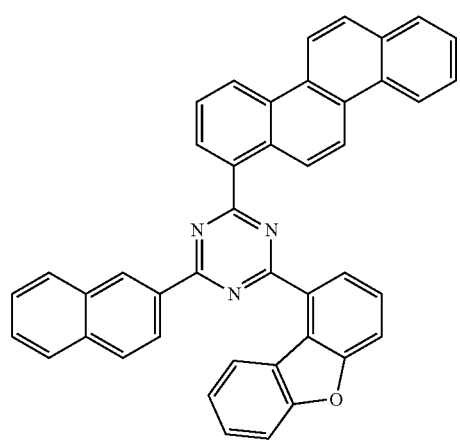
H4-19
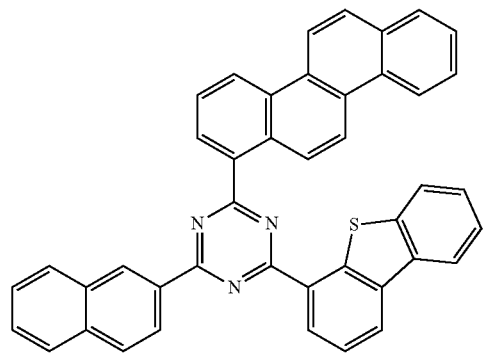
H4-20
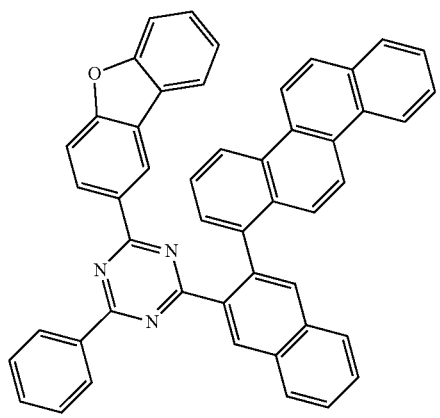
H4-21
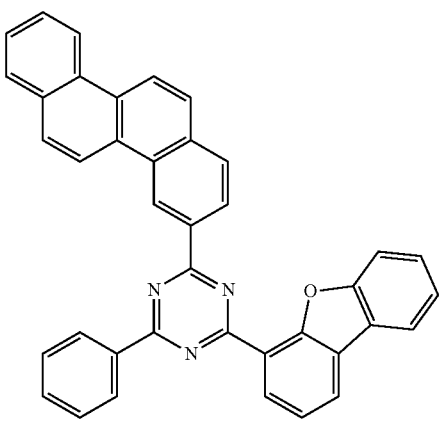
H4-22
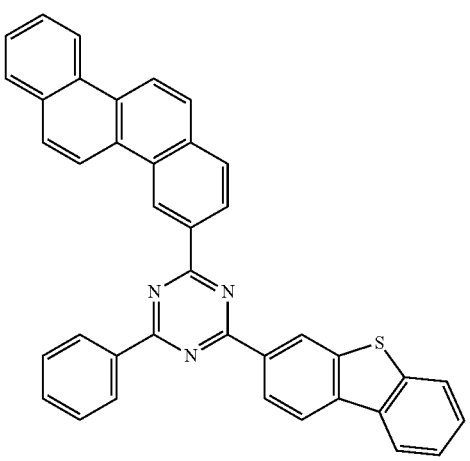

H4-23
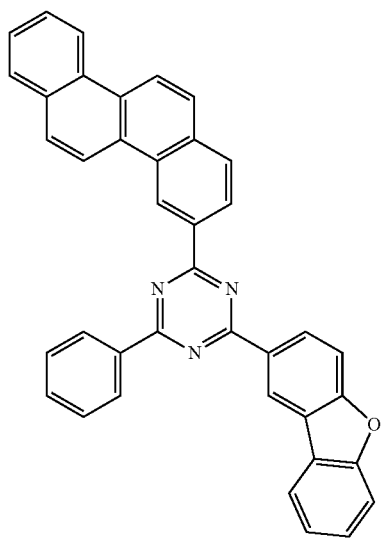
H4-24
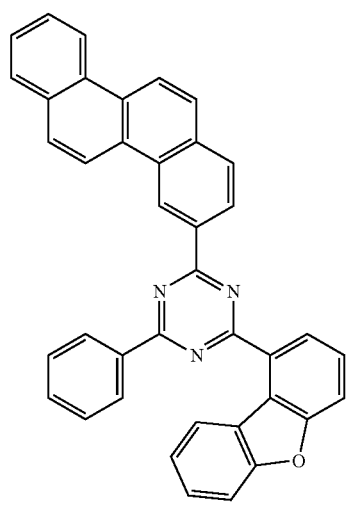
H4-25
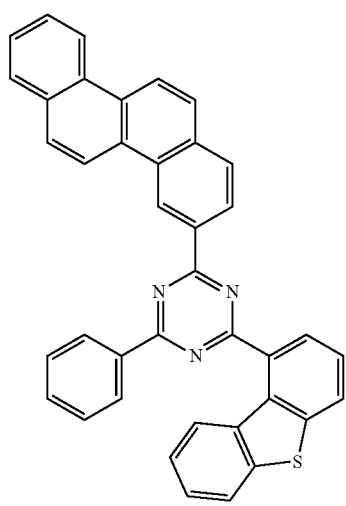
H4-26
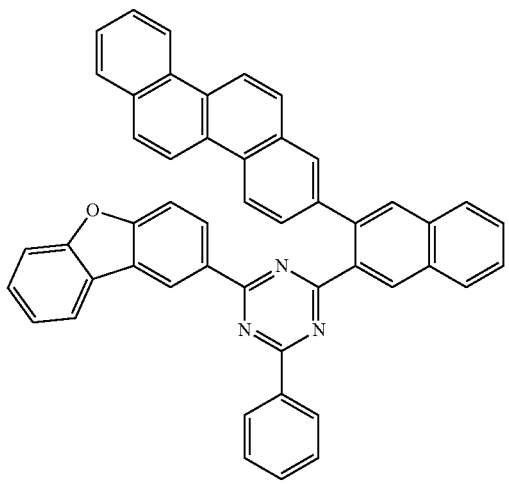
H4-27
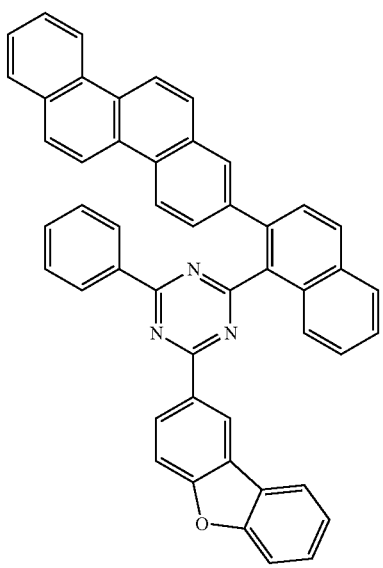
H4-28
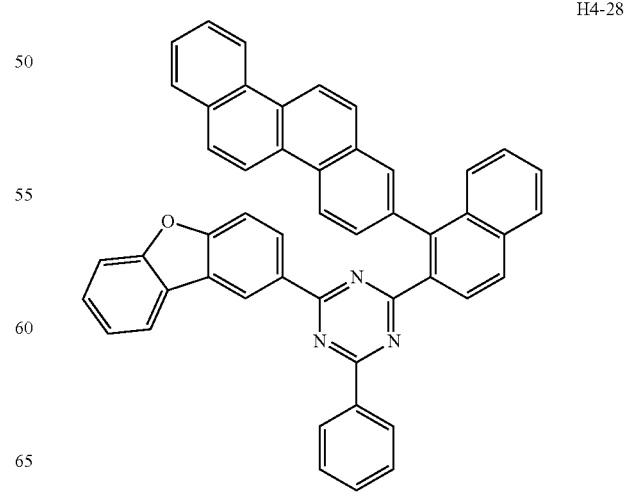

H4-29
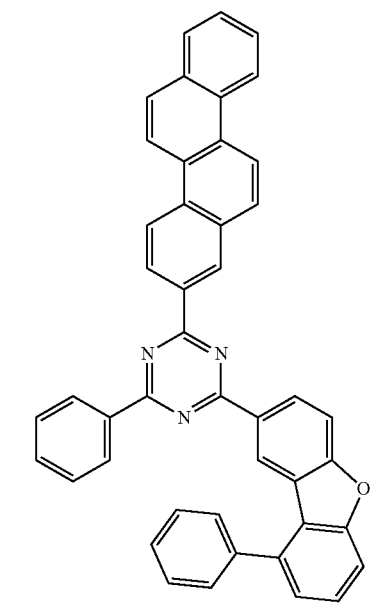
H4-30
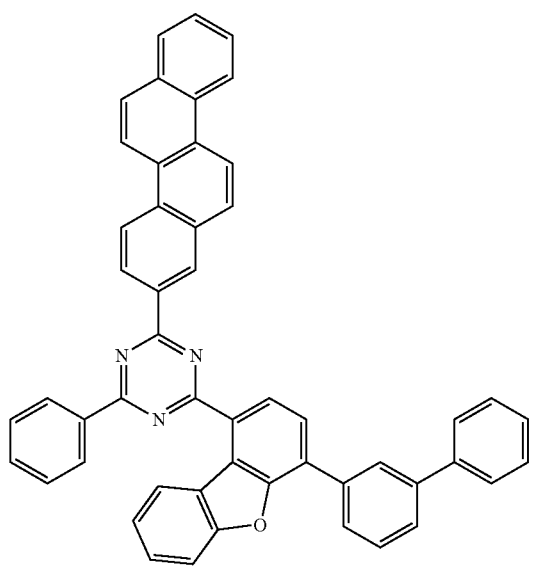
H4-31
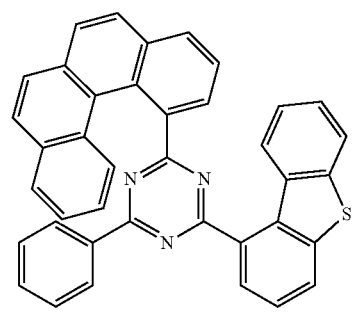
H4-32
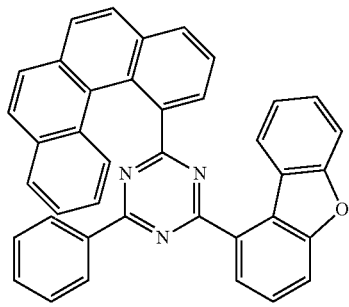
H4-33
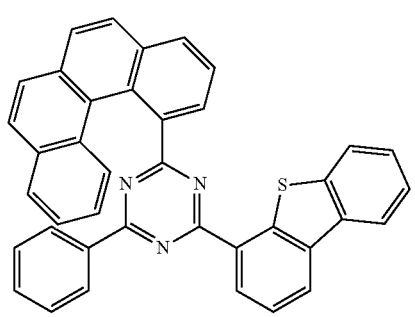
H4-34
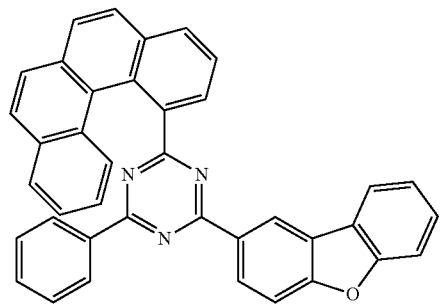
H4-35
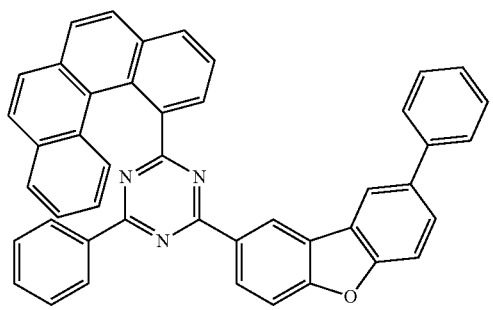

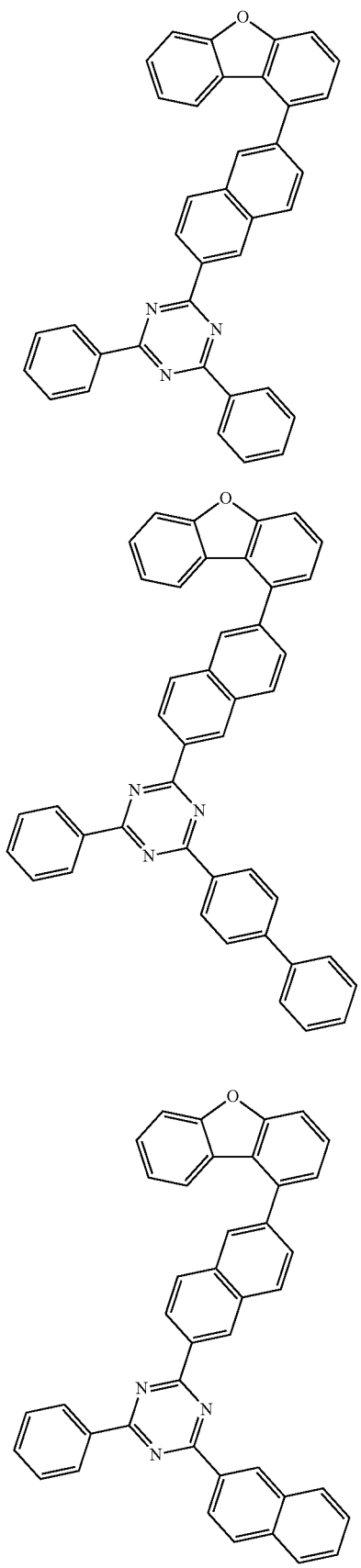
H4-36
H4-37
H4-38
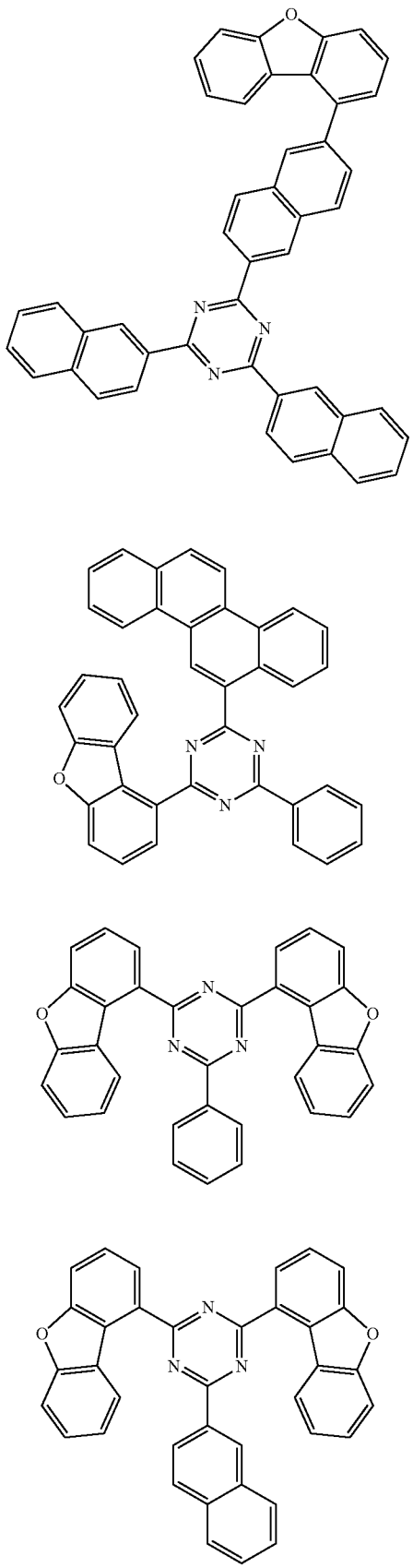
H4-39
H4-40
H4-41
H4-42

H4-43
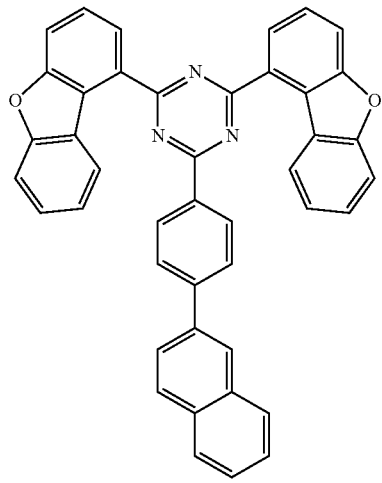
H4-44
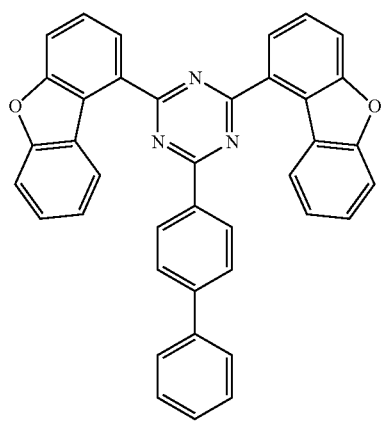
H4-45
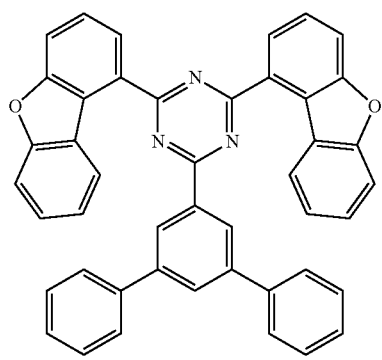
H4-46
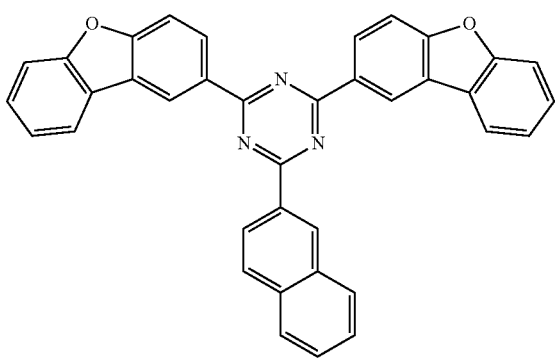
H4-47
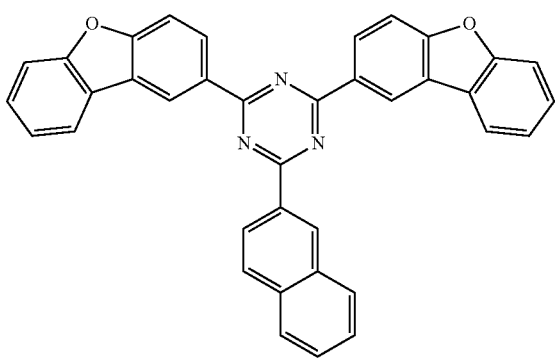
H4-48
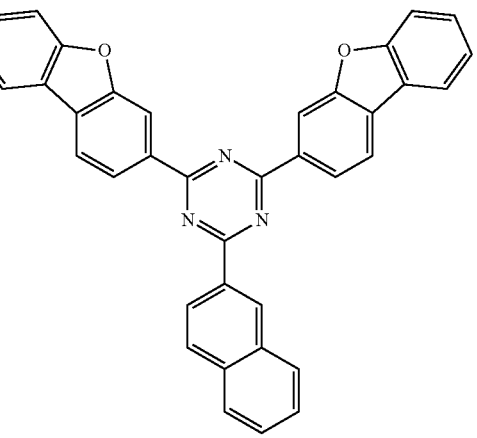

H4-49
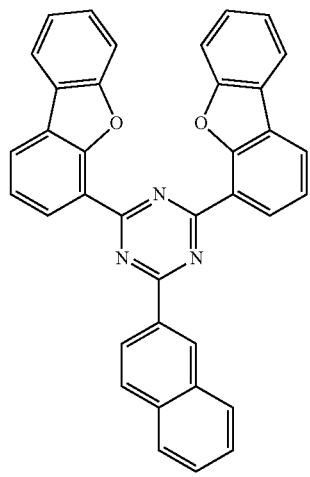
H4-52
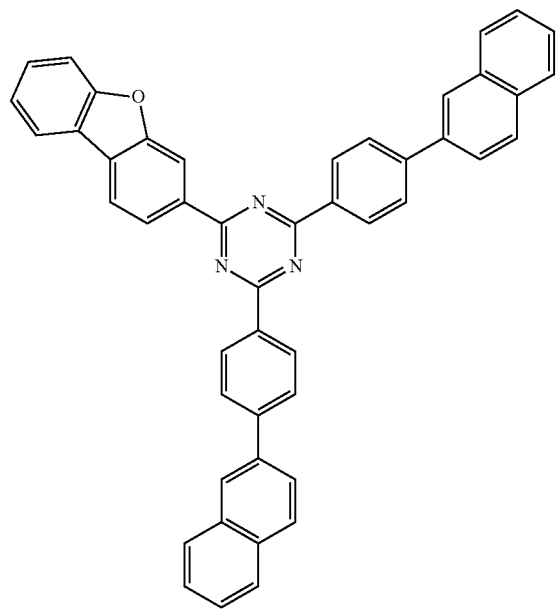
H4-50
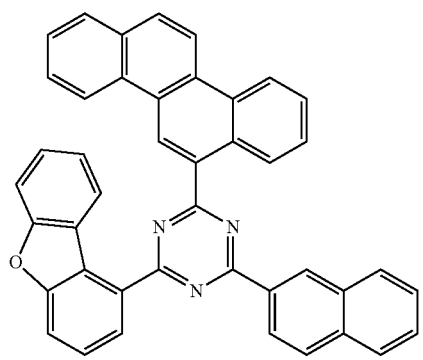
H4-53
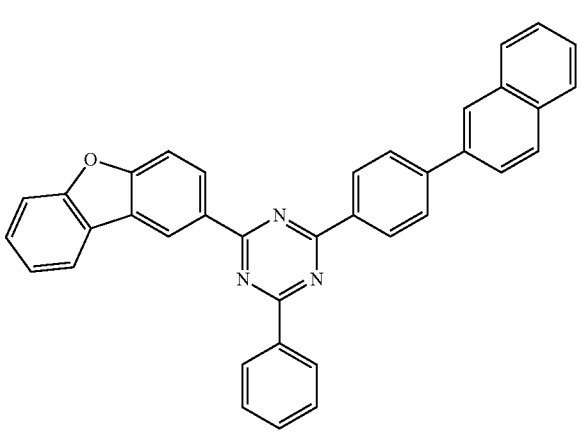
H4-51
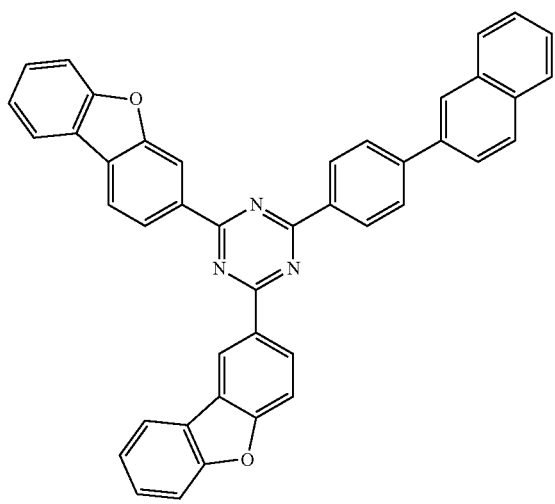
H4-54
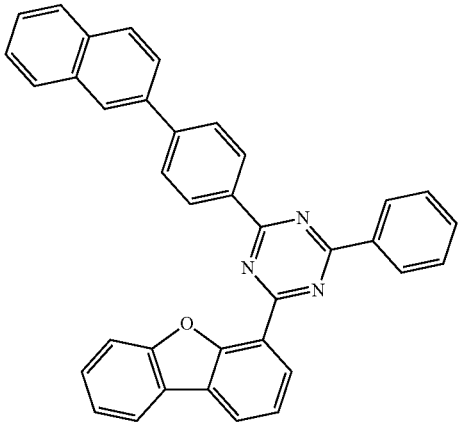

H4-55
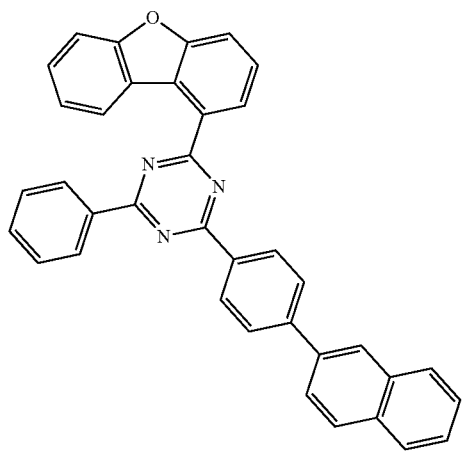
H4-56
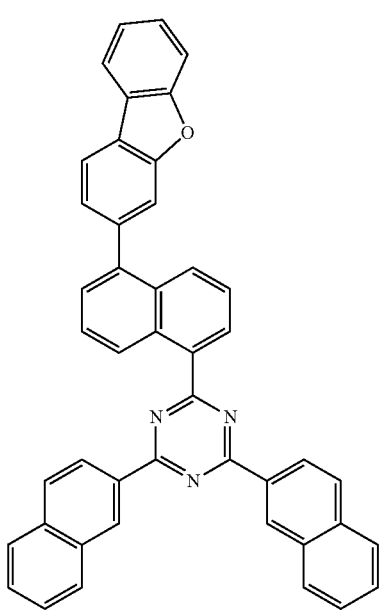
H4-57
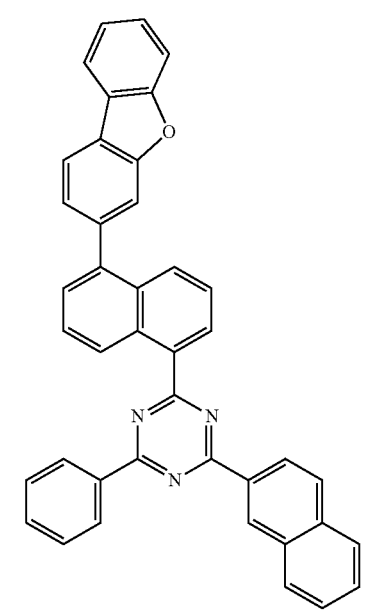
H4-58
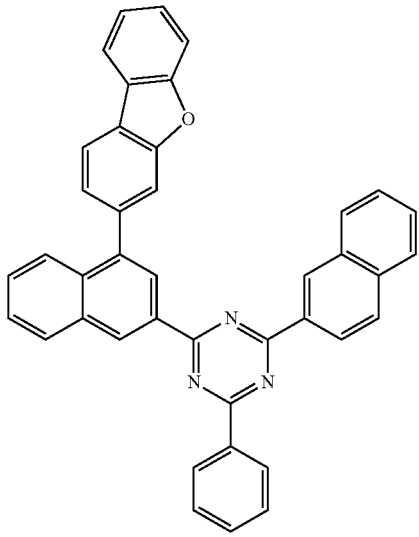
H4-59
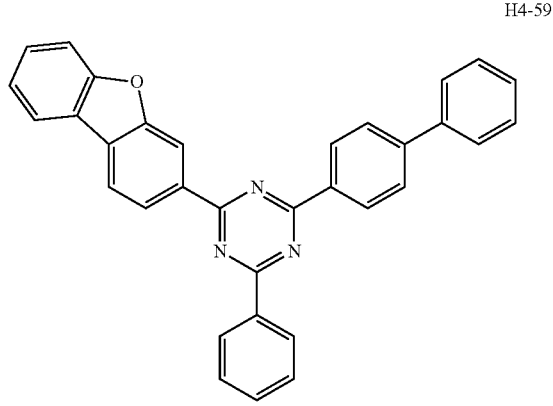
H4-60
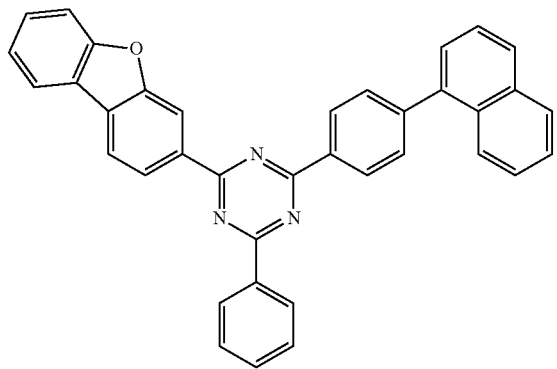

H4-61

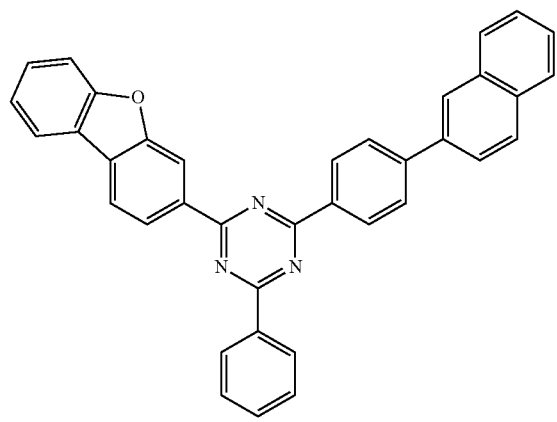

H4-62

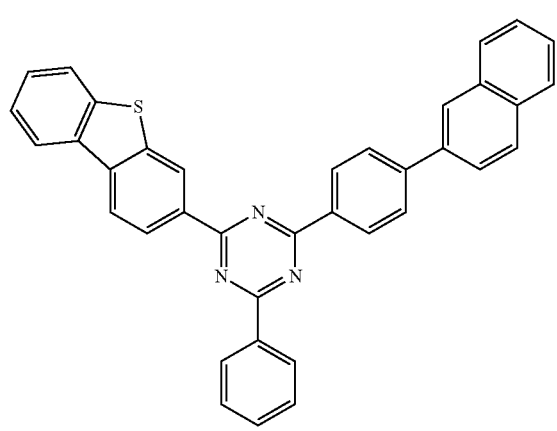

H4-63

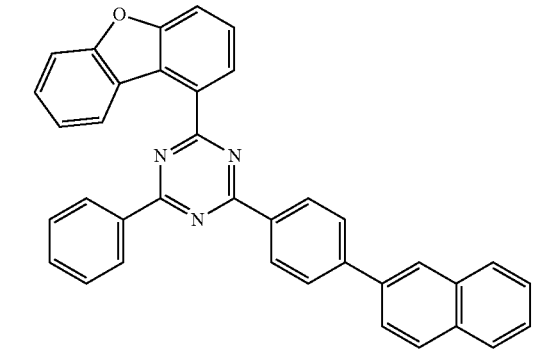

H4-64

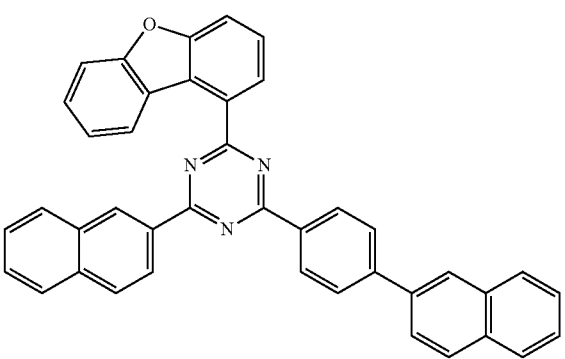

H4-65

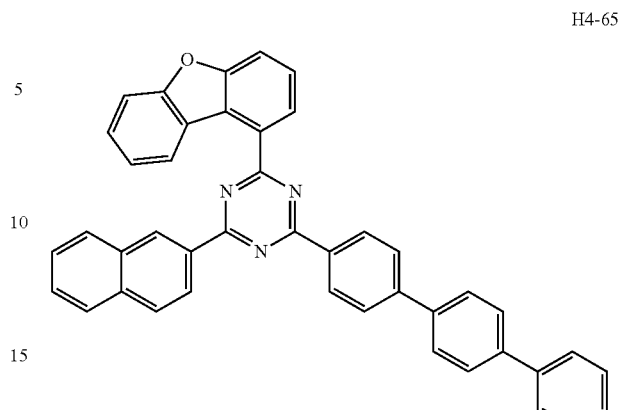

At least one of the compounds C-1 to C-695 and at least one of the compounds H1-1 to H1-136, the compounds H2-1 to H2-35 and the compounds H4-1 to H4-65 may be combined to be used in an organic electroluminescent device.

The compound of formula 1 according to the present disclosure may be prepared by a synthetic method known to one skilled in the art, for example, by referring to the following reaction schemes 1 to 4, but is not limited thereto.

[Reaction Scheme 1]

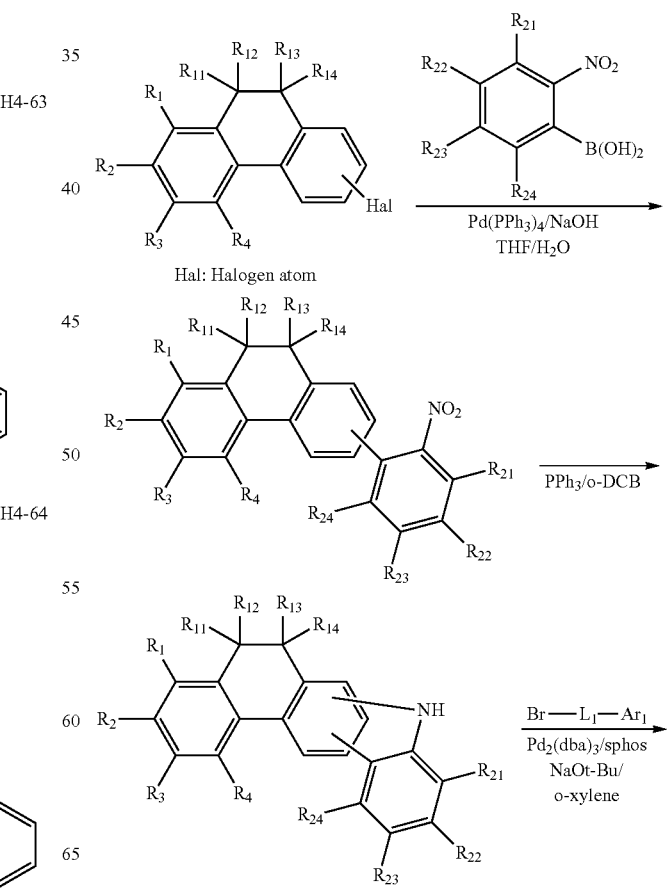

355
-continued
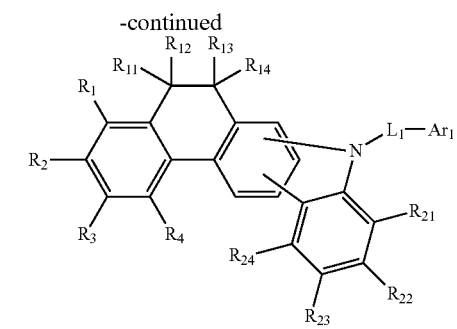
[Reaction Scheme 2]
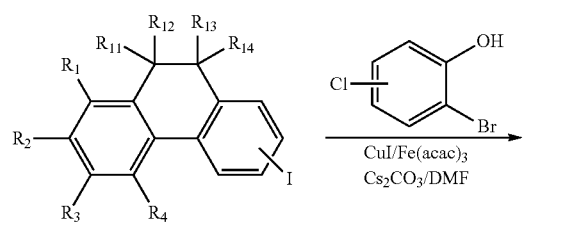
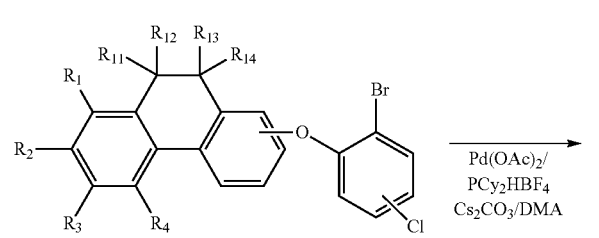
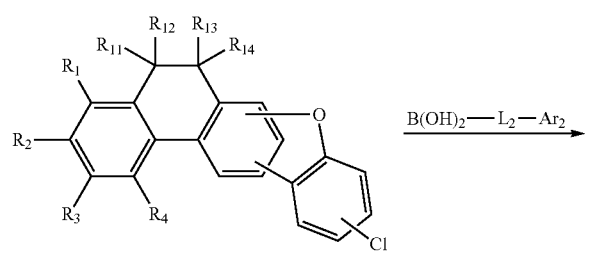
[Reaction Scheme 3]
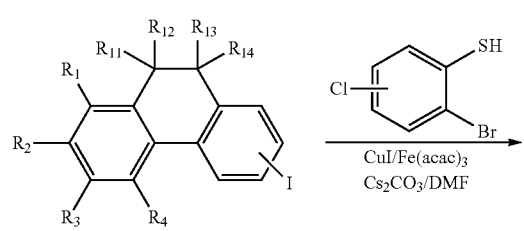
356
-continued
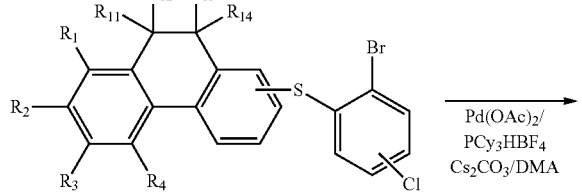
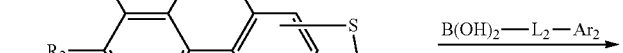
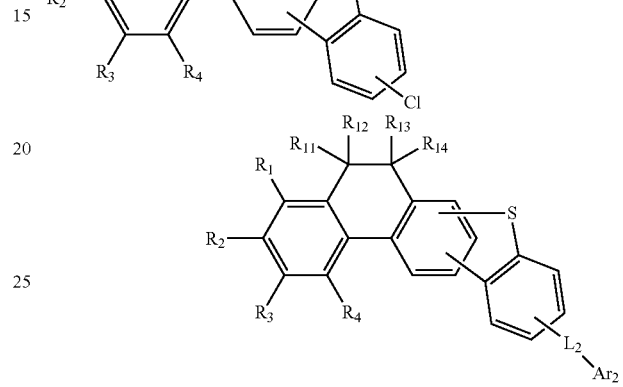
[Reaction Scheme 4]
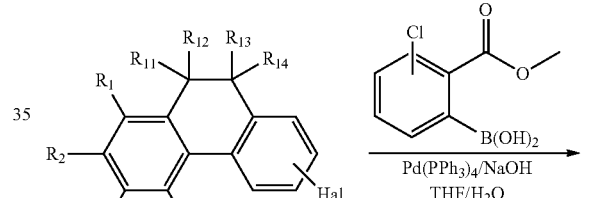
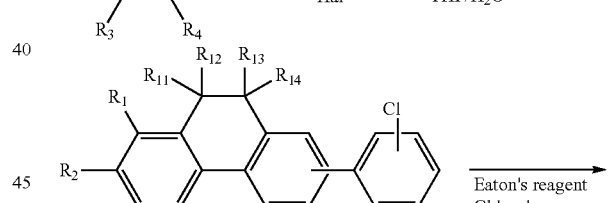
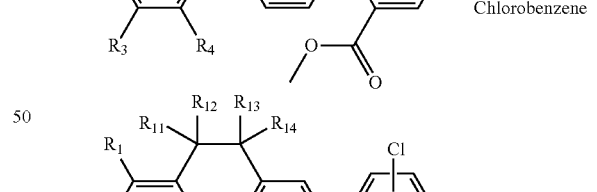
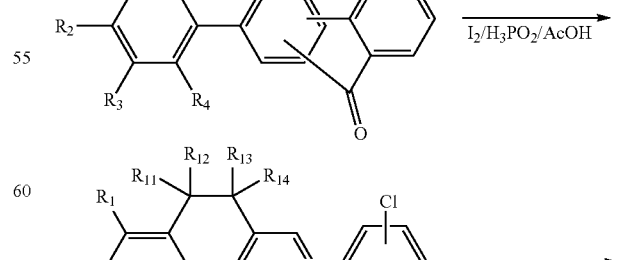

-continued

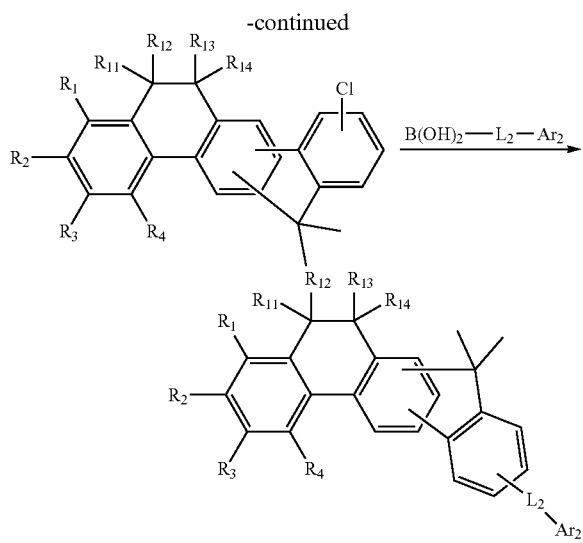

In reaction schemes 1 to 4, $R_1$ to $R_4$, $R_{11}$ to $R_{14}$, $R_{21}$ to $R_{24}$, $L_1$, $L_2$, $Ar_1$, and $Ar_2$ are as defined in in formula 1, and Hal is halogen atom.

The compound represented by formula 2 of the present disclosure may be prepared by a synthetic method known to one skilled in the art, for example, with reference to Korean Patent Appln. Laid-Open No. 2017-0022865 (published on Mar. 2, 2017), Korean Patent Appln. Laid-Open No. 2017-0051198 (published on May 11, 2017), Korean Patent Appln. Laid-Open No. 2018-0094572 (published on Aug. 24, 2018), etc., but is not limited thereto.

The compound represented by formula 3 of the present disclosure may be prepared by a synthetic method known to one skilled in the art.

The compound represented by formula 4 of the present disclosure may be prepared with reference to Korean Patent Appln. Laid-Open No. 2020-0026079 (published on Mar. 10, 2020), but is not limited thereto.

Although illustrative synthesis examples of the compounds represented by formula 1 are described above, one skilled in the art will be able to readily understand that all of them are based on a Buchwald-Hartwig cross-coupling reaction, an N-arylation reaction, H-mont-mediated etherification reaction, a Miyaura borylation reaction, a Suzuki cross-coupling reaction, an intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 1 but are not specified in the specific synthesis examples, are bonded.

The organic electroluminescent device of the present disclosure may comprise the compound of formula 1. Here, the compound of formula 1 may be included in a light-emitting layer.

In addition, the organic electroluminescent device of the present disclosure comprises an anode, a cathode, and at least one organic layer between the anode and the cathode, wherein the organic layer may comprise a plurality of organic electroluminescent materials including a compound represented by formula 1 as a first organic electroluminescent material and a compound represented by any one of formulas 2 to 4 as a second organic electroluminescent material. According to one embodiment of the present disclosure, the organic electroluminescent device of the present disclosure comprises an anode, a cathode, and at least one light-emitting layer between the anode and the cathode, wherein at least one layer of the light-emitting layer may comprise a plurality of host materials including a compound represented by formula 1 as a first host material and a compound represented by any one of formulas 2 to 4 as a second host material.

The electrode may be a transflective electrode or a reflective electrode, and may be a top emission type, a bottom emission type, or a both-sides emission type, depending on the materials. In addition, the hole injection layer may be additionally doped with a p-dopant, and the electron injection layer may be additionally doped with an n-dopant.

The light-emitting layer comprises a host(s) and a dopant, wherein the host includes a plurality of host materials, wherein the compound represented by formula 1 may be included as a first host compound among the plurality of host materials, and the compound represented by any one of formulas 2 to 4 may be included as a second host compound among the plurality of host materials. Here, the weight ratio of the first host compound to the second host compound is from about 1:99 to about 99:1, preferably from about 10:90 to about 90:10, more preferably from about 30:70 to about 70:30, more preferably about 40:60 to 60:40, and even more preferably about 50:50. When two or more materials are included in one layer, they may be mixture-evaporated or separately and simultaneously co-evaporated to form a layer.

In the present disclosure, the light-emitting layer is a layer that emits light, which may be a single layer or a plurality of layers in which two or more layers are stacked. In the plurality of host materials of the present disclosure, both the first and second host materials may be included in one layer or in different light-emitting layers, respectively. According to one embodiment of the present disclosure, the doping concentration of the dopant compound with respect to the host compound of the light-emitting layer may be less than 20 wt %.

The organic electroluminescent device of the present disclosure may comprise a hole transport zone between an anode and a light-emitting layer. The hole transport zone may comprise at least one of a hole injection layer, a hole transport layer, a hole auxiliary layer, a light-emitting auxiliary layer, and an electron blocking layer. The hole injection layer, the hole transport layer, the hole auxiliary layer, the light-emitting auxiliary layer, and the electron blocking layer may be a single layer or a plurality of layers in which two or more layers are stacked, respectively. The hole injection layer may be multilayers in order to lower the hole injection barrier (or hole injection voltage) from the anode to the hole transport layer or the electron blocking layer, wherein two compounds may be simultaneously used in each of the multilayers. The electron blocking layer may be placed between the hole transport layer (or hole injection layer) and the light-emitting layer, and may block overflow of electrons from the light-emitting layer and confine the excitons in the light-emitting layer to prevent light leakage.

In addition, the hole transport zone may comprise a p-doped hole injection layer, a hole transport and a light-emitting auxiliary layer. The p-doped hole injection layer means a hole injection layer doped with a p-dopant. The p-dopant is a material that contributes p-semiconductor properties. The p-semiconductor properties refer to the properties of injecting or transporting holes to HOMO energy level, that is, the properties of a material having high hole conductivity.

The organic electroluminescent device of the present disclosure may comprise an electron transport zone between a light-emitting layer and a cathode. The electron transport zone may comprise at least one of a hole blocking layer, an electron transport layer, an electron buffer layer, and an electron injection layer. The hole blocking layer, the electron transport layer, the electron buffer layer, and the electron injection layer may be a single layer or a plurality of layers in which two or more layers are stacked, respectively. The electron injection layer may be additionally doped with an n-dopant. The electron buffer layer may be multilayers in order to control electron injection and improve interfacial properties between the light-emitting layer and the electron injection layer, wherein two compounds may be simultaneously used in each of the multilayers. The hole blocking layer or the electron transport layer may also be multilayers, wherein a plurality of compounds may be used in each of the multilayers. According to one embodiment of the present disclosure, at least one layer of the electron transport zone, preferably an electron buffer layer, may comprise the compound represented by formula 1.

The light-emitting auxiliary layer is a layer placed between an anode and a light-emitting layer, or between a cathode and a light-emitting layer. When the light-emitting auxiliary layer is placed between the anode and the light-emitting layer, it may be used to facilitate injection and/or transport of holes or to prevent the overflow of electrons. When the light-emitting auxiliary layer is placed between the cathode and the light-emitting layer, it may be used to facilitate injection and/or transport of electrons or to prevent the overflow of holes. In addition, the light-emitting auxiliary layer may be placed between a hole transport layer (or a hole injection layer) and a light-emitting layer to exhibit an effect of facilitating or blocking transport rate (or injection rate) of holes, thereby enabling the charge balance to be controlled. When the organic electroluminescent device comprises two or more hole transport layers, the additionally included hole transport layer may be used as a hole auxiliary layer or an electron blocking layer. The light-emitting auxiliary layer, the hole auxiliary layer, or the electron blocking layer may have an effect of improving the efficiency and/or lifespan of the organic electroluminescent device.

The dopants that can be comprised in the organic electroluminescent device of the present disclosure may be at least one phosphorescent or fluorescent dopant, preferably a phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may be the compound represented by the following formula 101, but is not limited thereto.

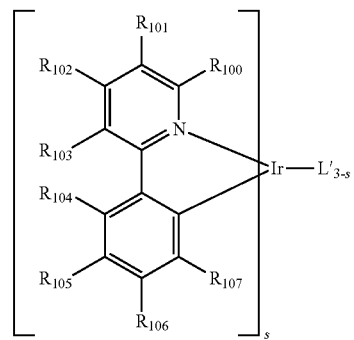

In formula 101,
L' is selected from the following structures 1 to 3:

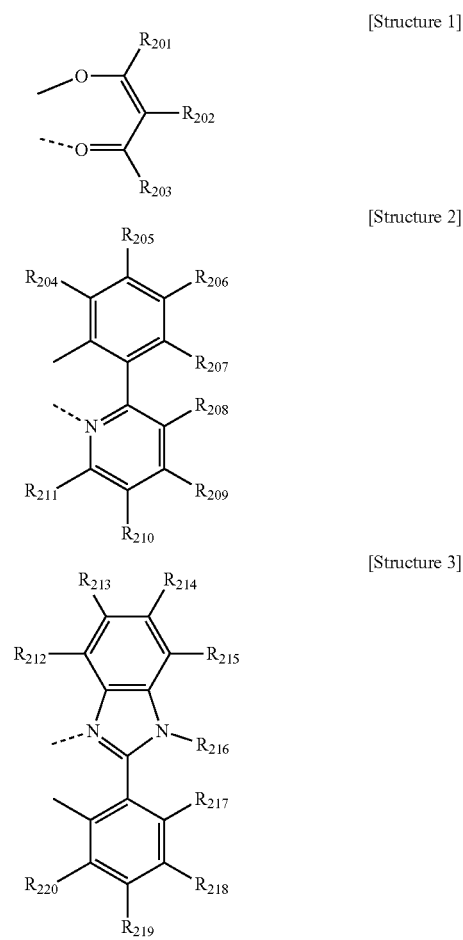

$R_{100}$ to $R_{103}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30) alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring, e.g., a substituted or unsubstituted, naphthalene, fluorene, dibenzothiophene, dibenzofuran, indenopyridine, benzofuropyridine, or benzothienopyridine ring, together with benzene;

$R_{201}$ to $R_{220}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, or a substituted or unsubstituted (C6-C30)aryl; or may be linked to an adjacent substituent to form a ring; and s represents an integer of 1 to 3.

The specific examples of the dopant compound are as follows, but are not limited thereto.

D-1

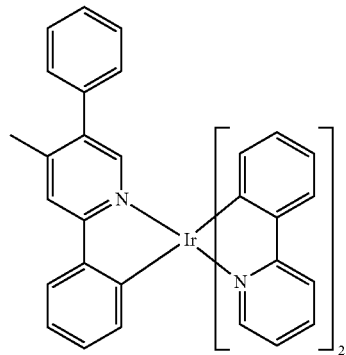

D-2

D-3

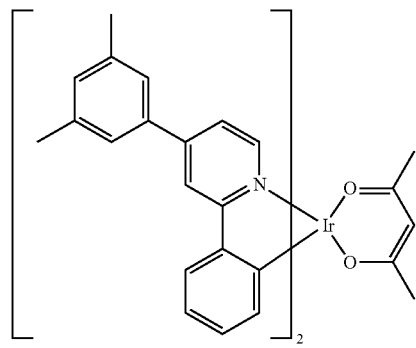

D-4

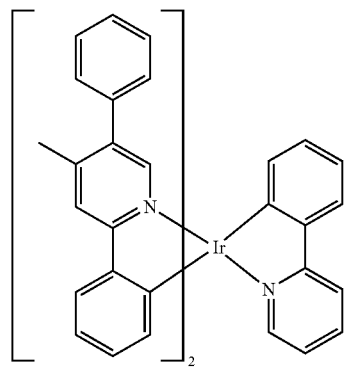

D-5

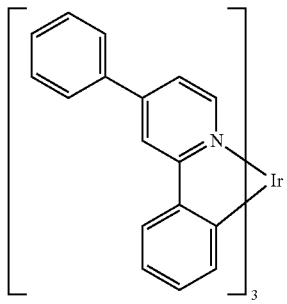

D-6

D-7
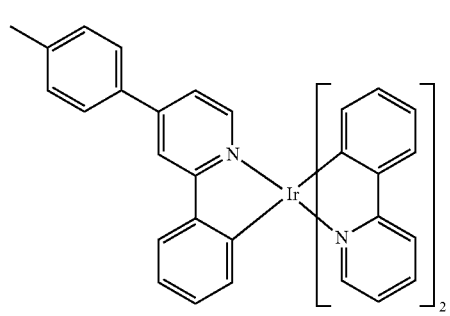
D-8
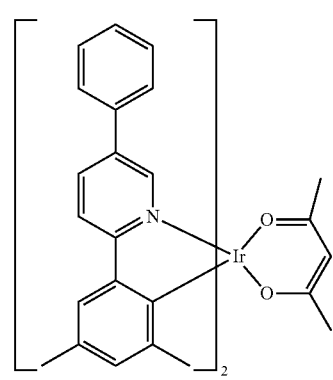
D-9
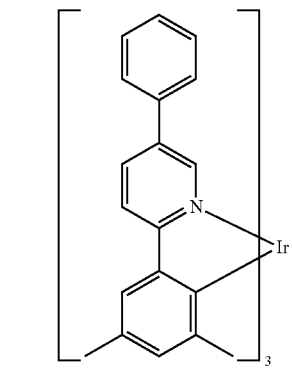
D-10
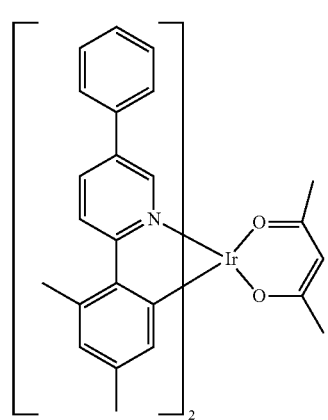
D-11
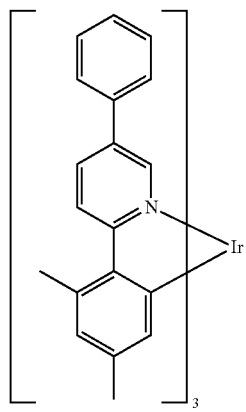
D-12
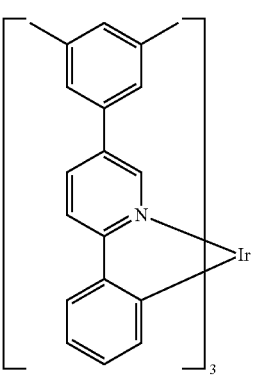
D-13
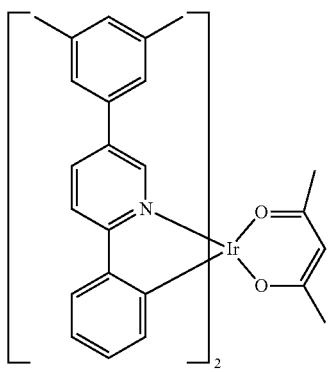
D-14
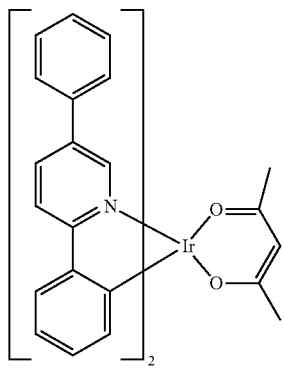

D-15 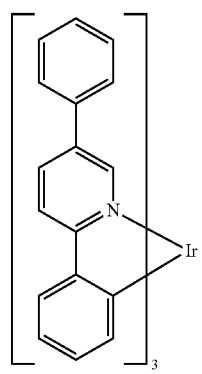
D-16 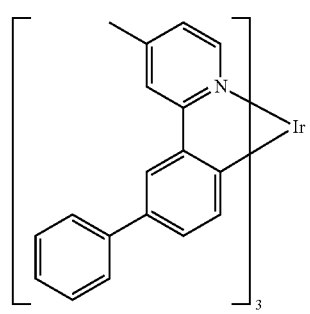
D-17 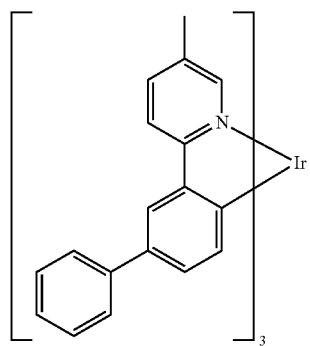
D-18 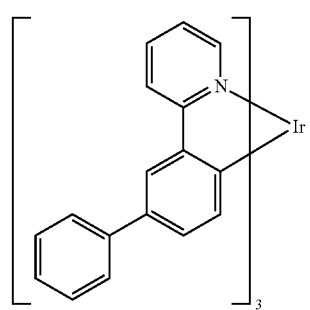
D-19 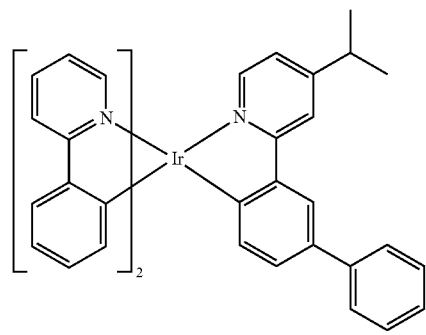
D-20 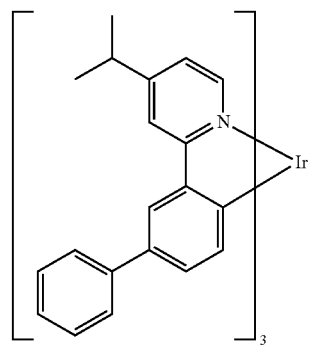
D-21 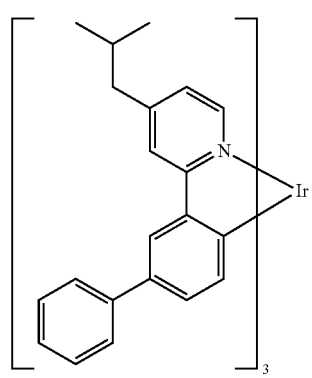
D-22 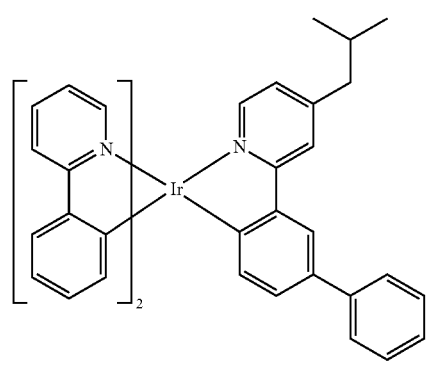

D-23
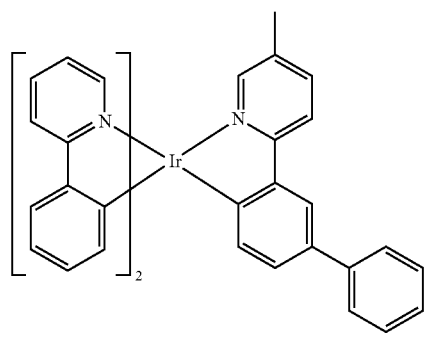
D-24
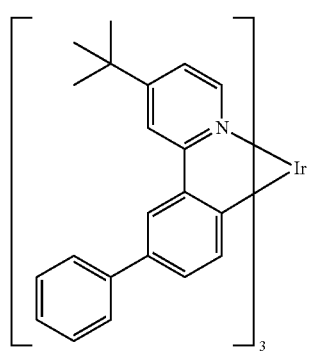
D-25
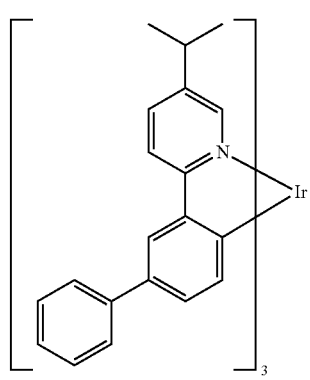
D-26
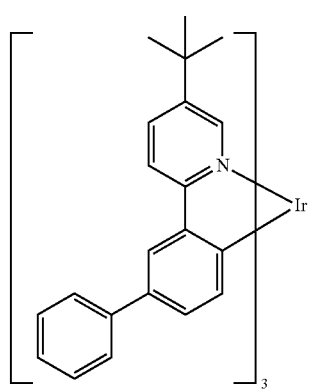
D-27
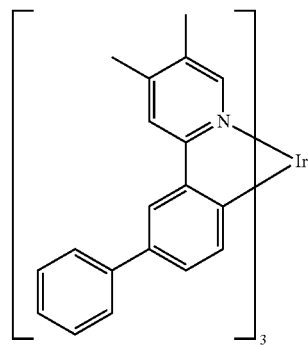
D-28
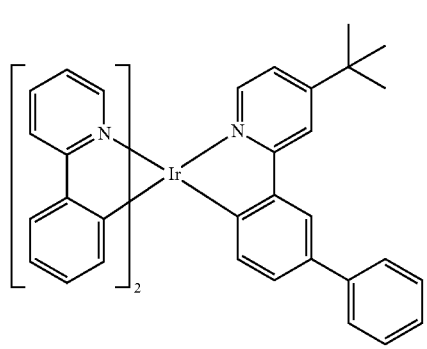
D-29
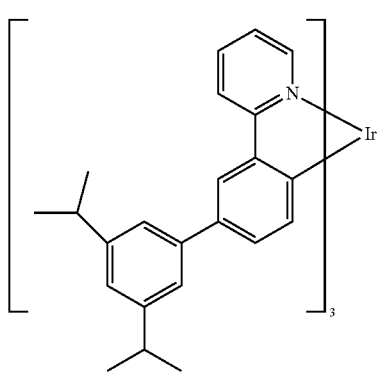
D-30
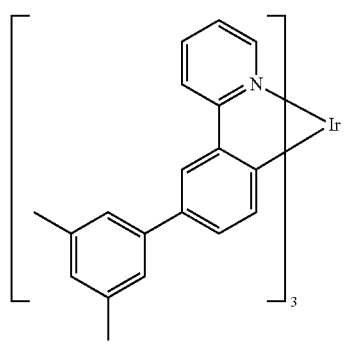

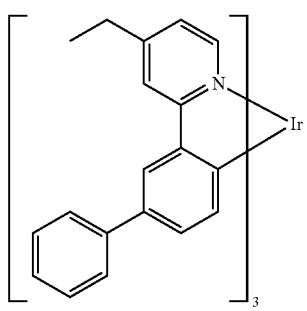 D-31
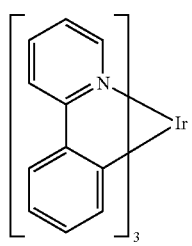 D-32
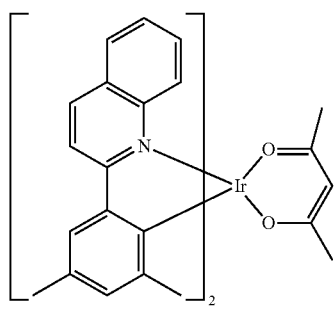 D-33
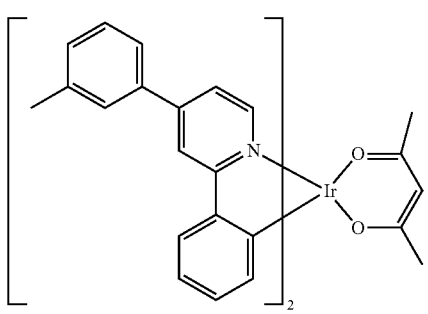 D-34
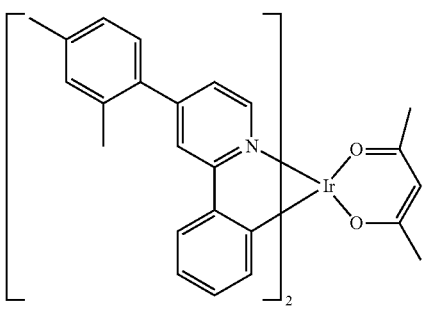 D-36
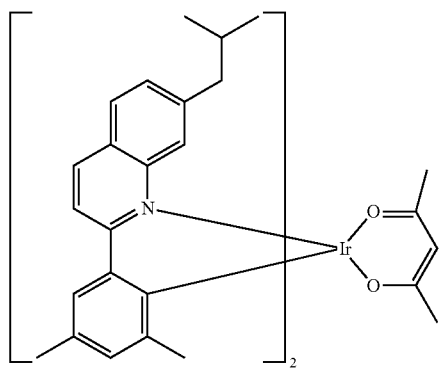 D-37
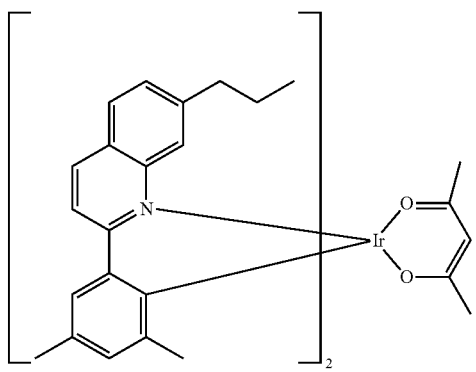 D-38
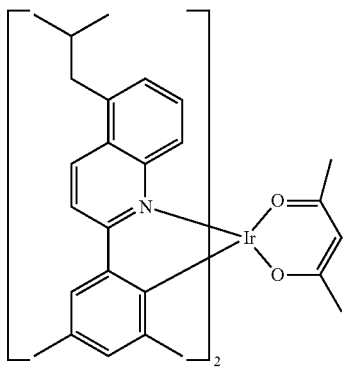 D-39
D-35

-continued
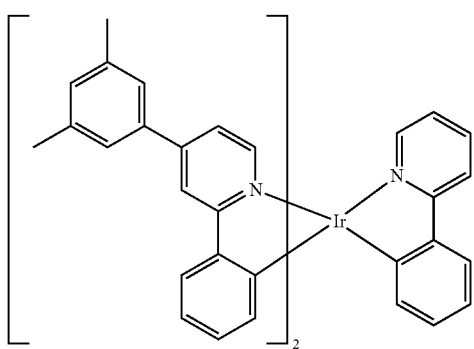
D-40
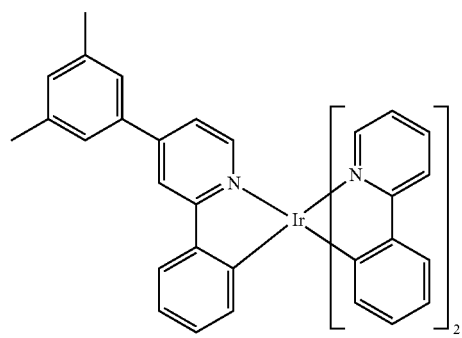
D-41
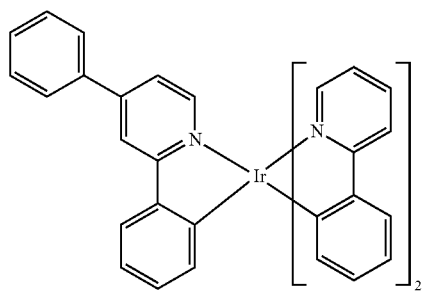
D-42
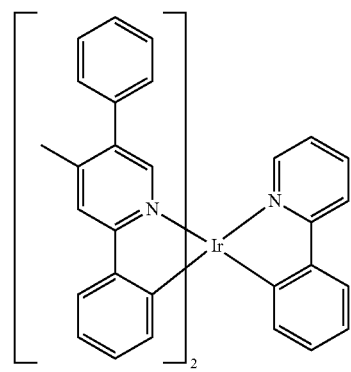
D-43
-continued
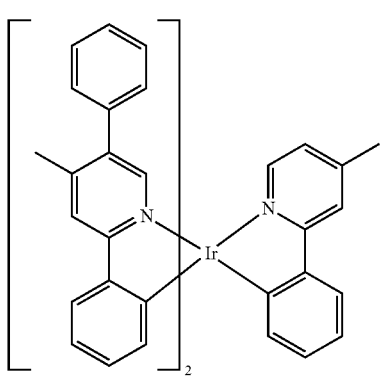
D-44
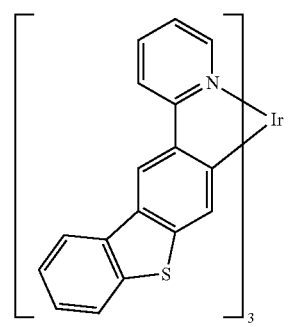
D-45
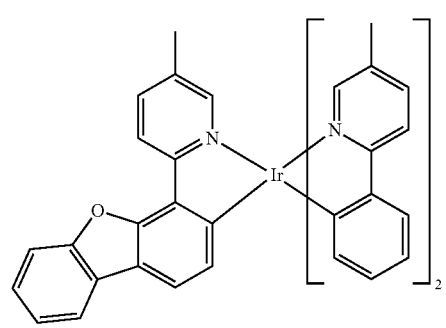
D-46
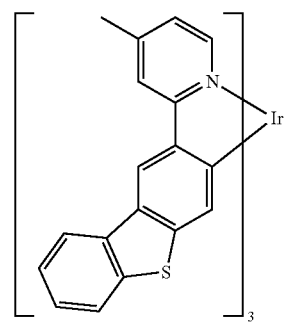
D-47
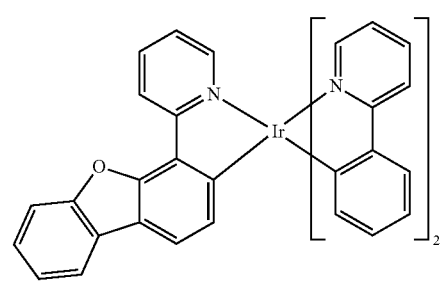
D-48

-continued
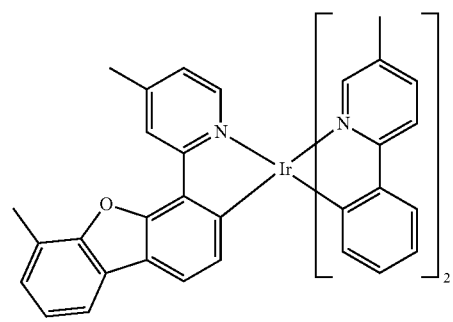
D-49
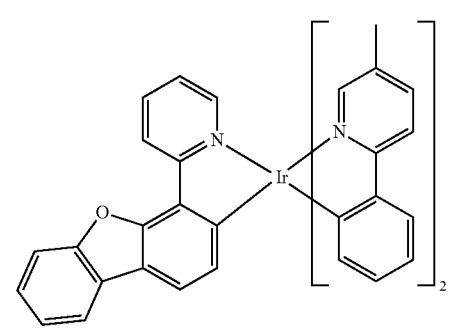
D-50
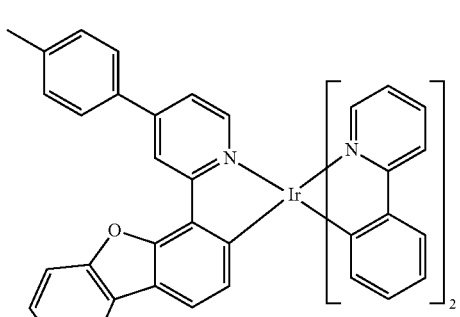
D-51
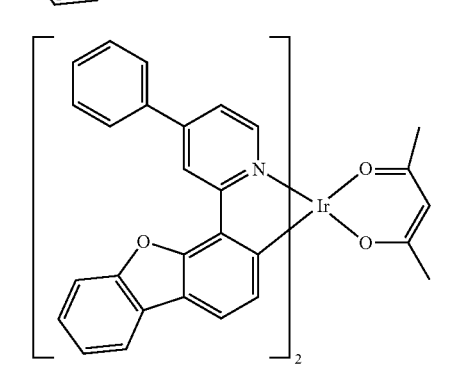
D-52
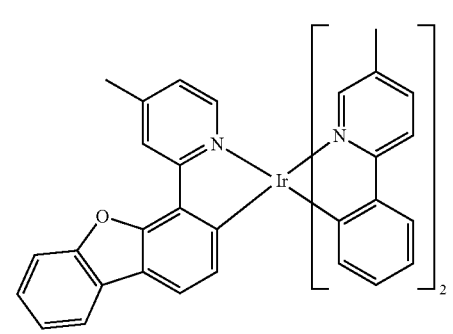
D-53
-continued
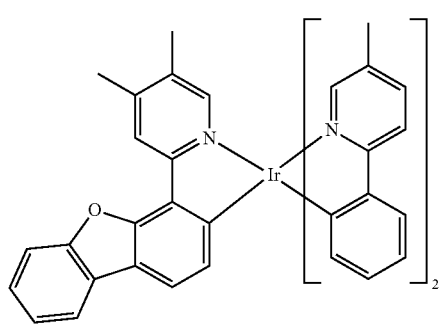
D-54
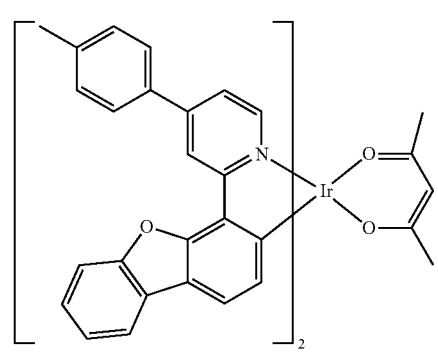
D-55
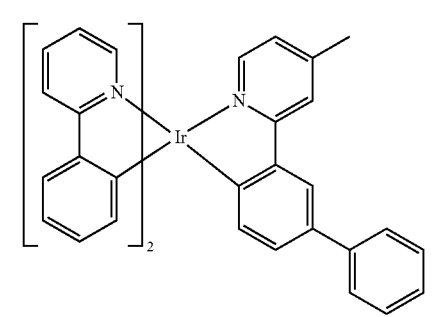
D-56
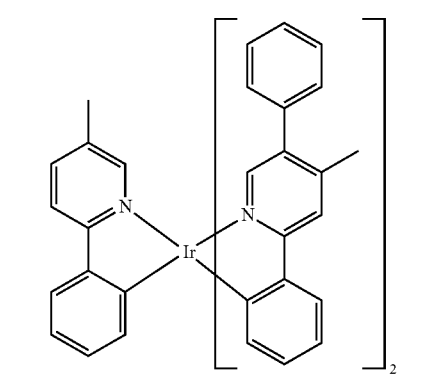
D-57

-continued
D-58
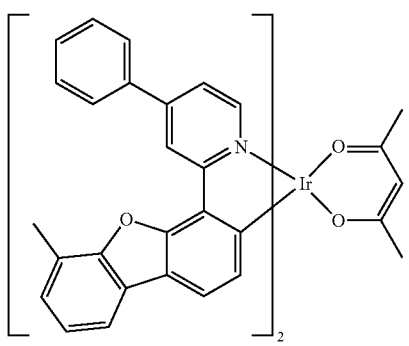
D-59
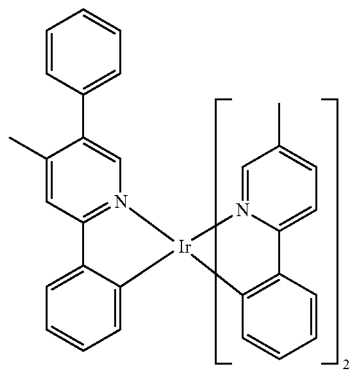
D-60
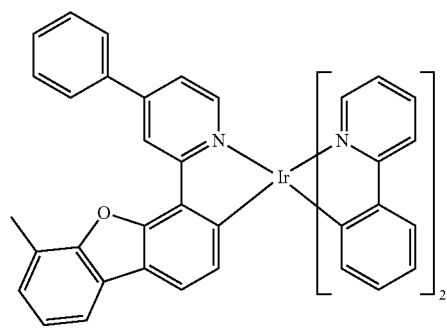
D-61
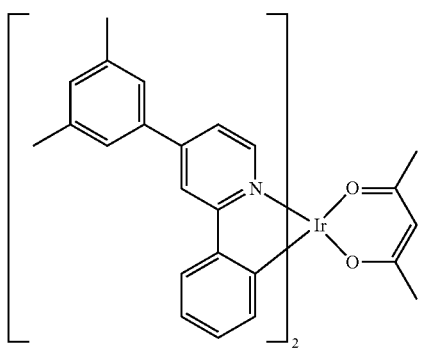
-continued
D-62
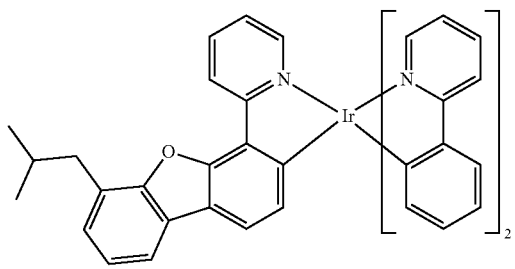
D-63
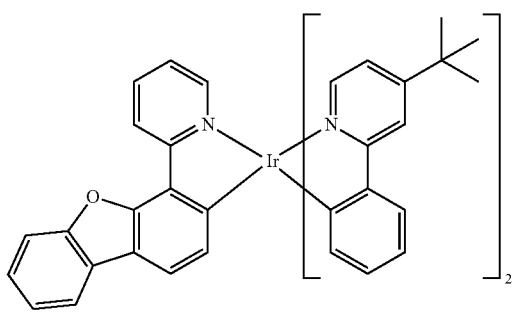
D-64
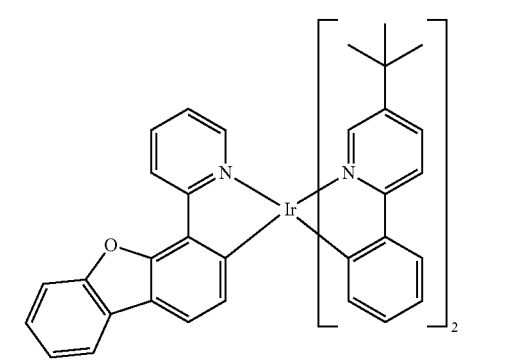
D-65
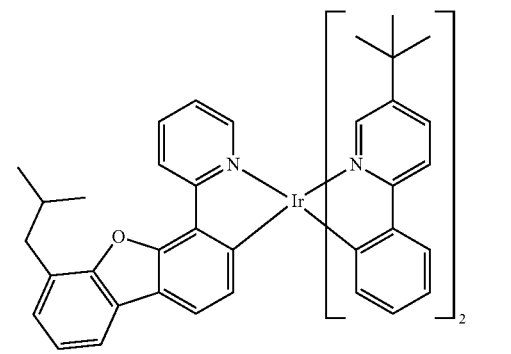

D-66
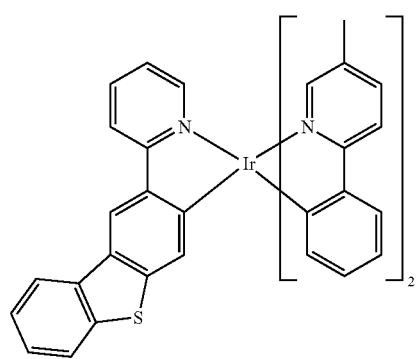
D-67
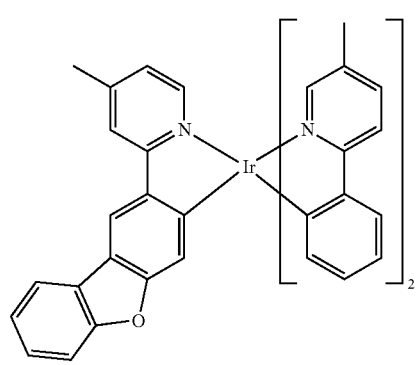
D-68
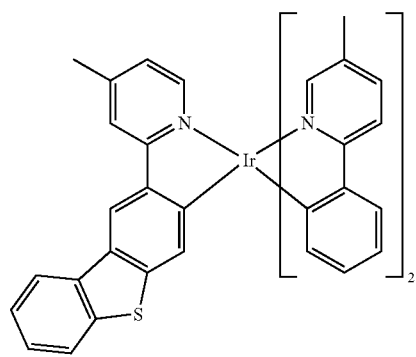
D-69
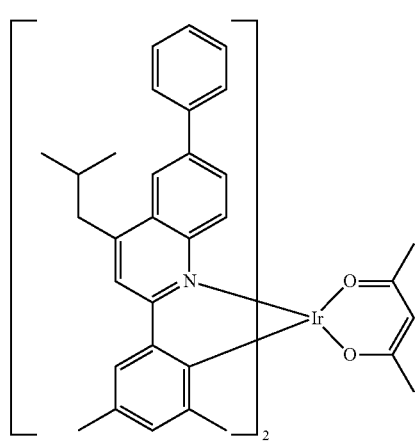
D-70
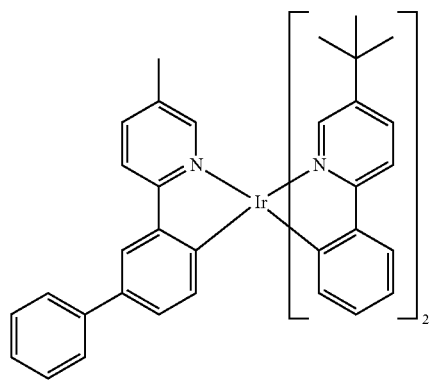
D-71
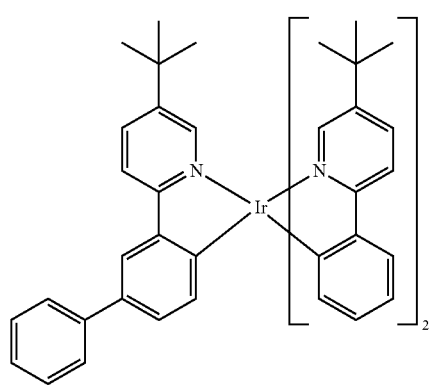
D-72
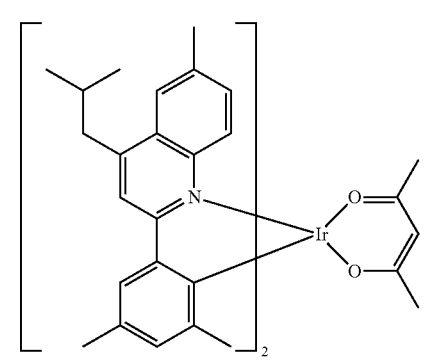
D-73
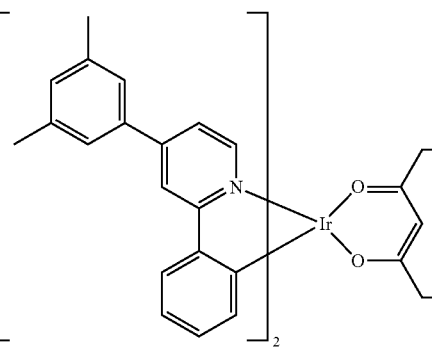

-continued
D-74
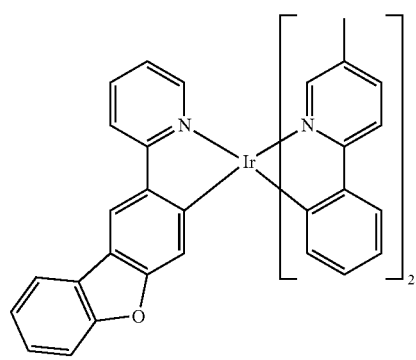
D-75
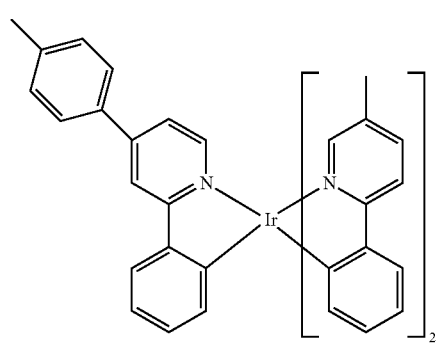
D-76
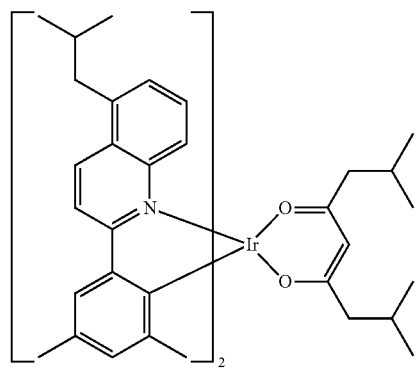
D-77
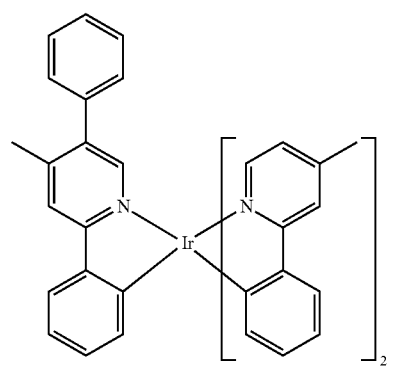
-continued
D-78
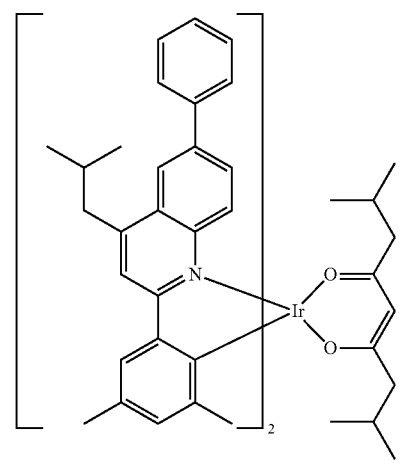
D-79
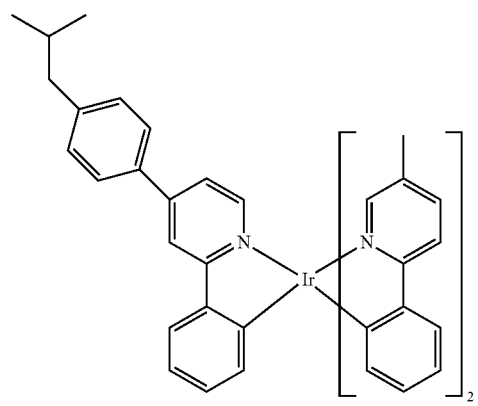
D-80
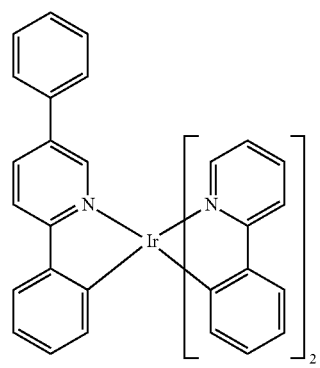

D-81
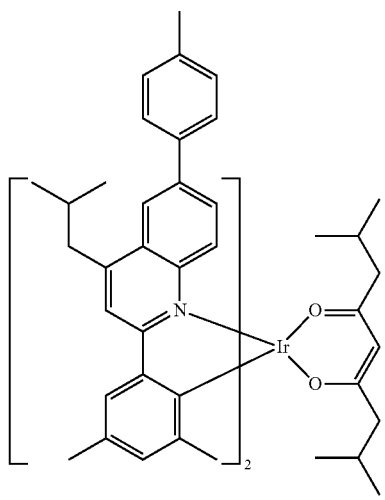
D-82
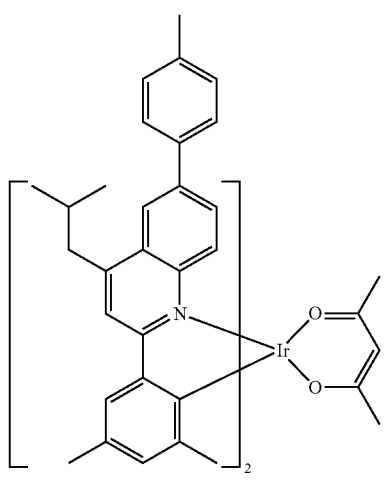
D-83
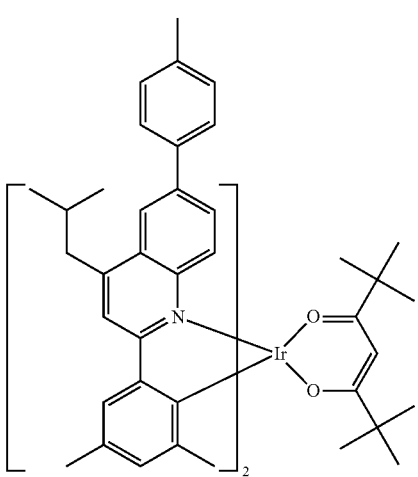
D-84
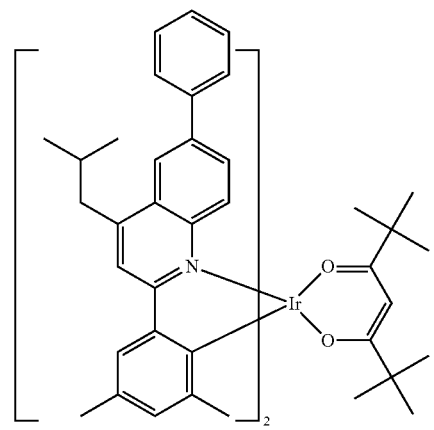
D-85
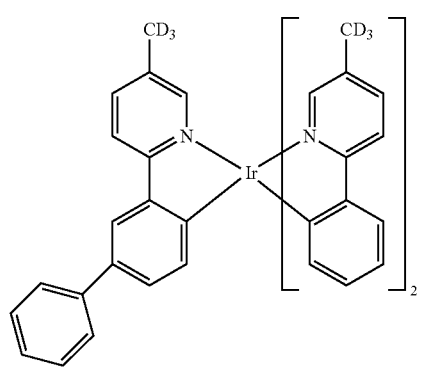
D-86
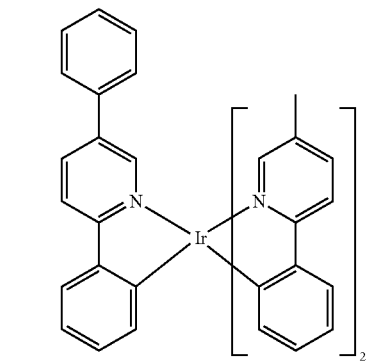
D-87
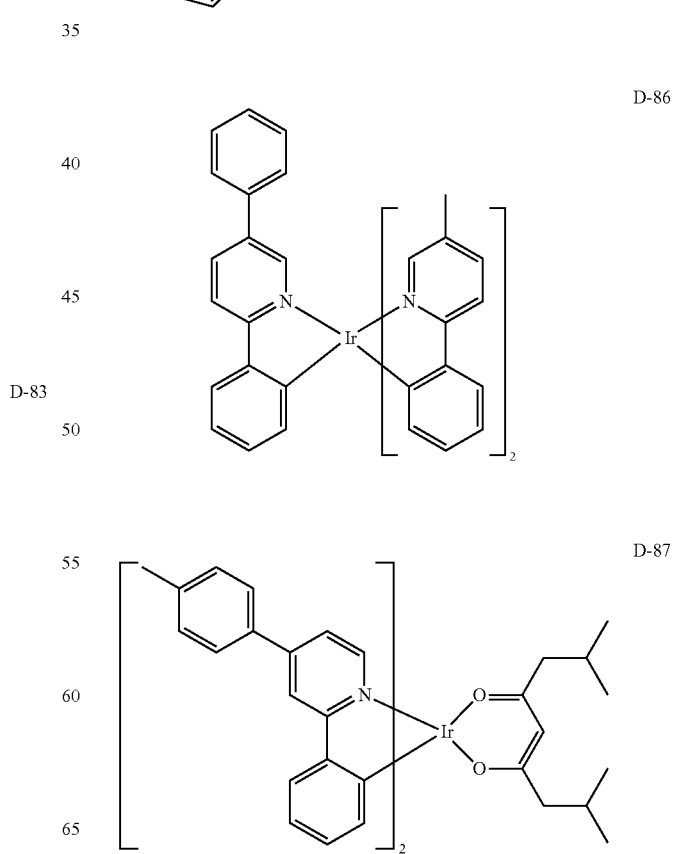

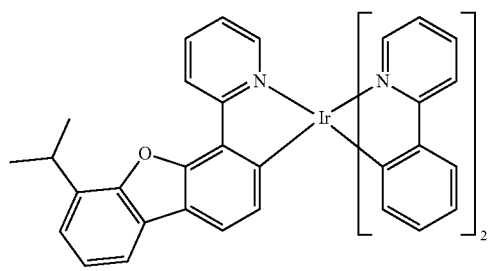
D-88
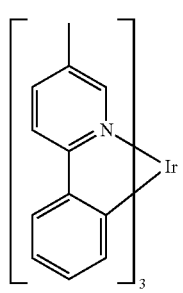
D-89
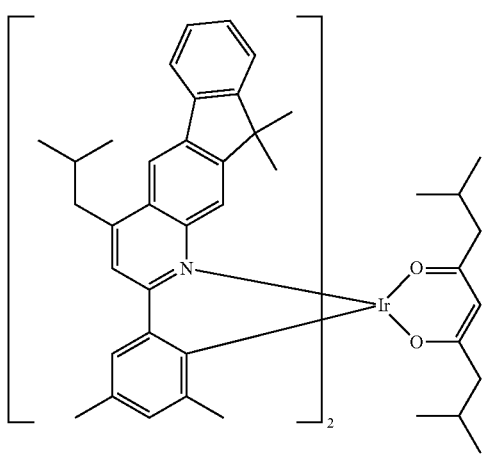
D-90
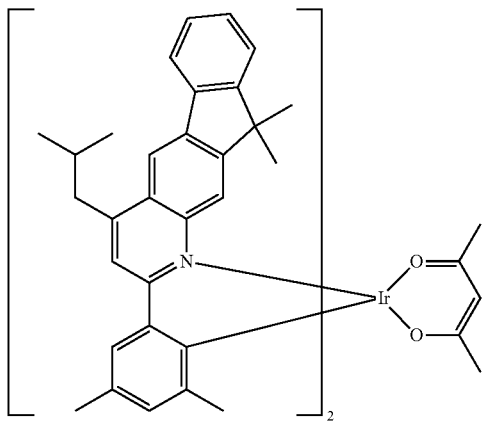
D-91
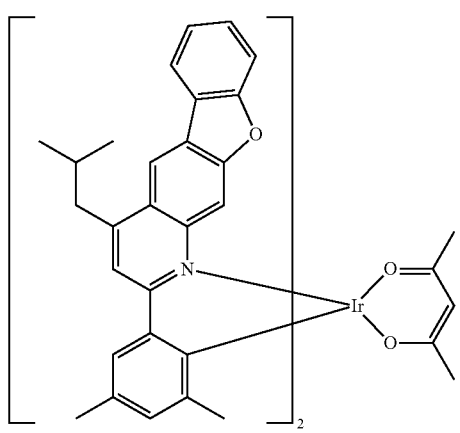
D-92
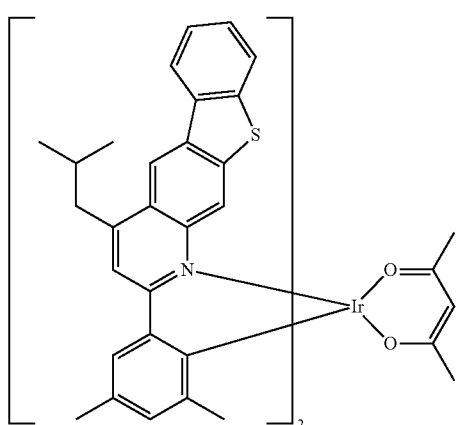
D-93
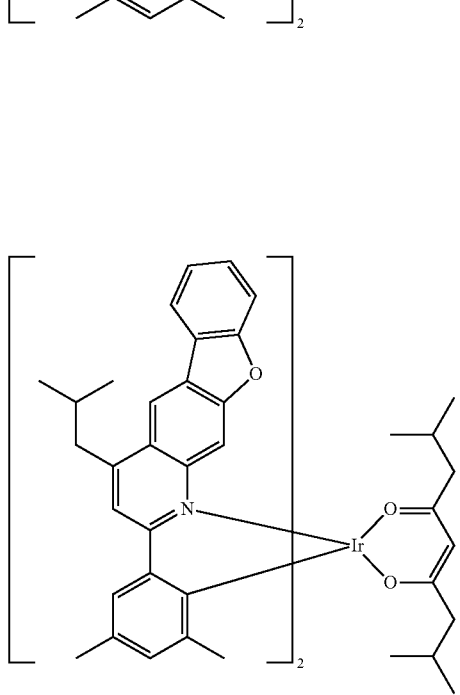
D-94

D-95
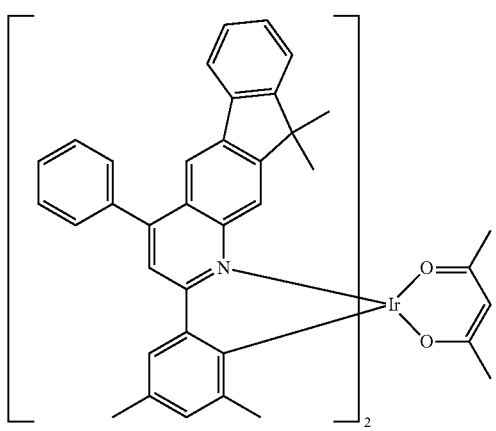
D-96
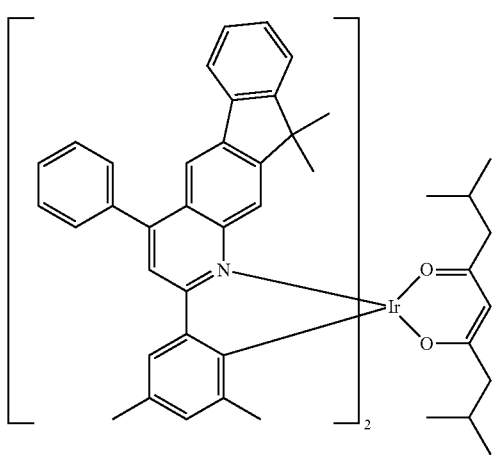
D-97
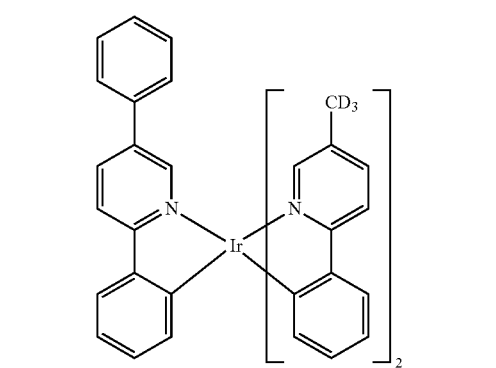
D-98
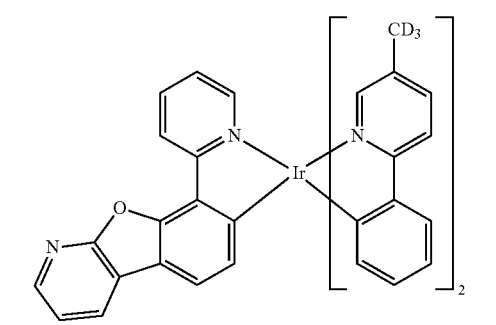
D-99
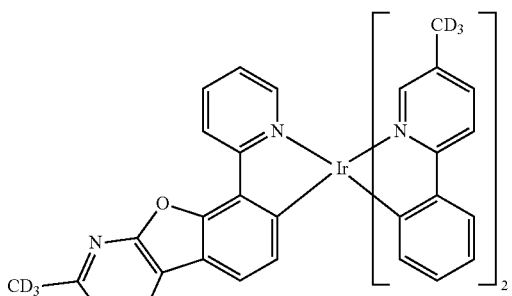
D-100
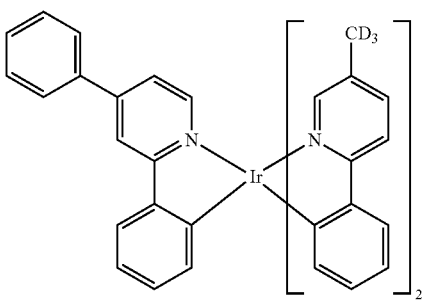
D-101
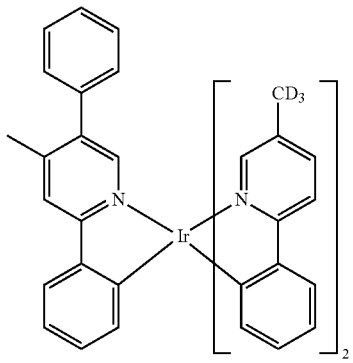
D-102
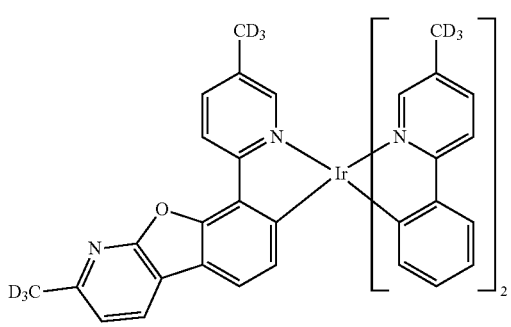

D-103
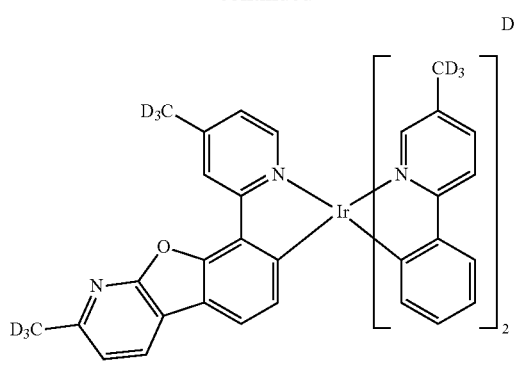
D-104
D-105
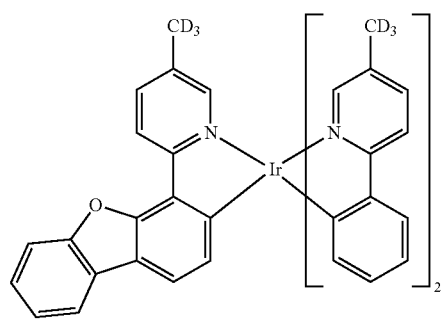
D-106
D-107
D-108
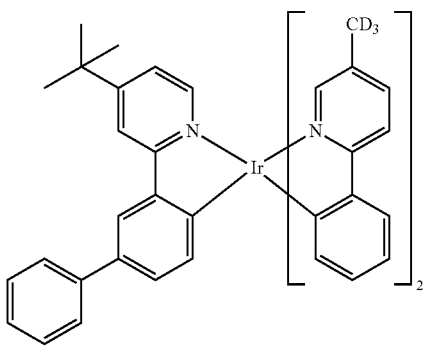
D-109
D-110
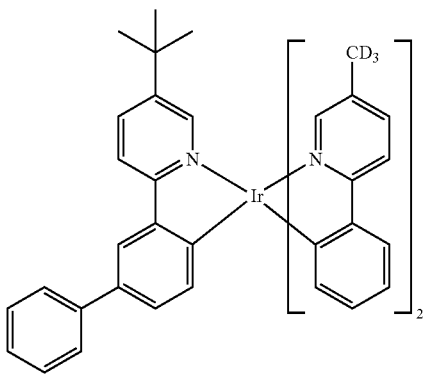
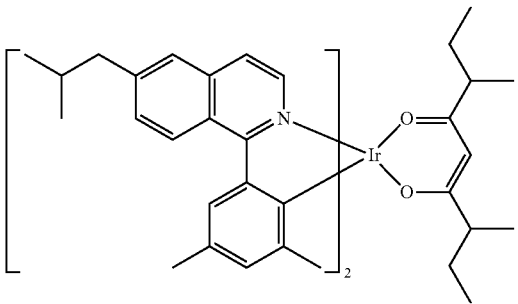
D-111
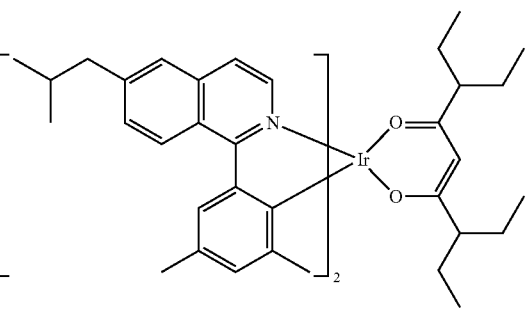

-continued
D-112
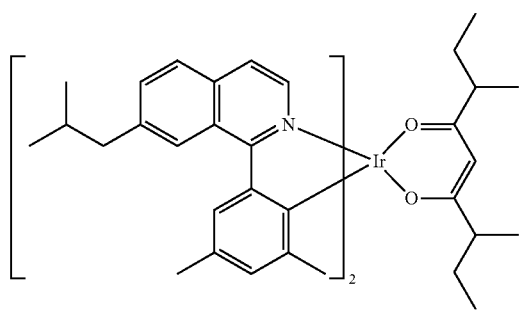
D-113
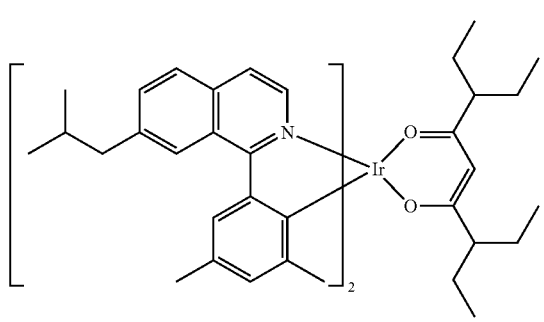
D-114
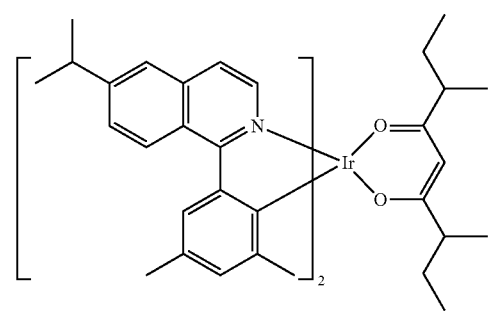
D-115
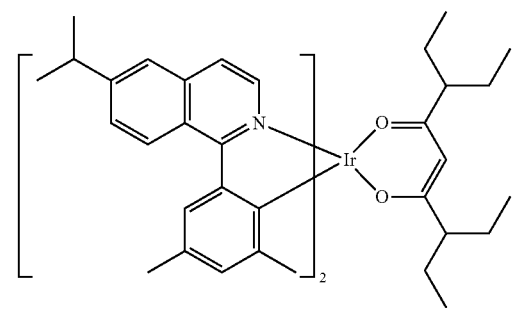
D-116
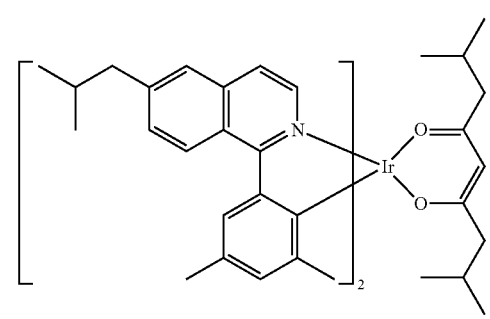
-continued
D-117
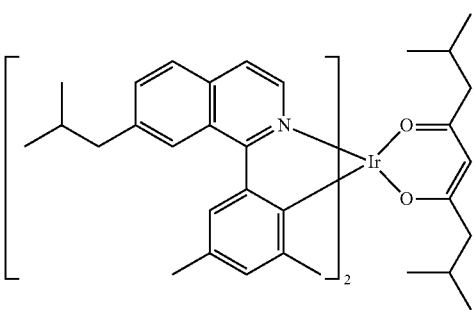
D-118
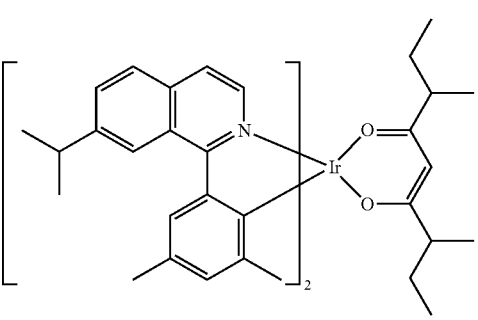
D-119
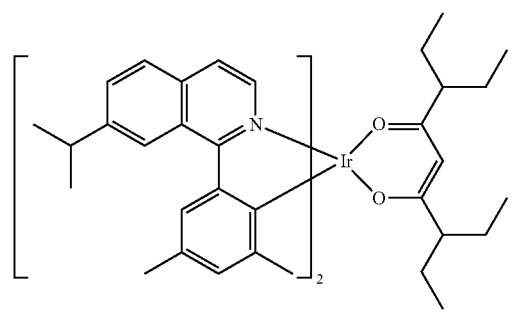
D-120
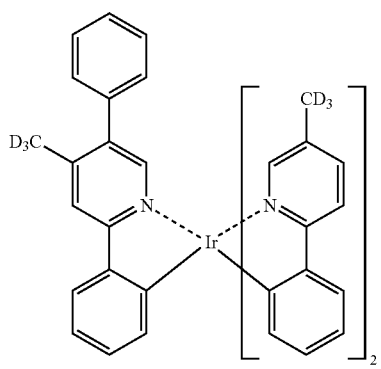

D-121
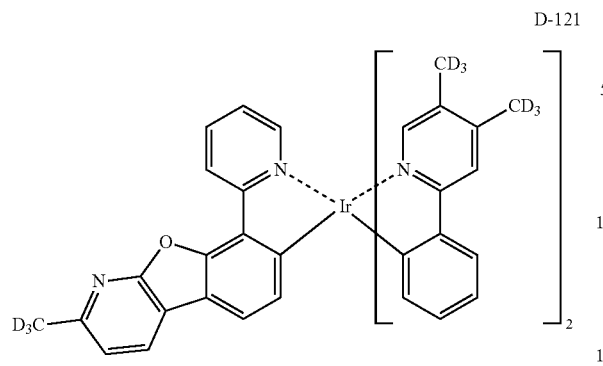
D-122
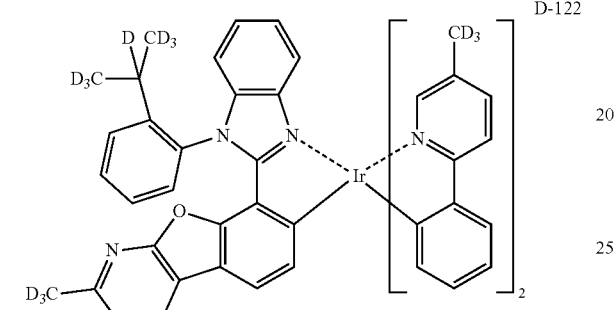
D-123
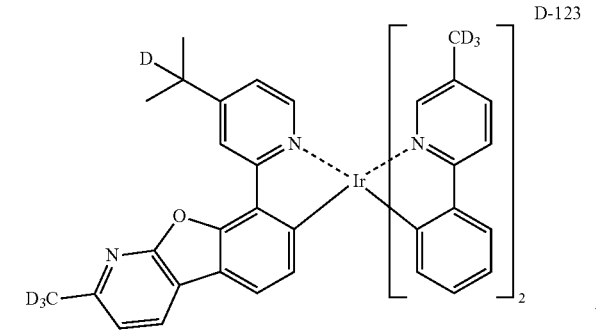
D-124
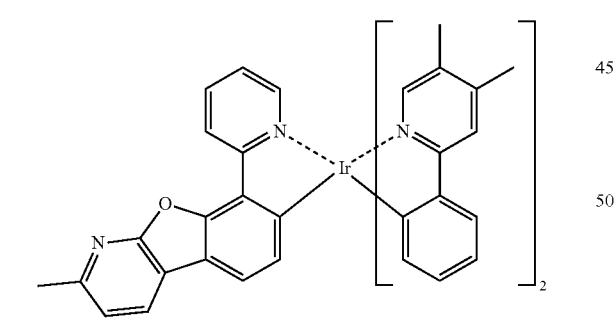
D-125
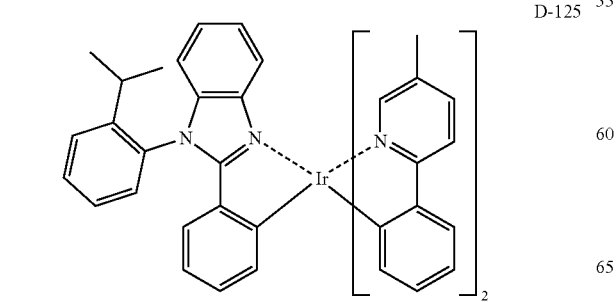
D-126
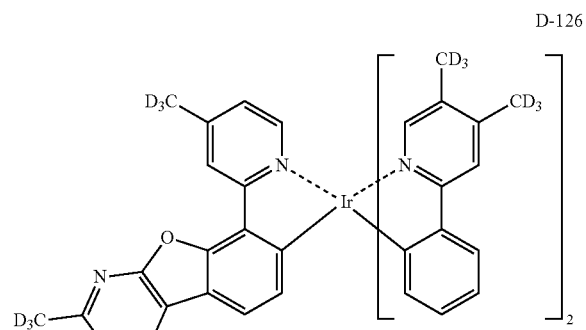
D-127
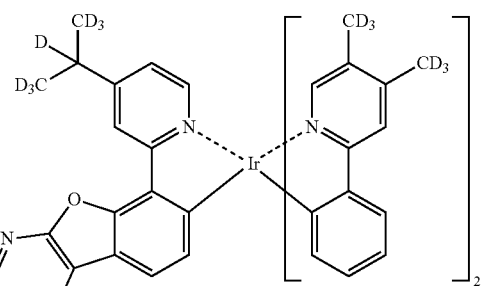
D-128
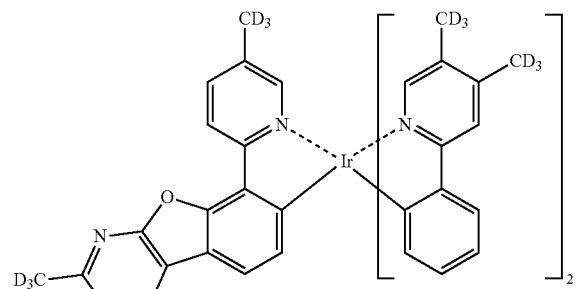
D-129
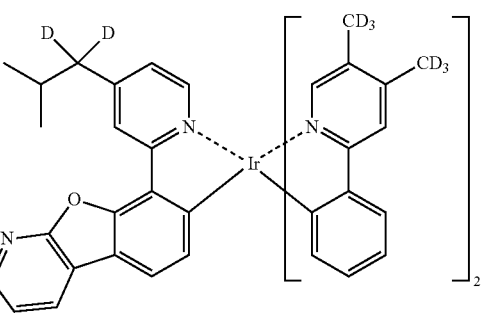

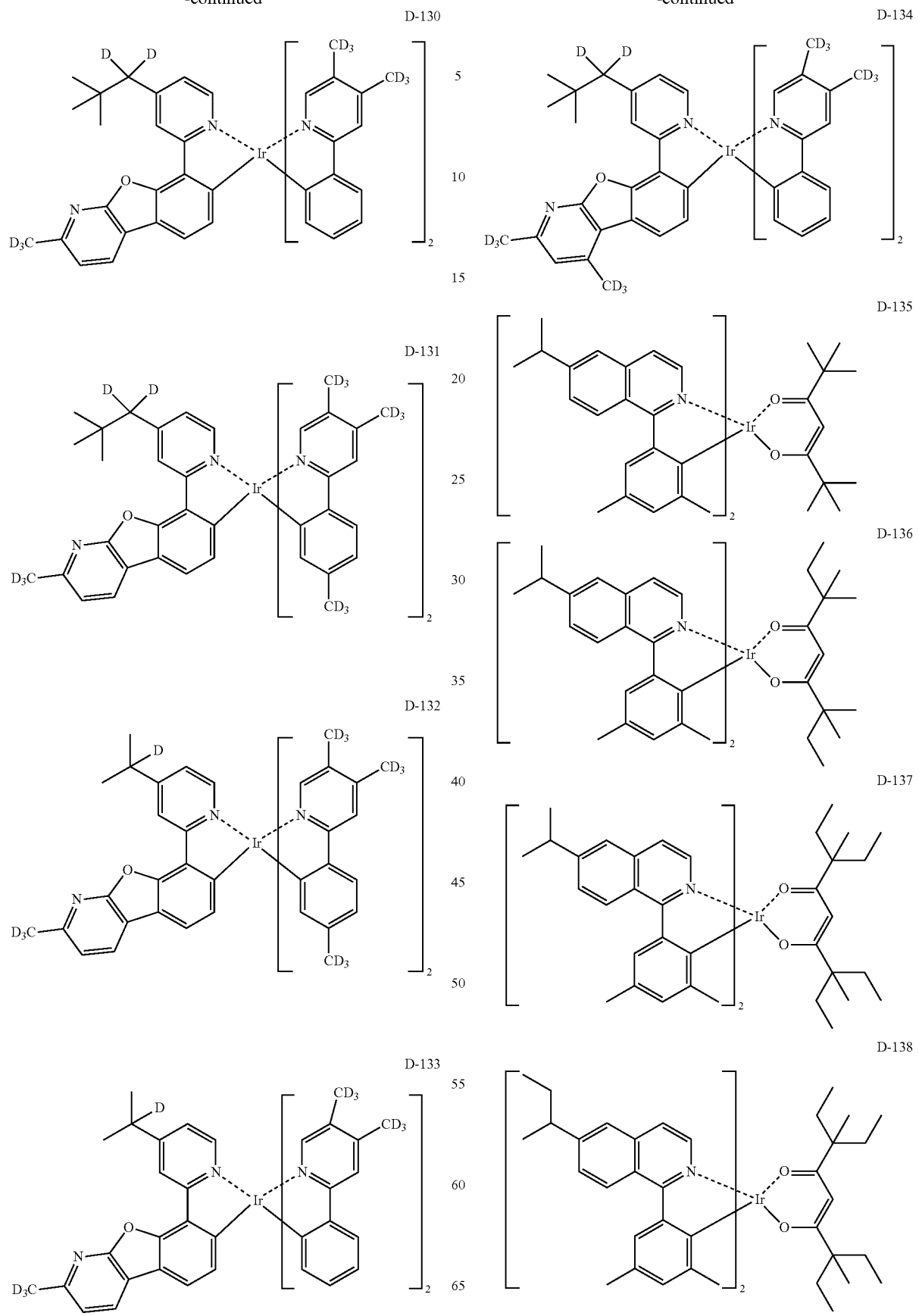

D-139
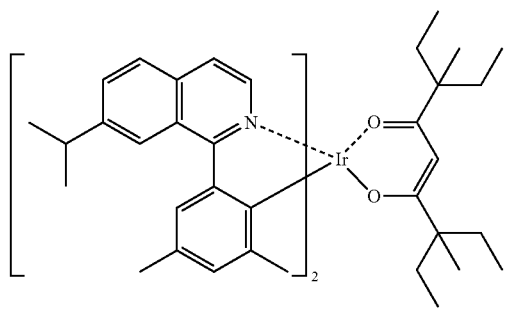
D-140
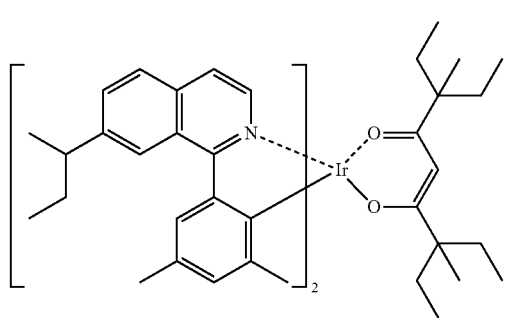
D-141
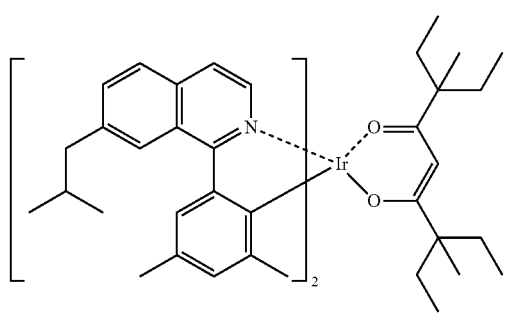
D-142
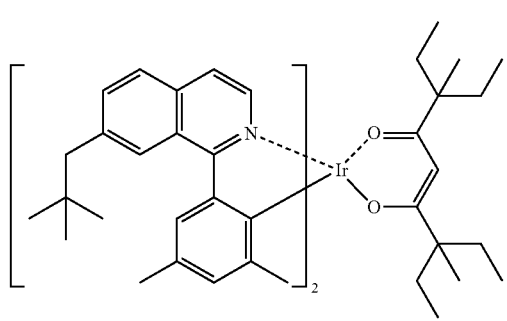
D-143
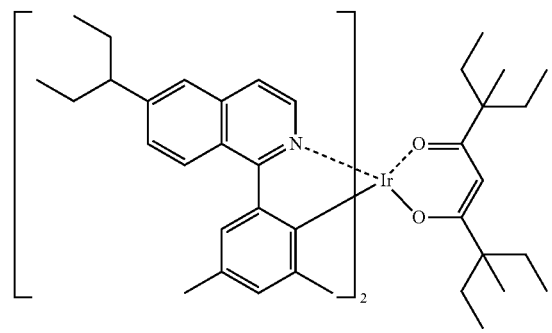
D-144
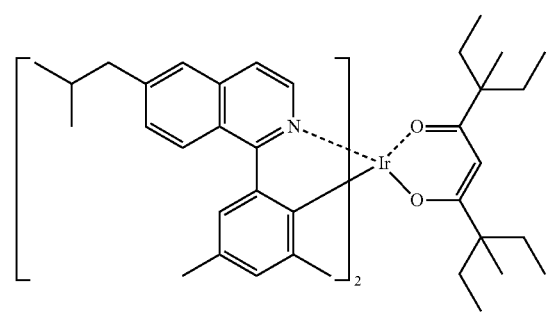
D-145
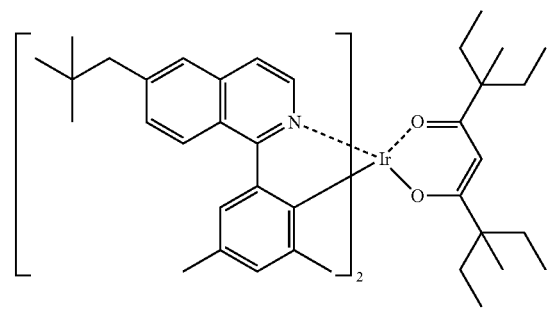
D-146
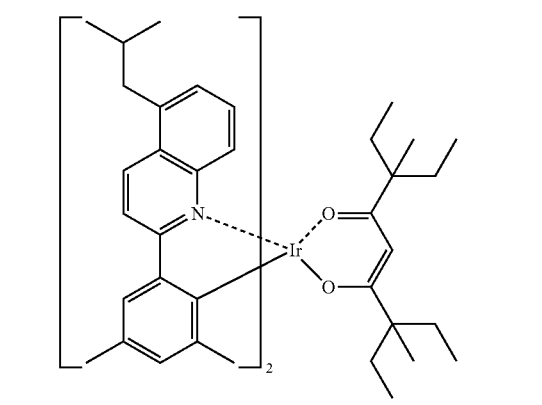

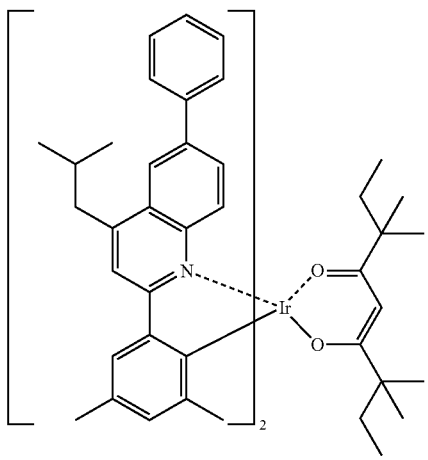

D-147

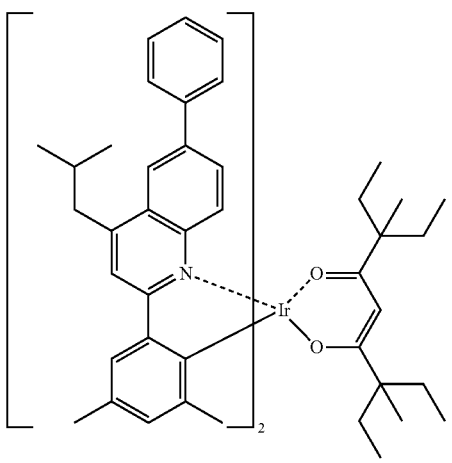

D-148

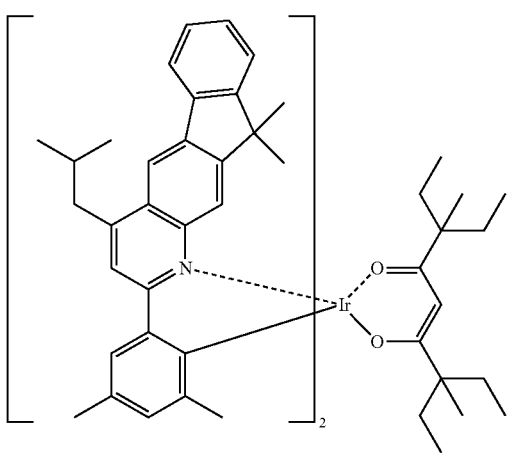

D-149

Each layer of the organic electroluminescent device of the present disclosure may be formed by any one of methods of dry film-forming methods such as vacuum evaporation, sputtering, plasma, ion plating, etc., or wet film-forming methods such as ink jet printing, nozzle printing, slot coating, spin coating, dip coating, flow coating, etc.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material forming each layer is soluble or dispersible in the solvents, which do not cause any problems in forming a film.

In addition, the compound represented by formula 1 and the compound represented by any one of formulas 2 to 4 may be formed by the aforementioned listed methods, commonly by co-evaporation or mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporation, and a current is applied to the cell to evaporate the materials. In addition, when the first and second host compounds are present in the same or different layer in an organic electroluminescent device, the two host compounds may be formed individually, respectively. For example, the second host compound may be evaporated after the first host compound is evaporated.

In addition, an organic electroluminescent material according to the present disclosure may be used as light-emitting materials for a white organic light-emitting device. The white organic light-emitting device has been suggested in various structures such as a side-by-side structure or a stacking structure depending on the arrangement of R (Red), G (Green) or YG (Yellowish Green), and B (Blue) light-emitting parts, or a color conversion material (CCM) method, etc. The present disclosure may be applied to such white organic light-emitting device. In addition, the organic electroluminescent material according to the present disclosure may also be used to the organic electroluminescent device comprising a QD (Quantum Dot).

The present disclosure may provide a display system by using a plurality of host materials comprising the compound represented by formula 1 and any one of the compounds represented by formulas 2 to 4. That is, it is possible to produce a display system or a lighting system by using the organic electroluminescent compound or a plurality of host materials of the present disclosure. Specifically, it is possible to produce a display system, e.g., a display system for white organic light-emitting device, smartphones, tablets, notebooks, PCs, TVs, or cars, or a lighting system, e.g., an outdoor or indoor lighting system, by using the plurality of host materials of the present disclosure.

Hereinafter, the preparation method of the compound of the present disclosure, and the properties thereof, and the properties of the organic electroluminescent device comprising the organic electroluminescent compound or a plurality of host materials according to the present disclosure will be explained in detail with reference to the representative compounds of the present disclosure. The following examples only describe the properties of the organic electroluminescent device comprising the compound or a plurality of host materials according to the present disclosure, but the present disclosure is not limited to the following examples.

Example 1: Preparation of Compound C-26

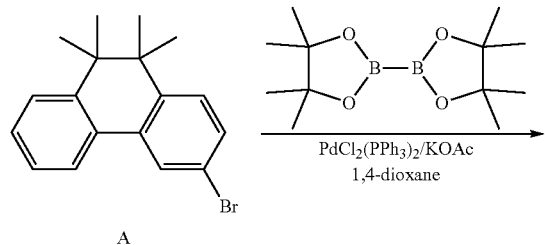

A

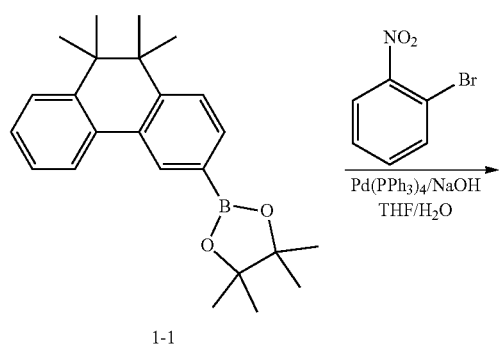

1-1

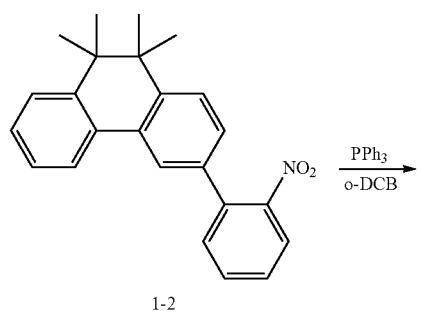

1-2

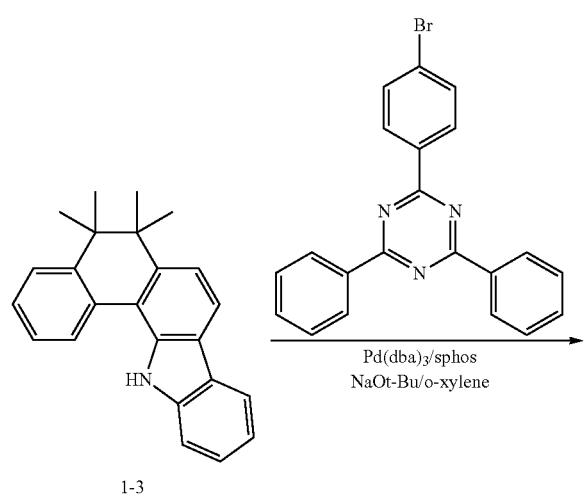

1-3

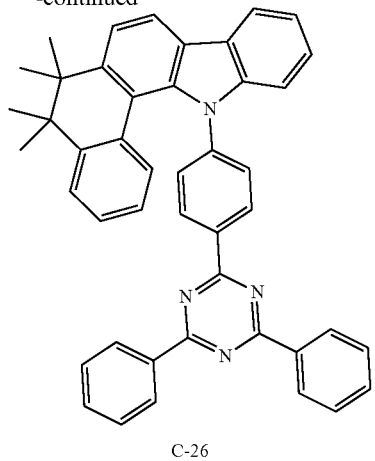

C-26

Synthesis of Compound 1-1

3-bromo-9,9,10,10-tetramethyl-9,10-dihydrophenanthrene (30 g, 95.2 mmol), 4,4,4',4',5,5,5',5'-octamethyl-2,2'-bi(1,3,2-dioxaborolane) (29.0 g, 114 mmol), PdCl$_2$(PPh$_3$)$_2$ (3.34 g, 4.76 mmol), KOAc (23.3 g, 238 mmol), and 500 mL of 1,4-dioxane were added to a flask and dissolved, followed by stirring under reflux at 140° C. for 3 hours. After the reaction was completed, the mixture was cooled to room temperature and separated through a silica filter to obtain compound 1-1 (31.0 g, yield: 90%).

Synthesis of Compound 1-2

Compound 1-1 (14.0 g, 38.6 mmol), 1-bromo-2-nitrobenzene (8.20 g, 40.6 mmol), tetrakis(triphenylphosphine)palladium(0) (4.47 g, 3.86 mmol), and NaOH (4.64 g, 116 mmol) were dissolved in a mixture of 130 mL of THF and 70 mL of H$_2$O in a flask, and the mixture was stirred under reflux at 110° C. for 3 hours. After the reaction was completed, ethyl acetate and water were added to separate the organic layer, and the silica filter was used to obtain compound 1-2 (17.0 g, yield: 116%).

Synthesis of Compound 1-3

Compound 1-2 (16.0 g, 44.8 mmol) and PPh$_3$ (29.4 g, 112 mmol) were dissolved in 220 mL of o-DCB in a flask, and the mixture was stirred under reflux at 230° C. for 1 day. After the reaction was completed, the solvent was removed through distillation and separated by column chromatography to obtain compound 1-3 (6.50 g, yield: 45%).

Synthesis of Compound C-26

Compound 1-3 (2.50 g, 7.68 mmol), 2-(4-bromophenyl)-4,6-diphenyl-1,3,5-triazine (3.13 g, 8.07 mmol), Pd$_2$(dba)$_3$ (0.350 g, 0.384 mmol), 2-dicyclohexylphosphino-2',6'-dimethoxybiphenyl (S-Phos) (0.315 g, 0.768 mmol), and NaOt-Bu (1.85 g, 19.2 mmol) were dissolved in 70 mL of o-xylene in a flask, and stirred under reflux at 180° C. for 1 hour. After the reaction was completed, the solvent was removed through filtration under reduced pressure and separated by column chromatography to obtain compound C-26 (1.10 g, yield: 22.6%).

|  | MW | M.P. | Color |
|---|---|---|---|
| C-26 | 521.61 | 269° C. | Yellow |

Example 2: Preparation of Compound C-582

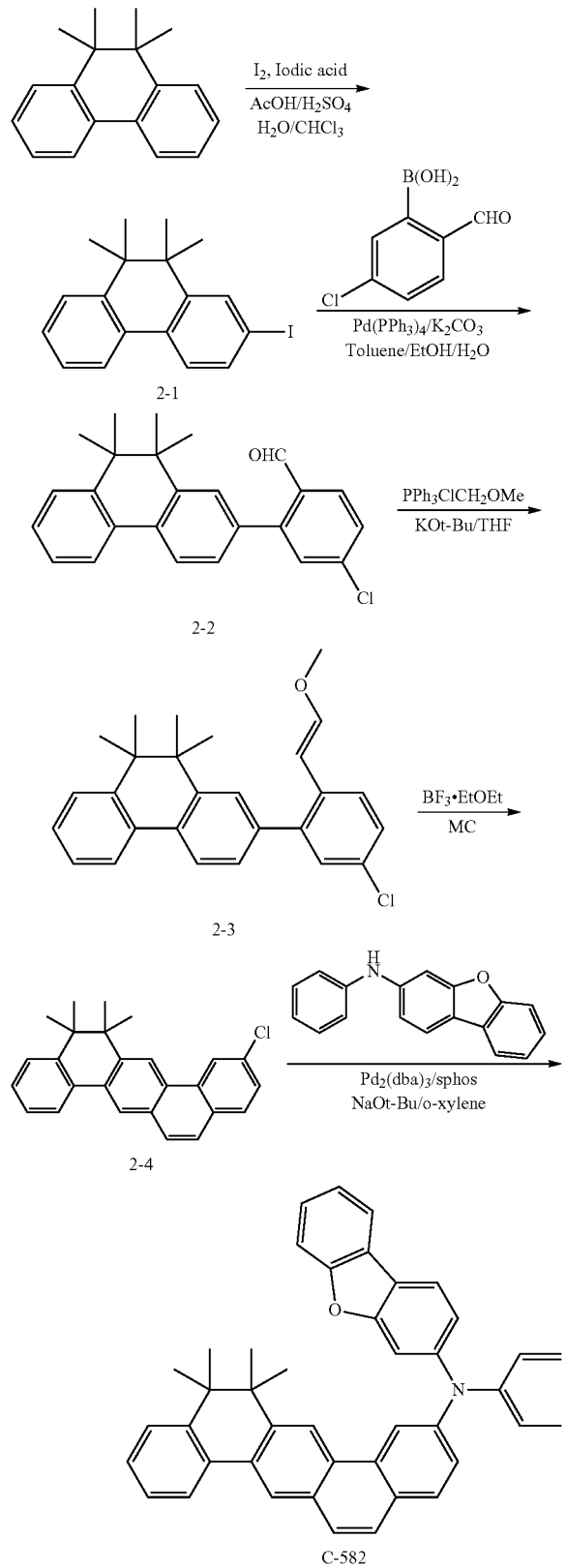

Synthesis of Compound 2-1

9,9,10,10-tetramethyl-9,10-dihydrophenanthrene (34.0 g, 144 mmol), $I_2$ (18.3 g, 71.9 mmol), iodic acid (12.7 g, 71.9 mmol), 280 mL of AcOH, 36 mL of $H_2SO_4$, 36 mL of $H_2O$, and 15 mL of $CHCl_3$ were added to a flask and stirred at 65° C. After the reaction was completed, the solvent was removed and the mixture was separated by column chromatography, and then MeOH was added thereto. The resulting solid was filtered under reduced pressure to obtain compound 2-1 (56.0 g, yield: 107%).

Synthesis of Compound 2-2

Compound 2-1 (35.0 g, 96.6 mmol), (5-chloro-2-formylphenyl)boronic acid (21.4 g, 116 mmol), $Pd(PPh_3)_4$ (5.58 g, 4.83 mmol), $K_2CO_3$ (33.4 g, 242 mmol), 300 mL of toluene, 100 mL of EtOH, and 100 mL of $H_2O$ were added to a flask and stirred at 140° C. After the reaction was completed, ethyl acetate and water were added to separate the layers, and then only the organic layer was separated. The solvent was removed by filtration under reduced pressure, followed by separation by column chromatography. MeOH was added thereto, and the resulting solid was filtered under reduced pressure to obtain compound 2-2 (36.0 g, yield: 99.4%).

Synthesis of Compound 2-3

Compound 2-2 (30.0 g, 80.0 mmol) and $PPh_3ClCH_2OMe$ (38.4 g, 112 mmol) were dissolved in 370 mL of THF in a flask, and 112 mL of a 1M solution of KOt-Bu in THF was added dropwise and stirred. After the reaction was completed, ethyl acetate and water were added to separate the layers, and then only the organic layer was separated. The solvent was removed by filtration under reduced pressure, and the residue was separated by column chromatography. MeOH was added thereto, and the resulting solid was filtered under reduced pressure to obtain compound 2-3 (20.0 g, yield: 62.0%).

Synthesis of Compound 2-4

Compound 2-3 (19.0 g, 47.2 mmol) was dissolved in 250 mL of methylene chloride (MC) in a flask, and 17.8 mL of $BF_3$-EtOEt solution was added dropwise and stirred at 0° C. After the reaction was completed, MC and $NaHCO_3$ (aq) were added to separate the layers, and then only the organic layer was separated. The solvent was removed by filtration under reduced pressure, and the residue was separated by column chromatography. MeOH was added thereto, and the resulting solid was filtered under reduced pressure to obtain compound 2-4 (16.0 g, Yield: 91.5%).

Synthesis of Compound C-582

Compound 2-4 (6.0 g, 16.2 mmol), N-phenyldibenzofuran-3-amine (4.40 g, 17.0 mmol), $Pd_2(dba)_3$ (0.741 g, 0.809 mmol), S-Phos (0.664 g, 1.62 mmol), NaOt-Bu (3.11 g, 32.4 mmol), and 80 mL of o-xylene were added to a flask and stirred under reflux at 180° C. After the reaction was completed, the solvent was removed by filtration under reduced pressure, and the residue was separated by column chromatography. MeOH was added thereto, and the resulting solid was filtered under reduced pressure to obtain compound C-582 (2.3 g, yield: 23.9%).

|  | MW | M.P. | Color |
| --- | --- | --- | --- |
| C-582 | 593.27 | 188.4° C. | White |

Example 3: Preparation of Compound H1-27

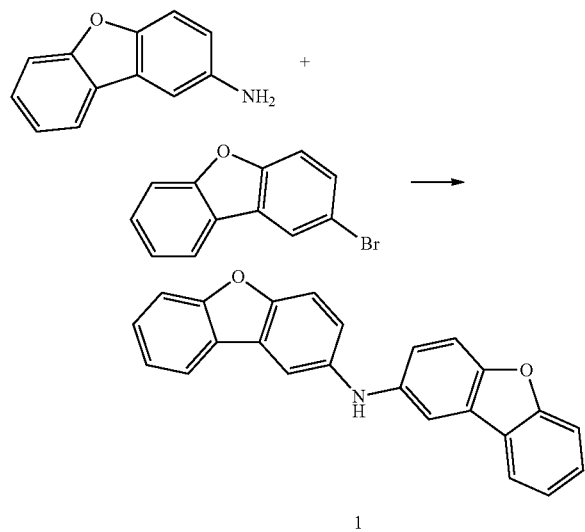

Synthesis of Compound 1

Dibenzofuran-2-amine (20 g, 144.7 mmol), 2-bromodibenzofuran (23.8 g, 96.47 mmol), Pd(OAc)$_2$ (1.1 g, 4.82 mmol), 2-dicyclohexylphosphino-2',6'-dimethoxybiphenyl (S-Phos) (3.9 g, 9.65 mmol), NaOt-Bu (13.9 g, 144.7 mmol), and 485 mL of o-xylene were added to a flask and stirred at 160° C. for 3 hours. After the reaction was completed, the mixture was cooled to room temperature. The organic layer was extracted with ethyl acetate, and residual moisture was removed using magnesium sulfate. The residue was dried, and separated by column chromatography to obtain compound 1 (4.9 g, yield: 10%).

Synthesis of Compound H1-27

Compound 1 (4.9 g, 12.76 mmol), compound 2 (4.2 g, 14.0 mmol), Pd(dba$_3$)$_2$ (0.584 g, 0.638 mmol), S-Phos (0.523 g, 1.276 mmol), NaOt-Bu (1.8 g, 19.14 mmol), and 65 mL of o-xylene were added to a flask and stirred at 160° C. for 2 hours. After the reaction was completed, the mixture was cooled to room temperature. The organic layer was extracted with ethyl acetate, and residual moisture was removed using magnesium sulfate. The residue was dried, and separated by column chromatography to obtain compound H1-27 (5.6 g, yield: 68.3%).

|  | MW | M.P. |
|---|---|---|
| H1-27 | 642.19 | 237° C. |

Example 4: Preparation of Compound H1-46

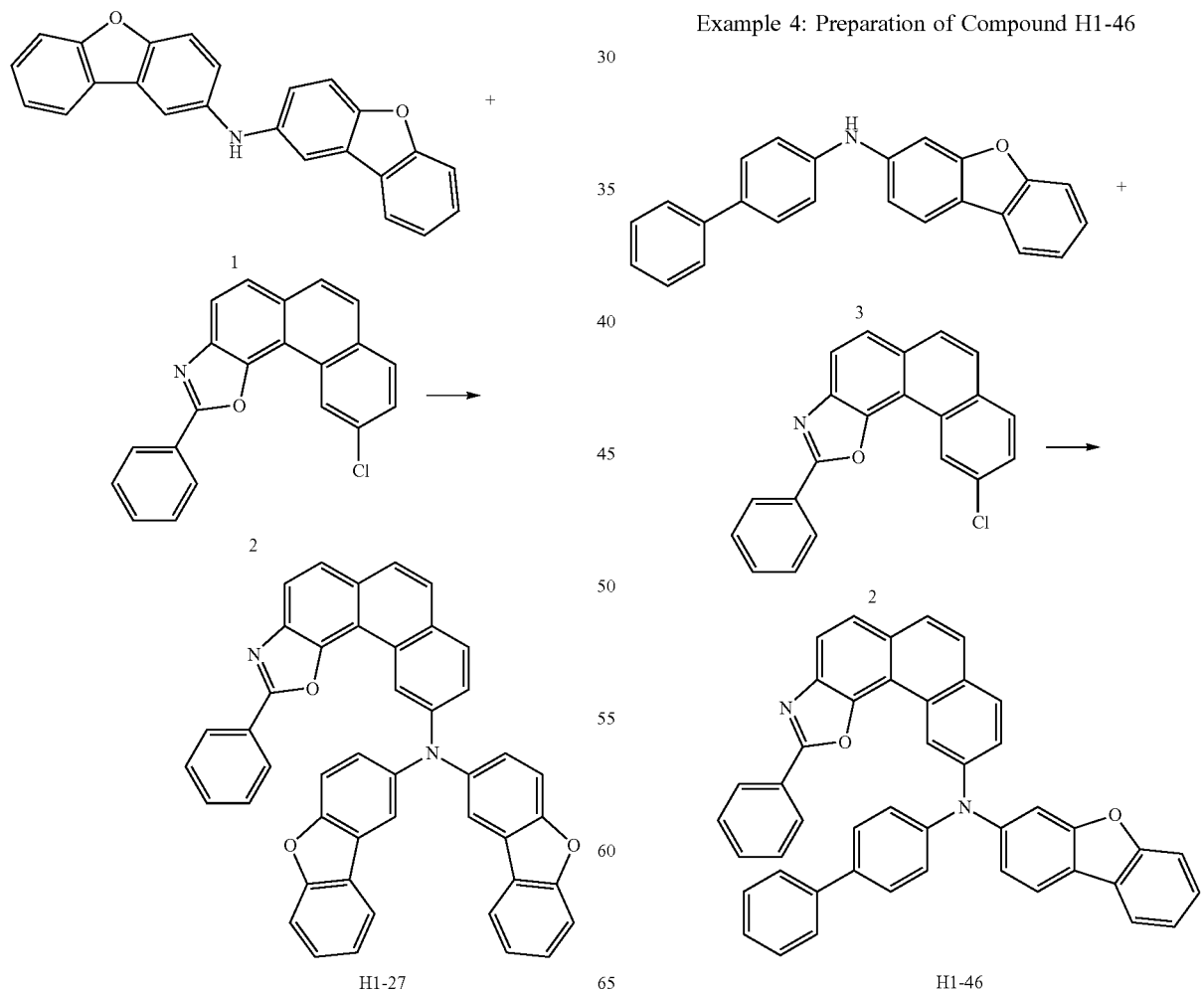

Compound 3 (25 g, 74.48 mmol), compound 2 (42.58 g, 81.93 mmol), Pd(OAc)$_2$ (0.16 g, 7.5 mmol), P(t-Bu)$_3$ (0.28 g, 7.5 mmol), NaOt-Bu (14.31 g, 150 mmol), and 284.09 mL of o-xylene were added to a flask and stirred at 160° C. for 2 hours. After the reaction was completed, the mixture was cooled to room temperature. The organic layer was extracted with ethyl acetate, and residual moisture was removed using magnesium sulfate. The residue was dried, and separated by column chromatography to obtain compound H1-46 (23.4 g, yield: 50%).

|  | MW | M.P. |
|---|---|---|
| H1-46 | 628.22 | 256.5° C. |

Example 5: Preparation of Compound H1-43

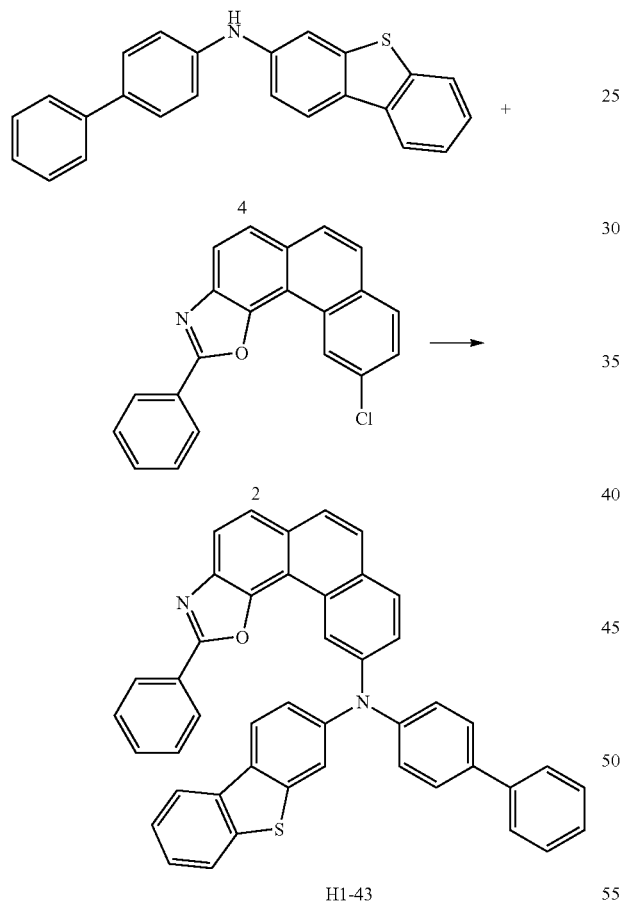

H1-43

Compound 4 (20 g, 56.96 mmol), compound 2 (18.8 g, 57.13 mmol), Pd(OAc)$_2$ (0.13 g, 5.7 mmol), P(t-Bu)$_3$ (0.22 g, 5.7 mmol), NaOt-Bu (11 g, 113.92 mmol), and 227.27 mL of o-xylene were added to a flask and stirred at 160° C. for 2 hours. After the reaction was completed, the reaction was cooled to room temperature. The organic layer was extracted with ethyl acetate, and residual moisture was removed using magnesium sulfate. The residue was dried, and separated by column chromatography to obtain compound H1-43 (12.5 g, yield: 34%).

|  | MW | M.P. |
|---|---|---|
| H1-43 | 644.19 | 249° C. |

Example 6: Preparation of Compound H1-123

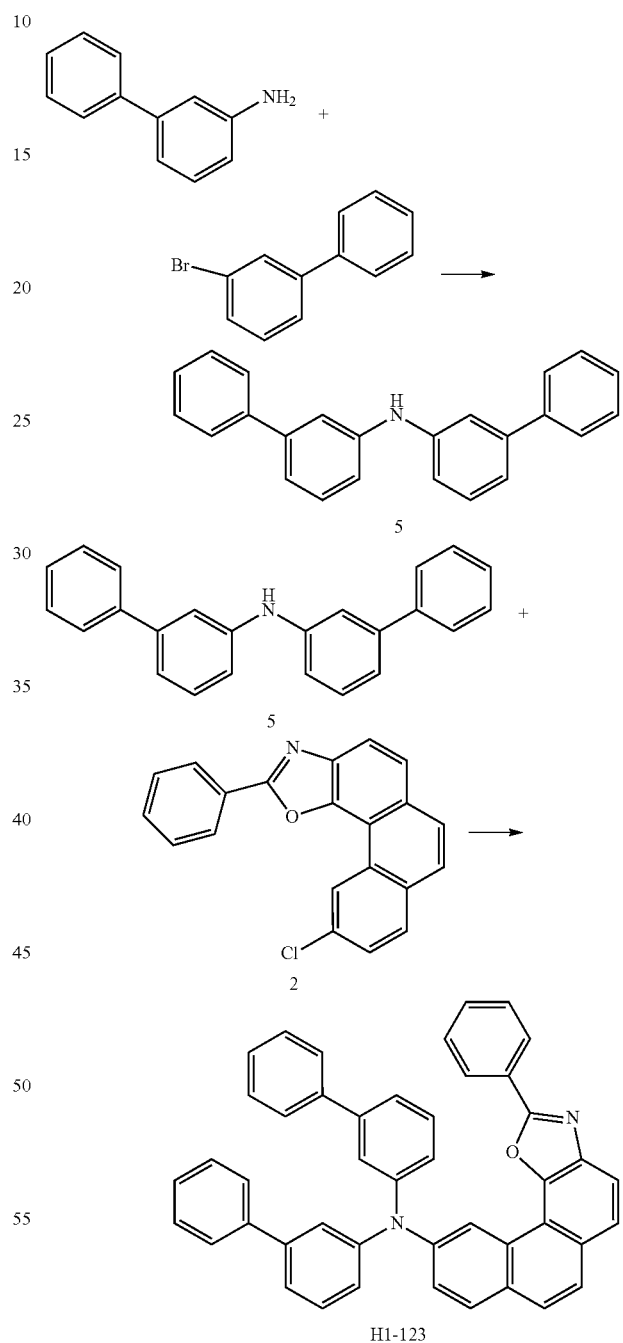

H1-123

Synthesis of Compound 5

3-aminobiphenyl (54 g, 319 mmol), 3-bromobiphenyl (70 g, 301 mmol), Pd(OAc)$_2$ (0.33 g, 1.47 mmol), tricyclohexylphosphine (0.84 g, 2.8 mmol), NaOt-Bu (57 g, 593 mmol), and 280 mL of toluene were added to a flask and stirred at 95° C. for 8 hours. After the reaction was completed, the mixture was cooled to room temperature. The organic layer was extracted with ethyl acetate, and residual moisture was removed using magnesium sulfate. The residue was dried, and separated by column chromatography to obtain compound 5 (60.23 g, yield: 85%).

Synthesis of Compound H1-123

Compound 5 (60.23 g, 187.5 mmol), compound 2 (60 g, 182.33 mmol), Pd(OAc)$_2$ (0.41 g, 1.83 mmol), S-Phos (1.74 g, 4.23 mmol), NaOt-Bu (26.23 g, 272 mmol), and 300 mL of xylene were added to a flask and stirred at 110° C. for 10 hours. After the reaction was completed, the mixture was cooled to room temperature. The organic layer was extracted with ethyl acetate, and residual moisture was removed using magnesium sulfate. The residue was dried, and separated by column chromatography to obtain compound H1-123 (36.9 g, yield: 33%).

|  | MW | M.P. |
|---|---|---|
| H1-123 | 614.24 | 210° C. |

Example 7: Preparation of Compound H1-136

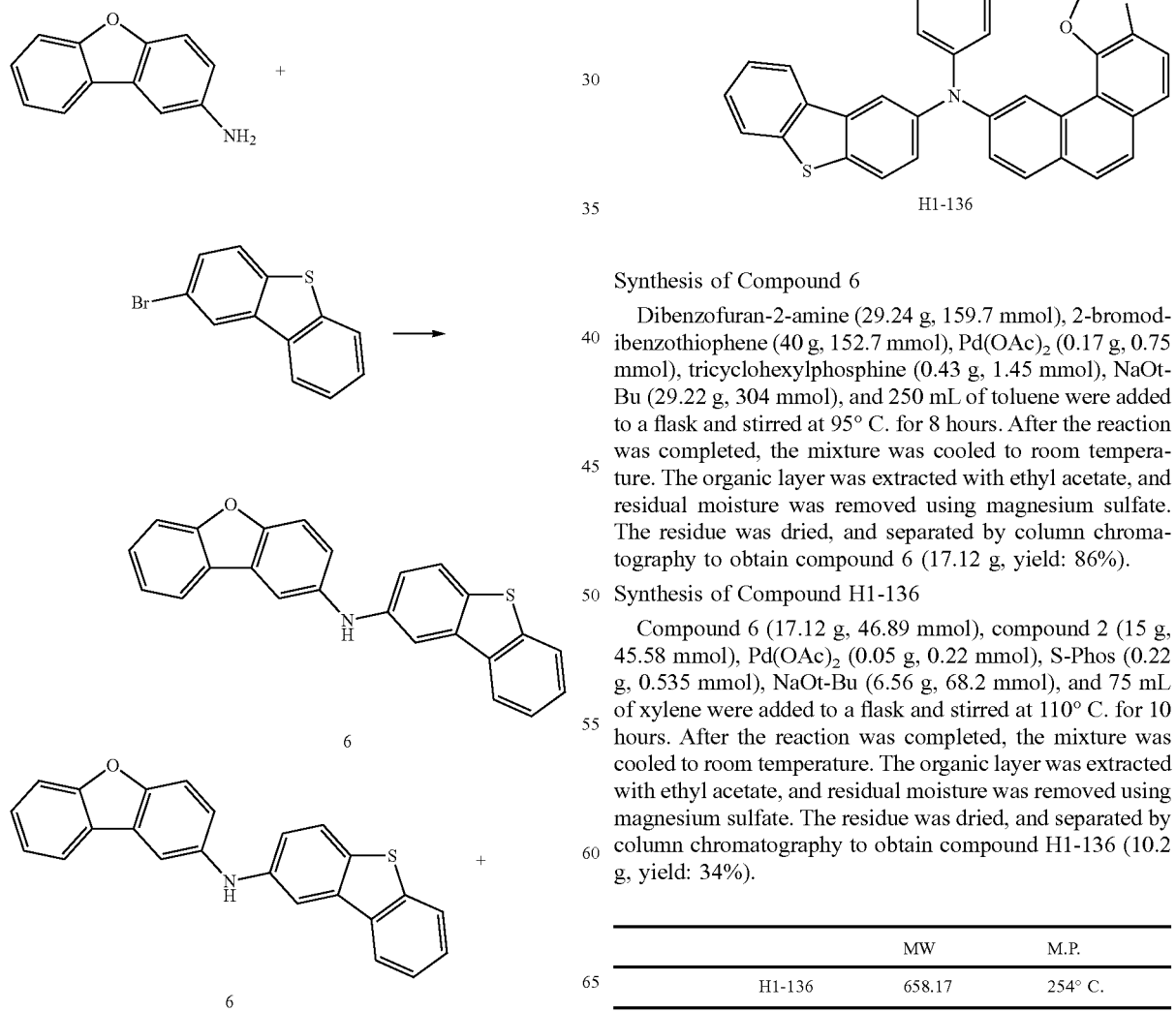

Synthesis of Compound 6

Dibenzofuran-2-amine (29.24 g, 159.7 mmol), 2-bromodibenzothiophene (40 g, 152.7 mmol), Pd(OAc)$_2$ (0.17 g, 0.75 mmol), tricyclohexylphosphine (0.43 g, 1.45 mmol), NaOt-Bu (29.22 g, 304 mmol), and 250 mL of toluene were added to a flask and stirred at 95° C. for 8 hours. After the reaction was completed, the mixture was cooled to room temperature. The organic layer was extracted with ethyl acetate, and residual moisture was removed using magnesium sulfate. The residue was dried, and separated by column chromatography to obtain compound 6 (17.12 g, yield: 86%).

Synthesis of Compound H1-136

Compound 6 (17.12 g, 46.89 mmol), compound 2 (15 g, 45.58 mmol), Pd(OAc)$_2$ (0.05 g, 0.22 mmol), S-Phos (0.22 g, 0.535 mmol), NaOt-Bu (6.56 g, 68.2 mmol), and 75 mL of xylene were added to a flask and stirred at 110° C. for 10 hours. After the reaction was completed, the mixture was cooled to room temperature. The organic layer was extracted with ethyl acetate, and residual moisture was removed using magnesium sulfate. The residue was dried, and separated by column chromatography to obtain compound H1-136 (10.2 g, yield: 34%).

|  | MW | M.P. |
|---|---|---|
| H1-136 | 658.17 | 254° C. |

Example 8: Preparation of Compound H1-85

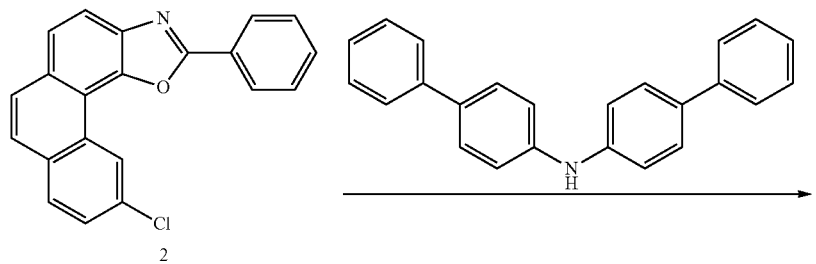

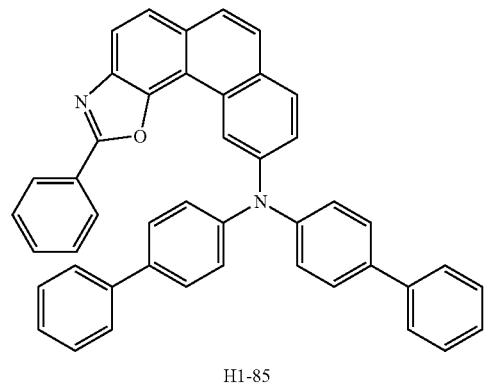

Compound 2 (5.0 g, 15.2 mmol), di([1,1'-biphenyl]-4-yl) amine (4.9 g, 15.2 mmol), Pd(OAc)$_2$ (0.2 g, 0.8 mmol), P(t-Bu)$_3$ (0.8 mL, 1.5 mmol), NaOt-Bu (2.9 g, 30.4 mmol), and 76 mL of xylene were added to a flask and stirred at 160° C. for 5 hours. After the reaction was completed, the mixture was cooled to room temperature. The precipitated solid was washed with distilled water and methanol, and separated by column chromatography to obtain compound H1-85 (5.5 g, yield: 59%).

Example 9: Preparation of Compound H1-51

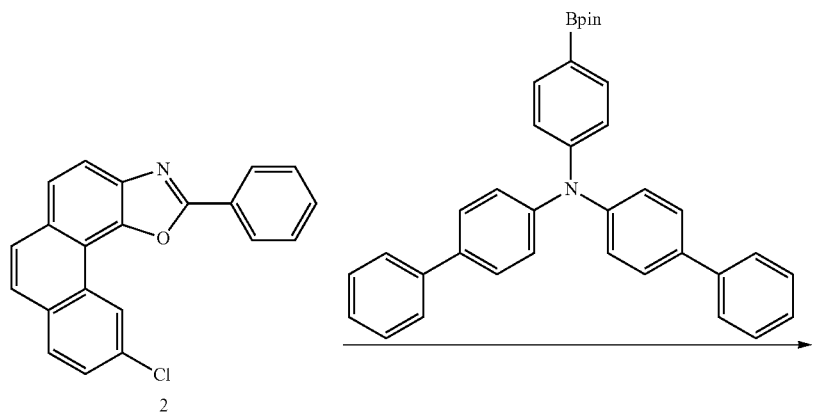

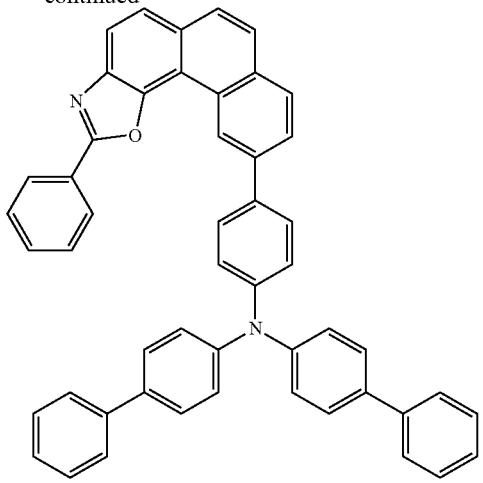

H1-51

Compound 2 (4 g, 12 mmol), bis(biphenyl-4-yl)[4-(4,4,5,5-tetramethyl-[1,3,2]-dioxaborolane-2-yl)phenyl]amine (6.8 g, 13 mmol), Pd(OAc)$_2$ (0.3 g, 1 mmol), S-Phos (0.9 g, 2 mmol), Cs$_2$CO$_3$ (11.5 g, 35 mmol), 60 mL of o-xylene, 15 mL of EtOH, and 15 mL of distilled water were added to a flask and stirred under reflux at 150° C. for 3 hours. After the reaction was completed, the mixture was cooled to room temperature and washed with distilled water. The organic layer was extracted with ethyl acetate, and residual moisture was removed using magnesium sulfate The residue was dried, and separated by column chromatography to obtain compound H1-51 (2.2 g, yield: 27%).

Example 10: Preparation of Compound H1-68

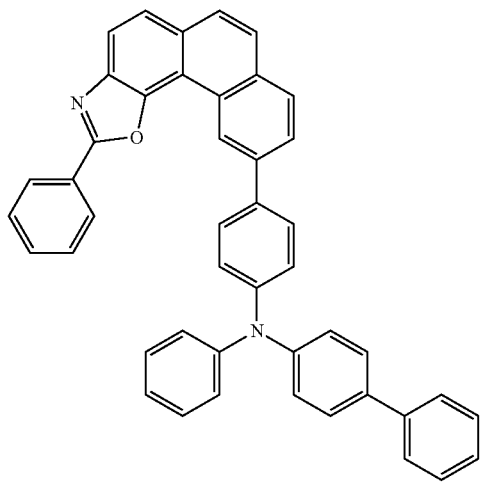

H1-68

Compound 7 (4.8 g, 11.34 mmol), N-(4-bromophenyl)-N-phenyl-[1,1'-biphenyl]-4-amine (5 g, 12.47 mmol), Pd(PPh$_3$)$_4$ (0.4 g, 0.34 mmol), Na$_2$CO$_3$ (3.0 g, 28.35 mmol), 57 mL of toluene, 14 mL of ethanol, and 14 mL of distilled water were added to a flask and stirred at 120° C. for 4 hours. After the reaction was completed, the mixture was added dropwise to methanol and the resulting solid was filtered. The resulting solid was purified by column chromatography to obtain compound H1-68 (1.4 g, yield: 20.0%).

Example 11: Preparation of Compound H1-15

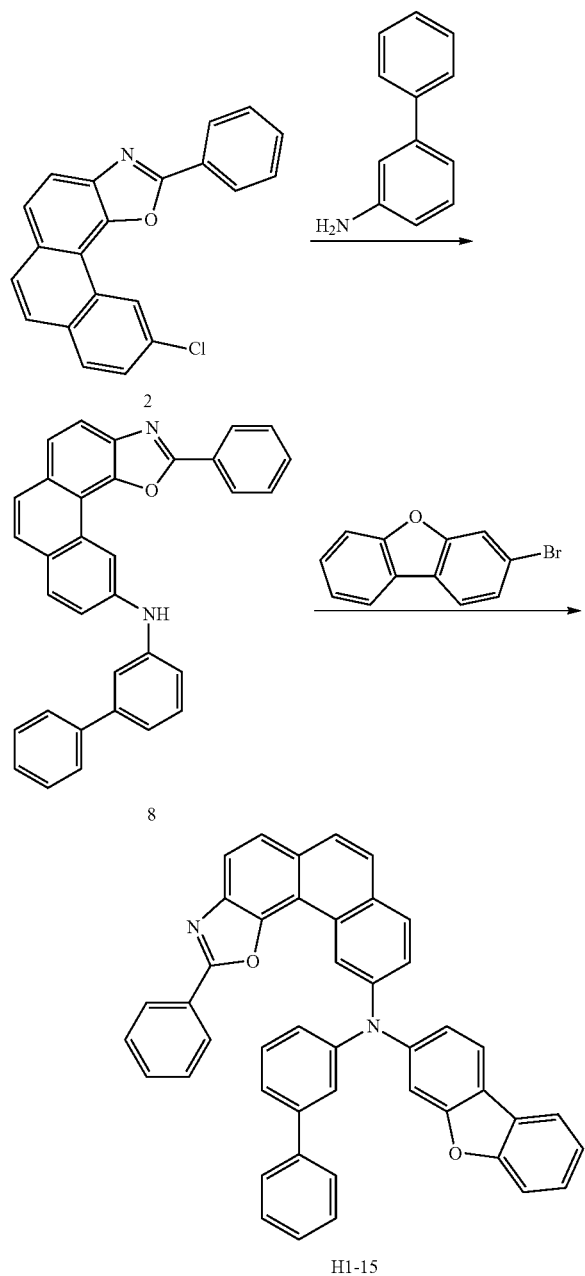

H1-15

Synthesis of Compound 8

Compound 2 (10.0 g, 30.3 mmol), [1,1'-biphenyl]-3-amine (6.7 g, 39.4 mmol), Pd(OAc)$_2$ (0.34 g, 1.5 mmol), P(t-Bu)$_3$ (1.5 mL, 3.03 mmol), NaOt-Bu (5.8 g, 60.6 mmol), and 150 mL of xylene were added to a flask and stirred at 160° C. for 6 hours. After the reaction was completed, the mixture was washed with distilled water. The organic layer was extracted with ethyl acetate and dried using magnesium sulfate. The solvent was removed using a rotary evaporator. The residue was separated by column chromatography to obtain compound 8 (10.8 g, yield: 36%).

Synthesis of Compound H1-15

Compound 8 (5.0 g, 10.8 mmol), 3-bromodibenzofuran (3.2 g, 12.9 mmol), Pd$_2$(dba)$_3$ (0.5 g, 0.54 mmol), S-Phos (0.45 g, 1.08 mmol), NaOt-Bu (2.0 g, 21.6 mmol), and 60 mL of o-xylene were added to a flask and stirred at 160° C. for 6 hours. After the reaction was completed, the mixture was cooled to room temperature. The organic layer was extracted with ethyl acetate, and residual moisture was removed using magnesium sulfate. The residue was dried, and separated by column chromatography to obtain compound H1-15 (1.45 g, yield: 21%).

|       | MW     | M.P.    |
|-------|--------|---------|
| H1-15 | 628.73 | 205° C. |

Device Example 1: Producing a Green Light-Emitting OLED Comprising a Compound According to the Present Disclosure An OLED comprising an organic electroluminescent compound according to the present disclosure was produced. First of all, a transparent electrode indium tin oxide (ITO) thin film (10 Ω/sq) on a glass substrate for an OLED (GEOMATEC CO., LTD., Japan) was subjected to an ultrasonic washing with acetone, and isopropyl alcohol, sequentially, and then was stored in isopropyl alcohol before use. The ITO substrate was mounted on a substrate holder of the vacuum vapor deposition apparatus. Compound HI-1 was introduced into a cell of the vacuum vapor deposition apparatus, and compound HT-1 was introduced into another cell. The two materials were evaporated at different rates to deposit a hole injection layer with a thickness of 10 nm by doping compound HI-1 in an amount of 3 wt % based to the total amount of compound HI-1 and compound HT-1. Subsequently, compound HT-1 was introduced into a cell of the vacuum vapor deposition apparatus and was evaporated by applying an electric current to the cell, thereby depositing a first hole transport layer on the hole injection layer with a thickness of 80 nm. Subsequently, compound HT-2 was introduced into another cell of the vacuum vapor deposition apparatus and was evaporated by applying an electric current to the cell, thereby depositing a second hole transport layer with a thickness of 30 nm on the first hole transport layer. After forming the hole injection layer and the hole transport layers, a light-emitting layer was deposited thereon as follows: Compound C-26 was introduced into a cell of the vacuum vapor deposition apparatus as a host and compound D-50 was introduced into another cell as a dopant, followed by doping a dopant in an amount of 10 wt % based on the total amount of the host and dopant to deposit a light-emitting layer having a thickness of 40 nm on the second hole transport layer. Subsequently, compound ETL-1: compound of EIL-1 were evaporated in a weight ratio of 40:60 to deposit an electron transport layer having a thickness of 35 nm on the light-emitting layer. After depositing compound EIL-1 as an electron injection layer having a thickness of 2 nm, an Al cathode having a thickness of 80 nm was deposited by another vacuum vapor deposition apparatus on the electron injection layer to produce an OLED. Each compound of materials was purified by vacuum sublimation under 10$^{-6}$ torr before use.

Comparative Example 1: Producing a Green Light-Emitting OLED Comprising a Conventional Compound as a Host An OLED was produced in the same manner as in Device Example 1, except that compound CBP (4,4'-N,N'-dicarbazole-biphenyl) was used as a host material of a light-emitting layer, Balq (aluminum(III)bis(2-methyl-8-quinolinato)4-phenylphenolate) was deposited to a thickness of 5 nm as a hole blocking layer, and compound ETL-1: compound of EIL-1 were evaporated in a weight ratio of 40:60 to deposit an electron transport layer having a thickness of 30 nm on the hole blocking layer.

The driving voltage, luminous efficiency, and luminous color based on a luminance of 1,000 nit of the organic electroluminescent device of Device Example 1 and Comparative Example 1 prepared as described above are shown in Table 1 below.

TABLE 1

|  | Host | Dopant | Driving Voltage (V) | Luminous Efficiency (cd/A) | Luminous Color |
|---|---|---|---|---|---|
| Device Example 1 | C-26 | D-50 | 2.8 | 80.5 | Green |
| Comparative Example 1 | CBP | D-50 | 5.7 | 75.8 | Green |

The organic electroluminescent device using the host material according to the present disclosure showed a lower driving voltage and higher luminous efficiency compared to the organic electroluminescent device using the host material of Comparative Example 1. In addition, the organic electroluminescent device using the host material according to the present disclosure may have excellent lifespan properties.

Device Examples 2 and 3: Producing a Red Light-Emitting OLED Comprising a Plurality of Host Materials According to the Present Disclosure An OLED according to the present disclosure was produced. First of all, a transparent electrode indium tin oxide (ITO) thin film (10 O/sq) on a glass substrate for an OLED (GEOMATEC CO., LTD., Japan) was subjected to an ultrasonic washing with acetone and isopropyl alcohol, sequentially, and then was stored in isopropyl alcohol before use. The ITO substrate was mounted on a substrate holder of the vacuum vapor deposition apparatus. Compound HI-1 was introduced into a cell of the vacuum vapor deposition apparatus, and compound HT-1 was introduced into another cell. The two materials were evaporated at different rates to deposit a hole injection layer with a thickness of 10 nm by doping compound HI-1 in an amount of 3 wt % based to the total amount of compound HI-1 and compound HT-1. Subsequently, compound HT-1 was introduced into a cell of the vacuum vapor deposition apparatus and was evaporated by applying an electric current to the cell, thereby depositing a first hole transport layer on the hole injection layer with a thickness of 80 nm. Subsequently, compound HT-3 was introduced into another cell of the vacuum vapor deposition apparatus and was evaporated by applying an electric current to the cell, thereby depositing a second hole transport layer with a thickness of 60 nm on the first hole transport layer. After forming the hole injection layer and the hole transport layers, a light-emitting layer was deposited thereon as follows: The first host compound and the second host compound as shown in Table 2 below were introduced into two cells of the vacuum vapor deposition apparatus as hosts, and compound D-39 was introduced into another cell as a dopant. The two host materials were evaporated at a rate of 1:1 and the dopant was evaporated at a different rate at the same time, thereby doping a dopant in an amount of 3 wt % based on the total amount of the host and dopant to deposit a light-emitting layer having a thickness of 40 nm on the second hole transport layer. Subsequently, compound ETL-1: compound of EIL-1 were evaporated in a weight ratio of 50:50 to deposit an electron transport layer having a thickness of 35 nm on the light-emitting layer. After depositing compound EIL-1 as an electron injection layer having a thickness of 2 nm on the electron transport layer, an Al cathode having a thickness of 80 nm was deposited by another vacuum vapor deposition apparatus on the electron injection layer to produce an OLED. Each compound of materials was purified by vacuum sublimation under $10^{-6}$ torr before use.

Comparative Examples 2 and 3: Producing a Red Light-Emitting OLED Comprising a Conventional Compound as a Host An OLED was produced in the same manner as in Device Examples 2 and 3, except that compound CBP or compound H1-9 was used as a single host material of a light-emitting layer.

The driving voltage, luminous efficiency, and luminous color based on a luminance of 1,000 nit, and the time taken for reduction of luminance from 100% to 95% (lifespan: T95) based on a luminance of 5,000 nit of the organic electroluminescent device of Device Examples 2 and 3 and Comparative Examples 2 and 3 prepared as described above are shown in Table 2 below.

TABLE 2

|  | First Host | Second Host | Dopant | Driving Voltage (V) | Luminous Efficiency (cd/A) | Luminous Color | Lifespan (T95, hr) |
|---|---|---|---|---|---|---|---|
| Device Example 2 | C-26 | H1-9 | D-39 | 3.0 | 31.0 | Red | 110 |
| Device Example 3 | C-582 | H4-24 | D-39 | 2.9 | 34.7 | Red | 180 |
| Comparative Example 2 | CBP | — | D-39 | 9.0 | 14.3 | Red | 0.31 |
| Comparative Example 3 | — | H1-9 |  | 4.23 | 6.9 | Red | 13.2 |

The organic electroluminescent device using a plurality of host materials according to the present disclosure showed a lower driving voltage, higher luminous efficiency, and excellent lifespan properties compared to the organic electroluminescent device using the host material of Comparative Examples 2 and 3.

Device Example 4: Producing a Green Light-Emitting OLED Comprising a Plurality of Host Materials According to the Present Disclosure An OLED according to the present disclosure was produced. First of all, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol before use. The ITO substrate was mounted on a substrate holder of the vacuum vapor deposition apparatus. Compound HI-1 was introduced into a cell of the vacuum vapor deposition apparatus, and compound HT-1 was introduced into another cell. The two materials were evaporated at different rates to deposit a hole injection layer with a thickness of 10 nm by doping compound HI-1 in an amount of 3 wt % based to the total amount of compound HI-1 and compound HT-1. Subsequently, compound HT-1 was introduced into a cell of the vacuum vapor deposition apparatus and was evaporated by applying an electric current to the cell, thereby depositing a first hole transport layer on the hole injection layer with a thickness of 80 nm. Subsequently, compound HT-2 was introduced into another cell of the vacuum vapor deposition apparatus and was evaporated by applying an electric current to the cell, thereby depositing a second hole transport layer with a thickness of 30 nm on the first hole transport layer. After forming the hole injection layer and the hole transport layers, a light-emitting layer was deposited thereon as follows: compound C-26 and compound H2-2 were introduced into cells of the vacuum vapor deposition apparatus as hosts and compound D-130 was introduced into another cell as a dopant. The two host materials were evaporated at a different rate of 2:1 and the dopant was evaporated at a different rate at the same time, thereby doping a dopant in an amount of 10 wt % based on the total amount of the host and dopant to deposit a light-emitting layer having a thickness of 40 nm on the second hole transport layer. Subsequently, compound ETL-1: compound of EIL-1 were evaporated in a weight ratio of 40:60 to deposit an electron transport layer having a thickness of 35 nm on the light-emitting layer. After depositing compound EIL-1 as an electron injection layer having a thickness of 2 nm on the electron transport layer, an Al cathode having a thickness of 80 nm was deposited by another vacuum vapor deposition apparatus on the electron injection layer to produce an OLED. Each compound of materials was purified by vacuum sublimation under $10^{-6}$ torr before use.

Comparative Example 4: Producing a Green Light-Emitting OLED Comprising a Conventional Compound as a Host An OLED was produced in the same manner as in Device Example 4, except that compound H2-2 was used as a single host material of a light-emitting layer.

The driving voltage, luminous efficiency, and luminous color based on a luminance of 1,000 nit of the organic electroluminescent device of Device Example 4 and Comparative Example 4 prepared as described above are shown in Table 3 below.

TABLE 3

| | First Host | Second Host | Dopant | Driving Voltage (V) | Luminous Efficiency (cd/A) | Luminous Color |
|---|---|---|---|---|---|---|
| Device Example 4 | C-26 | H1-9 | D-39 | 3.0 | 31.0 | Green |
| Comparative Example 4 | — | H1-9 | | 4.23 | 6.9 | Green |

The organic electroluminescent device using a plurality of host materials according to the present disclosure showed a lower driving voltage and higher luminous efficiency compared to the organic electroluminescent device using the host material of Comparative Example 4. In addition, the organic electroluminescent device using a plurality of host materials according to the present disclosure may have excellent lifespan properties.

Without being limited by theory, in the case of a compound in which all of $R_{11}$ to $R_{14}$ in the dihydrophenanthrene backbone of formula 1 are hydrogen, it is easily converted to a compound having a phenanthrene backbone by light irradiation (e.g., phenanthroindole structure). Compounds having a phenanthrene backbone (e.g., phenanthroindole) may act like an impurity, because phenanthrene has a lower triplet energy gap than dihydrophenanthrene. In this case, the characteristics of the OLED may be deteriorated. The present disclosure tried to solve such problem by introducing a protecting group such as a methyl group to $R_{11}$ to $R_{14}$. In particular, HOMO energy and LUMO energy are not affected when methyl is introduced.

TABLE 4

| Hole Injection Layer/First Hole Transport Layer | |
|---|---|
| | 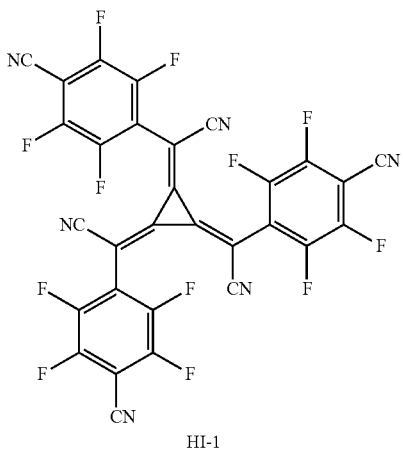 HI-1 |

TABLE 4-continued
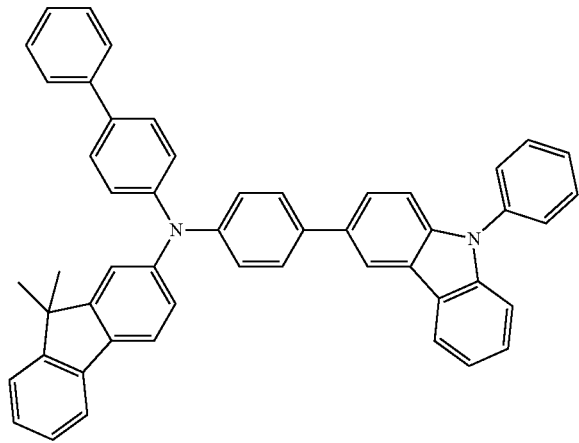 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-1
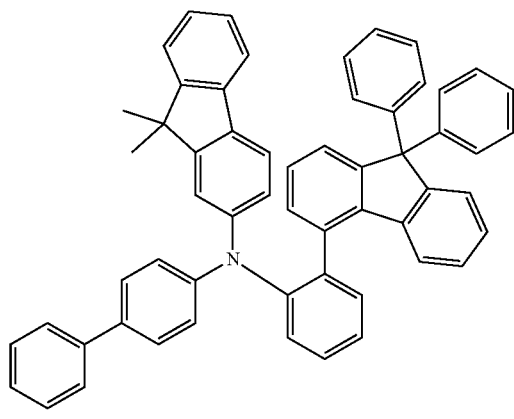 [SMILES: CC1(C)c2ccccc2-c2ccc(N(c3ccc(-c4ccccc4)cc3)c3ccccc3-c3cccc4c3-c3ccccc3C4(c3ccccc3)c3ccccc3)cc21]
HT-2
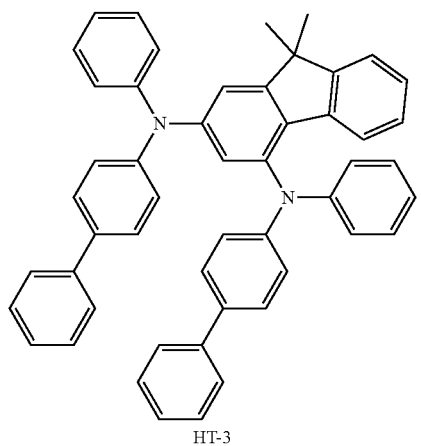
HT-3

TABLE 4-continued
Light-Emitting Layer
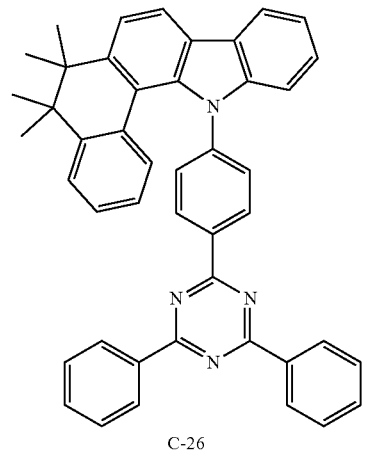
C-26
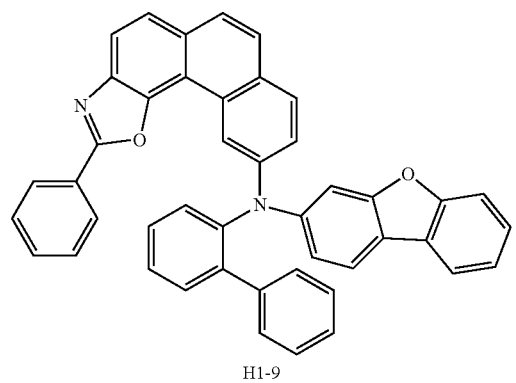
H1-9
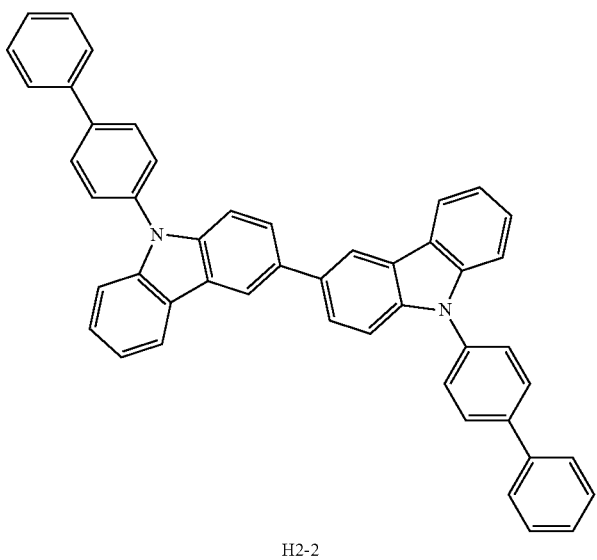
H2-2

TABLE 4-continued
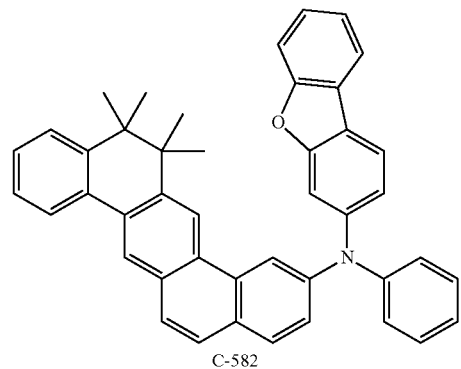
C-582
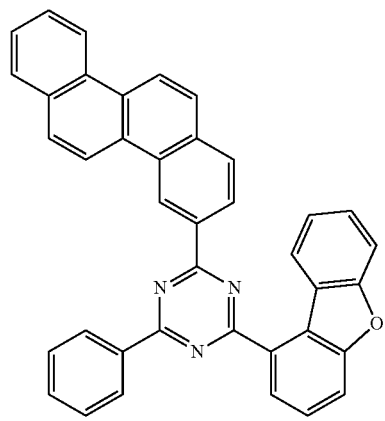 [SMILES: c1ccc(-c2nc(-c3ccc4ccc5c6ccccc6ccc5c4c3)nc(-c3cccc4oc5ccccc5c34)n2)cc1]
H4-24
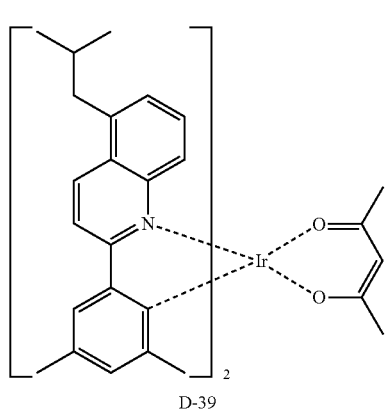
D-39
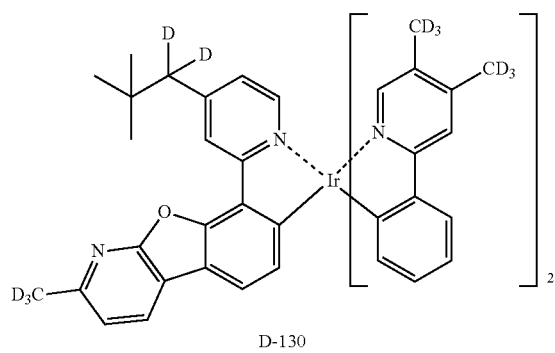
D-130

TABLE 4-continued

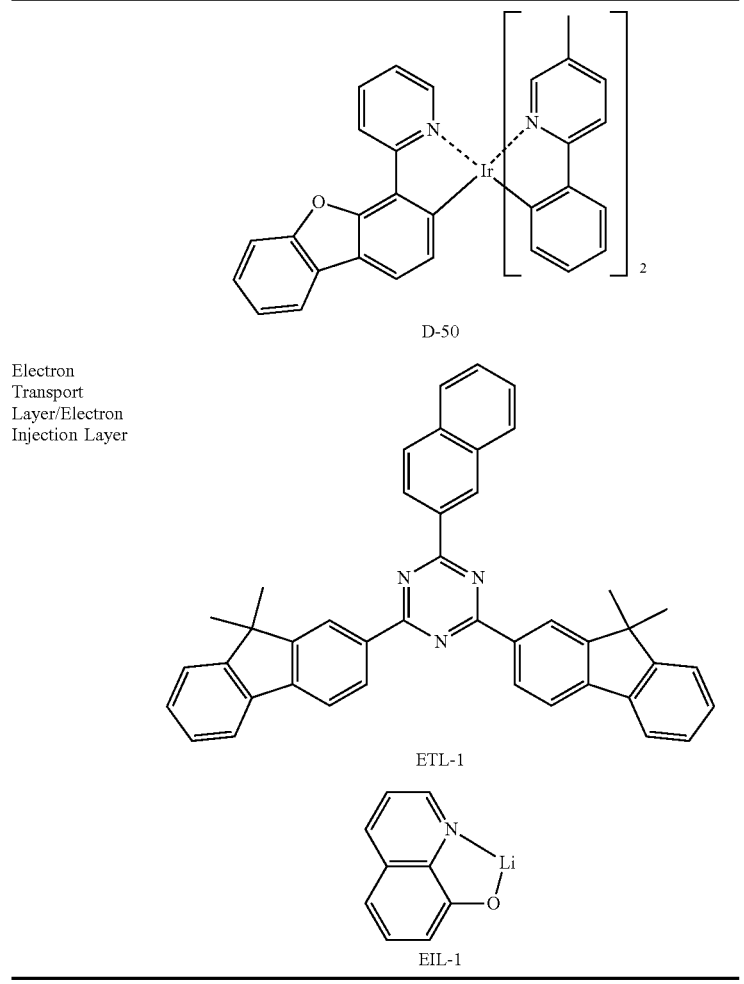

D-50

Electron Transport Layer/Electron Injection Layer

ETL-1

EIL-1

The invention claimed is:

1. An organic electroluminescent compound represented by at least one of the following formulas 1-11 to 1-13:

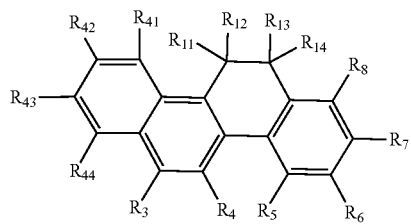

(1-11)

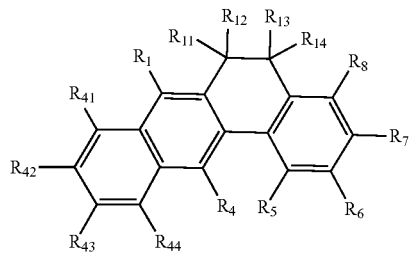

(1-12)

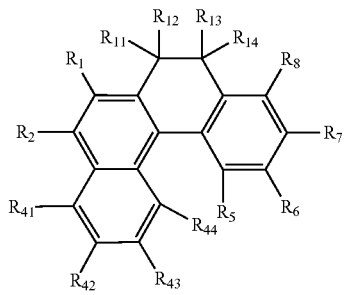

(1-13)

wherein $R_{11}$ to $R_{14}$ each independently represent hydrogen, deuterium, a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring, with a proviso that at least one of $R_{11}$ to $R_{14}$ is neither hydrogen nor deuterium;

$R_1$ to $R_8$ each independently represent hydrogen, deuterium, or -L-Ar, or may be linked to an adjacent substituent to form a ring, with a proviso that at least one pair of $R_1$ and $R_2$, $R_2$ and $R_3$, $R_3$ and $R_4$, $R_5$ and $R_6$, $R_6$ and $R_7$, and $R_7$ and $R_8$ is linked to each other to be fused as the following formula a;

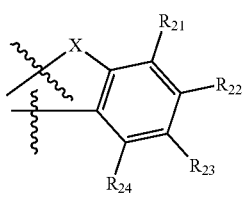

wherein

X represents $NR_{31}$, O, S, $CR_{32}R_{33}$, or —$CR_{34}$=$CR_{35}$—;

$R_{31}$ represents -$L_1$-$Ar_1$;

$R_{32}$ and $R_{33}$ each independently represent a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring;

$R_{34}$ and $R_{35}$ each independently represent hydrogen, deuterium, or -$L_5$-$Ar_5$;

$R_{21}$ to $R_{24}$ each independently represent hydrogen, deuterium, or -$L_2$-$Ar_2$, or may be linked to an adjacent substituent to form a ring:

L, $L_1$, $L_2$, and $L_5$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

Ar, $Ar_1$, $Ar_2$, and $Ar_5$ each independently represent a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, or a substituted or unsubstituted (C1-C30)alkoxy, or are represented by the following formula b or c;

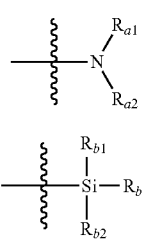

wherein $R_{a1}$, $R_{a2}$, $R_{b1}$, $R_{b2}$, and $R_{b3}$ each independently represent a substituted or unsubstituted (C6-C30)aryl, a substituted or unsubstituted (3- to 30-membered)heteroaryl, or a substituted or unsubstituted (C3-C30)cycloalkyl;

⸺ in formula a represents a bonding site with $R_1$ to $R_8$; and

⸺ in formulas b and c represents a bonding site with L, $L_1$, $L_2$, or $L_5$, respectively;

$R_{41}$ to $R_{44}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N($Ar_3$)($Ar_4$):

$L_3$ each independently represents a single bond, a substituted or unsubstituted (C6-C30)arylene, or a substituted or unsubstituted (3- to 30-membered)heteroarylene; and $Ar_3$ and $Ar_4$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

2. The organic electroluminescent compound according to claim 1, wherein formula a is represented by at least one of the following formulas a-1 to a-3:

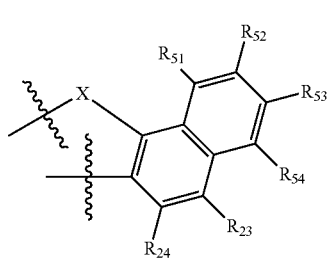

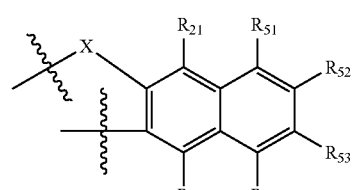

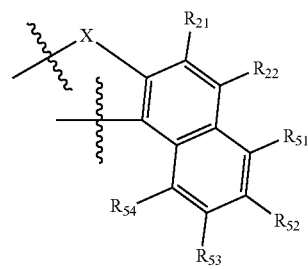

wherein $R_{21}$ to $R_{24}$ and X are as defined in claim 1;

$R_{51}$ to $R_{54}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-

C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -L$_3$'-N(Ar$_3$')(Ar$_4$');

L$_3$' each independently represents a single bond, a substituted or unsubstituted (C6-C30)arylene, or a substituted or unsubstituted (3- to 30-membered)heteroarylene; and Ar$_3$' and Ar$_4$' each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

3. The organic electroluminescent compound according to claim 1, wherein the substituents of the substituted alkyl, the substituted alkylene, the substituted cycloalkyl, the substituted cycloalkylene, the substituted alkoxy, the substituted aryl, the substituted arylene, the substituted heteroaryl, and the substituted heteroarylene in R$_{11}$ to R$_{14}$, R$_{32}$, R$_{33}$, L, L$_1$, L$_2$, L$_5$, Ar, Ar$_1$, Ar$_2$, Ar$_5$, R$_{a1}$, R$_{a2}$, and R$_{b1}$ to R$_{b3}$ each independently, are at least one selected from the group consisting of deuterium; a halogen; a cyano; a carboxyl; a nitro; a hydroxyl; a (C1-C30)alkyl; a halo (C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered) heterocycloalkyl; a (C6-C30)aryloxy; a (C6-C30)arylthio; a (3- to 30-membered) heteroaryl unsubstituted or substituted with at least one of a (C6-C30)aryl(s); a (C6-C30)aryl unsubstituted or substituted with at least one of a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino unsubstituted or substituted with a (C1-C30)alkyl(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl (3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

4. The organic electroluminescent compound according to claim 1, wherein the compound represented by formulas 1-11 to 1-13 is selected from the following compounds:

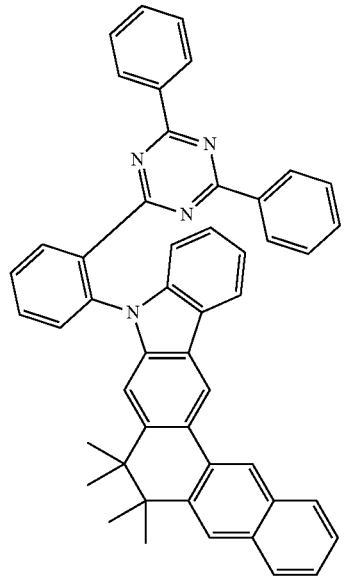

C-85

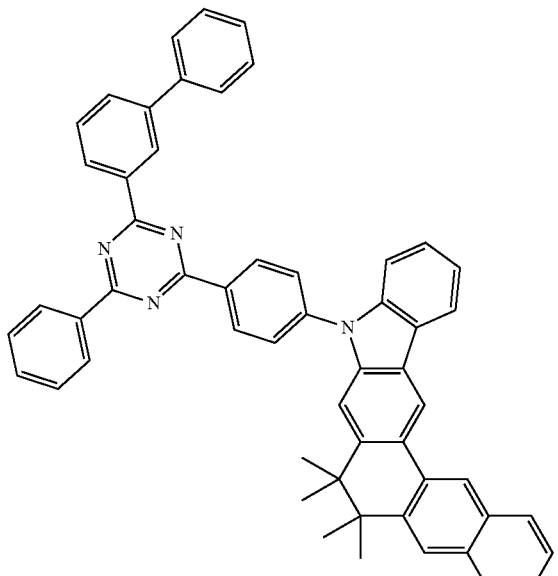

C-87

-continued
C-88
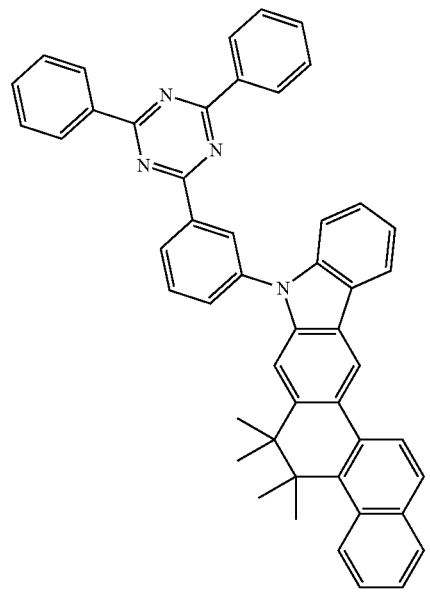
C-89
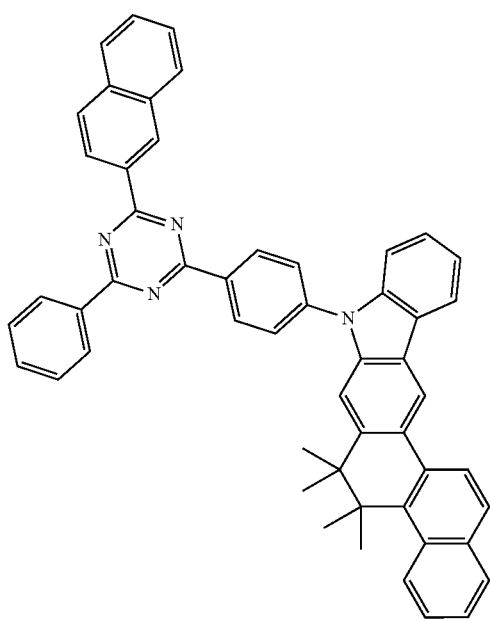
C-90
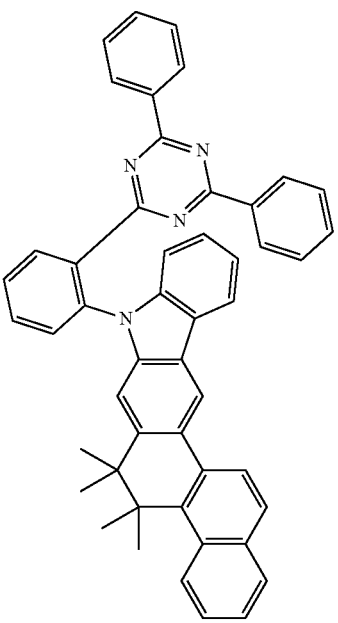
C-91
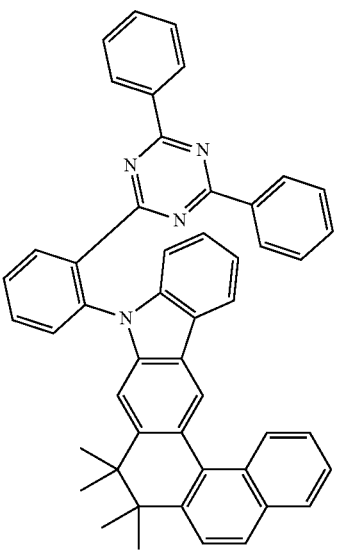

C-92
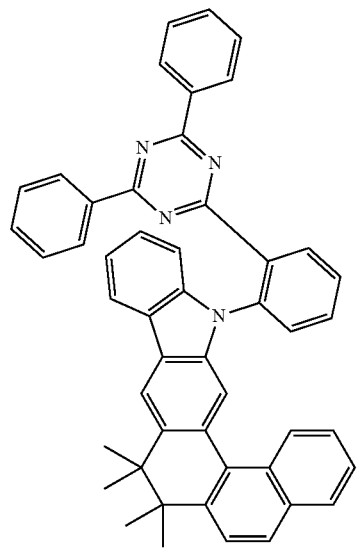
C-93
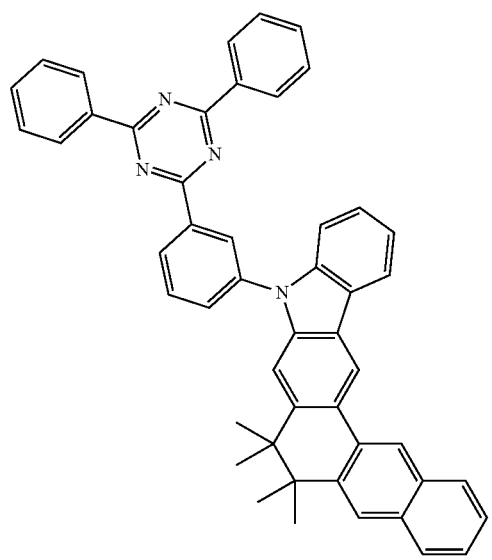
C-95
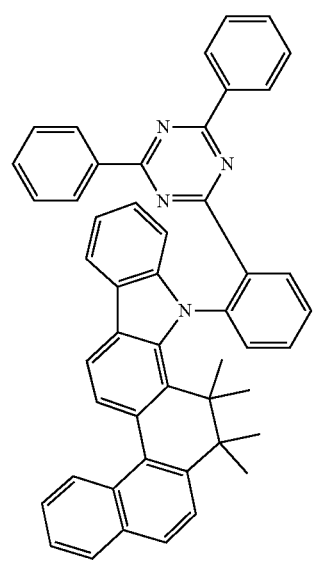
C-96
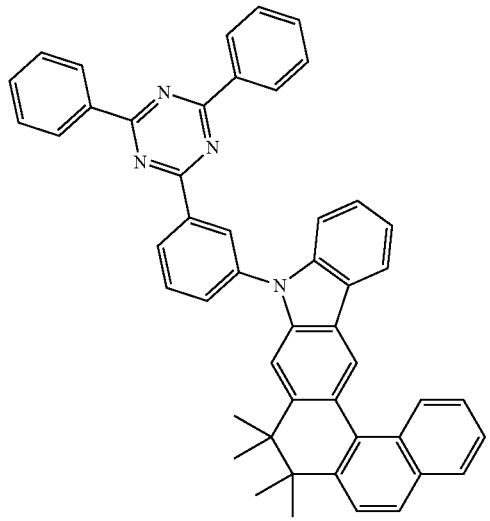
C-97
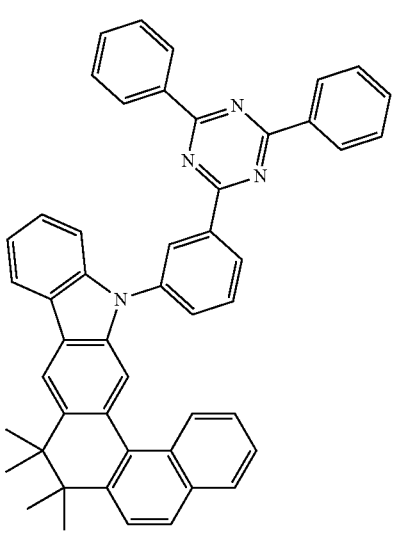
C-98
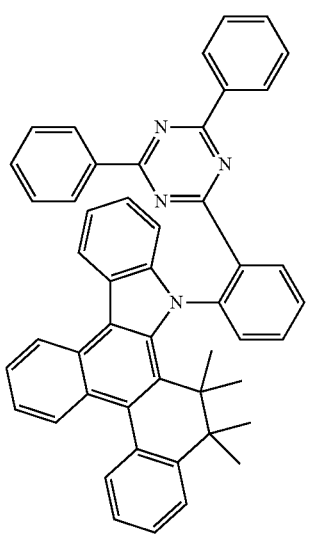

C-100
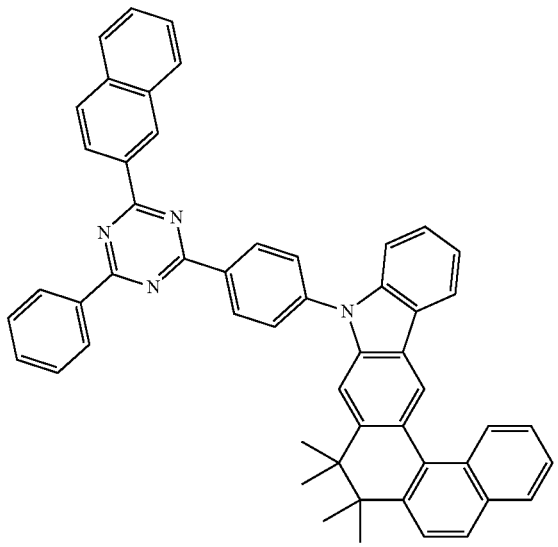
C-103
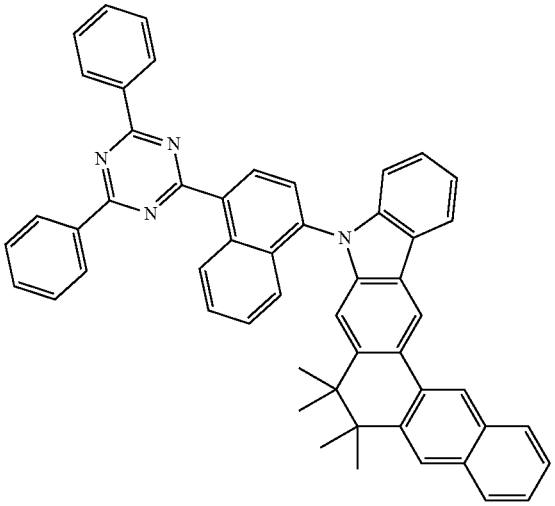
C-101
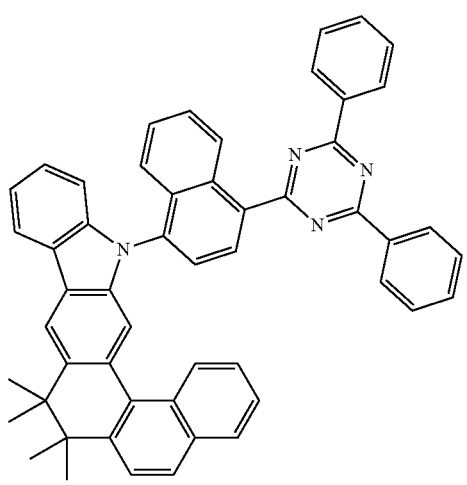
C-104
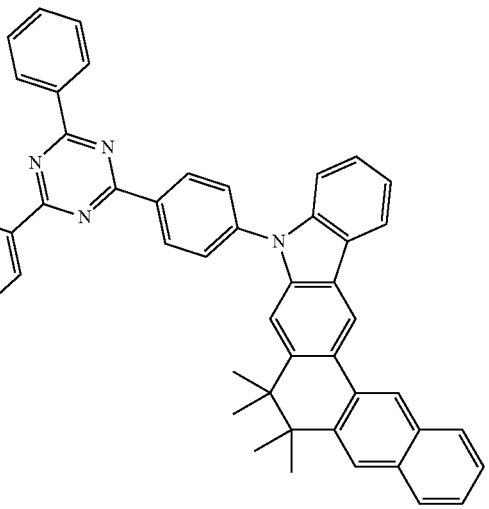
C-102
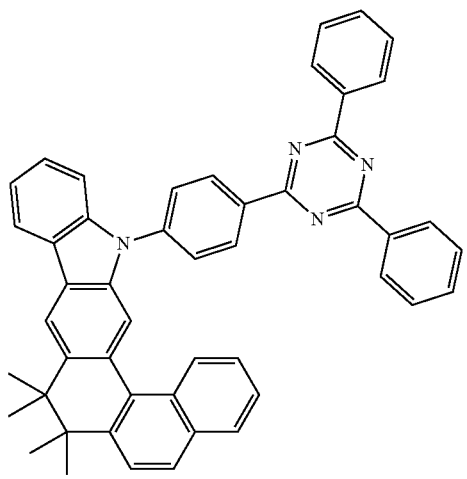
C-105
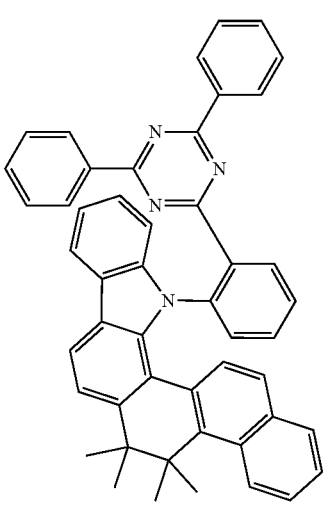

C-107
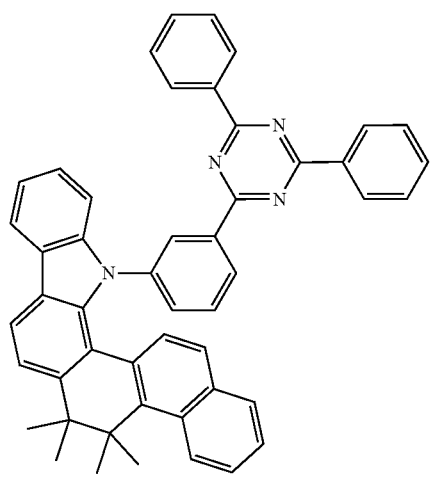
C-110
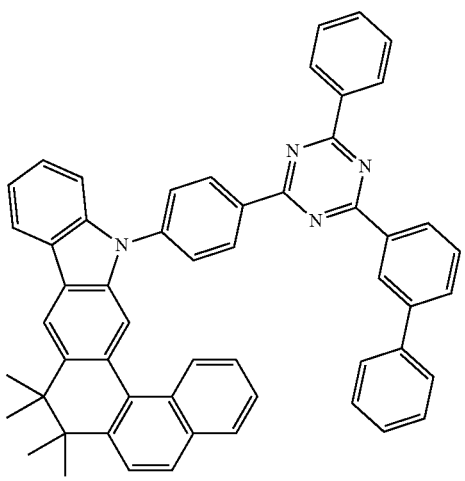
C-108
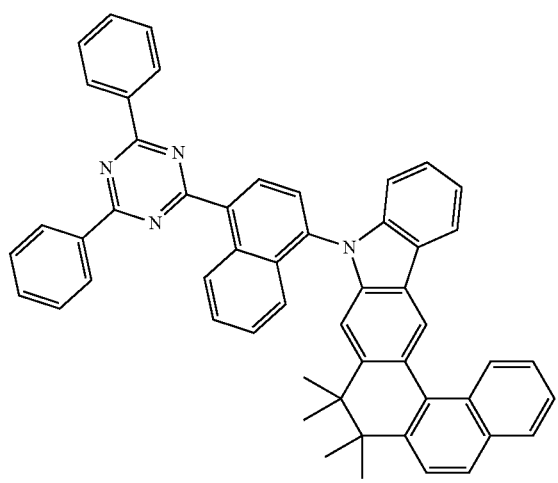
C-111
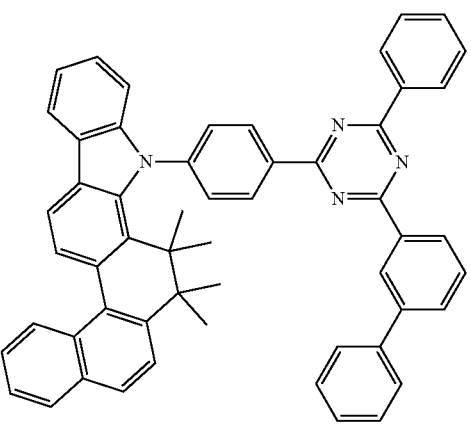
C-109
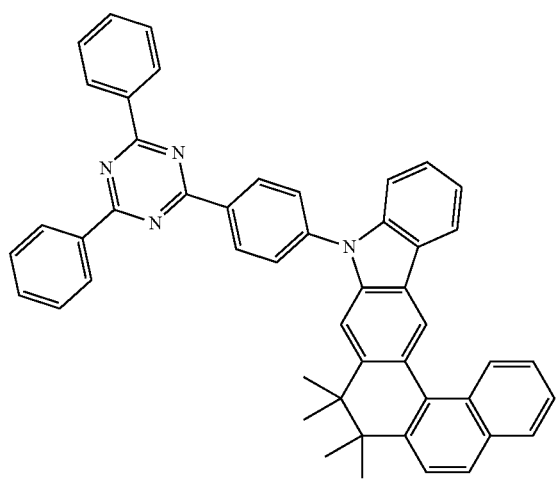
C-112
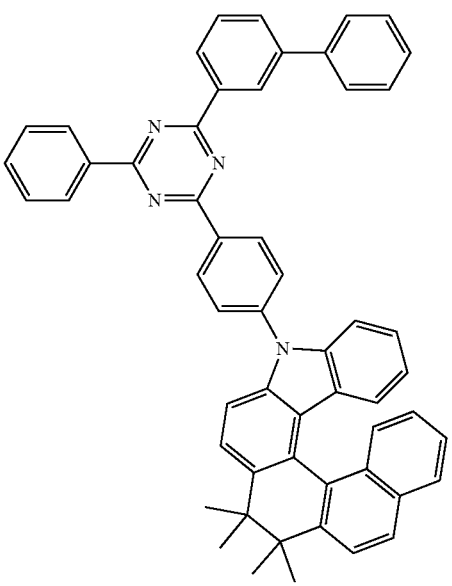

-continued
C-113
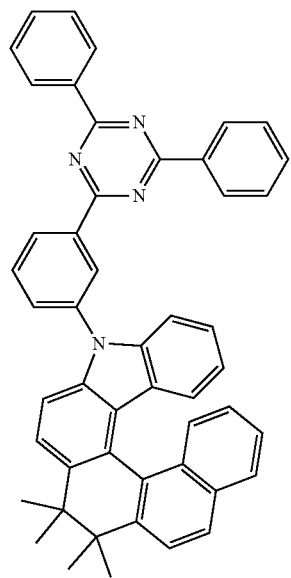
C-114
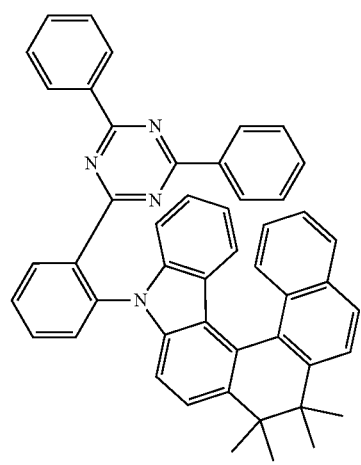
C-116
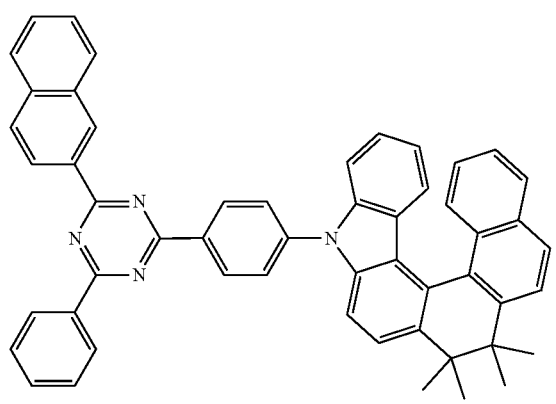
-continued
C-117
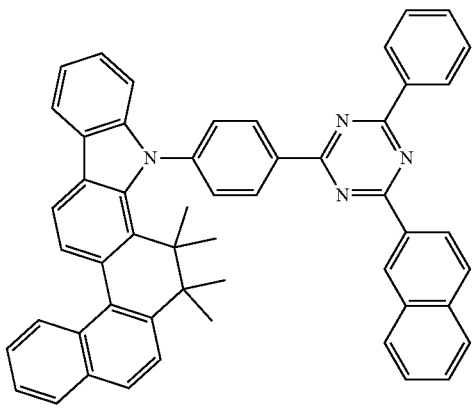
C-118
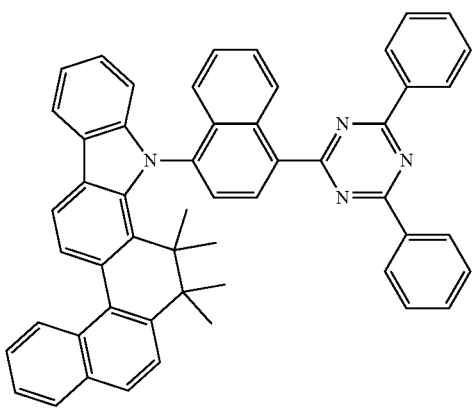
C-119
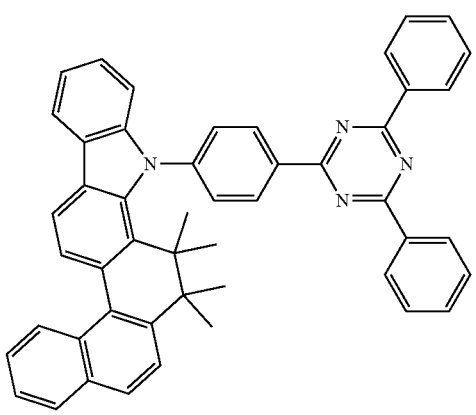
C-120
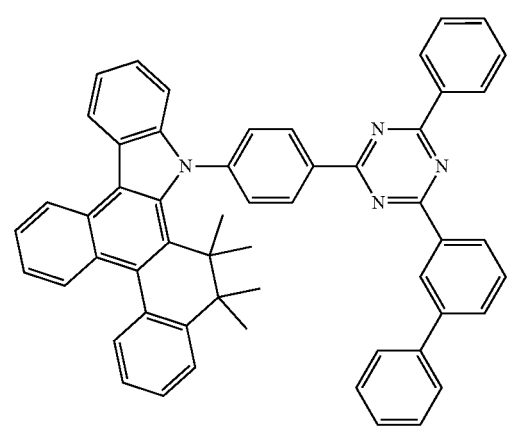

C-121
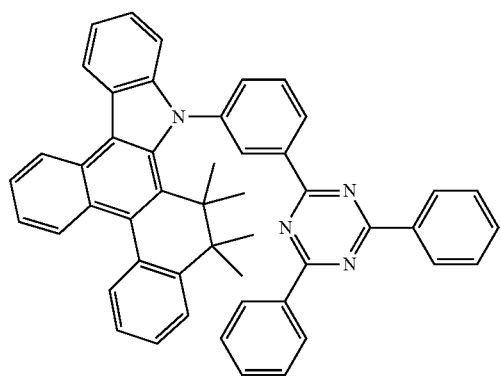
C-125
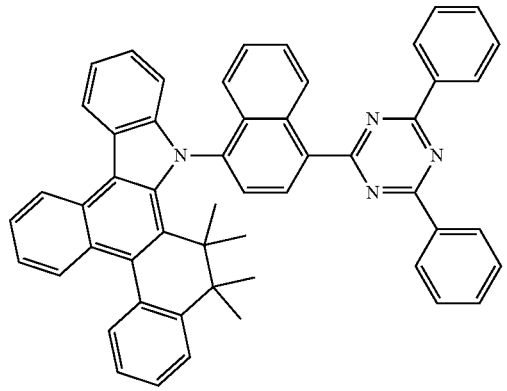
C-122
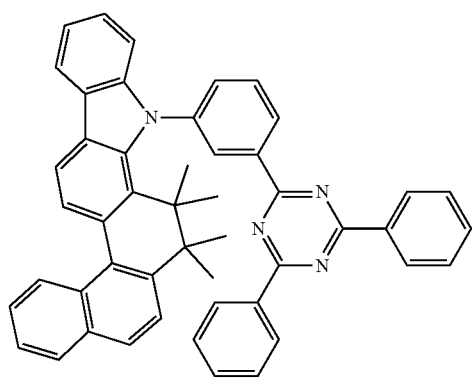
C-126
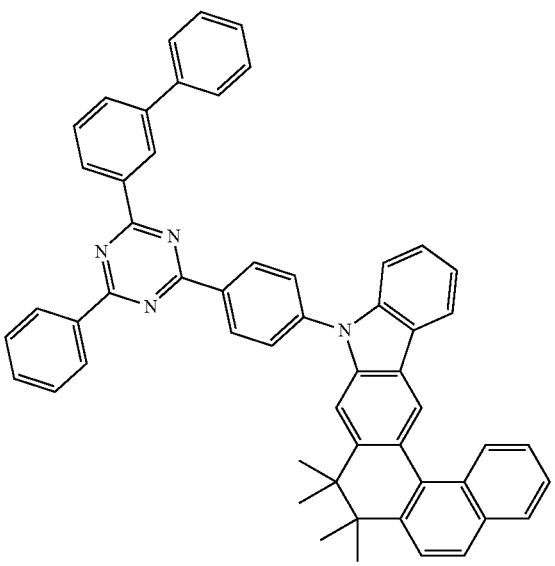
C-123
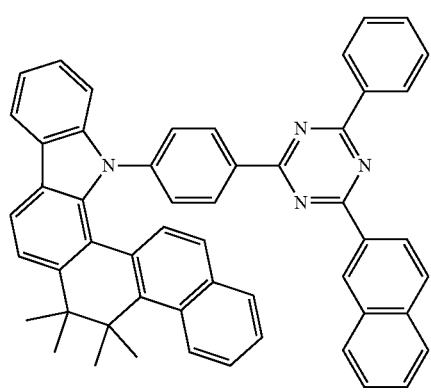
C-127
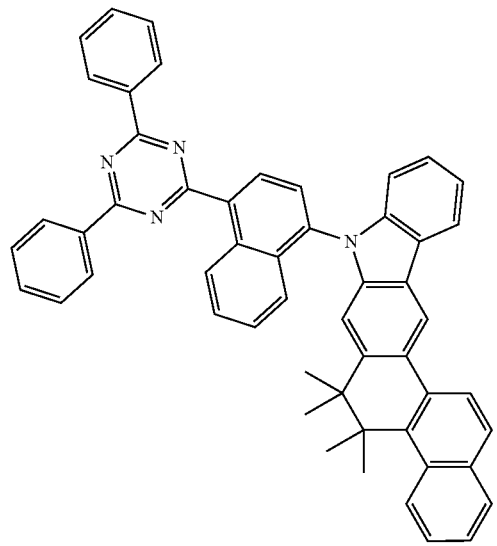
C-124
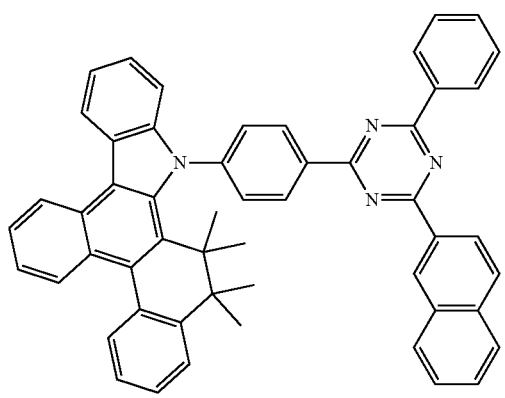

C-128
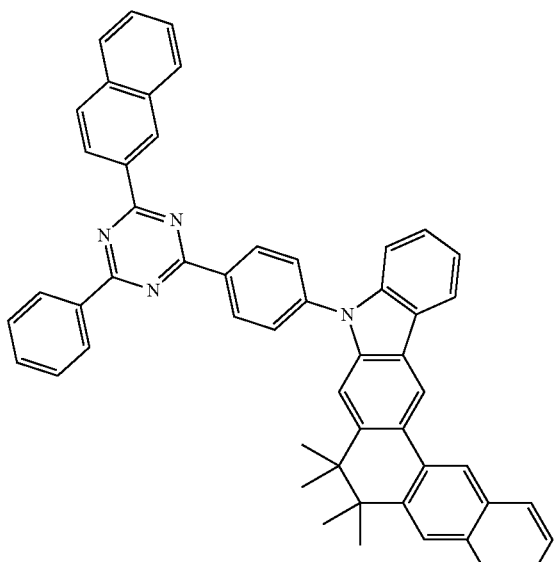
C-130
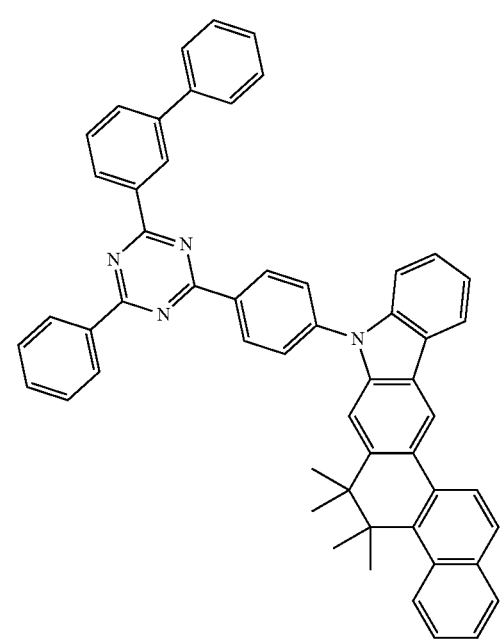
C-131
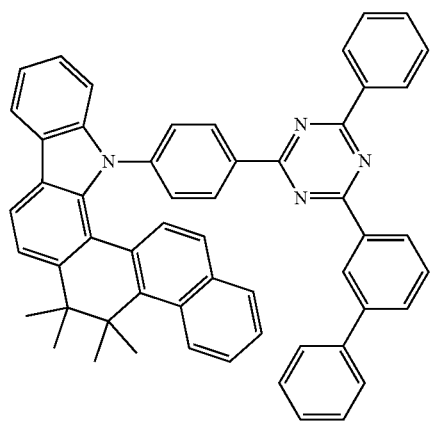
C-132
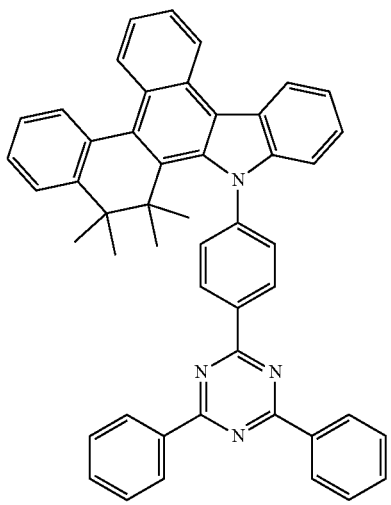
C-134
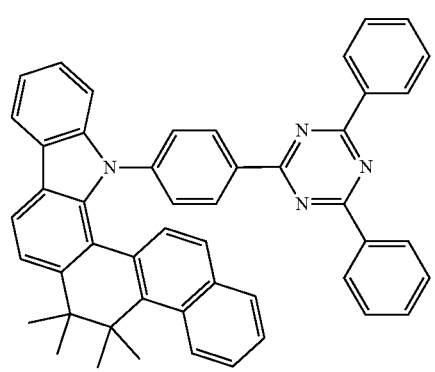
C-136
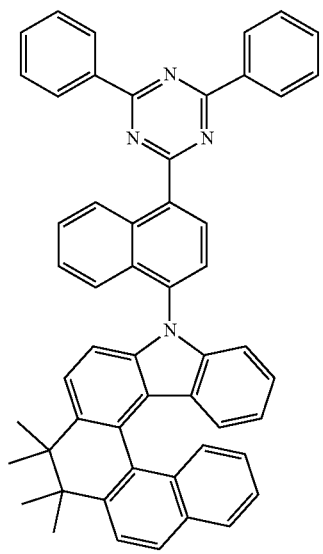

C-138
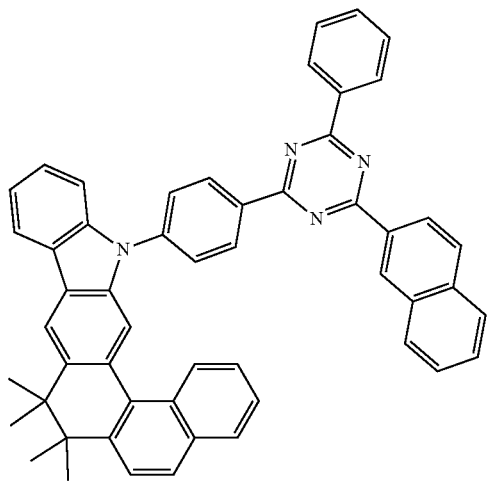
C-142
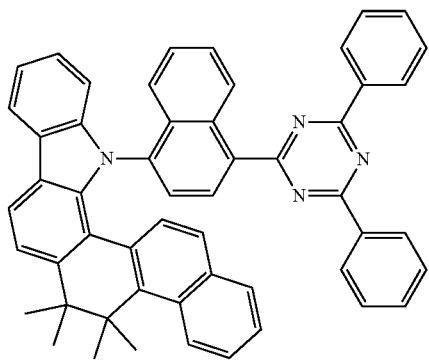
C-139
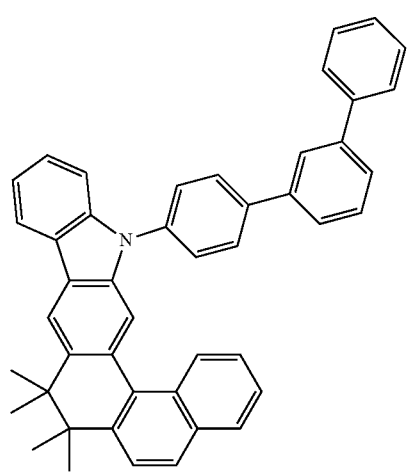
C-143
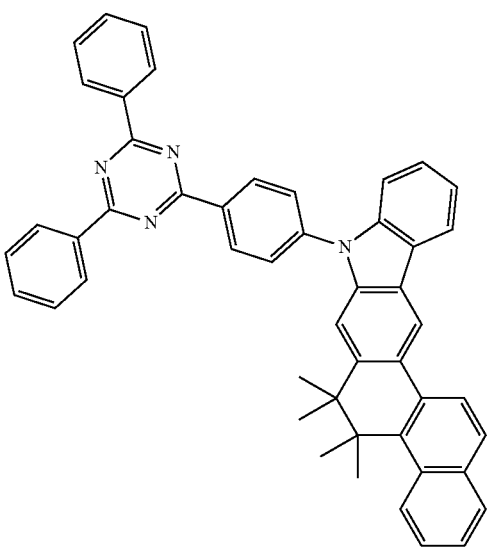
C-141
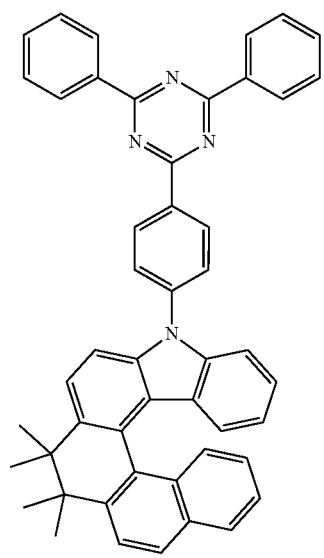
C-144
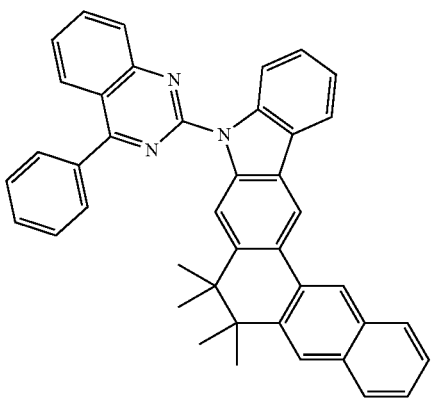

C-145 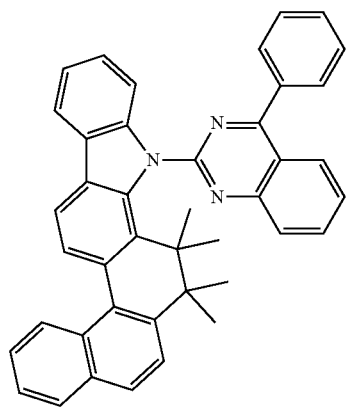
C-146 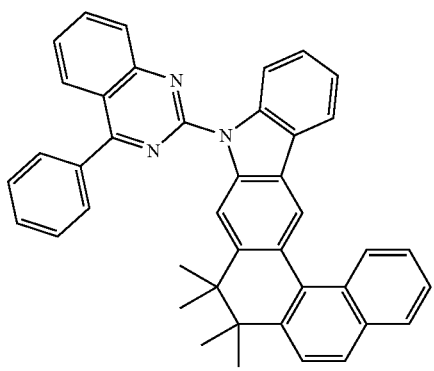
C-147 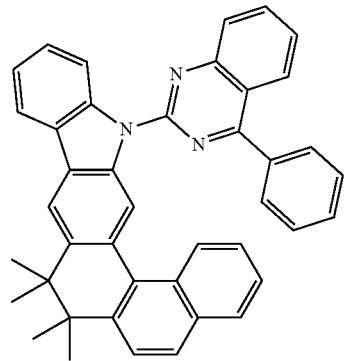
C-148 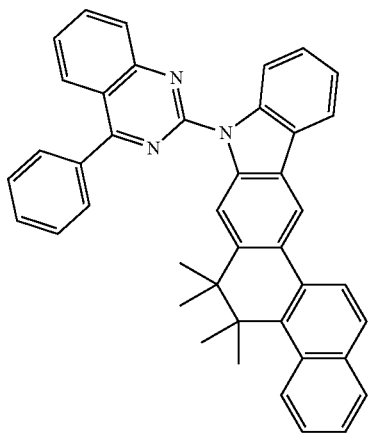
C-150 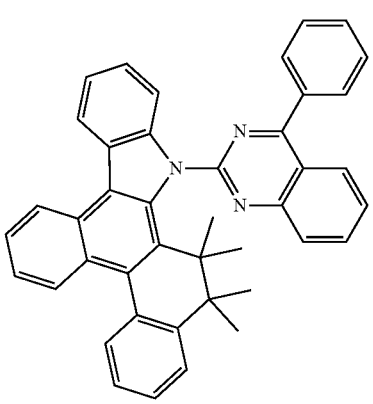
C-151 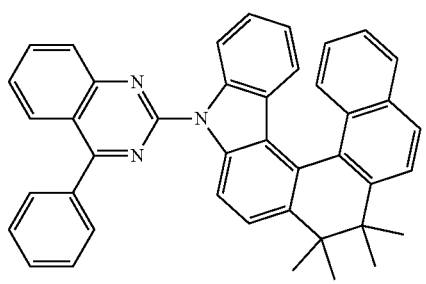
C-152 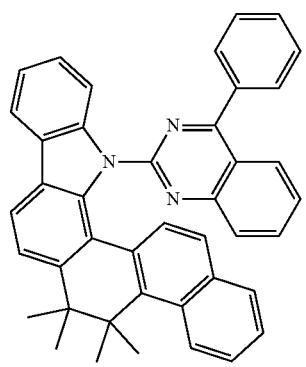
C-153 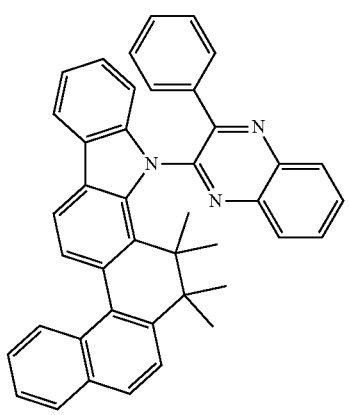

-continued
C-154
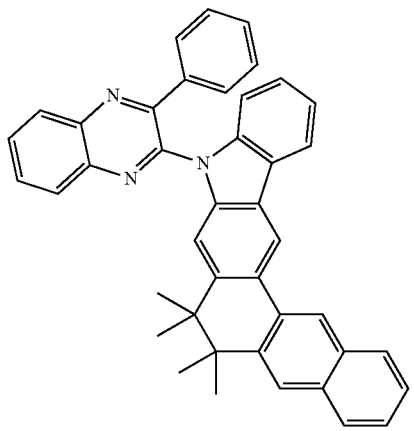
C-155
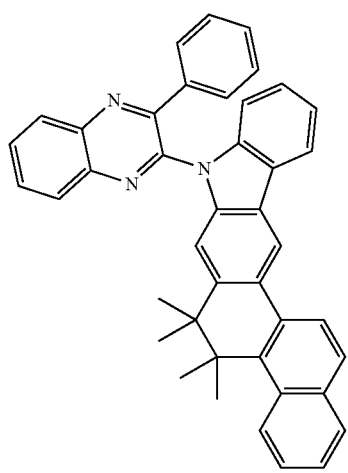
C-156
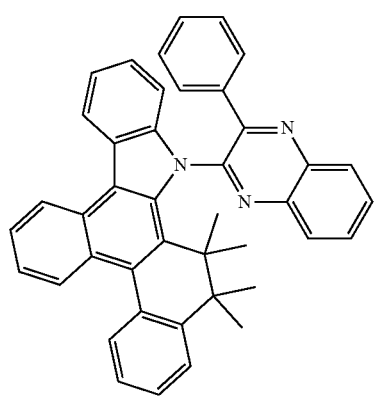
-continued
C-157
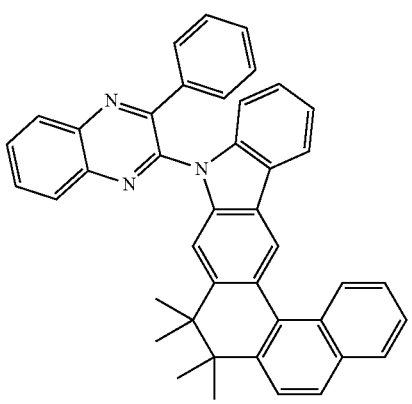
C-158
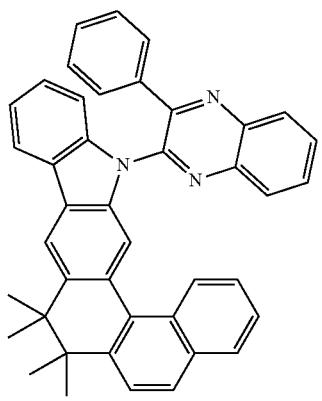
C-159
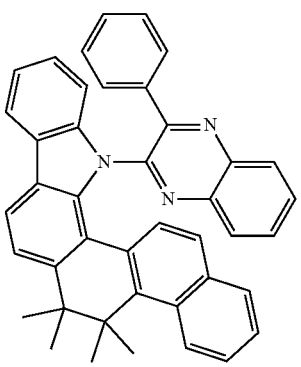
C-161
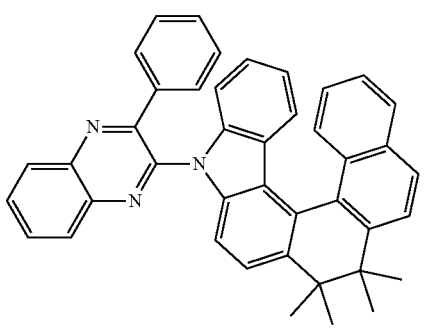

-continued
C-162
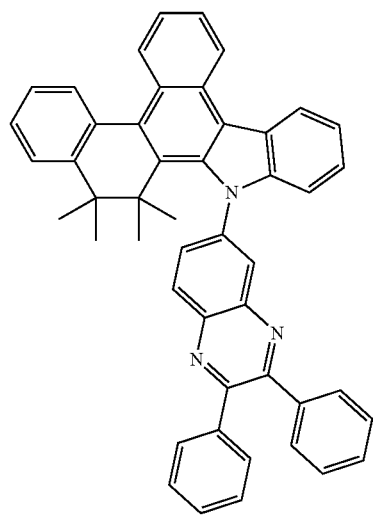
C-163
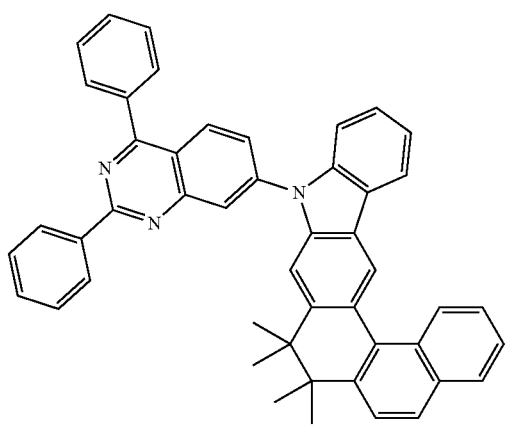
C-164
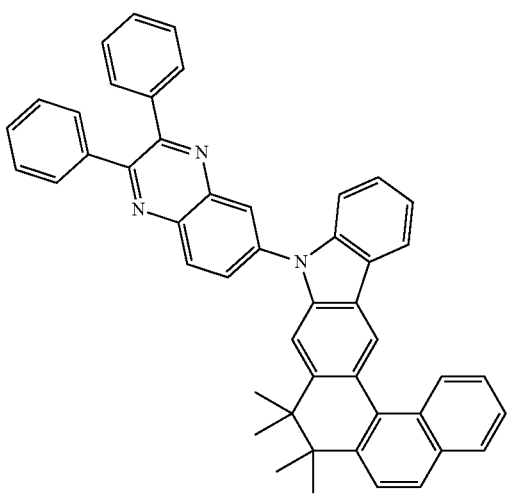
-continued
C-165
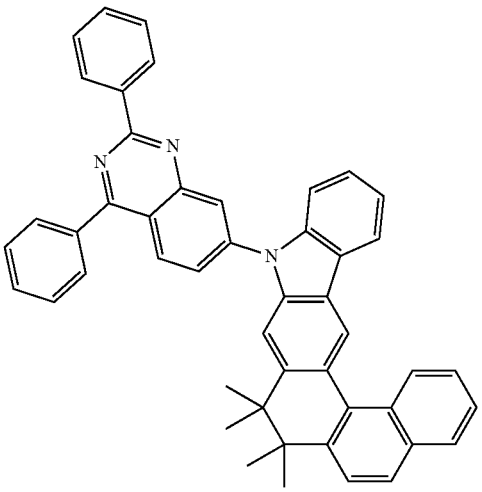
C-226
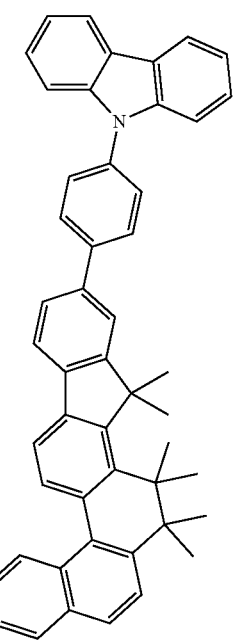

C-227
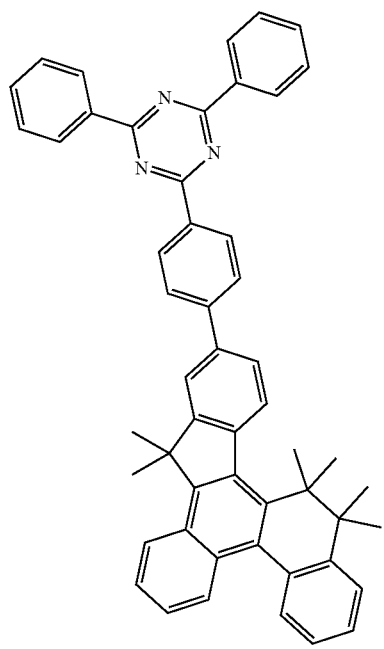
C-230
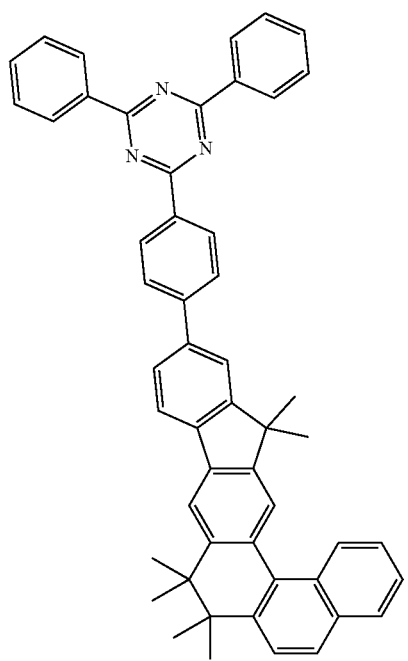
C-231
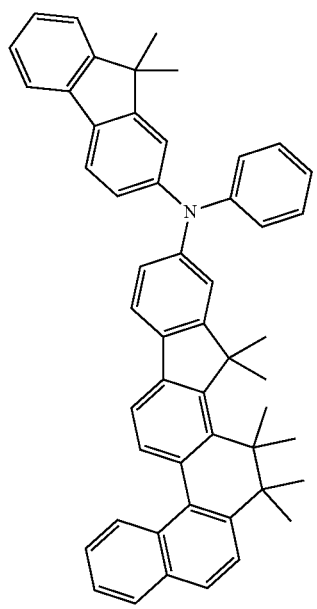
C-232
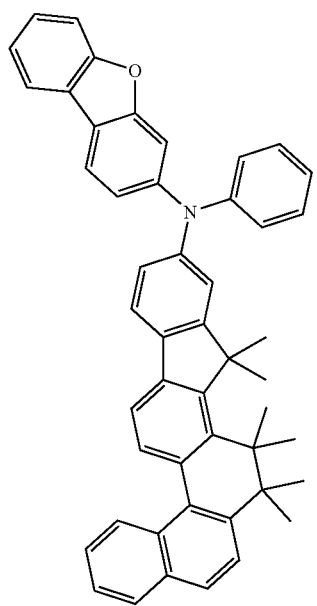

C-233
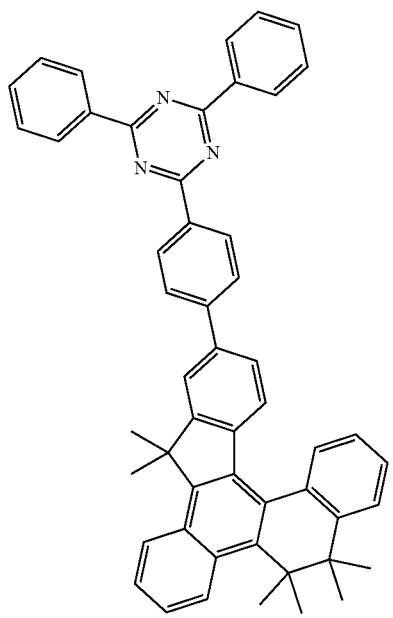
C-235
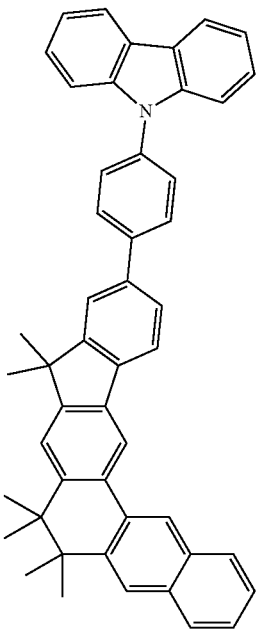
C-234
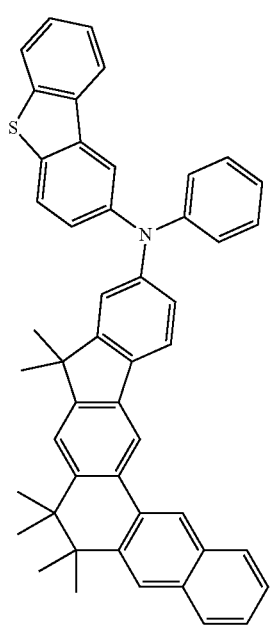
C-236
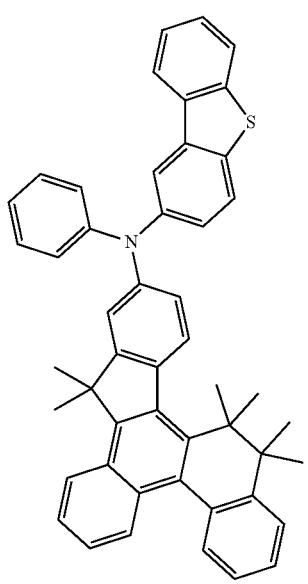

C-238
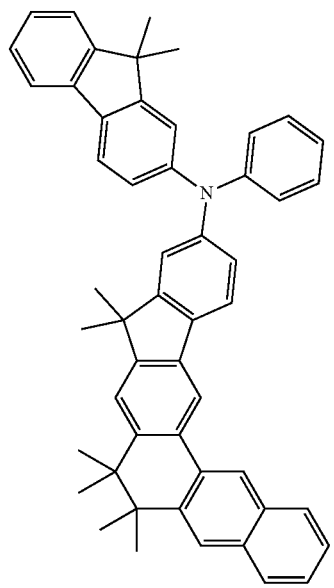
C-239
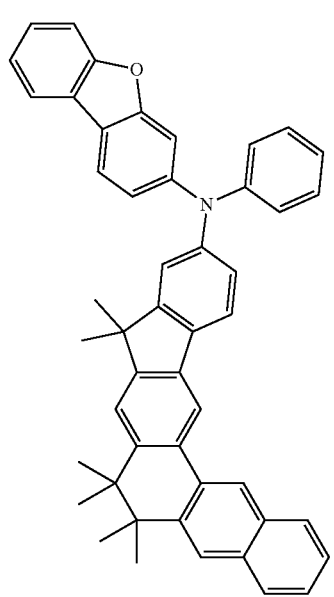
C-241
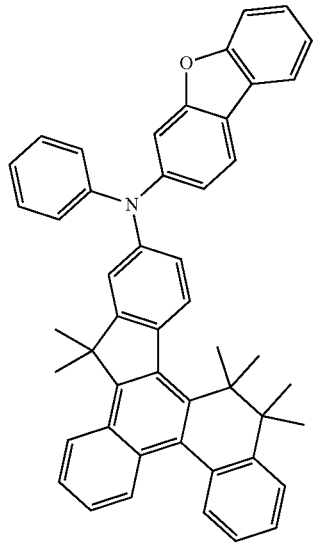
C-244
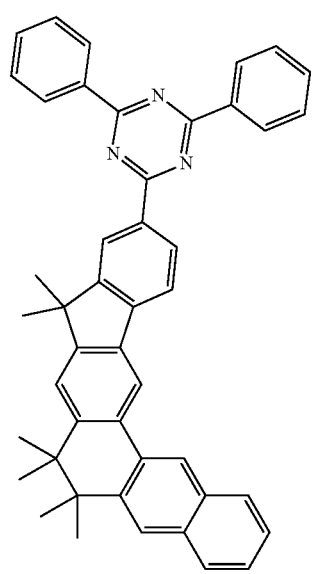

C-245
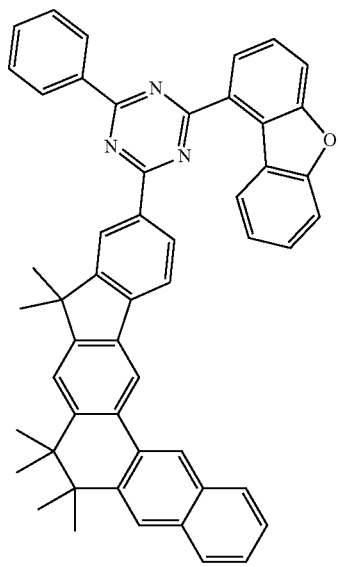
C-246
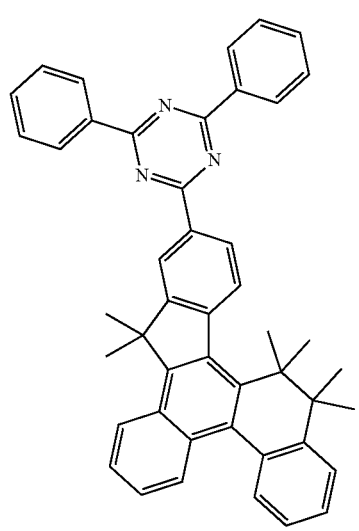
C-247
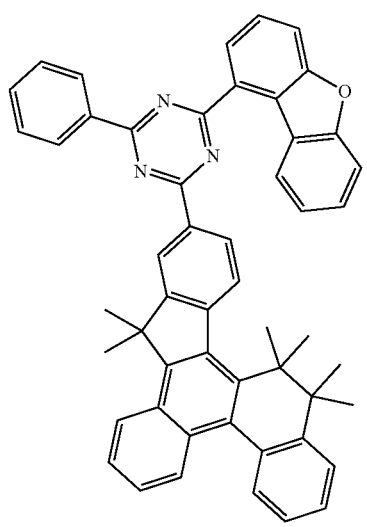
C-248
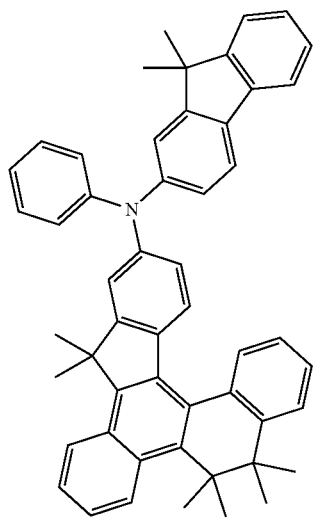
C-249
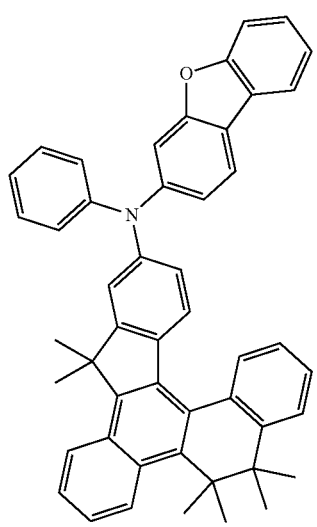
C-252
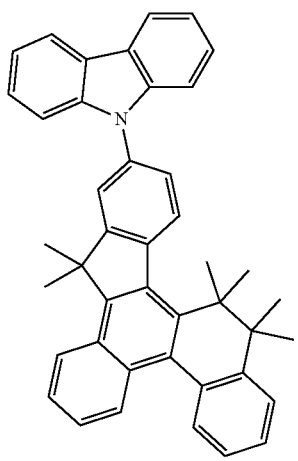

-continued
C-254
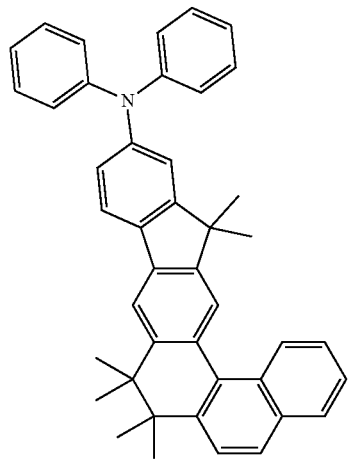
C-255
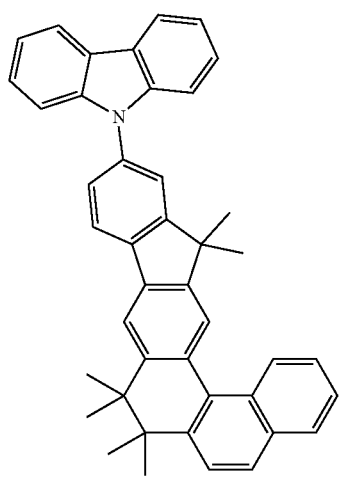
C-256
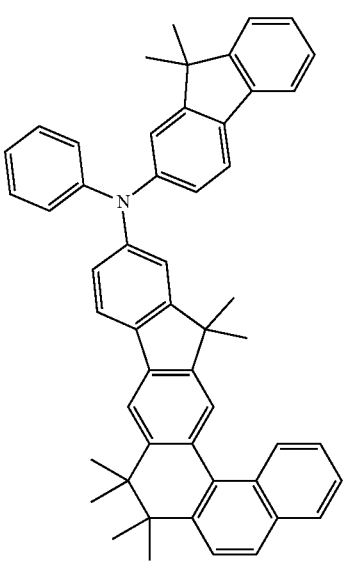
-continued
C-257
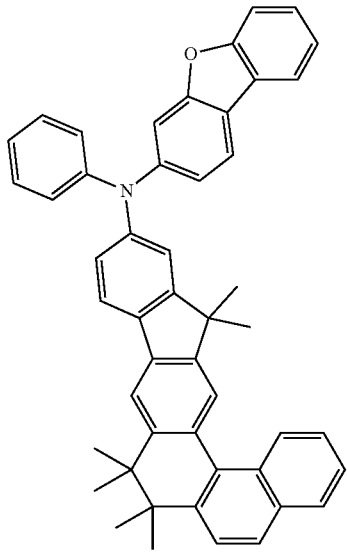
C-258
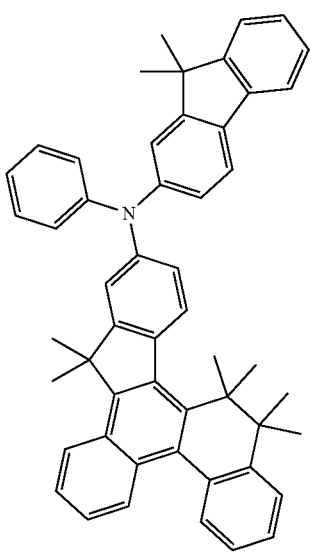
C-260
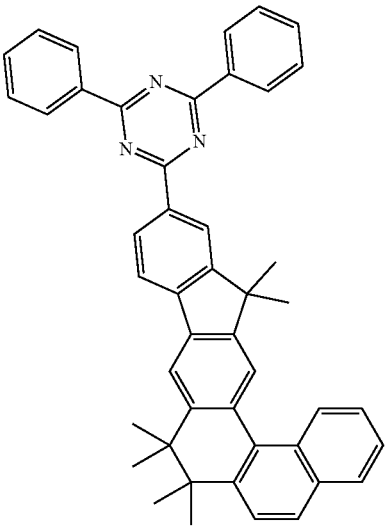

-continued
C-383
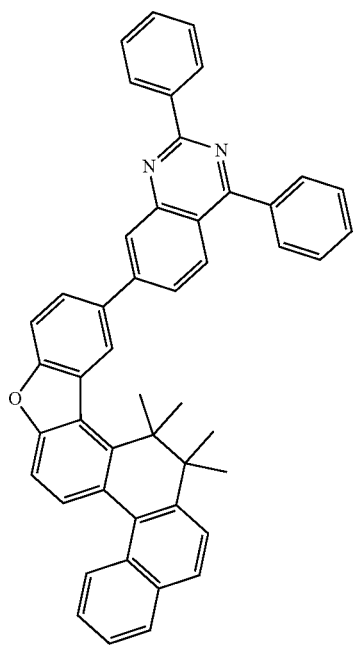
C-388
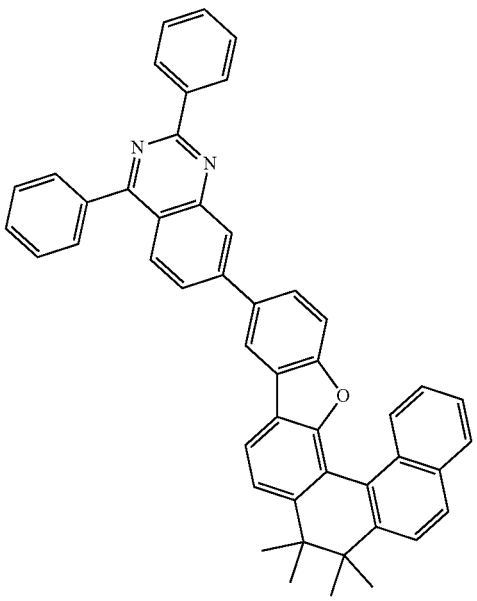
C-384
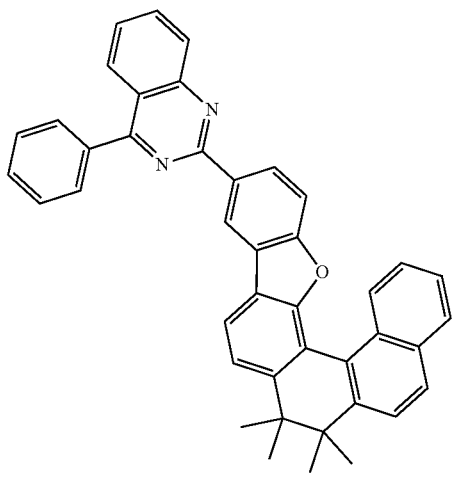
C-390
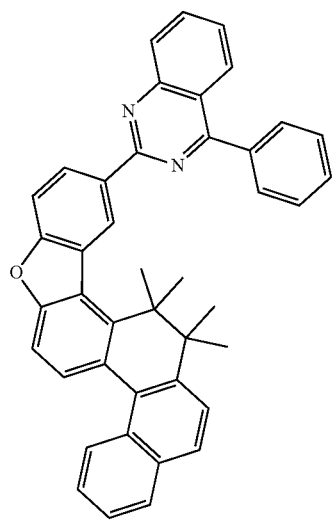
C-386
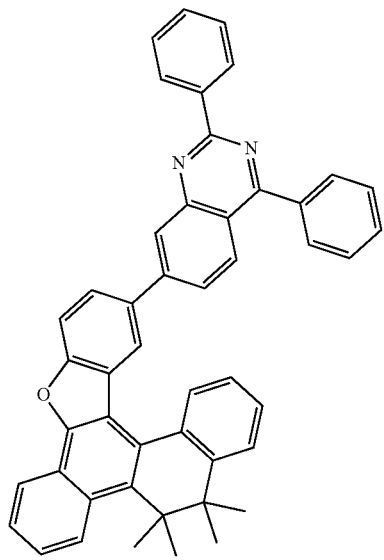
C-391
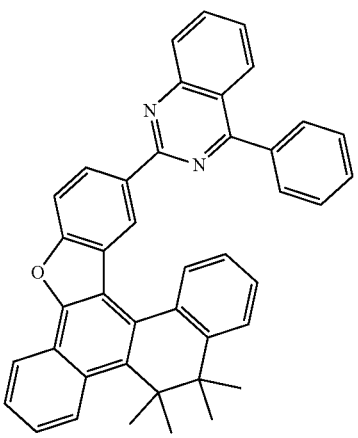

C-394
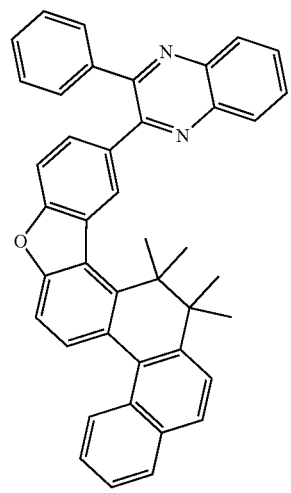
C-395
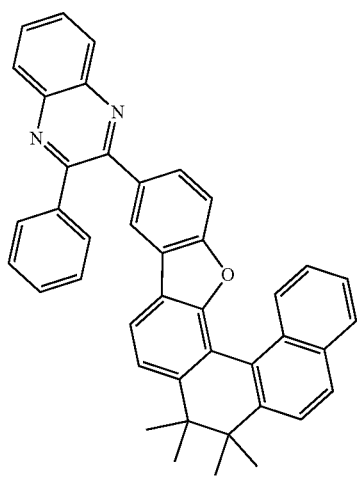
C-396
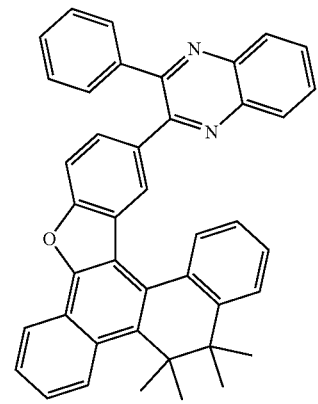
C-400
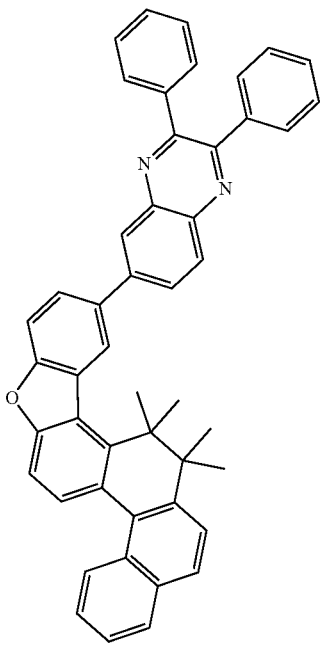
C-522
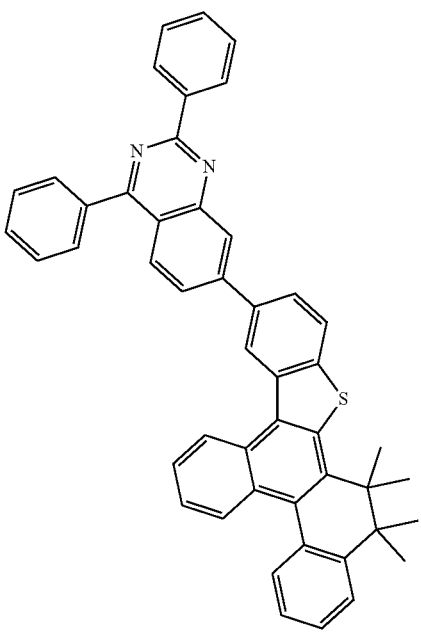

-continued
C-523
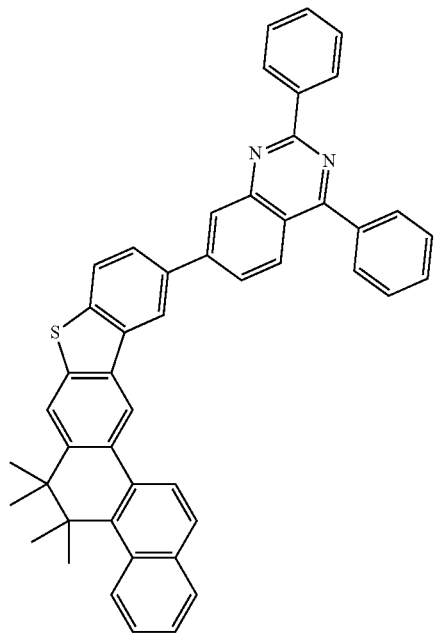
C-524
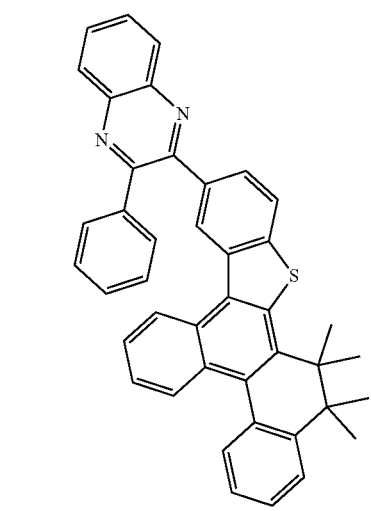
C-525
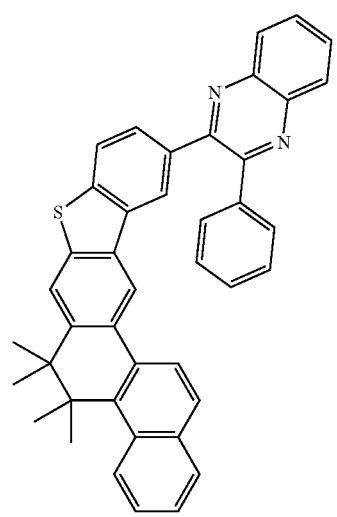
-continued
C-526
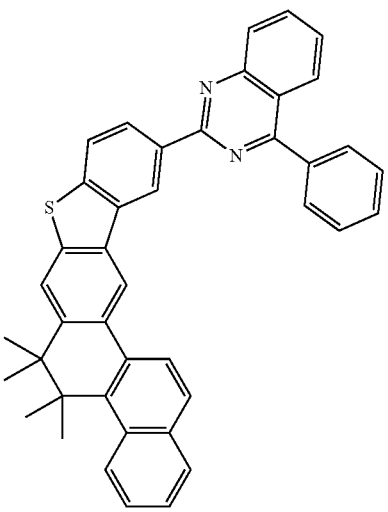
C-529
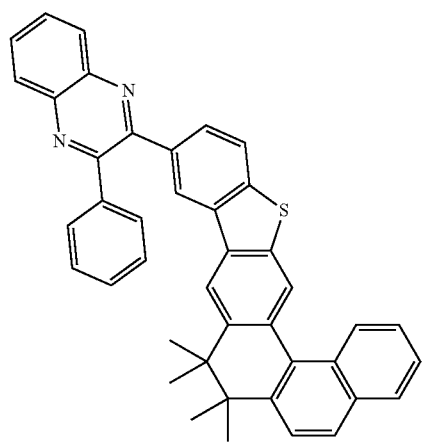
C-534
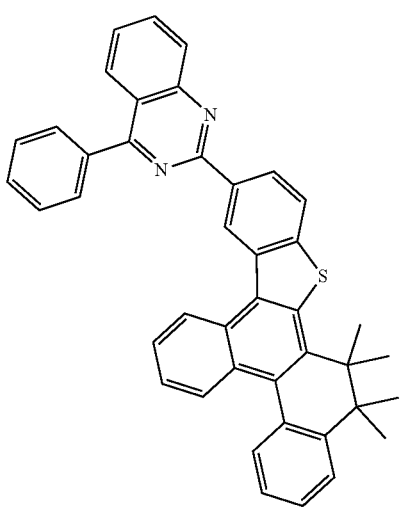

C-535
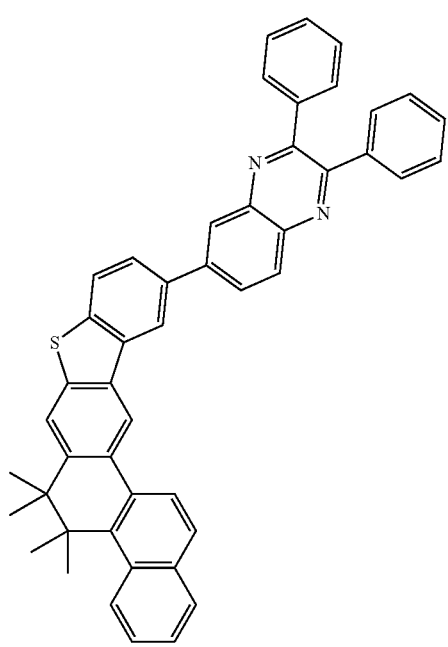
C-522
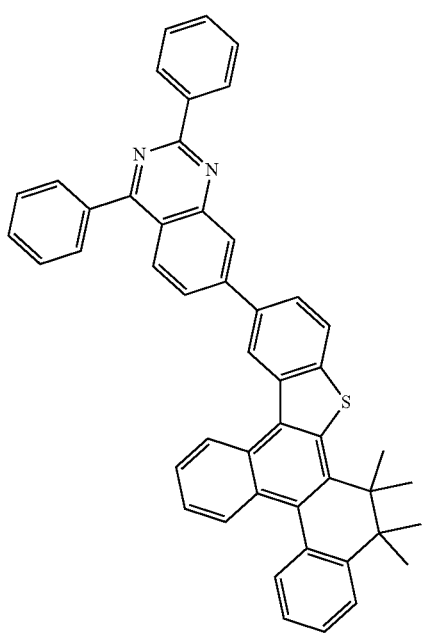
C-523
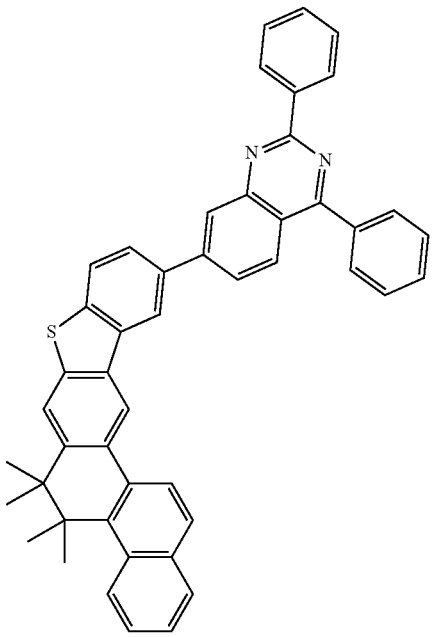
C-524
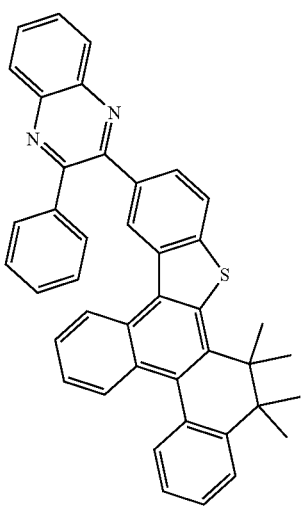
C-525
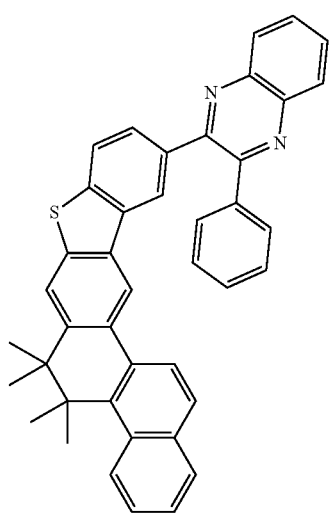

-continued
C-526
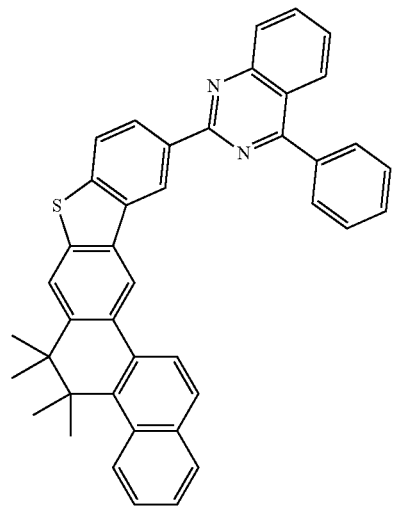
C-529
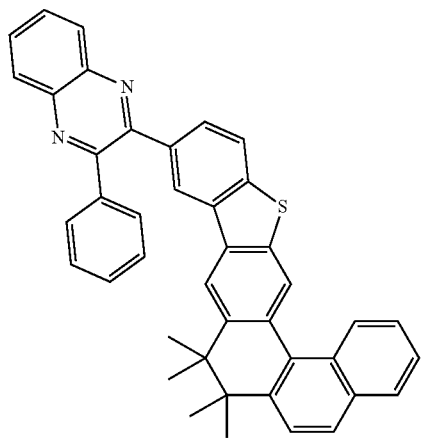
C-534
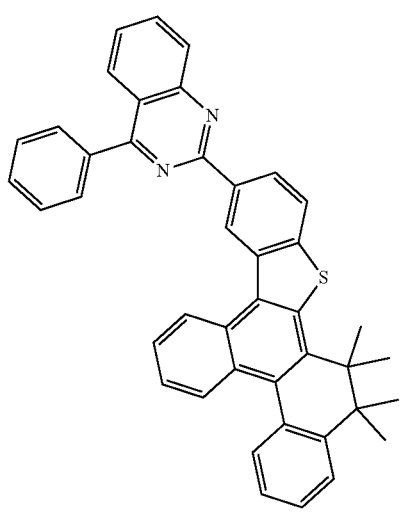
-continued
C-535
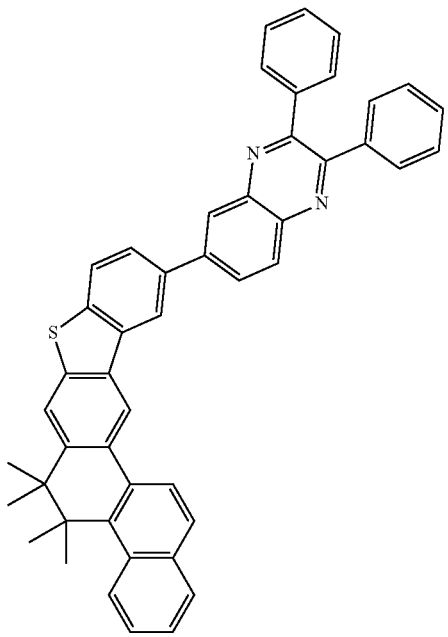
C-538
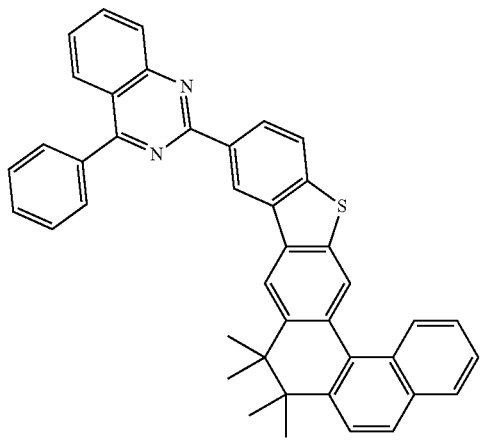

-continued
C-541
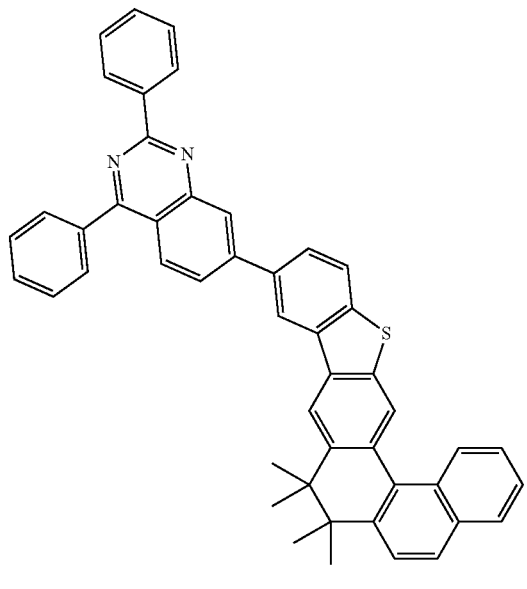
C-542
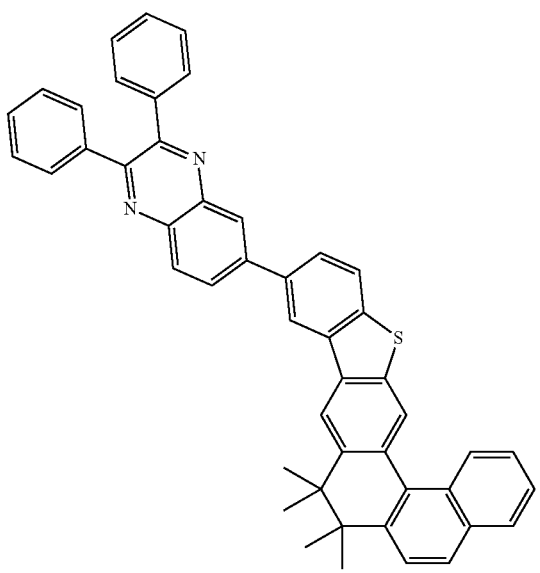
-continued
C-544
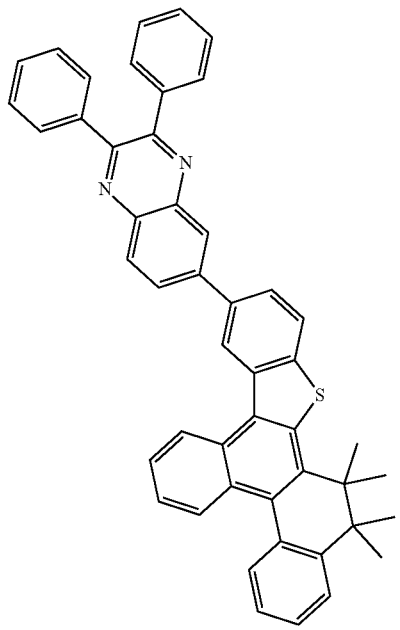
C-545
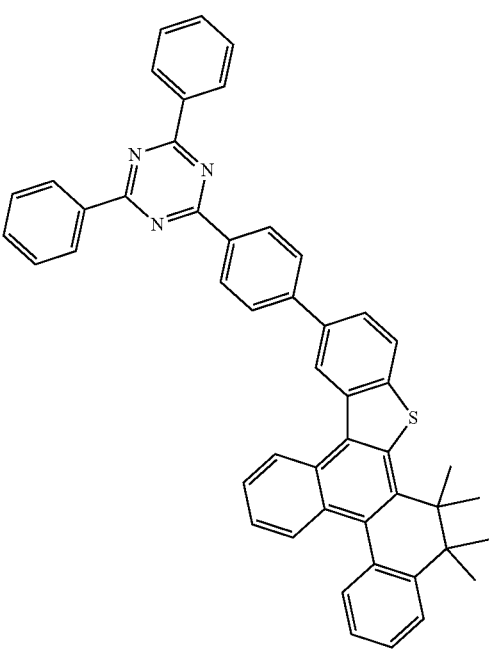

C-546
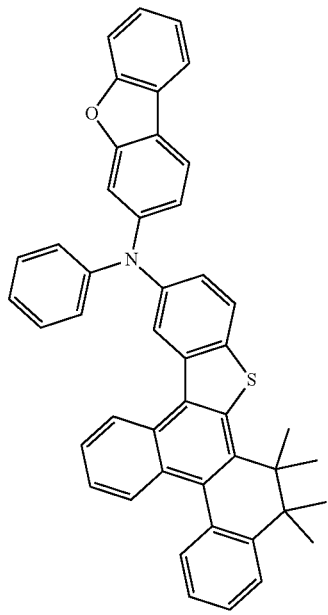
C-547
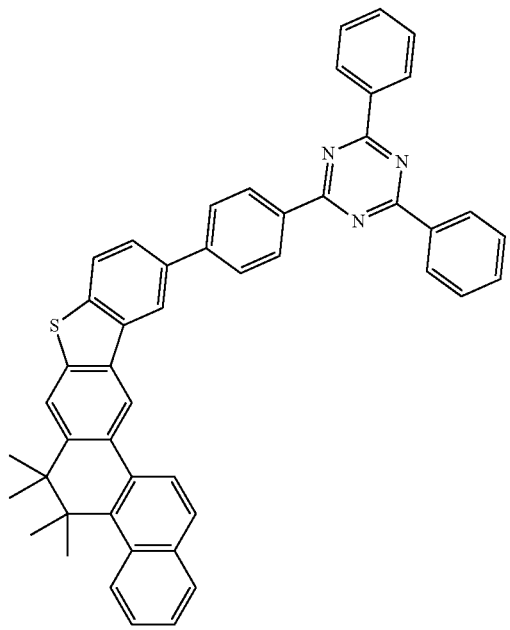
C-548
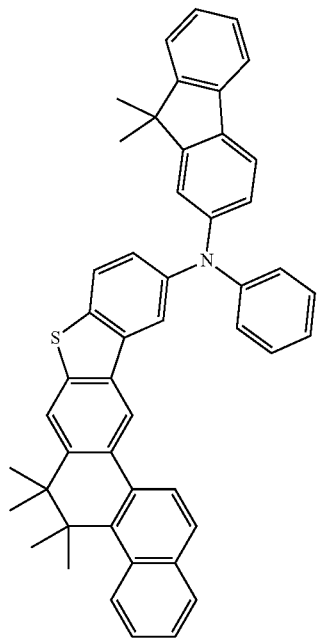
C-549
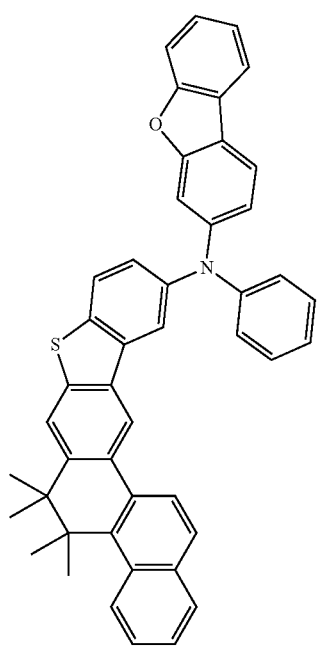

-continued
C-550
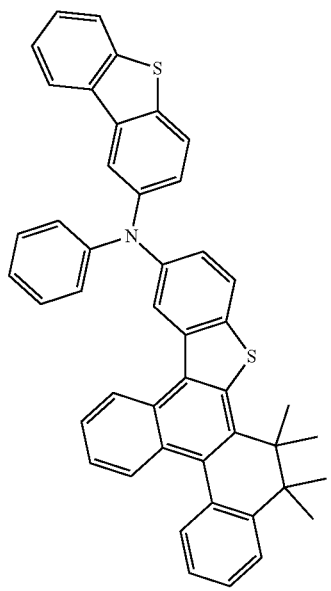
C-551
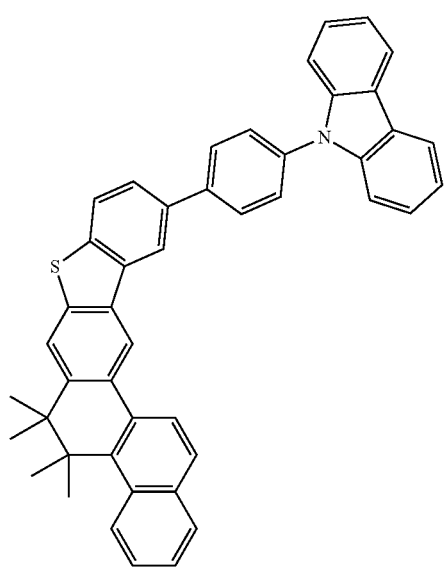
-continued
C-552
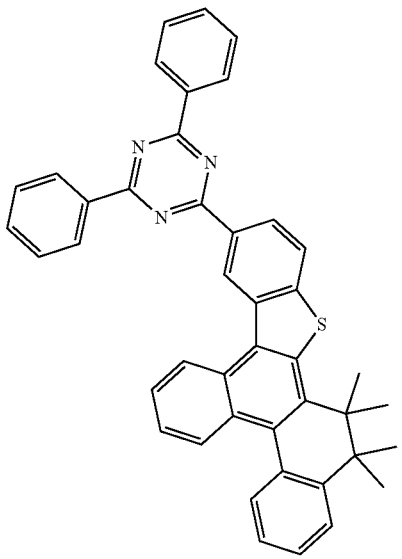
C-553
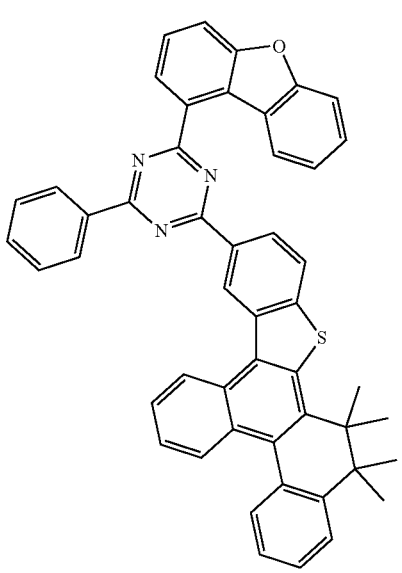

-continued
C-554
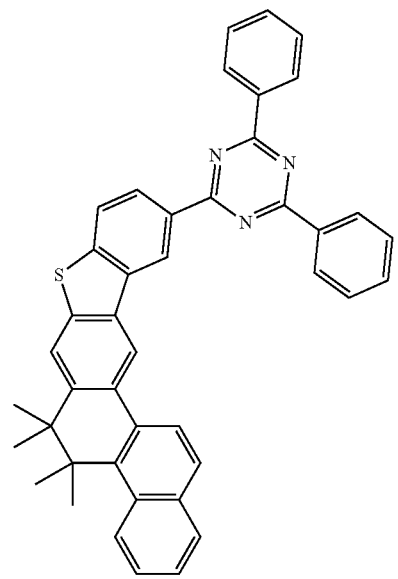
C-555
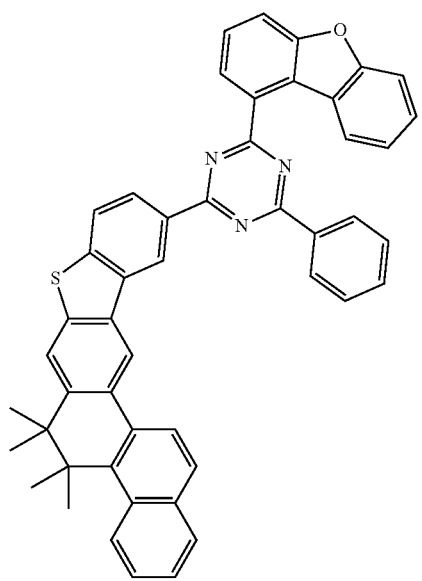
C-556
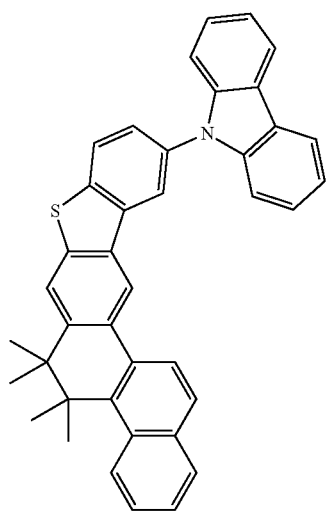
C-557
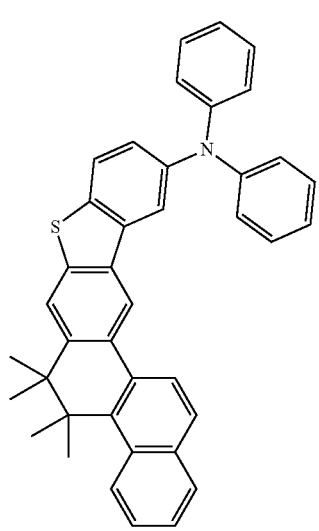
C-564
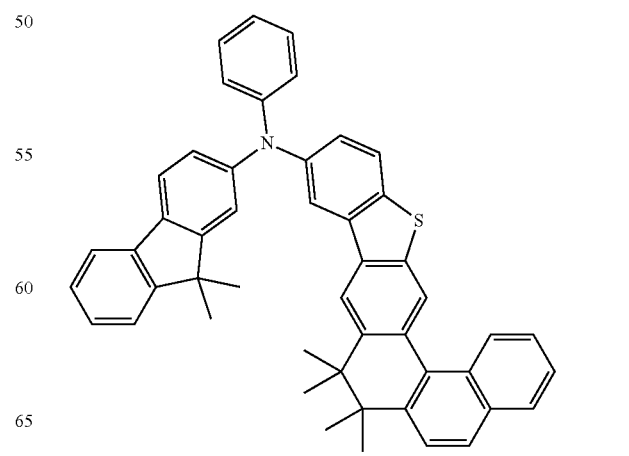

-continued

C-565

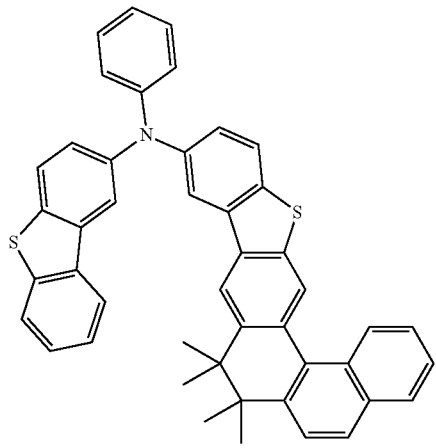

C-569

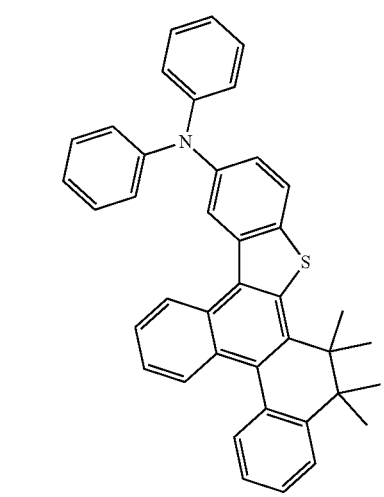

C-570

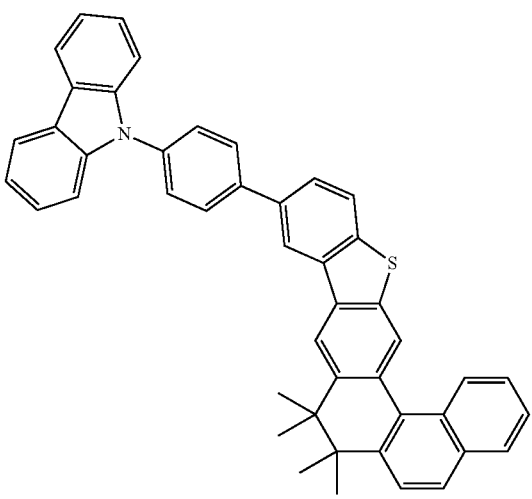

-continued

C-580

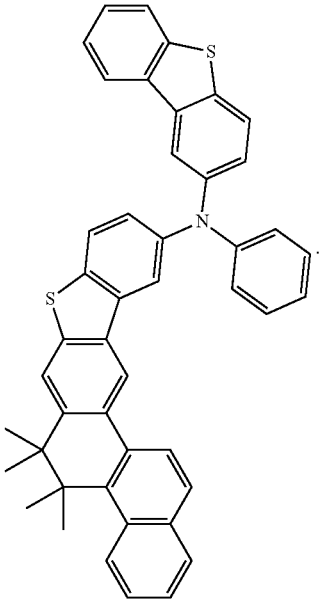

5. A plurality of host materials comprising a first host material comprising the organic electroluminescent compound represented by the following formula 1 and a second host material different from the first host material:

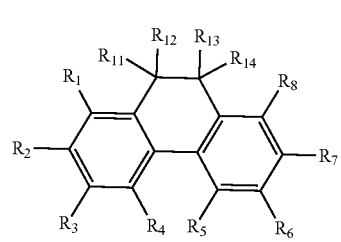

(1)

wherein
$R_{11}$ to $R_{14}$ each independently represent hydrogen, deuterium, a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring, with a proviso that at least one of $R_{11}$ to $R_{14}$ is neither hydrogen nor deuterium;
$R_1$ to $R_8$ each independently represent hydrogen, deuterium, or -L-Ar, or may be linked to an adjacent substituent to form a ring, with a proviso that at least one pair of $R_1$ and $R_2$, $R_2$ and $R_3$, $R_3$ and $R_4$, $R_5$ and $R_6$, $R_6$ and $R_7$, and $R_7$ and $R_8$ is linked to each other to be fused as the following formula a;

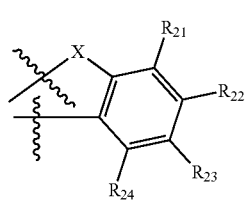

(a)

wherein

X represents $NR_{31}$, O, S, $CR_{32}R_{33}$, or —$CR_{34}$=$CR_{35}$—;

$R_{31}$ represents -$L_1$-$Ar_1$;

$R_{32}$ and $R_{33}$ each independently represent a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a ring;

$R_{34}$ and $R_{35}$ each independently represent hydrogen, deuterium, or -$L_5$-$Ar_5$;

$R_{21}$ to $R_{24}$ each independently represent hydrogen, deuterium, or -$L_2$-$Ar_2$, or may be linked to an adjacent substituent to form a ring:

L, $L_1$, $L_2$, and $L_5$ each independently represent a single bond, a substituted or unsubstituted (C1-C30)alkylene, a substituted or unsubstituted (C6-C30)arylene, a substituted or unsubstituted (3- to 30-membered) heteroarylene, or a substituted or unsubstituted (C3-C30)cycloalkylene;

Ar, $Ar_1$, $Ar_2$, and $Ar_5$ each independently represent a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, or a substituted or unsubstituted (C1-C30) alkoxy, or are represented by the following formula b or c;

(b)

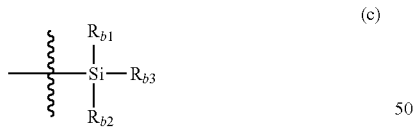

(c)

wherein $R_{a1}$, $R_{a2}$, $R_{b1}$, $R_{b2}$, and $R_{b3}$ each independently represent a substituted or unsubstituted (C6-C30)aryl, a substituted or unsubstituted (3- to 30-membered)heteroaryl, or a substituted or unsubstituted (C3-C30)cycloalkyl;

⁂ in formula a represents a bonding site with $R_1$ to $R_8$; and

⁂ in formulas b and c represents a bonding site with L, $L_1$, $L_2$, or $L_5$, respectively.

6. The plurality of host materials according to claim 5, wherein the second host material comprises the compound represented by the following formula 2:

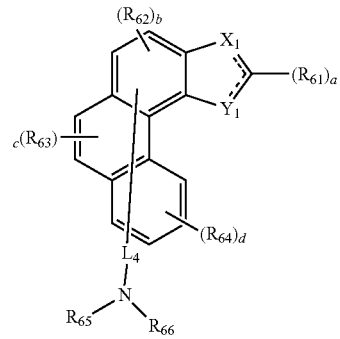

(2)

wherein $X_1$ and $Y_1$ each independently represent —N=, —$NR_{67}$—, —O—, or —S—, with a proviso that any one of $X_1$ and $Y_1$ represents —N=, and the other one of $X_1$ and $Y_1$ represents —$NR_{67}$—, —O—, or —S—;

$R_{61}$ represents a substituted or unsubstituted (C6-C30)aryl or a substituted or unsubstituted (3- to 30-membered) heteroaryl:

$R_{62}$ to $R_{64}$ and $R_{67}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$"-N($Ar_3$") ($Ar_4$"); or may be linked to an adjacent substituent to form a ring:

$L_3$" each independently represents a single bond, a substituted or unsubstituted (C6-C30)arylene, or a substituted or unsubstituted (3- to 30-membered)heteroarylene:

$Ar_3$" and $Ar_4$" each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl:

$R_{65}$ and $R_{66}$ each independently represent a substituted or unsubstituted (C6-C30)aryl or a substituted or unsubstituted (3- to 30-membered)heteroaryl:

$L_4$ represents a single bond, a substituted or unsubstituted (C6-C30)arylene, or a substituted or unsubstituted (3- to 30-membered)heteroarylene; and a represents 1, b and c each independently represent 1 or 2, d represents an integer of 1 to 4, and when b to d are an integer of 2 or more, each of $R_{62}$ to each of $R_{64}$ may be the same or different from each other.

7. The plurality of host materials according to claim 6, wherein the compound represented by formula 2 is at least one selected from the following compounds:

H1-1
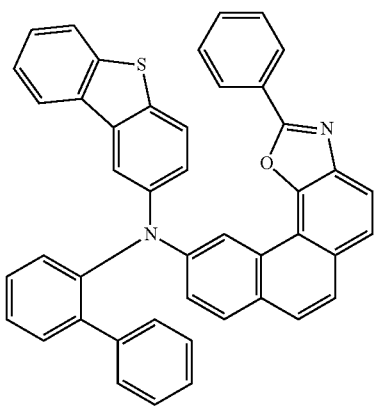
H1-2
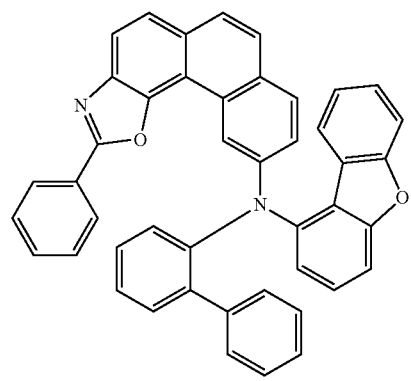
H1-3
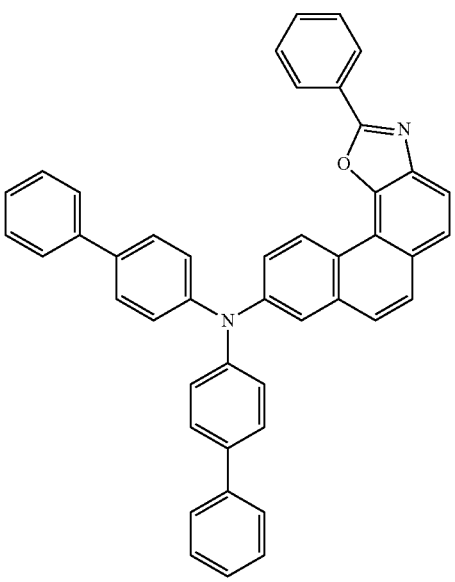
-continued
H1-4
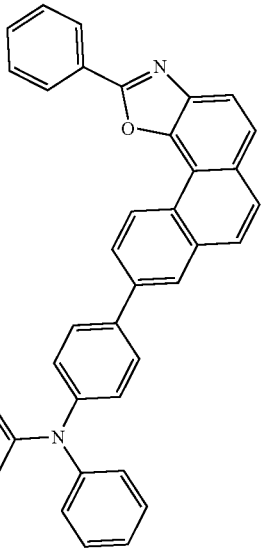
H1-5
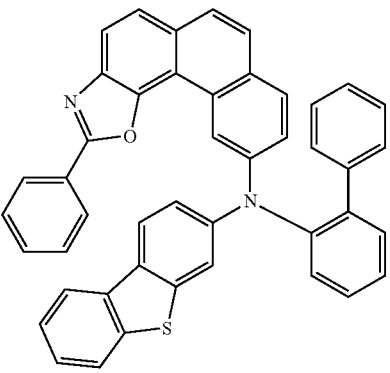
H1-6
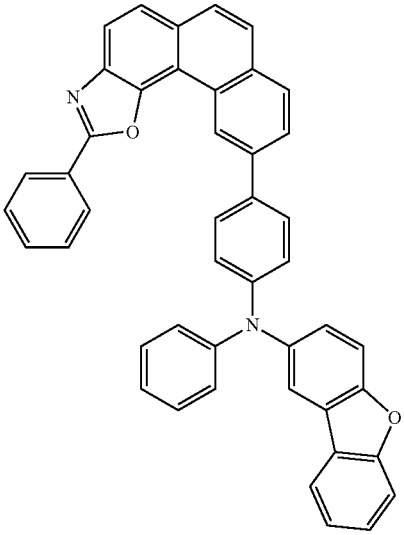

H1-7
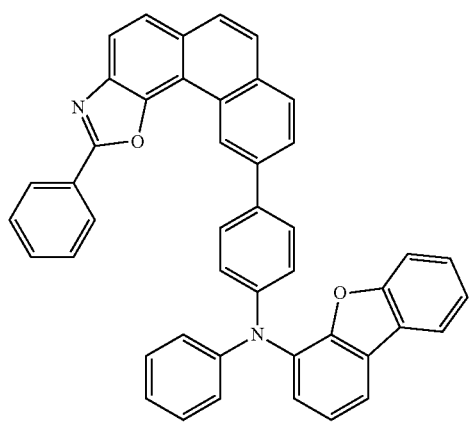
H1-8
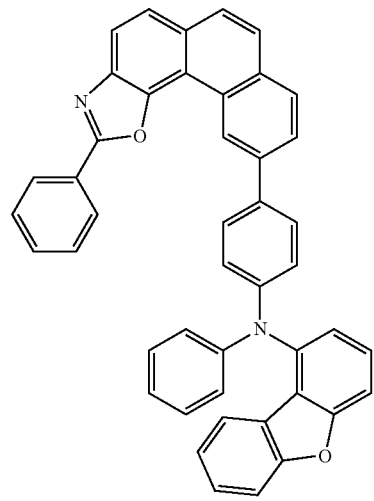
H1-9
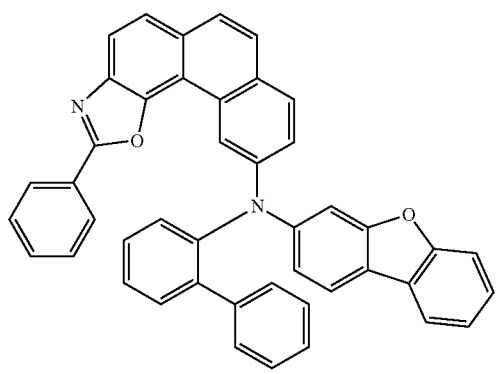
H1-10
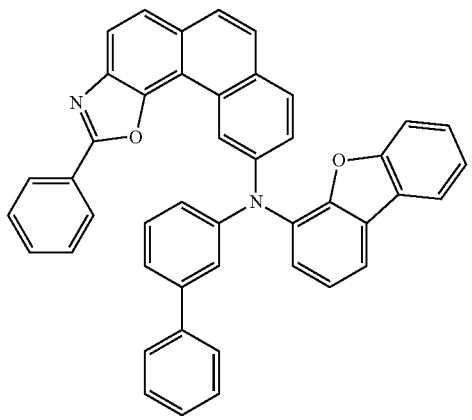
H1-11
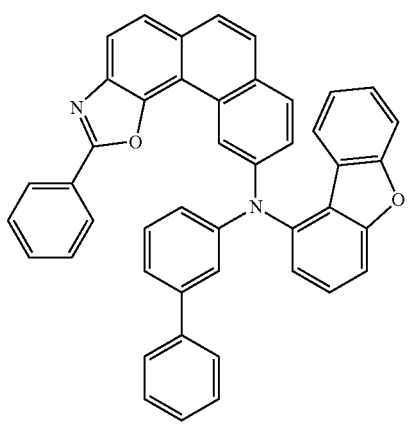
H1-12
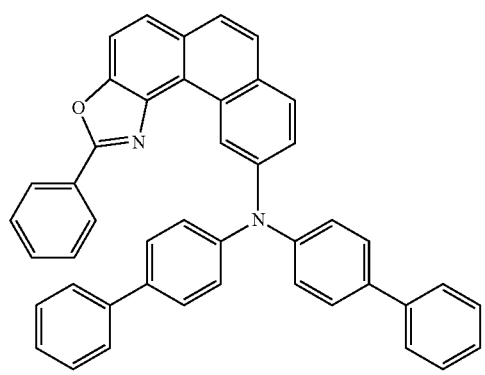
H1-13
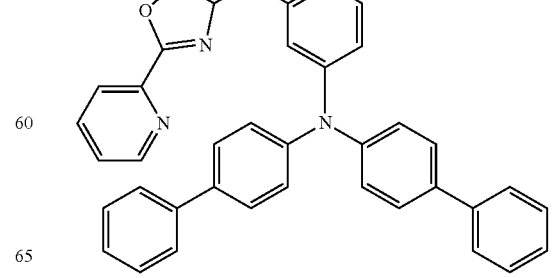

H1-14
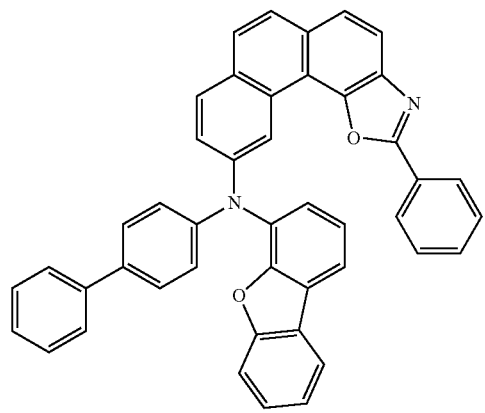
H1-15
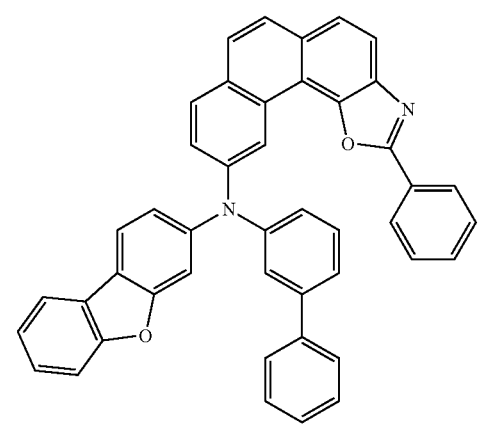
H1-16
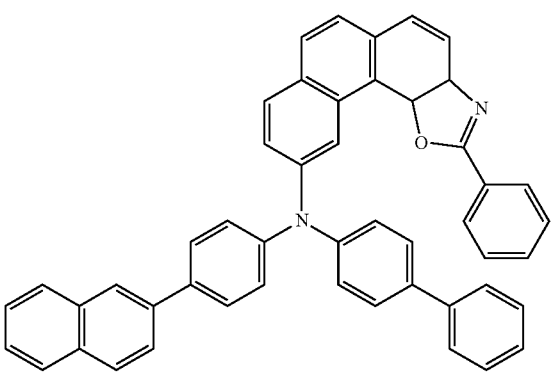
H1-17
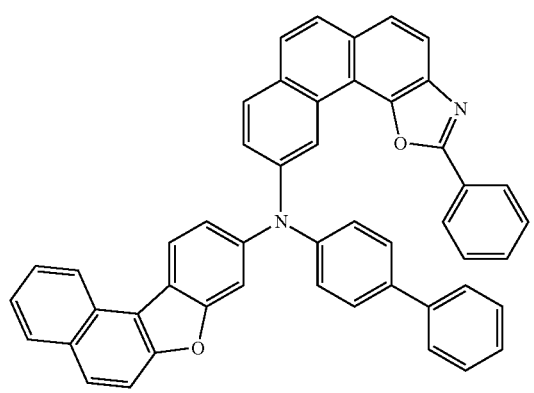
H1-18
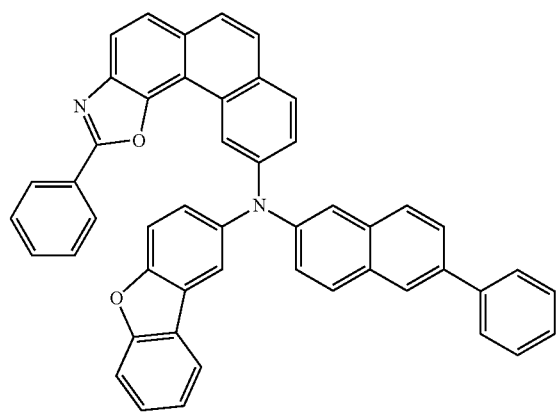
H1-19
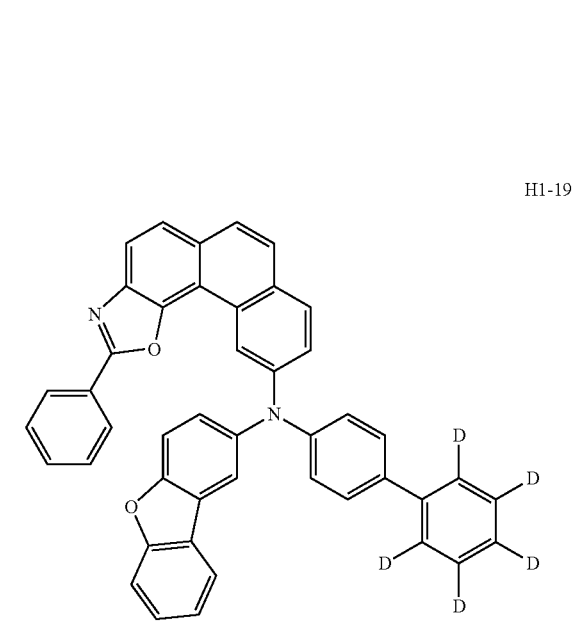
H1-20
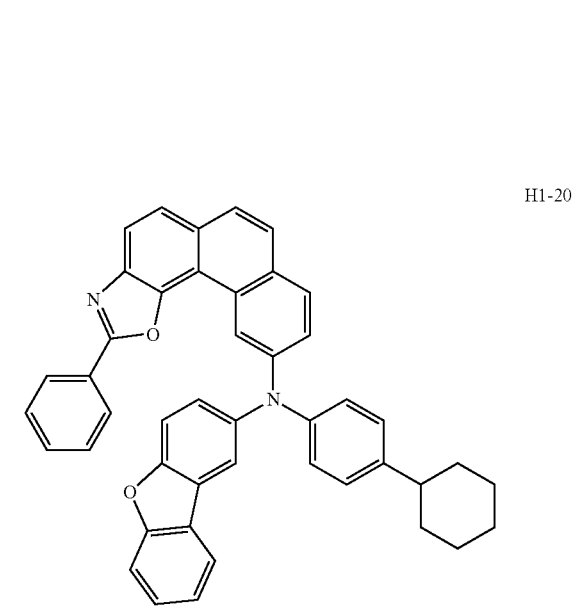

H1-21
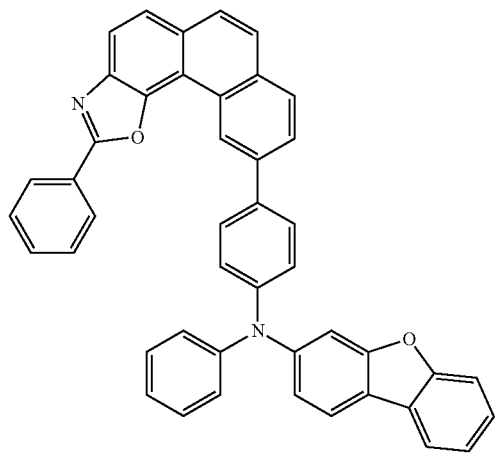
H1-22
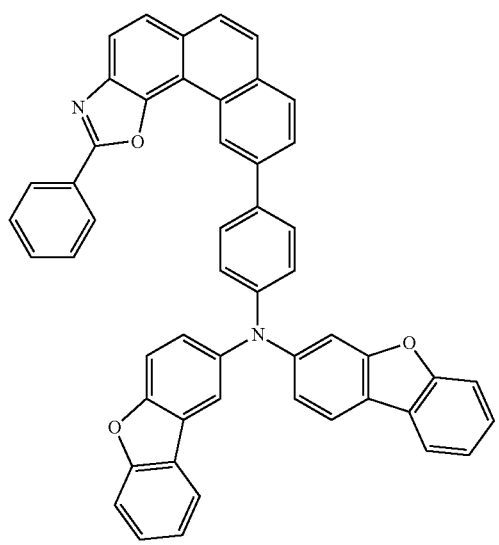
H1-23
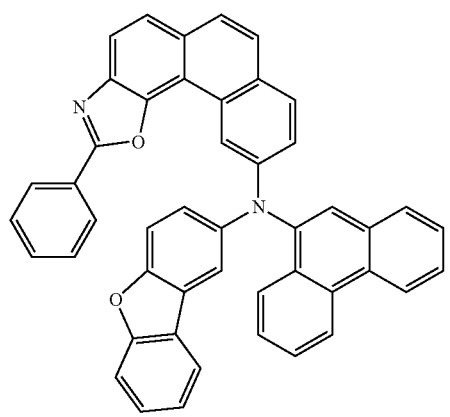
H1-24
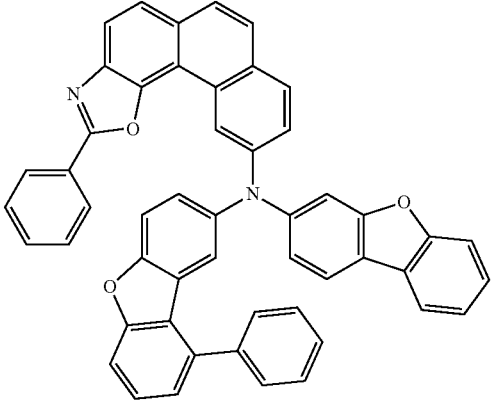
H1-25
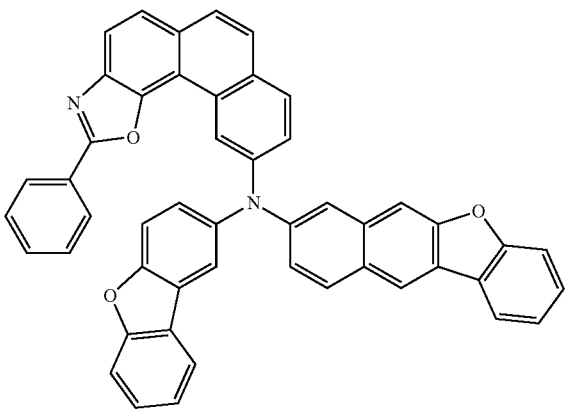
H1-26
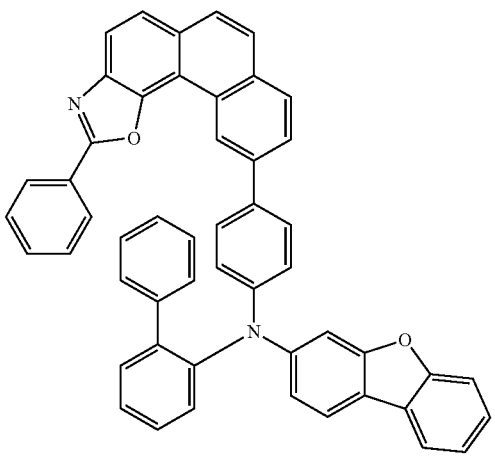

H1-27
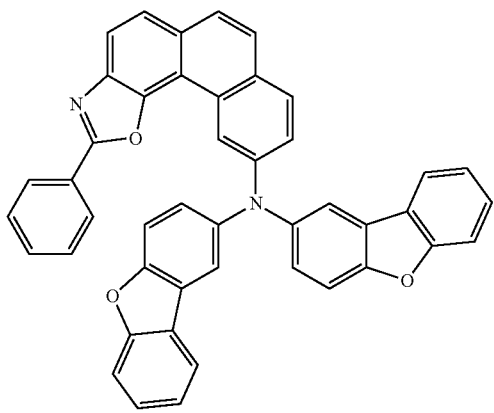
H1-28
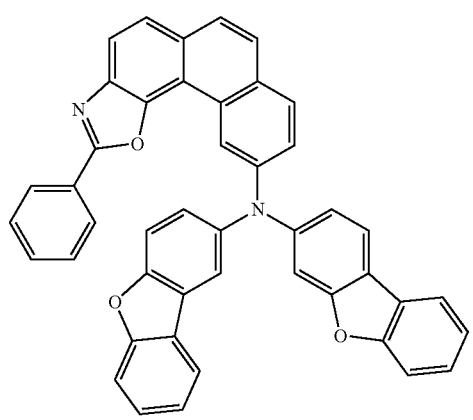
H1-29
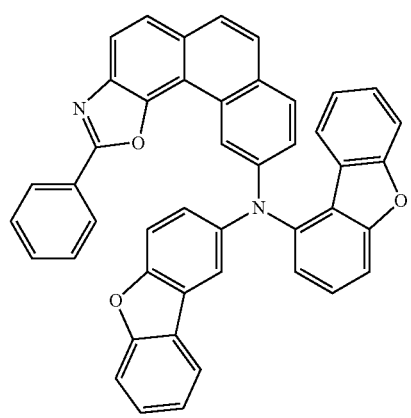
H1-30
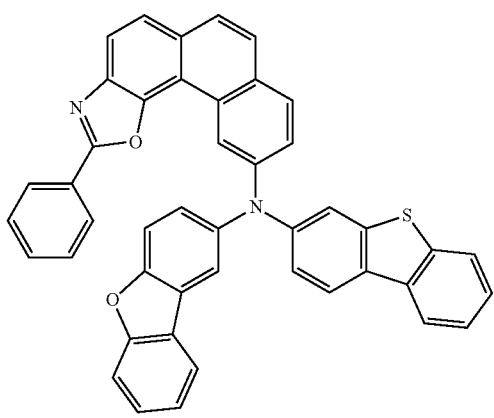
H1-31
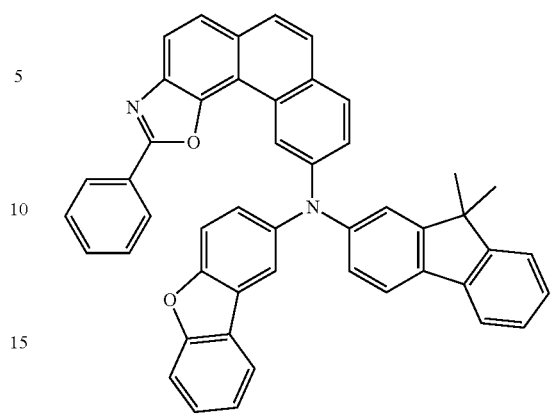
H1-32
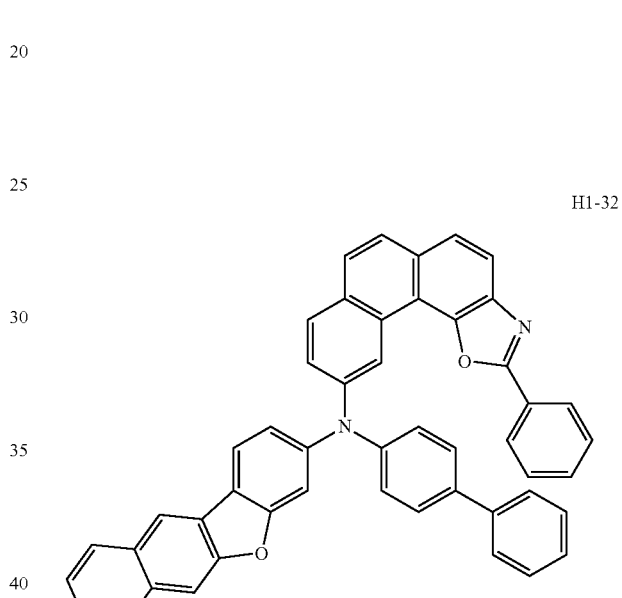
H1-33
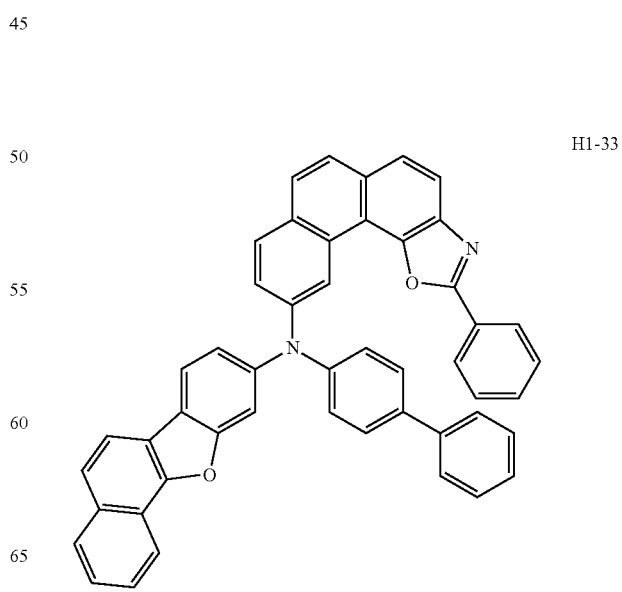

H1-34
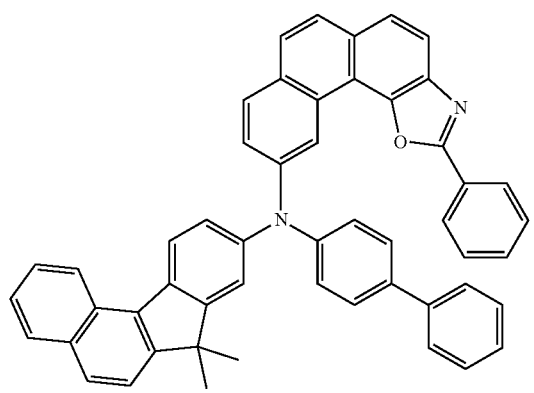
H1-35
H1-36
H1-37
H1-38
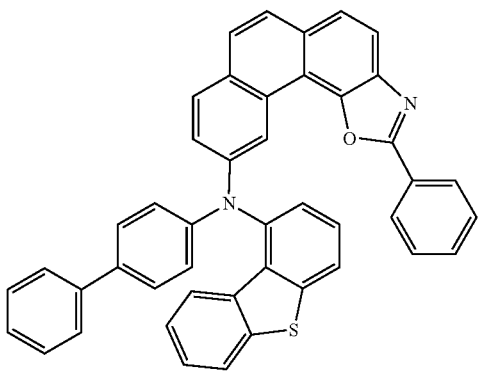
H1-39
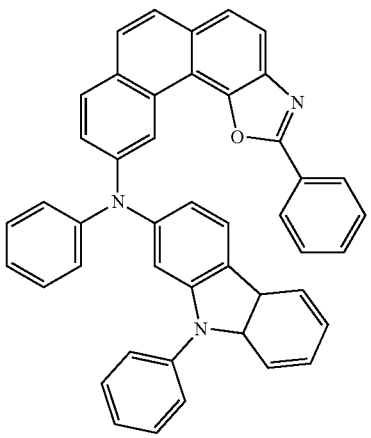
H1-40
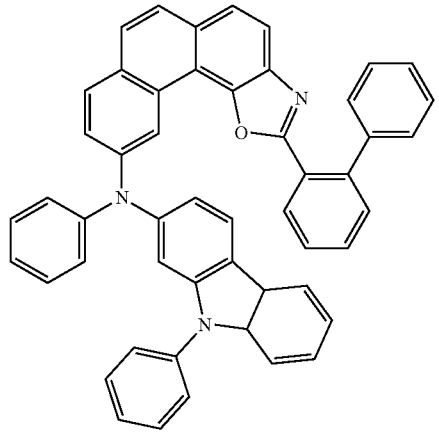
H1-41
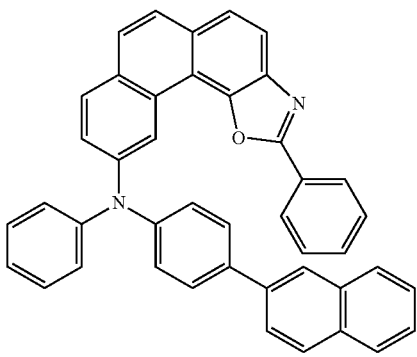

H1-42
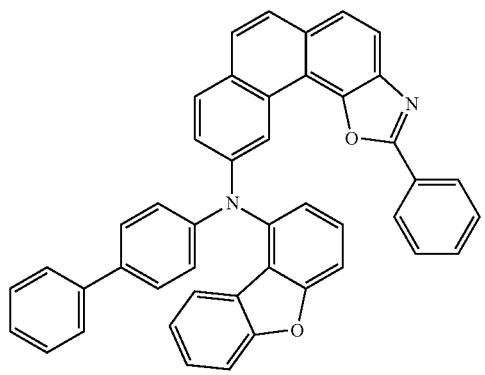
H1-43
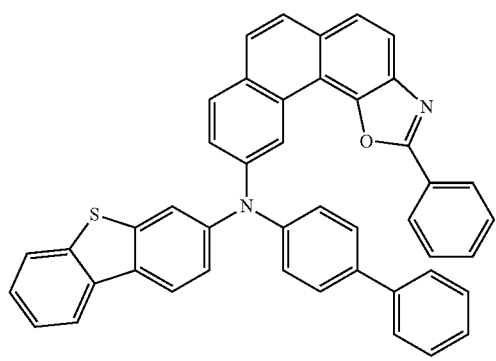
H1-44
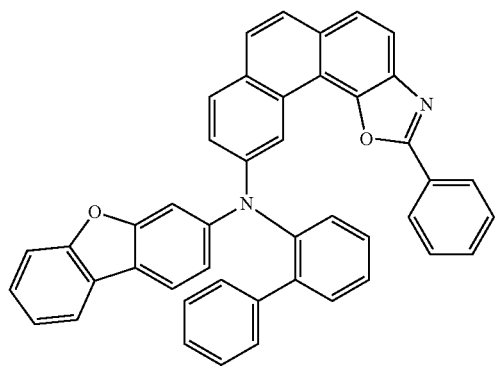
H1-45
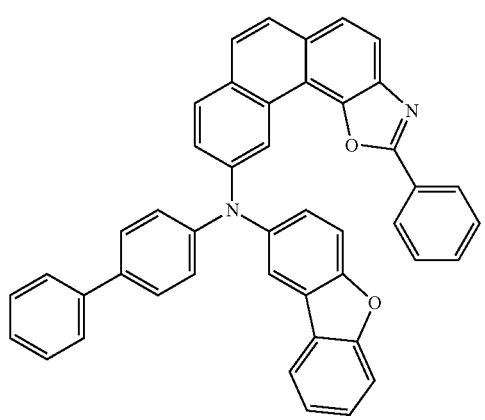
H1-46
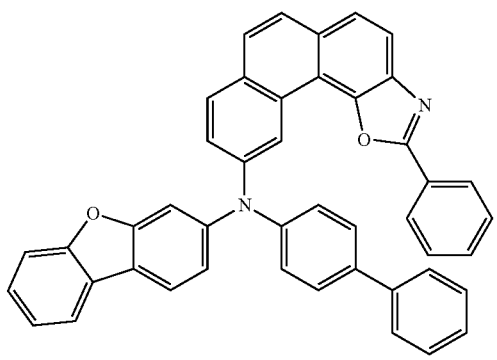
H1-47
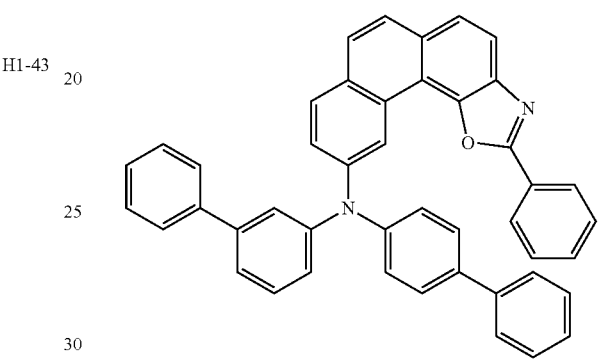
H1-48
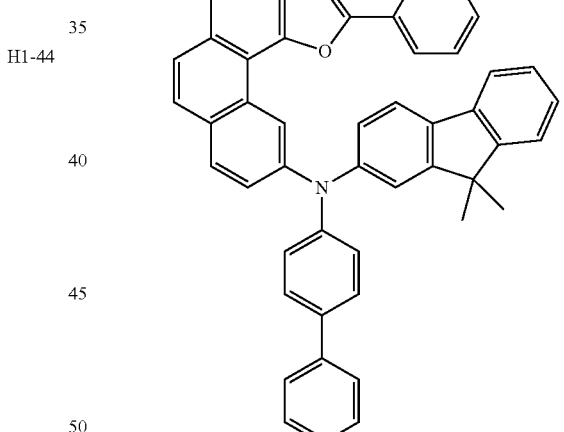
H1-49
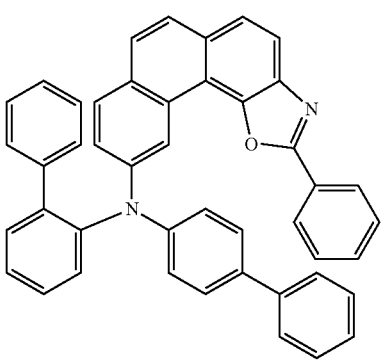

-continued
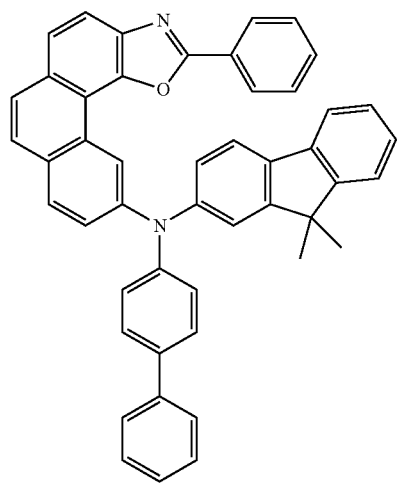
H1-50
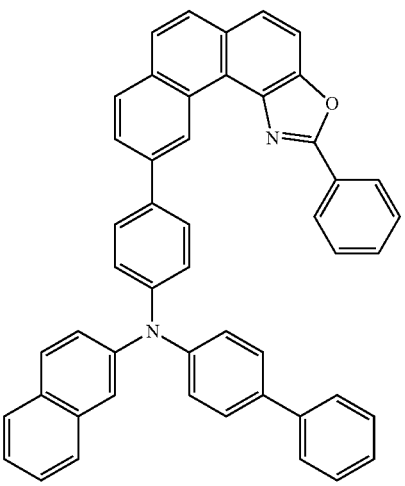
H1-53
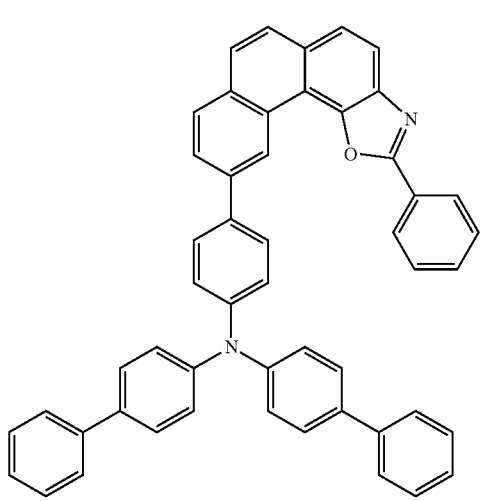
H1-51
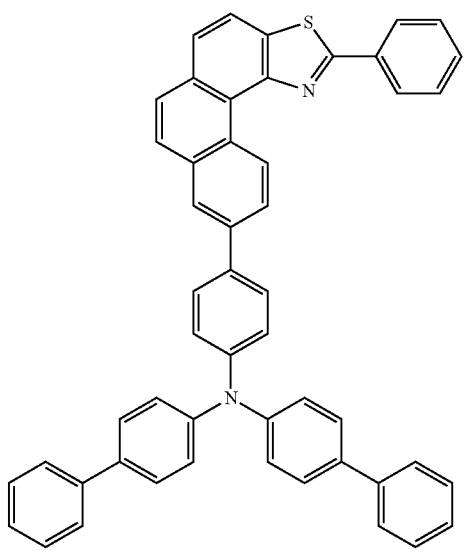
H1-54
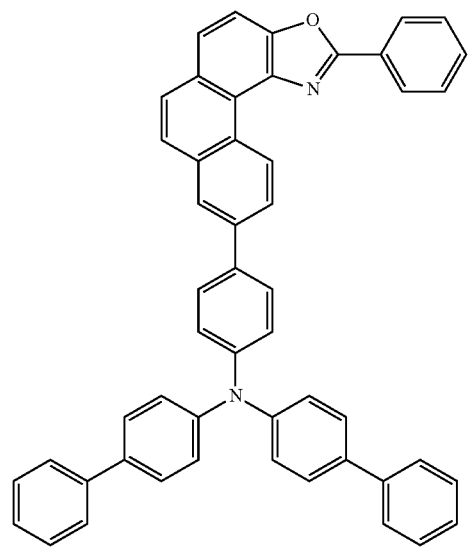
H1-52
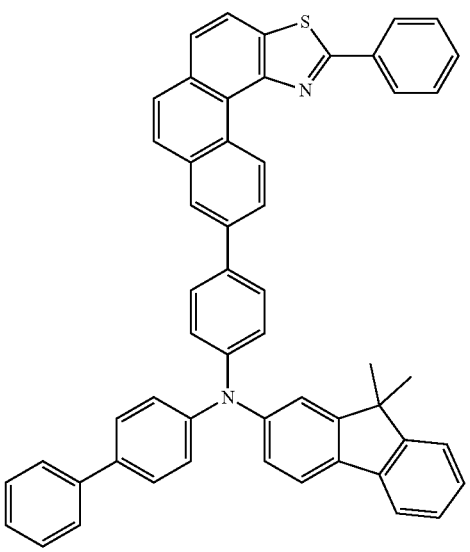
H1-55

H1-56
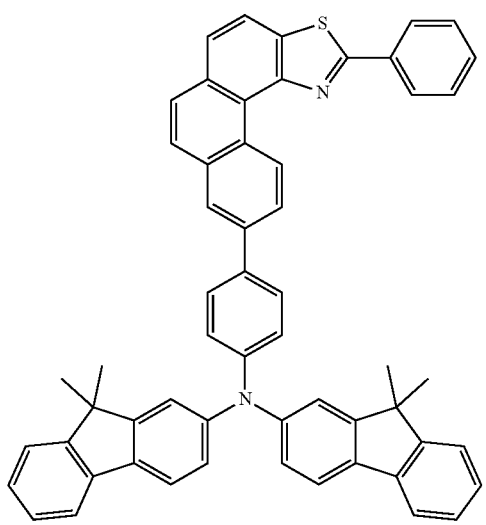
H1-57
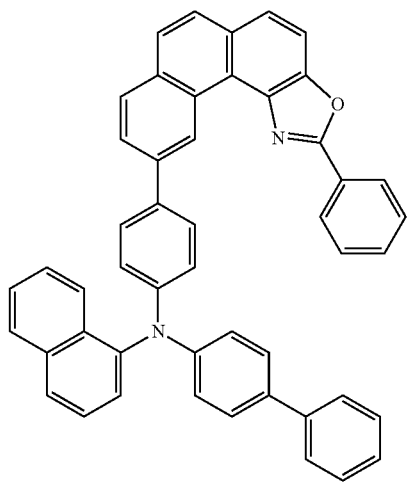
H1-58
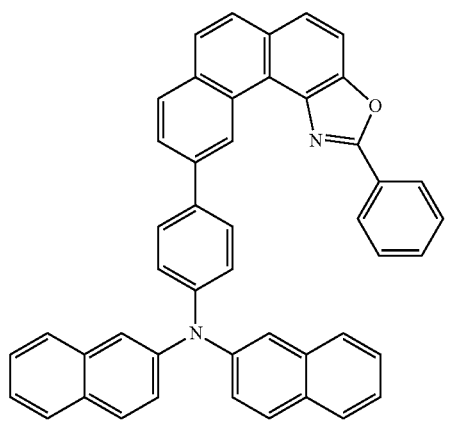
H1-59
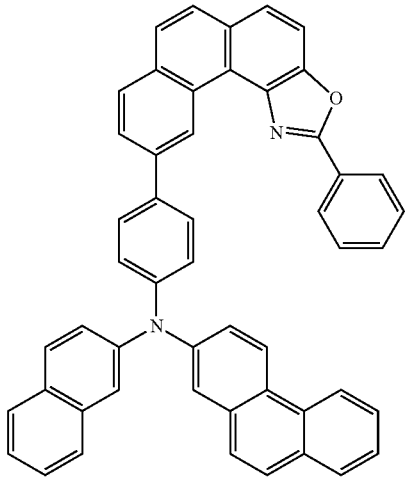
H1-60
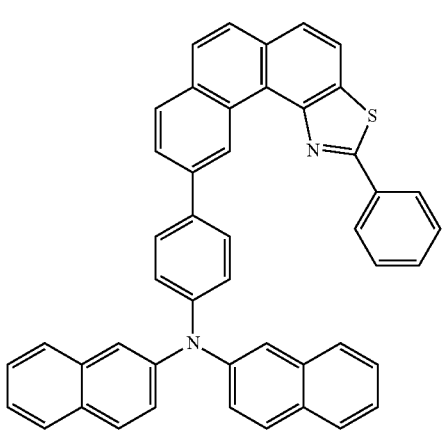
H1-61
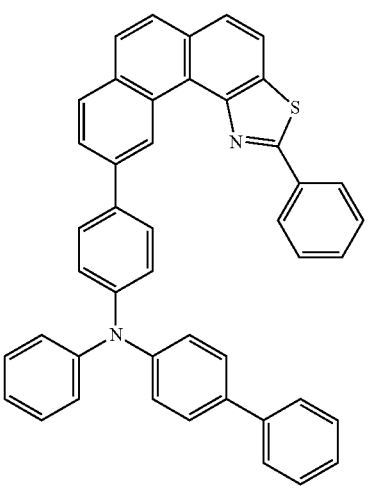

H1-62
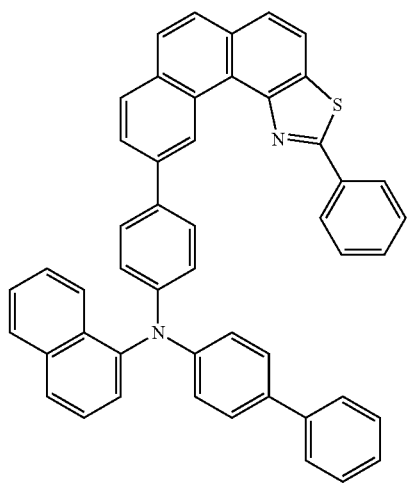
H1-63
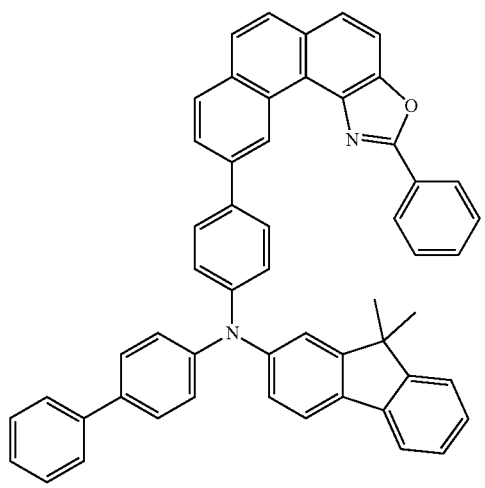
H1-64
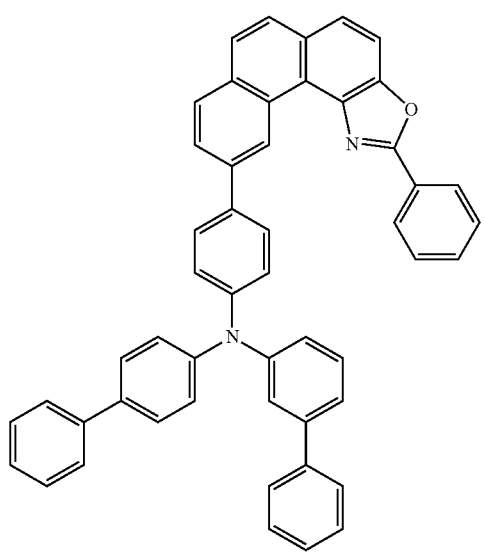
H1-65
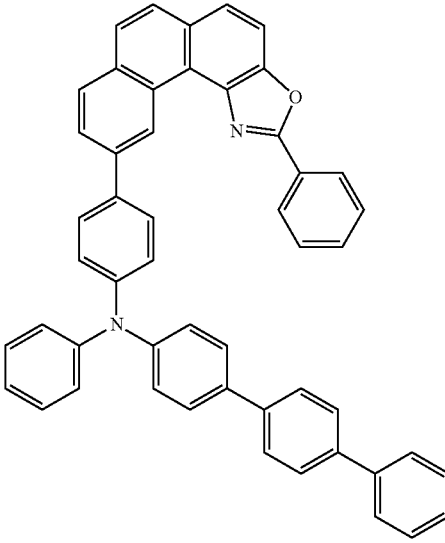
H1-66
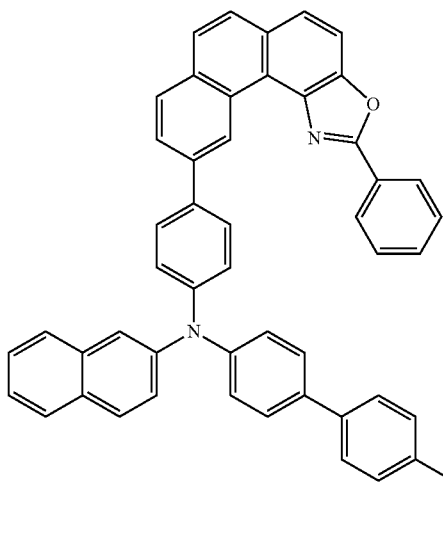
H1-67
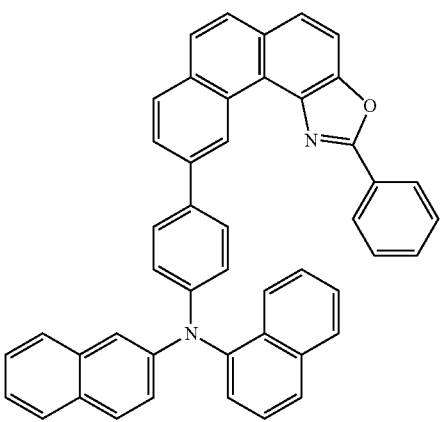

505
-continued
H1-68
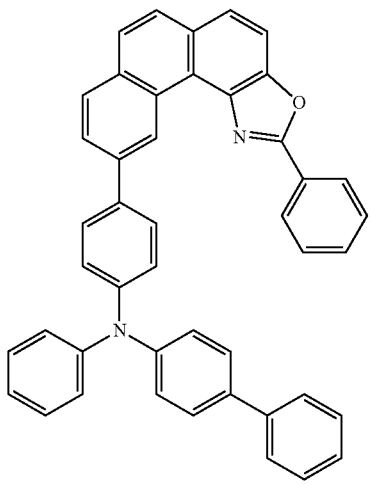
H1-69
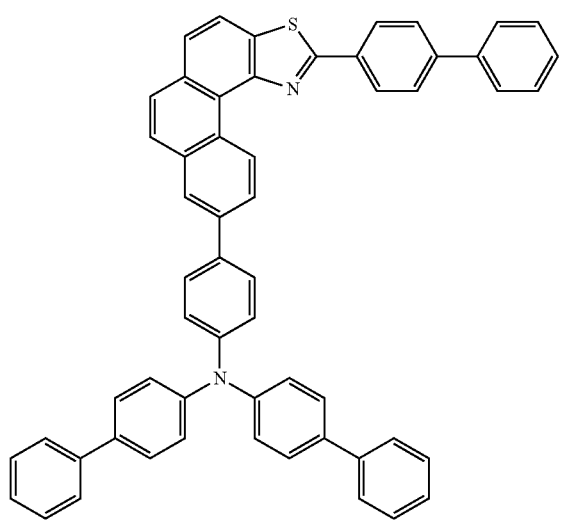
H1-70
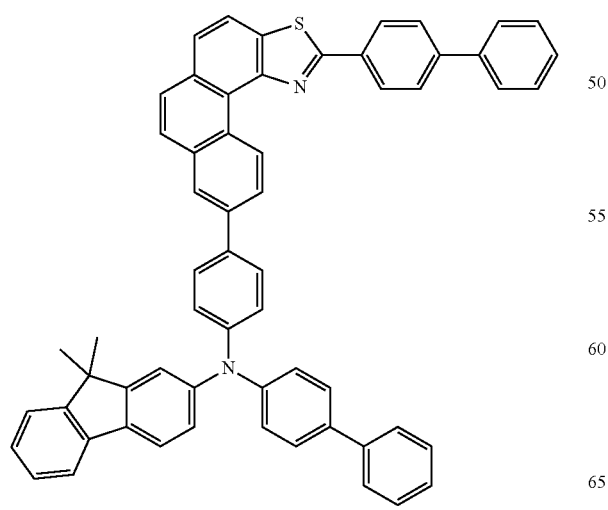
506
-continued
H1-71
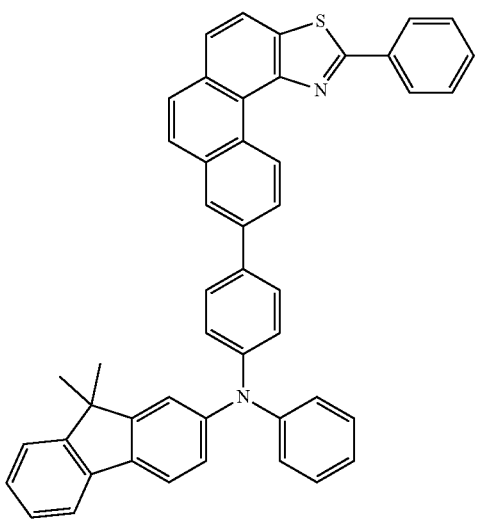
H1-72
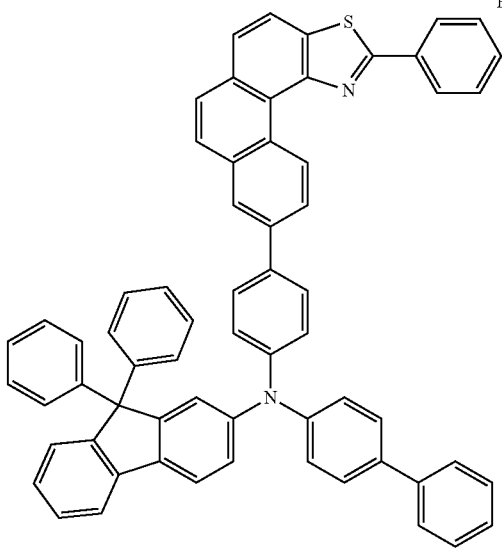
H1-73
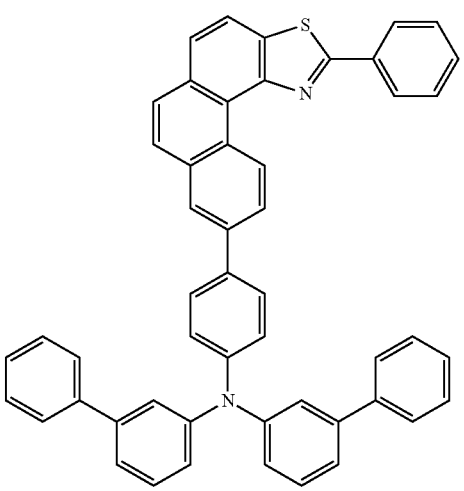

| 507 -continued | 508 -continued |
|---|---|
| H1-74 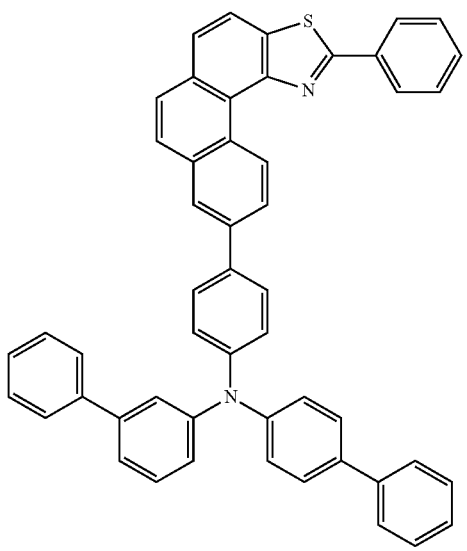 | H1-77 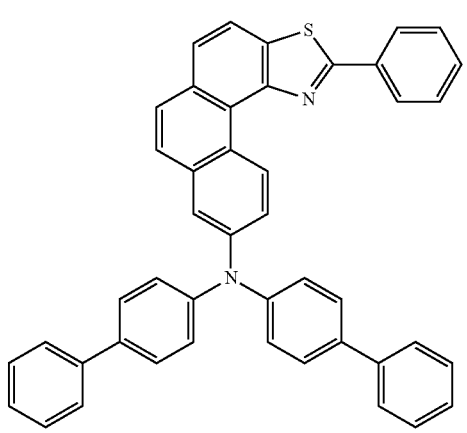 |
| H1-75 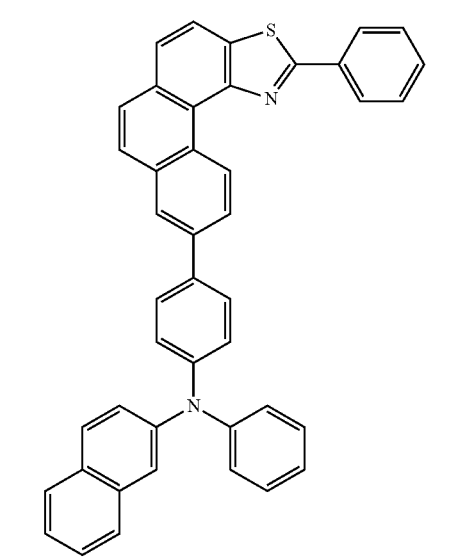 | H1-78 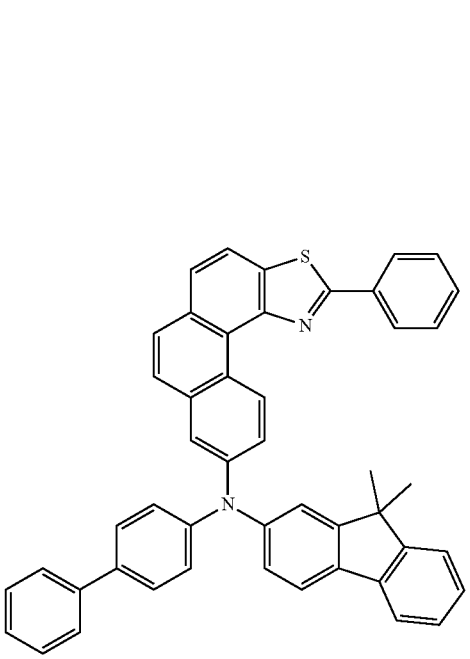 |
| H1-76 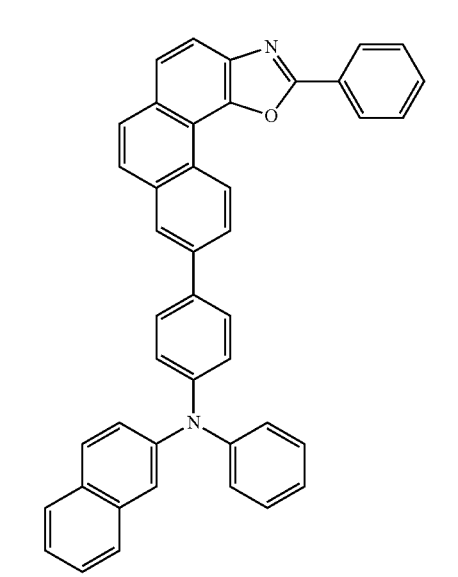 | H1-79 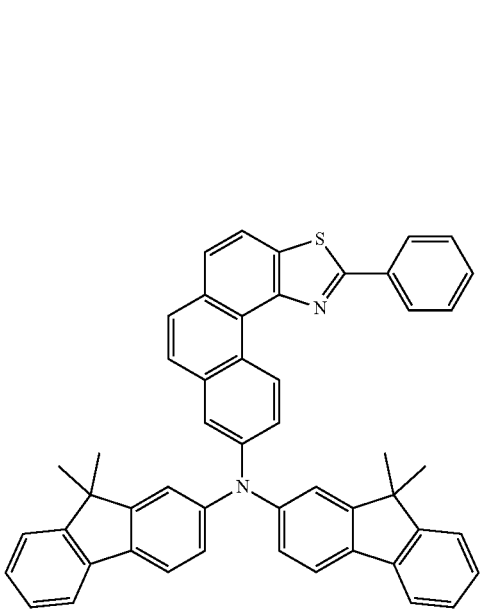 |

H1-80
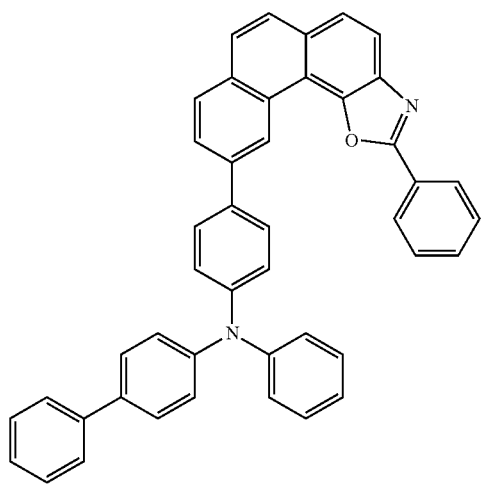
H1-81
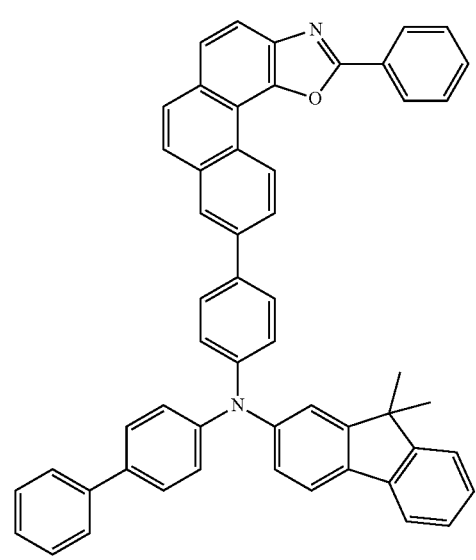
H1-82
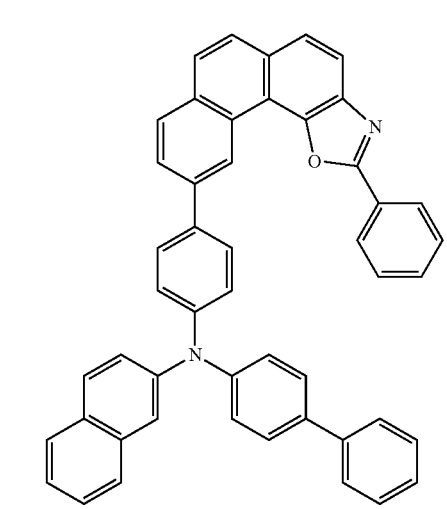
H1-83
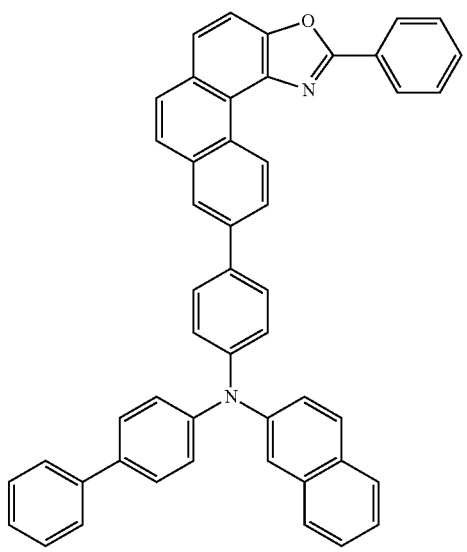
H1-84
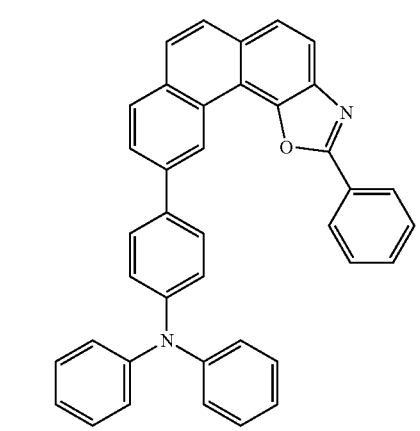
H1-85
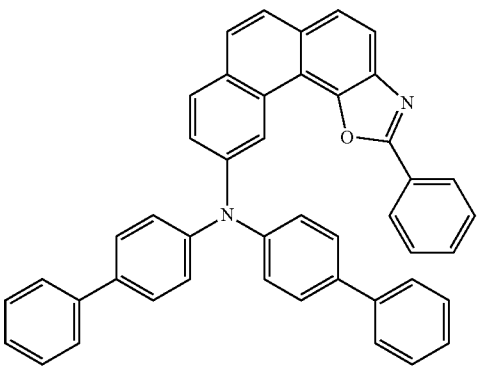

H1-86
H1-89
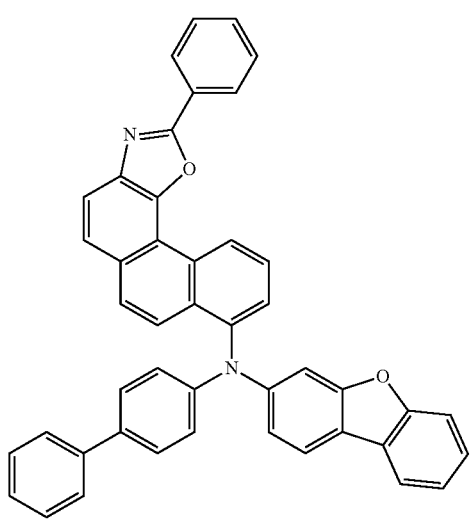
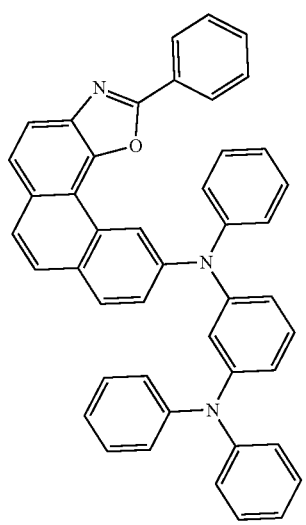
H1-87
H1-90
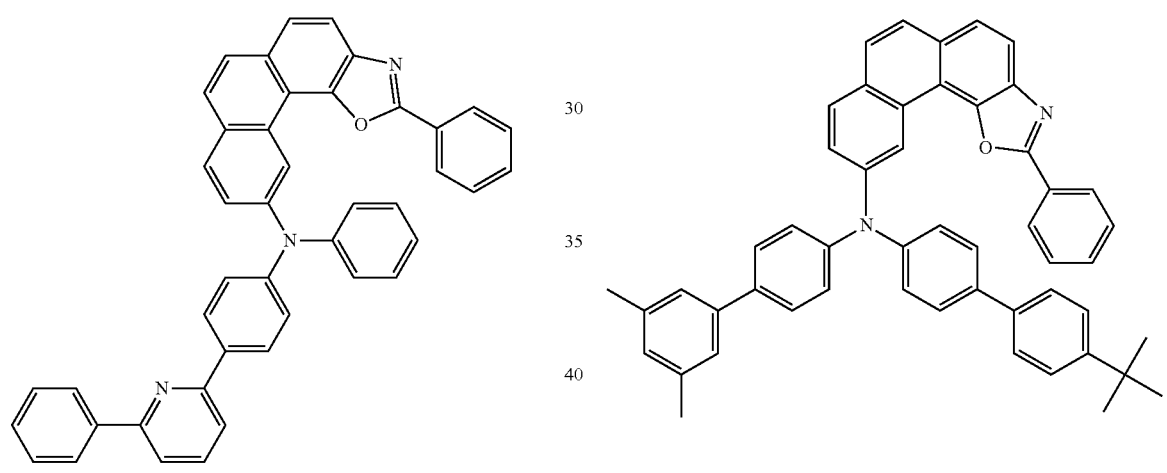
H1-88
H1-91
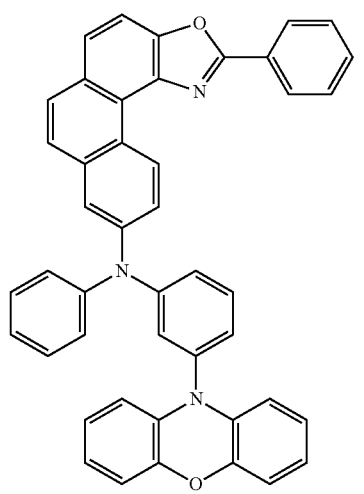
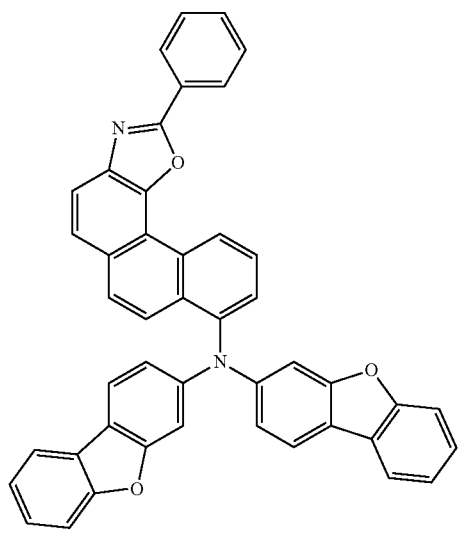

-continued
H1-92
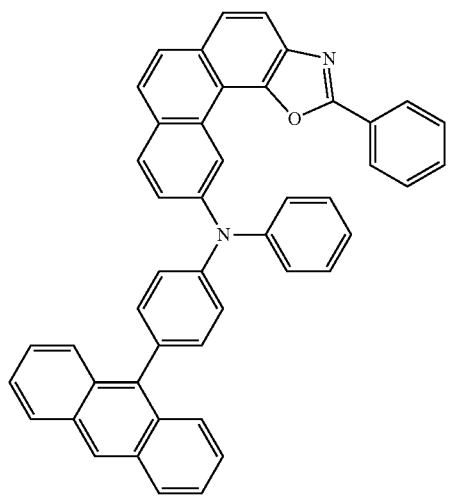
H1-93
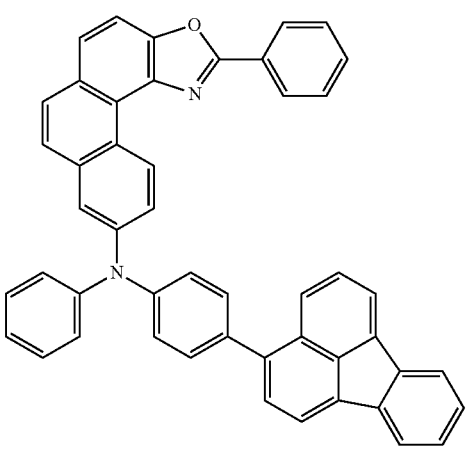
H1-94
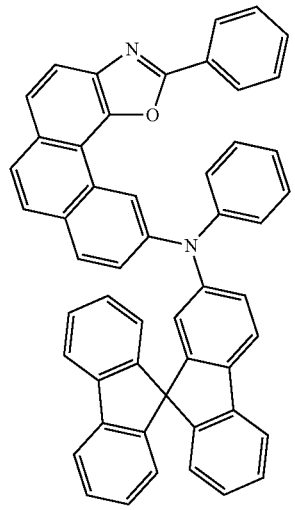
-continued
H1-95
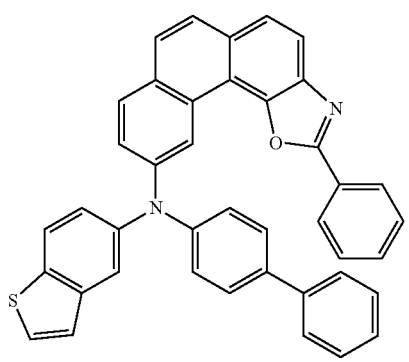
H1-96
H1-97
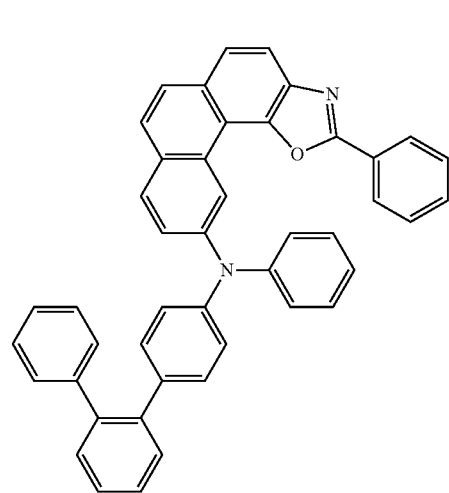

H1-98
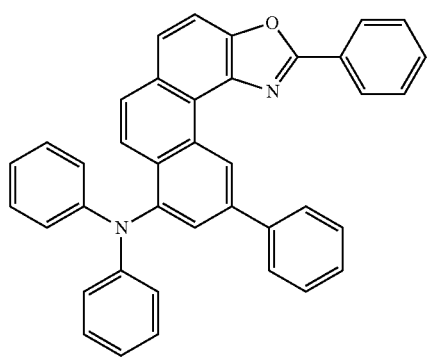
H1-101
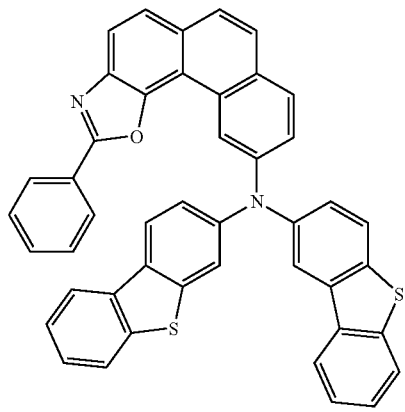
H1-99
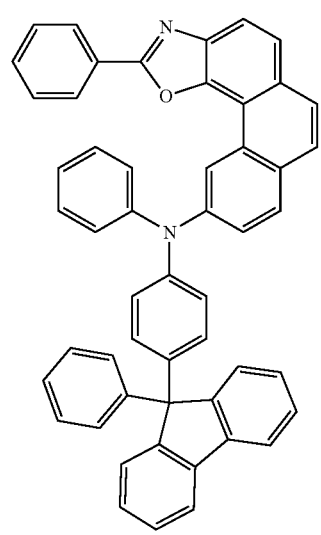
H1-102
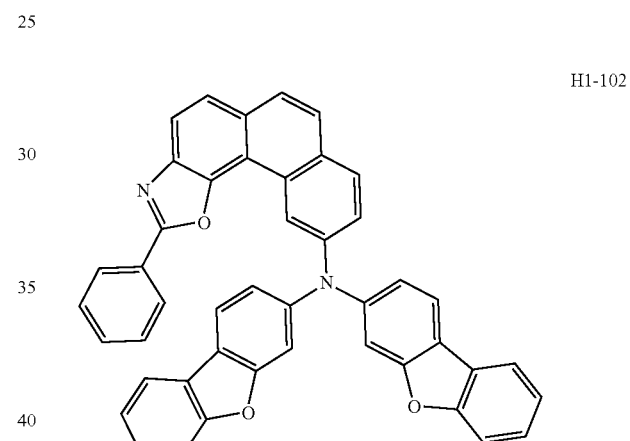
H1-100
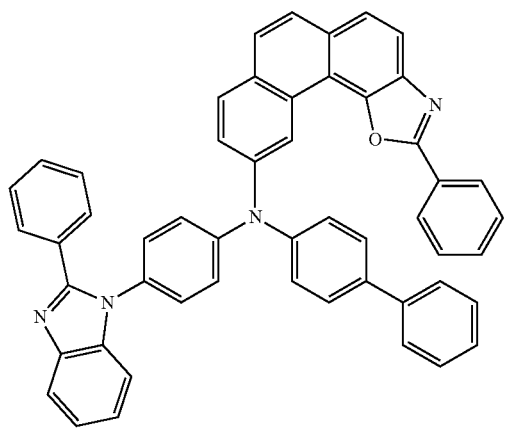
H1-103
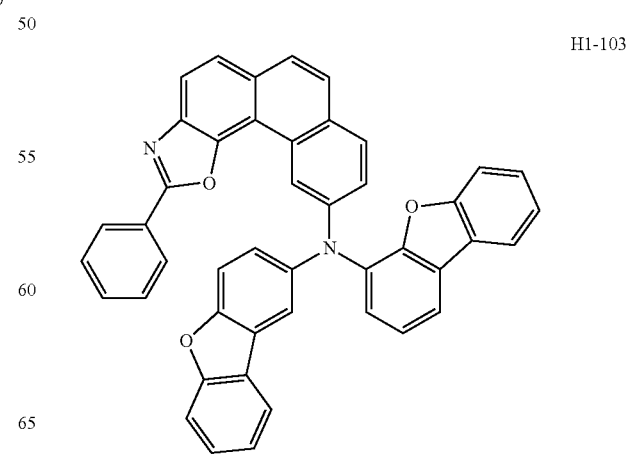

H1-104
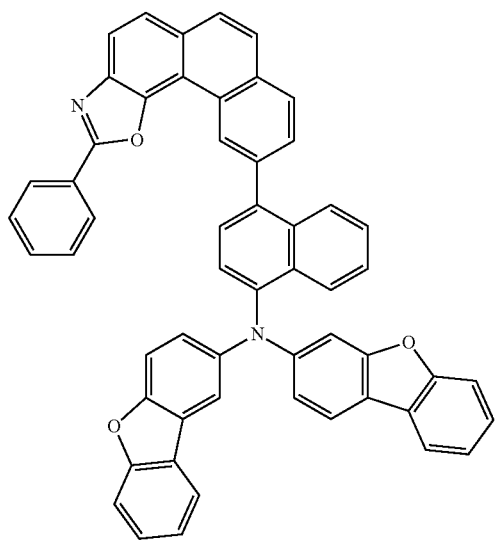
H1-105
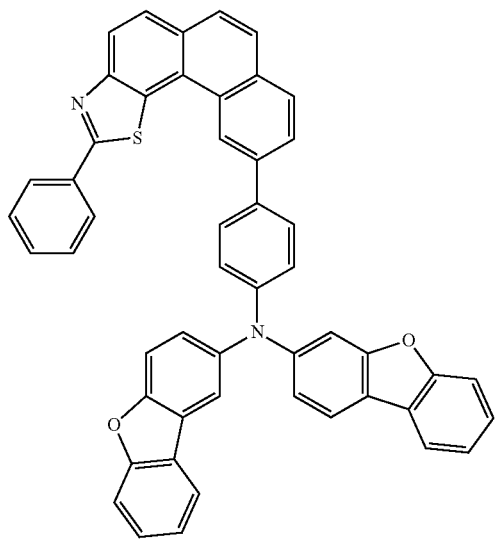
H1-106
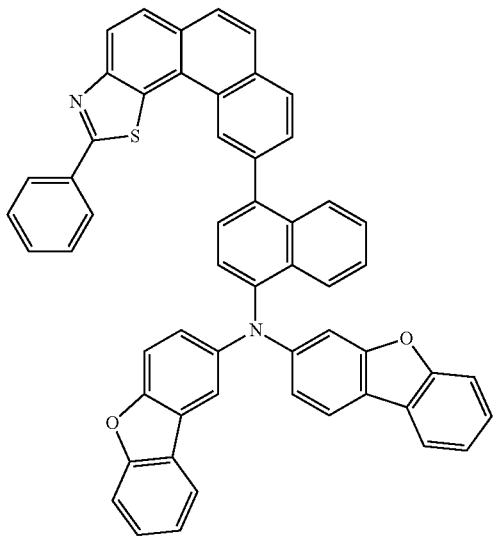
H1-107
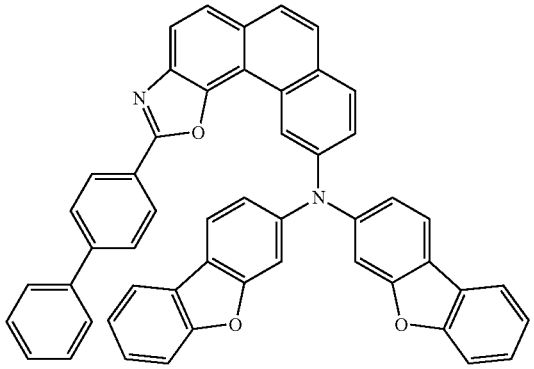
H1-108

H1-109
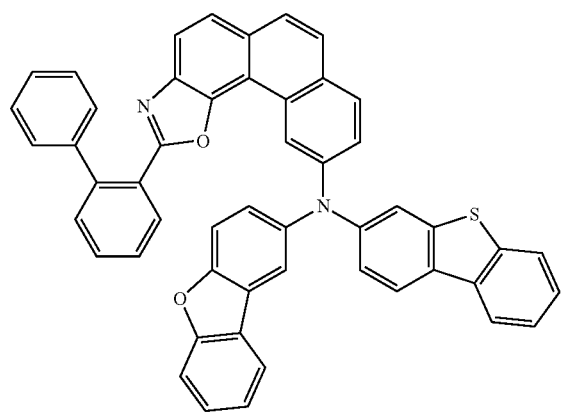
H1-110
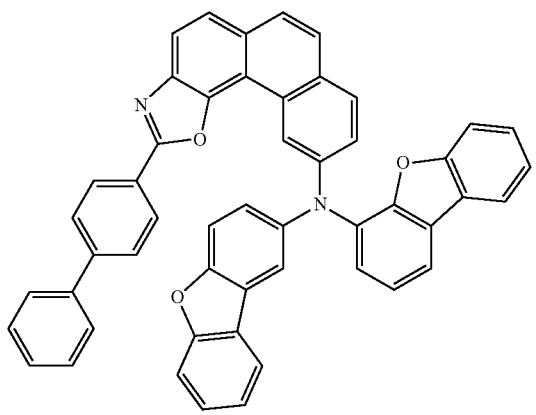
H1-111
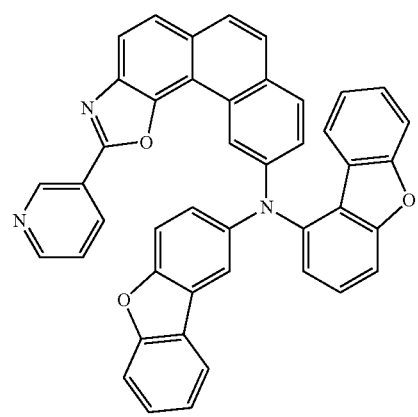
H1-112
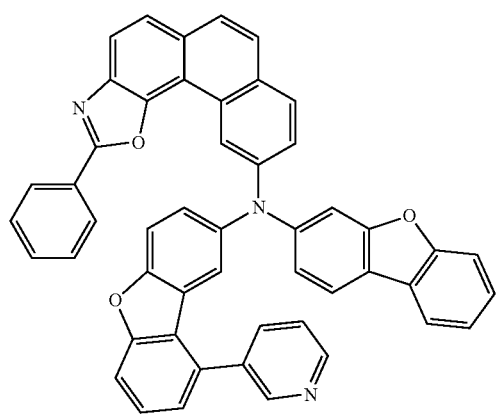
H1-113
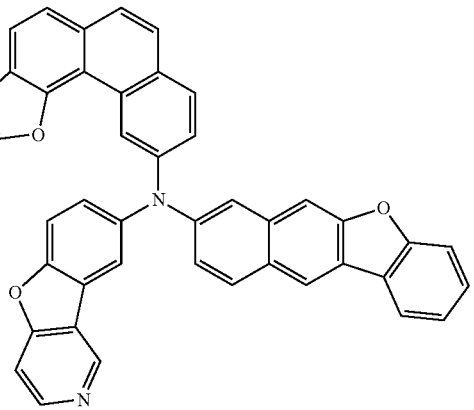
H1-114
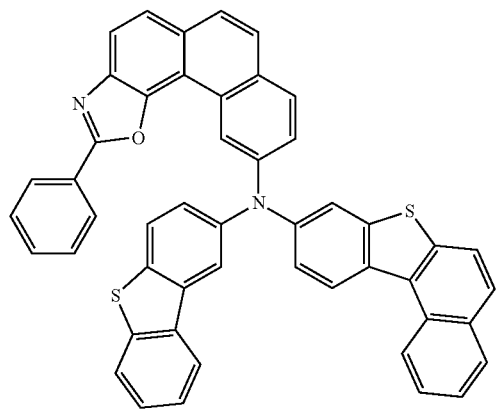

| 521 -continued | 522 -continued |
|---|---|
| H1-115 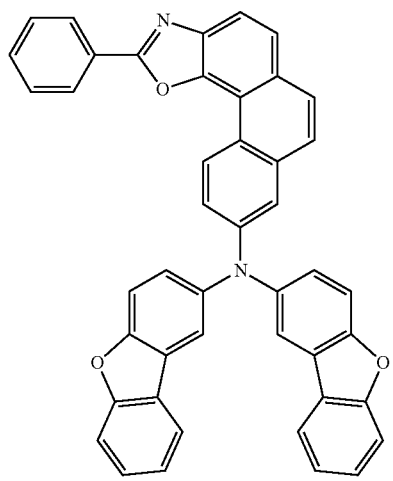 | H1-118 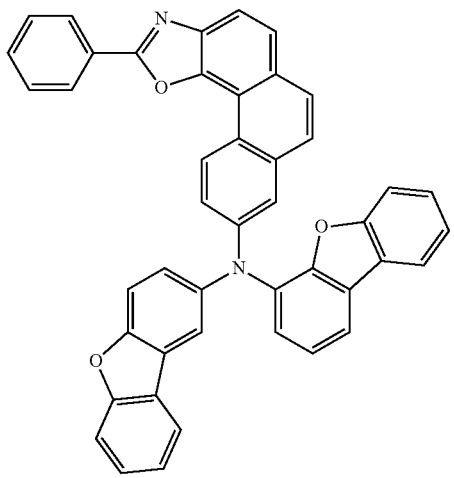 |
| H1-116 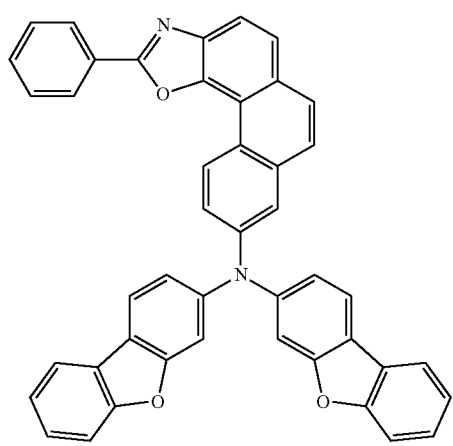 | H1-119 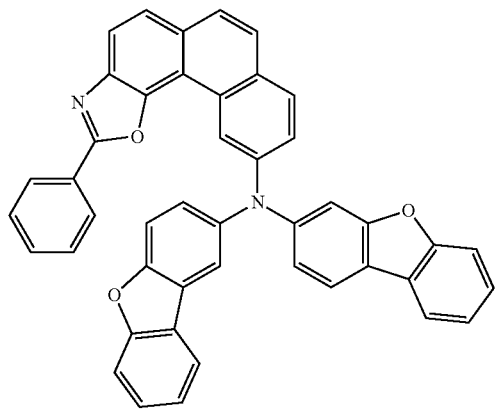 |
| H1-117 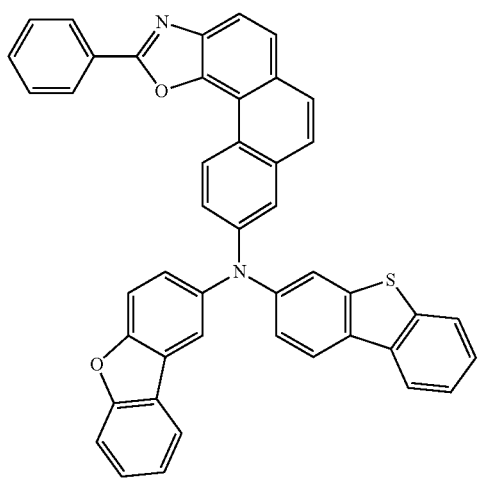 | H1-120 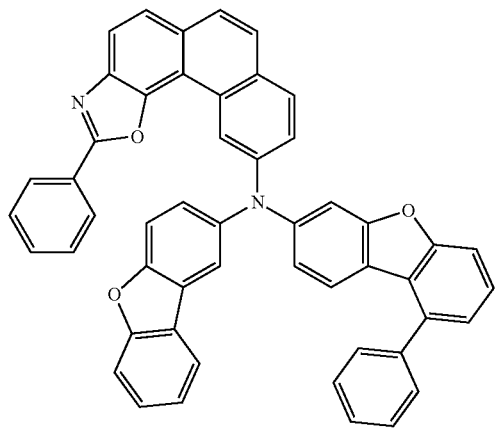 |

H1-121
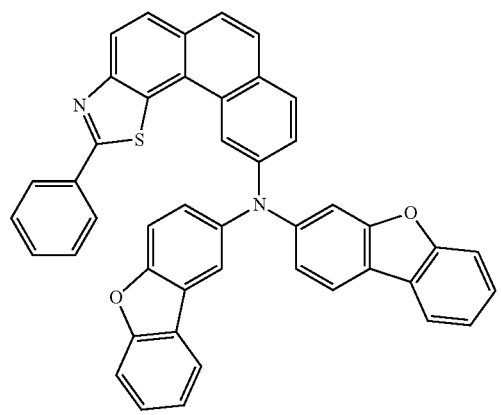
H1-124
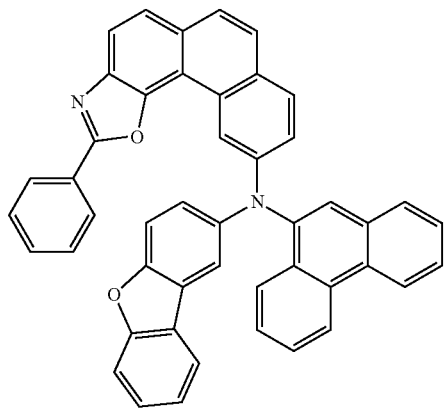
H1-122
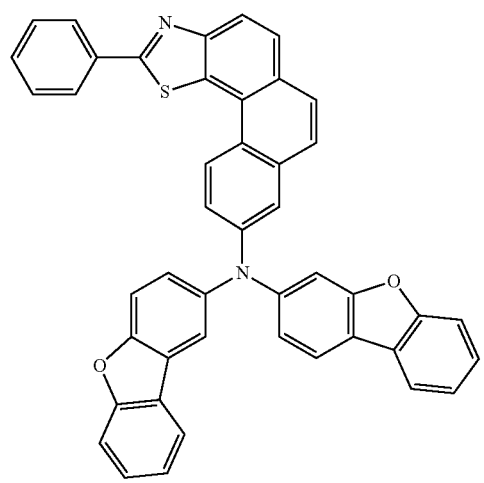
H1-125
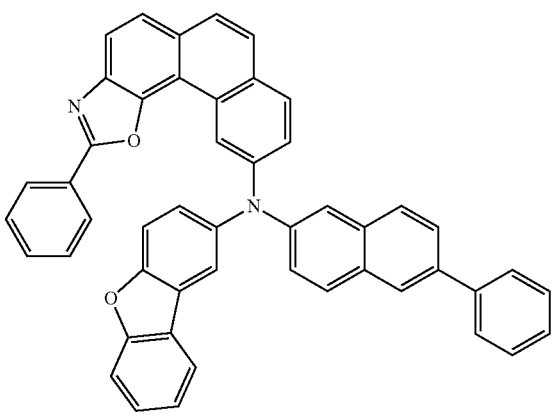
H1-123
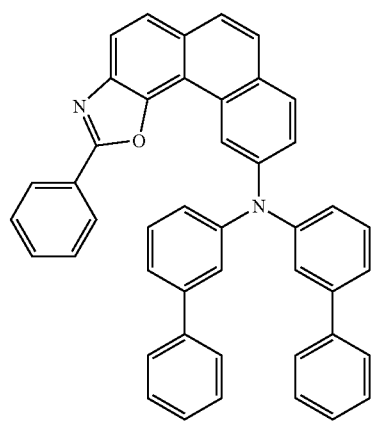
H1-126
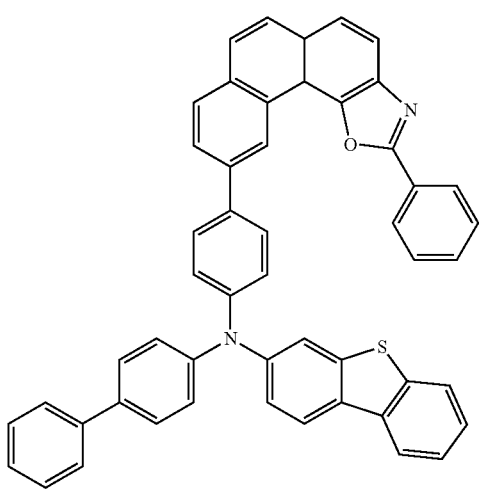

H1-127
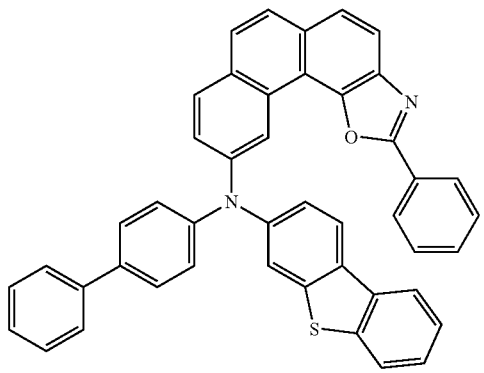
H1-128
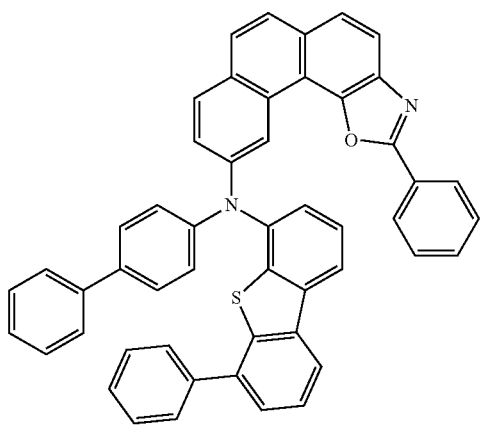
H1-129
H1-130
H1-131
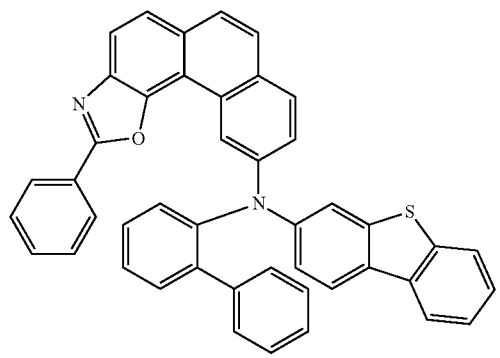
H1-132
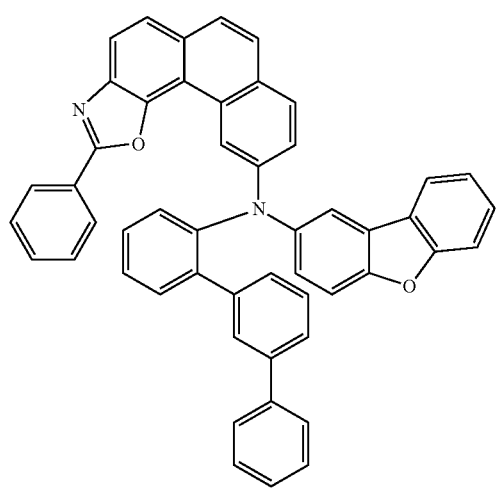
H1-133
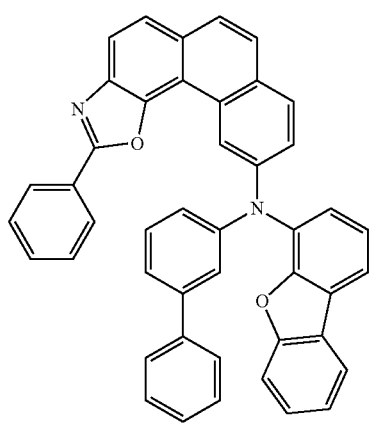

-continued

H1-134

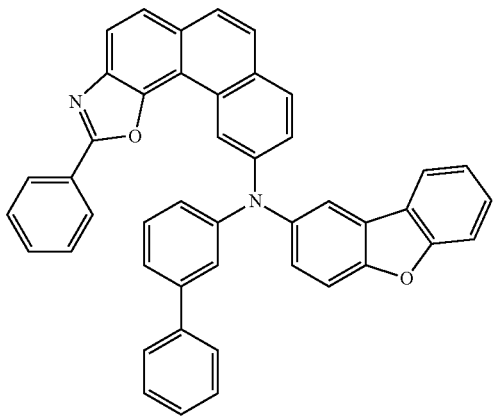

H1-135

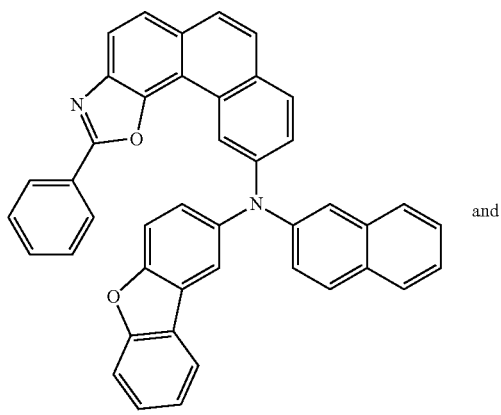

and

H1-136

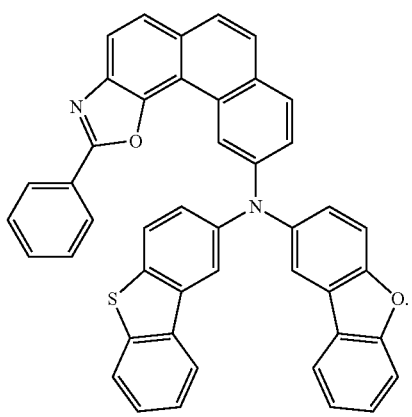

8. The plurality of host materials according to claim 5, wherein the second host material comprises the compound represented by the following formula 3:

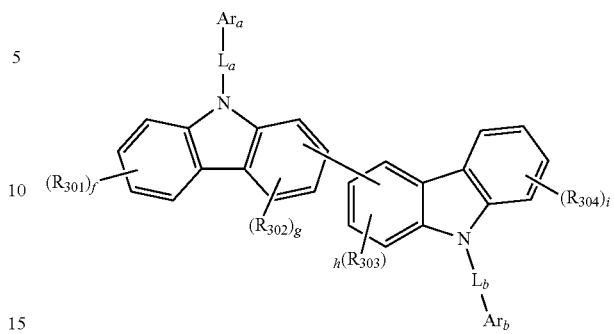

(3)

wherein $L_a$ and $L_b$ each independently represents a single bond, a substituted or unsubstituted (C6-C30)arylene, or a substituted or unsubstituted (3- to 30-membered)heteroarylene;

$Ar_a$ and $Ar_b$ each independently represent a substituted or unsubstituted (C1-C30)alkyl, a substituted or unsubstituted (C6-C30)aryl, or a substituted or unsubstituted (3- to 30-membered)heteroaryl;

$R_{301}$ to $R_{304}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or $-L_3'''-N(Ar_4''')(Ar_4''')$; or may be linked to an adjacent substituent to form a ring;

$L_3'''$ each independently represents a single bond, a substituted or unsubstituted (C6-C30)arylene, or a substituted or unsubstituted (3- to 30-membered)heteroarylene;

$Ar_3'''$ and $Ar_4'''$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl; and f and i each independently represent an integer of 1 to 4, g and h each independently represent an integer of 1 to 3, and when f to i are an integer of 2 or more, each of $R_{301}$ to each of $R_{304}$ may be the same or different from each other.

9. The plurality of host materials according to claim 8, wherein the compound represented by formula 3 is at least one selected from the following compounds:

H2-1
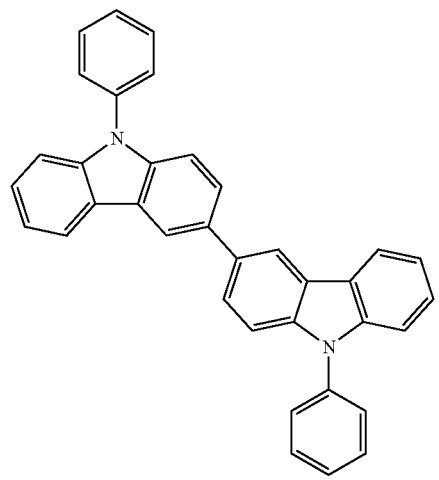
H2-2
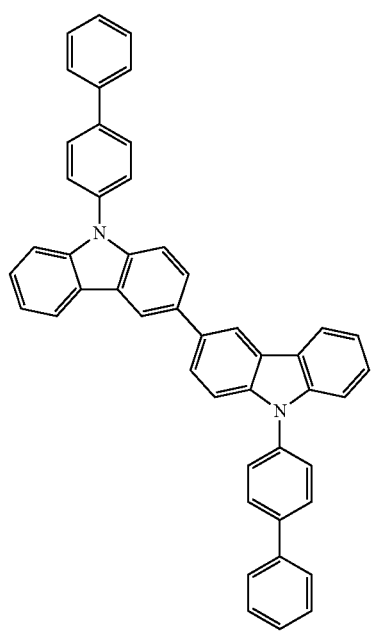
H2-3
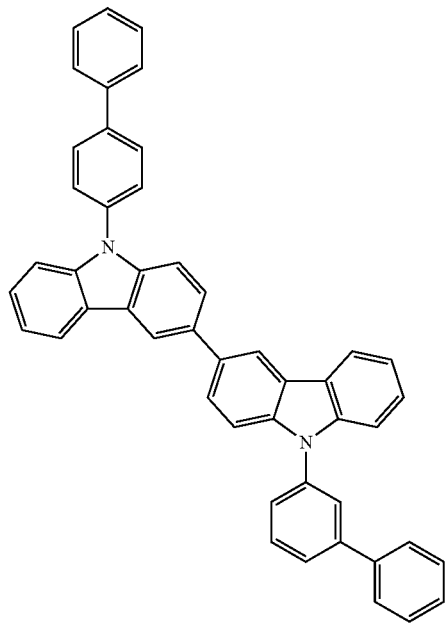
H2-4
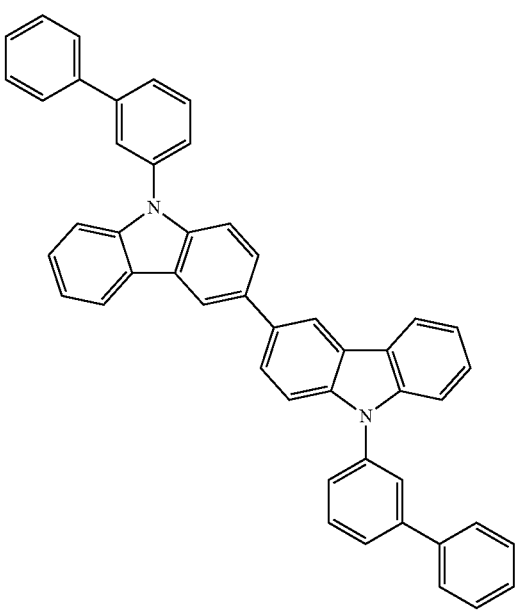

| 531 -continued | 532 -continued |
|---|---|
| H2-5 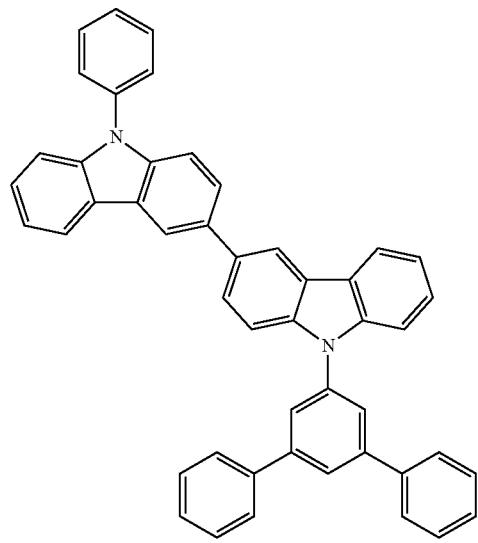 | H2-8 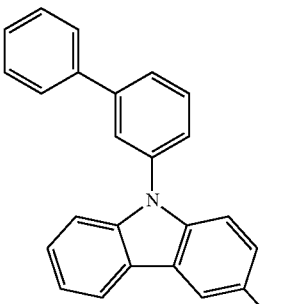 |
| H2-6 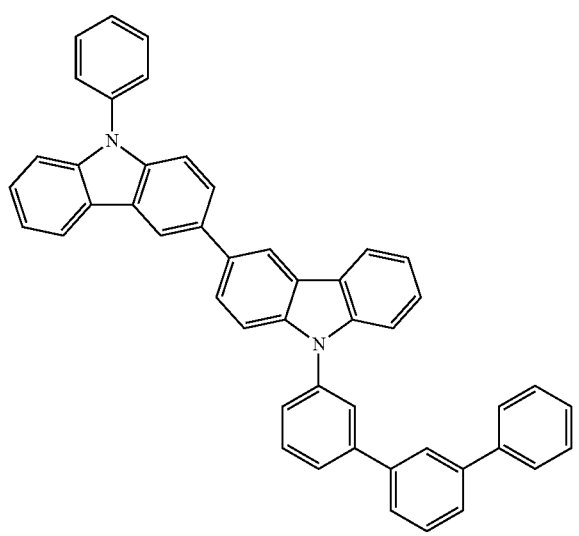 | H2-9 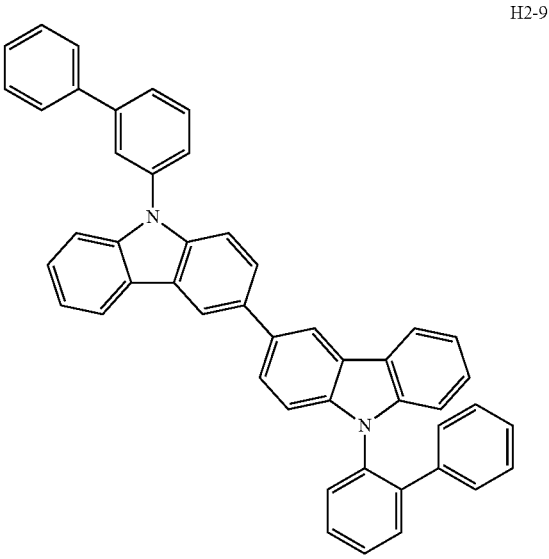 |
| H2-7 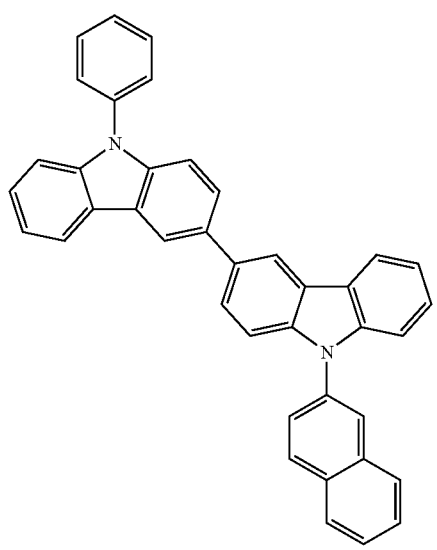 | H2-10 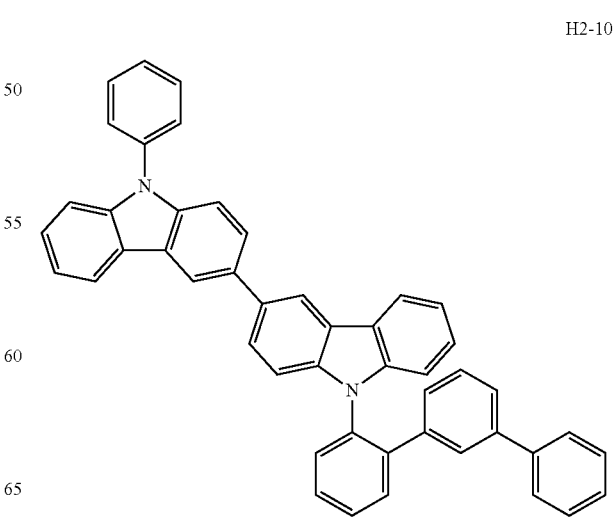 |

H2-11
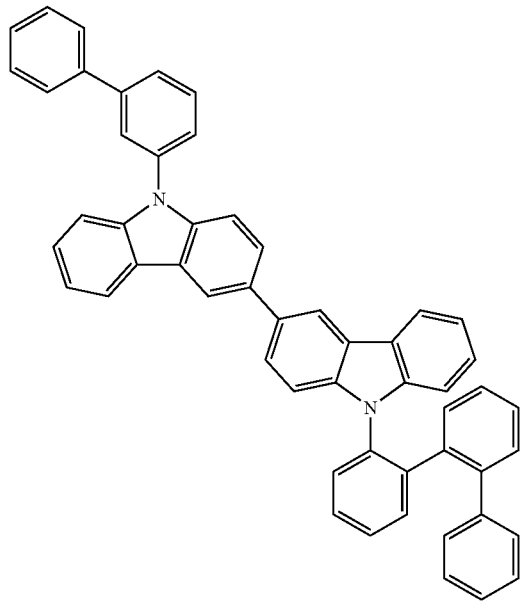
H2-13
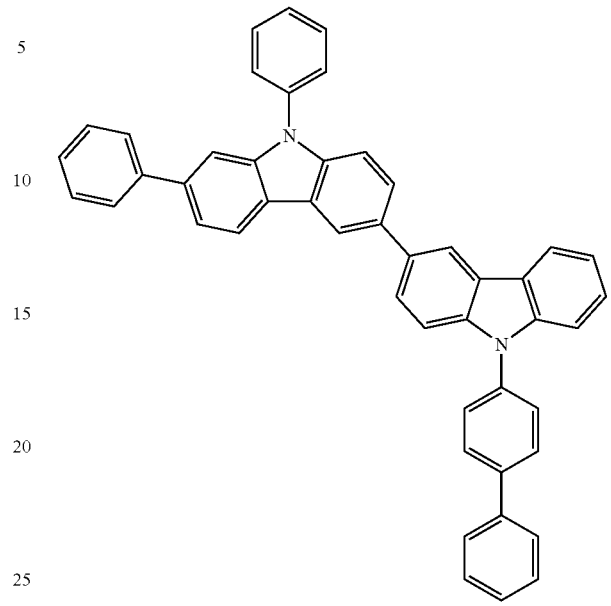
H2-12
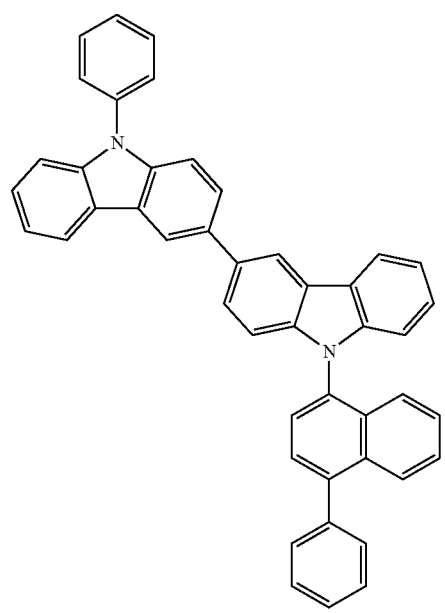
H2-14
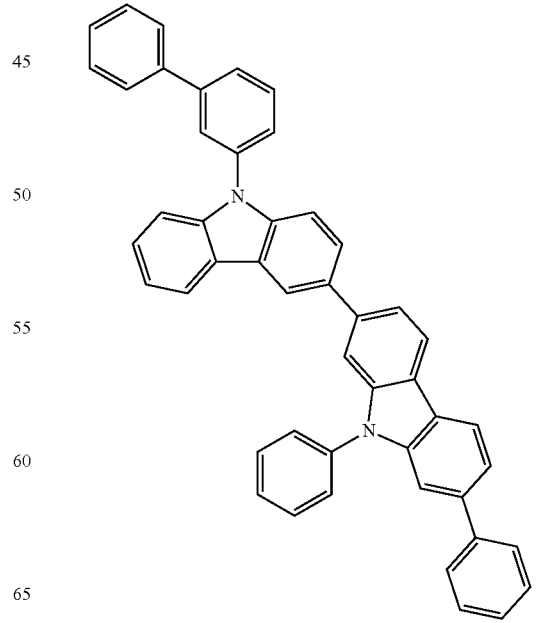

H2-15
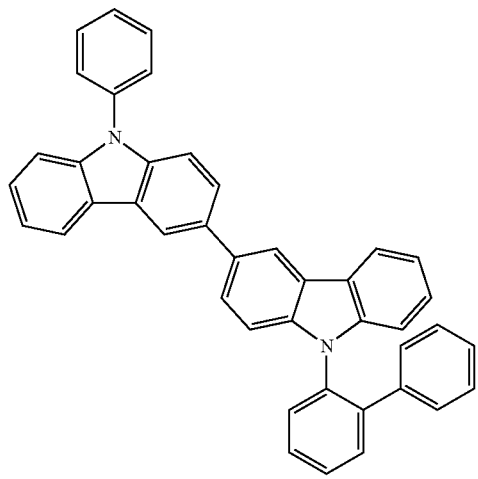
H2-18
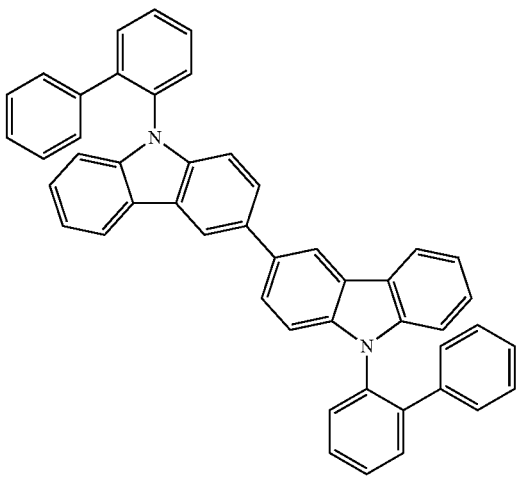
H2-16
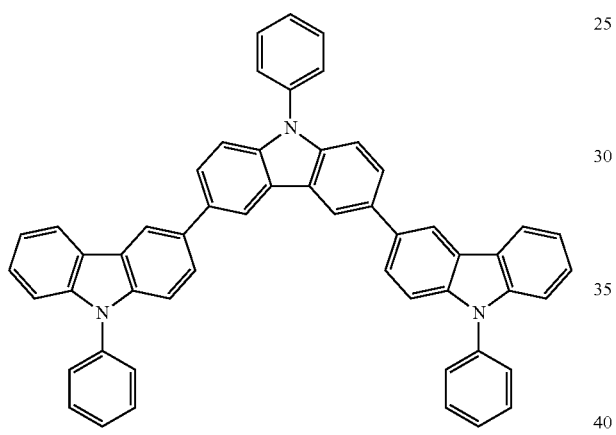
H2-19
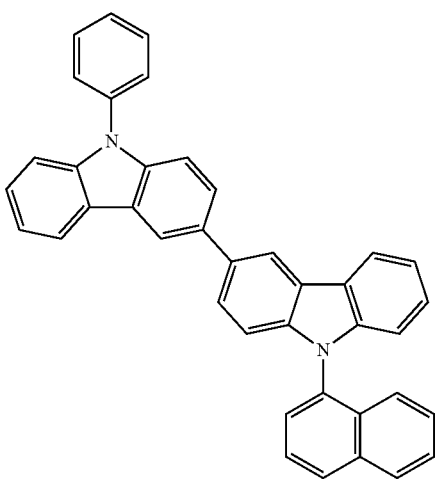
H2-17
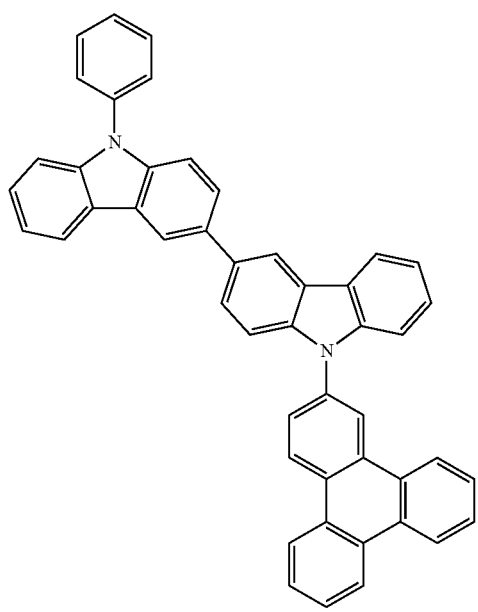
H2-20
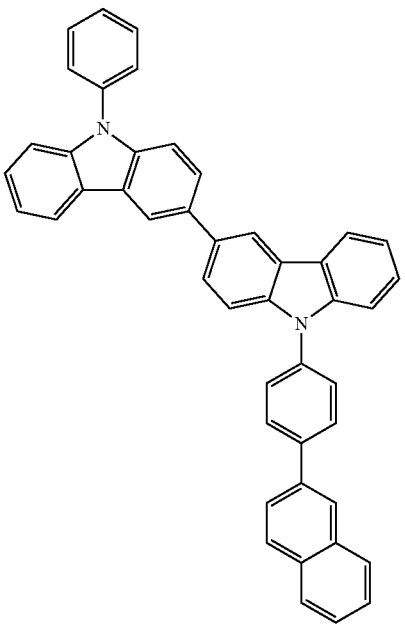

H2-21
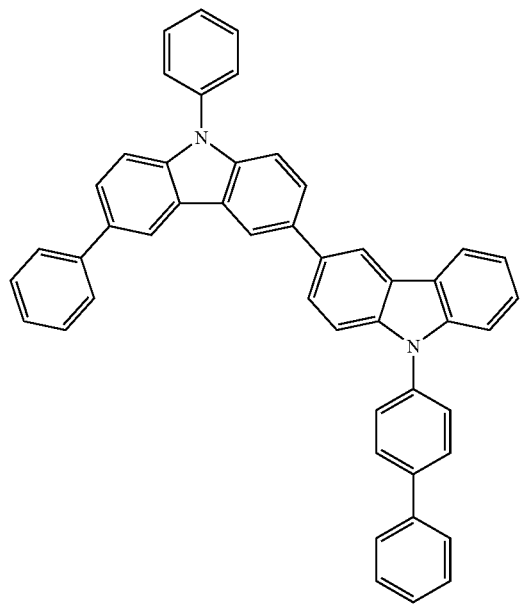
H2-22
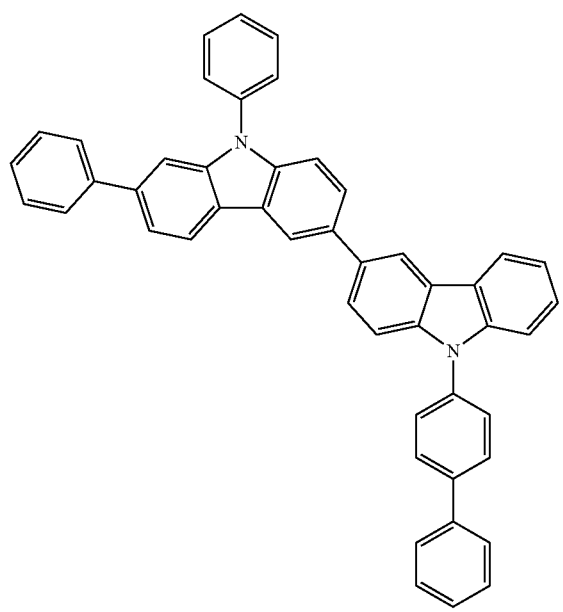
H2-23
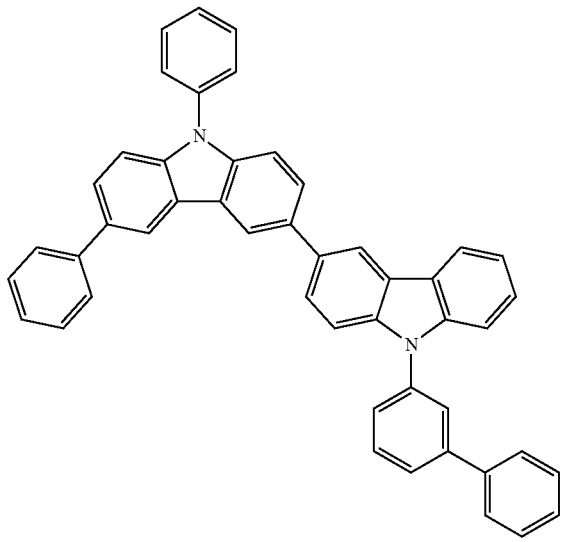
H2-24
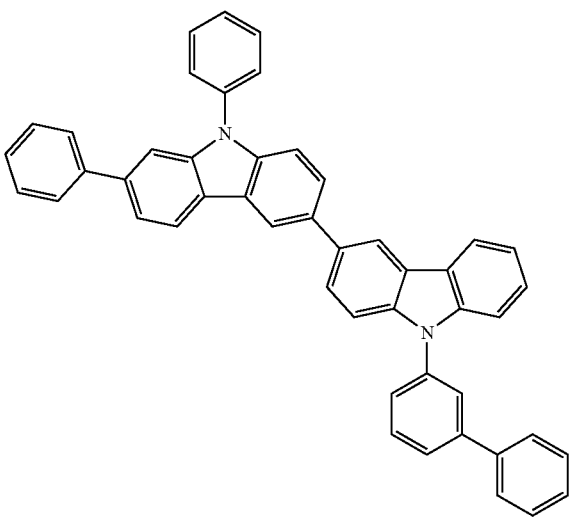

H2-25
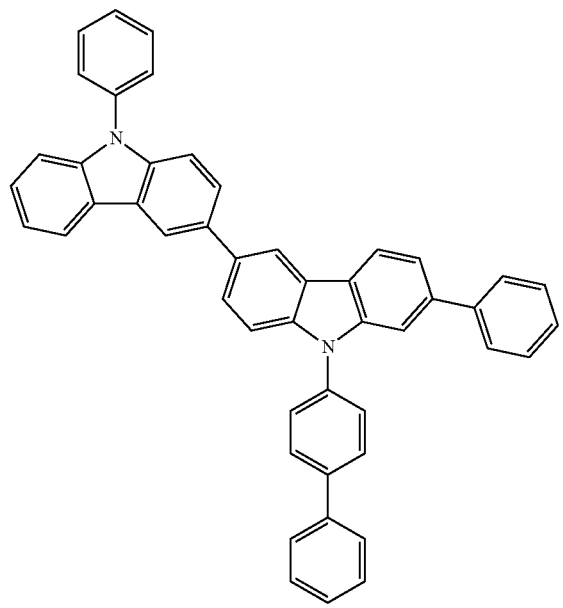
H2-26
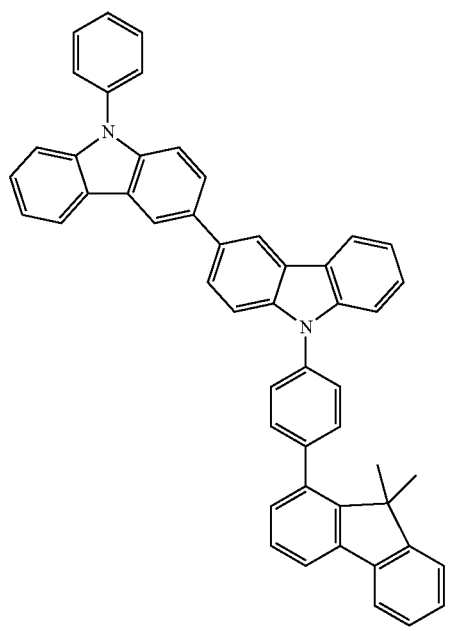
H2-27
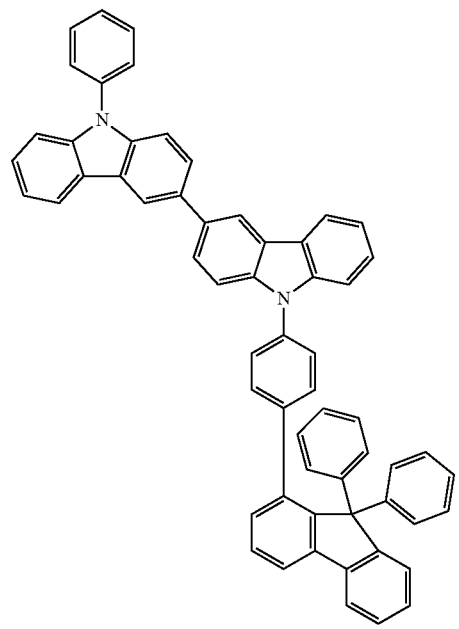
H2-28
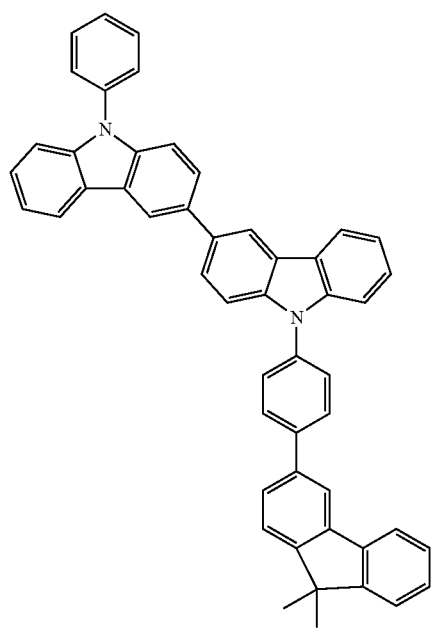

H2-29
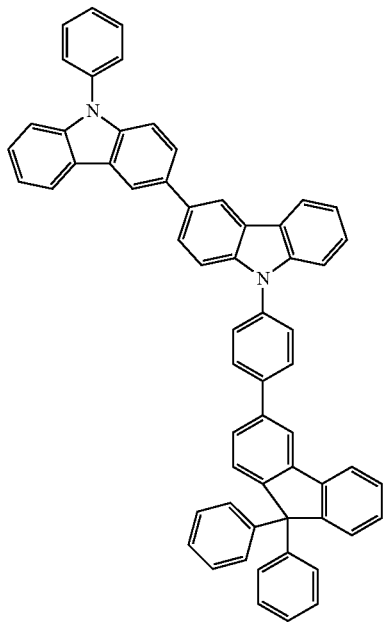
H2-30
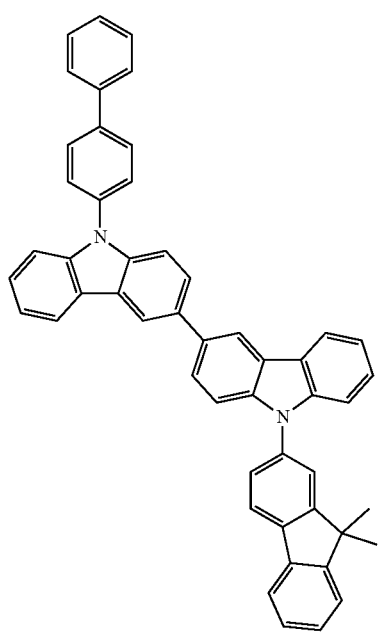
H2-31
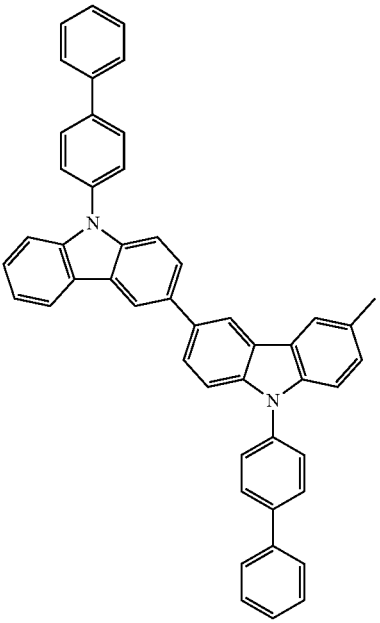
H2-32
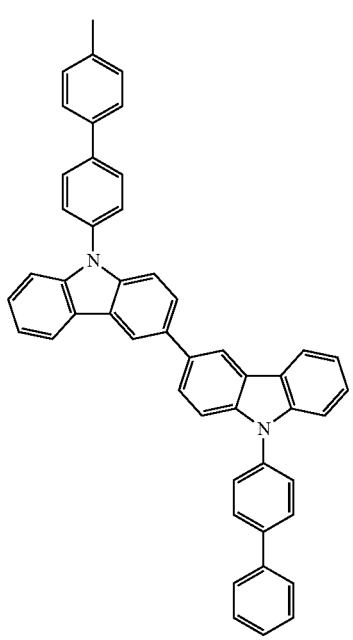

H2-33

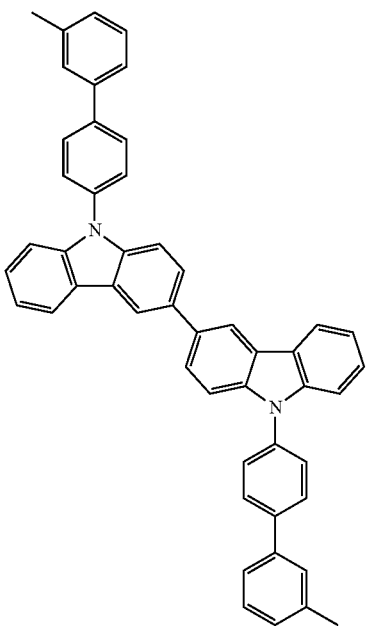

H2-35

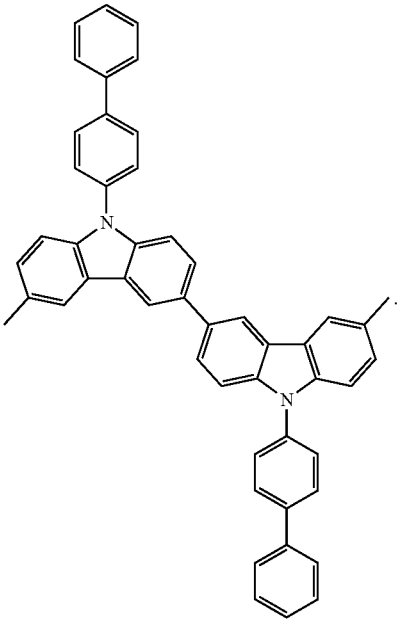

10. The plurality of host materials according to claim 5, wherein the second host material comprises the compound represented by the following formula 4:

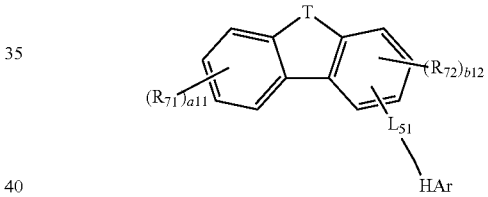

(4)

wherein
T represents —O— or —S—:
HAr represents a substituted or unsubstituted nitrogen-containing (3- to 30-membered)heteroaryl:
$L_{51}$ represents a single bond, a substituted or unsubstituted (C6-C30)arylene, or a substituted or unsubstituted (3- to 30-membered)heteroarylene:
$R_{71}$ and $R_{72}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino, or may be linked to an adjacent substituent to form a ring; and
$a_{11}$ represents an integer of 1 to 4, $b_{12}$ represents an integer of 1 to 3, and when $a_{11}$ and $b_{12}$ each represent an integer

H2-34

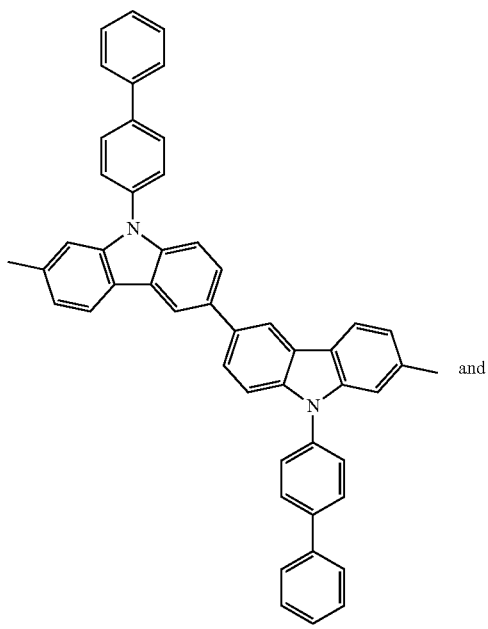

and of 2 or more, each of $R_{71}$ and each of $R_{72}$ may be the same or different from each other.
11. The plurality of host materials according to claim 10, wherein the compound represented by formula 4 is at least one selected from the following compounds:
H4-1
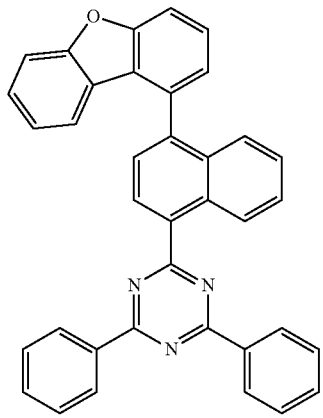
H4-2
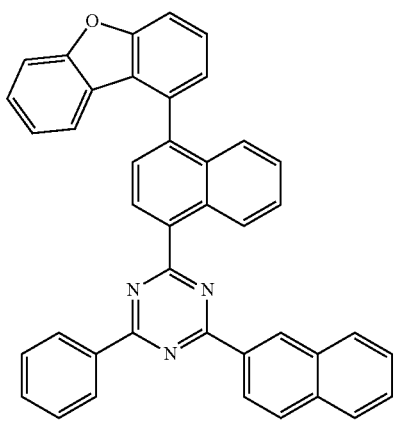
H4-3
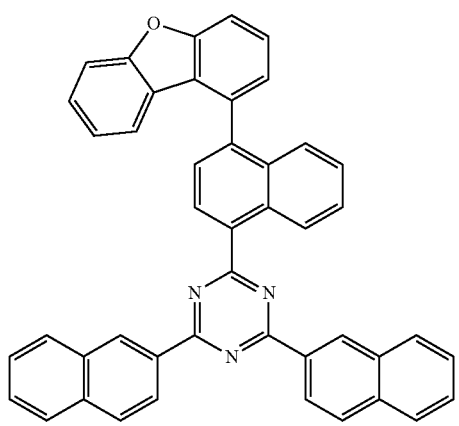
H4-4
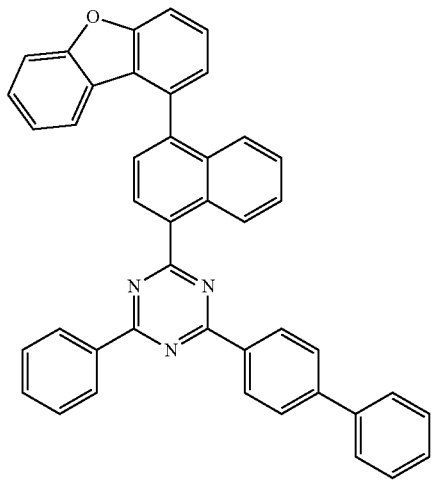
H4-5
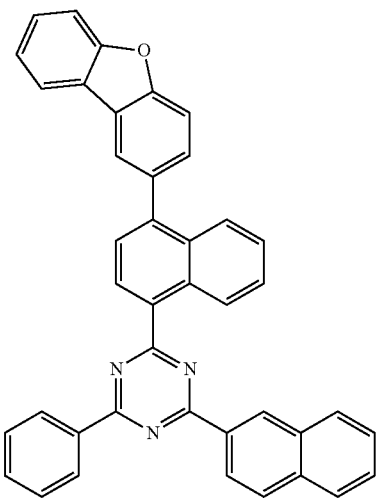
H4-6
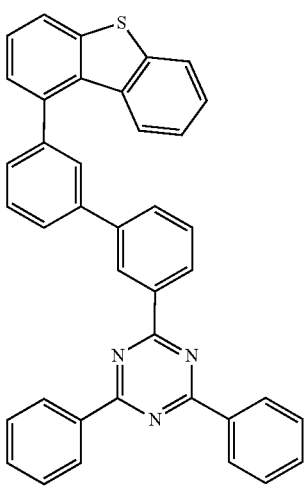

547                                                            548
-continued                                                     -continued
H4-7
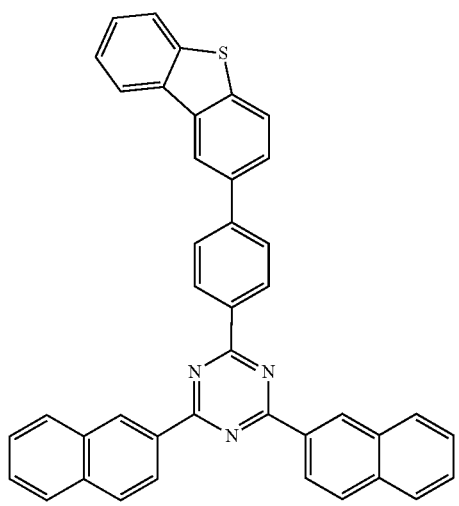
H4-10
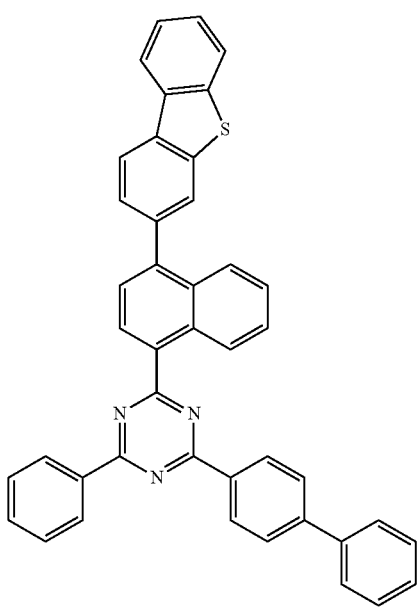
H4-8
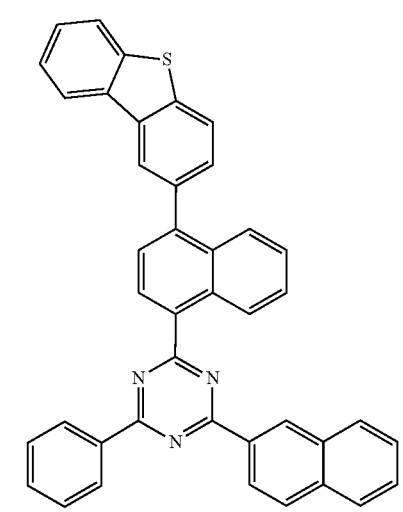
H4-11
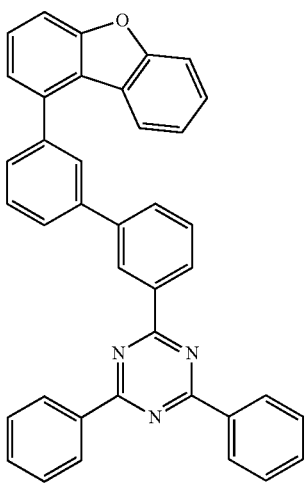
H4-9
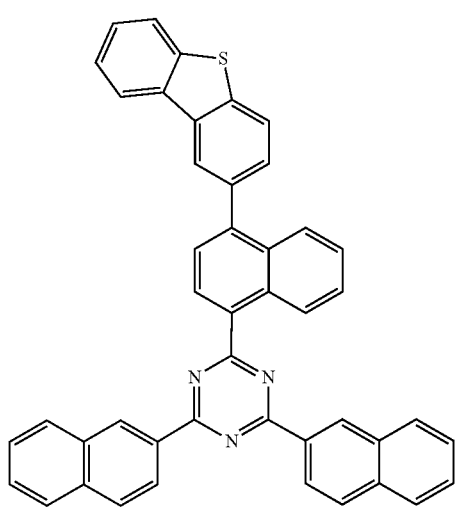
H4-12
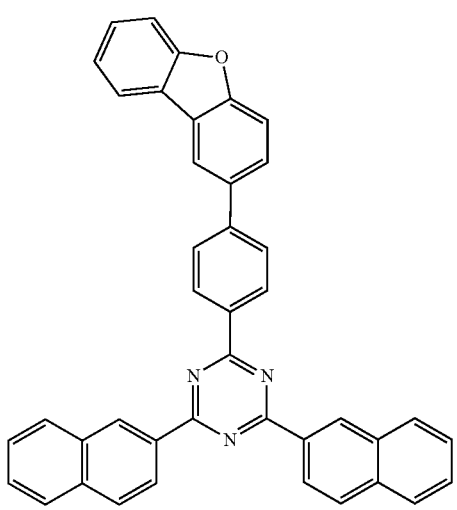

H4-13
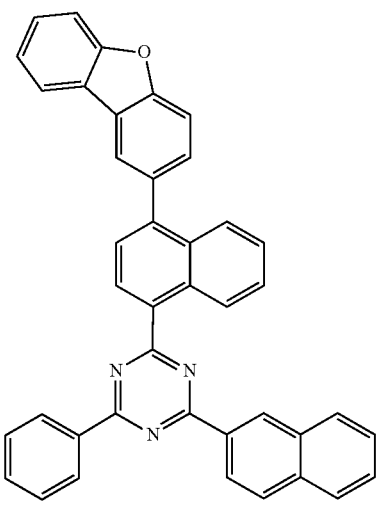
H4-14
H4-15
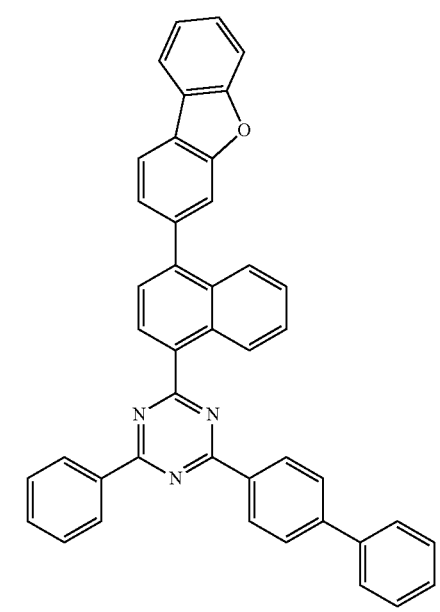
H-16
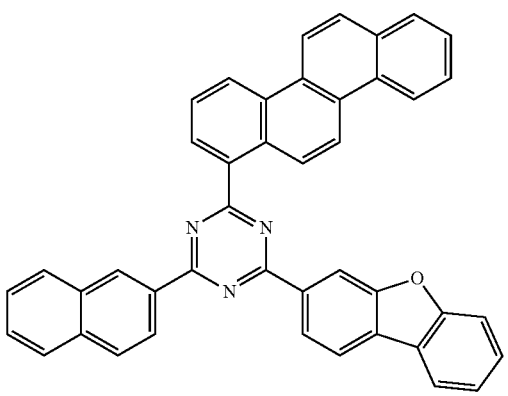
H-17
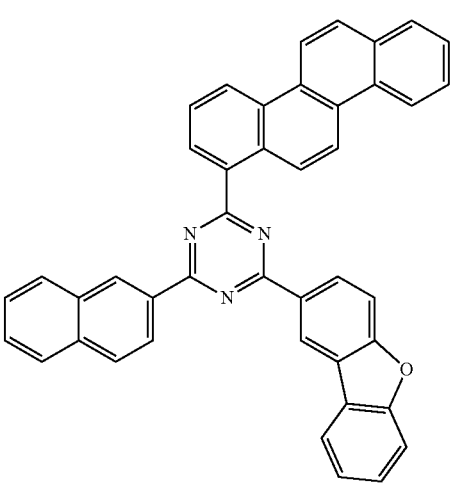
H-18
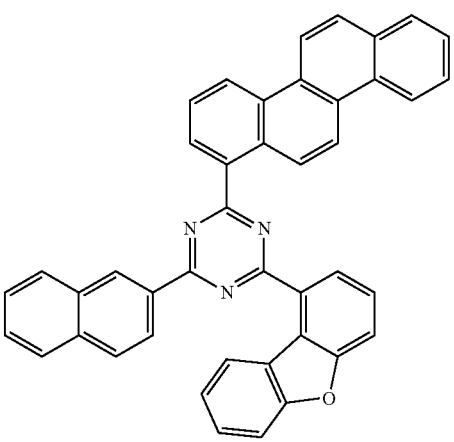

H-19
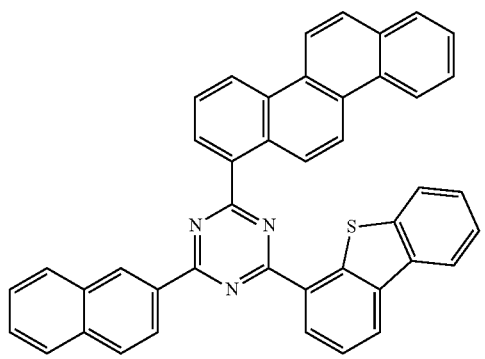
H4-22
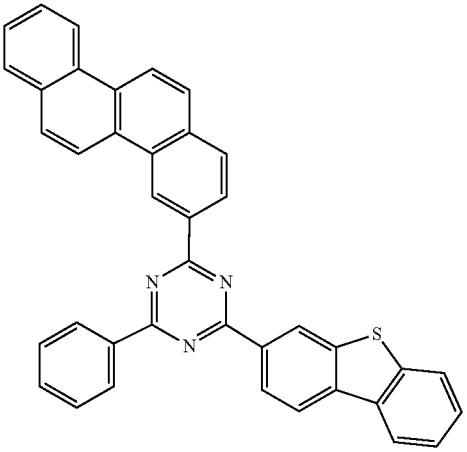
H4-20
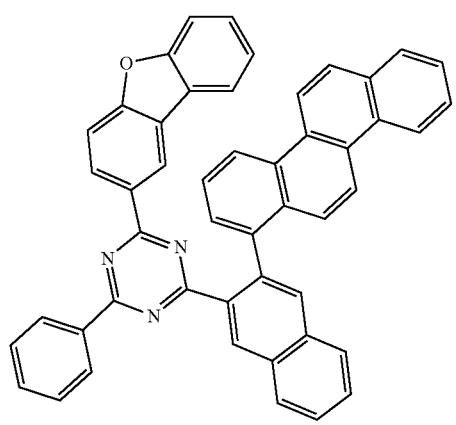
H4-23
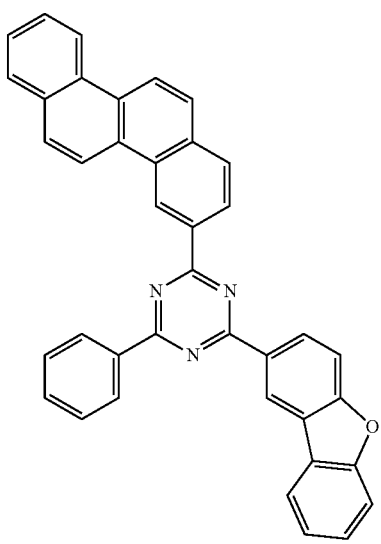
H4-21
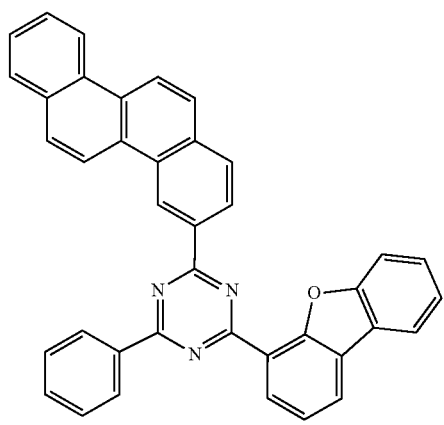
H4-24
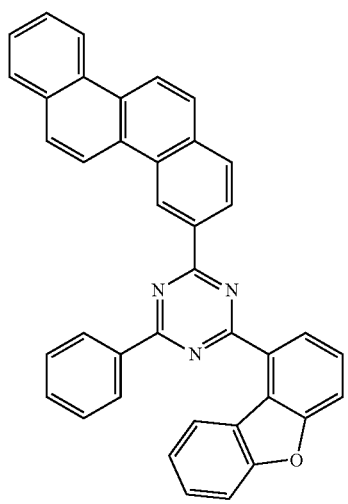

H4-25
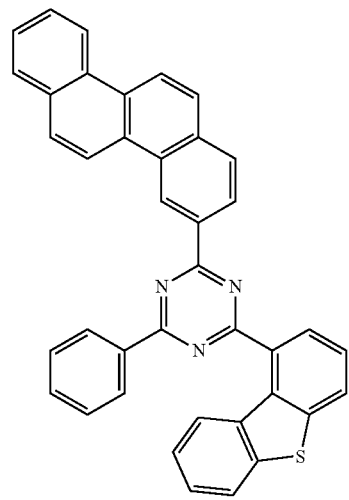
H4-26
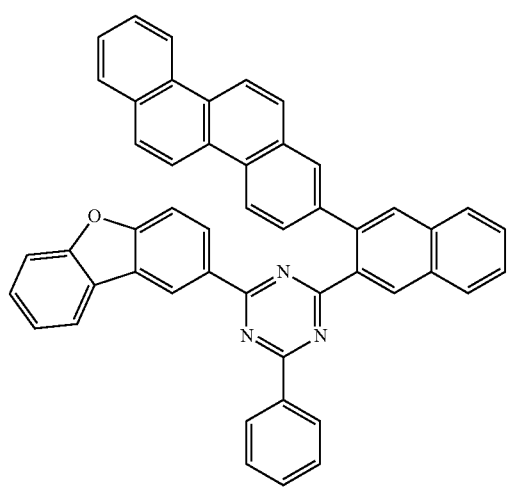
H4-27
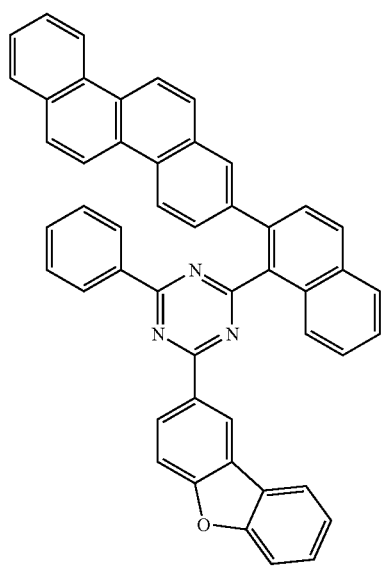
H4-28
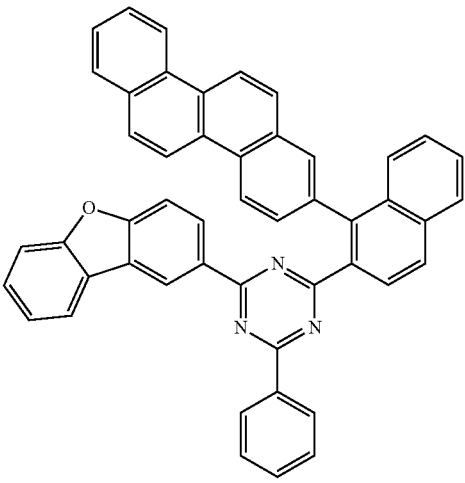
H4-29
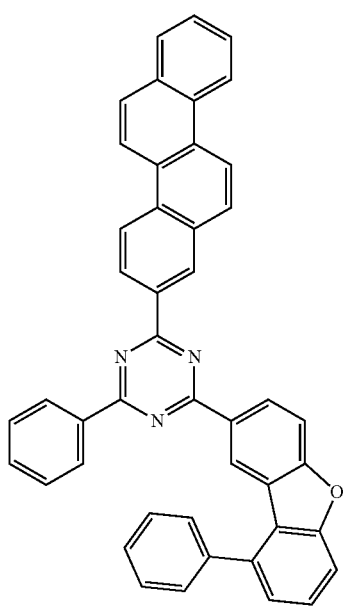
H4-30
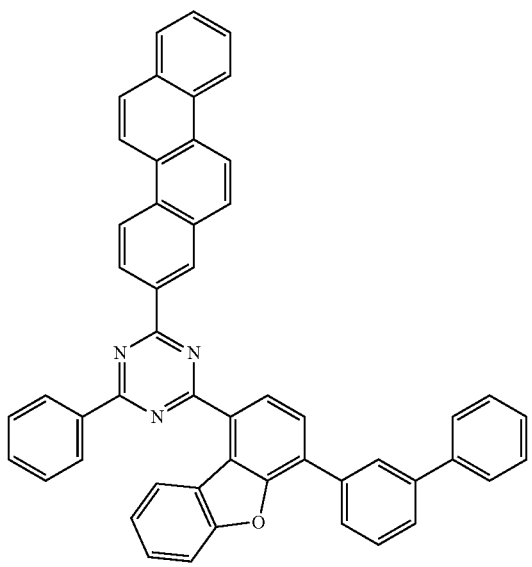

H4-31
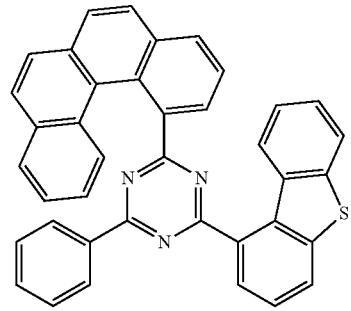
H4-32
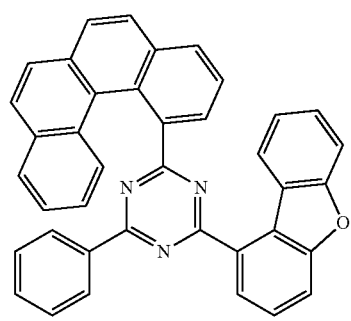
H4-33
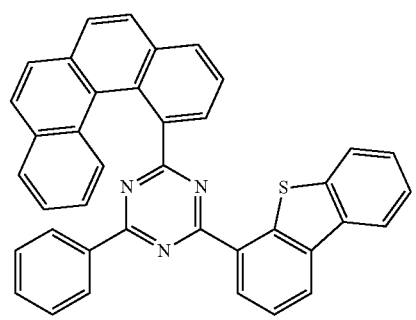
H4-34
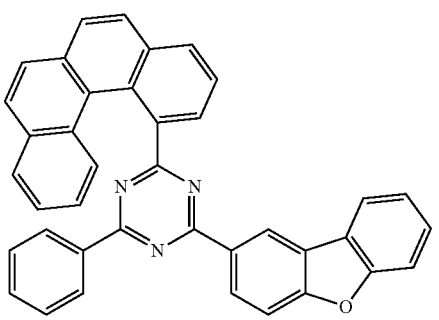
H4-35
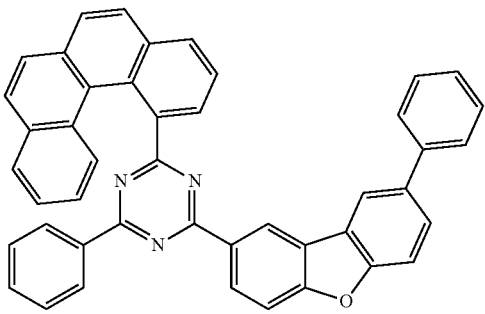
H4-36
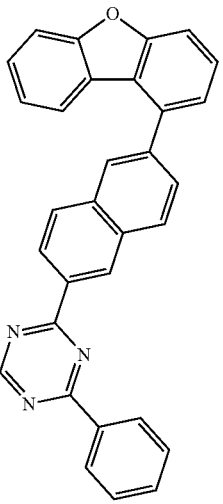
H4-37
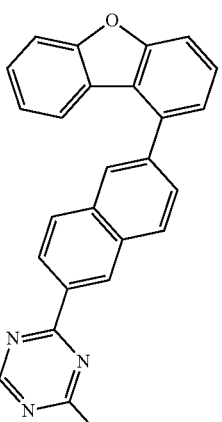
H4-38
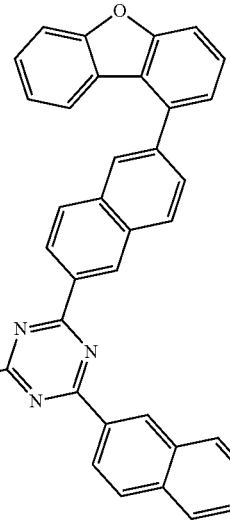

H4-39
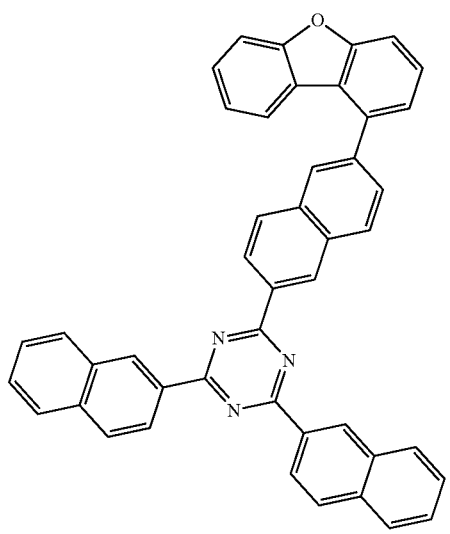
H4-40
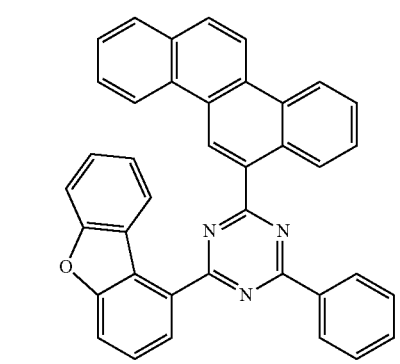
H4-41
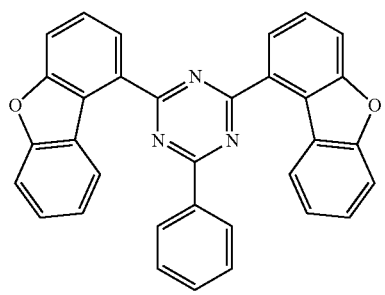
H4-42
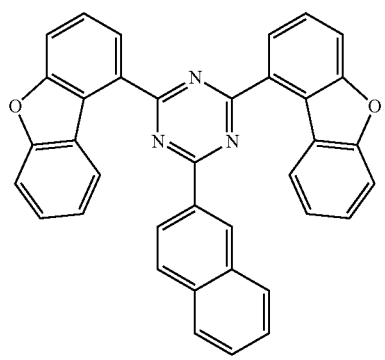
H4-43
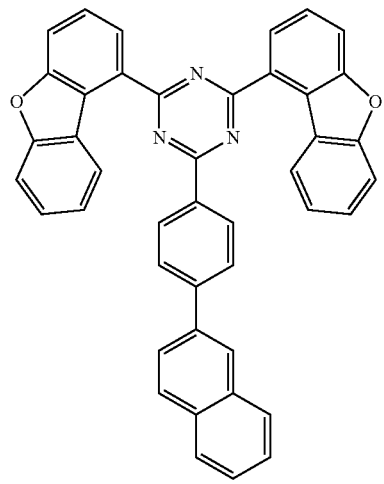
H4-44
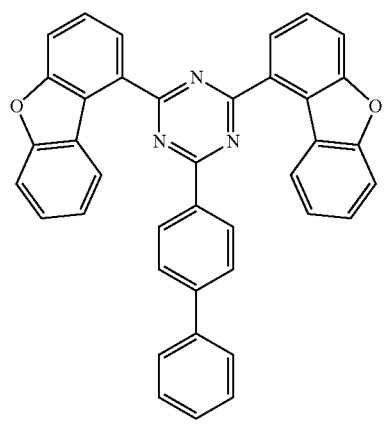
H4-45
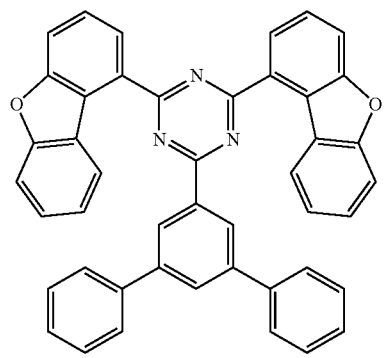

| 559 -continued | 560 -continued |
|---|---|
| H4-46 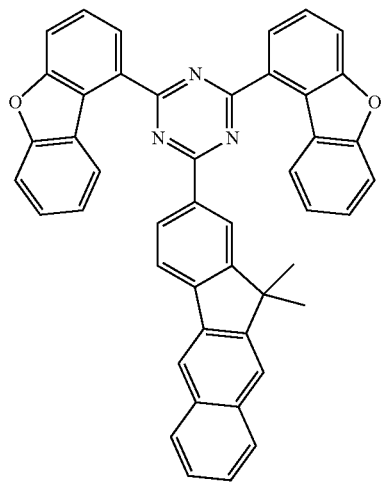 | H4-49 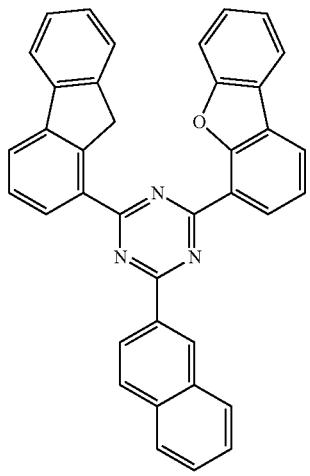 |
| H4-47 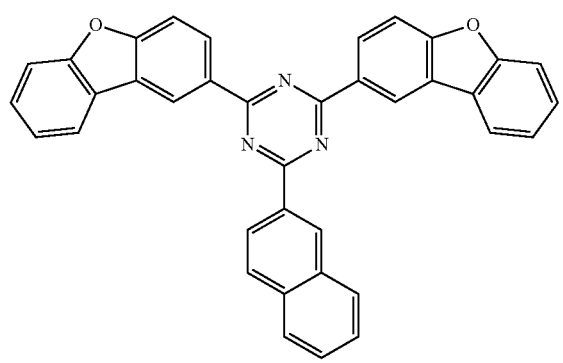 | H4-50 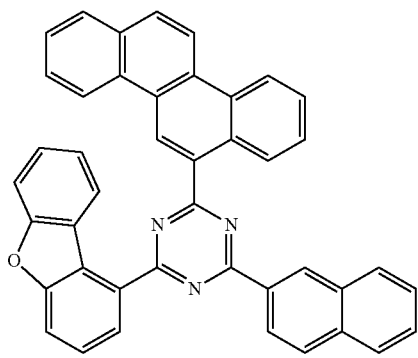 |
| H4-48 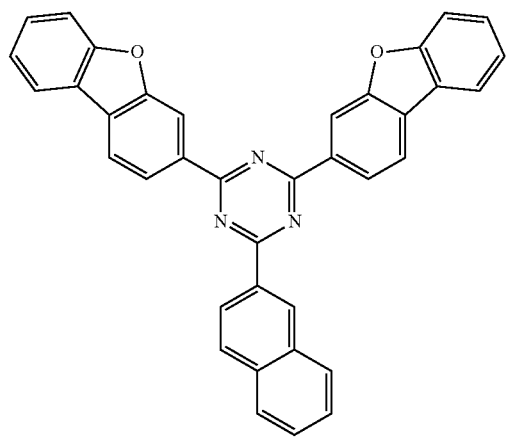 | H4-51 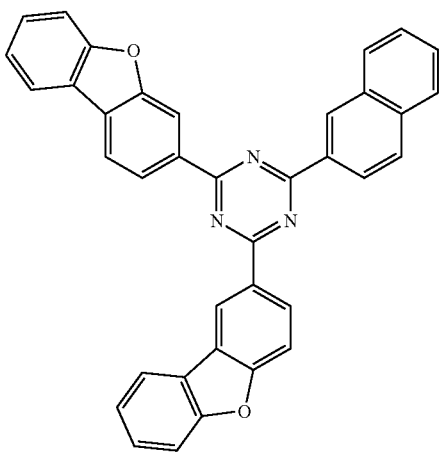 |

H4-52
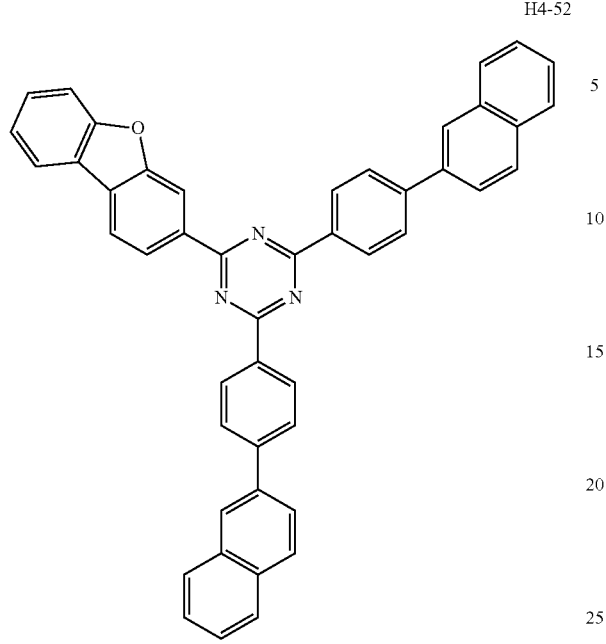
H4-55
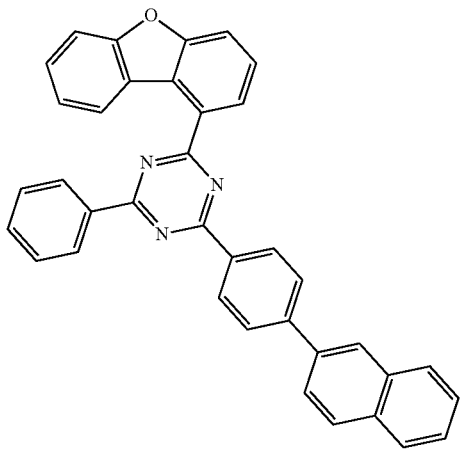
H4-53
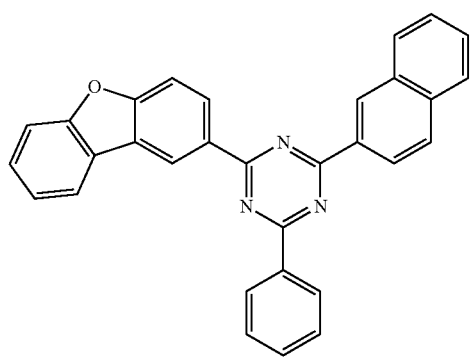
H4-54
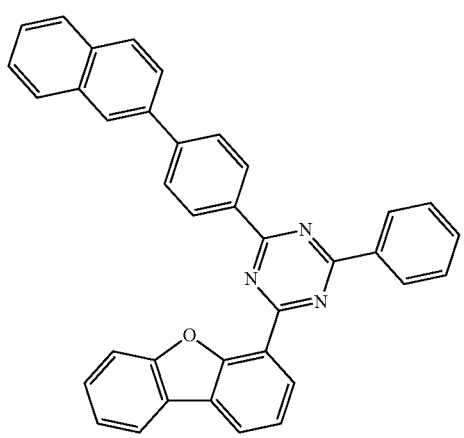
H4-56
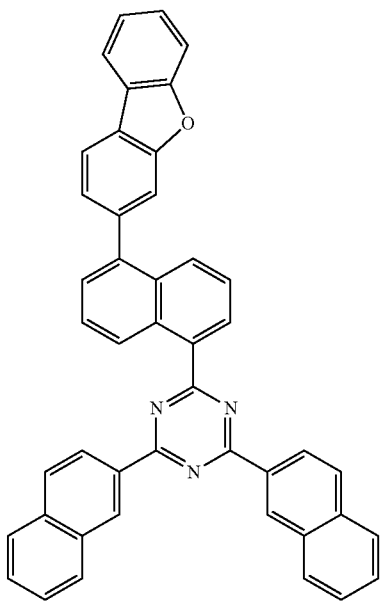

H4-57
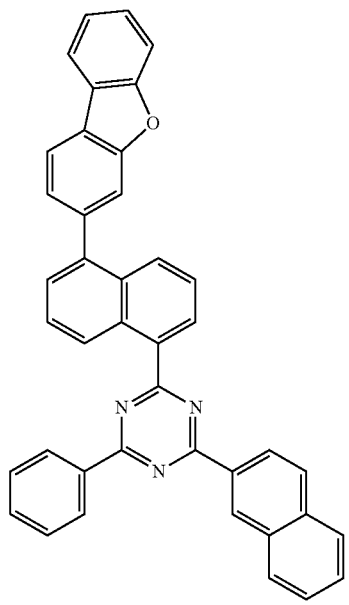
H4-58
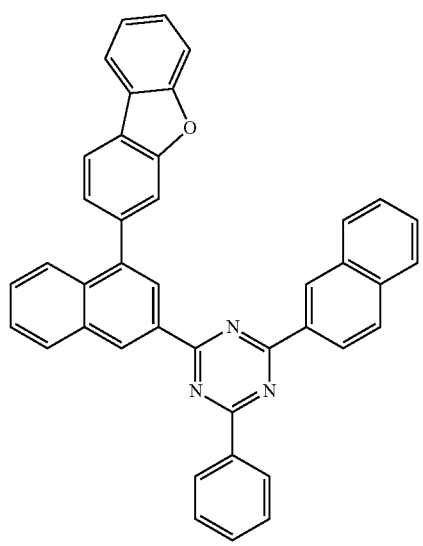
H4-59
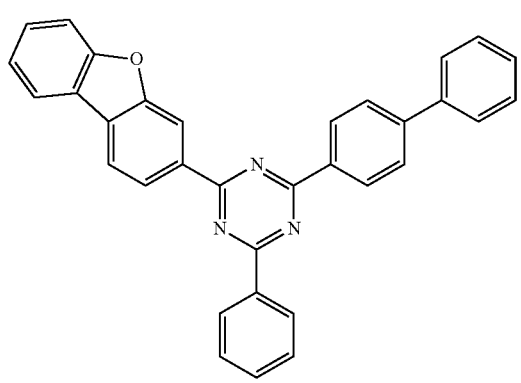
H4-60
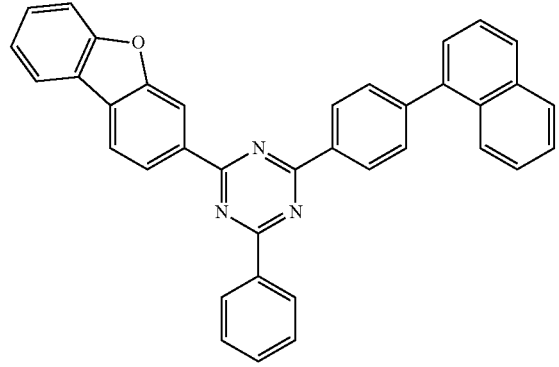
H4-61
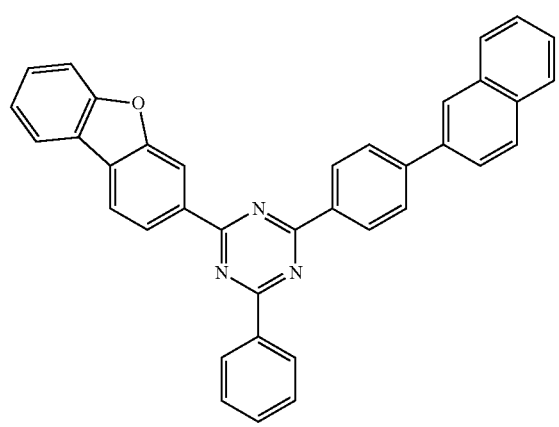
H4-62
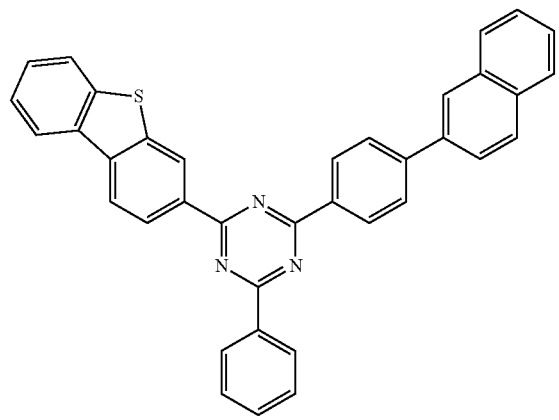

H4-63

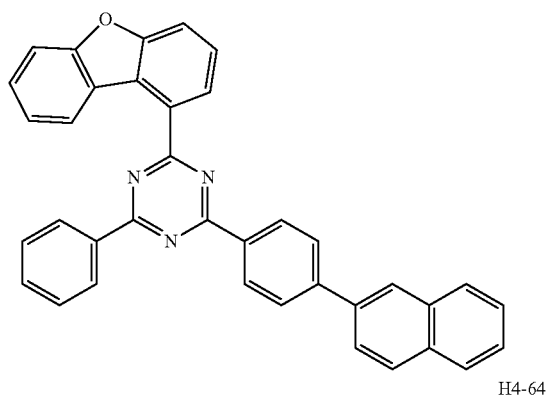

H4-65

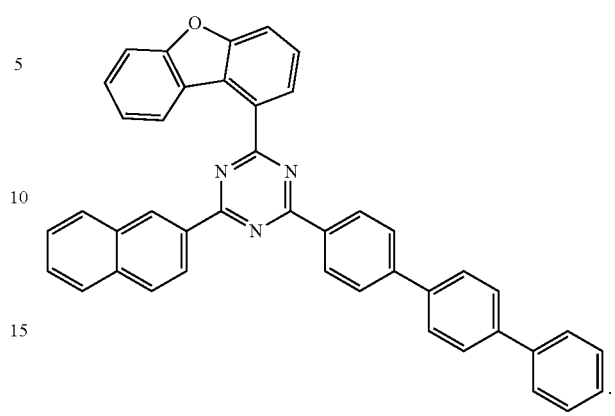

H4-64

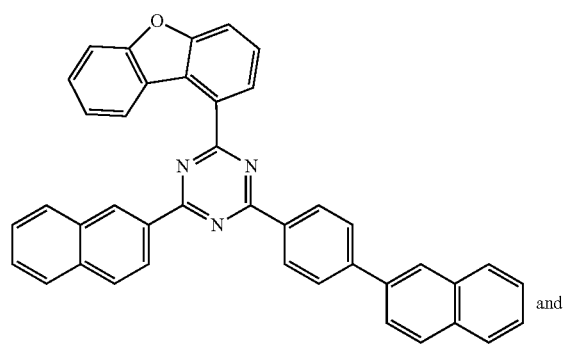

and

12. An organic electroluminescent device comprising the organic electroluminescent compound according to claim 1.

13. The organic electroluminescent device according to claim 12, wherein the organic electroluminescent compound is comprised in a light-emitting layer.

14. An organic electroluminescent device comprising an anode: a cathode; and at least one light-emitting layer between the anode and the cathode, wherein the at least one light-emitting layer comprises the plurality of host materials according to claim 5.

* * * * *

UNITED STATES PATENT AND TRADEMARK OFFICE
CERTIFICATE OF CORRECTION

PATENT NO. : 12,279,525 B2
APPLICATION NO. : 17/391166
DATED : April 15, 2025
INVENTOR(S) : Hyo-Soon Park Page 1 of 1

It is certified that error appears in the above-identified patent and that said Letters Patent is hereby corrected as shown below:

In the Claims

In Claim 4, the organic electroluminescent compounds C-522, C-523, C-524, C-525, C-526, C-529, C-534, and C-535 are inadvertently included twice. The compounds appearing from Column 469, Line 40 to Column 472, Line 30 therefore require deletion. These are:

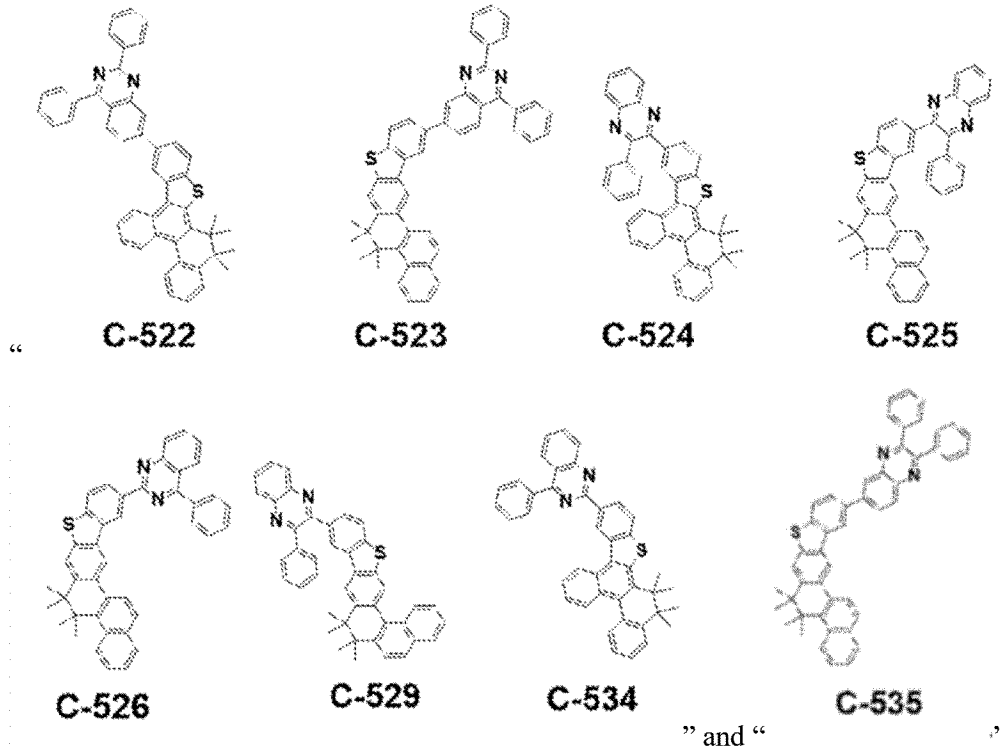

" and " ".

Signed and Sealed this
Twentieth Day of May, 2025

Coke Morgan Stewart
*Acting Director of the United States Patent and Trademark Office*